United States Patent
Chessari et al.

(10) Patent No.: US 10,544,132 B2
(45) Date of Patent: *Jan. 28, 2020

(54) ISOINDOLINONE INHIBITORS OF THE MDM2-P53 INTERACTION HAVING ANTICANCER ACTIVITY

(71) Applicants: ASTEX THERAPEUTICS LIMITED, Cambridge (GB); CANCER RESEARCH TECHNOLOGY LIMITED, London (GB)

(72) Inventors: Gianni Chessari, Cambridge (GB); Steven Howard, Cambridge (GB); Ildiko Maria Buck, London (GB); Benjamin David Cons, Cambridge (GB); Christopher Norbert Johnson, Saffron Walden (GB); Rhian Sara Holvey, Cambridge (GB); David Charles Rees, Cambridge (GB); Jeffrey David St. Denis, Cambridge (GB); Emiliano Tamanini, Cambridge (GB); Bernard Thomas Golding, Newcastle upon Tyne (GB); Ian Robert Hardcastle, Hexham (GB); Celine Florence Cano, Newcastle upon Tyne (GB); Duncan Charles Miller, Newcastle upon Tyne (GB); Martin Edward Mäntylä Noble, Newcastle upon Tyne (GB); Roger John Griffin; James Daniel Osborne, Cambridge (GB); Joanne Peach, Cambridge (GB); Arwel Lewis, Royston (GB); Kim Louise Hirst, Saffron Walden (GB); Benjamin Paul Whittaker, Potton (GB); David Wyn Watson, Duxford (GB); Dale Robert Mitchell, Saffron Walden (GB)

(73) Assignees: ASTEX THERAPEUTICS LIMITED, Cambridge (GB); CANCER RESEARCH TECHNOLOGY LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/763,698

(22) PCT Filed: Sep. 29, 2016

(86) PCT No.: PCT/GB2016/053042
§ 371 (c)(1),
(2) Date: Mar. 27, 2018

(87) PCT Pub. No.: WO2017/055860
PCT Pub. Date: Apr. 6, 2017

(65) Prior Publication Data
US 2019/0016708 A1    Jan. 17, 2019

(30) Foreign Application Priority Data

Sep. 29, 2015  (GB) .................. 1517217.4

(51) Int. Cl.
*C07D 405/14* (2006.01)
*C07D 403/06* (2006.01)
(Continued)

(52) U.S. Cl.
CPC ............ *C07D 405/14* (2013.01); *A61P 35/00* (2018.01); *C07D 209/48* (2013.01);
(Continued)

(58) Field of Classification Search
CPC .. C07D 405/14; C07D 209/48; C07D 403/06; C07D 405/12; C07D 413/12; A61P 35/00
(Continued)

(56) References Cited

U.S. PATENT DOCUMENTS 3,466,298 A   9/1969  Sulkowski et al.
3,763,178 A   10/1973 Sulkowski et al.
(Continued)

FOREIGN PATENT DOCUMENTS

CH    374071     12/1963
DE    2313227    9/1973
(Continued)

OTHER PUBLICATIONS

Chemical Inhibition of Wild-Type p-53-Induced phosphate 1 . . . Arman Esfandiari et al (Year: 2018).*
(Continued)

*Primary Examiner* — Rita J Desai
(74) *Attorney, Agent, or Firm* — Heslin Rothenberg Farley & Mesiti P.C.

(57) ABSTRACT

The invention provides a compound of formula (I):

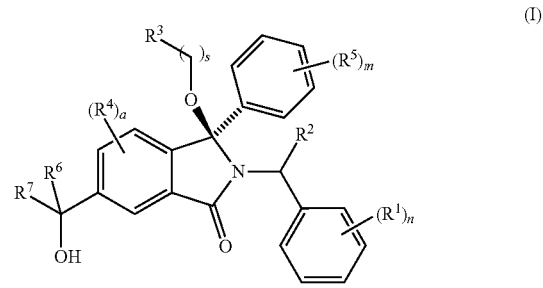

or tautomer or a solvate or a pharmaceutically acceptable salt thereof, wherein the various substituents are as defined in the claims.
Also provided are pharmaceutical compositions containing the compounds of formula (I), processes for making the compounds and the medical uses of the compounds.

27 Claims, No Drawings

(51) Int. Cl.
  *C07D 405/12* (2006.01)
  *C07D 413/12* (2006.01)
  *C07D 209/48* (2006.01)
  *A61P 35/00* (2006.01)

(52) U.S. Cl.
  CPC ......... *C07D 403/06* (2013.01); *C07D 405/12* (2013.01); *C07D 413/12* (2013.01); *C07B 2200/05* (2013.01)

(58) Field of Classification Search
  USPC ...................................................... 548/513
  See application file for complete search history.

(56) References Cited

U.S. PATENT DOCUMENTS

| | | | |
|---|---|---|---|
| 3,898,232 | A | 8/1975 | Cotrel et al. |
| 4,001,271 | A | 1/1977 | Cotrel et al. |
| 4,200,759 | A | 4/1980 | Dickinson |
| 4,244,966 | A | 1/1981 | Lippman et al. |
| 4,312,809 | A | 1/1982 | Haugwitz |
| 4,331,600 | A | 5/1982 | Golec, Jr. et al. |
| 4,505,921 | A | 3/1985 | Beregi et al. |
| 6,344,468 | B1 | 2/2002 | Schindler et al. |
| 8,258,175 | B2 | 9/2012 | Willems et al. |
| 8,618,158 | B2 | 12/2013 | Golding et al. |
| 9,358,222 | B2 | 6/2016 | Golding et al. |
| 2005/0004207 | A1 | 1/2005 | Straub et al. |
| 2006/0264473 | A1 | 11/2006 | Khazak et al. |
| 2012/0264738 | A1 | 10/2012 | Sugimoto et al. |
| 2014/0194486 | A1 | 7/2014 | Golding et al. |
| 2016/0355478 | A1 | 12/2016 | Golding et al. |
| 2018/0118684 | A1 | 5/2018 | Golding et al. |
| 2019/0055215 | A1 | 2/2019 | Chessari et al. |

FOREIGN PATENT DOCUMENTS

| | | |
|---|---|---|
| EP | 0461079 A2 | 12/1991 |
| EP | 1199306 A1 | 4/2002 |
| EP | 1566378 A1 | 8/2005 |
| EP | 2108642 A1 | 10/2009 |
| GB | 1325065 | 8/1973 |
| GB | 1601701 | 11/1981 |
| JP | 2000506163 A | 5/2000 |
| JP | 2004217591 | 8/2004 |
| JP | 2005255660 A | 9/2005 |
| KR | 20130088577 A | 8/2013 |
| WO | 9732846 A1 | 9/1997 |
| WO | 9942444 A1 | 8/1999 |
| WO | 0132928 A2 | 5/2001 |
| WO | 03051359 A1 | 6/2003 |
| WO | 03101450 A1 | 12/2003 |
| WO | 2005021532 A1 | 3/2005 |
| WO | 2005095341 A1 | 10/2005 |
| WO | 2006020879 A1 | 2/2006 |
| WO | 2006024837 A1 | 3/2006 |
| WO | 2007/021309 A1 | 2/2007 |
| WO | 2008/024892 A2 | 2/2008 |
| WO | 2008/117061 A2 | 10/2008 |
| WO | 2008151184 A1 | 12/2008 |
| WO | 2009156735 A2 | 12/2009 |
| WO | 2010031713 A1 | 3/2010 |
| WO | 2011076786 A1 | 6/2011 |
| WO | 2011098398 A1 | 8/2011 |
| WO | 2011153509 A1 | 12/2011 |
| WO | 2012175487 A1 | 12/2012 |
| WO | 2012175520 A1 | 12/2012 |
| WO | 2013/120835 A1 | 8/2013 |
| WO | 2013111105 A1 | 8/2013 |
| WO | 2014/070948 A1 | 5/2014 |
| WO | 2015161032 A1 | 10/2015 |
| WO | 2017/055859 A1 | 4/2017 |
| WO | 2017/055860 A1 | 4/2017 |
| WO | 2017/068412 A1 | 4/2017 |
| WO | 2017/087607 A1 | 5/2017 |

OTHER PUBLICATIONS

Degradation of MDM2 by interaction between Berberine and DAXX leads to potent apoptosis in MDM2-overexpressing cancer cells. . . Xiaoling Zhang et al. (Year: 2010).*
Small Molecule inhibitors of MDM2-p53 protein-protein Interaction based on Isoindole scaffold. Hardcastle Ian et al (Year: 2006).*
Great Britain Search Report for GB1517217.4, dated Jun. 27, 2016, 2 pp.
International Search Report for PCT/GB2016/053042, dated Nov. 30, 2016, 19 pp.
Prodrug [online, wikipedia], [retrieved on Mar. 11, 2007], Retrieved from the internet, URL http://en.wikipedia.org/wiki/Prodrugs.
Lala, P.K., et al., Role of nitric oxide in tumor progression: Lessons from experimental tumors, Cancer and Metastasis Reviews, vol. 17, No. 1, pp. 91-106 (1998).
Golub, T.R., et al., Molecular Classification of Cancer: Class Discovery and Class Prediction by Gene Expression Monitoring, Science, vol. 286, pp. 531-537 (1999).
Cancer [online, medline], [retrieved on Jul. 6, 2007], Retrieved from the internet, URL http://www.nlm.nih.gov/medlineplus/cancer.html.
Cancer [online, wikipedia], [retrieved on Jul. 6, 2007], Retrieved from the internet, URL http://en.wikipedia.org/wiki/Cancer.
Bartfeld, H.D., et al., 3-Oxo-Isoindole, Tetrahedron Letters, No. 10, pp. 757-760 (1970).
CAPLUS 95:150329 record for Lencbergs, I., et al., 3-Hydroxy-3-(α-aminobenzyl)-2-substituted 1-isoindolinones, Latvijas PSR Zinatnu Akademijas Vestis, Kimijas Serija (1981), (3), 335-40.
Rebek, Jr., J., et al., Olefin Epoxidation with α-Substituted Hydroperoxides, J. Am. Chem. Soc., vol. 102, pp. 5602-5605 (1980).
Griffiths, J., et al., Model Studies for Damage to Nucleic Acids Mediated by Thiyl Radicals, Tetrahedron, vol. 48, No. 26, pp. 5543-5556 (1992).
Park, J.S., et al., Noble 2-[3(Cyclopentyloxy)-4-Methoxyphenyl]-1-Isoindolinone Derivatives. Part I; Synthesis and SAR Studies for the Inhibition of TNF-α Production, Arch. Pharma. Res., vol. 24, No. 5, pp. 367-370 (2001).
Ito, Y., et al., Solid-State and Solution Photolyses of Tetracyanobenzene with Benzyl Cyanlides or Benzyl Alcohols, Tetrahedron, vol. 56, pp. 7139-7152 (2000).
Vivekananda Bhatt, M., et al., Aspects of Tautomerism. Part V. † Solvent, Substituent, and Steric Effects on the Ring-Chain Tautomerism of o-Benzoylbenzamides, Journal of the Chemical Society, Perkin Transactions II, pp. 1160-1166 (1973).
Topliss, J.G., Chemistry, et al., Antihypertensive Agents. III. 3-Hydroxy-3-phenylphthalimidines, Journal of Medicinal.vol. 7, pp. 453-456 (1964).
Charlesworth, E.H., et al., Fluoranthene studies. III. A synthesis of 3-bromo-6-nitrofluorenone, Canadian Journal of Chemistry, vol. 46, No. 3, pp. 463-465 (1968).
STN 1972:419475 (CAPLUS) record for Valters, R., et al., Ring-chain transformations involving the carbonyl group. XI. Acid chlorides and amides of 2-benzoyl-3-,4-, 5-, and 6-nitrobenzoic acids, Rizh. Politekh. Inst., Riga, USSR, Latvijas Psr Zinatnu Akademijas Vestis, Kimijas Serija, vol. 1, pp. 61-65 (1972).
Yang et al., "Practical Proline-Catalyzed Asymmetric Mannich Reaction of Aldehydes with N-Boc-Imines," Nature Protocols, vol. 2, No. 8, 2007, pp. 1937-1942.
Körmendy, Academiae K., Uber Reaktionen in Polyaminsynthesen Mit Phthaliminoakjylhaloiden, I., Acta Chimica.Scientiarum Hungaricae, pp. 255-264 (1958).
Inaba, M., et al., Reversal of Resistance to Vincristine in P388 Leukemia by Various Polycyclic Clinical Drugs, with a Special Emphasis on Quinacrine, Cancer Research, vol. 48, No. 8, pp. 2064-2067 (1988).
Croisy-Delcey, M., et al., Dipheyl Quinolines and Isoquinolines: Synthesis and Primary Biological Evaluation, Bioorganic and Medicinal Chemistry, vol. 8, pp. 2629-2641 (2000).
Kitching, M.S., et al., Synthesis of 3-Alkoxy- and 3-Alkylamino-2-alkyl-3-arylisoindolinones, Synlett, vol. 81, pp. 997-999 (1999).

(56) References Cited

OTHER PUBLICATIONS

Nikitin, K.V., et al., Synthesis of 5-alkyl- and 5-aryl-1,5-dihydro-2H-pyrrol-2-ones via coupling of 5-chloro-1,5-dihydro-2H-pyrrol-2-ones with organometallic compounds, Can. J. Chem., vol. 78, pp. 1285-1288 (2000).
Truitt, P., et al., 3-Phenylphthalimidines, New Compounds, J. Med. Chem., vol. 8, pp. 731-732 (1965).
Liebl, R., et al., Notiz zur Synthese von 3-[Aklyl(aryl)thio]isoindolinonen aus 2-Formylbenzoesäure-methylester, Liebigs Ann. Chem., pp. 1093-1094 (1985).
Usov, V.A., et al., Formation of Isoquinolones and Isoindolones in the Oxidation of 2-Aryl-l-phenylamino-3-phenyliminoindenes, Chemistry of Heterocyclic Compounds (Khimiya Geterotsiklicheskikh Soedinenil), vol. 5, No. 4, pp. 474-477
Ahmed, M., et al., Preparation of Some Isoindolo[2,1f]phenanthridine Derivatives, J. Chem. Soc., Perkins Trans. 1, pp. 601-605 (1977).
Beanlands, D.S., et al., Therapeutic Trial of a New Oral Diuretic, Canadian Medical Association Journal, vol. 84, pp. 91-95 (1961).
Chene, P., et al., A Small Synthetic Peptide, which Inhibits the p53-hdm2 Interaction, Stimulates the p53 Pathway in Tumour Cell Lines, J. Molecular Biology, vol. 299, pp. 245-253 (2000).
Donehower, L.A., et al., Mice deficient for p53 are developmentally normal but susceptible to spontaneous tumours, Nature, vol. 356, pp. 215-221 (1992).
Epsztajn, J., et al., Application of Organolithium and Related Reagents in Synthesis. Part 23: Synthetic Strategies Based on ortho-Aromatic Metallation. Synthesis of 4b-Arylisoindolo[2,1-α]quinolone derivatives, Tetrahedron, vol. 56 pp. 4837-4844 (2000).
Ghosh, M., et al., Overexpression of Mdm2 and MdmX Fusion Proteins Alters p53 Mediated Transactivation, Ubiquitination, and Degradation, American Chemical Society, Biochemistry, vol. 42, pp. 2291-2299 (2003).
Lane, D.P., p53, guardian of the genome, Nature, vol. 358, pp. 15-16 (1992).
Levine, A.J., p53, The Cellular Gatekeeper for Growth and Division, Cell, vol. 88, pp. 323-331 (1997).
Oliner, J.D., et al., Amplification of a gene encoding a p53-associated protein in human sarcomas, Nature, vol. 358, pp. 80-83 (1992).
Schon, O., et al., Molecular Mechanism of the Interaction between MDM2 and p53, Journal of Molecular Biology, vol. 323, pp. 491-501 (2002).
Toledo, F., et al., Regulating the p53 pathway: in vitro hypotheses, in vivo veritas, Nature Reviews Cancer, vol. 6, pp. 909-923 (2006).
Vassilev, L.T., et al., In Vivo Activation of the p53 Pathway by Small-Molecule Antagonists of MDM2, Science, vol. 303, pp. 844-848 (2004).
Golik, U., The Synthesis of some 2,4-Benzodiazepin-1-ones, Potent C.N.S. Agents (I), Journal of Heterocyclic Chemistry, vol. 12, No. 5, pp. 903-908 (1975).
Hardcastle, I.R., et al., Small-Molecule Inhibitors of the MDM2-p53 Protein-Protein Interaction Based on an Isoindolinone Scaffold, Journal of Medicinal Chemistry (2006), 49(21), 6209-6221.
Suzuki, T., et al., Novel Chemoselective Desulfurization of γ-Phenylthio-Substituted Aromatic Lactams: Application to the Synthesis of Isoindolobenzazepine Alkaloid, Lennoxamine, *Synlett*, No. 20, pp. 3407-3410 (2006).
Ying, H., et al., The Docking Based 3D-QSAR Studies on Isoindolinone Derived Inhibitors of p53-MDM2 Binding, Letters in Drug Design & Discovery, vol. 11, pp. 50-58 (2014).
Mondal, C., et al., Comparative validated molecular modeling of p53-HDM2 inhibitors as antiproliferative agents, European Journal of Medicinal Chemistry, vol. 90, pp. 860-875 (2015).
Dong, X., et al., OSAR Models for isoindolinone-based p53-MDM2 Interaction Inhibitors Using Linear and Non-linear Statistical Methods, Chem Biol Drug Des, vol. 79, pp. 691-702 (2012).
Watson, A.F., et al., MDM2-p53 protein-protein interactions inhibitors: A-ring substituted isoindolinones, Bioorganic & Medicinal Chemistry Letters, vol. 21, pp. 5916-5919 (2011).
Riedinger, C., et al., Understanding Small-Molecule Binding to MDM2: Insights into Structural Effects of Isoindolinone Inhibitors from NMR Spectroscopy, Chem Biol Drug Des, vol. 77, pp. 301-308 (2011).
Hardcastle, I.R., et al., "Isoindolinone Inhibitors of the Murine Double Minute 2 (MDM2)-p53 Protein—Protein Interaction: Structure—Activity Studies Leading to Improved Potency", Journal of Medicinal Chemistry, vol. 54, pp. 1233-1243 (2011).
Grigoreva, T.A., et al., "Proapoptotic modification of substituted isoindolinones as MDM2-p53 inhibitors", *Bioorganic & Medicinal Chemistry Letters*, vol. 27, pp. 5197-5202 (2017).
Riedinger, C., et al., "Analysis of Chemical Shift Changes Reveals the Binding Modes of Isoindolinone Inhibitors of the MDM2-p53 Interaction", Journal of the American Chemical Society, vol. 130, No. 47, pp. 16038-16044 (2008).
Howard et al., "Isoindolinone Inhibitors of the MDM2-P53 Interaction and Process for Making Them," U.S. Appl. No. 16/498,207, filed Sep. 26, 2019.
Chessari et al., "Combination of Isoindolinone Derivatives with SGI-110," U.S. Appl. No. 16/497,135, filed Sep. 24, 2019.

* cited by examiner

ISOINDOLINONE INHIBITORS OF THE MDM2-P53 INTERACTION HAVING ANTICANCER ACTIVITY

CROSS REFERENCE TO RELATED APPLICATIONS

This application is a national stage filing under section 371 of International Application No. PCT/GB2016/053042, filed on Sep. 29, 2016, and published on Apr. 6, 2017 as WO 2017/055860, which claims priority to Great Britain Application No. 1517217.4, filed on Sep. 29, 2015. The entire contents of WO 2017/055860 are hereby incorporated herein by reference.

FIELD OF THE INVENTION

The invention relates to new isoindolin-1-one derivatives, to pharmaceutical compositions comprising said compounds and to the use of said compounds in the treatment of diseases, e.g. cancer.

RELATED APPLICATIONS

This application is related to United Kingdom patent application number 1517217.4 filed 29 Sep. 2015, the contents of which are incorporated herein by reference in their entirety.

BACKGROUND OF THE INVENTION

The transformation-related protein 53 (TP53) gene encodes a 53 KDa protein—p53. The tumour suppressor protein p53 reacts to cellular stresses, such as hypoxia, DNA damage and oncogenic activation, via a number of post-translational modifications including phosphorylation, acetylation and methylation, and acts as a signalling node in the diverse pathways that become activated. p53 has additional roles in other physiological processes, including autophagy, cell adhesion, cell metabolism, fertility, and stem cell aging and development. Phosphorylation of p53, resulting from activation of kinases including ATM, CHK1 and 2, and DNA-PK, results in a stabilised and transcriptionally active form of the protein, thus producing a range of gene products. The responses to p53 activation include apoptosis, survival, cell-cycle arrest, DNA-repair, angiogenesis, invasion and autoregulation. The specific combination of which, in concert with the cell's genetic background, gives rise to the observed cellular effect i.e. apoptosis, cell-cycle arrest or senescence. For tumour cells, the apoptotic pathway may be favoured due to the loss of tumour suppressor proteins and associated cell cycle checkpoint controls, coupled with oncogenic stress.

Under conditions of stress such as hypoxia and DNA damage it is known that the cellular level of the protein p53 increases. p53 is known to initiate transcription of a number of genes which govern progression through the cell cycle, the initiation of DNA repair and programmed cell death. This provides a mechanism for the tumour suppressor role of p53 evidenced through genetic studies.

The activity of p53 is negatively and tightly regulated by a binding interaction with the MDM2 protein, the transcription of which is itself directly regulated by p53. p53 is inactivated when its transactivation domain is bound by the MDM2 protein. Once inactivated the functions of p53 are repressed and the p53-MDM2 complex becomes a target for ubiquitinylation.

In normal cells the balance between active p53 and inactive MDM2-bound p53 is maintained in an autoregulatory negative feedback loop. That is to say that p53 can activate MDM2 expression, which in turn leads to the repression of p53.

It has been found that inactivation of p53 by mutation is common in around half of all common adult sporadic cancers. Furthermore, in around 10% of tumours, gene amplification and over-expression of MDM2 results in the loss of functional p53, thereby allowing malignant transformation and uncontrolled tumour growth.

Inactivation of p53 by a range of mechanisms is a frequent causal event in the development and progression of cancer. These include inactivation by mutation, targeting by oncogenic viruses and, in a significant proportion of cases, amplification and/or an elevated rate of transcription of the MDM2 gene resulting in overexpression or increased activation of the MDM2 protein. Gene amplification of MDM2 giving rise to overexpression of MDM2 protein has been observed in tumour samples taken from common sporadic cancers. Overall, around 10% of tumours had MDM2 amplification, with the highest incidence found in hepatocellular carcinoma (44%), lung (15%), sarcomas and osteosarcomas (28%), and Hodgkin disease (67%) (Danovi et al., Mol. Cell. Biol. 2004, 24, 5835-5843, Toledo et al., Nat Rev Cancer 2006, 6, 909-923, Gembarska et al., Nat Med 2012, 18, 1239-1247). Normally, transcriptional activation of MDM2 by activated p53 results in increased MDM2 protein levels, forming a negative feedback loop. The essential nature of p53 regulation by MDM2 and MDMX is demonstrated by gene knockout mouse models. MDM2−/− knockout mice are embryonically lethal around the time of implantation. Lethality is rescued in the double knockout for Mdm2 and Trp53. MDM2 inhibits the activity of p53 directly, by binding to and occluding the p53 transactivation domain, and by promoting the proteosomal destruction of the complex, through its E3-ubiquitin ligase activity. In addition, MDM2 is a transcriptional target of p53, and so the two proteins are linked in an autoregulatory feedback loop, ensuring that p53 activation is transient.

The induction of the p14ARF protein, the alternate reading frame (ARF) product of the p16INK4a locus, is also a mechanism of negatively regulating the p53-MDM2 interaction. p14ARF directly interacts with MDM2 and leads to up-regulation of p53 transcriptional response. Loss of p14ARF by a homozygous mutation in the CDKN2A (INK4A) gene will lead to elevated levels in MDM2 and, therefore, loss of p53 function and cell cycle control.

Although MDMX shows strong amino acid sequence and structural homology to MDM2, neither protein can substitute for loss of the other; MDMX null mice die in utero, whereas MDM2 knockout is lethal during early embryogenesis, however both can be rescued by p53 knockout, demonstrating p53-dependence of the lethality. MDMX also binds p53 and inhibits p53-dependent transcription, but unlike MDM2 it is not transcriptionally activated by p53 and so does not form the same autoregulatory loop. Furthermore, MDMX has neither E3 ubiquitin ligase activity nor a nuclear localisation signal, however it is believed to contribute to p53 degradation by forming heterodimers with MDM2 and contributing to MDM2 stabilisation.

The therapeutic rationale for MDM2-p53 inhibition is that a potent inhibitor of the protein-protein interaction will liberate p53 from the repressive control of MDM2, and activate p53 mediated cell death in the tumour. In tumours, selectivity is envisioned to result from p53 sensing preexisting DNA-damage or oncogenic activation signals that had previously been blocked by the action of MDM2 at normal or overexpressed levels. In normal cells, p53 activation is anticipated to result in activation of non-apoptotic pathways and if anything a protective growth inhibition response. In addition due to the non-genotoxic mechanism of action for MDM2-p53 inhibitors they are suitable for the treatment of cancer in particular in the pediatric population.

About 50% of cancers harbour cells in which TP53, the gene that encodes for p53, is mutated resulting in a loss of the protein's tumour suppressor function and sometimes even in p53 protein versions that gain novel oncogenic functions.

Cancers where there is a high level of MDM2 amplification include liposarcoma (88%), soft tissue sarcoma (20%), osteosarcoma (16%) oesophageal cancer (13%), and certain paediatric malignancies including B-cell malignancies.

The present invention describes a novel series of compounds which selectively inhibit the MDM2-p53 interaction and which have anticancer activity.

SUMMARY OF THE INVENTION

In one aspect, the invention provides a compound of formula (I):

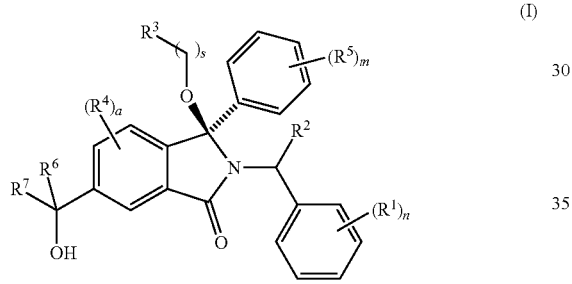

or a tautomer or a solvate or a pharmaceutically acceptable salt thereof, wherein:
$R^1$ is independently selected from hydroxy, halogen, nitro, nitrile, $C_{1-4}$ alkyl, haloC$_{1-4}$alkyl, hydroxyC$_{1-4}$alkyl, $C_{2-6}$alkenyl, $C_{1-4}$alkoxy, haloC$_{1-4}$alkoxy, $C_{2-4}$alkynyl, —O$_{0,1}$—(CR$^x$R$^y$)$_v$—CO$_2$H, —(CR$^x$R$^y$)$_v$—CO$_2$C$_{1-4}$ alkyl, —(CR$^x$R$^y$)$_v$—CON(C$_{1-4}$alkyl)$_2$, —P(=O)(R$^x$)$_2$, —S(O)$_d$—R$^x$, —S(O)$_d$-heterocyclic group with 3 to 6 ring members and —S(O)$_d$—N(R$^8$)$_2$;
$R^2$ is selected from hydrogen, $C_{1-4}$ alkyl, $C_{2-6}$alkenyl, hydroxyC$_{1-4}$alkyl, —(CR$^x$R$^y$)$_u$—CO$_2$H, —(CR$^x$R$^y$)$_u$—CO$_2$C$_{1-4}$alkyl, and —(CR$^x$R$^y$)$_u$—CONR$^x$R$^y$;
s is selected from 0 and 1;
$R^3$ is hydrogen or -(A)$_t$-(CR$^x$R$^y$)$_q$—X;
t is selected from 0 and 1;
q is selected from 0, 1 and 2;
wherein when $R^3$ is -(A)$_t$-(CR$^x$R$^y$)$_q$—X then (i) at least one of s, t and q is other than 0 and (ii) when t is 0 then s is 1 and q is other than 0;
A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN, —OR$^9$, —(CH$_2$)$_v$—CO$_2$H, —(CH$_2$)$_v$—CO$_2$C$_{1-4}$alkyl, —S(O)$_d$—R$^x$, —C(=O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;

$R^4$ and $R^5$ are independently selected from halogen, nitrile, $C_{1-4}$ alkyl, haloC$_{1-4}$alkyl, $C_{1-4}$alkoxy and haloC$_{1-4}$alkoxy;
$R^6$ and $R^7$ are independently selected from hydrogen, $C_{1-6}$alkyl, haloC$_{1-6}$alkyl, $C_{2-6}$alkenyl, $C_{2-6}$alkynyl, hydroxy, hydroxyC$_{1-6}$alkyl, —COOC$_{1-6}$alkyl, —(CH$_2$)$_j$—O—C$_{1-6}$alkyl, —(CH$_2$)$_j$—O-(hydroxyC$_{1-6}$ alkyl), —C$_{1-6}$alkyl-NR$^x$R$^y$, —(CR$^x$R$^y$)$_p$—CONR$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, $C_{3-8}$cycloalkyl, —CH$_2$—C$_{3-8}$cycloalkyl, —CH$_2$—O—C$_{3-8}$cycloalkyl, and $C_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;
or the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more R$^z$ groups;
$R^8$ and $R^9$ are independently selected from hydrogen, $C_{1-6}$alkyl, haloC$_{1-6}$alkyl, hydroxyC$_{1-6}$alkyl, —(CH$_2$)$_k$—O—C$_{1-6}$alkyl, —(CH$_2$)$_k$—O-(hydroxyC$_{1-6}$alkyl), hydroxyC$_{1-6}$alkoxy, —(CH$_2$)$_k$—CO$_2$C$_{1-6}$alkyl, —(CH$_2$)$_k$—CO$_2$H, —C$_{1-6}$ alkyl-N(H)$_e$(C$_{1-4}$alkyl)$_{2-e}$, —(CH$_2$)$_j$—C$_{3-8}$cycloalkyl and —(CH$_2$)$_j$—C$_{3-8}$cycloalkenyl;
$R^x$ and $R^y$ are independently selected from hydrogen, halogen, nitro, nitrile, $C_{1-6}$alkyl, haloC$_{1-6}$alkyl, $C_{2-6}$alkenyl, $C_{2-6}$alkynyl, hydroxy, hydroxyC$_{1-6}$alkyl, $C_{1-6}$alkoxy, —(CH$_2$)$_k$—O—C$_{1-6}$alkyl, hydroxyC$_{1-6}$ alkoxy, —COOC$_{1-6}$alkyl, —N(H)$_e$(C$_{1-4}$alkyl)$_{2-e}$, —C$_{1-6}$ alkyl-N(H)$_e$(C$_{1-4}$alkyl)$_{2-e}$, —(CH$_2$)$_k$—C(=O) N(H)$_e$(C$_{1-4}$alkyl)$_{2-e}$, $C_{3-8}$cycloalkyl and $C_{3-8}$cycloalkenyl;
or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;
or when on a carbon atom the $R^x$ and $R^y$ groups can join together to form a =CH$_2$ group;
$R^z$ is independently selected from halogen, nitro, nitrile, $C_{1-6}$alkyl, haloC$_{1-6}$alkyl, $C_{2-6}$alkenyl, $C_{2-6}$alkynyl, =O, hydroxy, hydroxyC$_{1-6}$alkyl, $C_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N (H)$_e$(C$_{1-4}$alkyl)$_{2-e}$, —(CH$_2$)$_r$—CO$_2$C$_{1-6}$alkyl, —(CH$_2$)$_r$—CO$_2$H, —N(H)$_e$(C$_{1-4}$alkyl)$_{2-e}$, —C$_{1-6}$alkyl-N(H)$_e$ (C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O) OC$_{1-4}$ alkyl, heterocyclyl group with 3 to 6 ring members substituted by —C(═O)N(H)$_e$(C$_{1-4}$alkyl)$_{2-e}$, —C(═O)heterocyclyl group with 3 to 6 ring members, C$_{3-8}$cycloalkyl and C$_{3-8}$cycloalkenyl, wherein if R$^7$ is pyridine then R$^z$ is other then —NH$_2$;

a, j, d, e, n, r and p are independently selected from 0, 1 and 2;

k and m are independently selected from 1 and 2;

u is selected from 0, 1, 2 and 3; and v and w are independently selected from 0 and 1.

In a further aspect, the invention provides a compound of formula (I):

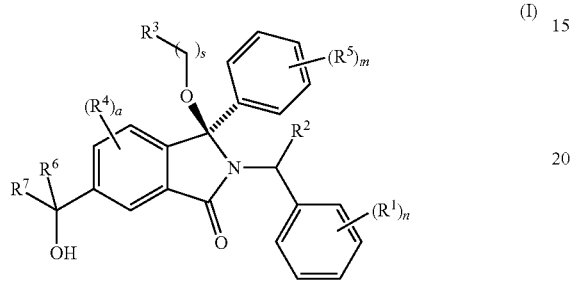

or a tautomer or a solvate or a pharmaceutically acceptable salt thereof, wherein:

R$^1$ is independently selected from hydroxy, halogen, nitro, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-6}$alkynyl, —(CR$^x$R$^y$)$_v$—CO$_2$H, —(CR$^x$R$^y$)$_v$CO$_2$C$_{1-4}$alkyl, —(CR$^x$R$^y$)$_v$—CON(C$_{1-4}$alkyl)$_2$, —P(═O)(R$^x$)$_2$, —S(O)$_d$—R$^x$, —S(O)$_d$-heterocyclic group with 3 to 6 ring members and —S(O)$_d$—N(R$^8$)$_2$;

R$^2$ is selected from hydrogen, C$_{1-4}$ alkyl, C$_{2-6}$alkenyl, hydroxyC$_{1-4}$alkyl, —(CR$^x$R$^y$)$_u$—CO$_2$H, —(CR$^x$R$^y$)$_u$—CO$_2$C$_{1-4}$alkyl, and —(CR$^x$R$^y$)$_u$—CONR$^x$R$^y$;

s is selected from 0 and 1;

R$^3$ is hydrogen or -(A)$_t$-(CR$^x$R$^y$)$_q$—X;

t is selected from 0 and 1;

q is selected from 0, 1 and 2;

wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —S(O)$_d$—R$^x$, —C(═O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(═O)NR$^x$R$^y$;

R$^4$ and R$^5$ are independently selected from halogen, nitrile, C$_{1-4}$ alkyl, haloC$_{1-4}$alkyl, C$_{1-4}$alkoxy and haloC$_{1-4}$alkoxy;

R$^6$ and R$^7$ are independently selected from hydrogen, C$_{1-6}$alkyl, haloC$_{1-6}$alkyl, C$_{2-6}$alkenyl, C$_{2-6}$alkynyl, hydroxy, hydroxyC$_{1-6}$alkyl, —COOC$_{1-6}$alkyl, —(CH$_2$)$_j$—O—C$_{1-6}$alkyl, —(CH$_2$)$_j$—O-(hydroxyC$_{1-6}$alkyl), —C$_{1-6}$alkyl-NR$^x$R$^y$, —(CR$^x$R$^y$)$_p$—CONR$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(═O)NH-heterocyclic group with 3 to 7 ring members, C$_{3-8}$cycloalkyl, —CH$_2$—C$_{3-8}$cycloalkyl, —CH$_2$—O—C$_{3-8}$cycloalkyl, and C$_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

or the R$^6$ and R$^7$ groups, together with the carbon atom to which they are attached, can join to form a C$_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said C$_{3-6}$cycloalkyl and heterocyclyl groups may be optionally substituted by one or more R$^z$ groups;

R$^8$ and R$^9$ are independently selected from hydrogen, C$_{1-6}$alkyl, haloC$_{1-6}$alkyl, hydroxyC$_{1-6}$alkyl, —(CH$_2$)$_k$—O—C$_{1-6}$alkyl, —(CH$_2$)$_k$—O-(hydroxyC$_{1-6}$alkyl), hydroxyC$_{1-6}$alkoxy, —(CH$_2$)$_k$—CO$_2$C$_{1-6}$alkyl, —(CH$_2$)$_k$—CO$_2$H, —C$_{1-6}$ alkyl-N(H)$_e$(C$_{1-4}$alkyl)$_{2-e}$, —(CH$_2$)$_j$—C$_{3-8}$cycloalkyl and —(CH$_2$)$_j$—C$_{3-8}$cycloalkenyl;

R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$alkyl, —N(H)$_e$(C$_{1-4}$alkyl)$_{2-e}$, —C$_{1-6}$ alkyl-N(H)$_e$(C$_{1-4}$alkyl)$_{2-e}$, —(CH$_2$)$_k$—C(═O)N(H)$_e$(C$_{1-4}$alkyl)$_{2-e}$, C$_{3-8}$cycloalkyl and C$_{3-8}$cycloalkenyl;

or the R$^x$ and R$^y$ groups, together with the carbon or nitrogen atom to which they are attached, can join to form a C$_{3-6}$cycloalkyl or saturated heterocyclyl group with 3 to 6 ring members which may be optionally fused to an aromatic heterocyclyl group of 3 to 5 ring members;

or when on a carbon atom the R$^x$ and R$^y$ groups can join together to form a ═CH$_2$ group;

R$^z$ is independently selected from halogen, nitro, nitrile, C$_{1-6}$alkyl, haloC$_{1-6}$alkyl, C$_{2-6}$alkenyl, C$_{2-6}$alkynyl, ═O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(═O)C$_{1-6}$ alkyl, —C(═O)C$_{1-6}$alkyl-OH, —C(═O)C$_{1-6}$alkyl-N(H)$_e$(C$_{1-4}$alkyl)$_{2-e}$, —C(═O)N(H)$_e$(C$_{1-4}$alkyl)$_{2-e}$, —(CH$_2$)$_r$—CO$_2$C$_{1-6}$alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(═O)C$_{1-4}$alkyl, heterocyclyl group with 3 to 6 ring members substituted by —C(═O)OC$_{1-4}$alkyl, heterocyclyl group with 3 to 6 ring members substituted by —C(═O)N(H)$_e$(C$_{1-4}$alkyl)$_{2-e}$, —C(═O)heterocyclyl group with 3 to 6 ring members, C$_{3-8}$cycloalkyl and C$_{3-8}$cycloalkenyl, wherein if R$^7$ is pyridine then R$^z$ is other then —NH$_2$;

a, j, d, e, n, r and p are independently selected from 0, 1 and 2;

k and m are independently selected from 1 and 2;

u is selected from 0, 1, 2 and 3; and v and w are independently selected from 0 and 1.

In further aspects of the invention there is provided a compound of formula (I) for use in the prophylaxis or treatment of a disease or condition as described herein, methods for the prophylaxis or treatment of a disease or condition as described herein comprising administering to a patient a compound of formula (I), pharmaceutical compositions comprising a compound of formula (I) and processes for the synthesis of a compound of formula (I).

Definitions

Unless the context indicates otherwise, references to formula (I) in all sections of this document (including the uses, methods and other aspects of the invention) include references to all other subformula, sub-groups, embodiments and examples as defined herein.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "antagonist" refers to a type of receptor ligand or drug that blocks or dampens agonist-mediated biological responses. Antagonists have affinity but no agonistic efficacy for their cognate receptors, and binding will disrupt the interaction and inhibit the function of any ligand (e.g. endogenous ligands or substrates, an agonist or inverse agonist) at receptors. The antagonism may arise directly or indirectly, and may be mediated by any mechanism and at any physiological level. As a result, antagonism of ligands may under different circumstances manifest itself in functionally different ways. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding.

As used herein, the term "mediated", as used e.g. in conjunction with MDM2/p53 as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence e.g. of cancer.

The combinations of the invention may produce a therapeutically efficacious effect relative to the therapeutic effect of the individual compounds/agents when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. A "synergistic" effect in the present context refers to a therapeutic effect produced by the combination which is larger than the sum of the therapeutic effects of the agents of the combination when presented individually. An "additive" effect in the present context refers to a therapeutic effect produced by the combination which is larger than the therapeutic effect of any of the agents of the combination when presented individually. The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term "combination", as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/ agents may unitary or non-unitary formulations. The unit dose(s) may be contained within a blister pack. The pharmaceutical pack may optionally further comprise instructions for use.

The term 'optionally substituted' as used herein refers to a group which may be unsubstituted or substituted by a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'halo' or 'halogen' as used herein refers to fluorine, chlorine, bromine or iodine, in particular fluorine or chlorine.

Each and every hydrogen in the compound (such as in an alkyl group or where referred to as hydrogen) includes all isotopes of hydrogen, in particular $^1H$ and $^2H$ (deuterium).

The term 'oxo' as used herein refers to the group =O.

The term '$C_{1-4}$alkyl' as used herein as a group or part of a group refers to a linear or branched saturated hydrocarbon group containing from 1 to 4 carbon atoms respectively. Examples of such groups include methyl, ethyl, n-propyl, isopropyl, n-butyl, isobutyl, sec-butyl, tert butyl and the like.

The term '$C_{2-4}$alkenyl' or '$C_{2-6}$alkenyl' as used herein as a group or part of a group refers to a linear or branched hydrocarbon group containing from 2 to 4, or 2 to 6 carbon atoms, respectively, and containing a carbon carbon double bond. Examples of such groups include $C_{3-4}$alkenyl or $C_{3-6}$alkenyl groups, such as ethenyl (vinyl), 1-propenyl, 2-propenyl (allyl), isopropenyl, butenyl, buta-1,4-dienyl, pentenyl, and hexenyl.

The term '$C_{2-4}$alkynyl' or '$C_{2-6}$alkynyl' as used herein as a group or part of a group refers to a linear or branched hydrocarbon group having from 2 to 4 or 2 to 6 carbon atoms, respectively, and containing a carbon carbon triple bond. Examples of such groups include $C_{3-4}$alkynyl or $C_{3-6}$alkynyl groups such as ethynyl and 2 propynyl (propargyl) groups.

The term '$C_{1-4}$alkoxy' as used herein as a group or part of a group refers to an —O—$C_{1-4}$alkyl group wherein $C_{1-4}$alkyl is as defined herein. Examples of such groups include methoxy, ethoxy, propoxy, butoxy, and the like.

The term '$C_{3-6}$cycloalkyl' as used herein refers to a saturated monocyclic hydrocarbon ring of 3 to 6 carbon atoms. Examples of such groups include cyclopropyl, cyclobutyl, cyclopentyl or cyclohexyl and the like.

The term '$C_{3-6}$cycloalkenyl' as used herein refers to a partially saturated monocyclic hydrocarbon ring of 3 to 6 carbon atoms having one or more (usually one) carbon carbon double bond(s). Examples of such groups include cyclopentenyl, cyclohexenyl, and cyclohexadienyl.

The term 'hydroxy$C_{1-4}$alkyl' as used herein as a group or part of a group refers to a $C_{1-4}$alkyl group as defined herein wherein one or more (e.g. 1, 2 or 3) than one hydrogen atom is replaced with a hydroxyl group. The term 'hydroxy$C_{1-4}$ alkyl' therefore includes monohydroxy$C_{1-4}$ alkyl, and also polyhydroxy$C_{1-4}$ alkyl. There may be one, two, three or more hydrogen atoms replaced with a hydroxyl group, so the hydroxy$C_{1-4}$alkyl may have one, two, three or more hydroxyl groups. Examples of such groups include hydroxymethyl, hydroxyethyl, hydroxypropyl and the like.

The term 'halo$C_{1-4}$alkyl' as used herein as a group or part of a group refers to a $C_{1-4}$alkyl group as defined herein wherein one or more (e.g. 1, 2 or 3) than one hydrogen atom is replaced with a halogen. The term 'halo$C_{1-4}$alkyl' therefore includes monohaloC$_{1-4}$alkyl and also polyhaloC$_{1-4}$alkyl. There may be one, two, three or more hydrogen atoms replaced with a halogen, so the haloC$_{1-4}$alkyl may have one, two, three or more halogens. Examples of such groups include fluoroethyl, fluoromethyl, difluoromethyl, trifluoromethyl or trifluoroethyl and the like.

The term 'haloC$_{1-4}$alkoxy' as used herein as a group or part of a group refers to a —O—C$_{1-4}$alkyl group as defined herein wherein one or more (e.g. 1, 2 or 3) than one hydrogen atom is replaced with a halogen. The terms 'haloC$_{1-4}$alkoxy' therefore include monohaloC$_{1-4}$alkoxy, and also polyhaloC$_{1-4}$alkoxy. There may be one, two, three or more hydrogen atoms replaced with a halogen, so the haloC$_{1-4}$alkoxy may have one, two, three or more halogens. Examples of such groups include fluoroethyloxy, difluoromethoxy or trifluoromethoxy and the like.

The term "heterocyclyl group" as used herein shall, unless the context indicates otherwise, include both aromatic and non-aromatic ring systems. Thus, for example, the term "heterocyclyl group" include within their scope aromatic, non-aromatic, unsaturated, partially saturated and saturated heterocyclyl ring systems. In general, unless the context indicates otherwise, such groups may be monocyclic or bicyclic (including fused, spiro and bridged bicyclic groups) and may contain, for example, 3 to 12 ring members, more usually 5 to 10 ring members. Reference to 4 to 7 ring members includes 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, or 4 to 7 and preferably 5, 6 or 7 ring members, more preferably 5 or 6 ring members. Examples of bicyclic groups are those containing 8, 9, 10, 11 and 12 ring members, and more usually 9 or 10 ring members. The heterocyclyl groups can be heteroaryl groups having from 5 to 12 ring members, more usually from 5 to 10 ring members. Where reference is made herein to a heterocyclyl group, the heterocyclyl ring can, unless the context indicates otherwise, be optionally substituted i.e. unsubstituted or substituted, by one or more (e.g. 1, 2, 3, or 4 in particular one or two) substituents as defined herein.

The heterocyclyl group can be, for example, a five membered or six membered monocyclic ring or a bicyclic structure formed from fused five and six membered rings or two fused six membered rings, or two fused five membered rings. Each ring may contain up to five heteroatoms particularly selected from nitrogen, sulfur and oxygen and oxidised forms of nitrogen or sulfur. Particularly the heterocyclyl ring will contain up to 4 heteroatoms, more particularly up to 3 heteroatoms, more usually up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

Examples of five membered aromatic heterocyclyl groups include but are not limited to pyrrolyl, furanyl, thienyl, imidazolyl, furazanyl, oxazolyl, oxadiazolyl, oxatriazolyl, isoxazolyl, thiazolyl, thiadiazolyl, isothiazolyl, pyrazolyl, triazolyl and tetrazolyl groups.

Examples of six membered aromatic heterocyclic groups include but are not limited to pyridinyl, pyrazinyl, pyridazinyl, pyrimidinyl and triazinyl.

The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 0, 1, 2 or 3 ring heteroatoms;
  c) a pyrimidine ring fused to a 5- or 6-membered ring containing 0, 1 or 2 ring heteroatoms;
  d) a pyrrole ring fused to a 5- or 6-membered ring containing 0, 1, 2 or 3 ring heteroatoms;
  e) a pyrazole ring fused to a 5- or 6-membered ring containing 0, 1 or 2 ring heteroatoms;
  f) an imidazole ring fused to a 5- or 6-membered ring containing 0, 1 or 2 ring heteroatoms;
  g) an oxazole ring fused to a 5- or 6-membered ring containing 0, 1 or 2 ring heteroatoms;
  h) an isoxazole ring fused to a 5- or 6-membered ring containing 0, 1 or 2 ring heteroatoms;
  i) a thiazole ring fused to a 5- or 6-membered ring containing 0, 1 or 2 ring heteroatoms;
  j) an isothiazole ring fused to a 5- or 6-membered ring containing 0, 1 or 2 ring heteroatoms;
  k) a thiophene ring fused to a 5- or 6-membered ring containing 0, 1, 2 or 3 ring heteroatoms;
  l) a furan ring fused to a 5- or 6-membered ring containing 0, 1, 2 or 3 ring heteroatoms;
  m) a cyclohexyl ring fused to a 5- or 6-membered ring containing 1, 2 or 3 ring heteroatoms; and
  n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]

triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiophene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

A nitrogen-containing heteroaryl ring must contain at least one ring nitrogen atom. The nitrogen-containing heteroaryl ring can be N-linked or C-linked. Each ring may, in addition, contain up to about four other heteroatoms particularly selected from nitrogen, sulfur and oxygen. Particularly the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, monocyclic groups such as pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, and bicyclic groups such as quinolinyl, isoquinolinyl, benzimidazolyl, benzoxazolyl, benzisoxazole, benzothiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazepinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic" embraces, unless the context indicates otherwise, unsaturated ring systems without aromatic character, partially saturated and saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "saturated" refers to rings where there are no multiple bonds between ring atoms. Saturated heterocyclyl groups include piperidinyl, morpholinyl, and thiomorpholinyl. Partially saturated heterocyclyl groups include pyrazolinyl, for example pyrazolin-2-yl and pyrazolin-3-yl.

Examples of non-aromatic heterocyclyl groups are groups having from 3 to 12 ring members, more usually 5 to 10 ring members. Such groups can be monocyclic or bicyclic, for example, have 3 to 7 ring members in particular 4 to 6 ring members. Such groups particularly have from 1 to 5 or 1 to 4 heteroatom ring members (more usually 1, 2, or 3 heteroatom ring members), usually selected from nitrogen, oxygen and sulfur and oxidised forms thereof. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, pyranyl (2H-pyran or 4H-pyran), dihydrothienyl, dihydropyranyl, dihydrofuranyl, dihydrothiazolyl, tetrahydrofuranyl, tetrahydrothienyl, dioxanyl, oxanyl (also known as tetrahydropyranyl) (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl. In general, typical non-aromatic heterocyclyl groups include saturated groups such as piperidinyl, pyrrolidinyl, azetidinyl, morpholinyl, piperazinyl and N-alkyl piperazines such as N-methyl piperazinyl.

The terms "oxan" and "oxanyl" as used herein refer to the group:

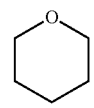

which may also be referred to as "tetrahydropyran" or tetrahydropyranyl".

In a nitrogen-containing non-aromatic heterocyclyl ring the ring must contain at least one ring nitrogen atom. The nitrogen-containing heterocyclyl ring can be N-linked or C-linked. The heterocylic groups can contain, for example, cyclic amine moieties (e.g. as in pyrrolidinyl), cyclic amides (such as a pyrrolidinonyl, piperidinonyl or caprolactamyl), cyclic sulfonamides (such as an isothiazolidinyl 1,1-dioxide, [1,2]thiazinanyl 1,1-dioxide or [1,2]thiazepanyl 1,1-dioxide) and combinations thereof.

Particular examples of nitrogen-containing non-aromatic heterocyclyl groups include aziridinyl, morpholinyl, thiomorpholinyl, piperidinyl (e.g. piperidin-1-yl, piperidin-2yl, piperidin-3-yl and piperidin-4-yl), pyrrolidinyl; (e.g. pyrrolidin-1-yl, pyrrolidin-2-yl and pyrrolidin-3-yl), pyrrolidonyl, dihydrothiazolyl, imidazolinyl, imidazolidinonyl, oxazolinyl, thiazolinyl, 6H-1,2,5-thiadiazinyl, pyrazolin-2-yl, pyrazolin-3-yl, pyrazolidinyl, piperazinyl, and N-alkyl piperazines such as N-methyl piperazinyl.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see Advanced Organic Chemistry, by Jerry March, 4th Edition, Wiley Interscience, pages 131-133, 1992.

Where, in a definition of a cyclic group or ring, it is stated that the cyclic group contains a certain number of heteroatom ring members, e.g. as in the phrase "a 5 or 6 membered ring containing 0, 1 or 2 nitrogen ring members", this is to be taken as meaning that apart from the certain number of heteroatom ring members specified, the remaining ring members are carbon atoms.

The compound of formula (I) may contain saturated cyclic groups that can be joined to the rest of the molecule by one or more bonds. When the cyclic group is joined to the rest of the molecule by two or more bonds, these bonds (or two of these bonds) can be made to the same atom (usually a carbon atom) of the ring or different atoms of the ring. Where the bonds are made to the same atom of the ring, this results in a cyclic group with a single atom (usually a quaternary carbon) bound to two groups. In other words, when the compound of formula (I) includes a cyclic group that group may either be linked to the rest of the molecule by a bond or the cyclic group and the rest of the molecule can have an atom in common e.g. a spiro compound.

The heterocyclyl group can each be unsubstituted or substituted by one or more (e.g. 1, 2 or 3) substituent groups. For example, heterocyclyl or carbocyclyl groups can be unsubstituted or substituted by 1, 2, 3 or 4 substituents and particularly it is unsubstituted or has 1, 2 or 3 substituents as defined herein. Where the cyclic group is saturated there may be 2 substituents joined to the same carbon (where the substituents are the same so called geminal or 'gem' disubstitution).

A combination of substituents is permissible only if such as combination results in a stable or chemically feasible compound (i.e. one that is not substantially altered when kept at 40° C. or less for at least a week).

The various functional groups and substituents making up the compounds of the invention are particularly chosen such that the molecular weight of the compound of the invention does not exceed 1000. More usually, the molecular weight of the compound will be less than 750, for example less than 700, or less than 650, or less than 600, or less than 550. More particularly, the molecular weight is less than 525 and, for example, is 500 or less.

DETAILED DESCRIPTION OF THE INVENTION

The invention provides a compound of formula (I):

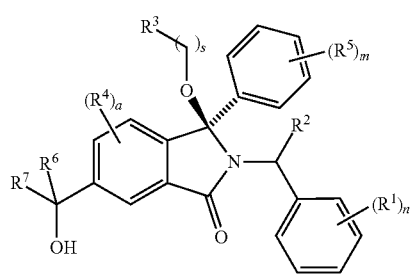

(I)

or a tautomer or a solvate or a pharmaceutically acceptable salt thereof, wherein Het, $R^1$, $R^2$, $R^3$, $R^4$, $R^5$, $R^6$, $R^7$, a, m, n and s are as defined herein.

The compounds of the formula (I) have a chiral centre, marked below with a "*":

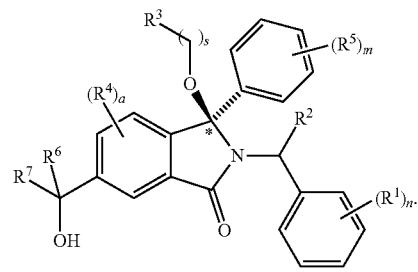

The compounds of formula (I) include a stereocentre at the position indicated (referred to herein as (3)) and are chiral non-racemic. Compounds of formula (I) have the stereochemistry shown by the hashed and solid wedged bonds and this stereoisomer predominates.

Typically, at least 55% (e.g. at least 60%, 65%, 70%, 75%, 80%, 85%, 90% or 95%) of the compound of the formula (I) is present as the shown stereoisomer. In one general embodiment, 97% (e.g. 99%) or more (e.g. substantially all) of the total amount of the compound of the formula (I) may be present as a single stereoisomer.

The compounds may also include one or more further chiral centres (e.g. in the —$CR^6R^7OH$ group and/or in the $R^3$ group and/or in the —$CHR^2$ group).

Typically, the compound of formula (I) has an enantiomeric excess of at least 10% (e.g. at least 20%, 40%, 60%, 80%, 85%, 90% or 95%). In one general embodiment, the compound of formula (I) has an enantiomeric excess of 97% (e.g. 99%) or more.

For the purposes of this section the isoindolin-1-one ring is numbered as followed:

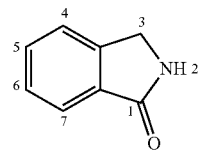

Compounds are named in accordance with protocols utilized by chemical naming software packages.

$R^1$ and n $R^1$ is the substituent(s) on the phenyl group bonded to —$CHR^2$—.

n is 0, 1, 2 or 3. In other words, the phenyl group bonded to —$CHR^2$— group may have 0, 1, 2 or 3 substituents $R^1$.

In one embodiment n is 1, 2 or 3. In one embodiment n is 1 or 2. In another embodiment n is 1.

When n is 2 or 3 (i.e. the phenyl group bonded to —$CHR^2$— group is substituted with more than one $R^1$) the substituents $R^1$ may be the same or different (i.e. are independently selected from the definitions of $R^1$).

$R^1$ may be attached at the ortho (or o-), meta (or m-) or para (or p-) position of the phenyl group, wherein the position is defined relative to the point of attachment of the phenyl group to the group —$CHR^2$—.

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$O_{0,1}$—$(CR^xR^y)_v$—$CO_2H$, —$(CR^xR^y)_v$—$CO_2C_{1-4}$alkyl, —$(CH_2)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$.

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $-O_{0,1}-(CH_2)_v-CO_2H$, $-(CH_2)_v-CO_2C_{1-4}$alkyl, $-(CH_2)_v-CON(C_{1-4}$alkyl$)_2$, $-P(=O)(R^x)_2$, $-S(O)_d-R^x$, $-S(O)_d$-heterocyclic group with 3 to 6 ring members and $-S(O)_d-N(R^8)_2$.

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $-(CH_2)_v-CO_2H$, $-(CH_2)_v-CO_2C_{1-4}$alkyl, $-(CH_2)_v-CON(C_{1-4}$alkyl$)_2$, $-P(=O)(R^x)_2$, $-S(O)_d-R^x$, $-S(O)_d$-heterocyclic group with 3 to 6 ring members and $-S(O)_d-N(R^8)_2$.

In one embodiment, $R^1$ is independently selected from halogen, hydroxy, nitrile, $C_{1-4}$alkyl, $C_{2-4}$alkynyl, or $C_{1-4}$alkoxy, for example $R^1$ is independently selected from chloro, hydroxy, nitrile, methyl or methoxy.

In one embodiment $R^1$ is independently selected from halogen (e.g. chloro), $C_{1-4}$alkyl (e.g. methyl), $C_{1-4}$alkoxy (e.g. methoxy), $-O_{0,1}-(CR^xR^y)_v-CO_2H$ (e.g. $-CO_2H$, $-(CH_2)-CO_2H$, $-(C(CH_3)_2)-CO_2H$, or $-O(CH_2)-CO_2H$) or $-S(O)_d-R^x$ (e.g. $SO_2CH_3$).

In one embodiment $R^1$ is $O_{0,1}-(CR^xR^y)_v-CO_2H$ in particular $-CO_2H$, $-(CH_2)-CO_2H$, $-(C(CH_3)_2)-CO_2H$, or $-O(CH_2)-CO_2H$), such as $-(C(CH_3)_2)-CO_2H$.

In one embodiment, $R^1$ is chloro or nitrile, in particular chloro.

In one embodiment, $R^1$ is nitro (e.g. p-$NO_2$).

In one embodiment, $R^1$ is nitro at the ortho or meta position.

In one embodiment, $R^1$ is independently selected from hydroxy, halogen, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $-(CH_2)_v-CO_2H$, $-(CH_2)_v-CO_2C_{1-4}$alkyl, $-(CH_2)_v-CON(C_{1-4}$alkyl$)_2$, $-P(=O)(R^x)_2$, $-S(O)_d-C_{1-6}$alkyl, $-S(O)_d$-heterocyclic group with 3 to 6 ring members and $-S(O)_d-N(R^8)_2$.

In another embodiment, n is 1 and $R^1$ is chloro or nitrile.

In another embodiment, n is 1 and $R^1$ is chloro.

In another embodiment, n is 1 and $R^1$ is nitrile.

In one embodiment, one of the $R^1$ groups or the $R^1$ group (where n=1) is at the para-position (i.e. para to the point of attachment of the phenyl ring). In one embodiment n is 1 and $R^1$ is p-chloro or p-nitrile.

In one embodiment, n is 1 and $R^1$ is halogen (e.g. Cl or F), nitrile, $C_{1-4}$alkoxy (e.g. $-OCH_3$) or $C_{1-4}$alkyl (e.g. $-CH_3$).

In one embodiment, $R^1$ is $-S(O)_d-C_{1-6}$alkyl, or $-S(O)_d$- heterocyclic group with 3 to 6 ring members and $-S(O)_d-N(R^8)_2$. In one embodiment, $R^1$ is $-S-C_{1-6}$alkyl, $-S(O)-C_{1-6}$alkyl, $-S(O)_2-C_{1-6}$alkyl, $-S(O)_d$-heterocyclic group with 3 to 6 ring members or $-S(O)_d-N(C_{1-6}$alkyl$)_2$.

In another embodiment, $R^1$ is $-S-CH_3$, $-S(O)-CH_3$, $-S(O)_2-CH_3$, or $-S(O)_2$-morpholinyl. In another embodiment, one or more $R^1$ is $-SO_2CH_3$, or $-SO_2$-heterocyclic group with 6 ring members e.g. $-SO_2$-(morpholinyl), in particular $-SO_2$-(1-morpholinyl).

In one embodiment, $R^1$ is o-($-S(O)_d-C_{1-4}$alkyl) or o-($-S(O)_d$-heterocyclic group with 3 to 6 ring members). In one embodiment, $R^1$ is o-$S-C_{1-4}$alkyl, o-($-S(O)_d-C_{1-4}$alkyl) or o-($-S(O)_d$-heterocyclic group with 3 to 6 ring members). In one embodiment, $R^1$ is o-($-S(O)_2-CH_3$)

In one embodiment, $R^1$ is $-(CH_2)_u-CO_2H$. In one embodiment, $R^1$ is $-CO_2H$. In one embodiment, $R^1$ is $-(CH_2)_u-CO_2H$ at the meta or para position. In one embodiment, $R^1$ is $-(CH_2)_u-CO_2H$ at the ortho position.

In one embodiment, $R^1$ is independently selected from hydroxy, halogen, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $-(CH_2)_v-CO_2C_{1-4}$alkyl, $-(CH_2)_v-CON(C_{1-4}$alkyl$)_2$, $-P(=O)(R^x)_2$, $-S(O)_d-C_{1-6}$alkyl, $-S(O)_d$-heterocyclic group with 3 to 6 ring members and $-S(O)_d-N(R^8)_2$.

In one embodiment, n is 2. In one embodiment when n is 2, the phenyl group is substituted with (i) o-($-S(O)_d-C_{1-4}$alkyl) or o-($-S(O)_d$-heterocyclic group with 3 to 6 ring members) and (ii) halogen (e.g. Cl or F), nitrile, or $C_{1-4}$alkyl, in particular chloro, nitrile or methyl.

In one embodiment, n is 2 and $R^1$ is (i) $-SO_2CH_3$ and (ii) chloro.

In one embodiment n is 2 and $R^1$ is (i) $-SO_2CH_3$ and (ii) chloro, nitrile or methyl.

In one embodiment, n is 2 and $R^1$ is (i) $-CO_2H$ and (ii) chloro.

In one embodiment n is 2 and $R^1$ is (i) $-CO_2H$ and (ii) chloro, or nitrile.

In one embodiment, when n is 2, the phenyl group bonded to $-CHR^2-$ is substituted with (i) hydroxyl and (ii) halogen (e.g. Cl or F), or nitrile, in particular chloro, or nitrile.

In one embodiment, the phenyl group bonded to $-CHR^2-$ and $R^1$ form a group:

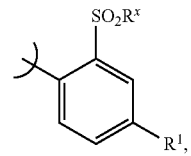

wherein in particular, $R^1$ is halogen (for example chloro), nitrile or $C_{1-4}$alkyl (for example $-CH_3$) and $R^x$ is $C_{1-4}$alkyl (for example $-CH_3$).

In one embodiment, the phenyl group bonded to $-CHR^2-$ and $R^1$ form a group:

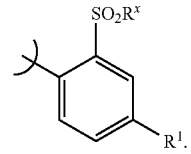

wherein in particular, $R^1$ is $C_{1-4}$alkyl (for example $-CH_3$) and $R^x$ is $C_{1-4}$alkyl (for example $-CH_3$).

In one embodiment when n is 2, the phenyl group is substituted with (i) o-OH or o-$CH_2OH$ and (ii) halogen (e.g. Cl or F), nitrile, or $C_{1-4}$ alkyl, in particular chloro, or nitrile. In one embodiment, when n is 2, the phenyl group is substituted with (i) hydroxy and (ii) halogen (e.g. Cl or F) or nitrile, in particular chloro or nitrile. In one embodiment, when n is 2, the phenyl group is substituted with (i) o-hydroxy and (ii) p-Cl or p-CN (e.g. p-Cl).

In one embodiment, n is 2 and $R^1$ is fluorine (e.g. at the ortho and para positions of the phenyl group).

In one embodiment, $R^1$ is halogen (e.g. Cl or F), $C_{1-4}$alkynyl (e.g. $-C\equiv CH$), nitrile, $-(CH_2)_v COOH$ (e.g. $-COOH$) or $SO_2C_{1-4}$alkyl (e.g. $SO_2CH_3$) and n is 1 or 2.

In one embodiment, $R^1$ is halogen (e.g. Cl), $C_{1-4}$alkynyl (e.g. $-C\equiv CH$), nitrile, hydroxy$C_{1-4}$alkyl (e.g. $CH_2OH$), —(CH$_2$)$_v$COOH (e.g. —COOH), —S(O)$_d$—C$_{1-4}$alkyl (e.g. SCH$_3$, SOCH$_3$, or SO$_2$CH$_3$), —SO$_2$-(1-morpholinyl) or —P(=O)(R$^x$)$_2$, (e.g. —P(=O)(CH$_3$)$_2$).

In one embodiment, n is 1 and R$^1$ is Cl (e.g. p-Cl), CN (e.g. p-CN), or C$_{2-4}$alkynyl (e.g. p-C$_1$alkynyl); or n is 2 and (i) R$^1$ is p-Cl, o-CH$_2$OH; (ii) p-CN, o-CH$_2$OH; or (iii) p-Cl, o-COOH, (iv) p-Cl, o-SCH$_3$, (v) p-Cl, o-S(O)CH$_3$, (vi) p-Cl, o-SO$_2$CH$_3$, (vii) p-Cl, o-SO$_2$-(1-morpholinyl), or (viii) p-Cl, o-P(O)(CH$_3$)$_2$.

In one embodiment, n is 1 and R$^1$ is Cl (e.g. p-Cl), CN (e.g. p-CN), or C$_{2-4}$alkynyl (e.g. p-C$_1$alkynyl).

In one embodiment, n is 2 and (i) R$^1$ is p-Cl, o-CH$_2$OH; (ii) p-CN, o-CH$_2$OH; or (iii) p-Cl, o-COOH, (iv) p-Cl, o-SCH$_3$, (v) p-Cl, o-S(O)CH$_3$, (vi) p-Cl, o-SO$_2$CH$_3$, (vii) p-Cl, o-SO$_2$-(1-morpholinyl), or (viii) p-Cl, o-P(O)(CH$_3$)$_2$.

In one embodiment n is 1 and R$^1$ is —Cl, —CN or —OMe (e.g. p-Cl, p-CN or p-OMe). In one embodiment n is 1 and R$^1$ is —Cl or —CN (e.g. p-Cl or p-CN).

In one embodiment, n is 2. When n is 2, typically the phenyl group is substituted at the o- and p-positions. In particular, n is 2 and R$^1$ is substituted by a p-chloro and either o-(—S(O)$_d$—C$_{1-4}$alkyl) or o-(—S(O)$_d$-heterocyclic group with 3 to 6 ring members).

In one embodiment, n is 2 and R$^1$ is o-CO$_2$H and p-chloro.
In one embodiment, n is 2 and R$^1$ is o-CO$_2$H and p-nitrile.
In one embodiment, n is 2 and R$^1$ is o-CH$_2$OH and p-chloro.
In one embodiment, n is 2 and R$^1$ is o-CH$_2$OH and p-nitrile.
In one embodiment, n is 2 and R$^1$ is o-OH and p-chloro.
In one embodiment, n is 2 and R$^1$ is o-OH and p-nitrile.
In one embodiment, n is 2 and R$^1$ is o-SO$_2$CH$_3$ and p-chloro.
In one embodiment n is 2 and R$^1$ is —SO$_2$-(1-morpholinyl) and p-chloro.

In one embodiment, R$^1$ is —O$_{0,1}$(CR$^x$R$^y$)$_v$COOH (e.g. —COOH, —CH$_2$COOH, —OCH$_2$COOH or —C(CH$_3$)$_2$COOH In one embodiment, n is 2 and R$^1$ is p-Cl and o-O$_{0,1}$(CR$^x$R$^y$)$_v$COOH (e.g. —COOH, —CH$_2$COOH, —OCH$_2$COOH or —C(CH$_3$)$_2$COOH).

In one embodiment, R$^1$ is halogen (e.g. Cl), hydroxyalkyl (e.g. —CH$_2$OH), C$_{1-4}$alkynyl (e.g. —C≡CH), nitrile, —O$_{0,1}$(CR$^x$R$^y$)$_v$COOH (e.g. —COOH, —CH$_2$COOH, —OCH$_2$COOH or —C(CH$_3$)$_2$COOH) or —SO$_2$C$_{1-4}$alkyl (e.g. —SO$_2$CH$_3$) and n is 1 or 2.

In one embodiment, R$^1$ is halogen (e.g. Cl), hydroxyalkyl (e.g. —CH$_2$OH), C$_{1-4}$alkynyl (e.g. —C≡CH), nitrile, —(CH$_2$)$_v$COOH (e.g. —COOH) or —SO$_2$C$_{1-4}$alkyl (e.g. —SO$_2$CH$_3$) and n is 1 or 2.

In one embodiment, R$^1$ is independently selected from hydroxy, halogen, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-4}$alkynyl, —(CH$_2$)$_v$—CO$_2$H, —O$_{0,1}$—(CR$^x$R$^y$)$_v$—CO$_2$C$_{1-4}$alkyl (e.g. —(CH$_2$)$_v$—CO$_2$C$_{1-4}$alkyl), —(CH$_2$)$_v$—CON(C$_{1-4}$alkyl)$_2$, —P(=O)(R$^x$)$_2$, —S(O)$_d$—C$_{1-6}$alkyl, —S(O)$_d$-heterocyclic group with 3 to 6 ring members and —S(O)$_d$—N(R$^8$)$_2$.

In one embodiment wherein n is 2, and one R$^1$ is —O$_{0,1}$—(CR$^x$R$^y$)$_v$—CO$_2$C$_{1-4}$alkyl, o-(—S(O)$_d$—C$_{1-4}$alkyl) or o-(—S(O)$_d$-heterocyclic group with 3 to 6 ring members) and one R$^1$ is halogen (e.g. Cl or F), nitrile, or C$_{1-4}$ alkyl, in particular chloro, nitrile or methyl.

In one embodiment wherein n is 2, and one R$^1$ is o-(—S(O)$_d$—C$_{1-4}$alkyl) or o-(—S(O)$_d$-heterocyclic group with 3 to 6 ring members) and one R$^1$ is halogen (e.g. Cl or F), nitrile, or C$_{1-4}$ alkyl, in particular chloro, nitrile or methyl.

In one embodiment wherein n is 2, and one R$^1$ is —O$_{0,1}$—(CR$^x$R$^y$)$_v$—CO$_2$C$_{1-4}$alkyl, and one R$^1$ is halogen (e.g. Cl or F), nitrile, or C$_{1-4}$ alkyl, in particular chloro, nitrile or methyl, such as chloro.

R$^2$

R$^2$ is selected from hydrogen, C$_{1-4}$ alkyl, C$_{2-6}$alkenyl, hydroxyC$_{1-4}$alkyl, —(CR$^x$R$^y$)$_u$—CO$_2$H, —(CR$^x$R$^y$)$_u$—CO$_2$C$_{1-4}$alkyl, and —(CR$^x$R$^y$)$_u$—CONR$^x$R$^y$.

In one embodiment u is selected from 0, 1, or 2. In one embodiment u is selected from 0 or 1.

In one embodiment, R$^2$ is selected from hydrogen, C$_{1-4}$ alkyl, C$_{2-6}$alkenyl, hydroxyC$_{1-4}$alkyl and —(CR$^x$R$^y$)$_u$—CO$_2$H. In one embodiment, R$^2$ is selected from hydrogen, C$_{1-4}$ alkyl, hydroxyC$_{1-4}$alkyl and —(CR$^x$R$^y$)$_u$—CO$_2$H. In one embodiment, R$^2$ is selected from hydrogen, C$_{1-4}$ alkyl, C$_{2-6}$alkenyl, and hydroxyC$_{1-4}$alkyl. In another embodiment R$^2$ is selected from hydrogen and —(CH$_2$)$_u$—CO$_2$H (e.g. —CH$_2$—CO$_2$H).

In one embodiment, R$^2$ is hydrogen, C$_{1-4}$ alkyl (e.g. —CH$_3$), hydroxyC$_{1-4}$alkyl (e.g. CH$_2$OH) or —(CH$_2$)$_u$COOH (e.g. —COOH, —CH$_2$COOH, —CH$_2$CH$_2$—CO$_2$H, —(CH(CH$_3$))—CO$_2$H or —(C(CH$_3$)$_2$—CO$_2$H, such as —COOH, —CH$_2$COOH, —CH$_2$CH$_2$—CO$_2$H, or —(CH(CH$_3$))—CO$_2$H).

In one embodiment, R$^2$ is selected from hydrogen, C$_{1-4}$alkyl, C$_{2-6}$alkenyl, and hydroxyC$_{1-4}$alkyl.

In one embodiment, R$^2$ is hydrogen, C$_{1-4}$ alkyl (e.g. —CH$_3$), hydroxyC$_{1-4}$alkyl (e.g. CH$_2$OH) or —(CH$_2$)$_u$COOH (e.g. —CH$_2$COOH). In one embodiment, R$^2$ is selected from hydrogen, —CH$_3$, —CH$_2$OH, and —CH$_2$CO$_2$H.

In one embodiment, R$^2$ is selected from hydrogen, —CH$_3$, —CH$_2$OH, —CH=CH$_2$ and —CH(OH)CH$_2$OH.

In one embodiment, R$^2$ is selected from hydrogen, —CH$_3$, —CH$_2$OH, and —CH$_2$CO$_2$H.

In one embodiment, R$^2$ is hydrogen or C$_{1-4}$ alkyl (e.g. —CH$_3$ or —CH$_2$CH$_3$).

In one embodiment, R$^2$ is selected from hydrogen, —CH$_3$ and —CH$_2$CH$_3$. In one embodiment, R$^2$ is selected from hydrogen and methyl.

In one embodiment, R$^2$ is selected from hydrogen and —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H).

In one embodiment, R$^2$ is —(R$^x$R$^y$)$_u$COOH (e.g. —CH$_2$COOH, —CH$_2$CH$_2$—CO$_2$H, —(CH(CH$_3$))—CO$_2$H (e.g. ⫶⫶⫶△CO$_2$H)

or —(C(CH$_3$)$_2$—CO$_2$H).

In one embodiment, R$^2$ is hydrogen, C$_{1-4}$ alkyl (e.g. —CH$_3$) or —(CH$_2$)$_u$COOH (e.g. —CH$_2$COOH, —CH$_2$CH$_2$—CO$_2$H or —(CH(CH$_3$))—CO$_2$H).

In one embodiment, R$^2$ is hydrogen, C$_{1-4}$ alkyl (e.g. —CH$_3$) or —(CH$_2$)$_u$COOH (e.g. —CH$_2$COOH).

In one embodiment, R$^2$ is —(CR$^x$R$^y$)$_u$—CO$_2$H (e.g. —CH$_2$—CO$_2$H).

In another embodiment, R$^2$ is selected from —(CH(CH$_3$))—CO$_2$H and —(C(CH$_3$)$_2$—CO$_2$H)

(e.g. ⫶⫶⫶△CO$_2$H, △CO$_2$H)

or —(C(CH$_3$)$_2$—CO$_2$H.

In another embodiment, $R^2$ is hydrogen and the compound of formula (I) is a compound of formula (Ie) or a tautomer or a solvate or a pharmaceutically acceptable salt thereof:

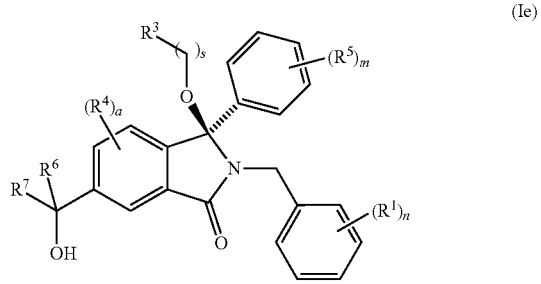
(Ie)

When $R^2$ is other than hydrogen, the compound of formula (I) can exist as at least two diastereoisomers:

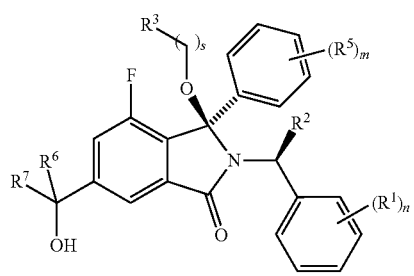
Diastereoisomer 1A

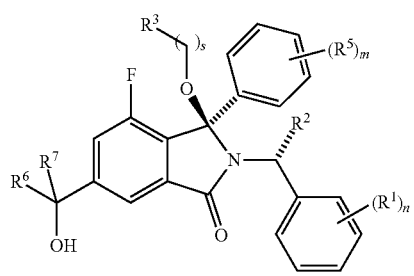
Diastereoisomer 1B

For the avoidance of doubt, the general formula (I) and all subformulae cover both individual diastereoisomers and mixtures of the diastereoisomers which are related as epimers at the —CHR$^2$— group. In one embodiment the compound of formula I is diastereoisomer 1A or a tautomer or a solvate or a pharmaceutically acceptable salt thereof. In one embodiment the compound of formula I is diastereoisomer 1B or a tautomer or a solvate or a pharmaceutically acceptable salt thereof.

In one embodiment, the compound is diastereoisomer 1A and $R^2$ is selected from:
i. $C_{1-4}$ alkyl, $C_{2-6}$alkenyl, hydroxyC$_{1-4}$alkyl, —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H), —(CH$_2$)$_u$—CO$_2$C$_{1-4}$alkyl, and —(CH$_2$)$_u$—CONR$^x$R$^y$; or
ii. $C_{1-4}$ alkyl, $C_{2-6}$alkenyl, and hydroxyC$_{1-4}$alkyl.

In one embodiment, the compound is diastereoisomer 1A and $R^2$ is selected from:
i. $C_{1-4}$ alkyl, $C_{2-6}$alkenyl, hydroxyC$_{1-4}$alkyl, —(CH$_2$)$_u$—CO$_2$H, —(CH$_2$)$_u$—CO$_2$C$_{1-4}$alkyl, and —(CH$_2$)$_u$—CONR$^x$R$^y$; or
ii. $C_{1-4}$ alkyl, $C_{2-6}$alkenyl, and hydroxyC$_{1-4}$alkyl.

In another embodiment $R^2$ is selected from hydrogen and —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$ —CO$_2$H), In another embodiment $R^2$ is selected from hydrogen and —(CH$_2$)$_u$—CO$_2$H (e.g. —CH$_2$—CO$_2$H).

In one embodiment, the compound is diastereoisomer 1A and $R^2$ is selected from:
i. —CH$_3$, —CH$_2$OH, —CH=CH$_2$ and —CH(OH)CH$_2$OH; or
ii. $C_{1-4}$ alkyl (e.g. —CH$_3$ or —CH$_2$CH$_3$); or
iii. —CH$_3$ and —CH$_2$CH$_3$.

In one embodiment, the compound is diastereoisomer 1B and $R^2$ is selected from:
i. $C_{1-4}$ alkyl, $C_{2-6}$alkenyl, hydroxyC$_{1-4}$alkyl, —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H), —(CH$_2$)$_u$—CO$_2$C$_{1-4}$alkyl, and —(CH$_2$)$_u$—CONR$^x$R$^y$; or
ii. $C_{1-4}$ alkyl, $C_{2-6}$alkenyl, and hydroxyC$_{1-4}$alkyl.

In one embodiment, the compound is diastereoisomer 1B and $R^2$ is selected from:
i. $C_{1-4}$ alkyl, $C_{2-6}$alkenyl, hydroxyC$_{1-4}$alkyl, —(CH$_2$)$_u$—CO$_2$H, —(CH$_2$)$_u$—CO$_2$C$_{1-4}$alkyl, and —(CH$_2$)$_u$—CONR$^x$R$^y$; or
ii. $C_{1-4}$ alkyl, $C_{2-6}$alkenyl, and hydroxyC$_{1-4}$alkyl.

In another embodiment $R^2$ is selected from hydrogen and —(CH$_2$)$_u$—CO$_2$H (e.g. —CH$_2$—CO$_2$H).

In one embodiment, the compound is diastereoisomer 1B and $R^2$ is selected from:
i. —CH$_3$, —CH$_2$OH, —CH=CH$_2$ and —CH(OH)CH$_2$OH; or
ii. $C_{1-4}$ alkyl (e.g. —CH$_3$ or —CH$_2$CH$_3$); or
iii. —CH$_3$ and —CH$_2$CH$_3$.

In another embodiment $R^2$ is selected from hydrogen and —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$ —CO$_2$H), In one embodiment $R^2$ is selected from $C_{1-4}$ alkyl, hydroxyC$_{1-4}$alkyl, —(CH$_2$)$_u$—CO$_2$H, —(CH$_2$)$_u$—CO$_2$C$_{1-4}$ alkyl, and —(CH$_2$)$_u$—CONR$^x$R$^y$ (in particular —CH$_2$—CO$_2$H) and the compound is diastereoisomer 1A.

In one embodiment $R^2$ is selected from $C_{1-4}$ alkyl, hydroxyC$_{1-4}$alkyl, —(CH$_2$)$_u$—CO$_2$H, —(CH$_2$)$_u$—CO$_2$C$_{1-4}$ alkyl, and —(CH$_2$)$_u$—CONR$^x$R$^y$ (in particular —CH$_2$—CO$_2$H) and the compound is diastereoisomer 1B.

In one embodiment $R^2$ is hydroxyC$_{1-4}$alkyl (e.g. —CH$_2$OH) and the compound is diastereoisomer 1A.

In one embodiment $R^2$ is —(CH$_2$)$_u$—CO$_2$H (e.g. —CH$_2$—CO$_2$H) and the compound is diastereoisomer 1A.

In one embodiment $R^2$ and the hydrogen on the carbon to which it is attached are $^2$H (i.e. deuterium).

$R^3$ and s $R^3$ is hydrogen or -(A)$_t$-(CR$^x$R$^y$)$_q$—X;

s is selected from 0 and 1;

t is selected from 0 and 1;

q is selected from 0, 1 and 2;

wherein when $R^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —S(O)$_d$—R$^x$, —C(=O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;

R$^9$ is independently selected from hydrogen, C$_{1-6}$alkyl, haloC$_{1-6}$alkyl, hydroxyC$_{1-6}$alkyl, —(CH$_2$)$_k$—O—C$_{1-6}$alkyl, —(CH$_2$)$_k$—O-(hydroxyC$_{1-6}$alkyl), hydroxyC$_{1-6}$alkoxy, —(CH$_2$)$_k$—CO$_2$C$_{1-6}$alkyl, —(CH$_2$)$_k$—CO$_2$H, —C$_{1-6}$ alkyl-N(H)$_e$(C$_{1-4}$alkyl)$_{2-e}$, —(CH$_2$)$_j$—C$_{3-8}$cycloalkyl and —(CH$_2$)$_j$—C$_{3-8}$cycloalkenyl;

R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$alkyl, —N(H)$_e$(C$_{1-4}$alkyl)$_{2-e}$, —C$_{1-6}$alkyl-N(H)$_e$(C$_{1-4}$alkyl)$_{2-e}$, —(CH$_2$)$_k$—C(=O)N(H)$_e$(C$_{1-4}$alkyl)$_{2-e}$, C$_{3-8}$cycloalkyl and C$_{3-8}$cycloalkenyl;

or the R$^x$ and R$^y$ groups, together with the carbon or nitrogen atom to which they are attached, can join to form a C$_{3-6}$cycloalkyl or saturated heterocyclyl group with 3 to 6 ring members which may be optionally fused to an aromatic heterocyclyl group of 3 to 5 ring members or can join to form a =CH group;

j, d, and e are independently selected from 0, 1 and 2;
k is selected from 1 and 2; and
v is independently selected from 0 and 1.

In one embodiment when t is 1 the group —(CR$^x$R$^y$)$_q$—X and the rest of the molecule are attached to the same carbon atom in the group A. In one embodiment when t is 1 the group (CR$^x$R$^y$)$_q$—X and the rest of the molecule are attached to different carbon atoms in the group A.

In one embodiment, R$^3$ is hydrogen or -(A)$_t$-(CR$^x$R$^y$)$_q$—X;
s is selected from 0 and 1;
t is selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —S(O)$_d$—R$^x$, —C(=O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;

R$^9$ is independently selected from hydrogen and C$_{1-6}$alkyl;

R$^x$ and R$^y$ are independently selected from hydrogen and C$_{1-6}$alkyl;

d and e are independently selected from 0, 1 and 2;
v is independently selected from 0 and 1.

In one embodiment, R$^3$ is hydrogen or -(A)$_t$-(CR$^x$R$^y$)$_q$—X;
s is selected from 0 and 1;
t is selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —C(=O)—C$_{1-4}$alkyl, —NR$^x$R$^y$, —NR$^x$COR$^y$, and —C(=O)NR$^x$R$^y$;

R$^9$ is independently selected from hydrogen and C$_{1-6}$alkyl;

R$^x$ and R$^y$ are independently selected from hydrogen and C$_{1-6}$alkyl;

v is independently selected from 0 and 1.

In one embodiment, R$^3$ is hydrogen or -(A)$_t$-(CR$^x$R$^y$)$_q$—X;
s is selected from 0 and 1;
t is selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —NR$^x$COR$^y$, and —C(=O)NR$^x$R$^y$;

R$^9$ is independently selected from hydrogen and C$_{1-6}$alkyl;

R$^x$ and R$^y$ are independently selected from hydrogen and C$_{1-6}$alkyl;

v is independently selected from 0 and 1.

In one embodiment, R$^3$ is hydrogen or -(A)$_t$-(CR$^x$R$^y$)$_q$—X;
s is selected from 0 and 1;
t is selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen (e.g. fluoro), —OR$^9$, —NR$^x$COR$^y$; and —C(=O)NR$^x$R$^y$;

R$^9$ is independently selected from hydrogen and C$_{1-6}$alkyl;

R$^x$ and R$^y$ are independently selected from hydrogen and C$_{1-6}$alkyl;

v is independently selected from 0 and 1.

In one embodiment, R$^3$ is hydrogen and s is 1 i.e. the moiety —(CH$_2$)$_s$R$^3$ is —CH$_3$.

In one embodiment, R$^3$ is hydrogen and s is 0 i.e. the moiety —(CH$_2$)$_s$R$^3$ is —H.

In one embodiment, t is 1 and A is a C$_{3-6}$cycloalkyl group or a heterocyclic group with 3 to 6 ring members, wherein the heterocyclic group comprises one or more (e.g. 1 or 2) heteroatoms selected from N, O, S and oxidised forms thereof.

In one embodiment, t is 1 and A is a C$_{3-6}$cycloalkyl group. In one embodiment, A is a C$_{3-5}$cycloalkyl group. For example, A is selected from a cyclopropyl group, a cyclobutyl group and a cyclopentyl group. In one embodiment, A is a cyclopropyl group. In one embodiment, A is a cyclobutyl group.

In particular, t is 1 and A is cyclopropyl.

In one embodiment, t is 1 and A is a heterocyclic group with 3 to 6 ring members, wherein the heterocyclic group comprises one or more (e.g. 1, 2, or 3) heteroatoms selected from N, O, S and oxidised forms thereof.

In one embodiment, t is 1 and A is a heterocyclic group with 3 to 5 ring members, wherein the heterocyclic group comprises one or more (e.g. 1, 2, or 3) heteroatoms selected from N, O, S and oxidised forms thereof.

In one embodiment, t is 1 and A is an unsaturated heterocyclic group with 3 to 5 ring members, wherein the heterocyclic group comprises one or more (e.g. 1, 2, or 3) heteroatoms selected from N, O, S and oxidised forms thereof, in particular O.

In one embodiment, t is 1 and A is a saturated heterocyclic group with 3 to 5 ring members, wherein the heterocyclic group comprises one or more (e.g. 1, 2, or 3) heteroatoms selected from N, O, S and oxidised forms thereof, in particular O.

In one embodiment, t is 1 and A is a heterocyclic group which is selected from morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, oxetanyl, pyranyl (2H-pyran or 4H-pyran), dihydrothienyl, dihydropyranyl, dihydrofuranyl, dihydrothiazolyl, tetrahydrofuranyl (e.g. tetrahydrofuran-3-yl), tetrahydrothienyl, dioxanyl, oxanyl (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl.

In one embodiment, t is 1 and A is a heterocyclic group which is selected from morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, oxetanyl, pyranyl (2H-pyran or 4H-pyran), dihydropyranyl, dihydrofuranyl, dihydrothiazolyl, tetrahydrofuranyl (e.g. tetrahydrofuran-3-yl), dioxanyl, oxanyl (e.g. oxan-4-yl), imidazolinyl, imidazolidinonyl, oxazolinyl, pyrazolin-2-yl, pyrazolidinyl, piperazinonyl, piperazinyl, and N-alkyl piperazines such as N-methyl piperazinyl.

In particular, t is 1 and A is a heterocyclic group which is oxetanyl (e.g. oxetan-3-yl).

In particular, t is 1 and A is a heterocyclic group which is tetrahydrofuranyl (e.g. tetrahydrofuran-3-yl).

In one embodiment, X is hydrogen, s is 0 and q is 0, and $R^3$ is a heterocyclic group with 3 to 6 ring members, wherein the heterocyclic group comprises one or more (e.g. 1, 2, or 3) heteroatoms selected from N, O, S and oxidised forms thereof. In particular, $R^3$ is tetrahydrofuranyl (e.g. tetrahydrofuran-3-yl).

In one embodiment, s is 0 and t is 1 and A is attached directly to the oxygen atom bound to the isoindolinone. In one embodiment s is 1 and the cycloalkyl group is attached via a methylene group (i.e. —CH$_2$—) to the oxygen atom bound to the isoindolinone.

In one embodiment, A is tetrahydrofuranyl and X is hydrogen.

In one embodiment A is selected from cyclopropyl, oxetanyl and tetrahydrofuranyl.

In one embodiment, q is 0. In one embodiment, q is 1. In one embodiment, q is 2.

In one embodiment, A is oxetanyl and X is fluorine.

When q is not 0, $R^x$ and $R^y$ are selected from hydrogen, halogen (e.g. fluorine), hydroxy and methyl e.g. hydrogen and methyl, in particular hydrogen.

In one embodiment, q is 1 and at least one $R^x$ and $R^y$ is hydrogen. In one embodiment, q is 2 and at least two $R^x$ and $R^y$ are hydrogen e.g. three $R^x$ and $R^y$ are hydrogen.

In one embodiment, —(CR$^x$R$^y$)$_q$— is selected from —CH$_2$— and —CH$_2$CH$_2$—.

In one embodiment, $R^x$ and $R^y$ together form a saturated heterocyclyl group with 3 to 6 ring members.

In one embodiment t is 0 and —(CR$^x$R$^y$)$_q$— is —CH$_2$—. In one embodiment t is 0, s is 0, —(CR$^x$R$^y$)$_q$— is —CH$_2$— and X is hydroxy.

In one embodiment, X is selected from —CN, —OH, —O—C$_{1-4}$alkyl, —O-hydroxyC$_{1-4}$alkyl, —S(O)$_d$—C$_{1-4}$alkyl, —C(=O)—C$_{1-4}$alkyl, —NR$^x$R$^y$, —NR$^x$COR$^y$ and —C(=O)NR$^x$R$^y$.

In one embodiment, X is selected from —CN, —OH, —O—CH$_2$CH$_2$OH, —S(O)$_d$—C$_{1-4}$alkyl and —C(=O)NR$^x$R$^y$ (e.g. —C(=O)NH$_2$ or —C(=O)NH(CH$_3$)). In one embodiment X is selected from —CN, —OH, —C(=O)NH$_2$ or —C(=O)NH(CH$_3$).

In one embodiment, X is selected from hydrogen, halogen, —CN, —OR$^9$, and —C(=O)NR$^x$R$^y$. In another embodiment, X is selected from hydrogen, halogen, —CN, —OH, —OCH$_3$, and —C(=O)NH$_2$. In another embodiment, X is selected from hydrogen, fluorine, —CN, —OH, and —C(=O)NH$_2$.

In one embodiment, X is selected from hydrogen, fluorine, —CN, —OH and —C(=O)NH$_2$. In one embodiment, X is selected from hydrogen, —CN, —OH and —C(=O)NH$_2$. In one embodiment, X is selected from —CN, —OH and —C(=O)NH$_2$.

In one embodiment X is selected from —OH and —C(=O)NH$_2$ e.g. —OH.

In one embodiment, X is —C(=O)NR$^x$R$^y$ (e.g. —C(=O)NH$_2$ or —C(=O)NH(CH$_3$)).

In one embodiment, $R^x$ and $R^y$ are hydrogen, halogen (e.g. fluorine), hydroxy and methyl. In one embodiment, $R^x$ and $R^y$ are hydrogen and methyl. In one embodiment, $R^x$ and $R^y$ together form a saturated heterocyclyl group with 3 to 6 ring members.

In one embodiment, A is a C$_{3-6}$cycloalkyl group (i.e. g is 1, 2 or 3) and t is 1 and s is 0 or 1, and the compound of formula (I) is a compound of formula (If) or a tautomer or a solvate or a pharmaceutically acceptable salt thereof:

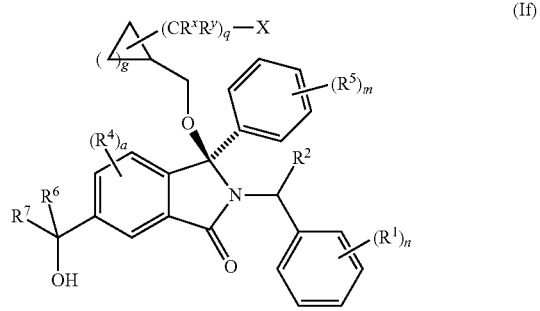

(If)

In one embodiment, A is a C$_{3-6}$cycloalkyl group (i.e. g is 1, 2 or 3) and t is 1 and s is 1, and the compound of formula (I) is a compound of formula (Ig) or a tautomer or a solvate or a pharmaceutically acceptable salt thereof:

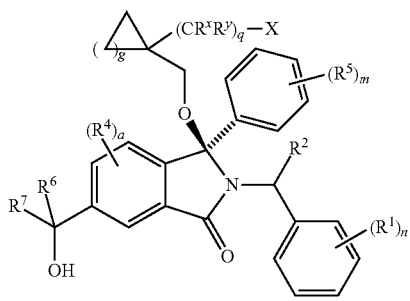
(Ig)

In one embodiment, A is a $C_{3-6}$cycloalkyl group (i.e. g is 1, 2 or 3) and t is 1 and s is 0, and the compound of formula (I) is a compound of formula (Ig') or a tautomer or a solvate or a pharmaceutically acceptable salt thereof:

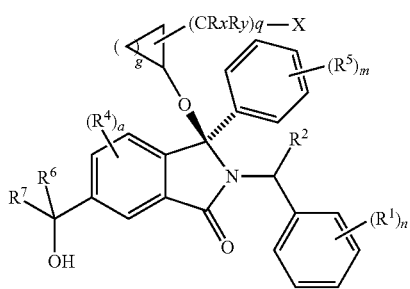
(Ig')

In one embodiment, the compound of formula (I) is a compound of formula (Ig') and g is 2.

In one embodiment, A is a $C_{3-6}$cycloalkyl group (i.e. g is 1, 2 or 3) and t is 1 and s is 1, and the cycloalkyl group is geminally disubstituted (i.e. the group —$(CR^xR^y)_q$—X and the —$CH_2$—O-isoindolinone group are both attached to the same atom of the cycloalkyl group), and the compound of formula (I) is a compound of formula (Ih) or a tautomer or a solvate or a pharmaceutically acceptable salt thereof:

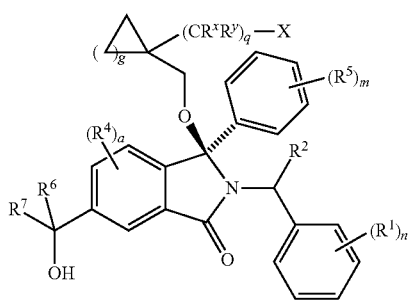
(Ih)

In one embodiment, A is a cyclopropyl group (i.e. g is 1), t is 1 and s is 1. Therefore the cycloalkyl group is a cyclopropyl group and the compound of formula (I) is a compound of formula (Ii) or a tautomer or a solvate or a pharmaceutically acceptable salt thereof:

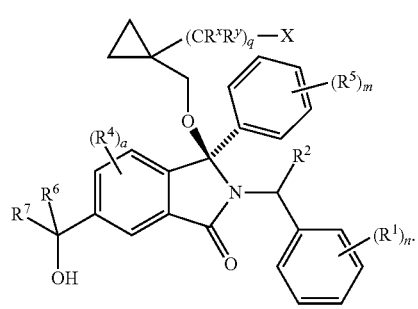
(Ii)

In one embodiment, A is a $C_{3-6}$cycloalkyl group (i.e. g is 1, 2 or 3), t is 1, s is 1 and X is hydroxy, and the compound of formula (I) is a compound of the formula (Ij) or a tautomer or a solvate or a pharmaceutically acceptable salt thereof:

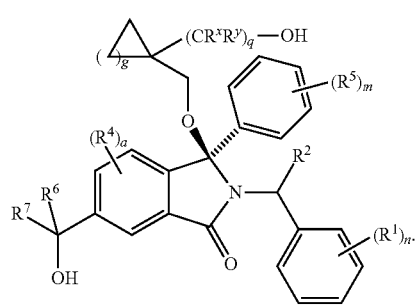
(Ij)

In one embodiment, A is a $C_{3-6}$cycloalkyl group (i.e. g is 1, 2 or 3), t is 1, s is 1 and X is —C(=O)NH$_2$ and the compound of formula (I) is a compound of the formula (Ik) or a tautomer or a solvate or a pharmaceutically acceptable salt thereof:

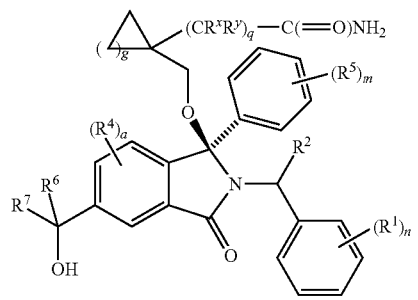
(Ik)

In one embodiment, A is a $C_{3-6}$cycloalkyl group (i.e. g is 1, 2 or 3), t is 1, s is 1 and X is —CN and the compound of formula (I) is a compound of the formula (Ik') or a tautomer or a solvate or a pharmaceutically acceptable salt thereof:

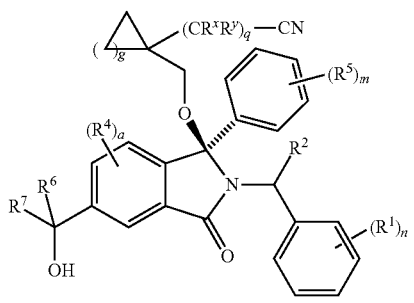

(Ik')

In another embodiment, A is a $C_{3-6}$cycloalkyl group (i.e. g is 1, 2 or 3), t is 1, s is 1 and $R^x$ and $R^y$ are hydrogen (including $^1H$ and $^2H$) and the compound of formula (I) is a compound of formula (IL) or a tautomer or a solvate or a pharmaceutically acceptable salt thereof:

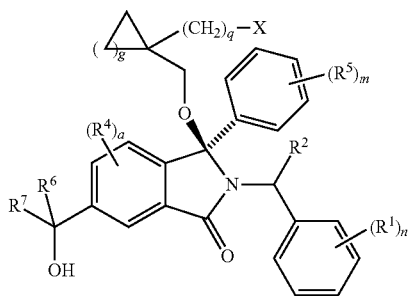

(IL)

In one embodiment, A is a cyclopropyl or cyclobutyl group (i.e. g is 1 or 2), t is 1, s is 1 and X is hydroxy and the compound of formula (IL) is a compound of formula (Im) or a tautomer or a solvate or a pharmaceutically acceptable salt thereof:

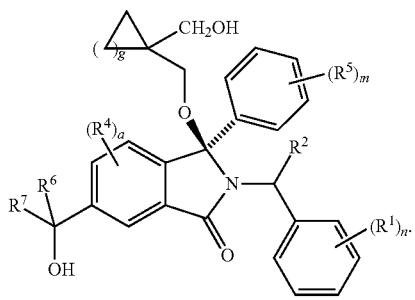

(Im)

In one embodiment, g is 1 and the compound of formula (Im) is a compound of the formula (Im') or a tautomer or a solvate or a pharmaceutically acceptable salt thereof:

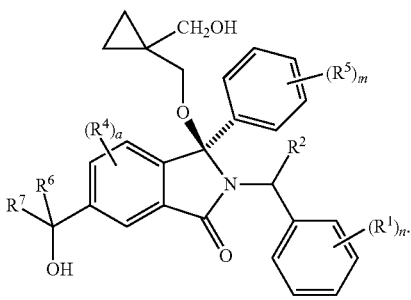

(Im')

In one embodiment, A is a $C_3$-cycloalkyl group (i.e. g is 1), t is 1, s is 1 and X is —C(=O)NH$_2$ and the compound of formula (I) is a compound of formula (In) or a tautomer or a solvate or a pharmaceutically acceptable salt thereof:

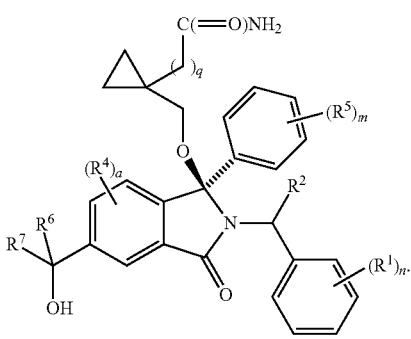

(In)

wherein q is 0 or 1. In one embodiment of the compound (In), q is 0.

In one embodiment, A is a $C_3$-cycloalkyl group (i.e. g is 1), t is 1, s is 1 and X is —CN and the compound of formula (I) is a compound of formula (In') or a tautomer or a solvate or a pharmaceutically acceptable salt thereof:

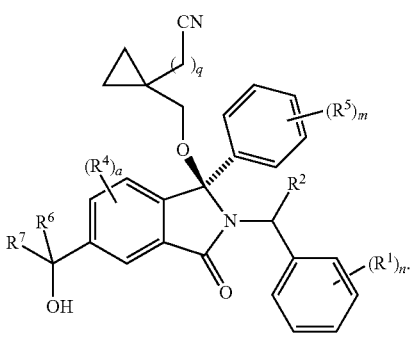

(In')

wherein q is 0 or 1. In one embodiment of the compound (In), q is 0.

In one embodiment of formula (I) and subformulae thereof, the hydrogens in the —(CR$^x$R$^y$)— group of R$^3$ are $^2H$ (i.e. deuterium, D). In one embodiment, the hydrogens in the group —CH$_2$—O group are $^2H$ (i.e. deuterium, D). In one embodiment, the hydrogens in the —(CR$^x$R$^y$)— and —CH$_2$—O groups are $^2H$ (i.e. deuterium, D).

In one embodiment q is 0 or 1 and R$^x$ and R$^y$ are hydrogen or deuterium.

In one embodiment, A is cyclopropyl (i.e. g is 1), t is 1, s is 1, X is hydroxy and the hydrogens in the —(CR$^x$R$^y$)— and —CH$_2$—O groups are $^2$H (or D), and the compound of formula (I) is a compound of formula (Io) or a tautomer or a solvate or a pharmaceutically acceptable salt thereof:

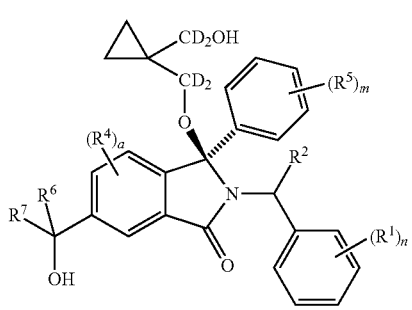
(Io)

In one embodiment the compound of formula (I) is a compound of formula (Io') or (Io'') or a tautomer or a solvate or a pharmaceutically acceptable salt thereof:

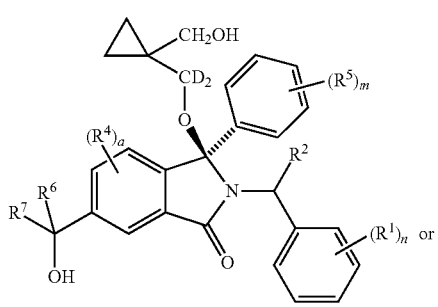
(Io')

or

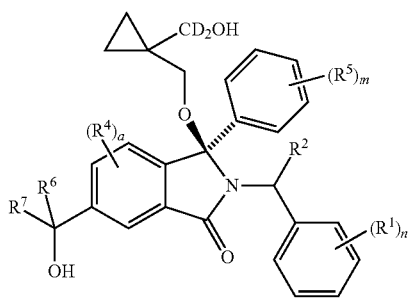
(Io'')

In one embodiment, R$^3$ is —(CR$^x$R$^y$)$_q$—X and s is 1, t is 0 and q is 1 or 2, and the compound of formula (I) is a compound of the formula (Ip):

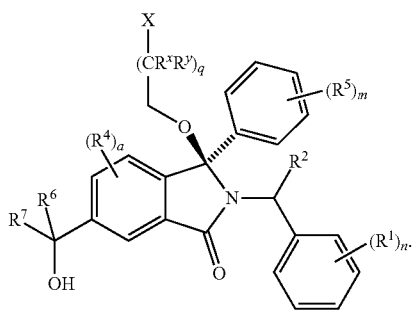
(Ip)

In one embodiment, R$^x$ and R$^y$ are H, and the compound of formula (Ip) is a compound of the formula (Ip') or a tautomer or a solvate or a pharmaceutically acceptable salt thereof:

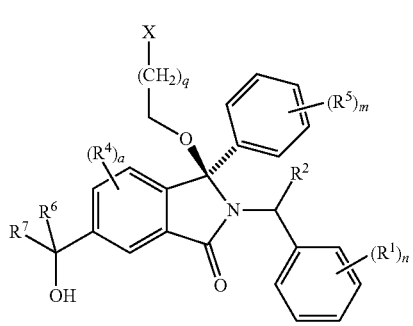
(Ip')

In one embodiment, A is a C$_{3-6}$cycloalkyl group or saturated heterocyclic group with 3 to 6 ring members, wherein t is 1, and s is 1, Y is independently selected from —CH$_2$—, O, or SO$_2$, i is 0 or 1, g is 1, 2, 3 or 4 and i+g is 1, 2, 3 or 4 and the compound of formula (I) is a compound of the formula (Iq) or a tautomer or a solvate or a pharmaceutically acceptable salt thereof:

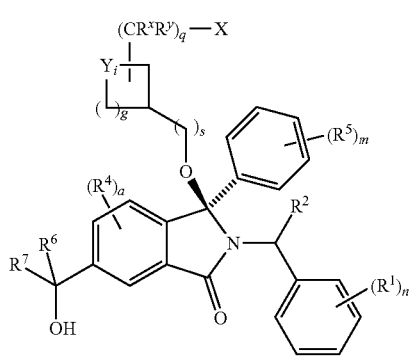
(Iq)

In one embodiment the compound of formula (I) is a compound of the formula (Iq') or a tautomer or a solvate or a pharmaceutically acceptable salt thereof:

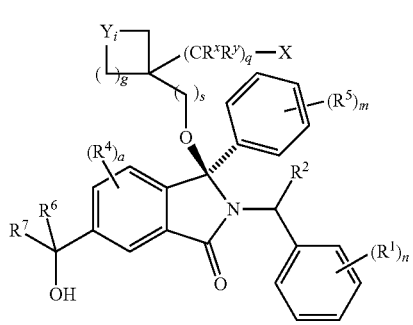
(Iq')

In one embodiment of the compound of formula (Iq'), q is 1 and R$^x$, R$^y$ and X are hydrogen.

In one embodiment of the compound of formula (Iq'), q is 1, R$^x$ and R$^y$ are hydrogen, and X is hydroxy.

In one embodiment of the compound of formula (Iq'), q is 1, $R^x$ and $R^y$ are hydrogen, and X is fluorine.

In one embodiment of the compound of formula (Iq'), q is 0. In one embodiment of the compound of formula (Iq'), q is 0 and X is fluorine.

In one embodiment q is 0 and X is fluorine and the compound of formula (Iq') is a compound of the formula (Iq") or a tautomer or a solvate or a pharmaceutically acceptable salt thereof:

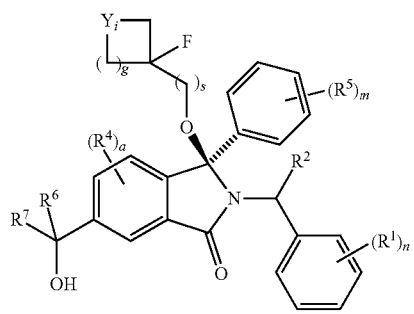

(Iq")

In one embodiment of the compound of (Iq') or the compound of (Iq"), g is 1, i is 1 and Y is O.

In one embodiment g is 1, i is 1, Y is O, q is 0 and X is F and the compound of formula (Iq') is a compound of the formula (Iq''') or a tautomer or a solvate or a pharmaceutically acceptable salt thereof:

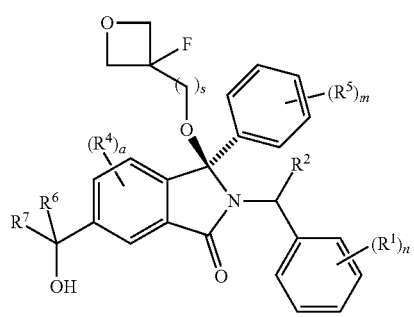

(Iq''')

In one embodiment, i is 1 and Y is O or SO$_2$, in particular O. In one embodiment, the compound of formula (Iq) is a compound of formula (Iq"") or a tautomer or a solvate or a pharmaceutically acceptable salt thereof:

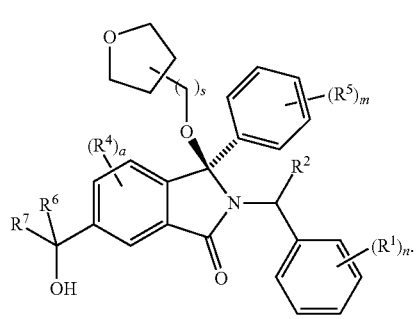

(Iq"")

In one embodiment, s is 0, t is 1, A is tetrahydrofuranyl, q is 0 and X is hydrogen. In one embodiment, $R^3$ is tetrahydrofuranyl and s is 0.

In one embodiment, —(CH$_2$)$_s$R$^3$ is selected from the following table (point of attachment to the oxygen represented by dashed bond or bond terminus marked "*"):

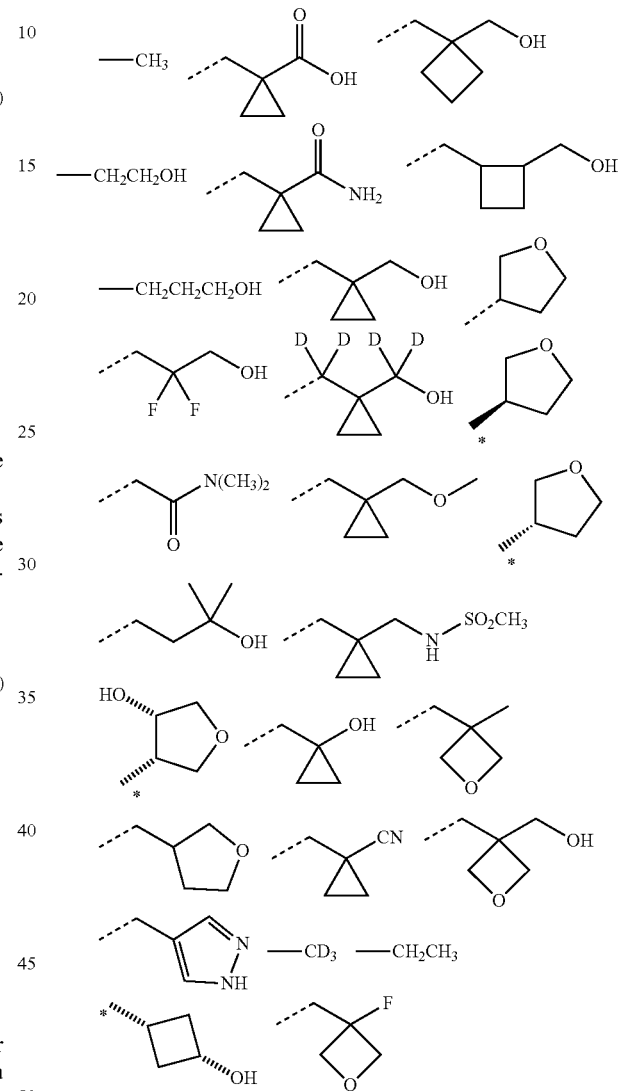

In one embodiment, —(CH$_2$)$_s$R$^3$ is selected from the following table (point of attachment to the oxygen represented by dashed bond or bond terminus marked "*"):

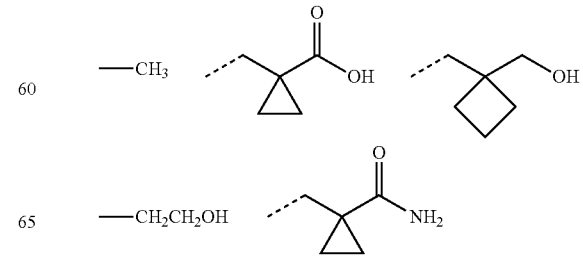

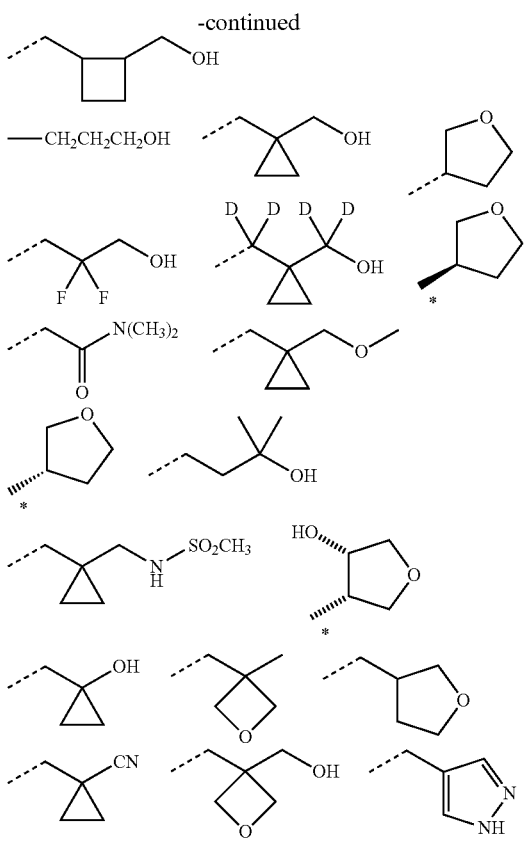

In one embodiment A is cyclopropyl, t is 1, s is 1, $R^x$ and $R^y$ are hydrogen and X is —OH.

In one embodiment A is cyclopropyl, t is 1, s is 1, $R^x$ and $R^y$ are hydrogen and X is —CN.

In one embodiment $R^3$ is hydrogen and s is 1. In one embodiment, X is hydrogen and s, t, and q are 0.

$R^4$ and a a is 0, 1, 2 or 3. In other words, the phenyl group of the isoindolin-1-one may have 0, 1, 2 or 3 substituents $R^4$.

In one embodiment a is 0 or 1. In another embodiment a is 0. In another embodiment a is 1.

When a is 2 or 3 (i.e. the phenyl group of the isoindolin-1-one is substituted with more than one $R^4$) the substituents $R^4$ may be the same or different (i.e. are independently selected from the definitions of $R^4$).

In one embodiment, a is 1 and the substituent $R^4$ is at the 4-position of the isoindolin-1-one, and the compound of formula (I) is a compound of formula (Ir) or a tautomer or a solvate or a pharmaceutically acceptable salt thereof:

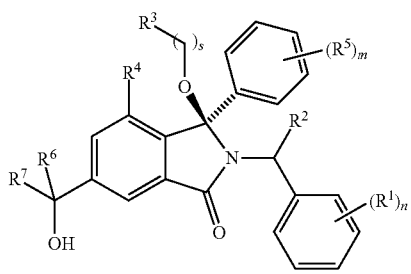

$R^4$ is independently selected from halogen, nitrile, $C_{1-4}$ alkyl, halo$C_{1-4}$alkyl, $C_{1-4}$alkoxy and halo$C_{1-4}$alkoxy.

In one embodiment, $R^4$ is halogen. In one embodiment, $R^4$ is fluoro or chloro. In another embodiment, $R^4$ is fluoro.

In one embodiment, a is 1, the substituent $R^4$ is at the 4-position of the isoindolin-1-one, and $R^4$ is F and the compound of formula (I) is a compound of formula (Is) or a tautomer or a solvate or a pharmaceutically acceptable salt thereof:

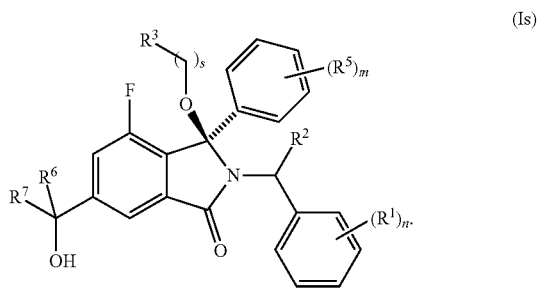

In one embodiment, a is 0, and the compound of formula (I) is a compound of formula (It) or a tautomer or a solvate or a pharmaceutically acceptable salt thereof:

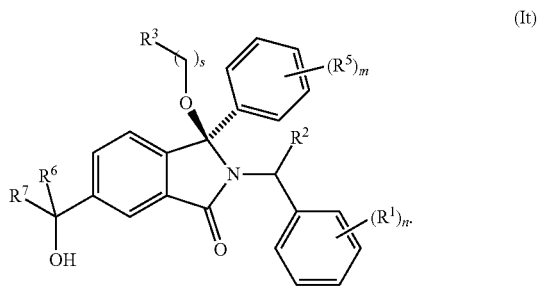

In one embodiment, $R^4$ is $C_{1-4}$ alkyl (e.g. —CH$_3$), or halogen (e.g. F or Cl) and a is 1.

In one embodiment, a is 0 and $R^4$ is absent (i.e. hydrogen).

In one embodiment a is 0 or 1 and $R^4$ is halogen (e.g. fluorine).

$R^5$ and m m is 1 or 2. In other words, the phenyl group may have 1 or 2 substituents $R^5$.

In one embodiment, m is 1 and the phenyl group has one substituent.

$R^5$ may be attached at the ortho (or o-), meta (or m-) or para (or p-) position of the phenyl group, wherein the position is defined relative to the point of attachment of the phenyl group to the 3-position of the isoindolin-1-one ring.

When m is 2 (i.e. the phenyl group is substituted with more than one $R^5$) the substituents $R^5$ may be the same or different (i.e. are independently selected from the definitions of $R^5$).

In one embodiment, m is 1 and the substituent $R^4$ is at the p-position of the phenyl group, and the compound of formula (I) is a compound of formula (Iu) or a tautomer or a solvate or a pharmaceutically acceptable salt thereof:

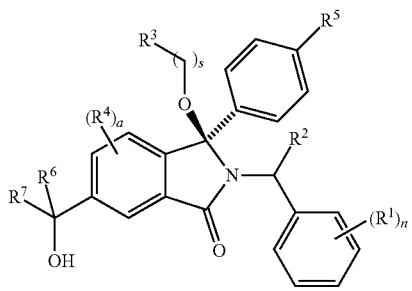

(Iu)

$R^5$ is independently selected from halogen, nitrile, $C_{1-4}$ alkyl, halo$C_{1-4}$alkyl, $C_{1-4}$alkoxy and halo$C_{1-4}$alkoxy.

In one embodiment, $R^5$ is halogen, $C_{1-4}$ alkyl, halo$C_{1-4}$alkyl or $C_{1-4}$alkoxy. In another embodiment $R^5$ is halogen (e.g. chloro).

In one embodiment, $R^5$ is halogen (e.g. Cl or F), $C_{1-4}$ alkyl (e.g. —$CH_2CH_3$), nitrile, halo$C_{1-4}$alkyl (e.g. —$CF_3$, or —$CF_2CH_3$), or halo$C_{1-4}$alkoxy (e.g. —$OCF_3$), and m is 1 or 2.

In one embodiment, m is 1 and $R^5$ is selected from halogen, nitrile, $C_{1-4}$ alkyl, halo$C_{1-4}$alkyl, $C_{1-4}$alkoxy and halo$C_{1-4}$alkoxy.

In one embodiment, m=1 and $R^5$ is —Cl (e.g. p-Cl), —F (e.g. 4-F), —CN (e.g. p-CN), —$CF_3$ (e.g. p-$CF_3$), —$OCF_3$ (e.g. p-$OCF_3$), $CF_2CH_3$ (e.g. p-$CF_2CH_3$) or —$CH_2CH_3$ (e.g. p-$CH_2CH_3$), or m=2 and $R^5$ is p-F or m-F.

In one embodiment, m=1 and $R^5$ is —Cl (e.g. p-Cl)

$R^6$ and $R^7$ $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)_j$—O—$C_{1-6}$ alkyl, —$(CH_2)_j$—O-(hydroxy$C_{1-6}$alkyl), —$C_{1-6}$alkyl-NR$^x$R$^y$, —$(CR^xR^y)_p$—CONR$^x$R$^y$, —$(CR^xR^y)_p$—NR$^x$COR$^y$, —$(CR^xR^y)_p$—O—$CH_2$—CONR$^x$R$^y$, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, —$CH_2$—$C_{3-8}$cycloalkyl, —$CH_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more $R^z$ groups;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —COO$C_{1-6}$alkyl, —N(H)$_e$($C_{1-4}$alkyl)$_{2-e}$, —$C_{1-6}$alkyl-N(H)$_e$($C_{1-4}$alkyl)$_{2-e}$, —$(CH_2)_k$—C(=O)N(H)$_e$($C_{1-4}$alkyl)$_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$—CO$_2$$C_{1-6}$ alkyl, —$(CH_2)_r$—CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O) O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl, wherein if $R^7$ is pyridine then $R^z$ is other then —$NH_2$;

j, e, r and p are independently selected from 0, 1 and 2; and k is selected from 1 and 2.

In one embodiment, $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)_j$—O—$C_{1-6}$alkyl, —$(CH_2)_j$—O-(hydroxy$C_{1-6}$alkyl), —$C_{1-6}$alkyl-NR$^x$R$^y$, —$(CR^xR^y)_p$—CONR$^x$R$^y$, —$(CR^xR^y)_p$—NR$^x$COR$^y$, —$(CR^xR^y)_p$—O—$CH_2$—CONR$^x$R$^y$, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—N ($C_{1-6}$alkyl)-heterocyclic group with 3 to 7 ring members, —C(=O)NH-heterocyclic group with 3 to 7 ring members, $C_{3-8}$cycloalkyl, —$CH_2$—$C_{3-8}$cycloalkyl, —$CH_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

In one embodiment $R^7$ is a cycloalkyl, cycloalkenyl or heterocyclic group optionally substituted by one or more $R^z$ selected from $C_{1-6}$alkyl (e.g. methyl), $C_{1-6}$alkoxy (e.g. methoxy) and —C(=O)$C_{1-6}$alkyl (e.g. —C(=O)$CH_3$).

In one embodiment $R^7$ is a cycloalkyl or cycloalkenyl group optionally substituted by one or more $R^z$ groups wherein $R^z$ is hydroxy.

$R^6$ and $R^7$ may be the same or different.

When $R^6$ and $R^7$ are different, the compound of formula (I) can exist as at least two diastereoisomers:

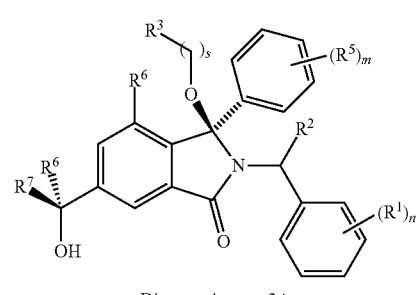

Diastereoisomer 2A

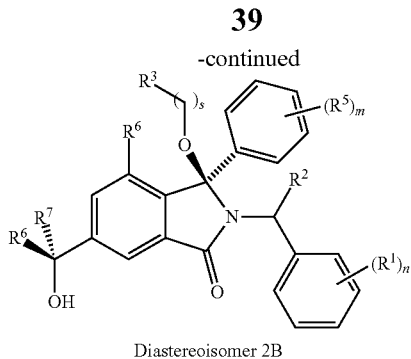

Diastereoisomer 2B

For the avoidance of doubt, the general formula (I) and all subformulae cover both individual diastereoisomers and mixtures of the diastereoisomers which are related as epimers at the —CR$^6$R$^7$OH group.

In one embodiment of the compound of formula (I) R$^6$ and R$^7$ are different and the compound is diastereoisomer 2A or a tautomer or a solvate or a pharmaceutically acceptable salt thereof.

In one embodiment of the compound of formula (I) R$^6$ and R$^7$ are different and the compound is diastereoisomer 2B or a tautomer or a solvate or a pharmaceutically acceptable salt thereof.

In one embodiment, R$^6$ is methyl and the compound of formula (I) is a compound of formula (Iv) or a tautomer or a solvate or a pharmaceutically acceptable salt thereof:

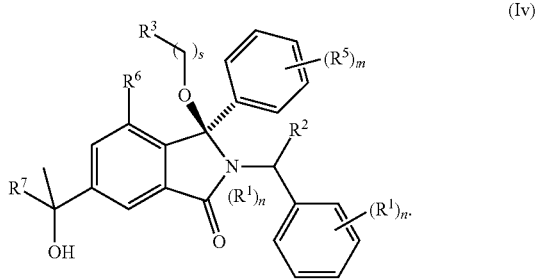

(Iv)

In one embodiment, R$^6$ is ethyl and the compound of formula (I) is a compound of formula (Iv') or a tautomer or a solvate or a pharmaceutically acceptable salt thereof:

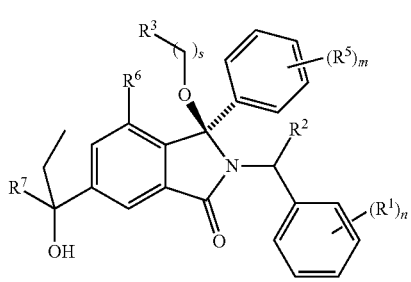

(Iv')

In one embodiment, R$^7$ is selected from C$_{1-6}$alkyl or haloC$_{1-6}$alkyl. In one embodiment R$^7$ is a C$_{3-6}$cycloalkyl (e.g. cyclopropyl, cyclobutyl or cyclohexyl) optionally substituted by one or more R$^z$ groups (e.g. —OH).

In one embodiment, R$^7$ is selected from C$_{1-6}$alkyl, hydroxyC$_{1-6}$alkyl, —(CH$_2$)$_j$—O—C$_{1-6}$alkyl, —(CH$_2$)$_j$—O— (hydroxyC$_{1-6}$alkyl), —C$_{1-6}$alkyl-NR$^x$R$^y$ (e.g. —C$_{1-6}$alkyl-N (H)$_e$(C$_{1-4}$alkyl)$_{2-e}$), —(CR$^x$R$^y$)$_p$—NR$^x$COR$^y$, heterocyclic group with 3 to 7 ring members, —CH$_2$-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof.

In one embodiment, R$^7$ is selected from C$_{1-6}$alkyl, hydroxyC$_{1-6}$alkyl, —(CH$_2$)$_j$—O—C$_{1-6}$alkyl, —(CH$_2$)$_j$—O-(hydroxyC$_{1-6}$alkyl), —C$_{1-6}$alkyl-N(H)$_e$(C$_{1-4}$alkyl)$_{2-e}$, heterocyclic group with 3 to 7 ring members, —CH$_2$-heterocyclic group with 3 to 7 ring members, —C(=O)NH-heterocyclic group with 3 to 7 ring members, C$_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof.

In one embodiment, R$^7$ is selected from heterocyclic group with 3 to 7 ring members, —CH$_2$-heterocyclic group with 3 to 7 ring members, —C(=O)NH-heterocyclic group with 3 to 7 ring members, C$_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof.

In one embodiment, R$^7$ is selected from heterocyclic group with 3 to 7 ring members and —CH$_2$-heterocyclic group with 3 to 7 ring members, wherein said heterocyclic groups may be optionally substituted by one or more R$^z$ groups, and wherein in each instance the heterocyclic group comprises one or more (e.g. 1, or 2) heteroatoms selected from N, O, S and oxidised forms thereof.

In embodiment, the heterocyclic group is saturated. In one embodiment, R$^7$ is saturated heterocyclic group with 3 to 6 ring members or —CH$_2$-(saturated heterocyclic group with 3 to 6 ring members) such as wherein the heterocyclic group is selected from oxetanyl, oxanyl, piperidinyl, piperazinyl, morpholinyl, pyrrolidinyl, imidazolinyl, azetidinyl, thiomorpolinyl, such as oxanyl, piperdinyl or piperazinyl.

In one embodiment, R$^7$ is selected from saturated heterocyclic group with 3 to 6 ring members and —CH$_2$-saturated heterocyclic group with 3 to 6 ring members, wherein said heterocyclic groups may be optionally substituted by one or more R$^z$ groups, and wherein in each instance the heterocyclic group comprises one or more (e.g. 1, 2, or 3) heteroatoms selected from N, O, S. In one embodiment, R$^7$ is selected from a nitrogen containing saturated heterocyclic group with 3 to 6 ring member and —CH$_2$-(nitrogen containing saturated heterocyclic group with 3 to 6 ring members), wherein said heterocyclic groups may be optionally substituted by one or more R$^z$ groups, and wherein the heterocyclic group may optionally contain one or more (e.g. 1, 2, or 3) additional heteroatoms selected from N, O, S.

In one embodiment, R$^7$ is nitrogen containing saturated heterocyclic group with 3 to 7 ring members or —CH$_2$-(nitrogen containing saturated heterocyclic group with 3 to 7 ring members), wherein said nitrogen containing saturated heterocyclic groups may be optionally substituted by one or more R$^z$ groups and wherein the nitrogen containing saturated heterocyclic group may optionally contain one or more (e.g. 1, 2, or 3) additional heteroatoms selected from N, O, S. In one embodiment the nitrogen containing saturated heterocyclic group with 3 to 7 ring members (such as 3 to 6 ring members) is selected from piperidinyl, piperazinyl, morpholinyl, pyrrolidinyl, imidazolidinyl, azetidinyl, thiomorpolinyl, such as piperdinyl or piperazinyl.

In one embodiment, $R^7$ is nitrogen containing aromatic heterocyclic group with 3 to 6 ring members or —$CH_2$-(nitrogen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, $R^7$ is nitrogen containing aromatic heterocyclic group with 3 to 6 ring members, wherein said heterocyclic group may be unsubstituted or substituted by one or more $R^z$ groups, for example selected from halogen (e.g. fluorine), $C_{1-6}$alkyl (e.g. methyl), $C_{1-6}$alkoxy (e.g. methoxy), and —$C(=O)C_{1-6}$alkyl (e.g. —$C(=O)CH_3$).

In one embodiment, $R^7$ is oxygen containing aromatic heterocyclic group with 3 to 6 ring members or —$CH_2$-(oxygen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, $R^7$ is oxygen containing aromatic heterocyclic group with 3 to 6 ring members, wherein said heterocyclic group may be unsubstituted or substituted by one or more $R^z$ groups, for example $R^z$ groups selected from halogen (e.g. fluorine), $C_{1-6}$alkyl (e.g. methyl), $C_{1-6}$alkoxy (e.g. methoxy), and —$C(=O)C_{1-6}$alkyl (e.g. —$C(=O)CH_3$).

In one embodiment $R^7$ is selected from heterocyclyl groups containing 5 or 6 ring members optionally substituted by one or more $R^z$.

In one embodiment $R^7$ is selected from aromatic heterocyclyl groups containing 5 ring members optionally substituted by one or more $R^z$. In one embodiment $R^7$ is selected from an aromatic nitrogen containing (e.g. diaza) heterocyclyl group containing 5 ring members optionally substituted by one or more $R^z$. In one embodiment $R^7$ is pyrazolyl (e.g. pyrazol-4-yl or pyrazol-3-yl).

In one embodiment $R^7$ is selected from a saturated heterocyclyl group containing 6 ring members optionally substituted by one or more $R^z$. In one embodiment $R^7$ is selected from a saturated oxygen or nitrogen containing heterocyclyl group containing 6 ring members optionally substituted by one or more $R^z$.

In one embodiment $R^7$ is selected from oxanyl, piperidinyl, pyrazolyl or imidazolyl optionally substituted by one or more $R^z$. In one embodiment $R^7$ is selected from oxanyl, piperidinyl, pyrazolyl or imidazolyl optionally substituted by one or more $R^z$, where $R^z$ is selected from halo (e.g. —F) or $C_{1-4}$alkyl (e.g. methyl).

In one embodiment $R^7$ is selected from oxanyl (also known as tetrahydropyranyl) or piperidinyl optionally substituted by one or more $R^z$. In one embodiment $R^7$ is selected from oxanyl or piperidinyl unsubstituted or substituted by one or more $R^z$, where $R^z$ is selected from halo (e.g. —F) or $C_{1-4}$alkyl (e.g. methyl), in particular halo (e.g. —F).

In one embodiment, $R^7$ is $C_{3-8}$cycloalkyl such as $C_{3-6}$cycloalkyl (e.g. cyclobutyl or cyclohexyl) optionally substituted by one or more $R^z$, for example where $R^z$ is hydroxy. In one embodiment, $R^7$ is cyclohexyl optionally substituted by one or more hydroxy. In one embodiment $R^7$ is cyclohexyl optionally substituted by one or more hydroxyl, in the trans stereochemistry (e.g. trans-4-hydroxycyclohexane).

In one embodiment $R^7$ is selected from —$CH_2$—NH-heterocyclic group with 3 to 7 ring members (e.g. —$CH_2$—NH-oxanyl and —$CH_2$—N($C_{1-6}$alkyl)-heterocyclic group with 3 to 7 ring members (e.g. —$CH_2NCH_3$-(piperidinyl) optionally substituted by one or more $R^z$ groups (e.g. methyl, —$COCH_3$).

In one embodiment, $R^7$ is —$(CR^xR^y)_p$—$CONR^xR^y$ or —$C(=O)NH$-heterocyclic group with 3 to 7 ring members. In one embodiment, $R^7$ is —$C(=O)NH$-heterocyclic group with 4 to 6 ring members (e.g. piperidinyl, pyrazolyl, or azetidinyl).

In one embodiment, $R^7$ is —$(CR^xR^y)_p$—$CONR^xR^y$. In one embodiment $R^7$ is —$(CR^xR^y)_p$—$CONH(C_{1-4}alkyl)$, in particular —$(CO)NHCH_3$, —$(CO)NHCH_2CH_3$ or —$(CO)NH(CH(CH_3)_2)$.

In one embodiment $R^7$ is —$C(=O)NH$-heterocyclic group with 3 to 7 ring members (e.g. —$C(=O)NH$-piperidinyl, —$C(=O)NH$-azetidinyl or —$C(=O)NH$-pyrazolyl) optionally substituted by one or more $R^z$ groups (e.g. methyl, —$COCH_3$).

In one embodiment, $R^7$ is —$C_{1-6}$alkyl-$NR^xR^y$ (e.g. —$C_{1-6}$alkyl-$N(H)_e(C_{1-4}$alkyl$)_{2-e}$). In one embodiment $R^7$ is —$CH_2NH_2$, —$CH_2NHCH_3$, or —$CH_2N(CH_3)_2$. In one embodiment $R^7$ is —$C_{1-6}$alkyl-$NR^xR^y$ wherein $R^x$ is $C_{3-8}$cycloalkyl. In one embodiment $R^7$ is —$C_{1-2}$alkyl-NH—$C_{3-6}$cycloalkyl (e.g. —$CH_2$—NH-cyclopropyl).

In one embodiment, $R^7$ is —$C_{1-6}$alkyl-$NR^xR^y$ wherein the $R^x$ and $R^y$ groups, together with the nitrogen atom to which they are attached, can join to form a $C_{3-6}$cycloalkyl or heterocyclyl group with 3 to 6 ring members. In one embodiment, $R^x$ and $R^y$ together form a saturated heterocyclyl group with 3 to 6 ring members e.g. piperazinyl.

In one embodiment $R^7$ is —$C_{1-6}$alkyl-$NR^xR^y$, wherein the $R^x$ and $R^y$ groups, together with the nitrogen atom to which they are attached, join to form a $C_{3-6}$cycloalkyl or saturated heterocyclyl group with 3 to 6 ring members which may be optionally fused to an aromatic heterocyclyl group of 3 to 5 ring members. In one embodiment $R^7$ is —$C_{1-6}$alkyl-$NR^xR^y$, wherein the $R^x$ and $R^y$ groups, together with the nitrogen atom to which they are attached, join to form a saturated heterocyclyl group with 3 to 6 ring members which is fused to an aromatic heterocyclyl group of 3 to 5 ring members. $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$ alkyl, hydroxy$C_{1-6}$alkoxy, —$C(=O)C_{1-6}$alkyl, —$C(=O)C_{1-6}$alkyl-OH, —$C(=O)C_{1-6}$alkyl-$N(H)_e(C_{1-4}$alkyl$)_{2-e}$, —$C(=O)N(H)_e(C_{1-4}$alkyl$)_{2-e}$, —$(CH_2)_r$—$CO_2C_{1-6}$ alkyl, —$(CH_2)_r$—$CO_2H$, —$N(H)_e(C_{1-4}$alkyl$)_{2-e}$, —$C_{1-6}$alkyl-$N(H)_e(C_{1-4}$alkyl$)_{2-e}$, heterocyclyl group with 3 to 6 ring members, heterocyclyl group with 3 to 6 ring members substituted by —$C(=O)C_{1-4}$alkyl, heterocyclyl group with 3 to 6 ring members substituted by —$C(=O)OC_{1-4}$alkyl, heterocyclyl group with 3 to 6 ring members substituted by —$C(=O)N(H)_e(C_{1-4}$alkyl$)_{2-e}$, —$C(=O)$heterocyclyl group with 3 to 6 ring members, $C_{3-8}$cycloalkyl and $C_{3-8}$cycloalkenyl.

In one embodiment $R^z$ is independently selected from halogen (e.g. fluorine), $C_{1-6}$alkyl (e.g. methyl), $C_{1-6}$alkoxy (e.g. methoxy), and —$C(=O)C_{1-6}$alkyl (e.g. —$C(=O)CH_3$).

In one embodiment R$^z$ is independently selected from C$_{1-6}$alkyl (e.g. methyl), C$_{1-6}$alkoxy (e.g. methoxy), and —C(=O)C$_{1-6}$alkyl (e.g. —C(=O)CH$_3$).

In one embodiment, R$^7$ is C$_{1-6}$alkyl (e.g. methyl or ethyl), haloC$_{1-6}$alkyl (e.g. trifluoromethyl), C$_{2-6}$alkenyl (e.g. C$_2$alkenyl), hydroxyC$_{1-6}$alkyl (e.g. —CH$_2$OH, —CH$_2$CH$_2$OH), —C$_{1-6}$alkyl-NR$^x$R$^y$ (e.g. —CH$_2$NH$_2$, —CH$_2$NHCH$_3$, —CH$_2$N(CH$_3$)$_2$, or —CH$_2$—NH-cyclopropyl), —(CR$^x$R$^y$)$_p$—CONR$^x$R$^y$ (e.g. —(CO)NHCH$_3$, —(CO)NHCH$_2$CH$_3$, —(CO)NHCH$_2$CH$_2$NH$_2$ or —(CO)NH(CH(CH$_3$)$_2$), —(CH$_2$)$_j$—O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHCOCH$_3$), —(CR$^x$R$^y$)$_p$—O—CH$_2$—CONR$^x$R$^y$ (e.g. —CH$_2$—O—CH$_2$CON(CH$_3$)$_2$), —(CH$_2$)$_j$—O-(hydroxyC$_{1-6}$alkyl) (e.g. —CH$_2$—O—CH$_2$CH$_2$OH), —C(=O)NH- heterocyclic group with 3 to 7 ring members, C$_{3-6}$cycloalkyl, heterocyclic group with 3 to 7 ring members (e.g. oxanyl), or —CH$_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more R$^z$ groups (for example selected from C$_{1-6}$alkyl (e.g. methyl), C$_{1-6}$alkoxy (e.g. methoxy) and —C(=O)C$_{1-6}$alkyl (e.g. —C(=O)CH$_3$)). In one embodiment, R$^6$ is methyl or ethyl and R$^7$ is C$_{1-6}$alkyl (e.g. methyl), hydroxyC$_{1-6}$alkyl, —C$_{1-6}$alkyl-NR$^x$R$^y$, —(CR$^x$R$^y$)$_p$—CONR$^x$R$^y$, —(CH$_2$)$_j$—O—C$_{1-6}$alkyl, —(CR$^x$R$^y$)$_p$—NR$^x$COR$^y$, —(CR$^x$R$^y$)$_p$—O—CH$_2$—CONR$^x$R$^y$, —(CH$_2$)$_j$—O-(hydroxyC$_{1-6}$alkyl), heterocyclic group with 3 to 7 ring members (e.g. oxanyl), or —CH$_2$-heterocyclic group with 3 to 7 ring members wherein the heterocyclic group comprises one or more (e.g. 1, 2, or 3) heteroatoms selected from N, O, S and oxidised forms and may be optionally substituted by one or more R$^z$ groups selected from C$_{1-6}$alkyl (e.g. methyl), C$_{1-6}$alkoxy (e.g. methoxy) and —C(=O)C$_{1-6}$alkyl (e.g. —C(=O)CH$_3$).

In one embodiment, R$^6$ is selected from hydrogen, C$_{1-6}$alkyl (e.g. —CH$_3$, —CH$_2$CH$_3$ or —CH$_2$CH$_2$CH$_3$), C$_{2-6}$alkenyl (e.g. —CH=CH$_2$) and haloC$_{1-6}$alkyl (e.g. —CF$_3$).

In one embodiment, R$^6$ is selected from hydrogen or C$_{1-6}$alkyl (e.g. —CH$_3$ or —CH$_2$CH$_3$).

In one embodiment, R$^7$ is C$_{1-6}$alkyl (e.g. —CH$_3$ or —CH$_2$CH$_3$), hydroxyC$_{1-6}$alkyl (e.g. —CH$_2$OH), —C$_{1-6}$alkyl-NR$^x$R$^y$ (e.g. —CH$_2$N(CH$_3$)$_2$), —(CR$^x$R$^y$)$_p$—CONR$^x$R$^y$ (e.g. —C(=O)N(CH$_3$)$_2$ or —C(=O)NHCH$_3$ or

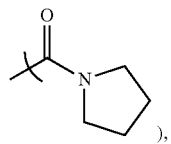

),

—(CH$_2$)$_j$—O—C$_{1-6}$alkyl (e.g. —CH$_2$OCH$_3$), C$_{3-8}$cycloalkyl (e.g. cyclobutyl or cyclohexyl), heterocyclic group with 3 to 7 ring members e.g.
(point of attachment represented by dashed bond):

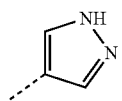 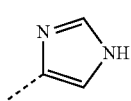 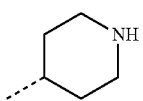

or —CH$_2$-heterocyclic group with 3 to 7 ring members e.g.
(point of attachment represented by dashed bond)

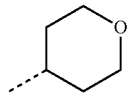

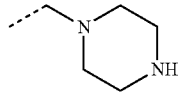

wherein when the moiety R$^7$ comprises a heterocyclic or cycloalkyl group, the heterocyclic group may be optionally substituted by one or more R$^z$ groups selected from C$_{1-6}$alkyl (e.g. methyl), hydroxy, halogen (e.g. fluoro), —C(=O)C$_{1-6}$alkyl (e.g. —C(=O)C(CH$_3$)$_3$), —(CH$_2$)$_r$—CO$_2$H (e.g. —CH$_2$COOH or CH$_2$CH$_2$COOH or —(CH$_2$)$_r$—CO$_2$C$_{1-6}$alkyl (e.g. CH$_2$CH$_2$COOCH$_3$).

In one embodiment, R$^7$ is C$_{1-6}$alkyl (e.g. methyl or ethyl), haloC$_{1-6}$alkyl (e.g. trifluoromethyl), C$_{2-6}$alkenyl (e.g. C$_2$alkenyl), hydroxyC$_{1-6}$alkyl (e.g. —CH$_2$OH, —CH$_2$CH$_2$OH), —C$_{1-6}$alkyl-NR$^x$R$^y$ (e.g. —CH$_2$NH$_2$, —CH$_2$NHCH$_3$, —CH$_2$N(CH$_3$)$_2$, or —CH$_2$—NH-cyclopropyl), —(CR$^x$R$^y$)$_p$—CONR$^x$R$^y$ (e.g. —(CO)NHCH$_3$, —(CO)NHCH$_2$CH$_3$, —(CO)NHCH$_2$CH$_2$NH$_2$ or —(CO)NH(CH(CH$_3$)$_2$), —(CH$_2$)$_j$—O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHCOCH$_3$), —(CR$^x$R$^y$)$_p$—O—CH$_2$—CONR$^x$R$^y$ (e.g. —CH$_2$—O—CH$_2$CON(CH$_3$)$_2$), —(CH$_2$)$_j$—O-(hydroxyC$_{1-6}$alkyl) (e.g. —CH$_2$—O—CH$_2$CH$_2$OH), —C(=O)NH- heterocyclic group with 3 to 7 ring members, C$_{3-6}$cycloalkyl, heterocyclic group with 3 to 7 ring members (e.g. oxanyl), or —CH$_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more R$^z$ groups (for example selected from C$_{1-6}$alkyl (e.g. methyl), C$_{1-6}$alkoxy (e.g. methoxy) and —C(=O)C$_{1-6}$alkyl (e.g. —C(=O)CH$_3$)). In one embodiment, R$^6$ is methyl or ethyl and R$^7$ is C$_{1-6}$alkyl (e.g. methyl), hydroxyC$_{1-6}$alkyl, —C$_{1-6}$alkyl-NR$^x$R$^y$, —(CR$^x$R$^y$)$_p$—CONR$^x$R$^y$, —(CH$_2$)$_j$—O—C$_{1-6}$alkyl, —(CR$^x$R$^y$)$_p$—NR$^x$COR$^y$, —(CR$^x$R$^y$)$_p$—O—CH$_2$—CONR$^x$R$^y$, —(CH$_2$)$_j$—O-(hydroxyC$_{1-6}$alkyl), heterocyclic group with 3 to 7 ring members (e.g. oxanyl), or —CH$_2$-heterocyclic group with 3 to 7 ring members wherein the heterocyclic group comprises one or more (e.g. 1, 2, or 3) heteroatoms selected from N, O, S and oxidised forms and may be optionally substituted by one or more R$^z$ groups selected from C$_{1-6}$alkyl (e.g. methyl), C$_{1-6}$alkoxy (e.g. methoxy) and —C(=O)C$_{1-6}$alkyl (e.g. —C(=O)CH$_3$).

In one embodiment, R$^6$ is selected from hydrogen or C$_{1-6}$alkyl (e.g. —CH$_3$ or —CH$_2$CH$_3$).

In one embodiment, R$^7$ is C$_{1-6}$alkyl (e.g. —CH$_3$ or —CH$_2$CH$_3$), hydroxyC$_{1-6}$alkyl (e.g. —CH$_2$OH o), —C$_{1-6}$alkyl-NR$^x$R$^y$ (e.g. —CH$_2$N(CH$_3$)$_2$), —(CR$^x$R$^y$)$_p$—CONR$^x$R$^y$ (e.g. —C(=O)N(CH$_3$)$_2$ or

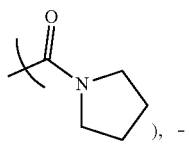

$(CH_2)_j$—O—$C_{1-6}$alkyl (e.g. —$CH_2OCH_3$), heterocyclic group with 3 to 7 ring members e.g.
(point of attachment represented by dashed bond):

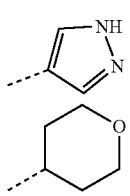 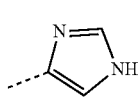 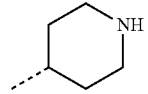

or —$CH_2$-heterocyclic group with 3 to 7 ring members e.g.
(point of attachment represented by dashed bond)

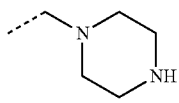

wherein when the moiety $R^7$ comprises a heterocyclic group, the heterocyclic group may be optionally substituted by one or more $R^z$ groups selected from $C_{1-6}$alkyl (e.g. methyl).

In one embodiment of formula (I) $R^7$ is a heterocyclic group with 3 to 7 ring members optionally substituted by one or more $R^z$ groups e.g.
(point of attachment represented by dashed bond)

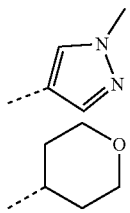 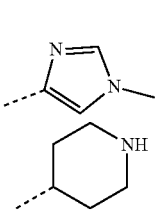 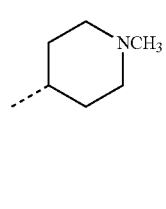

In one embodiment of formula (I) $R^7$ is a heterocyclic group with 3 to 7 ring members optionally substituted by one or more $R^z$ groups e.g.
(point of attachment represented by dashed bond)

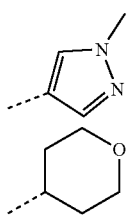 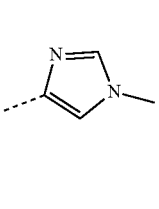 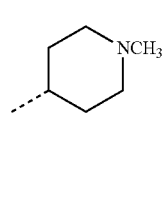

In one embodiment, $R^7$ is a —$CH_2$-heterocyclic group with 3 to 7 ring members optionally substituted by by one or more $R^z$ groups e.g.
(point of attachment represented by dashed bond)

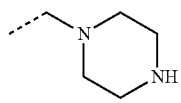 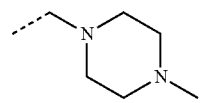

In one embodiment, $R^7$ is selected from:
(point of attachment represented by dashed bond):

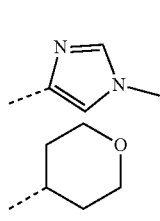 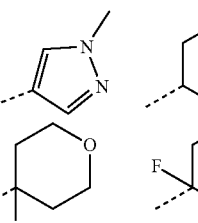 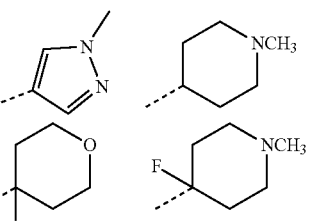

In one embodiment, $R^7$ is selected from:
(point of attachment represented by dashed bond):

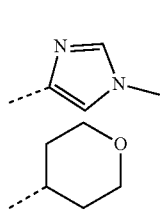 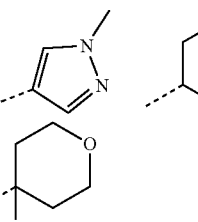 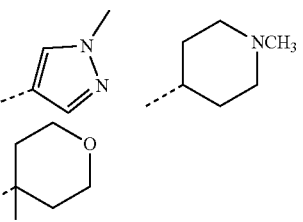

In one embodiment, $R^6$ is hydrogen or $C_{1-6}$alkyl. In one embodiment, $R^6$ is $C_{1-6}$alkyl. In one embodiment, $R^6$ is methyl or ethyl. In one embodiment, $R^6$ is ethyl.

In one embodiment, $R^6$ is $C_{1-6}$alkyl (such as methyl or ethyl e.g. methyl) and $R^7$ is selected from hydroxy$C_{1-6}$alkyl and —$(CH_2)$—O—$C_{1-6}$alkyl, In one embodiment, $R^6$ is methyl and $R^7$ is selected from methyl, —$CH_2$—OH and —$CH_2$—$OCH_3$. In one embodiment $R^6$ is methyl and $R^7$ is methyl, ethyl, or propyl.

In one embodiment $R^6$ is methyl and $R^7$ is methyl.

In one embodiment, $R^6$ is $C_{1-6}$alkyl or halo$C_{1-6}$alkyl (e.g. methyl, -monofluoromethyl, trifluoromethyl or ethyl).

In one embodiment, $R^6$ is $C_{3-8}$cycloalkyl such as $C_{3-6}$cycloalkyl (e.g. cyclopropyl).

In one embodiment $R^6$ is $C_{1-6}$alkyl (such as methyl or ethyl e.g. ethyl) and $R^7$ is selected from: (point of attachment represented by dashed bond or bond terminus marked "*"):

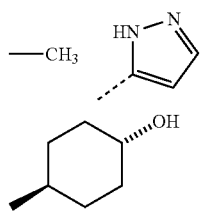 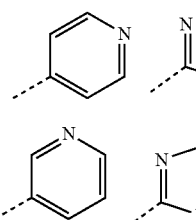 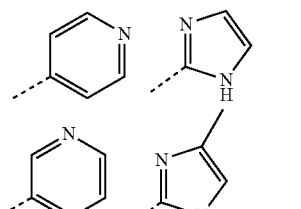

-continued

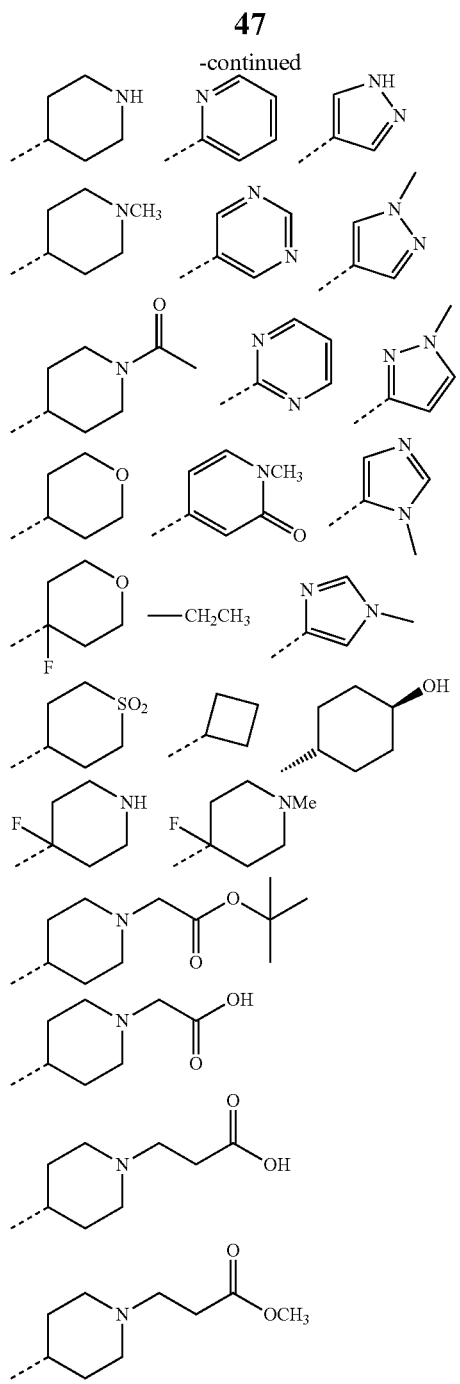

In one embodiment $R^6$ is $C_{1-6}$alkyl (such as methyl or ethyl e.g. ethyl) and $R^7$ is selected from: (point of attachment represented by dashed bond or bond terminus marked "*"):

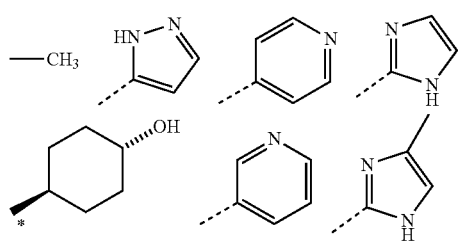

-continued

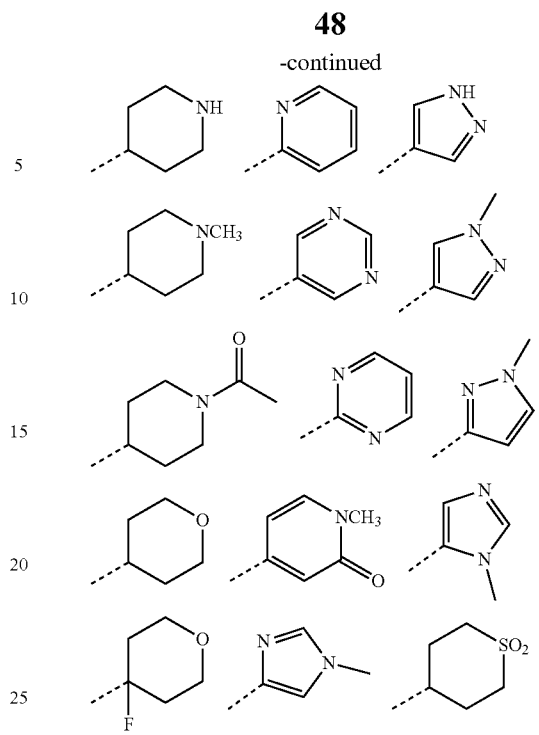

In particular, $R^7$ is:
(point of attachment represented by dashed bond):

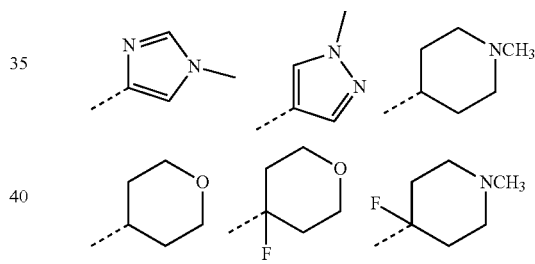

In one embodiment, $R^6$ is $C_{1-6}$alkyl (such as methyl or ethyl e.g. methyl) and $R^7$ is oxanyl, and the compound of formula (I) is a compound of formula (Iw):

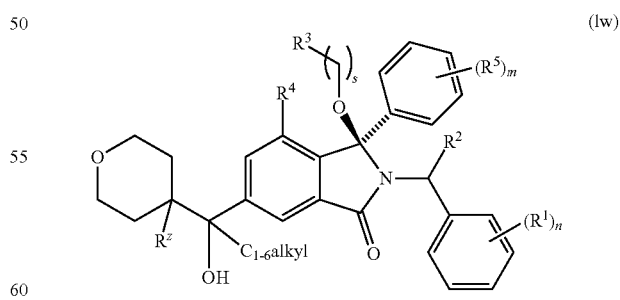

In one embodiment of formula (Iw) $R_z$ is hydrogen or fluorine.

In one embodiment, $R^7$ is imidazolyl and the compound of formula (I) is a compound of formula (Ix) or a tautomer or a solvate or a pharmaceutically acceptable salt thereof:

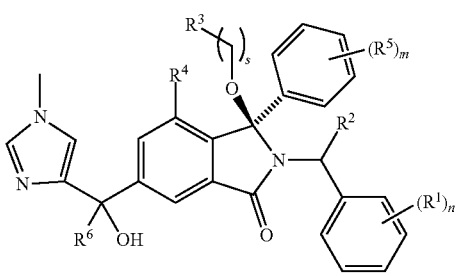

(Ix)

In one embodiment, R⁷ is N-methyl piperidinyl and the compound of formula (I) is a compound of formula (Ix') or a tautomer or a solvate or a pharmaceutically acceptable salt thereof:

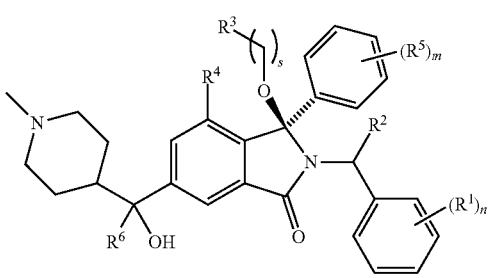

(Ix')

In one embodiment, R⁷ is 4-fluoro-1-methylpiperidin-4-yl and the compound of formula (I) is a compound of formula (Ix") or a tautomer or a solvate or a pharmaceutically acceptable salt thereof:

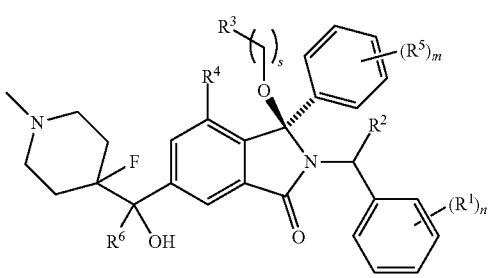

(Ix")

In one embodiment, R⁷ is pyrazolyl optionally substituted by one or more R$^z$ groups (e.g. methyl). In one embodiment, R⁷ is N-methylpyrazol-3-yl or N-methylpyrazol-4-yl.

In one embodiment, R⁷ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxyl).

In one embodiment, R⁷ is selected from piperidinyl optionally substituted by one or more R$^z$ groups (e.g. methyl, fluorine, or hydroxyl, in particular methyl and fluorine).

In one embodiment, the compound of formula (I) is a compound of formula (Ix) and R⁶ is C$_{1-4}$alkyl.

In one embodiment, R⁶ is C$_{1-6}$alkyl (e.g. —CH$_3$, —CH$_2$CH$_3$ or —CH$_2$CH$_2$CH$_3$ such as methyl or ethyl e.g. ethyl) and R⁷ is a heterocyclic group with 3 to 7 ring members optionally substituted by one or more R$^z$ groups.

In one embodiment, R⁶ is C$_{1-6}$alkyl (e.g. —CH$_3$, —CH$_2$CH$_3$ or —CH$_2$CH$_2$CH$_3$ such as methyl or ethyl e.g. ethyl) and R⁷ is imidazolyl optionally substituted by one or more R$^z$ groups (e.g. methyl imidazolyl).

In one embodiment, R⁶ is C$_{1-6}$alkyl (e.g. —CH$_3$, —CH$_2$CH$_3$ or —CH$_2$CH$_2$CH$_3$ such as methyl or ethyl e.g. ethyl) and R⁷ is piperidinyl optionally substituted by one or more R$^z$ groups (e.g. methyl piperidinyl).

In one embodiment R⁶ is C$_{1-6}$alkyl (e.g. —CH$_3$, —CH$_2$CH$_3$ or —CH$_2$CH$_2$CH$_3$ such as methyl or ethyl e.g. ethyl) and R⁷ is C$_{1-4}$alkyl, hydroxylC$_{1-4}$alkyl, methoxyC$_{1-4}$alkyl, a heterocyclic group with 5 or 6 ring members or C$_{3-6}$cycloalkyl, wherein the heterocyclic group or C$_{3-6}$cycloalkyl group is optionally substituted by one or more R$^z$ (e.g. methyl, halogen (such as fluorine), C(=O)Me, or —OH).

In one embodiment R⁶ is C$_{1-6}$alkyl (e.g. —CH$_3$, —CH$_2$CH$_3$ or —CH$_2$CH$_2$CH$_3$ such as methyl or ethyl e.g. ethyl) and R⁷ is methyl, ethyl, hydroxylmethyl, hydroxyethyl, methoxymethyl, piperidinyl, oxanyl, imidazolyl, pyrazolyl, cyclobutyl, cyclohexyl, optionally substituted by one or more R$^z$ (e.g. methyl, halogen (such as fluorine), C(=O)Me, or —OH).

In one embodiment, R⁶ and R⁷ are both the same. In one embodiment, R⁶ and R⁷ are both methyl, and the compound of formula (I) is a compound of formula (Iy) or a tautomer or a solvate or a pharmaceutically acceptable salt thereof:

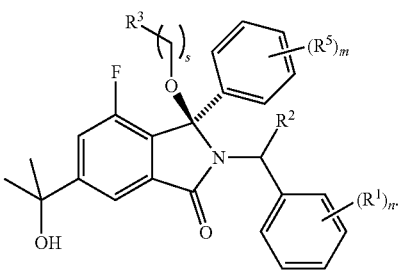

(Iy)

In one embodiment the group —CR⁶R⁷OH is other than —C(CH$_3$)$_2$OH.

In one embodiment, R⁷ is selected from the group consisting of:

(point of attachment represented by dashed bond)

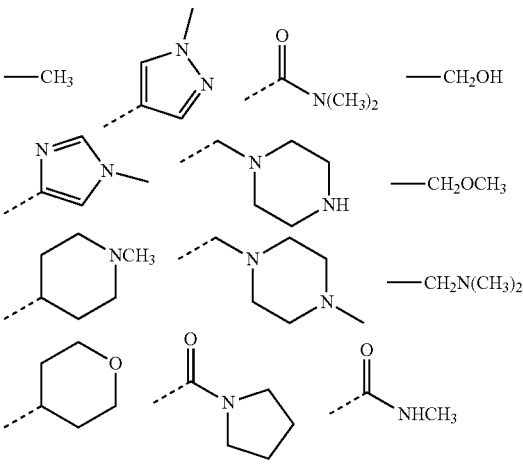

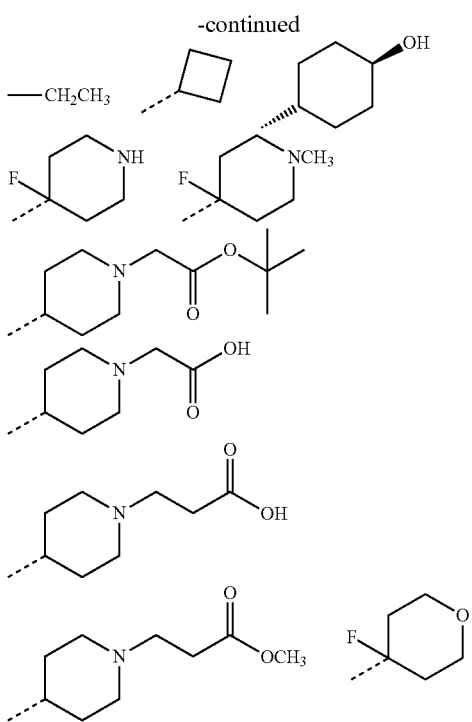

In one embodiment, R⁷ is selected from the group consisting of:
(point of attachment represented by dashed bond)

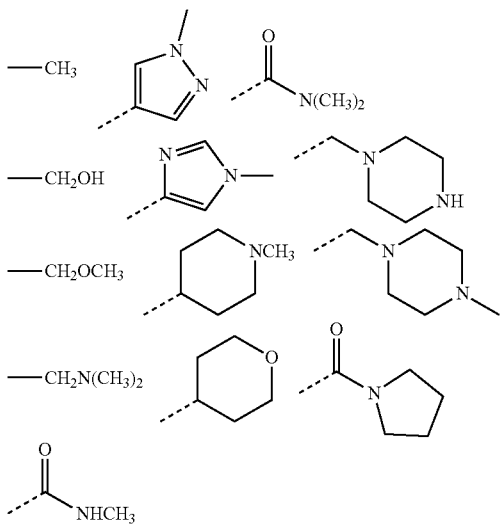

In one embodiment $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_k$—$CO_2C_{1-6}$alkyl, —$(CH_2)_r$—$CO_2H$, —NH($C_{1-4}$alkyl), —N($C_{1-4}$alkyl)$_2$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

In another embodiment $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$—$CO_2C_{1-6}$alkyl, —$(CH_2)_r$—$CO_2H$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

In another embodiment when $R^7$ contains a saturated heterocyclic group then $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$—$CO_2C_{1-6}$alkyl, —$(CH_2)_r$—$CO_2H$, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

Subformulae

In one embodiment, the compound of formulae (I) is a compound of formulae (II) or a tautomer or a solvate or a pharmaceutically acceptable salt thereof:

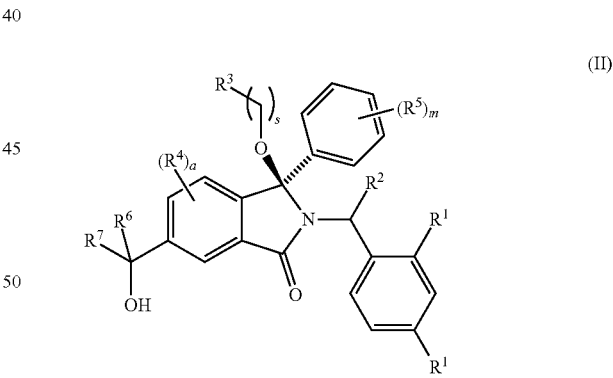

(II)

wherein $R^1$, $R^2$, $R^3$, $R^4$, $R^5$, $R^6$, $R^7$, a, m and s are as defined herein.

In one embodiment, $R^1$ is chloro, nitrile, methyl or methoxy. In one embodiment, $R^1$ is hydroxy or hydroxy$C_{1-4}$alkyl (e.g. hydroxyl).

In one embodiment, $R^1$ is $O_{0,1}(CR^xR^y)_v$COOH (e.g. —COOH, —$CH_2$COOH, —O$CH_2$COOH or —C(CH$_3$)$_2$COOH.

In another embodiment, $R^1$ is chloro or nitrile and the compound of formula (II) is a compound of formula (IIa) or (IIb) or a tautomer or a solvate or a pharmaceutically acceptable salt thereof:

(IIa)

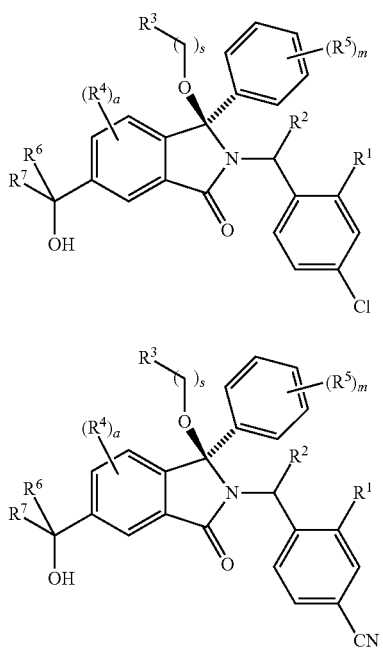

(IIb)

wherein $R^2$, $R^3$, $R^4$, $R^5$, $R^7$, m and s are as defined herein. In one embodiment, $R^1$ is —$SO_2R^x$. In particular, $R^x$ is —$SO_2$—$C_{1-4}$alkyl, for example —$SO_2$—$CH_3$ or —$SO_2$-heterocyclic group with 5 to 6 ring members (e.g. —$SO_2$-morpholinyl, typically —$SO_2$-(1-morpholinyl). In another embodiment In one embodiment, $R^1$ is hydroxy or hydroxy$C_{1-4}$alkyl (e.g. —$CH_2OH$ or —OH).

In one embodiment, $R^6$ is methyl or ethyl, and the compound of formula (I) is a compound of formula (IIIa) or (IIIb) or a tautomer or a solvate or a pharmaceutically acceptable salt thereof:

(IIIa)

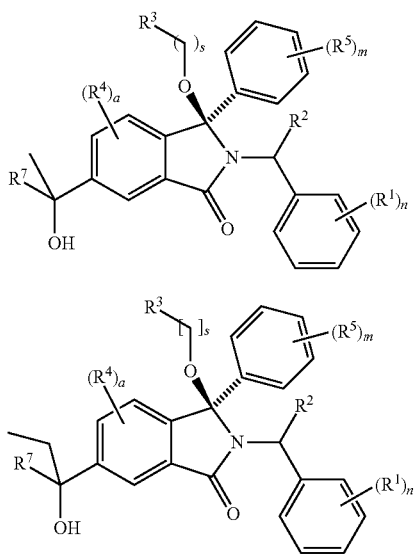

(IIIb)

wherein $R^1$, $R^2$, $R^3$, $R^4$, $R^5$, $R^7$, a, m and s are as defined herein.

In one embodiment, a is 1 and the compound of formula (I) is a compound of formula (IVa) or a tautomer or a solvate or a pharmaceutically acceptable salt thereof:

(IVa)

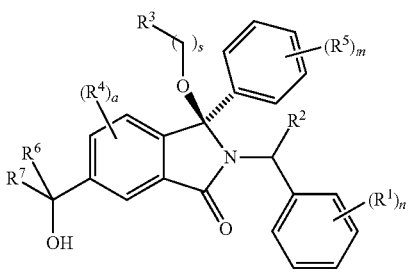

wherein $R^1$, $R^2$, $R^3$, $R^4$, $R^5$, $R^7$, a, m and s are as defined herein.

In one embodiment, s is 0 and the compound of formula (I) is a compound of formula (IVb) or a tautomer or a solvate or a pharmaceutically acceptable salt thereof:

(IVb)

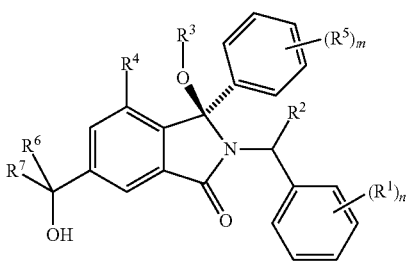

wherein $R^1$, $R^2$, $R^3$, $R^4$, $R^5$, $R^7$, a, m and s are as defined herein.

In one embodiment, $R^4$ is F and the compound of formula (IVa) is a compound of formula (V) or a tautomer or a solvate or a pharmaceutically acceptable salt thereof:

(V)

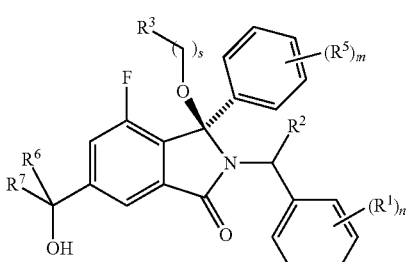

wherein $R^1$, $R^2$, $R^3$, $R^5$, $R^7$, m and s are as defined herein.

In one embodiment, m is 1 and the substituent $R^4$ is at the 4-position of the phenyl group, and the compound of formula (I) is a compound of formula (VI) or a tautomer or a solvate or a pharmaceutically acceptable salt thereof:

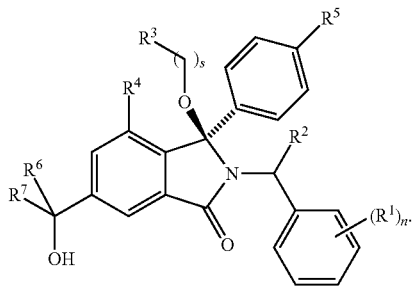

(VI)

In one embodiment, $R^5$ is chloro and the compound of formula (VI) is a compound of formula (VIa) or a tautomer or a solvate or a pharmaceutically acceptable salt thereof:

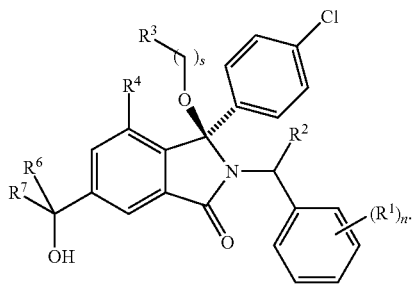

(VIa)

In one embodiment, A is a $C_{3-6}$cycloalkyl group (g is 1, 2 or 3) and t is 1, and the compound of formula (VI) is a compound of formula (VII) or a tautomer or a solvate or a pharmaceutically acceptable salt thereof:

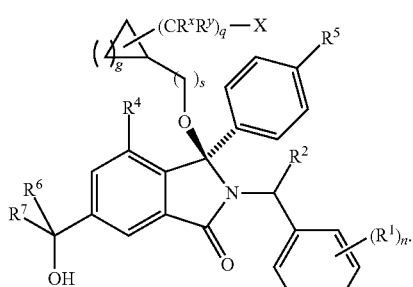

(VII)

In one embodiment, A is a $C_{3-6}$cycloalkyl group (g is 1, 2 or 3) and t is 1, and the cycloalkyl group is geminally disubstituted (i.e. the group —$(CR^xR^y)$—X and the $CH_2$ group (where s is 1) or the oxygen atom (where s is 0) are both attached to the same atom of the cycloalkyl group, and the compound of formula (VII) is a compound of formula (VIIa) or a tautomer or a solvate or a pharmaceutically acceptable salt thereof:

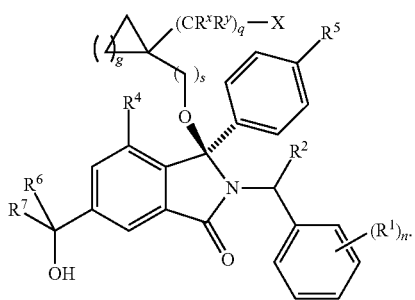

(VIIa)

In one embodiment, g is 1, and so the cycloalkyl group is a cyclopropyl group and the compound of formula (VIIa) is a compound of formula (VIIb) or a tautomer or a solvate or a pharmaceutically acceptable salt thereof:

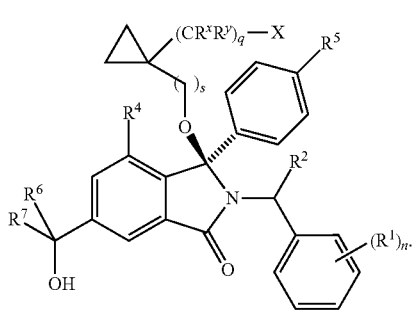

(VIIb)

In one embodiment, s is 1, and the compound of formula (VIIb) is a compound of formula (VIIc) or a tautomer or a solvate or a pharmaceutically acceptable salt thereof:

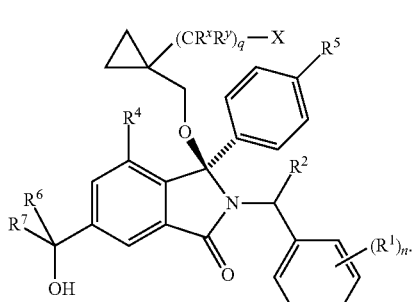

(VIIc)

In one embodiment, $R^x$ and $R^y$ are hydrogen (including $^1H$ and $^2H$) and q is 1 and the compound of formula (VIIc) is a compound of (VIId) or a tautomer or a solvate or a pharmaceutically acceptable salt thereof:

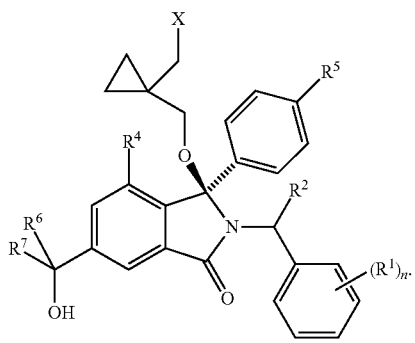

(VIId)

In one embodiment, the compound of formula (VIId) is a compound of (VIId') or a tautomer or a solvate or a pharmaceutically acceptable salt thereof:

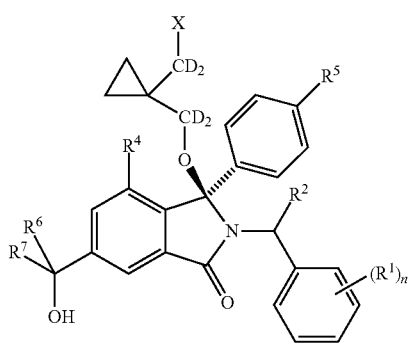

(VIId')

In one embodiment, the compound of formula (VIId) is a compound of (VIId') and X is hydroxy.

In one embodiment, X is hydroxy, and the compound of formula (VIId) is a compound of the formula (VIIe) or a tautomer or a solvate or a pharmaceutically acceptable salt thereof:

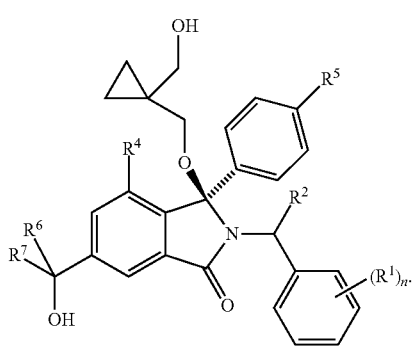

(VIIe)

In one embodiment, X is —C(=O)NH$_2$ and the compound of formula (VIIe) is a compound of the formula (VIIe') or a tautomer or a solvate or a pharmaceutically acceptable salt thereof:

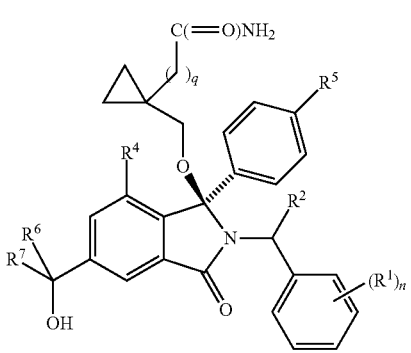

(VIIe')

wherein q is 0 or 1, and in particular q is 0.

In one embodiment, X is —CN and the compound of formula (VIId) is a compound of the formula (VIIe'') or a tautomer or a solvate or a pharmaceutically acceptable salt thereof:

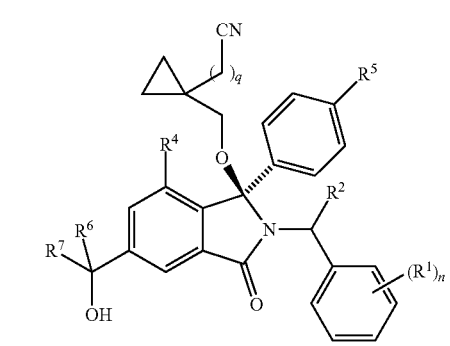

(VIIe'')

wherein q is 0 or 1, and in particular q is 0.

In one embodiment, R$^3$ is methyl, and the compound of formula (VI) is a compound of formula (VIIf) or a tautomer or a solvate or a pharmaceutically acceptable salt thereof:

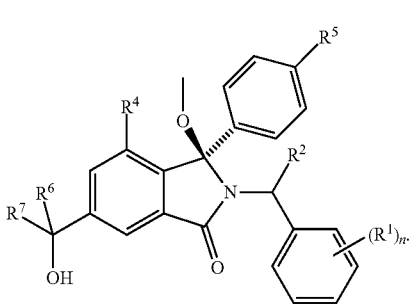

(VIIf)

In one embodiment of Formula (VIIa-e') R$^6$ is methyl. In one embodiment of Formula (VIIa-e') R$^6$ is ethyl.

In one embodiment of Formula (VIIe'') or (VIIf) R$^6$ is methyl. In one embodiment of Formula (VIIe'') or (VIIf) R$^6$ is ethyl.

In one embodiment of Formula (VIIe'') or (VIIf) R$^6$ is methyl. In one embodiment of Formula (VIIe'') or (VIIf) R$^6$ is ethyl.

In one embodiment of the compound of formula (VIIa-e'), R$^7$ is selected from methyl, oxanyl, pyrazolyl, imidazolyl, piperidinyl, and cyclohexyl wherein said cycloalkyl and heterocyclic groups are optionally substituted by one or more R<sup>z</sup> groups (e.g. methyl, fluorine, or hydroxy).

In one embodiment of the compound of formula (VIIa-e'), R$^7$ is selected from oxanyl and methyl.

In one embodiment of the compound of formula (VIIe") or (VIIf), R$^7$ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (VIIe") or (VIIf), R$^7$ is selected from oxanyl and methyl.

In one embodiment of the compound of formula (VIIa-f), R$^7$ is selected from piperidinyl optionally substituted by one or more R$^z$ groups (e.g. methyl, fluorine, or hydroxy).

In another embodiment, the compound of formula (I) is a compound of formula (a) or a tautomer or a solvate or a pharmaceutically acceptable salt thereof:

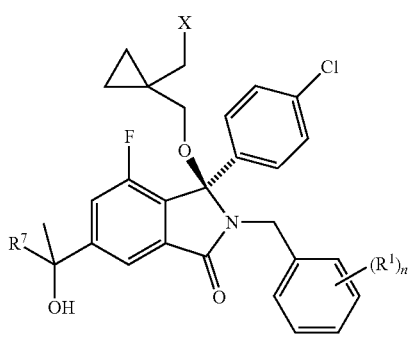

(a)

wherein R$^1$ is chloro or nitrile, when s is 1 then X is hydroxyl or when s is 0 then X is —C(=O)NH$_2$.

In another embodiment, the compound of formula (I) is a compound of formula (a') or a tautomer or a solvate or a pharmaceutically acceptable salt thereof:

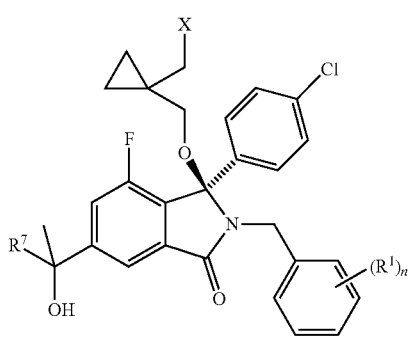

(a')

wherein R$^1$ is chloro or nitrile, when s is 1 then X is hydroxyl or when s is 0 then X is —CN.

In another embodiment, the compound of formula (I) is a compound of formula (a") or a tautomer or a solvate or a pharmaceutically acceptable salt thereof:

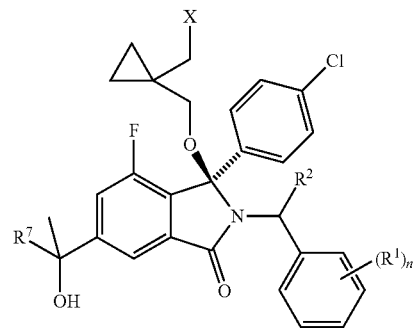

(a")

wherein R$^1$ is chloro or nitrile, when s is 1 then X is hydroxyl or when s is 0 then X is —C(=O)NH$_2$.

In another embodiment, the compound of formula (I) is a compound of formula (a') or a tautomer or a solvate or a pharmaceutically acceptable salt thereof:

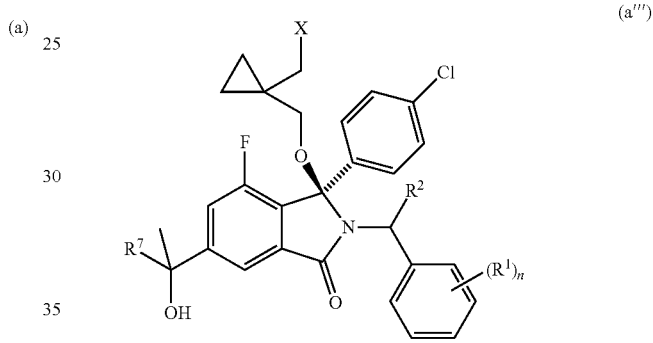

(a''')

wherein R$^1$ is chloro or nitrile, when s is 1 then X is hydroxyl or when s is 0 then X is —CN.

In one embodiment of the compound of formula (a), R$^7$ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (a), R$^7$ is oxanyl or methyl.

In one embodiment of the compound of formula (a), R$^7$ is piperidinyl, optionally substituted with C$_{1-6}$ alkyl (e.g. methyl) and/or halo (e.g. flouro).

In one embodiment of the compound of formula (a'), (a") or (a''') R$^7$ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (a'), (a") or (a''') R$^7$ is oxanyl or methyl.

In one embodiment of the compound of formula (a'), (a") or (a''') R$^7$ is piperidinyl, optionally substituted with C$_{1-6}$ alkyl (e.g. methyl) and/or halo (e.g. flouro).

In one embodiment, A is a heterocyclyl group with 3 to 6 ring members, wherein the heterocyclic group comprises one or more (e.g. 1, 2, or 3) heteroatoms selected from N, O, S and oxidised forms thereof (t is 1; g is 1, 2, 3 or 4; Z represents N, O, S and oxidised forms thereof; i is 1, 2, or 3; and i+g=2, 3, 4 or 5), and the compound of formula (VI)

is a compound of formula (b) or a tautomer or a solvate or a pharmaceutically acceptable salt thereof:

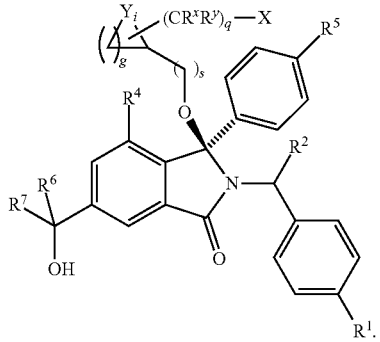

(b)

In one embodiment, Y is O and i is 1 and the compound of formula (b) is a compound of formula (ba) or a tautomer or a solvate or a pharmaceutically acceptable salt thereof:

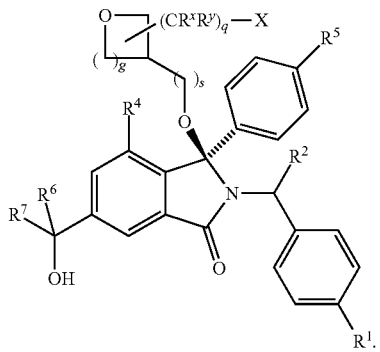

(ba)

In one embodiment, s is 0, g is 2, q is 0 and X is hydrogen, and the compound of formula (b) is a compound of formula (bb) or a tautomer or a solvate or a pharmaceutically acceptable salt thereof:

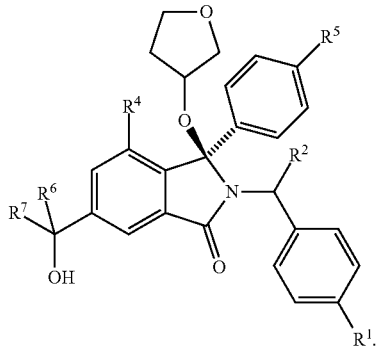

(bb)

In one embodiment, s is 0, g is 1, Y is O and i is 1 and the compound of formula (b) is a compound of formula (bc) or a tautomer or a solvate or a pharmaceutically acceptable salt thereof:

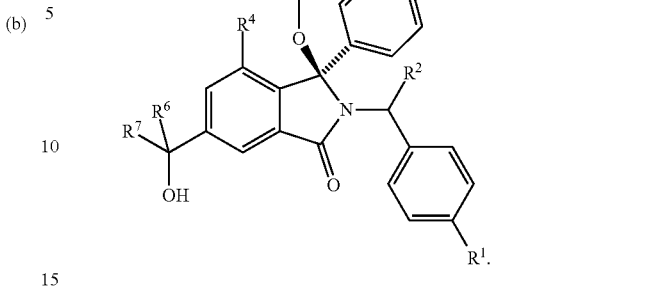

(bc)

In one embodiment, the compound of formula (bc) is where q is 0 and X is fluorine.

In another embodiment, the compound of formula (I) is a compound of formula (c) or a tautomer or a solvate or a pharmaceutically acceptable salt thereof:

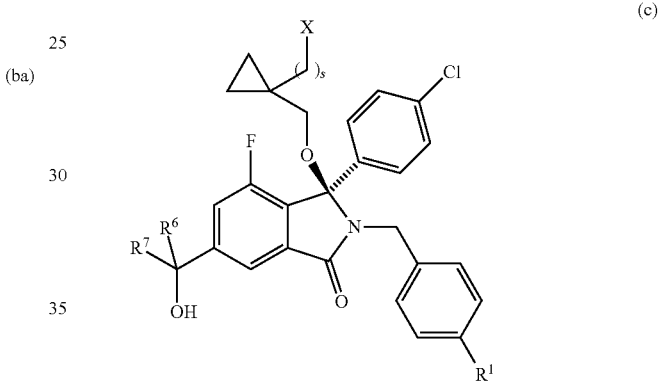

(c)

wherein $R^1$ is chloro or nitrile, s is 1 and X is hydroxyl or s is 0 and X is —C(=O)NH$_2$.

In another embodiment, the compound of formula (I) is a compound of formula (c') or a tautomer or a solvate or a pharmaceutically acceptable salt thereof:

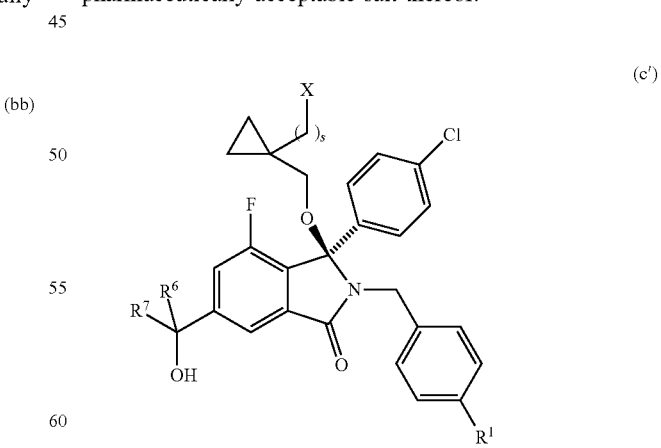

(c')

wherein $R^1$ is chloro or nitrile, s is 1 and X is hydroxyl or s is 0 and X is —CN.

In another embodiment, the compound of formula (I) is a compound of formula (c") or a tautomer or a solvate or a pharmaceutically acceptable salt thereof:

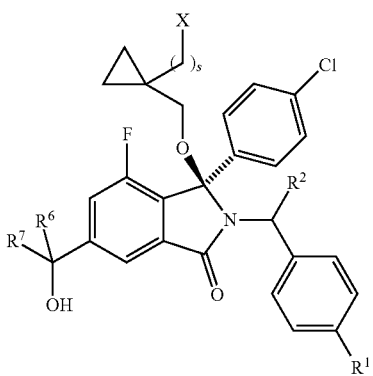

wherein $R^1$ is chloro or nitrile, s is 1 and X is hydroxyl or s is 0 and X is —C(=O)NH$_2$.

In another embodiment, the compound of formula (I) is a compound of formula (c''') or a tautomer or a solvate or a pharmaceutically acceptable salt thereof:

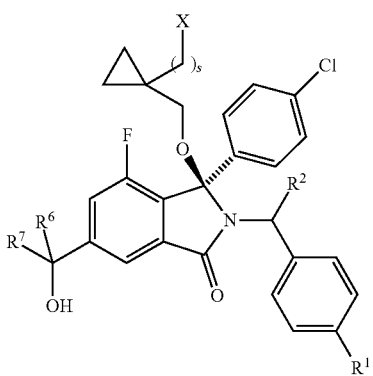

wherein $R^1$ is chloro or nitrile, s is 1 and X is hydroxyl or s is 0 and X is —CN.

In one embodiment of the compound of formula (c), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (c), $R^7$ is oxanyl or methyl.

In one embodiment of the compound of formula (c), $R^7$ is piperidinyl, optionally substituted with $C_{1-6}$ alkyl (e.g. methyl) and/or halo (e.g. flouro).

In one embodiment of the compound of formula (c'), (c'') or (c''') $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (c'), (c'') or (c''') $R^7$ is oxanyl or methyl.

In one embodiment of the compound of formula (c'), (c'') or (c''') $R^7$ is piperidinyl, optionally substituted with $C_{1-6}$ alkyl (e.g. methyl) and/or halo (e.g. flouro).

In another embodiment of the subsformulae described hereinabove, $R^2$ is selected from hydrogen and —$(R^xR^y)_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H).

In another embodiment of the subsformulae described hereinabove, $R^2$ is selected from —(CH(CH$_3$))—CO$_2$H and —(C(CH$_3$)$_2$—CO$_2$H).

In another embodiment, $R^2$ is selected from —(CH (CH$_3$))—CO$_2$H and —(C(CH$_3$)$_2$—CO$_2$H)

(e.g. 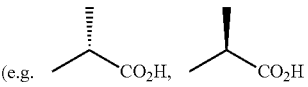

or —(C(CH$_3$)$_2$—CO$_2$H.

In one embodiment, the invention provides a compound of formula (I) or a tautomer or a solvate or a pharmaceutically acceptable salt thereof wherein:

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, and $C_{2-4}$alkynyl;

$R^2$ is selected from hydrogen, $C_{1-4}$ alkyl, $C_{2-6}$alkenyl, hydroxy$C_{1-4}$alkyl and —CH$_2$CO$_2$H;

$R^3$ is hydrogen or -(A)$_t$-(CR$^x$R$^y$)$_q$—X;

s and t are independently selected from 0 and 1;

q is selected from 0, 1 and 2;

wherein when $R^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —C(=O)—C$_{1-4}$alkyl, —NR$^x$R$^y$, —NHSO$_2$R$^x$, —NR$^x$COR$^y$; and —C(=O)NR$^x$R$^y$;

$R^4$ and $R^5$ are independently selected from halogen, nitrile, $C_{1-4}$ alkyl, halo$C_{1-4}$alkyl, $C_{1-4}$alkoxy and halo$C_{1-4}$alkoxy;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COOC$_{1-6}$alkyl, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, $C_{3-8}$cycloalkyl, —CH$_2$—C$_{3-8}$cycloalkyl, —CH$_2$—O—C$_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

$R^9$ is selected from hydrogen, $C_{1-6}$alkyl, halo$C_{1-6}$alkyl, hydroxy$C_{1-6}$alkyl, —(CH$_2$)$_k$—O—C$_{1-6}$alkyl, —(CH$_2$)$_k$—O-(hydroxy$C_{1-6}$alkyl), hydroxy$C_{1-6}$alkoxy, —(CH$_2$)$_k$—CO$_2$C$_{1-6}$alkyl, —(CH$_2$)$_k$—CO$_2$H, —C$_{1-6}$alkyl-N(H)$_e$(C$_{1-4}$alkyl)$_{2-e}$, —(CH$_2$)$_j$—C$_{3-8}$cycloalkyl and —(CH$_2$)$_j$—C$_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —(CH$_2$)$_k$—O—C$_{1-6}$alkyl, hydroxy$C_{1-6}$alkoxy, —COOC$_{1-6}$alkyl, —N(H)$_e$(C$_{1-4}$alkyl)$_{2-e}$, —C$_{1-6}$alkyl-N(H)$_e$(C$_{1-4}$alkyl)$_{2-e}$, —(CH$_2$)$_k$—C(=O)N(H)$_e$(C$_{1-4}$alkyl)$_{2-e}$ $C_{3-8}$cycloalkyl and $C_{3-8}$cycloalkenyl;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$ alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$—CO$_2$C$_{1-6}$ alkyl, —$(CH_2)_r$—CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl;

n, e, r and j are independently selected from 0, 1 and 2;
k and m are independently selected from 1 and 2; and
v and a are independently selected from 0 and 1.

In one embodiment, the invention provides a compound of formula (I) or a tautomer or a solvate or a pharmaceutically acceptable salt thereof, wherein:

$R^1$ is independently selected from hydroxy, halogen, nitro, nitrile and $C_{1-4}$alkyl;

$R^2$ is selected from hydrogen, $C_{1-4}$ alkyl, $C_{2-6}$alkenyl, hydroxy$C_{1-4}$alkyl and —CH$_2$CO$_2$H;

$R^3$ is hydrogen or -(A)$_t$-(CR$^x$R$^y$)$_q$—X;
s and t are independently selected from 0 and 1;
q is selected from 0, 1 and 2;
wherein when $R^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —C(=O)—C$_{1-4}$alkyl, —NR$^x$R$^y$, —NHSO$_2$R$^x$, —NR$^x$COR$^y$; and —C(=O)NR$^x$R$^y$;

$R^4$ and $R^5$ are independently selected from halogen, nitrile and $C_{1-4}$ alkyl;

$R^6$ is selected from hydrogen, $C_{1-6}$alkyl, halo$C_{1-6}$alkyl, $C_{2-6}$alkenyl, and $C_{2-6}$alkynyl;

$R^7$ is selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COOC$_{1-6}$alkyl, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, $C_{3-8}$cycloalkyl, —CH$_2$—C$_{3-8}$cycloalkyl, —CH$_2$—O—C$_{3-8}$cycloalkyl, and $C_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

$R^9$ is selected from hydrogen, $C_{1-6}$alkyl, halo$C_{1-6}$alkyl, hydroxy$C_{1-6}$alkyl, —(CH$_2$)$_k$—O—$C_{1-6}$alkyl, —(CH$_2$)$_k$—O-(hydroxy$C_{1-6}$alkyl), hydroxy$C_{1-6}$alkoxy, —(CH$_2$)$_k$—CO$_2$C$_{1-6}$alkyl, —(CH$_2$)$_k$—CO$_2$H, —$C_{1-6}$ alkyl-N(H)$_e$(C$_{1-4}$alkyl)$_{2-e}$, —(CH$_2$)$_j$—C$_{3-8}$cycloalkyl and —(CH$_2$)$_j$—C$_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —(CH$_2$)$_k$—O—$C_{1-6}$alkyl, hydroxy$C_{1-6}$alkoxy, —COOC$_{1-6}$alkyl, —N(H)$_e$(C$_{1-4}$alkyl)$_{2-e}$, —C$_{1-6}$alkyl-N(H)$_e$(C$_{1-4}$alkyl)$_{2-e}$, —(CH$_2$)$_k$—C(=O)N(H)$_e$(C$_{1-4}$alkyl)$_{2-e}$, $C_{3-8}$cycloalkyl and $C_{3-8}$cycloalkenyl;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —(CH$_2$)$_k$—O—$C_{1-6}$ alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —(CH$_2$)$_r$—CO$_2$C$_{1-6}$ alkyl, —(CH$_2$)$_r$—CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl;

n, e, r and j are independently selected from 0, 1 and 2;
k and m are independently selected from 1 and 2; and
v and a are independently selected from 0 and 1.

In one embodiment, the invention provides a compound of formula (I) or a tautomer or a solvate or a pharmaceutically acceptable salt thereof, wherein:

$R^1$ is independently selected from hydroxy, halogen, nitro, nitrile and $C_{1-4}$alkyl;

$R^2$ is selected from hydrogen, $C_{1-4}$ alkyl, $C_{2-6}$alkenyl, hydroxy$C_{1-4}$alkyl and —CH$_2$CO$_2$H;

$R^3$ is hydrogen or -(A)$_t$-(CR$^x$R$^y$)$_q$—X;
s and t are independently selected from 0 and 1;
q is selected from 0, 1 and 2;
wherein when $R^3$ is -(A)$_t$-(CR$^x$R$^y$)$_q$—X then (i) at least one of s, t and q is other than 0 and (ii) when t is 0 then s is 1 and q is other than 0;

A is a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN and —OR$^9$;

$R^4$ and $R^5$ are independently selected from halogen, nitrile and $C_{1-4}$ alkyl;

$R^6$ is selected from hydrogen and $C_{1-6}$alkyl;

$R^7$ is selected from heterocyclic group with 3 to 7 ring members, —CH$_2$-heterocyclic group with 3 to 7 ring members, $C_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

$R^9$ is selected from hydrogen and $C_{1-6}$alkyl;

$R^x$ and $R^y$ are independently selected from hydrogen and $C_{1-6}$alkyl;

$R^z$ is independently selected from halogen, nitro, nitrile, $C_{1-6}$alkyl, halo$C_{1-6}$alkyl, $C_{2-6}$alkenyl, hydroxy, hydroxy$C_{1-6}$alkyl, $C_{1-6}$alkoxy, —C(=O)$C_{1-6}$alkyl, and —N(H)$_e$(C$_{1-4}$alkyl)$_{2-e}$;

n and e are independently selected from 0, 1 and 2
m is selected from 1 and 2; and
a is selected from 0 and 1.

In one embodiment, the invention provides a compound of formula (I) or a tautomer or a solvate or a pharmaceutically acceptable salt thereof, wherein:

$R^1$ is independently selected from halogen, hydroxy and nitrile;

R² is selected from hydrogen, C₁₋₄ alkyl and —CH₂CO₂H;

R³ is -(A)ₜ-(CRˣRʸ)_q—X;

A is a heterocyclic group with 3 to 6 ring members, wherein the heterocyclic group comprises one or more (e.g. 1, 2, or 3) heteroatoms selected from N, O, S and oxidised forms thereof;

s and t are independently selected from 0 and 1;

q is selected from 0, 1 and 2;

wherein (i) at least one of s, t and q is other than 0 and (ii) when t is 0 then s is 1 and q is other than 0;

X is selected from hydrogen, halogen or —OR⁹;

R⁴ and R⁵ are independently selected from halogen;

R⁶ is selected from hydrogen and C₁₋₆alkyl;

R⁷ is selected from heterocyclic group with 3 to 7 ring members, —CH₂-heterocyclic group with 3 to 7 ring members, C₃₋₈cycloalkyl, and —CH₂—C₃₋₈cycloalkyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

R⁹ is selected from hydrogen and C₁₋₆alkyl;

Rˣ and Rʸ are independently selected from hydrogen and C₁₋₆alkyl;

R$^z$ is independently selected from halogen, nitro, nitrile, and C₁₋₆alkyl;

n is 1 and m is 1; and a is selected from 0 and 1.

In one embodiment, the invention provides a compound of formula (I) or a tautomer or a solvate or a pharmaceutically acceptable salt thereof, wherein:

R¹ is independently selected from halogen, hydroxy and nitrile;

R² is selected from hydrogen, C₁₋₄ alkyl and —CH₂CO₂H;

R³ is -(A)ₜ-(CRˣRʸ)_q—X;

A is a heterocyclic group with 3 to 6 ring members, wherein the heterocyclic group comprises one or more (e.g. 1, 2, or 3) heteroatoms selected from N, O, S and oxidised forms thereof;

s and t are independently selected from 0 and 1;

q is selected from 0, 1 and 2;

wherein (i) at least one of s, t and q is other than 0 and (ii) when t is 0 then s is 1 and q is other than 0;

X is selected from hydrogen, halogen and —OR⁹;

R⁴ and R⁵ are independently selected from halogen;

R⁶ is selected from hydrogen and C₁₋₆alkyl;

R⁷ is a heterocyclic group with 3 to 7 ring members optionally substituted by one or more R$^z$ groups;

R⁹ is selected from hydrogen and C₁₋₆alkyl;

Rˣ and Rʸ are independently selected from hydrogen and C₁₋₆alkyl;

R$^z$ is independently selected from halogen and C₁₋₆alkyl; and n is, 1 and m is 1; and a is 1.

In one embodiment, the invention provides a compound of formula (I) or a tautomer or a solvate or a pharmaceutically acceptable salt thereof, wherein:

R¹ is halogen (e.g. Cl), C₁₋₄alkynyl (e.g. —C≡CH), nitrile, hydroxyC₁₋₄alkyl (e.g. CH₂OH), —O₀,₁(CRˣRʸ)ᵥCOOH (e.g. —COOH, —CH₂COOH, —OCH₂COOH or —C(CH₃)₂COOH, —S(O)_d—C₁₋₄alkyl (e.g. SCH₃, SOCH₃, or SO₂CH₃), —SO₂-(1-morpholinyl) or —P(=O)(Rˣ)₂, (e.g. —P(=O)(CH₃)₂);

n is 1 or 2;

R² is hydrogen, C₁₋₄ alkyl (e.g. —CH₃), hydroxyC₁₋₄alkyl (e.g. CH₂OH) or —(CH₂)_uCOOH (e.g. —CH₂COOH, —CH₂CH₂—CO₂H or —(CH(CH₃))—CO₂H);

the moiety —(CH₂)ₛR³ is selected from:

(point of attachment to the oxygen represented by dashed bond or bond terminus indicated by *):

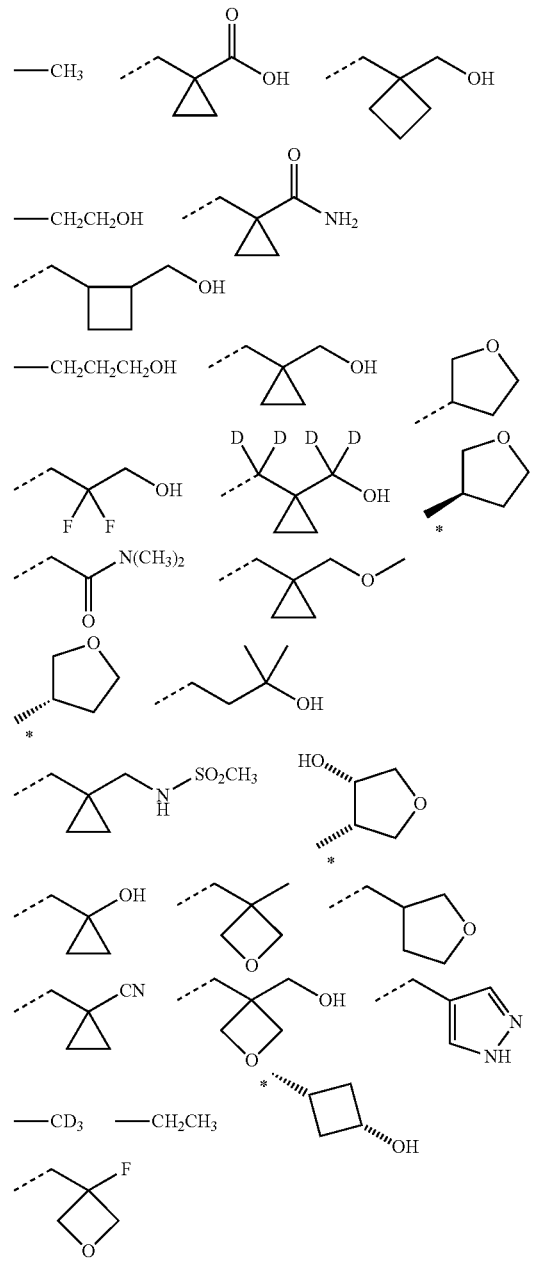

R⁴ is halogen (e.g. F);

a is 0 or 1;

R⁵ is halogen (e.g. Cl);

m is 1;

R⁶ is hydrogen or C₁₋₆alkyl (e.g. —CH₃ or —CH₂CH₃);

R⁷ is C₁₋₆alkyl (e.g. —CH₃ or —CH₂CH₃), hydroxyC₁₋₆alkyl (e.g. —CH₂OH), —C₁₋₆alkyl-NRˣRʸ (e.g. —CH₂N(CH₃)₂), —(CRˣRʸ)_p—CONRˣRʸ (e.g. —C(=O)N(CH₃)₂ or —C(=O)NHCH₃ or

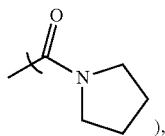

—(CH$_2$)$_j$—O—C$_{1-6}$alkyl (e.g. —CH$_2$OCH$_3$), C$_{3-8}$cycloalkyl (e.g. cyclobutyl or cyclohexyl), heterocyclic group with 3 to 7 ring members e.g.
(point of attachment represented by dashed bond)

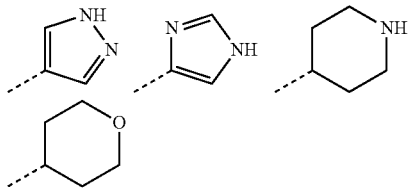

or —CH$_2$-heterocyclic group with 3 to 7 ring members e.g.
(point of attachment represented by dashed bond)

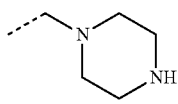

wherein when the moiety R$^7$ comprises a heterocyclic or cycloalkyl group, the heterocyclic group may be optionally substituted by one or more R$^z$ groups selected from C$_{1-6}$alkyl (e.g. methyl), hydroxy, halogen (e.g. fluoro), —C(═O)C$_{1-6}$alkyl (e.g. —C(═O)C(CH$_3$)$_3$), —(CH$_2$)$_r$—CO$_2$H (e.g. —CH$_2$COOH or CH$_2$CH$_2$COOH or —(CH$_2$)$_r$—CO$_2$C$_{1-6}$alkyl (e.g. CH$_2$CH$_2$COOCH$_3$).

In one embodiment, the invention provides a compound of formula (I) or a tautomer or a solvate or a pharmaceutically acceptable salt thereof, wherein:

R$^1$ is halogen (e.g. Cl), C$_{1-4}$alkynyl (e.g. —C≡CH), nitrile, hydroxyC$_{1-4}$alkyl (e.g. CH$_2$OH), —(CH$_2$)$_v$COOH (e.g. —COOH), —S(O)$_d$—C$_{1-4}$alkyl (e.g. SCH$_3$, SOCH$_3$, or SO$_2$CH$_3$), —SO$_2$-(1-morpholinyl) or —P(═O)(R$^x$)$_2$, (e.g. —P(═O)(CH$_3$)$_2$);

n is 1 or 2;

R$^2$ is hydrogen, C$_{1-4}$ alkyl (e.g. —CH$_3$), hydroxyC$_{1-4}$alkyl (e.g. CH$_2$OH) or —(CH$_2$)$_u$COOH (e.g. —CH$_2$COOH);

the moiety —(CH$_2$)$_s$R$^3$ is selected from:
(point of attachment to the oxygen represented by dashed bond or bond terminus indicated by *):

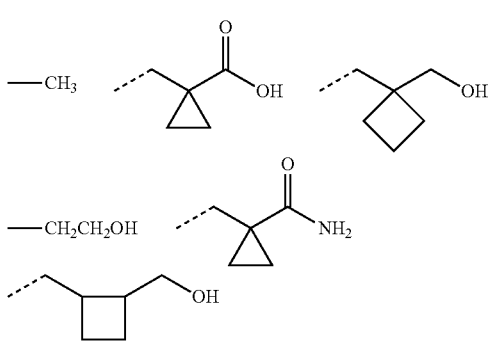

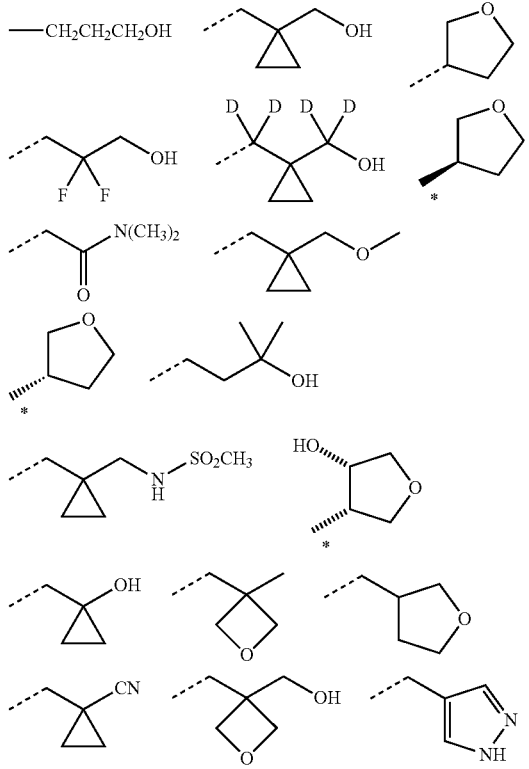

R$^4$ is halogen (e.g. F);

a is 0 or 1;

R$^5$ is halogen (e.g. Cl);

m is 1;

R$^6$ is hydrogen or C$_{1-6}$alkyl (e.g. —CH$_3$ or —CH$_2$CH$_3$);

R$^7$ is C$_{1-6}$alkyl (e.g. —CH$_3$), hydroxyC$_{1-6}$alkyl (e.g. —CH$_2$OH), —(CH$_2$)$_j$—O—C$_{1-6}$alkyl (e.g. —CH$_2$OCH$_3$), —C$_{1-6}$alkyl-NR$^x$R$^y$ (e.g. —CH$_2$N(CH$_3$)$_2$), —(CR$^x$R$^y$)$_p$—CONR$^x$R$^y$ (e.g. —C(═O)N(CH$_3$)$_2$ or —C(═O)NHCH$_3$) or

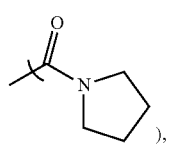

heterocyclic group with 3 to 7 ring members e.g.
(point of attachment represented by dashed bond)

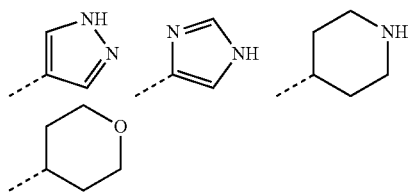

or —CH$_2$-heterocyclic group with 3 to 7 ring members e.g.

(point of attachment represented by dashed bond)

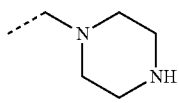

wherein when R⁷ comprises a heterocyclic group, the heterocyclic group may be optionally substituted by one or more R$^z$ groups selected from C$_{1-6}$alkyl (e.g. methyl).

In one embodiment of formula (I) R⁷ is a heterocyclic group with 3 to 7 ring members e.g.

(point of attachment represented by dashed bond)

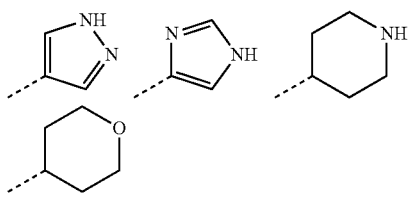

In one embodiment of formula wherein when R⁷ comprises a heterocyclic group, the heterocyclic group may be R⁷ is a heterocyclic group with 3 to 7 ring members optionally substituted by one or more R$^z$ groups e.g.

(point of attachment represented by dashed bond)

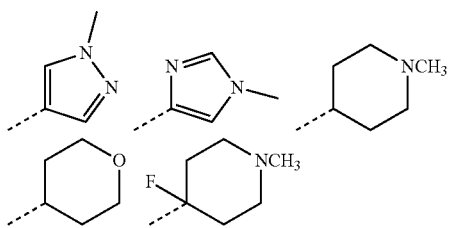

or a —CH$_2$-heterocyclic group with 3 to 7 ring members optionally substituted by one or more R$^z$ groups e.g.

(point of attachment represented by dashed bond)

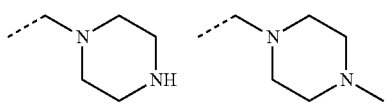

In one embodiment of formula wherein when R⁷ comprises a heterocyclic group, the heterocyclic group may be R⁷ is a heterocyclic group with 3 to 7 ring members optionally substituted by one or more R$^z$ groups e.g.

(point of attachment represented by dashed bond)

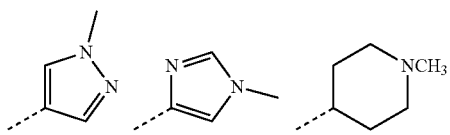

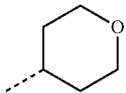

or a —CH$_2$-heterocyclic group with 3 to 7 ring members optionally substituted by one or more R$^z$ groups e.g.

(point of attachment represented by dashed bond)

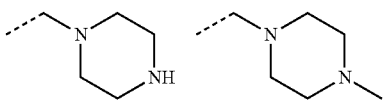

In one embodiment, the invention provides a compound of formula (I) or a tautomer or a solvate or a pharmaceutically acceptable salt thereof, wherein:
R¹ is —Cl, —CN, —OH or —OCH$_3$;
n is 1;
R² is hydrogen;
R³ is hydrogen or -(A)$_s$-(CR$^x$R$^y$)$_q$—X;
s is 0 or 1, and t is 1;
A is selected from cyclopropyl, oxetanyl and tetrahydrofuranyl;
X is selected from hydrogen, fluorine, —CN, —OH and —C(=O)NH$_2$;
q is 0 or 1 and R$^x$ and R$^y$ are hydrogen or deuterium;
a is 0 or 1 and R⁴ is halogen (e.g. fluorine);
R⁵ is halogen (e.g. Cl);
m is 1;
R⁶ is C$_{1-4}$alkyl (e.g. methyl or ethyl);
R⁷ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-6}$cycloalkyl (e.g. cyclobutyl or cyclohexyl) wherein said heterocyclic group with 5 or 6 ring members and C$_{3-6}$cycloalkyl groups may be optionally substituted with one or two R$^z$ groups independently selected from methyl, halogen (such as fluorine), —C(=O)Me, and —OH.

In one embodiment, the invention provides a compound of formula (I) or a tautomer or a solvate or a pharmaceutically acceptable salt thereof, wherein:
R¹ is —Cl, —CN, —OH or —OCH$_3$;
n is 1;
R² is hydrogen or —(CH$_2$)$_u$—CO$_2$H wherein u is independently selected from 0 and 1; R³ is hydrogen and s is 1 or R³ is -(A)$_s$-(CR$^x$R$^y$)$_q$—X and t is 1 and q is 1;
A is selected from cyclopropyl;
X is —OH;
R$^x$ and R$^y$ are hydrogen or deuterium;
a is 0 or 1 and R⁴ is halogen (e.g. fluorine);
R⁵ is halogen (e.g. Cl);
m is 1;
R⁶ is C$_{1-4}$alkyl (e.g. methyl or ethyl);
R⁷ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-6}$cycloalkyl (e.g. cyclobutyl or cyclohexyl); wherein said heterocyclic group with 5 or 6 ring members and C$_{3-6}$cycloalkyl groups may be optionally substituted with one or two R$^z$ groups independently selected from methyl, halogen (such as fluorine), —C(=O)Me, and —OH.

In one embodiment, the invention provides a compound of formula (I) or a tautomer or a solvate or a pharmaceutically acceptable salt thereof, wherein:
$R^1$ is halogen (e.g. Cl) or nitrile;
n is 1;
$R^2$ is hydrogen or —$(CH_2)_u$COOH (e.g. —$CH_2$COOH);
$R^3$ is hydrogen and s is 1 or $R^3$ is -(A)$_t$-(C$R^xR^y$)$_q$—X and t is 1 and q is 1;
A is selected from cyclopropyl;
X is —OH;
$R^x$ and $R^y$ are hydrogen or deuterium (e.g. hydrogen);
$R^4$ is halogen (e.g. F);
a is 0 or 1;
$R^5$ is halogen (e.g. Cl);
m is 1;
$R^6$ is hydrogen or $C_{1-6}$alkyl (e.g. —$CH_3$ or —$CH_2CH_3$);
$R^7$ is $C_{1-4}$alkyl (e.g. methyl), hydroxyl$C_{1-4}$alkyl (e.g. hydroxylmethyl), methoxy$C_{1-4}$alkyl (e.g. methoxymethyl), a heterocyclic group with 5 or 6 ring members (e.g. piperidinyl, oxanyl, imidazolyl or pyrazolyl));
wherein said heterocyclic group with 5 or 6 ring members may be optionally substituted with one or two $R^z$ groups independently selected from $C_{1-4}$alkyl (e.g. methyl).

In one embodiment, the invention provides a compound of formula (I) or a tautomer or a solvate or a pharmaceutically acceptable salt thereof, wherein: $R^1$ is halogen (e.g. Cl), nitrile, $O_{0,1}$(C$R^xR^y$)$_v$COOH (e.g. —COOH, —$CH_2$COOH, —$OCH_2$COOH or —$C(CH_3)_2$COOH;
n is 1 or 2;
$R^2$ is selected from hydrogen and —$(R^xR^y)_u$—$CO_2$H (e.g. —COOH, —$CH_2$COOH, —$CH_2CH_2$—$CO_2$H, —(CH($CH_3$))—$CO_2$H and —$(C(CH_3)_2$—$CO_2$H).
$R^3$ is hydrogen and s is 1;
$R^4$ is halogen (e.g. F);
$R^5$ is halogen (e.g. Cl);
m is 1;
$R^6$ is hydrogen or $C_{1-6}$alkyl (e.g. —$CH_3$ or —$CH_2CH_3$);
$R^7$ is $C_{1-4}$alkyl (e.g. methyl), hydroxyl$C_{1-4}$alkyl (e.g. hydroxylmethyl), methoxy$C_{1-4}$alkyl (e.g. methoxymethyl), a heterocyclic group with 5 or 6 ring members (e.g. piperidinyl, oxanyl, imidazolyl or pyrazolyl));
wherein said heterocyclic group with 5 or 6 ring members may be optionally substituted with one or two $R^z$ groups independently selected from $C_{1-4}$alkyl (e.g. methyl).

In one embodiment, the invention provides a compound of formula (I) which is one of the Examples 1-137 or is selected from the Examples 1-137 or a tautomer, N-oxide, pharmaceutically acceptable salt or solvate thereof.

In one embodiment, the invention provides a compound of formula (I) which is one of the Examples 1-97 or is selected from the Examples 1-97 or a tautomer, N-oxide, pharmaceutically acceptable salt or solvate thereof.

In one embodiment, the invention provides a compound of formula (I) which is selected from the following compounds, or a tautomer, N-oxide, pharmaceutically acceptable salt or solvate thereof:
4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile; and
(3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid.

In one embodiment, the invention provides a compound of formula (I) which is diastereoisomer 2A and is selected from the following compounds, or a tautomer, N-oxide, pharmaceutically acceptable salt or solvate thereof:

4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile; and
(3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid.

In one embodiment, the invention provides a compound of formula (I) which is diastereoisomer 2B and is selected from the following compounds, or a tautomer, N-oxide, pharmaceutically acceptable salt or solvate thereof:
4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile; and
(3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid.

In one embodiment, the invention provides a compound of formula (I) which is 2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)-2-methylpropanoic acid, or a tautomer, N-oxide, pharmaceutically acceptable salt or solvate thereof.

In one embodiment, the invention provides a compound of formula (I) which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, or a tautomer, N-oxide, pharmaceutically acceptable salt or solvate thereof.

For the avoidance of doubt, it is to be understood that each general and specific embodiment and example for one substituent may be combined with each general and specific embodiment and example for one or more, in particular all, other substituents as defined herein and that all such embodiments are embraced by this application.

Salts, Solvates, Tautomers, Isomers, N-Oxides, Esters, Prodrugs and Isotopes

A reference to a compound of the formula (I), sub-groups thereof (e.g. formulae I(c), I(f), I(g), I(g'), I(h), I(i), I(j), I(k), I(L), I(m), I(m'), I(n), I(o), I(o'), I(o''), I(p), I(p'), I(q), I(q'), I(q''), I(q'''), I(q''''), I(r), I(s), I(t), I(u), I(v), I(v'), I(w), I(x), I(x'), I(y), (II), (IIa), (IIb), (IIIa), (IIIb), (IVa), (IVb), (V), (VI), (Via), (VII), (VIIa), (VIIb), (VIIc), (VIId), (VIId'), (VIIe), (VIIe'), (a), (b), (ba), (bb), (bc) or (c)) and any example also includes ionic forms, salts, solvates, isomers (including geometric and stereochemical isomers unless specified), tautomers, N-oxides, esters, prodrugs, isotopes and protected forms thereof, for example, as discussed below; in particular, the salts or tautomers or isomers or N-oxides or solvates thereof; and more particularly the salts or tautomers or N-oxides or solvates thereof. In one embodiment reference to a compound of the formula (I), sub-groups thereof (e.g. formulae I(c), I(f), I(g), I(g'), I(h), I(i), I(j), I(k), I(L), I(m), I(m'), I(n), I(o), I(o'), I(o''), I(p), I(p'), I(q), I(q'), I(q''), I(q'''), I(q''''), I(r), I(s), I(t), I(u), I(v), I(v'), I(w), I(x), I(x'), I(y), (II), (IIa), (IIb), (IIIa), (IIIb), (IVa), (IVb), (V), (VI), (Via), (VII), (VIIa), (VIIb), (VIIc), (VIId), (VIId'), (VIIe), (VIIe'), (a), (b), (ba), (bb), (bc) or (c)) and any example also includes the salts or tautomers or solvates thereof.

Salts

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

In one embodiment the compound is the tris(hydroxymethyl)aminomethane (TRIS) salt.

If the compound is anionic, or has a functional group which may be anionic (e.g., —COOH may be —COO—), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/ml, typically greater than 15 mg/ml and typically greater than 20 mg/ml.

N-Oxides

Compounds of the formula (I) containing an amine function may also form N-oxides. A reference herein to a compound of the formula (I) that contains an amine function also includes the N-oxide.

Where a compound contains several amine functions one, or more than one, nitrogen atom may be oxidised to form an N-oxide. Particular examples of N-oxides are the N-oxides of a tertiary amine or a nitrogen atom of a nitrogen-containing heterocyclic group.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

In one embodiment of the invention, the compound is an N-oxide, e.g. from a nitrogen atom on the $R^6$ or $R^7$ group, for example a pyridine N-oxide.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, certain heteroaryl rings can exist in the two tautomeric forms such as A and B shown below. For simplicity, a formula may illustrate one form but the formula is to be taken as embracing both tautomeric forms.

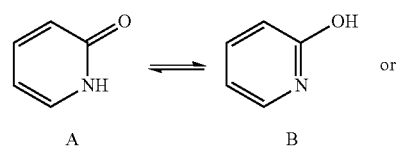

A        B    or

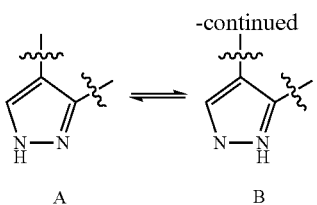

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

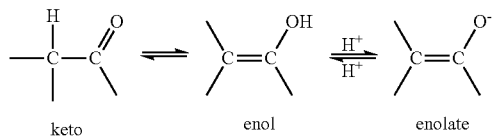

Stereoisomers

Unless otherwise mentioned or indicated, the chemical designation of compounds denotes the mixture of all possible stereochemically isomeric forms.

Stereocentres are illustrated in the usual fashion, using 'hashed' or 'solid' wedged lines. e.g.

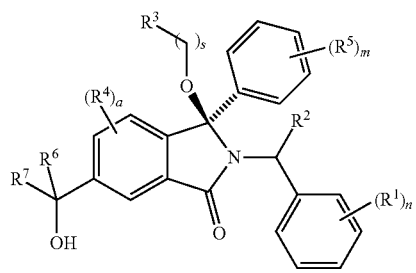

Where a compound is described as a mixture of two diastereoisomers/epimers, the configuration of the stereocentre is not specified and is represented by straight lines.

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic or scalemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2H$ (D) and $^3H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as 15O, 17O and $^{18}O$, phosphorus, such as $^{32}P$, and sulfur, such as $^{35}S$.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be used in some circumstances.

In particular, every reference to hydrogen in the application should be constructed to cover $^1$H and $^2$H, whether hydrogen is defined explicitly, or hydrogen is present implicitly to satisfy the relevant atom's (in particular carbon's) valency.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-12}$ heterocyclyl group, or a $C_{5-12}$ aryl group, typically a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-6}$ alkyl group, a $C_{3-12}$ heterocyclyl group, or a $C_{5-12}$ aryl group, typically a $C_{1-6}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph. Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described herein, can be used to establish whether solvates had formed.

Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);

$C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-oxanyloxy) carbonyloxymethyl; 1-(4- oxanyloxy)carbonyloxyethyl; (4-oxanyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I) does not include pro-drugs of the compounds of the formula (I) within its scope.

Methods for the Preparation of Compounds of Formula (I)

In this section, as in all other sections of this application unless the context indicates otherwise, references to formula (I) also include all other subformula (e.g. formulae I(c), I(f), I(g), I(g'), I(h), I(i), I(j), I(k), I(L), I(m), I(m'), I(n), I(o), I(o'), I(o''), I(p), I(p'), I(q), I(q'), I(q''), I(q'''), (q''''), I(r), I(s), I(t), I(u), I(v), I(v'), I(w), I(x), I(x'), I(y), (II), (IIa), (IIb), (IIIa), (IIIb), (IVa), (IVb), (V), (VI), (Via), (VII), (VIIa), (VIIb), (VIIc), (VIId), (VIId'), (VIIe), (VIIe'), (a), (b), (ba), (bb), (bc) or (c)) and examples thereof as defined herein, unless the context indicates otherwise.

Compounds of the formula (I) can be prepared in accordance with synthetic methods well known to the skilled person.

According to a further aspect of the invention there is provided a process for preparing a compound of formula (I), or a tautomer, stereoisomer, N-oxide, pharmaceutically acceptable salt, or solvate thereof which comprises:

According to a further aspect of the invention there is provided a process for preparing a compound of formula (I) as hereinbefore defined which comprises:

(a) reacting a compound of formula (XV) with an organometallic reagent of the formula $R^7M$ (where M is a metal), for example a Grignard reagent of the formula $R^7MgBr$:

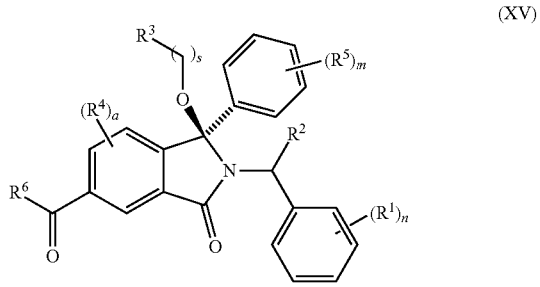

(XV)

wherein $R^1$, $R^2$, $R^3$, $R^4$, $R^5$, $R^6$, a, s m and n are as defined herein;

(b) interconversion of a compound of formula (I) or protected derivative thereof to a further compound of formula (I) or protected derivative thereof; and/or (c) deprotection of a protected derivative of a compound of formula (I); and/or (d) providing a compound of formula (I) and forming a pharmaceutically acceptable salt of the compound.

The required intermediates are either commercially available, known in the literature, prepared by methods analogous to those in the literature or prepared by methods analogous to those described in the example experimental procedures below. Other compounds may be prepared by functional group interconversion of the groups using methods well known in the art.

The general synthetic route for the preparation of compounds of formula XV, a key intermediate is set out in the Schemes below.

Scheme 1

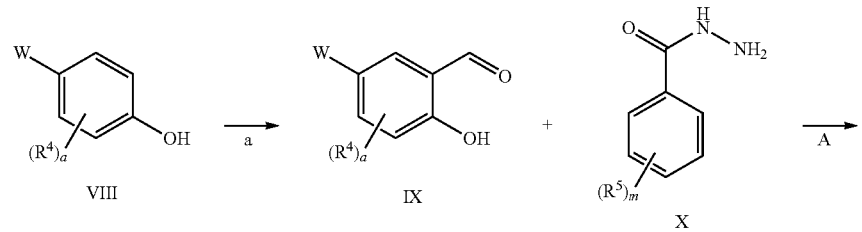

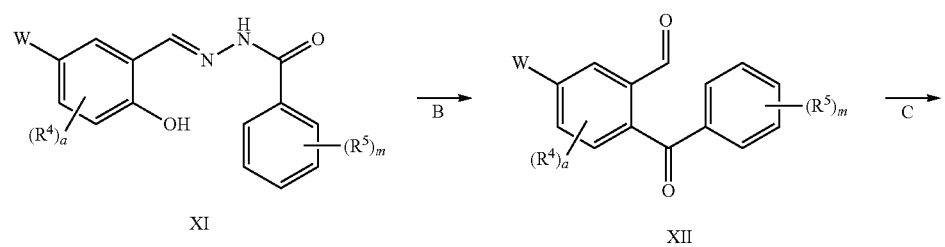

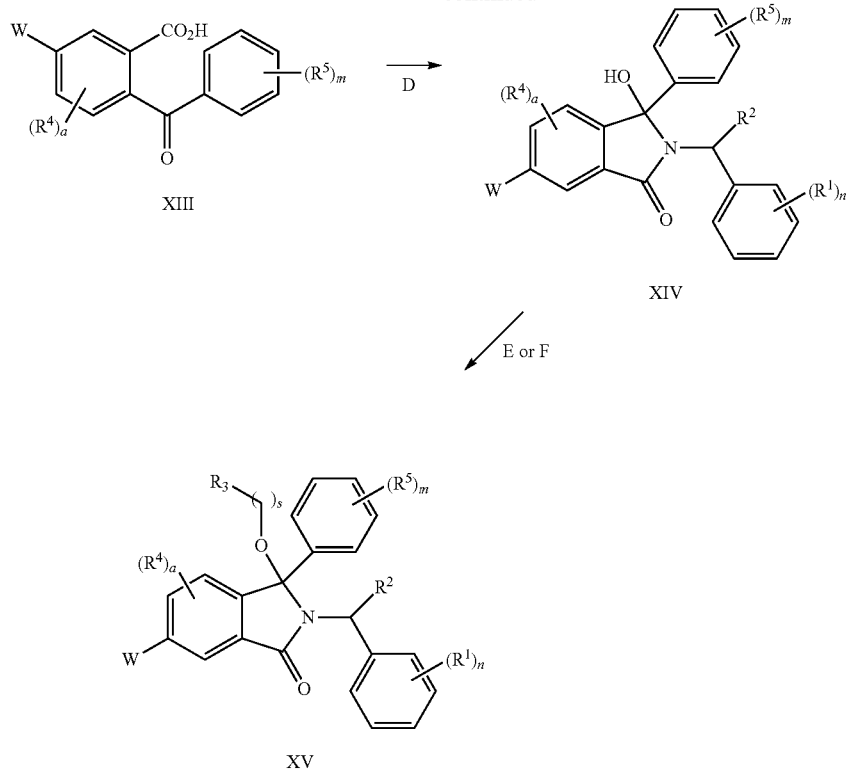

Example reagents and conditions for Scheme 1: a) NaOH, H₂O, CHCl₃, 85° C.; A) AcOH, rt; B) Pb(OAc)₄, THF, 0° C.; C) NaClO₂, H₂NSO₃H, CH₃CN, H₂O, rt; D) i) SOCl₂, DMF, THF, ii) amine, i-Pr₂EtN, THF; E) i) SOCl₂, DMF, THF, ii) R³(CH₂)ₛ—OH, K₂CO₃, THF; F) InBr₃, R³(CH₂)ₛ—OH, DCE, 85° C.; separation and isolation of the 3(R) enantiomer can be achieved at this stage by chiral HPLC.

In Scheme 1, $R^1$, $R^2$, $R^3$, $R^4$ and $R^5$ are as described herein and W represents a leaving group, such as for example halo, e.g. bromo, or a carbonyl group, such as for example acetyl.

N-aroylhydrazone (XI) can be prepared by condensing benzaldehyde (IX) with benzohydrazide (X). Reaction with Pb(OAc)₄ yields aldehyde (XII), from which a Pinnick oxidation provides acid (XIII). The appropriate benzylamine can then be used to provide 3-hydroxyisoindolinone (XIV), and the $R^3$—containing side chain added using thionyl chloride or InBr₃ and the appropriate alcohol.

Intermediates of formula (XV) can be used as a starting point for the synthesis of compounds of the present invention having varying functionality in the $R^3$, $R^6$ and $R^7$ positions of Formula I.

Scheme 2 below sets out example procedures for introducing various $R^6$ moieties starting from intermediates of formula (XVI) (which is the compound of formula (XV) wherein W is Br).

Scheme 2

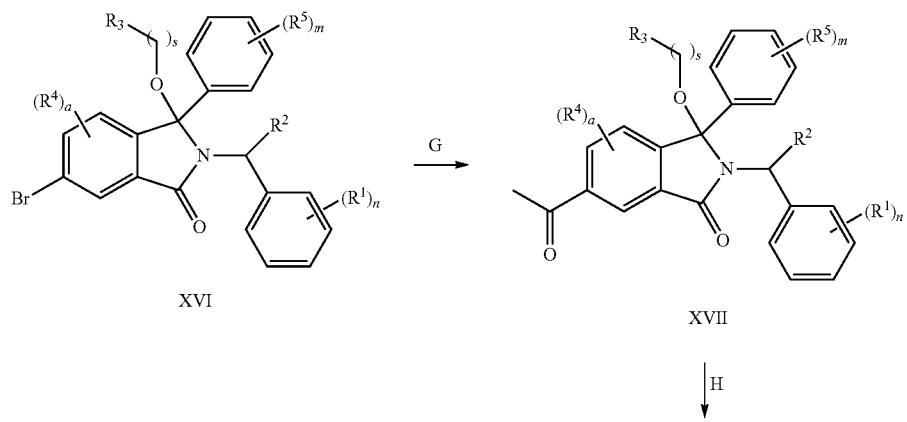

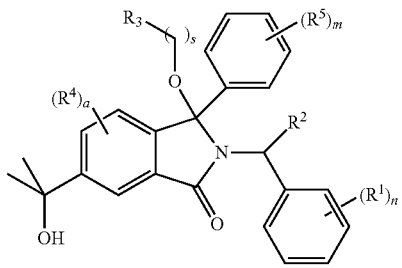

XVIII

Example reagents and conditions for Scheme 2: G) (i) toluene, 1,4-dioxane, LiCl, tributyl(1-ethoxyvinyl)tin, Pd(PPh$_3$)$_4$, (ii) HCl, H$_2$O/THF. H) MeMgCl, in the presence of ZnCl$_2$ and/or LaCl$_3$-2LiCl, THF. Separation and isolation of the 3(R) enantiomer can be achieved at any stage by chiral HPLC.

Bromide (XVI) can be converted to methyl ketone (XVII) for example using 1,4-dioxane, LiCl, tributyl(1-ethoxyvinyl)tin, Pd(PPh$_3$)$_4$, and further converted to the alcohol XVIII by reaction with a methyl Grignard reagent.

Compounds wherein R$^6$ and R$^7$ are hydrogen, can also be prepared according to the general synthetic Scheme 3. Where R$^3$ contains a hydroxyl group, this can be protected during the synthesis by using standard protecting groups (e.g. TBDMS, TBDPS). Deprotection can be performed using standard conditions (e.g. TBAF).

Example reagents and conditions for Scheme 3: I) HCOOLi.H$_2$O, Ac$_2$O, Et$_3$N, 4,5-Bis(diphenylphosphino)-9,9-dimethylxanthene, Pd(OAc)$_2$, DMF; J) LiBH$_4$, THF.

Compounds of formula (XVIII), first shown in Scheme 2, wherein R$^6$ and R$^7$ are methyl, can also be prepared according to the general synthetic Scheme 4.

In Scheme 4, an intermediate of formula (XXIV) is prepared from an intermediate of formula (XXIII) according to procedure F (InBr$_3$ with R$^3$(CH$_2$)$_s$—OH). The intermediate of formula (XXIV) is then converted to the compound of formula (XVIII) by a Grignard reaction.

Scheme 3

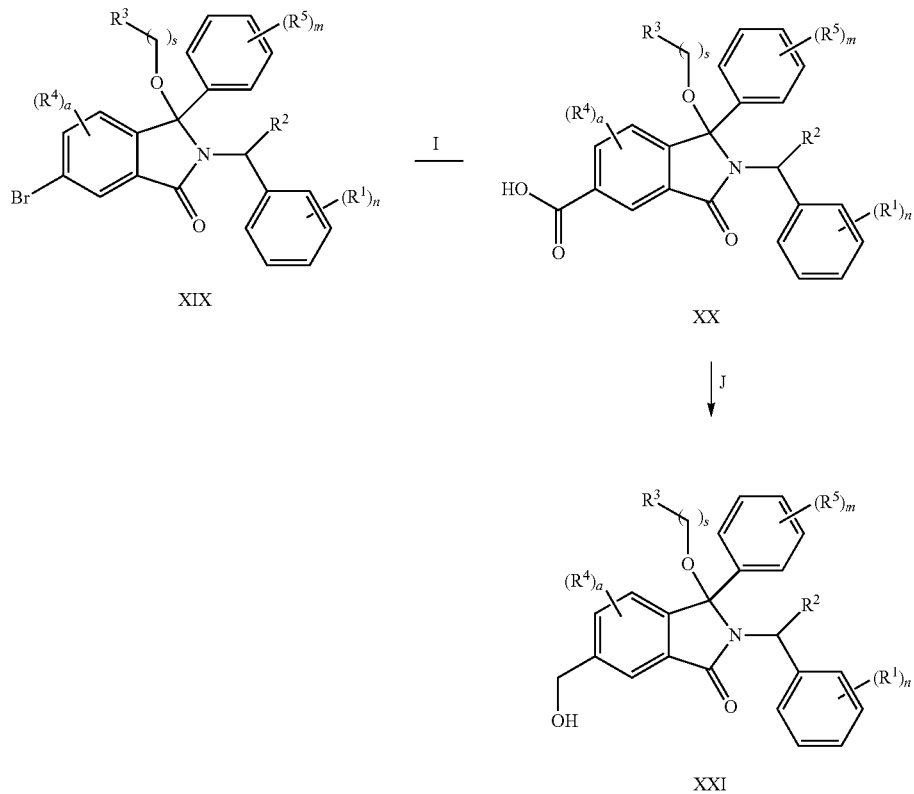

Scheme 4
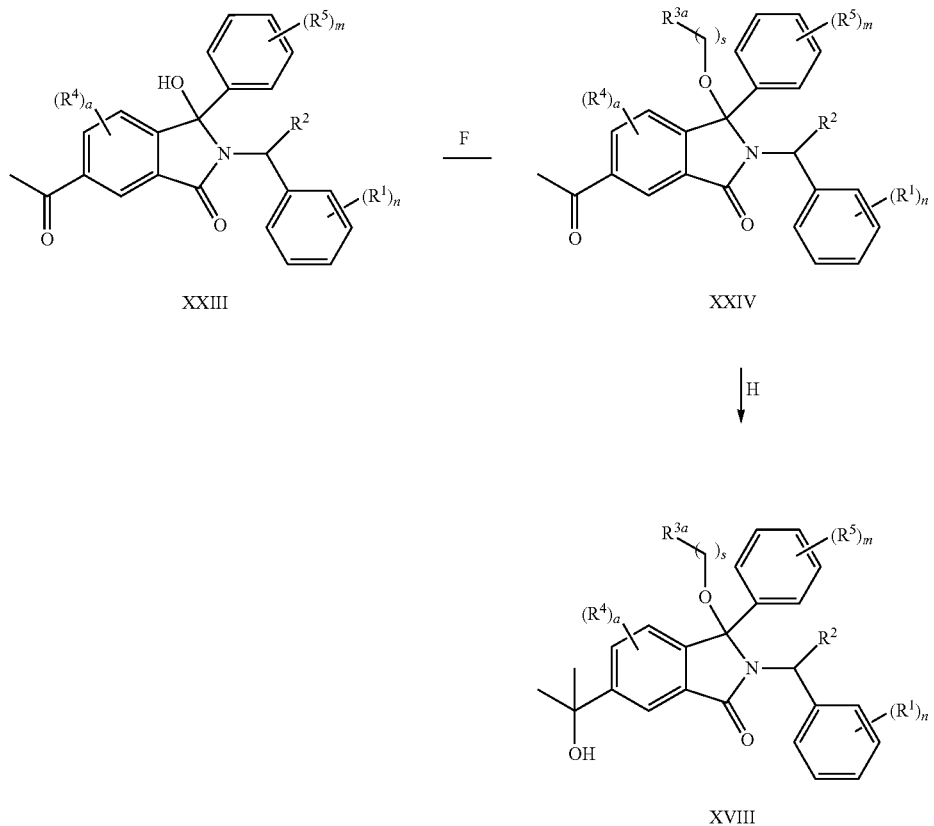
Example reagents and conditions: F) InBr₃, R³(CH₂)ₛ—OH, DCE, 85° C.; H) MeMgCl, ZnCl₂, THF, 0° C. Separation and isolation of the 3(R) enantiomer can be achieved at stage F or H by chiral HPLC.
Compounds of general formula XXX can also be prepared according to Schemes 5 and 6.
Scheme 5
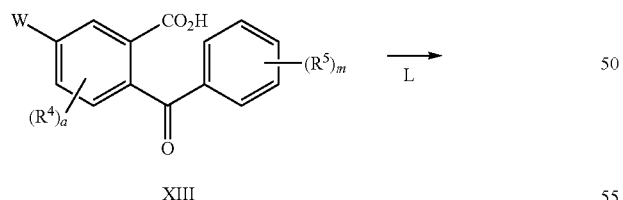
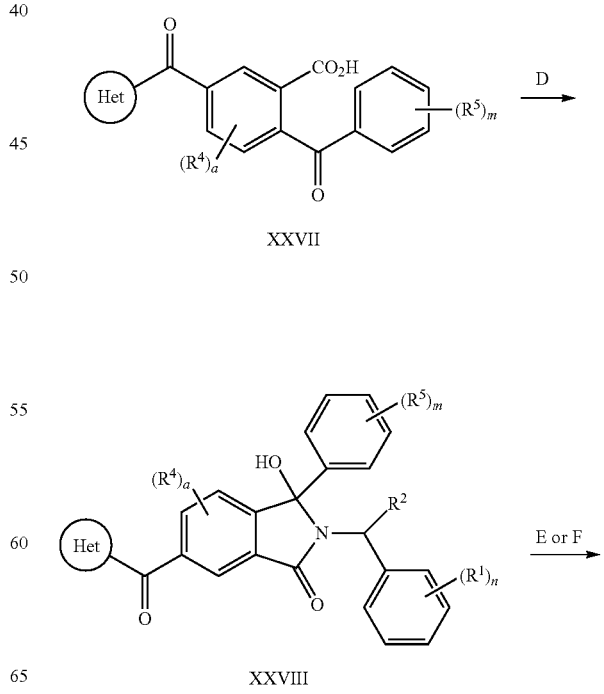
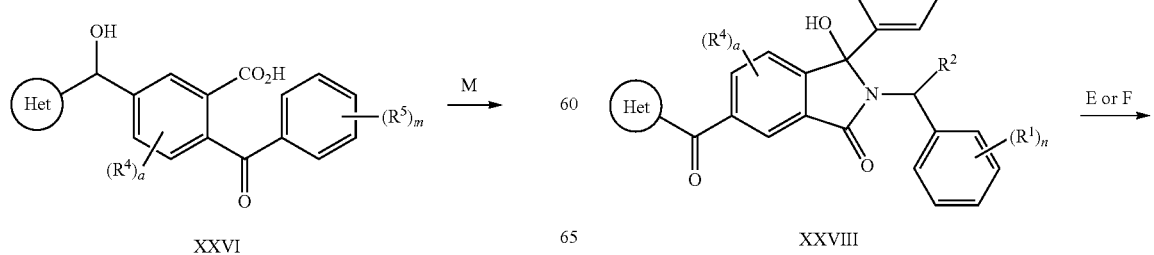

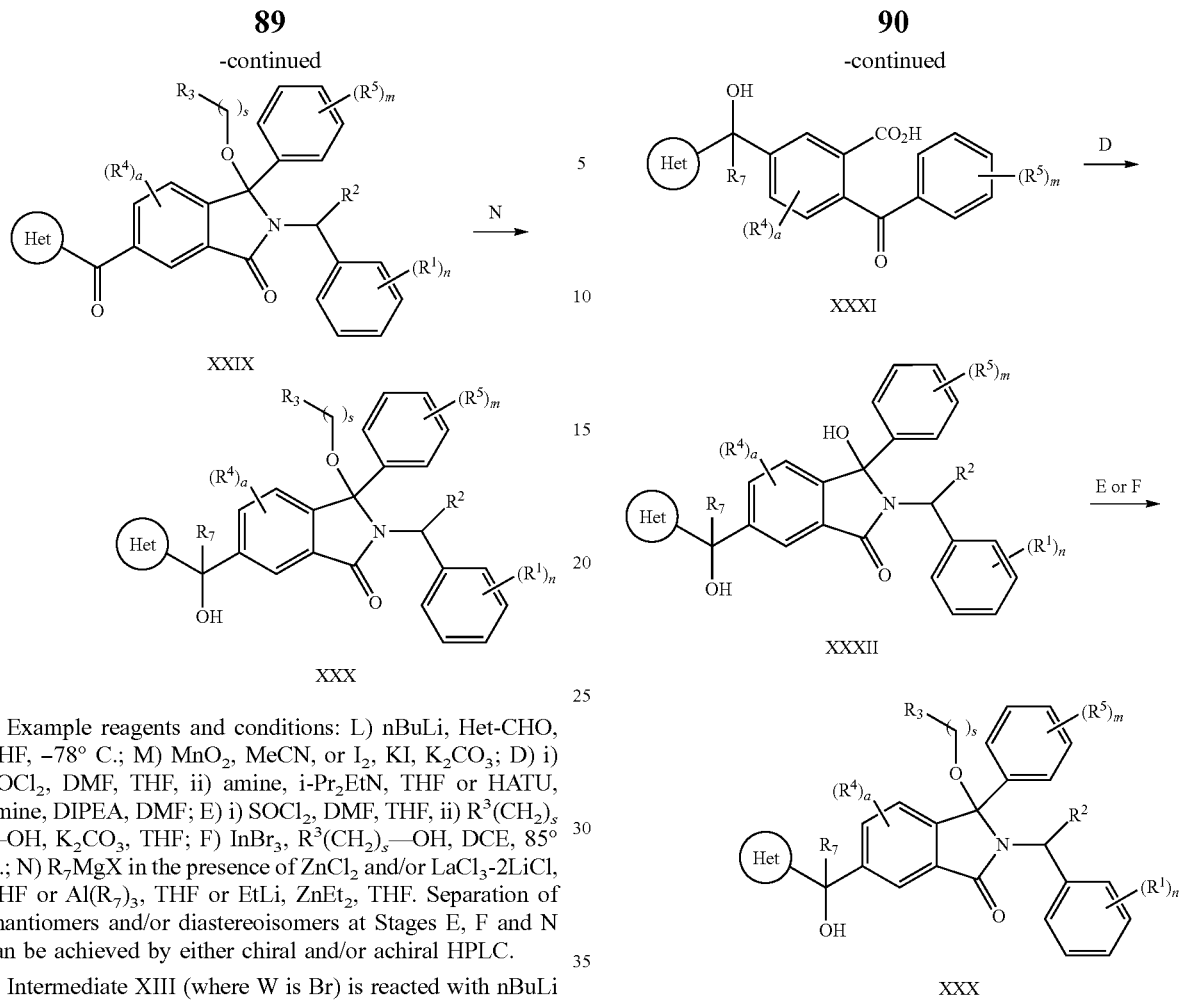

Example reagents and conditions: L) nBuLi, Het-CHO, THF, −78° C.; M) MnO$_2$, MeCN, or I$_2$, KI, K$_2$CO$_3$; D) i) SOCl$_2$, DMF, THF, ii) amine, i-Pr$_2$EtN, THF or HATU, amine, DIPEA, DMF; E) i) SOCl$_2$, DMF, THF, ii) R$^3$(CH$_2$)$_s$—OH, K$_2$CO$_3$, THF; F) InBr$_3$, R$^3$(CH$_2$)$_s$—OH, DCE, 85° C.; N) R$_7$MgX in the presence of ZnCl$_2$ and/or LaCl$_3$-2LiCl, THF or Al(R$_7$)$_3$, THF or EtLi, ZnEt$_2$, THF. Separation of enantiomers and/or diastereoisomers at Stages E, F and N can be achieved by either chiral and/or achiral HPLC.

Intermediate XIII (where W is Br) is reacted with nBuLi and an appropriate aldehyde to provide alcohol XXVI which is oxidised to the corresponding ketone (XXVII) either using MnO$_2$ or I$_2$/KI. Intermediate XXVII is then converted into the 3-hydroxyisoindolinone XXIX following procedures D and E (of F) described above.

Intermediates of formula XXIX can be used as a starting point for the synthesis of compounds of the present invention having varying functionality in the R$^7$ position of Formula I Alternatively the R$^7$ substituents are introduced earlier in the synthesis as shown in Scheme 6. Intermediates of formula XXVII can react with organometallic reagents to provide tertiary alcohol (XXXI) which is then converted to final compounds of Formula I following procedures D and E (or F) (Scheme 6).

Scheme 6

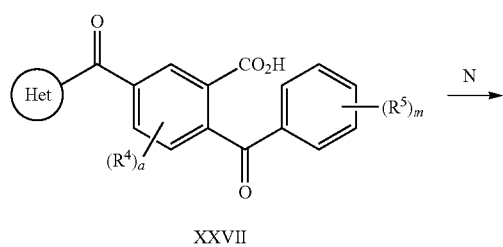

Example reagents and conditions: N) R$_7$MgX in the presence of ZnCl$_2$ and/or LaCl$_3$-2LiCl, THF or Al(R$_7$)$_3$, THF or EtLi, ZnEt$_2$, THF; D) i) SOCl$_2$, DMF, THF, ii) amine, i-Pr$_2$EtN, THF or HATU, amine, DIPEA, DMF; E) i) SOCl$_2$, DMF, THF, ii) R$^3$(CH$_2$)$_s$—OH, K$_2$CO$_3$, THF; F) InBr$_3$ R$^3$(CH$_2$)$_s$—OH, DCE, 85° C. Separation of enantiomers and/or diastereoisomers at Stages N and E/F can be achieved by either chiral and/or achiral HPLC.

Compounds of formula XVI (first shown in Scheme 2) can also be used to make compounds of formula XXIX using methods outlined in Scheme 7. In this case, XVI can be converted into a suitable boronate using, for example, Miyaura conditions. The boronate is then treated with an appropriate heterocyclic iodide (or heterocyclic bromide) in the presence of carbon monoxide, a suitable catalyst (such as Pd(dppf)Cl$_2$.) and a solvent (such as toluene or ansole).

Alternatively, compounds of formula XVI can be treated with an appropriate heterocyclic stannane in the presence of carbon monoxide, a suitable catalyst [such as Pd(dppf)Cl$_2$] and a solvent (such as DMF) to give compounds of formula XXIX (Scheme 7). Separation and isolation of the 3(R) intermediate can be achieved at any stage using chiral HPLC. Compounds of formula XXIX can then be progressed to compounds of formula XXX (as shown in Scheme 5), Scheme 7

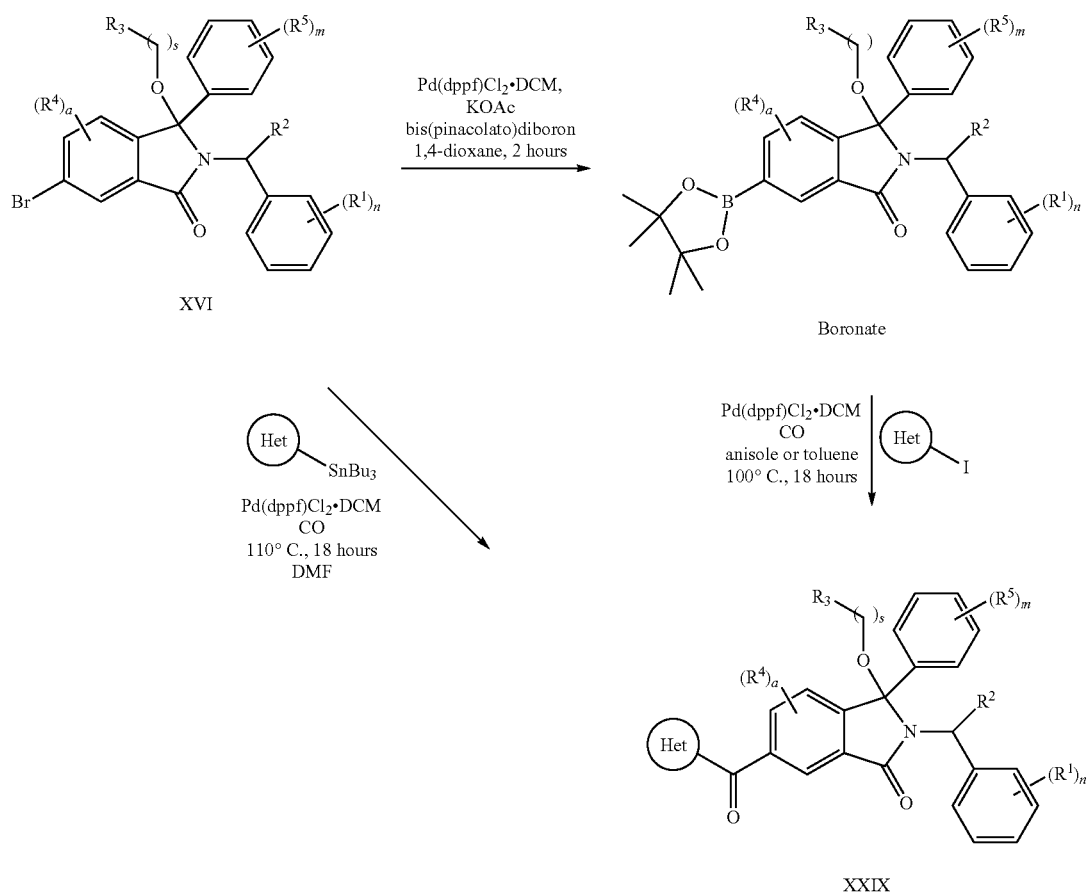

Compounds of formula XVI can also be used to make compounds of formula XXIX using methods outlined in Scheme 8. In this case, compounds of formula XVI can be used to make a Weinreb amide derivative using N,O-dimethylhydroxylamine hydrochloride in the presence of carbon monoxide and a suitable palladium catalyst (e.g. Xantphos G3 catalyst). The Weinreb amide can then be reacted with an appropriate metallated heterocycle (e.g. the product of 4-bromo-1-methyl-1H-pyrazole and nBuLi in THF) to give compounds of formula XXIX (Scheme 8). Separation and isolation of the 3(R) intermediate can be achieved at any stage using chiral HPLC. Compounds of formula XXIX can then be progressed to compounds of formula XXX (as shown in Scheme 5).

Scheme 8

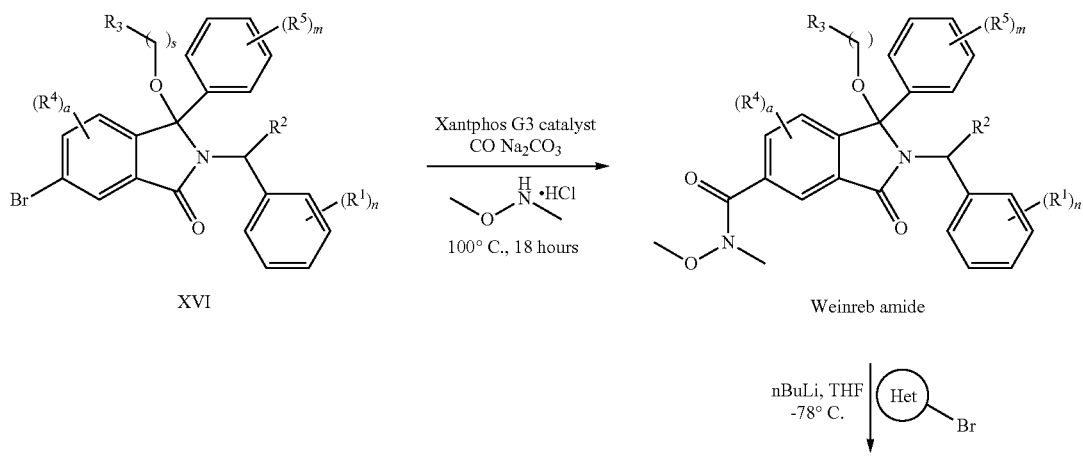

-continued

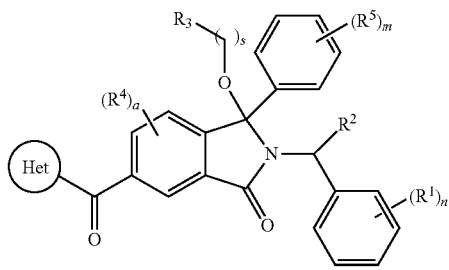

XXIX

It will be appreciated that certain compounds can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid (or enantiomerically pure base such as (1R)-1-phenylethan-1-amine); or enantiomer separation of a diastereomeric derivative formed by covalently linking a enantiomerically pure chiral auxiliary onto the compound, followed by separation using conventional methods such as chiral or non-chiral chromatography. The aforementioned covalent linkage is then cleaved to generate the appropriate enantiomerically pure product.

A wide range of well known functional group interconversions are known by a person skilled in the art for converting a precursor compound to a compound of formula I and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described below are followed or preceded by one or more reactions known to the skilled of the art and are performed in an appropriate order to achieve the requisite substitutions defined above to afford other compounds of formula (I). Non-limiting examples of such reactions whose conditions can be found in the literature include:
  protection of reactive functions,
  deprotection of reactive functions,
  halogenation,
  dehalogenation,
  dealkylation,
  alkylation or arylation of amine, aniline, alcohol and phenol,
  Mitsunobu reaction on hydroxyl groups,
  cycloaddition reactions on appropriate groups,
  reduction of nitro, esters, cyano, aldehydes,
  transition metal-catalyzed coupling reactions,
  acylation,
  sulfonylation/introduction of sulfonyl groups,
  saponification/hydrolysis of ester groups,
  amidification or transesterification of ester groups,
  esterification or amidification of carboxylic groups,
  halogen exchange,
  nucleophilic substitution with amine, thiol or alcohol,
  reductive amination,
  oxime formation on carbonyl and hydroxylamine groups,
  S-oxidation,
  N-oxidation,
  salification.

It will be appreciated that certain compounds e.g. compounds of formulae (I), I(c), I(f), I(g), I(g'), I(h), I(i), I(j), I(k), I(L), I(m), I(m'), I(n), I(o), I(o'), I(o"), I(p), I(p'), I(q), I(q'), I(q"), I(q'''), I(q''''), I(r), I(s), I(t), I(u), I(v), I(v'), I(w), I(x), I(x'), I(y), (II), (IIa), (IIb), (IIIa), (IIIb), (IVa), (IVb), (V), (VI), (Via), (VII), (VIIa), (VIIb), (VIIc), (VIId), (VIId'), (VIIe), (VIIe'), (a), (b), (ba), (bb), (bc) or (c) can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid; or enantiomer separation of a diastereomeric derivative formed by covalently linking a enantiomerically pure chiral auxiliary onto the compound, followed by separation using conventional methods such as chiral chromatography. The aforementioned covalent linkage is then cleaved to generate the appropriate enantiomerically pure product.

Certain of the required intermediates, are either commercially available, known in the literature, prepared by methods analogous to those in the literature or prepared by methods analogous to those described in the example experimental procedures below. Other compounds may be prepared by functional group interconversion using methods well known in the art.

In a further embodiment the invention provides a novel intermediate. In one embodiment the invention provides a novel intermediate of (VII), (VIII), (IX), (X), (XI), (XII), (XIII), (XIV), (XV), (XVI), (XVII), (XIX), (XX), (XXI), (XXIII) and (XXIV).

Protecting Groups

In many of the reactions described herein, it may be necessary to protect one or more groups to prevent reaction from taking place at an undesirable location on the molecule. Examples of protecting groups, and methods of protecting and deprotecting functional groups, can be found in *Protec-* tive Groups in Organic Synthesis (T. Green and P. Wuts; 3rd Edition; John Wiley and Sons, 1999).

In particular the compound may be synthesised in protected forms and the protecting groups removed to generate a compound of formula (I).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Bpoc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH-Psec).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. An example of such a system for purifying compounds via preparative LC-MS is described below in the Examples section of this application (under the heading "Mass Directed Purification LC-MS System").

Methods of recrystallisation of compounds of formula (I) and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes an heating step under vacuum for example using a cold finger, and crystallization from melt (Crystallization Technology Handbook 2nd Edition, edited by A. Mersmann, 2001).

Biological Effects

It is envisaged that the compound of the invention will be useful in medicine or therapy. The compounds of the invention, subgroups and examples thereof, have been shown to inhibit the interaction of p53 with MDM2. Such inhibition leads to cell proliferative arrest and apoptosis, which may be useful in preventing or treating disease states or conditions described herein, for example the diseases and conditions discussed below and the diseases and conditions described in the "Background of the Invention" section above in which p53 and MDM2 play a role. Thus, for example, it is envisaged that the compounds of the invention may be useful in alleviating or reducing the incidence of cancer.

The compounds of the present invention may be useful for the treatment of the adult population. The compounds of the present invention may be useful for the treatment of the pediatric population.

The compounds of the present invention have been shown to be good inhibitors of the formation of MDM2-p53 complex. The antagonist compounds of formula (I) are capable of binding to MDM2 and exhibiting potency for MDM2. The efficacies of the compounds of the present invention have been determined against MDM2/p53 using the assay protocol described herein and other methods known in the art. More particularly, the compounds of the formula (I) and sub-groups thereof have affinity for MDM2/p53.

Certain compounds of the invention are those having $IC_{50}$ values of less than 0.1 µM in particular less than 0.01 or 0.001 µM.

MDM2/p53 function has been implicated in many diseases due to its role in a variety of process for example vascular remodelling and antiangiogenic processes and regulation of metabolic pathways, as well as in oncogenesis. As a consequence of their affinity for MDM2 it is anticipated that the compounds may prove useful in treating or preventing a range of diseases or conditions including autoimmune conditions; diabetes mellitus; chronic inflammatory diseases, for example lupus nephritis, systemic lupus erythematosus (SLE), autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; hyperkeratotic diseases such as autosomal recessive congenital ichthyosis (ARCI); kidney diseases including glomerular disorders, chronic kidney disease (CKD) renal inflammation, podocyte loss, glomerulosclerosis, proteinuria, and progressive kidney disease; cardiovascular diseases for example cardiac hypertrophy, restenosis, arrhythmia, atherosclerosis; ischemic injury associated myocardial infarctions, vascular injury, stroke and reperfusion injury; vascular proliferative diseases; ocular diseases such as age-related macular degeneration in particular wet form of age-related macular degeneration, ischemic proliferative retinopathies such as retinopathy of prematurity (ROP) and diabetic retinopathy, and hemangioma.

As a consequence of their affinity for MDM2 it is anticipated that the compounds may prove useful in treating or preventing proliferative disorders such as cancers.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, bowel, colorectal, rectum and anus), liver (hepatocellular carcinoma), gall bladder and biliary system, exocrine pancreas, kidney (for example renal cell carcinoma), lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, testes, cervix, myometrium, endometrium, thyroid (for example thyroid follicular carcinoma), brain, adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas (e.g. gliomas), neuromas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer.

Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent. The compounds may be beneficial in the treatment of diseases such as cancer and metastasis, ocular diseases, arthritis and hemangioma.

Therefore, the compounds of the invention may be useful in the treatment of metastasis and metastatic cancers. Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body. In particular, the compounds of the invention may be useful in the treatment of metastasis and metastatic cancers.

In one embodiment the haematological malignancies is a leukaemia. In another embodiment the haematological malignancies is a lymphoma. In one embodiment the cancer is AML. In another embodiment the cancer is CLL.

In one embodiment the compound of the invention is for use in the prophylaxis or treatment of leukemia, such as acute or chronic leukaemia, in particular acute myeloid leukaemia (AML), acute lymphocytic leukaemia (ALL), chronic lymphocytic leukaemia (CLL), or chronic myeloid leukemia (CML). In one embodiment the compound of the invention is for use in the prophylaxis or treatment of lymphoma, such as acute or chronic lymphoma, in particular Burkitt lymphoma, Hodgkin lymphoma, non-Hodgkin lymphoma or diffuse large B-cell lymphoma.

In one embodiment the compound of the invention is for use in the prophylaxis or treatment of acute myeloid leukaemia (AML) or acute lymphocytic leukaemia (ALL).

One embodiment includes a compound of the invention for use in the prophylaxis or treatment of cancer in a patient selected from a sub-population possessing cancers which are p53 wild-type or have an MDM2 amplification The cancers may be cancers which are sensitive to treatment with MDM2 inhibitors. The cancers may be cancers which overexpress MDM2. The cancer may be cancers which are p53 wild-type.

Particular cancers include those with an MDM2 amplification and/or MDM2 overexpression, for example, hepatocellular carcinoma, lung, sarcomas, osteosarcomas, and Hodgkin disease.

Particular cancers include those with wild-type p53. Particulars cancers include those cancer cells with wild-type p53, particularly but not exclusively, if MDM2 is highly expressed.

In one embodiment the cancer is a p53 functional tumours. In one embodiment this disease to be treated is p53 functional solid and haematological malignancies. In another embodiment the patient to be treated has p53 mutant tumour for example AML patients with p53 mutant tumour.

In one embodiment the cancer is a tumour of the brain, for example glioma, or neuroblastoma.

In one embodiment the cancer is a cancer of the skin, for example melanoma.

In one embodiment the cancer is a cancer of the lung, for example mesothelioma. In one embodiment the mesothelioma is malignant peritoneal mesothelioma or malignant pleural mesothelioma.

In one embodiment the cancer is a cancer of the gastro-intestinal tract, for example GIST, gastric, colorectal or bowel.

In one embodiment the cancer is osteosarcoma.

In one embodiment the cancer is liposarcoma.

In one embodiment the cancer is Ewing's sarcoma.

In one embodiment, the cancer is liposarcoma, soft tissue sarcoma, osteosarcoma, oesophageal cancer, and certain paediatric malignancies including B-cell malignancies.

In one embodiment, the cancer is colorectal, breast, lung and brain

In one embodiment, the cancer is a paediatric cancer.

Whether a particular cancer is one which is sensitive to MDM2 inhibitors, may be determined by a method as set out in the section headed "Methods of Diagnosis".

A further aspect provides the use of a compound for the manufacture of a medicament for the treatment of a disease or condition as described herein, in particular cancer.

Certain cancers are resistant to treatment with particular drugs. This can be due to the type of the tumour (most common epithelial malignancies are inherently chemoresistant and prostate is relatively resistant to currently available regimens of chemotherapy or radiation therapy) or resistance can arise spontaneously as the disease progresses or as a result of treatment. In this regard, references to prostate includes prostate with resistance towards anti-androgen therapy, in particular abiraterone or enzalutamide, or castrate-resistant prostate. Similarly references to multiple myeloma includes bortezomib-insensitive multiple myeloma or refractory multiple myeloma and references to chronic myelogenous leukemia includes imitanib-insensitive chronic myelogenous leukemia and refractory chronic myelogenous leukemia. In this regard, references to mesothelioma includes mesothelioma with resistance towards topoisomerase poisons, alkylating agents, antitubulines, antifolates, platinum compounds and radiation therapy, in particular cisplatin-resistant mesothelioma.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. Inhibitors of MDM2/p53 represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

In one embodiment the invention provides a compound for use in the treatment of a disease or condition which is mediated by MDM2. In a further embodiment the disease or condition which is mediated by MDM2 is a cancer which is characterised by overexpression and/or increased activity of MDM2, or high copy number MDM2 and/or wildtype p53.

A further aspect provides the use of a compound for the manufacture of a medicament for the treatment of a disease or condition as described herein, in particular cancer.

In one embodiment there is provided a compound for use in the prophylaxis or treatment of a disease or condition mediated by MDM2/p53. In one embodiment there is provided a compound for inhibiting the interaction between of MDM2 protein with p53.

In one embodiment there is provided a pharmaceutical composition comprising an effective amount of at least one compound as defined. In a further aspect of the present invention, there is provided a compound as defined in the present In one embodiment there is provided a method for the prophylaxis or treatment of cancer comprising the steps of administering to a mammal a medicament comprising at least one compound as defined.

Methods of Diagnosis

Prior to administration of a compound of the formula (I), a patient may be screened to determine whether a disease or condition from which the patient is or may be suffering is one which would be susceptible to treatment with a compound which inhibits Mdm2/p53. The term 'patient' includes human and veterinary subjects such as primates, in particular human patients.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of MDM2 or to upregulation of a biochemical pathway downstream of MDM2/p53.

Examples of such abnormalities that result in activation or sensitisation of MDM2, loss of, or inhibition of regulatory pathways impacting on MDM2 expression, up-regulation of receptors or their ligands, cytogenetic aberrations or presence of mutant variants of the receptors or ligands. Tumours with up-regulation of MDM2/p53, in particular over-expression of MDM2 or exhibit wild-type p53, may be particularly sensitive to inhibitors of MDM2/p53. For example, amplification of MDM2 and/or deletion of its negative regulator such as p14ARF has been identified in a range of cancers as discussion in the Introduction section.

The term up-regulation includes elevated expression or over-expression, including gene amplification (i.e. multiple gene copies), cytogenetic aberration and increased expression by a transcriptional or post-translational effect. Thus, the patient may be subjected to a diagnostic test to detect a marker characteristic of up-regulation of MDM2. The term diagnosis includes screening. By marker we include genetic markers including, for example, the measurement of DNA composition to identify presence of mutations in p53 or amplification MDM2 or deletion (loss) of p14ARF. The term marker also includes markers which are characteristic of up regulation of MDM2/p53, including protein levels, protein state and mRNA levels of the aforementioned proteins. Gene amplification includes greater than 7 copies, as well as gains of between 2 and 7 copies.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal smears, skin biopsy or urine.

Methods of identification and analysis of cytogenetic aberration, genetic amplification, mutations and up-regulation of proteins are known to a person skilled in the art. Screening methods could include, but are not limited to, standard methods such as DNA sequence analysis by conventional Sanger or next-generation sequencing methods, reverse-transcriptase polymerase chain reaction (RT-PCR), RNA sequencing (RNAseq), nanostring hybridisation proximity RNA nCounter assays, or in-situ hybridization such as fluorescence in situ hybridization (FISH) or allele-specific polymerase chain reaction (PCR).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Certain probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA using a (dT)24 oligomer for priming first-strand cDNA synthesis from polyadenylated mRNA, followed by second strand cDNA synthesis with random hexamer primers. The double-stranded cDNA is used as a template for in vitro transcription of cRNA using bioti-nylated ribonucleotides. cRNA is chemically fragmented according to protocols described by Affymetrix (Santa Clara, Calif., USA), and then hybridized overnight to gene-specific oligonucleotide probes on Human Genome Arrays.

Alternatively, single nucleotide polymorphism (SNP) arrays, a type of DNA microarray, can be used to detect polymorphisms within a population.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins e.g. capillary electrophoresis. Detection methods would include the use of site specific antibodies. The skilled person will recognize that all such well-known techniques can be used for detection of upregulation of MDM2 and p53, detection of MDM2 or p53 variants or mutants, or loss of negative regulators of MDM2 in the present case.

Abnormal levels of proteins such as MDM2 or p53 can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured. Assay methods also include the use of markers.

In other words, p53 and MDM2 overexpression can be measured by tumour biopsy.

Methods for assessing gene copy changes include techniques commonly used in cytogenetic laboratories such as MLPA (Multiplex Ligation-dependent Probe Amplification) a multiplex PCR method detecting abnormal copy numbers, or other PCR techniques which can detect gene amplification, gain and deletion.

Ex-functional assays could also be utilised where appropriate, for example measurement of circulating leukemia cells in a cancer patient, to assess the response to challenge with an MDM2/p53 inhibitor.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with an MDM2/p53 inhibitor.

Another aspect of the invention includes a compound of the invention for use in the prophylaxis or treatment of cancer in a patient selected from a sub-population possessing amplification of MDM2.

Another aspect of the invention includes a compound of the invention for use in the prophylaxis or treatment of cancer in a patient selected from a sub-population possessing p53 wild-type.

Another aspect of the invention includes a compound of the invention for use in the prophylaxis or treatment of cancer in a patient possessing loss of a MDM2 negative regulator such as p14ARF.

MRI determination of vessel normalization (e.g. using MRI gradient echo, spin echo, and contrast enhancement to measure blood volume, relative vessel size, and vascular permeability) in combination with circulating biomarkers may also be used to identify patients suitable for treatment with a compound of the invention.

Thus a further aspect of the invention is a method for the diagnosis and treatment of a disease state or condition mediated by MDM2/p53, which method comprises (i) screening a patient to determine whether a disease or condition from which the patient is or may be suffering is one which would be susceptible to treatment with MDM2/p53 inhibitor; and (ii) where it is indicated that the disease or condition from which the patient is thus susceptible, thereafter administering to the patient a compound of formula (I) and sub-groups or examples thereof as defined herein.

Advantages of Compounds of the Invention

The compounds of the formula (I) have a number of advantages over prior art compounds.

Compounds of the invention may have particular advantage in one or more of the following aspects:
(i) Superior potency;
(ii) Superior in vivo efficacy
(iii) Superior PK;
(iv) Superior metabolic stability;
(v) Superior oral bioavailability; and
(vi) Superior physiochemical properties.

Superior Potency and In Vivo Efficacy

The compounds of the formula (I) have increased affinity for MDM2 and in particular increased cell potency against cell lines known to be sensitive to MDM2 antagonists.

Enhanced target engagement is a highly desirable property in a pharmaceutical compound as it allows for a reduced dosage of drug and a good separation ('therapeutic window') between MDM2 activity and toxic effects.

The compounds of the formula (I) have improved cell potency and/or improved selectivity for p53 WT vs mutant p53 cell lines. As a result of increased potency against MDM2 compounds of the invention may have increased in vivo efficacy in cancer cell lines and in vivo models. In addition the compounds show selectivity for MDM2 over MDMX, despite the close sequence, structural and functional similarity between these genetic paralogues.

Superior PK and Metabolic Stability

The compounds of the formula (I) may have advantageous ADMET properties for example better metabolic stability (for example as determined with mouse liver microsomes), a better P450 profile, short half-life and/or beneficial clearance (e.g. low or high clearance). It has also been found that many compounds of the formula (I) have an improved PK profile.

These features could confer the advantage of having more drug available in the systemic circulation to reach the appropriate site of action to exert its therapeutic effect. Increased drug concentrations to exert pharmacological action in tumours potentially leads to improved efficacy which thereby allows reduced dosages to be administered. Thus, the compounds of formula (I) should exhibit reduced dosage requirements and should be more readily formulated and administered.

This results in a good separation ('therapeutic window') between MDM2 activity and toxic effects.

Many compounds of the formula (I) have a reduction in Cmax required for efficacy (due to better MDM2 potency and/or PK).

Superior Oral Bioavailability

Potentially the compounds of the invention have physiochemical properties suitable for oral exposure (oral exposure or AUC). In particular, compounds of the formula (I) may exhibit improved oral bioavailability or improved reproducibility of oral absorption. Oral bioavailability can be defined as the ratio (F) of the plasma exposure of a compound when dosed by the oral route to the plasma exposure of the compound when dosed by the intravenous (i.v.) route, expressed as a percentage.

Compounds having an oral bioavailability (F value) of greater than 10%, 20% or 30%, more particularly greater than 40%, are particularly advantageous in that they may be administered orally rather than, or as well as, by parenteral administration.

Superior Physiochemical Properties

The compounds of the formula (I) may have advantageous physiochemical properties in particular chemical stability in acidic conditions and reduced lipophilicity.

Lipophilicity can be measured using a partition-coefficient (log P) or a distribution-coefficient (log D). The partition coefficient is a ratio of concentrations of un-ionized compound between two immiscible phases (n-octanol and water) at equilibrium whereas the distribution coefficient is the ratio of the sum of the concentrations of all forms of the compound (ionized plus un-ionized) in each of the two phases. High lipophilicity is associated with poor drug like properties such us low aqueous solubility, poor pharmacokinetics properties (low oral bioavailability), undesired drug metabolism and high promiscuity. Compounds with optimal lipophilicity might have greater chances of success in drug development. However reduced log P (or calculated log P, clogP) can be challenging to achieve whilst retaining an acceptable level of potency for inhibition of protein-protein interactions (PPIs) due to the lipophilic nature of the targets involved.

Pharmaceutical Formulations

While it is possible for the active compound to be administered alone, it is generally presented as a pharmaceutical composition (e.g. formulation).

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short-term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one typical embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another typical embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% active ingredient and from 99% (w/w) to 5% (w/w) of a pharmaceutically acceptable excipient or combination of excipients. Typically, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, typically from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g. solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose).

They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described herein. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by MDM2/p53. Examples of such disease states and conditions are set out above.

The compounds are generally administered to a subject in need of such administration, for example a human or animal patient, typically a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

Dosages may also be expressed as the amount of drug administered relative to the body surface area of the patient (mg/m$^2$). A typical daily dose of the compound of formula (I) can be in the range from 3700 pg/m$^2$ to 3700 mg/m$^2$, more typically 185 ng/m$^2$ to 925 mg/m$^2$, and more usually 370 ng/m$^2$ to 555 mg/m$^2$ (e.g. 370 ng/m$^2$ to 370 mg/m$^2$, and more typically 37 mg/m$^2$ to 740 mg/m$^2$, for example 37 mg/m$^2$ to 370 mg/m$^2$) although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 0.1 to 5000 mg, or 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles. This discontinuous treatment can also be based upon numbers of days rather than a full week. For example, the treatment can comprise daily dosing for 1 to 6 days, no dosing for 1 to 6 days with this pattern repeating during the treatment protocol. The number of days (or weeks) wherein the compounds of the invention are not dosed do not necessarily have to equal the number of days (or weeks) wherein the compounds of the invention are dosed.

In one embodiment, the compounds of the invention can be administered in amounts from 3 mg/m$^2$ to 125 mg/m$^2$ daily. Treatment can be by continuous daily dosing or more usually consist of multiple cycles of treatment separated by treatment breaks. One example of a single treatment cycle is 5 consecutive daily doses followed by 3 weeks without treatment.

One particular dosing regimen is once a day (e.g. orally) for a week (e.g. 5 days of treatment), followed by a treatment break of 1, 2, or 3 weeks. An alternative dosing regimen is once a week (e.g. orally), for 1, 2, 3 or 4 weeks.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

The compounds of the invention can also be administered by bolus or continuous infusion. The compound of the invention can be given daily to once every week, or once every two weeks, or once every three weeks, or once every four weeks during the treatment cycle. If administered daily during a treatment cycle, this daily dosing can be discontinuous over the number of weeks of the treatment cycle: for example, dosed for a week (or a number of days), no dosing for a week (or a number of days, with the pattern repeating during the treatment cycle.

In a further particular dosing schedule, a patient is given a continuous infusion for a period of 12 hours to 5 days, and in particular a continuous infusion of 24 hours to 72 hours.

Ultimately, however, the quantity of compound administered and the type of composition used will be commensurate with the nature of the disease or physiological condition being treated and will be at the discretion of the physician.

It may be beneficial to use a compound of the invention as a single agent or to combine the compound of the invention with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferase inhibitors
Cytokines and retinoids
Chromatin targeted therapies
Radiotherapy, and,
Other therapeutic or prophylactic agents.

Particular examples of anti-cancer agents or adjuvants (or salts thereof), include but are not limited to any of the agents selected from groups (i)-(xlviii), and optionally group (xlix), below:

(i) Platinum compounds, for example cisplatin (optionally combined with amifostine), carboplatin or oxaliplatin;

(ii) Taxane compounds, for example paclitaxel, paclitaxel protein bound particles (Abraxane™), docetaxel, cabazitaxel or larotaxel;

(iii) Topoisomerase I inhibitors, for example camptothecin compounds, for example camptothecin, irinotecan (CPT11), SN-38, or topotecan;

(iv) Topoisomerase II inhibitors, for example anti-tumour epipodophyllotoxins or podophyllotoxin derivatives for example etoposide, or teniposide;

(v) Vinca alkaloids, for example vinblastine, vincristine, liposomal vincristine (Onco-TCS), vinorelbine, vindesine, vinflunine or vinvesir;

(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;

(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);

(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;
(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;
(xi) DNA methyl transferase inhibitors, for example temozolomide, azacytidine, or decitabine;
(xii) Antifolates, for example methotrexate, pemetrexed disodium, or raltitrexed;
(xiii) Cytotoxic antibiotics, for example antinomycin D, bleomycin, mitomycin C, dactinomycin, carminomycin, daunomycin, levamisole, plicamycin, or mithramycin;
(xiv) Tubulin-binding agents, for example combrestatin, colchicines or nocodazole;
(xv) Signal Transduction inhibitors such as Kinase inhibitors for example receptor tyrosine kinase inhibitors (e.g. EGFR (epithelial growth factor receptor) inhibitors, VEGFR (vascular endothelial growth factor receptor) inhibitors, PDGFR (platelet-derived growth factor receptor) inhibitors, Axl inhibitors, MTKI (multi target kinase inhibitors), Raf inhibitors, ROCK inhibitors, mTOR inhibitors, MEK inhibitors or PI3K Inhibitors) for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032 or RG7204), dabrafenib, encorafenib, selumetinib (AZD6244), trametinib (GSK121120212), dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, sonolisib (PX-866), or AT13148.
(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;
(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, ZK-304709, or AZD-5438 and including CDK4 inhibitors such as palbociclib (PD332991) and ribociclib (LEE-011);
(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);
(xix) Hsp90 inhibitors for example onalespib (AT13387), herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;
(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxomab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (1L6) or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (a anti-PD-1), BMS-936559 (anti-PD-L1), MPDL320A, AMP-514 or MED14736 (anti-PD-L1), or tremelimumab (formerly ticilimumab, CP-675,206, anti-CTLA-4);
(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;
(xxii) Aromatase inhibitors and related drugs, such as exemestane, anastrozole, letrazole, testolactone aminoglutethimide, mitotane or vorozole;
(xxiii) Antiandrogens (i.e. androgen receptor antagonists) and related agents for example bicalutamide, nilutamide, flutamide, cyproterone, or ketoconazole;
(xxiv) Hormones and analogues thereof such as medroxyprogesterone, diethylstilbestrol (a.k.a. diethylstilboestrol) or octreotide;
(xxv) Steroids for example dromostanolone propionate, megestrol acetate, nandrolone (decanoate, phenpropionate), fluoxymestrone or gossypol,
(xxvi) Steroidal cytochrome P450 17alpha-hydroxylase-17, 20-lyase inhibitor (CYP17), e.g. abiraterone;
(xxvii) Gonadotropin releasing hormone agonists or antagonists (GnRAs) for example abarelix, goserelin acetate, histrelin acetate, leuprolide acetate, triptorelin, buserelin, or deslorelin;
(xxviii) Glucocorticoids, for example prednisone, prednisolone, dexamethasone;
(xxix) Differentiating agents, such as retinoids, rexinoids, vitamin D or retinoic acid and retinoic acid metabolism blocking agents (RAMBA) for example accutane, alitretinoin, bexarotene, or tretinoin;
(xxx) Farnesyltransferase inhibitors for example tipifarnib;
(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;
(xxxii) Drugs targeting the ubiquitin-proteasome pathway including proteasome Inhibitors for example bortezomib, carfilzomib, CEP-18770, MLN-9708, or ONX-0912; NEDD8 inhibitors; HDM2 antagonist and deubiquitinases (DUBs);
(xxxiii) Photodynamic drugs for example porfimer sodium or temoporfin;
(xxxiv) Marine organism-derived anticancer agents such as trabectidin;
(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab or alpha radium 223;
(xxxvi) Telomerase inhibitors for example telomestatin;
(xxxvii) Matrix metalloproteinase inhibitors for example batimastat, marimastat, prinostat or metastat;
(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;
(xxxix) Selective immunoresponse modulators for example thalidomide, or lenalidomide;
(xl) Therapeutic Vaccines such as sipuleucel-T (Provenge) or OncoVex;
(xli) Cytokine-activating agents include Picibanil, Romurtide, Sizofiran, Virulizin, or Thymosin;
(xlii) Arsenic trioxide;
(xliii) Inhibitors of G-protein coupled receptors (GPCR) for example atrasentan;
(xliv) Enzymes such as L-asparaginase, pegaspargase, rasburicase, or pegademase;
(xlv) DNA repair inhibitors such as PARP inhibitors for example, olaparib, velaparib, iniparib, INO-1001, AG-014699, or ONO-2231;
(xlvi) Agonists of Death receptor (e.g. TNF-related apoptosis inducing ligand (TRAIL) receptor), such as mapatumumab (formerly HGS-ETR1), conatumumab (formerly AMG 655), PR095780, lexatumumab, dulanermin, CS-1008, apomab or recombinant TRAIL ligands such as recombinant Human TRAIL/Apo2 Ligand;
(xlvii) Immunotherapies such as immune checkpoint inhibitors; cancer vaccines and CAR-T cell therapy;
(xlviii) Regulators of Cell death (apoptosis) including Bcl-2 (B-cell lymphoma 2) antagonists such as venetoclax (ABT-199 or GDC-0199), ABT-737, ABT-263, TW-37, sabutoclax, obatoclax, and MIM1 and IAP antagonists including LCL-161 (Novartis), Debio-1143 (Debiopharma/Ascenta), AZD5582, Birinapant/TL-32711 (TetraLogic), CUDC-427/GDC-0917/RG-7459 (Genentech), JP1201 (Joyant), T-3256336 (Takeda), GDC-0152 (Genentech) or HGS-1029/AEG-40826 (HGS/Aegera);
(xlix) Prophylactic agents (adjuncts); i.e. agents that reduce or alleviate some of the side effects associated with chemotherapy agents, for example
anti-emetic agents,
agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim),
agents that inhibit bone resorption such as denosumab or bisphosphonates e.g. zoledronate, zoledronic acid, pamidronate and ibandronate,
agents that suppress inflammatory responses such as dexamethasone, prednisone, and prednisolone,
agents used to reduce blood levels of growth hormone and IGF-I (and other hormones) in patients with acromegaly or other rare hormone-producing tumours, such as synthetic forms of the hormone somatostatin e.g. octreotide acetate,
antidote to drugs that decrease levels of folic acid such as leucovorin, or folinic acid,
agents for pain e.g. opiates such as morphine, diamorphine and fentanyl,
non-steroidal anti-inflammatory drugs (NSAID) such as COX-2 inhibitors for example celecoxib, etoricoxib and lumiracoxib,
agents for mucositis e.g. palifermin,
agents for the treatment of side-effects including anorexia, cachexia, oedema or thromoembolic episodes, such as megestrol acetate.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, typically 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

Where the compound of the formula (I) is administered in combination therapy with one, two, three, four or more other therapeutic agents (typically one or two, more typically one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the typical method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets. Radiotherapy may be for radical, palliative, adjuvant, neoadjuvant or prophylactic purposes.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all components. In an alternative, the individual therapeutic agents may be formulated separately and presented together in the form of a kit, optionally with instructions for their use.

In one embodiment the pharmaceutical composition comprises a compound of formula I together with a pharmaceutically acceptable carrier and optionally one or more therapeutic agent(s)

In another embodiment the invention relates to the use of a combination according to the invention in the manufacture of a pharmaceutical composition for inhibiting the growth of tumour cells.

In a further embodiment the invention relates to a product containing a compound of formula I and one or more anticancer agent, as a combined preparation for simultaneous, separate or sequential use in the treatment of patients suffering from cancer.

EXAMPLES

The invention will now be illustrated, but not limited, by reference to the specific embodiments described in the following examples. Compounds are named using an automated naming package such as AutoNom (MDL) or ChemAxon Structure to Name or are as named by the chemical supplier. In the examples, the following abbreviations are used:

AcOH acetic acid
Boc tert-butyloxycarbonyl
Boc-Abu-OH (S)-2-(Boc-amino)butyric acid
BuLi butyllithium
CDI 1,1-carbonyldiimidazole
DAST Diethylaminosulfur trifluoride
DCM dichloromethane
DCMA Dicyclohexyylmethylamine
DIPEA N-ethyl-N-(1-methylethyl)-2-propylamine
DMC dimethyl carbonate
DMF N,N-dimethylformamide
DMSO dimethyl sulfoxide
EDC 1-ethyl-3-(3'-dimethylaminopropyl)-carbodiimide hydrochloride
Et$_3$N triethylamine
EtOAc ethyl acetate
EtOH ethanol
Et$_2$O diethyl ether
HATU 2-(7-aza-1H-benzotriazole-1-yl)-1,1,3,3-tetramethyluronium hexafluorophosphate
HBTU O-benzotriazole-N,N,N',N'-tetramethyl-uronium-hexafluoro-phosphate
HCl hydrochloric acid
HOAc acetic acid
HOAt 1-hydroxyazabenzotriazole
HOBt 1-hydroxybenzotriazole
HPLC high pressure liquid chromatography
IPA isopropyl alcohol
KHMDS potassium hexamethyldisilazide
LiHMDS lithium bis(trimethylsilyl)amide
MeCN acetonitrile
MeOH methanol
mins. minutes
MS mass spectrometry
MW microwave
NaBH(OAc)$_3$ sodium triacetoxyborohydride
NaOtBu potassium tert-butoxide
NMP N-methyl-2-pyrrolidinone
NMR nuclear magnetic resonance spectroscopy
Pd$_2$(dba)$_3$ tris(dibenzylideneacetone)dipalladium (o)
Pd(OAc)$_2$ palladium (2) acetate
Pd(PPh$_3$)$_4$ tetrakis(triphenylphosphine)palladium (0)
petrol petroleum ether fraction with boiling point range 40-60° C.
PyBrop bromo-tris-pyrrolidino-phosphonium hexafluorophosphate
RT room temperature
SiO$_2$ silica
TBTU N,N,N',N'-tetramethyl-O-(benzotriazol-1-yl)uronium tetrafluoroborate
TEA triethylamine
TFA trifluoroacetic acid
THF tetrahydrofuran
UV Ultraviolet
Column Chromatography Purification using column chromatography can be achieved, for example using a Biotage automated flash purification system with UV monitoring at 298 nm and collection at 254 nm. Biotage automated chromatography pre-packed silica cartridges were used in most cases. Where stated, the purification of some compounds was performed using Biotage C18 reversed phase silica columns, which have octadecyl (end-capped) functionalised silica or Biotage KP-NH cartridges were used for the separation of highly polar compounds, which uses primary amine bonded silica.

Where necessary, semi-preparative HPLC can be carried out, for example using one of the following machines: (i) Varian Prostar Modular HPLC system with a binary pumping system, UV detector and fraction collector and controlled by Varian Star software. (ii) Agilent 1200 HPLC system with a binary pump, autosampler, fraction collector and diode array detector and controlled by Agilent ChemStation software.

Analytical LC-MS System Description

In the following examples, many of the compounds prepared were characterised by mass spectroscopy using the systems and suitable operating conditions set out below. Where atoms with different isotopes are present and a single mass quoted, the mass quoted for the compound is the monoisotopic mass (i.e. $^{35}$Cl; $^{79}$Br etc.). Several systems can be used, as described below, and these can be equipped with, and can be set up to run under, closely similar operating conditions. Possible operating conditions are also described below.

Agilent 1200SL-6140 LC-MS System—RAPID:
HPLC System: Agilent 1200 series SL
Mass Spec Detector: Agilent 6140 single quadrupole
Second Detector: Agilent 1200 MWD SL
Agilent MS Running Conditions:
Capillary voltage: 3000V on ES pos (2700V on ES Neg)
Fragmentor/Gain: 190 on ES pos (160 on ES neg)
Gain: 1

Drying gas flow: 12.0 L/min
Gas Temperature: 345° C.
Nebuliser Pressure: 60 psig
Scan Range: 125-800 amu
Ionisation Mode: ElectroSpray Positive-Negative switching Shimadzu Nexera LC-MS System
HPLC System: Shimadzu SIL-30AC autosampler/2× Shimadzu LC-30AD pumps
Mass Spec Detector: Shimadzu LCMS-2020 single quadrupole MS
Second Detector: Shimadzu SPD-M20A diode array detector Shimadzu MS Running Conditions:
Qarray DC voltage: 20V on ES Pos (−20V on ES Neg)
Drying gas flow: 20.0 L/min
DL Temperature: 300° C.
Heat Block Temperature: 350° C.
Nebulising Gas Flow: 1.5 L/min
Scan Range: 100-750 amu
Ionisation Mode: ElectroSpray Positive-Negative switching Mass Directed Purification LC-MS System Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Several systems for purifying compounds via preparative LC-MS are described below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Preparative LC-MS System Description:
Waters Fractionlynx System:
Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Software:
Masslynx 4.1

Waters MS Running Conditions:
Capillary voltage: 3.5 kV (3.2 kV on ES Negative)
Cone voltage: 25 V
Source Temperature: 120° C.
Multiplier: 500 V
Scan Range: 125-800 amu
Ionisation Mode: ElectroSpray Positive or
ElectroSpray Negative Agilent 1100 LC-MS Preparative System:
Hardware:
Autosampler: 1100 series "prepALS"
Pump: 1100 series "PrepPump" for preparative flow gradient and 1100 series "QuatPump" for pumping modifier in prep flow
UV detector: 1100 series "MWD" Multi Wavelength Detector
MS detector: 1100 series "LC-MSD VL"
Fraction Collector: 2×"Prep-FC"
Make Up pump: "Waters RMA"
Agilent Active Splitter
Software:
Chemstation: Chem32
Agilent MS Running Conditions:
Capillary voltage: 4000 V (3500 V on ES Negative)
Fragmentor/Gain: 150/1
Drying gas flow: 13.0 L/min
Gas Temperature: 350° C.
Nebuliser Pressure: 50 psig
Scan Range: 125-800 amu
Ionisation Mode: ElectroSpray Positive or
ElectroSpray Negative Columns:
A range of commercially available columns—both achiral and chiral—may be used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge Prep Phenyl 5μ OBD 100×19 mm, XBridge Prep C18 5μ OBD 100×19 mm, Waters Atlantis Prep T3 OBD 5μ 100×19 mm and SunFire Prep C18 OBD 5μ 100×19 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.

Eluents:
Mobile phase eluent was chosen in conjunction with column manufacturers recommended stationary phase limitations in order to optimise a columns separation performance.

Methods:
According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen.

Solvent:
All compounds were usually dissolved in 100% MeOH or 100% DMSO or 90:10 Methanol:Water+0.2% Formic Acid.

Supercritical Fluid Chromatography (SFC)

In some cases, final compounds were purified by Supercritcal Fluid Chromatography (SFC) using a Waters Thar Prep100 preparative SFC system (P200 CO2 pump, 2545 modifier pump, 2998 UV/VIS detector, 2767 liquid handler with Stacked Injection Module). The Waters 2767 liquid handler acted as both auto-sampler and fraction collector.

The column used for the preparative purification of the compounds was a Diacel Chiralpak IA/IB/IC, YMC Amylose/Cellulose C or Phenomenex Lux Cellulose-4 at 5 um 20-21.2×250 mm unless otherwise stated.

Appropriate isocratic methods were selected based on methanol, ethanol or isopropanol solvent systems under un-modified or basic conditions. The standard method used was typically 5-55% modifier/CO2, 100 ml/min, 120 Bar backpressure, 40° C. column temperature.

All compounds were screened analytically prior to the purification step. Each sample was run under both un-modified and basic conditions (5.0 ul injection, 5/95 gradient for 5 minutes) across ethanol, methanol and isopropanol. If necessary, secondary screen across extended solvents such as acetonitrile, ethyl acetate and THF may also be considered. A decision was then made by the analyst as to what pH and which isocratic condition to use depending on where the desired product elutes and the separation achieved.

The modifier used under basic conditions was diethyl amine (0.1% V/V). Occasionally formic acid (0.1% V/V) may be used as an acidic modifier.

The purification was controlled by Waters Fractionlynx software through monitoring at 210-400 nm and triggered a threshold collection value at 260 nm unless otherwise started. Collected fractions were analysed by SFC (Waters/Thar SFC systems with Waters SQD). The fractions that contained the desired product were concentrated by vacuum centrifugation.

From the information provided someone skilled in the art could purify the compounds described herein by preparative LC-MS.

Synthetic Methods

By following methods similar and/or analogous to general procedures below, the compounds set out below were prepared.

The following synthetic procedures are provided for illustration of the methods used; for a given preparation or step the precursor used may not necessarily derive from the individual batch synthesised according to the step in the description given.

Where a compound is described as a mixture of two diastereoisomers/epimers, the configuration of the stereocentre is not specified and is represented by straight lines.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

Some of the compounds below are isolated as the salt, for example depending on the acid used in the purification method. Some compounds are isolated as the free base.

Compounds containing a single stereocentre (R-configuration) at the 3-position are typically isolated as a single isomer using preparative chiral HPLC (as described in general methods); at (or towards) the final stage of the synthetic sequence. In these cases the stereochemistry at the 3-position is designated in accordance with IUPAC, using 'hashed' or 'solid' wedged lines. Unless stated otherwise, a straight line at a stereocentre indicates the compound exists as a mixture of both isomers.

An example (3R)-3-(4-chlorophenyl)-2-[(4-chlorophenyl)methyl]-3-{[1-(hydroxymethyl)cyclopropyl]methoxy}-6-(2-hydroxypropan-2-yl)-2,3-dihydro-1H-isoindol-1-one is shown in Figure A.

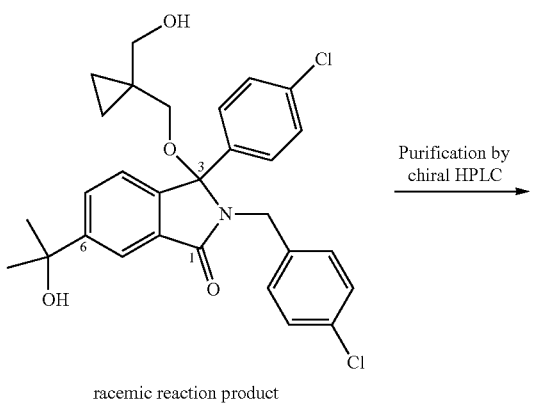

racemic reaction product

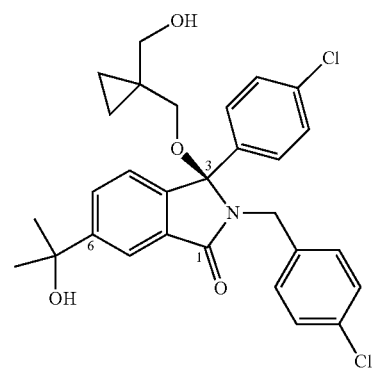

Example (single enantiomer with R-configuration)

Figure A: Example showing purification of 3R-isomer by chiral HPLC

Compounds containing a second stereocentre (e.g. adjacent to the 6-position) are typically isolated as a single isomer by preparative achiral and/or chiral HPLC. In these cases, the stereochemistry at the 3 position is designated in the usual fashion, using 'hashed' or 'solid' wedged lines. An asterisk (*) at the second stereocentre indicates one (or both) of the diastereoisomers associated with this position was/were isolated separately. For example, the 2 isomers of (3R)-2-[(4-chloro-2-methanesulfonylphenyl)methyl]-3-(4-chlorophenyl)-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one were separated by preparative achiral and/or chiral HPLC to give two separate Examples (Figure B).

Note: Depending on the specific substitution pattern, the numbering system in some analogues may differ, according to the formal convention of nomenclature.

125

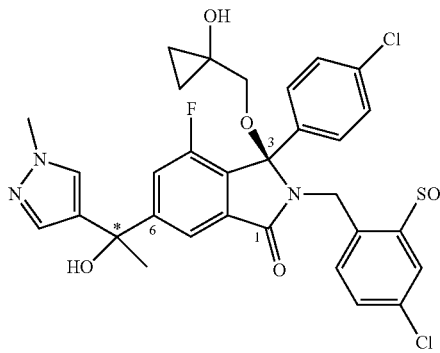

126

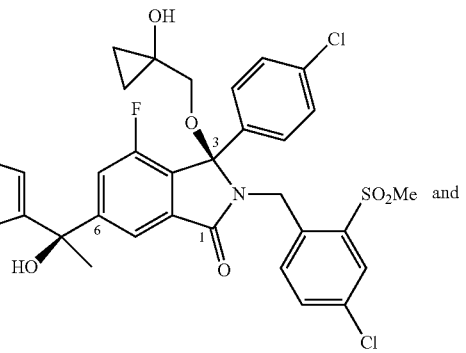

R,R-isomer and

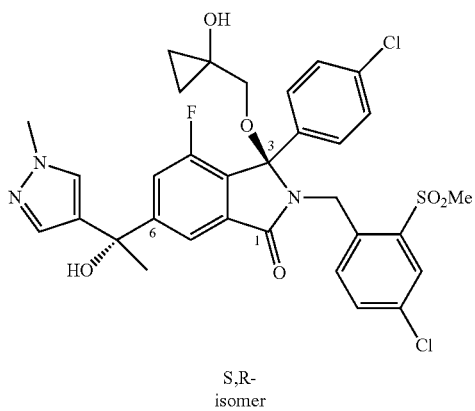

S,R-isomer

Figure B: Asterisk (*) means the two isomers were separated and isolated to give the two diastereoisomeric examples (Example 75 and 76)

In other cases, isomers were separated at an intermediate stage in the synthesis and only one isomer progressed to the final Example. The relevant isomers can be characterised by either optical rotation of linearly polarized light and/or or relative retention time on a chiral HPLC column. In these cases, an asterisk (*) indicates that the compound was isolated as a single isomer. This is illustrated by Example 80 (Figure C)

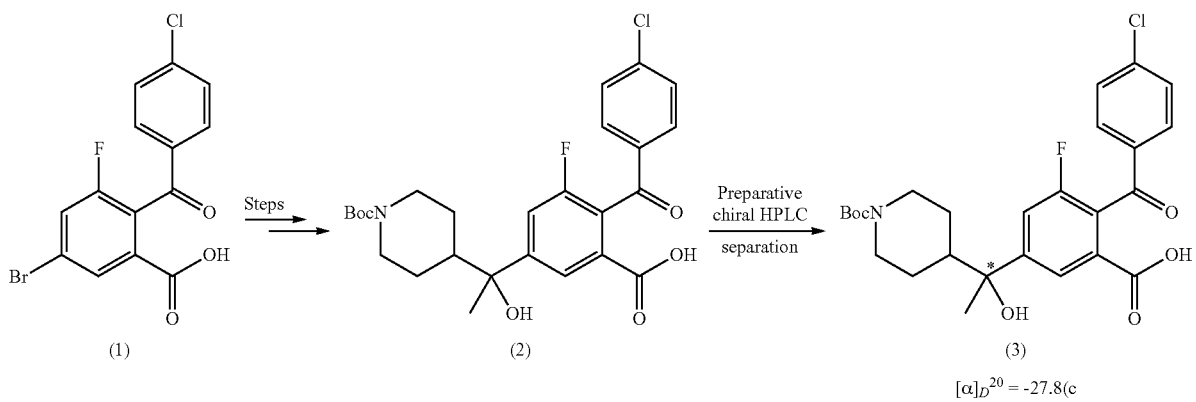

$[\alpha]_D^{20} = -27.8$(c 1.8, MeOH).
'slower' running enatiomer by chiral HPLC Steps

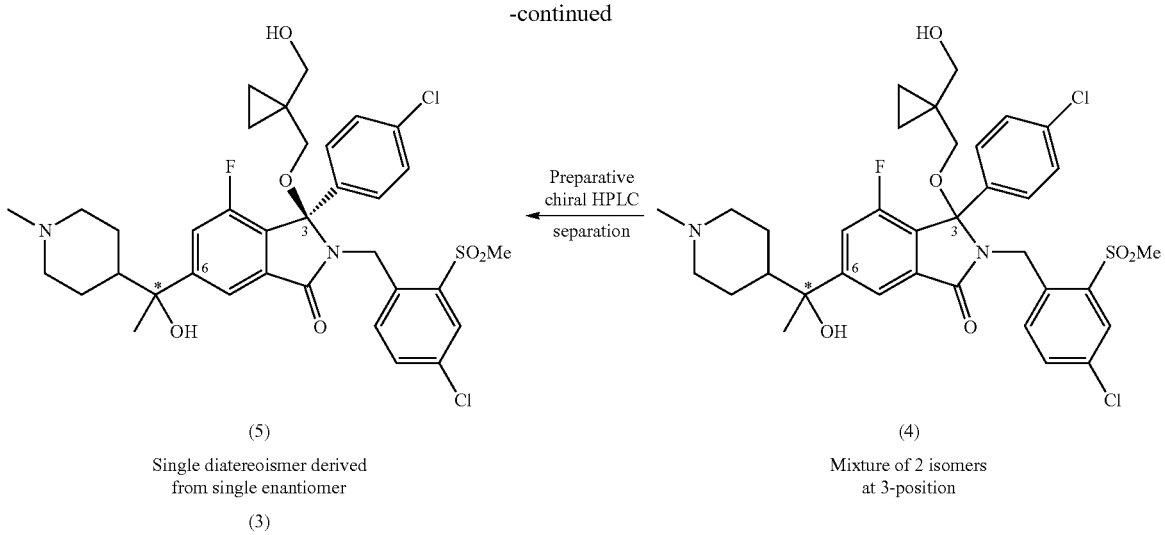

(5)
Single diatereoismer derived
from single enantiomer
(3)

(4)
Mixture of 2 isomers
at 3-position

Figure C: Synthesis of Example 80, (3R)-2-[(4-chloro-2-methanesulfonylphenyl)methyl]-3-(4-chlorophenyl)-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one. Example is derived from the levorotary enantiomer of compound (3), followed by a preparative chiral HPLC at the final stage.

The optical isomers may be characterised by their optical activity (i.e. as + and − isomers, or d and l isomers). The stereocentre can also assigned as "R or S" according to the nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers of basic compounds can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomeric salts by preferential crystallisation, and then dissociating the salts to give the individual enantiomer of the free base. Likewise, optical isomers of acidic compounds can be separated by forming diastereoisomeric salts with chiral amines such as Brucine, Cinchonidine, quinine etc.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product. Examples could include making menthol esters of an acidic compound.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Examples 1-137

Preparation 1. 4-Fluoro-2-hydroxybenzaldehyde

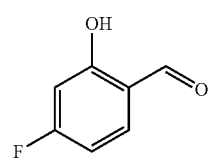

To a mixture of 3-fluorophenol (415 mg, 3.70 mmol) and anhydrous MgCl₂ powder (1.06 g, 11.1 mmol) in anhydrous acetonitrile (20 mL) was added anhydrous triethylamine (1.94 mL) and paraformaldehyde (811 mg, 27.0 mmol). The mixture was heated to reflux for 4.25 h, during which time there was a colour change from white to pink to yellow. The reaction mixture was cooled to room temperature and 5% aqueous HCl was added (20 mL). The product was extracted with EtOAc (2×50 mL) and the combined organic extracts washed with $H_2O$ (3×50 mL), brine (50 mL), dried over anhydrous $MgSO_4$ and the solvent removed in vacuo. FCC [dichloromethane-methanol (100:0)→(97:3)] of the crude residue afforded the title Preparation 1 (367 mg, 71%) as a white solid; $R_f$ 0.83 (10% $MeOH:CH_2Cl_2$); $^1$H NMR (500 MHz, $CDCl_3$) δ 11.35 (1H, d, J=1.6 Hz, CHO), 9.82 (1H, s), 7.55 (1H, dd, J=6.3 and 8.6 Hz), 6.71 (1H, dt, J=2.4 and 8.3 Hz) and 6.66 (1H, dd, J=2.4 and 10.4 Hz), $^{19}$F NMR (470.7 MHz, $CDCl_3$) δ −97.53 (m).

Preparation 2: N'-(5'-Bromo-2'-hydroxybenzylidene)-4-chlorobenzohydrazide

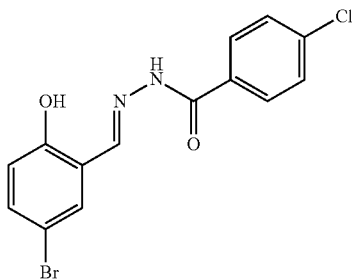 [SMILES: O=C(N/N=C/c1cc(Br)ccc1O)c1ccc(Cl)cc1]

By following a similar procedure to Preparation 3,5-bromo-2-hydroxybenzaldehyde (10 g, 49.7 mmol) and 4-chlorobenzhydrazide (8.5 g, 49.7 mmol) gave Preparation 2 as an off white solid which was used in the next step without further purification (16.5 g, 94%), $δ_{max}/cm^{-1}$ 1014, 1266, 1354, 1476, 1642, 3069, 3218; $δ_H$(500 MHz; DMSO) 6.91 (1H, d, J=8.6, 3'-H), 7.44 (1H, dd, J=2.3, 8.7, 4'-H), 7.61-7.67 (2H, m, Ar—H), 7.81 (1H, d, J=2.3, 6'-H), 7.94-8.01 (2H, m, Ar—H), 8.62 (1H, s, 1'-CH), 11.2 (1H, br. s, NH), 12.24 (1H, br. s, OH).

Preparation 3: (E)-N'-(5-Bromo-3-fluoro-2-hydroxybenzylidene)-4-chlorobenzohydrazide

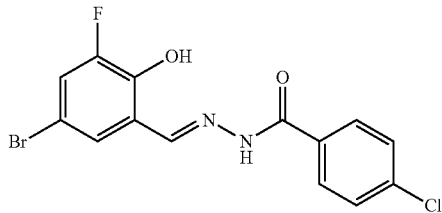 [SMILES: O=C(N/N=C/c1cc(Br)cc(F)c1O)c1ccc(Cl)cc1]

To a solution of 5-bromo-3-fluoro-2-hydroxybenzaldehyde (1.06 g, 4.83 mmol) in acetic acid (23 mL) was added 4-chlorobenzhydrazide (824 mg, 4.83 mmol) at room temperature and the resulting mixture stirred for 15 min. The suspension was poured onto water (20 mL) at 0° C. and the resulting precipitate collected by filtration. The solid was washed with water (3×20 mL), then petrol (3×20 mL) and the product dried overnight in the vacuum oven to afford (E)-N'-(5-bromo-3-fluoro-2-hydroxybenzylidene)-4-chlorobenzohydrazide Preparation 3 (1.69 g, 94%) as a pale yellow solid, which was used without further purification; $R_f$ 0.84 (10% $MeOH:CH_2Cl_2$); $λ_{max}$(EtOH)/nm 237.8, 292.6, 303.6 and 333.0; IR (cm$^{-1}$) 1098, 1158, 1242, 1463, 1521, 1591, 1660, 2360 and 3261; mp 245° C. (decomp.); 1H NMR (500 MHz, DMSO) δ 12.39 (1H, br.s), 11.64 (1H, br.s), 8.63 (1H, s, HC═N), 7.98 (1H, d, J=8.5 Hz, 2×ArH), 7.69 (1H, s, ArH), 7.65 (2H, d, J=8.5 Hz, 2×ArH) and 7.60 (1H, dd, J=2.2 and 10.4 Hz, ArH). LRMS (ESI+) m/z 371.2 [M]$^+$.

Preparation 4:
5-Bromo-2-(4-chlorobenzoyl)benzaldehyde

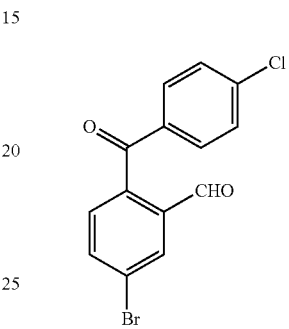

By following a similar procedure to preparation 5, N'-(5'-bromo-2'-hydroxybenzylidene)-4-chlorobenzohydrazide (Preparation 2) (16.53 g, 46.7 mmol), Pb(OAc)$_4$ (20.7 g, 46.7 mmol) and THF (492 mL). Purified on silica gel eluting with 20→85% EtOAc/Hexane to give the Preparation 4 as an orange solid (13.41, 88%). $δ_{max}/cm^{-1}$ 764, 927, 1189, 1277, 1585, 1663, 1698, 2354, 2840, 3086; $δ_H$(500 MHz; CDCl$_3$) 7.37 (1H, d, J=8.2, 3-H), 7.43-7.46 (1H, m, Ar—H), 7.70-7.73 (2H, m, Ar—H), 7.82 (1H, dd, J=2.0, 7.9, 4-H), 8.14 (1H, d, J=2.0, 6-H). m/z (ESI+) 323 (M+80%) 325 (100%).

Preparation 5:
5-Bromo-2-(4-chlorobenzoyl)-3-fluorobenzaldehyde

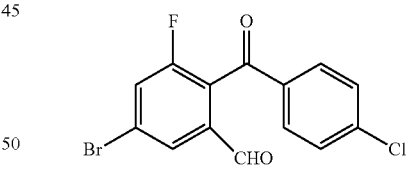

To a suspension of (E)-N'-(5-bromo-4-fluoro-2-hydroxybenzylidene)-4-chlorobenzohydrazide (Preparation 3) (1.67 g, 4.49 mmol) in THF (45 mL) was added Pb(OAc)$_4$ (1.99 g, 4.49 mmol) portionwise. The resulting orange solution was stirred at room temperature for 2 h and then filtered through Celite®, eluting with EtOAc (30 mL). The organics were washed with saturated aqueous NaHCO$_3$ (50 mL), brine (50 mL) dried over anhydrous Na$_2$SO$_4$, and the solvent removed in vacuo. FCC [petrol-ethyl acetate (100:0)→(95:5)] of the crude residue afforded 5-Bromo-2-(4-chlorobenzoyl)-3-fluorobenzaldehyde Preparation 5 (1.29 g, 84%) as a yellow solid; $R_f$ 0.87 (40% EtOAc:Petrol); $λ_{max}$ (EtOH)/nm 201.8 and 258.4; IR (cm$^{-1}$) 1095, 1249, 1271, 1586, 1649, 1710, 2920 and 3072; mp 120.6-122.0° C.; 1H NMR (500 MHz, DMSO) δ 9.87 (1H, s, CHO), 8.27 (1H, d, J=1.6

Hz, HCCBr), 8.15 (1H, dd, J=1.6 and 8.8 Hz, HCCF) 7.75 (2H, d, J=8.5 Hz, 2×Ar) and 7.59 (2H, d, J=8.5 Hz, 2×ArH). LRMS (ESI+) m/z 341.2 [M]+.

Preparation 6: 5-Bromo-2-(4-chlorobenzoyl)benzoic Acid

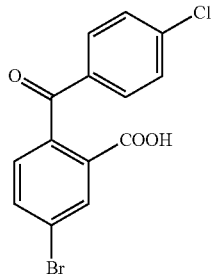 [SMILES: O=C(O)c1cc(Br)ccc1C(=O)c1ccc(Cl)cc1]

Following procedures similar to these described in Preparation 7; 5-bromo-2-(4-chlorobenzoyl)benzaldehyde (Preparation 4) (7.4 g, 22.9 mmol), sodium chlorite (2.9 g, 29.7 mmol), sulfamic acid (2.77 g, 30.6 mmol), acetonitrile (213 mL) and water (72 mL) gave Preparation 6 as a beige solid and was used in the next step without further purification (7.4 g, 95%). $\delta_{max}$/cm$^{-1}$ 1014, 1090, 1252, 1270, 1288, 1305, 1423, 1481, 1582, 1671, 2551, 2658, 2800; $\delta_H$(500 MHz; DMSO) 7.44 (1H, d, J=8.0, 4-H), 7.56-7.60 (2H, m, Ar—H), 7.63-7.67 (2H, m, Ar—H), 7.96 (1H, dd, J=2.0, 8.0, 4-H), 8.11 (1H, d, J=2.0, 6-H), 13.64 (1H, br s, COOH). m/z (ESI−) 337 (75%) 339 (M+100%) 341 (25%).

Preparation 7: 5-Bromo-2-(4-chlorobenzoyl)-3-fluorobenzoic Acid

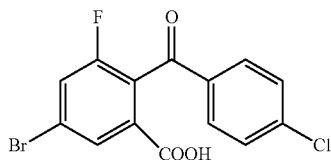 [SMILES: O=C(O)c1cc(Br)cc(F)c1C(=O)c1ccc(Cl)cc1]

To a solution of 5-Bromo-2-(4-chlorobenzoyl)-3-fluorobenzaldehyde (Preparation 5) (1.27 g, 3.71 mmol) in acetonitrile (48 mL) was added a solution of sodium chlorite (436 mg, 4.82 mmol) in water (5.4 mL), followed by a solution of sulfamic acid (468 mg, 4.82 mmol) in water (5.4 mL). The resulting yellow solution was stirred at room temperature for 3 h and then the solvent removed in vacuo. The resulting yellow solid was dissolved in ethyl acetate (30 mL) and washed with water (30 mL), brine (30 mL), dried over anhydrous Na$_2$SO$_4$ and the solvent removed to give 5-bromo-2-(4-chlorobenzoyl)-3-fluorobenzoic acid Preparation 7 (1.33 g, 100%) as a pale yellow solid, which was used without any further purification; R$_f$ 0.23 (10% MeOH: CH$_2$Cl$_2$); $\lambda_{max}$ (EtOH)/nm 207.0 and 258.0; IR (cm$^{-1}$) 1087, 1269, 1397, 1590, 1678, 1711 and 3072; mp 155° C. (decomp.); $^1$H NMR (500 MHz, DMSO) δ 13.93 (1H, br. s, COOH), 8.07 (1H, dd, J=1.5 and 9.0 Hz, HCCF), 8.00 (1H, d, J=1.5 Hz, HCCBr), 7.74 (2H, d, J=8.5 Hz, 2×Ar) and 7.59 (2H, d, J=8.5 Hz, 2×ArH). LRMS (ESI−) m/z 357.0 [M]−.

Preparation 8: 6-Bromo-2-(4-chlorobenzyl)-3-(4-chlorophenyl)-3-hydroxyisoindolin-1-one

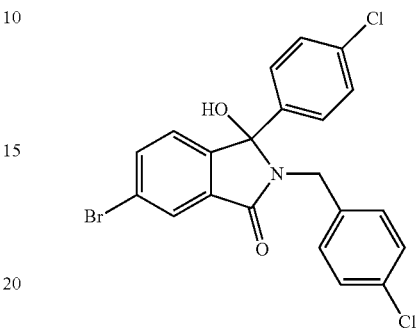

The title compound was prepared from 5-bromo-2-(4-chlorobenzoyl)benzoic acid (7.4 g, 21.8 mmol) using a procedure similar to that described for Preparation 9. The product was obtained as a yellow solid (6.78 g, 66%) m/z (ESI−) 462 (100%) (M+H$^+$)$^+$ Preparation 9: 6-Bromo-2-(4-chlorobenzyl)-3-(4-chlorophenyl)-4-fluoro-3-hydroxyisoindolin-1-one

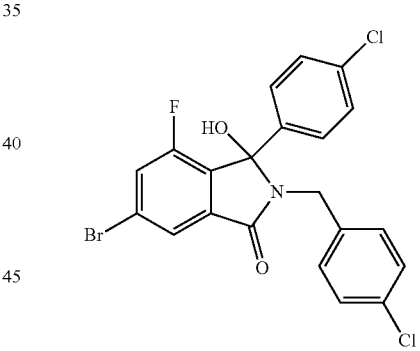

To a solution of 5-bromo-2-(4-chlorobenzoyl)-3-fluorobenzoic acid (Preparation 7) (509 mg, 1.42 mmol) in anhydrous THF (7.1 mL) was added thionyl chloride (0.21 mL, 2.85 mmol) and a catalytic quantity of DMF (1 drop) and the yellow mixture stirred at room temperature for 4 h, then concentrated under reduced pressure. The residue was dissolve in anhydrous THF (7.1 mL) and 4-chlorobenzylamine (0.19 mL, 1.56 mmol) and Hünigs base (0.27 mL, 1.56 mmol) were added and the mixture stirred at room temperature for 16 h. The reaction was diluted with EtOAc (20 mL) and the solution washed with water (3×20 mL) and brine (20 mL), dried over anhydrous MgSO$_4$ and concentrated in vacuo to give a dark orange oil. FCC [petrol-ethyl acetate (100:0)→(95:5)→(80:20)] of the crude residue afforded 6-bromo-2-(4-chlorobenzyl)-3-(4-chlorophenyl)-4-fluoro-3-hydroxyisoindolin-1-one Preparation 9 (624 mg, 91%) as a pale yellow solid; LRMS (ESI−) m/z 480.1 [M−H]−.

Preparation 10: 6-Bromo-2-(4-chlorobenzyl)-3-(4-chlorophenyl)-3-((1-(hydroxymethyl) cyclopropyl)methoxy)isoindolin-1-one

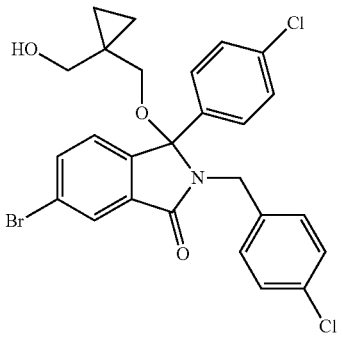 [SMILES: O=C1c2cc(Br)ccc2C(OCC2(CO)CC2)(c2ccc(Cl)cc2)N1Cc1ccc(Cl)cc1]

To a solution of 6-bromo-2-(4-chlorobenzyl)-3-(4-chlorophenyl)-3-hydroxyisoindolin-1-one (Preparation 8) (1 g, 2.1 mmol) and 1,1-Bis(hydroxymethyl)cyclopropane (0.604 mL, 6.3 mmol) in DCE (21 mL) was added InBr$_3$ (76 mgs, 0.21 mmol) and the resulting mixture was heated to 95° C. for 3 hours. The reaction was cooled to room temperature before being washed with water, brine, and the organic phase dried (MgSO$_4$), filtered and conc. in vacuo. Purification on silica gel (Biotage SP4) eluting with 20%→95% EtOAc/pet gave Preparation 10 as a brown gum (921 mgs; 80%). (500 MHz, CDCl$_3$) 0.10-0.19 (2H, m), 0.37-0.46 (2H, m), 1.53 (1H, t), 2.65 (1H, d), 2.81 (1H, d), 3.36 (1H, dd), 3.50 (1H, dd), 4.17 (1H, d), 4.50 (1H, d), 7.01 (1H, d), 7.08-7.22 (8H, m), 7.63 (1H, dd), 8.02 (1H, d).

Preparation 11: 6-Bromo-3-((1-(((tert-butyldimethylsilyl)oxy)methyl)cyclopropyl)methoxy)-2-(4-chlorobenzyl)-3-(4-chlorophenyl)isoindolin-1-one

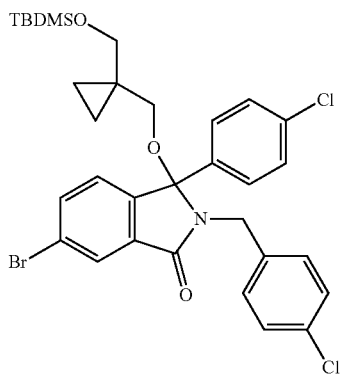 [SMILES: CC(C)(C)[Si](C)(C)OCC1(COC2(c3ccc(Cl)cc3)c3ccc(Br)cc3C(=O)N2Cc2ccc(Cl)cc2)CC1]

Preparation 10 (0.8 g, 1.46 mmol), imidazole (0.370 g, 5.44 mmol), TBDMSCl (0.496 g, 3.29 mmol) in THF (10 mL/0.7 mmol) was heated at 85° C. for 7 hours. After work-up, the crude material was purified using chromatography on silica (Pet:EtOAc 1:0 to 4:1) to give the desired product Preparation 11 as a colorless oil (0.928 g, 1.403 mol) in 96 $^1$H NMR (500 MHz, CDCl$_3$) δ (ppm) −0.02 (s, 3H), 0.00 (s, 3H), 0.06-0.15 (m, 2H), 0.30-0.43 (m, 2H), 0.83 (s, 9H), 2.61 (d, 1H), 2.87 (d, 1H), 3.35 (d, 1H), 3.65 (d, 1H), 4.30 (d, 1H), 4.37 (d, 1H), 6.97 (d, 1H), 7.04 (d, 2H), 7.10 (d, 2H, J=8.5 Hz, Ar—H), 7.12-7.20 (m, 4H, Ar—H), 7.60 (dd, 1H), 8.02 (d, 1H); MS(ES+) m/z 456.4 [M+H]$^+$.

Preparation 12: 6-Bromo-2-(4-chlorobenzyl)-3-(4-chlorophenyl)-4-fluoro-3-((1-(hydroxymethyl)cyclopropyl)methoxy)isoindolin-1-one

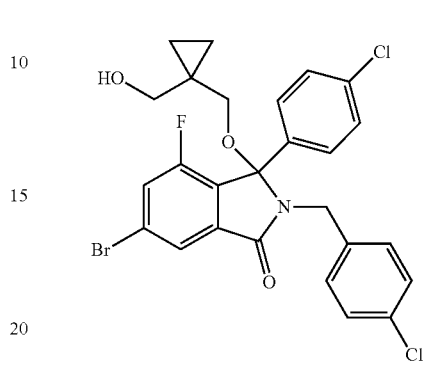

To a solution of 6-bromo-2-(4-chlorobenzyl)-3-(4-chlorophenyl)-4-fluoro-3-hydroxyisoindolin-1-one (Preparation 9) (603 mg, 1.25 mmol) in anhydrous THF (7 mL) was added thionyl chloride (0.18 mL, 2.50 mmol) and a catalytic quantity of DMF (2 drops) and the orange mixture stirred at room temperature for 4 h, then concentrated under reduced pressure. The residue was dissolved in anhydrous THF and then a solution of 1,1-bis(hydroxymethyl)cyclopropane (0.24 mL, 2.50 mmol) and K$_2$CO$_3$ (345 mg, 2.50 mmol) were added and the reaction mixture stirred at room temperature for 18 h. The reaction mixture was diluted with EtOAc (10 mL) and washed with water (3×20 mL), brine (20 mL), dried over Na$_2$SO$_4$, filtered and the solvent removed in vacuo. FCC [petrol-ethyl acetate (100:0)→(80:20)] of the crude residue afforded 6-bromo-2-(4-chlorobenzyl)-3-(4-chlorophenyl)-4-fluoro-3-((1-(hydroxymethyl)cyclopropyl)methoxy)isoindolin-1-one Preparation 12 (389 mg, 55%) as a yellow gum; $^1$H NMR (500 MHz, DMSO) δ 0.13 (2H, m), 0.34 (2H, m), 2.81 (1H, d), 2.86 (1H, d), 3.28 (1H, dd), 3.35 (1H, dd), 4.28 (1H, d), 4.34 (1H, d), 7.05 (2H, d), 7.19 (2H, d, J=8.5 Hz, 2×ArH), 7.25 (2H, d, J=8.4 Hz, 2×ArH), 7.30 (2H, d), 7.82 (1H, dd) and 7.89 (1H, dLRMS (ESI+) m/z 464.2 [M-C$_5$H$_9$O$_2$]$^+$ Preparation 13: 2-(4-Chlorobenzyl)-3-(4-chlorophenyl)-3-((1-(hydroxymethyl) cyclopropyl) methoxy)-6-(prop-1-en-2-yl)isoindolin-1-one

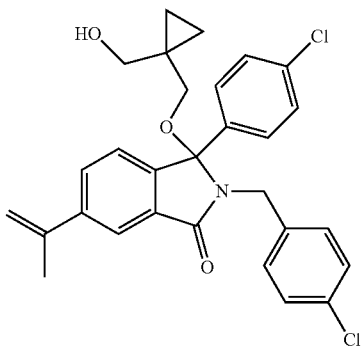 [SMILES: C=C(C)c1ccc2c(c1)C(=O)N(Cc1ccc(Cl)cc1)C2(OCC1(CO)CC1)c1ccc(Cl)cc1]

A suspension of isopropenylboronic acid ester (239 µL, 1.27 mmol), 6-bromo-2-(4-chlorobenzyl)-3-(4-chlorophenyl)-3-((1-(hydroxymethyl) cyclopropyl)methoxy)isoindolin-1-one (Preparation 10) (465 g, 0.85 mmol), NaOH (35.7 mgs, 0.89 mmol), and N,N-dicyclohexylmethyl amine (0.191 mL, 0.894 mmol) in THF (4.63 mL) was degassed for 10 minutes before the addition of Pd(dppf)Cl$_2$ (62 mgs, 0.09 mmol). The resulting mixture was heated to a rapid reflux for 3 hours. The reaction was cooled to room temperature, diluted with DCM and washed with HCl (1M), water, brine, dried (MgSO$_4$), filtered and conc. in vacuo. Purification on silica gel eluting with 30% EtOAc/Hexanes gave Preparation 13 as a white foam (316 mgs; 73%); m/z (ESI+) 508.4 (10%), 406.3, 408.3 (70%).

Preparation 14: 2-(4-Chlorobenzyl)-3-(4-chlorophenyl)-4-fluoro-3-((1-(hydroxymethyl)cyclopropyl) methoxy)-6-(prop-1-en-2-yl)isoindolin-1-one

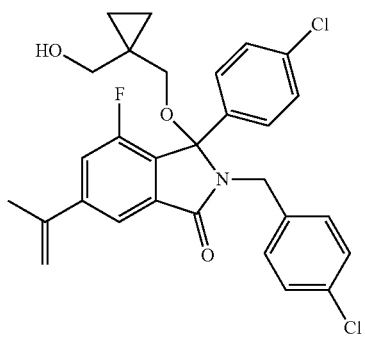 [SMILES: C=C(C)c1cc(F)c2c(c1)C(=O)N(Cc1ccc(Cl)cc1)C2(OCC1(CO)CC1)c1ccc(Cl)cc1]

6-bromo-2-(4-chlorobenzyl)-3-(4-chlorophenyl)-4-fluoro-3-((1-(hydroxymethyl)cyclopropyl)methoxy)isoindolin-1-one (Preparation 12) (194 mg, 0.343 mmol) was dissolved in anhydrous THF (4.6 mL) and powdered NaOH (14 mg, 0.343 mmol), DCMA (0.07 mL, 0.343 mmol) and iso-propenylboronic acid pinacol ester (0.1 mL, 0.514 mmol) were added sequentially at room temperature under a N$_2$ atmosphere. The solution was degassed with N$_2$ for 20 min, then Pd(dppf)Cl$_2$.CH$_2$Cl$_2$ (28 mg, 0.100 mmol) was added and the solution heated at reflux for 3.5 h. After cooling to room temperature, the reaction mixture was filtered through Celite®, rinsed with EtOAc, then transferred to a separating funnel and washed with 1M aq. HCl (20 mL), brine (20 mL), dried over Na$_2$SO$_4$, filtered and the solvent removed in vacuo. FCC [petrol-ethyl acetate (100: 0)→(85:15))→(70:30)] of the crude residue, followed by preparative HPLC, afforded 2-(4-chlorobenzyl)-3-(4-chlorophenyl)-4-fluoro-3-((1-(hydroxymethyl)cyclopropyl) methoxy)-6-(prop-1-en-2-yl)isoindolin-1-one Preparation 14 (150 mg, 83%) as a pale yellow gum; LRMS (ESI+) m/z 426.3 [M-C$_5$H$_9$O$_2$]$^+$.

Preparation 15: 6-Acetyl-2-(4-chlorobenzyl)-3-(4-chlorophenyl)-3-((3'-(hydroxymethyl) cyclopropyl) methoxy)isoindolin-1-one

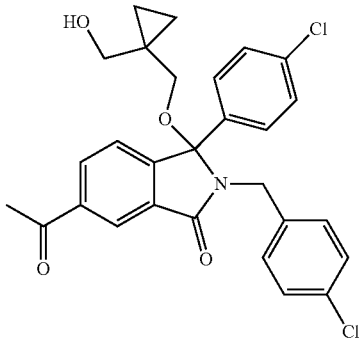 [SMILES: CC(=O)c1ccc2c(c1)C(=O)N(Cc1ccc(Cl)cc1)C2(OCC1(CO)CC1)c1ccc(Cl)cc1]

To a solution of 2-(4-chlorobenzyl)-3-(4-chlorophenyl)-3-((1-(hydroxymethyl) cyclopropyl) methoxy)-6-(prop-1-en-2-yl)isoindolin-1-one (preparation 13) (64 mgs, 0.125 mmol) in dioxane/H$_2$O (3:1, 1.23 mL) at room temperature was added 2,6-Lutidine (30 µL, 0.251 mmol), OsO$_4$ (~1 mg, 0.0025 mmol) and NaIO$_4$ (106 mg, 0.5 mmol) and the resulting mixture stirred until TLC indicted the complete consumption of the starting material. The reaction was diluted with water and DCM and the organic phase separated. The aqueous layer was extracted DCM (x3) and the combined organic phases washed with brine, dried (MgSO$_4$) and conc. in vacuo. Purification on silica gel (Biotage SP4) eluting with 20%→85% EtOAc/Pet gave Preparation 15 as white foam (37 mgs; 60%). HRMS (ESI+) 510.121 (MH$^+$).

Preparation 16: 3-(4-chlorophenyl)-2-((S)-1-(4-chlorophenyl)ethyl)-3-hydroxy-6-(prop-1-en-2-yl)isoindolin-1-one

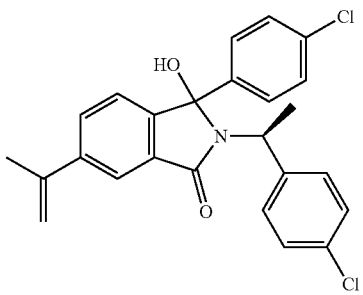 [SMILES: C=C(C)c1ccc2c(c1)C(=O)N([C@@H](C)c1ccc(Cl)cc1)C2(O)c1ccc(Cl)cc1]

The title compound was prepared using a mixture of Preparations 25a and 25b, by following a procedure similar to that described for Preparation 13. The crude material was purified using chromatography on silica (Pet:EtOAc 1:0 to 2:1) to give the desired diastereoisomers as a beige solid (2.255 g, 5.14 mmol).

Preparation 16a R$_f$=0.30 (Pet:EtOAc/9:1); MS(ES+) m/z 484.3 [M+H

Preparation 16b: R$_f$=0.15 (Pet:EtOAc/9:1);

Preparation 17: (E)-N'-(5-acetyl-2-hydroxybenzylidene)-4-chlorobenzohydrazide

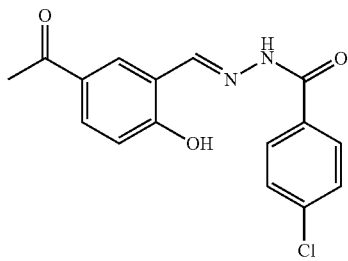 [SMILES: CC(=O)c1ccc(O)c(/C=N/NC(=O)c2ccc(Cl)cc2)c1]

The title compound was prepared from 5-acetyl-2-hydroxybenzaldehyde (500 mg, 3.1 mmol) using a procedure similar to that described for Preparation 3. The product was obtained as a yellow coloured solid (923 mg, 96. LRMS (ES$^+$) m/z 317.2 [M+H

Preparation 18: 5-Acetyl-2-(4-chlorobenzoyl)benzaldehyde

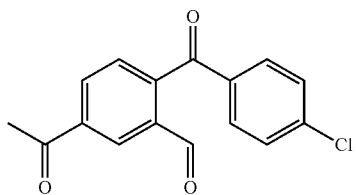 [SMILES: CC(=O)c1ccc(C(=O)c2ccc(Cl)cc2)c(C=O)c1]

The title compound was prepared from (E)-N'-(5-acetyl-2-hydroxybenzylidene)-4-chlorobenzohydrazide, (Preparation 17), (0.90 g, 2.8 mmol) and Pb(OAc)$_4$ (2.5 g, 5.7 mmol) using a procedure similar to that described for Preparation 5. LRMS (ES$^+$) m/z 287.3 [M+H]$^+$;

Preparation 19: 5-Acetyl-2-(4-chlorobenzoyl)benzoic Acid

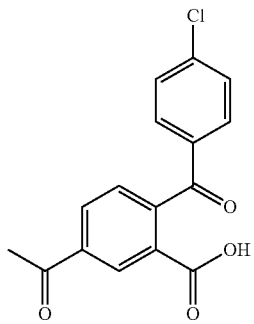 [SMILES: CC(=O)c1ccc(C(=O)c2ccc(Cl)cc2)c(C(=O)O)c1]

The title compound was prepared from 5-acetyl-2-(4-chlorobenzoyl)benzaldehyde, Preparation 18, (690 mg, 2.4 mmol) using a procedure similar to that described for Preparation 7. The product was obtained as an off-white coloured solid (753 mg, 100%). LRMS (ES) m/z 301.2 [M−H]$^-$;

Preparation 20: 6-Acetyl-2-(4-chlorobenzyl)-3-(4-chlorophenyl)-3-hydroxyisoindolin-1-one

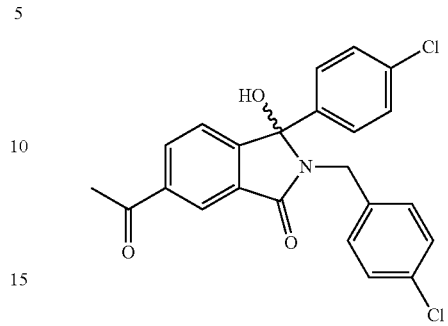

To a solution of 5-acetyl-2-(4-chlorobenzoyl)benzoic acid, Preparation 19, (2.0 g, 6.6 mmol) in THF (8 mL) was added thionyl chloride (0.96 mL, 13.2 mmol) and stirred at rt for 2 h before being concentrated in vacuo. The residue was dissolved in THF (8 mL) and 4-chlorobenzylamine (0.89 mL, 7.3 mmol) and Hünig's base (1.3 mL, 7.3 mmol) were added and stirred at rt for 2 h before being diluted with EtOAc (8 mL). Washed with water (8 mL), brine (8 mL), dried (MgSO$_4$) and concentrated in vacuo. Purification (SP4, silica, EtOAc/petrol, 40%) gave Preparation 20 as a yellow solid (1.52 g, 54%). $^1$H NMR (500 MHz, CDCl$_3$) δ 2.61 (3H, s, CH$_3$), 3.21 (1H, br s, OH), 4.18 (1H, d, J=15.0 Hz, NCHH), 4.68 (1H, d, J=15.0 Hz, NCHH), 7.14-7.26 (8H, m, H—Ar), 7.31 (1H, d, J=8.0 Hz, H-4), 8.07 (1H, dd, J=1.6, 8.0 Hz, H-5), 8.26 (1H, d, J=1.6 Hz, H-7). LRMS (ES$^-$) m/z 424.2 [M−H]$^-$;

Preparation 21: 6-Acetyl-2-(4-chlorobenzyl)-3-(4-chlorophenyl)-3-(2-hydroxyethoxy)isoindolin-1-one

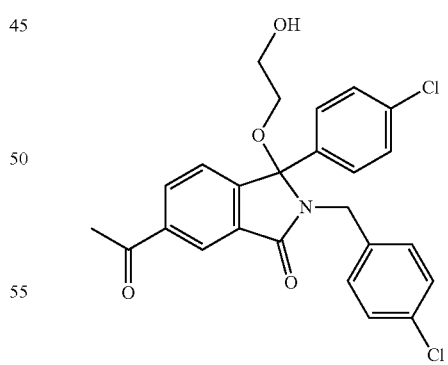

The title compound was prepared in a similar fashion to Preparation 10, but using 0.8 mol. eq of InBr$_3$ and 20 mol. eq of ethylene glycol. $^1$H NMR (500 MHz, CDCl$_3$) δ (ppm) 1.48-1.55 (m, 1H), 2.67 (s, 3H), 1.62 (s, 6H), 2.80-2.92 (m, 2H), 3.32-3.52 (m, 2H), 4.11 (d, 1H), 4.67 (d, 1H), 7.14-7.19 (m, 4H), 7.20-7.27 (m), 8.14 (dd, 1H), 8.43-8.46 (m). HMS(ES+) m/z 486.3 [M+H]$^+$;

Preparation 22: 6-Acetyl-3-(3-bromo-2,2-bis(hydroxymethyl)propoxy)-2-(4-chlorobenzyl)-3-(4-chlorophenyl)isoindolin-1-one

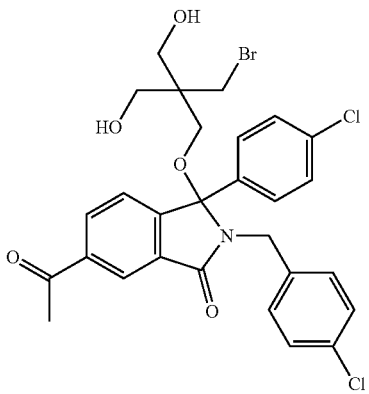 [SMILES: CC(=O)c1ccc2c(c1)C(=O)N(Cc1ccc(Cl)cc1)C2(OCC(CO)(CO)CBr)c1ccc(Cl)cc1]

6-Acetyl-isoindolinone derivative (Preparation 20) (0.3 g, 0.704 mmol) in THF (5 mL) under a dried atmosphere of $N_2$ was added $SOCl_2$ (0.103 mL, 1.41 mmol). The mixture was stirred for 2 hours at room temperature before to be concentrated in vacuo. To the residue were added 2-(bromomethyl)-2-(hydroxymethyl)-1,3-propanediol (0.42 g, 2.11 mmol) and anhydrous $K_2CO_3$ (0.194 g, 1.41 mmol), followed by THF (5 mL) and the reaction mixture was stirred overnight. After work-up, crude material was purified using chromatography on silica (Pet:EtOAc 1:0 to 0:1) to give a yellow solid Preparation 22 (0.186 g, 0.306 mmol. 1H NMR (500 MHz, CDCl$_3$) δ (ppm) 2.67 (s, 3H, COCH$_3$), 2.78 (d, 1H, J=9.0 Hz, OCCHHC), 3.00 (d, 1H, J=9.0 Hz, CCHHC), 3.45-3.65 (m, 6H, CCH$_2$Br, C(CH$_2$OH)$_2$), 4.41 (d, 1H, J=15.1 Hz, NCHH), 4.45 (d, 1H, J=15.1 Hz, NCHH), 7.02-7.11 (m, 4H, Ar—H), 7.13 (d, 2H, J=8.5 Hz, Ar—H), 7.18 (d, 2H, J=8.7 Hz, Ar—H), 7.27 (d, 1H, J=8.0 Hz, isoindolinone-H), 8.15 (dd, 1H, J=7.9, 1.6 Hz, isoindolinone-H), 8.45 (d, 1H, J=1.2 Hz, isoindolinone-H; MS(ES+) m/z 456.4 [M+H]$^+$;

Preparation 23: 6-Acetyl-2-(4-chlorobenzyl)-3-(4-chlorophenyl)-3-((3-(hydroxymethyl)oxetan-3-yl)methoxy)isoindolin-1-one

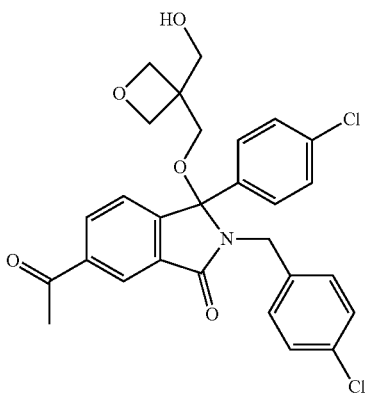 [SMILES: CC(=O)c1ccc2c(c1)C(=O)N(Cc1ccc(Cl)cc1)C2(OCC1(CO)COC1)c1ccc(Cl)cc1]

Bromo-diol (Preparation 22) (0.215 g, 0.354 mmol) was dissolved in EtOH (10 mL). KOH (0.023 g, 0.407 mmol) was added and the mixture was heated to 90° C. and stirred for 6 hours. Once back to room temperature, H$_2$O (10 mL) was added followed by introduction of an aqueous 1M solution of HCL until pH ~2-3. The mixture was extracted with EtOAc (3×20 mL) and the combined organic phases were washed with brine, dried over MgSO$_4$, filtered and evaporated in vacuo. Crude material purified using chromatography on silica (Pet:EtOAc 1:0 to 1:3) to give the desired product as a white foamy solid Preparation 23 (0.104 g, 0198 mmol) in 56 $^1$H NMR (500 MHz, CDCl$_3$) δ (ppm) 1.73 (bs, 1H, OH), 2.67 (s, 3H), 2.92 (d, 1H), 3.05 (d, 1H), 3.67-3.77 (m, 2H), 4.22 (d, 1H), 4.24-4.29 (m, 2H), 4.31 (d, 1H), 4.36 (d, 1H), 4.57 (d, 1H), 7.10 (d, 1H), 7.12-7.18 (m, 4H, H), 7.19-7.24 (m, 3H), 8.15 (dd, 1H), 8.46 (d, 1H); MS(ES+) m/z [M+H]$^+$; 456.1624.

Preparation 24: (R)-3-(4-Chlorophenyl)-2-((S)-1-(4-chlorophenyl)ethyl)-3-((2-(hydroxymethyl)allyl)oxy)-6-(prop-1-en-2-yl)isoindolin-1-one

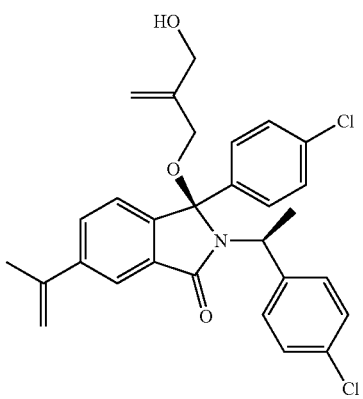 [SMILES: C=C(CO)CO[C@]1(c2ccc(Cl)cc2)c2ccc(C(=C)C)cc2C(=O)N1[C@@H](C)c1ccc(Cl)cc1]

3-(4-Chlorophenyl)-2-((S)-1-(4-chlorophenyl)ethyl)-3-hydroxy-6-(prop-1-en-2-yl)isoindolin-1-one, Preparation 16, (250 mg, 0.57 mmol), 2-methylene-1,3-propandiol (0.23 mL, 2.85 mmol), InBr$_3$ (305 mg, 0.86 mmol) and DCE (5 mL). Purification (SP4, silica, EtOAc/petrol, 25%) gave Preparation 24 as a white glassy solid (88 mg, 30%). R$_f$=0.64 (silica, EtOAc/petrol. $^1$H NMR (500 MHz, CDCl$_3$) δ 1.85 (3H, d, J=7.3 Hz, benzylic CH$_3$), 2.17 (3H, s, isopropene CH$_3$), 3.59 (1H, d, J=12.2 Hz, -iso-OCHH), 3.81 (1H, d, J=12.2 Hz, -iso-OCHH), 4.16-4.23 (2H, m, CH$_2$OH), 4.40 (1H, q, J=7.3 Hz, H-benzylic), 5.17-5.18 (1H, m, H-isopropene), 5.21-5.24 (2H, m, side-chain alkene CH$_2$), 5.44-5.45 (1H, m, H-isopropene), 6.95-7.10 (9H, m, H—Ar), 7.59 (1H, dd, J=1.7, 7.9 Hz, H-5), 7.92 (1H, d, J=1.7 Hz, H-7). LRMS (ES$^+$) m/z 508.4 [M+H]$^+$.

Preparation 25a and 25b: 6-Bromo-3-(4-chlorophenyl)-2-((S)-1-(4-chlorophenyl)ethyl)-3-hydroxy-isoindolin-1-one 25a

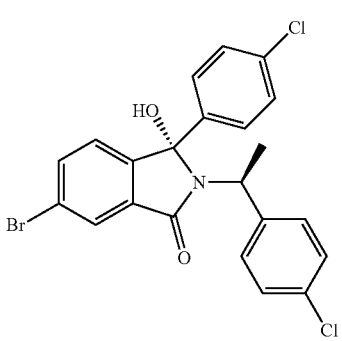

-continued

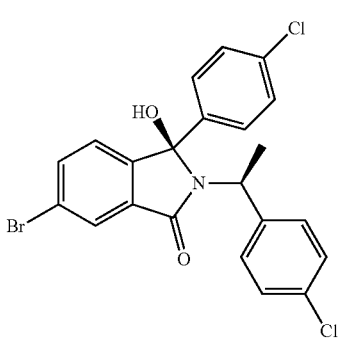
25b

Starting from 5-bromo-2-(4-chlorobenzoyl)benzoic acid (Preparation 6) and (1S)-1-(4-chlorophenyl)ethan-1-amine the title compounds, Preparation 25a and 25b were prepared using procedures similar to those described for Preparation 9. Products obtained as off white solids.

25a (S,S): MS (ES+) 477.3 [M+H]$^+$. R$_f$=0.73 (1:1 EtOAc/petrol);

25b (R,S): MS (ES+) 477.3 [M+H]$^+$. R$_f$=0.64 (1:1 EtOAc/petrol

Preparations 26a and 26b: 6-Bromo-3-(4-chlorophenyl)-2-((S)-1-(4-chlorophenyl)ethyl)-3-((1-hydroxymethyl)cyclopropyl) methoxy)isoindolin-1-one

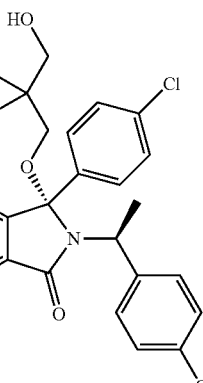
26a

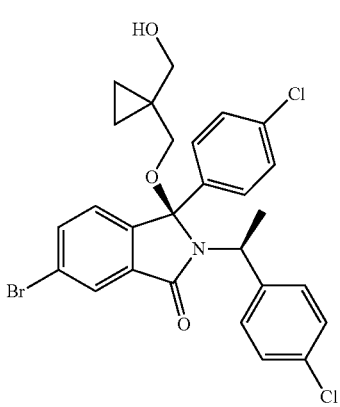
26b

Preparations 26a and 26b were prepared using procedures similar to those described for Preparation 12.

26a (S,S): MS (ES+) 460.2 [M−HOCH$_2$(c-Pr)CH$_2$O]$^+$.): R$_f$=0.51 (2:3 EtOAc/petrol);

26b (R,S): MS (ES+) 460.2 [M−HOCH$_2$(c-Pr)CH$_2$O, R$_f$=0.42 (2:3 EtOAc/petrol);

Preparation 27: (R)-3-(4-Chlorophenyl)-2-((S)-1-(4-chlorophenyl)ethyl)-3-((1-(hydroxymethyl)cyclopropyl)methoxy)-6-(prop-1-en-2-yl)isoindolin-1-one

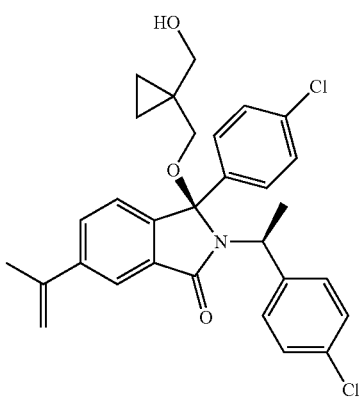 [SMILES: C=C(C)c1ccc2c(c1)C(=O)N([C@@H](C)c1ccc(Cl)cc1)[C@@]2(OCC1(CO)CC1)c1ccc(Cl)cc1]

Starting from intermediate 26b (500 mg, 0.89 mmol), Preparation 27 was prepared using similar procedures to those described for Preparation 13. MS (ES+) 522.5 [M+H]$^+$.

Preparation 28: (R)-6-Acetyl-3-(4-chlorophenyl)-2-((S)-1-(4-chlorophenyl)ethyl)-3-((1-(hydroxymethyl)cyclopropyl)methoxy)isoindolin-1-one

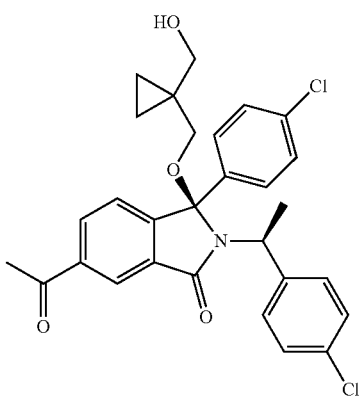 [SMILES: CC(=O)c1ccc2c(c1)C(=O)N([C@@H](C)c1ccc(Cl)cc1)[C@@]2(OCC1(CO)CC1)c1ccc(Cl)cc1]

Starting from Preparation 27, Preparation 28 was prepared using similar procedures to those described for Preparation 15. MS (ES+) 524.5 [M+H]$^+$.

Preparation 29: (R)-3-((1-(((tert-Butyldimethylsilyl)oxy)methyl)cyclopropyl)methoxy)-3-(4-chlorophenyl)-2-((S)-1-(4-chlorophenyl)ethyl)-6-(prop-1-en-2-yl)isoindolin-1-one

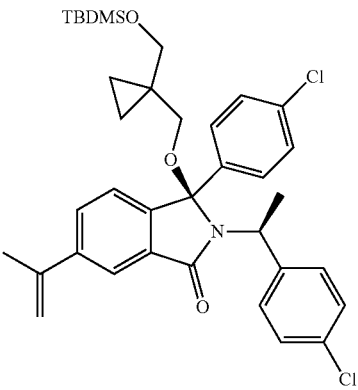 [SMILES: C=C(C)c1ccc2c(c1)C(=O)N([C@@H](C)c1ccc(Cl)cc1)[C@@]2(OCC1(CO[Si](C)(C)C(C)(C)C)CC1)c1ccc(Cl)cc1]

To a solution of (R)-3-(4-chlorophenyl)-2-((S)-1-(4-chlorophenyl)ethyl)-3-((1-(hydroxymethyl)cyclopropyl)methoxy)-6-(prop-1-en-2-yl)isoindolin-1-one, Preparation 27 (2.20 g, 4.21 mmol) in THF (50 mL) was added TBDMSCl (1.27 g, 8.42 mmol) and imidazole (860 mg, 12.6 mmol) and the mixture heated at 85° C. for 5 h. The reaction was cooled to RT, extracted into EtOAc (100 mL), washed with 0.3 M aqueous HCl (150 mL), water (150 mL), brine (150 mL), dried over $MgSO_4$ and concentrated under vacuum. MPLC (95:5 petrol to EtOAc then 99:1 petrol/EtOAc) gave the title compound, Preparation 29 as a colourless oil (1.83 g, 68%); MS (ES+) 422.3 $[M-(TBDMSOCH_2(c-Pr)CH_2O)]^+$.

Preparation 30: (3R)-3-((1-(((tert-Butyldimethylsilyl)oxy)methyl)cyclopropyl)methoxy)-3-(4-chlorophenyl)-2-((S)-1-(4-chlorophenyl)ethyl)-6-(2-methyloxiran-2-yl)isoindolin-1-one

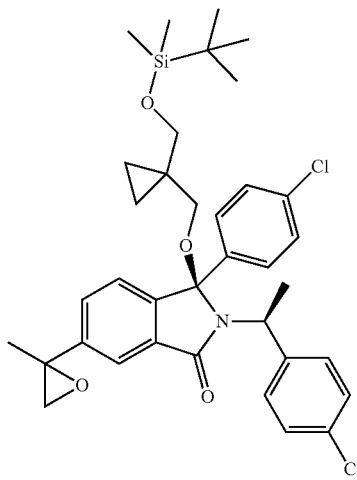

At 0° C., to a solution of (R)-3-((1-(((tert-butyldimethylsilyl)oxy)methyl)cyclopropyl)methoxy)-3-(4-chlorophenyl)-2-((S)-1-(4-chlorophenyl)ethyl)-6-(prop-1-en-2-yl)isoindolin-1-one, Preparation 29 (500 mg, 0.79 mmol) in DCM (43 mL) was added portionwise mCPBA (271 mg, 1.57 mmol) and the resulting solution stirred at RT for 18 h. The reaction was quenched by addition of saturated aqueous $NaHCO_3$ (25 mL) and stirred at RT for 30 min. The organic layer was separated, washed with brine (40 mL), dried over $MgSO_4$ and concentrated under vacuum. The crude product, Preparation 30 was obtained as a colourless oil and carried forward to the next step without purification (708 mg); MS (ES+) 436.3 $[M-(TBDMSOCH_2(c-Pr)CH_2O)]^+$.

Preparation 31: (3R)-3-((1-(((tert-Butyldimethylsilyl)oxy)methyl)cyclopropyl)methoxy)-3-(4-chlorophenyl)-2-((S)-1-(4-chlorophenyl)ethyl)-6-(2-hydroxy-1-methoxypropan-2-yl)isoindolin-1-one

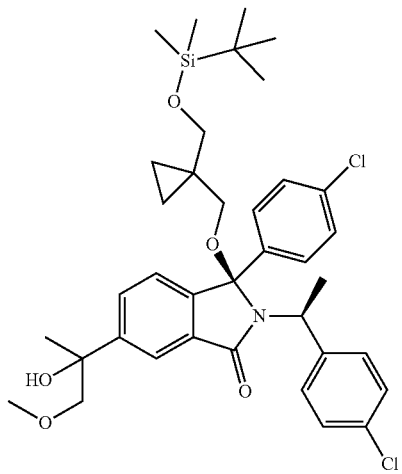 [SMILES: COCC(C)(O)c1ccc2c(c1)C(=O)N([C@@H](C)c1ccc(Cl)cc1)[C@@]2(OCC1(CO[Si](C)(C)C(C)(C)C)CC1)c1ccc(Cl)cc1]

To a solution of sodium (249 mg, 10.8 mmol) in MeOH (1.5 mL) was added dropwise a solution of (3R)-3-((1-(((tert-butyldimethylsilyl)oxy)methyl)cyclopropyl)methoxy)-3-(4-chlorophenyl)-2-((S)-1-(4-chlorophenyl)ethyl)-6-(2-methyloxiran-2-yl)isoindolin-1-one, Preparation 30 (708 mg, 1.08 mmol) in MeOH (1.5 mL) and the resulting solution stirred at RT for 18 h then at 65° C. for 5 h. The reaction was cooled to RT, NaOMe (292 mg, 5.4 mmol) was added and the mixture heated at 65° C. for 2 h then cooled to RT. The reaction was quenched by addition of water (100 mL), neutralised with aqueous 1.0 M HCl solution, extracted into EtOAc (2×100 mL), washed with brine (100 mL), dried over $MgSO_4$ and concentrated under vacuum. MPLC (3:2 petrol/EtOAc) gave the title compound, Preparation 31 as a colourless oil as a diastereoisomeric mixture (151 mg, 20; MS (ES+) 468.3 $[M-(TBDMSOCH_2(c-Pr)CH_2O)]^+$.

Preparation 32: 3-((1-(((tert-Butyldimethylsilyl)oxy)methyl)cyclopropyl)methoxy)-2-(4-chlorobenzyl)-3-(4-chlorophenyl)-6-(prop-1-en-2-yl)isoindolin-1-one

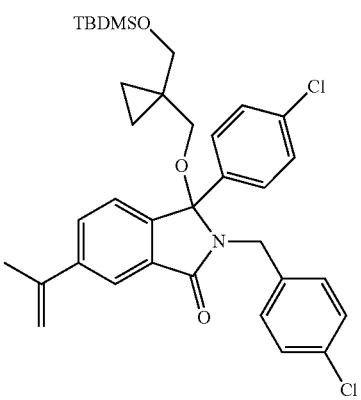 [SMILES: C=C(C)c1ccc2c(c1)C(=O)N(Cc1ccc(Cl)cc1)C2(OCC1(CO[Si](C)(C)C(C)(C)C)CC1)c1ccc(Cl)cc1]

To a solution of 2-(4-chlorobenzyl)-3-(4-chlorophenyl)-3-((1-(hydroxymethyl)cyclopropyl)methoxy)-6-(prop-1-en-2-yl)isoindolin-1-one, Preparation 13 (2.73 g, 5.37 mmol) in THF (68 mL) was added TBDMSCl (1.62 g, 10.7 mmol) and imidazole (1.10 g, 16.1 mmol) and the resulting suspension heated at 85° C. for 5 h then cooled to RT. The mixture was diluted with EtOAc (150 mL), washed with aqueous 0.3 M HCl (150 mL), water (150 mL), brine (150 mL) and dried over MgSO$_4$. Purification by MPLC (100% petrol to 95:5 petrol/EtOAc) gave the title compound, Preparation 32 as a colourless oil (1.12 g, 34%); λ$_{max}$ (EtOH/nm) 214; IR (cm$^{-1}$) 2928, 2855, 1704 (C=O), 1433; $^1$H NMR (500 MHz, CDCl$_3$) δ −0.11 (3H, s, SiCH$_3$), −0.09 (3H, s, SiCH$_3$), 0.00-0.03 (2H, m, 2×c-PrH), 0.25-0.27 (2H, m, 2×c-PrH), 0.73 (9H, s, SiC(CH$_3$)$_3$), 2.08 (3H, m, CH$_3$), 2.52 (1H, d, J=9.2 Hz, CHH'), 2.80 (1H, d, J=9.2 Hz, CHH'), 3.27 (1H, d, J=10.3 Hz, C'HH'), 3.56 (1H, d, J=10.3 Hz, C'HH'), 4.22 (1H, d, J=14.7 Hz, NCHH'), 4.30 (1H, d, J=14.7 Hz, NCHH'), 5.08 (1H, m, alkene-CH), 5.35 (1H, s, alkene-CH'), 6.94 (1H, d, J=8.0 Hz, ArH), 6.95-7.01 (4H, m, 4×ArH), 7.05-7.09 (4H, m, 4×ArH), 7.48 (1H, dd, J=1.7 and 8.0 Hz, ArH), 7.86 (1H, d, J=1.7 Hz, ArH); $^{13}$C (125 MHz, CDCl$_3$) δ −5.2, −5.3, 7.9, 8.1, 18.3, 12.9, 25.9, 42.2, 65.9, 66.1, 94.3, 114.3, 120.4, 122.8, 128.0, 128.2, 128.4, 130.1, 130.5, 131.6, 133.0, 134.3, 136.0, 137.4, 142.1, 168.3; MS (ES+) 408.3 [M-(TBDMSOCH$_2$(c-Pr)CH$_2$O)]$^+$.

Preparation 33: 3-((1-(((tert-Butyldimethylsilyl)oxy)methyl)cyclopropyl)methoxy)-2-(4-chlorobenzyl)-3-(4-chlorophenyl)-6-(2-methyloxiran-2-yl)isoindolin-1-one

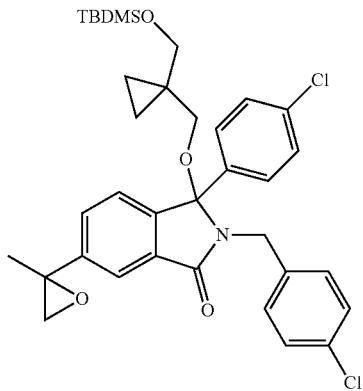 [SMILES: CC1(c2ccc3c(c2)C(=O)N(Cc2ccc(Cl)cc2)C3(OCC2(CO[Si](C)(C)C(C)(C)C)CC2)c2ccc(Cl)cc2)CO1]

At 0° C., to a solution of 3-((1-(((tert-butyldimethylsilyl)oxy)methyl)cyclopropyl)methoxy)-2-(4-chlorobenzyl)-3-(4-chlorophenyl)-6-(prop-1-en-2-yl)isoindolin-1-one, Preparation 32 (640 mg, 1.03 mmol) in DCM (50 mL) was added mCPBA (355 mg, 2.05 mmol) and the resulting solution stirred at RT for 18 h. The reaction was quenched by addition of saturated aqueous NaHCO$_3$ (50 mL) and stirred vigorously for 4 h. The organic layer was separated, washed with brine (50 mL), dried over MgSO$_4$ and concentrated under vacuum. The crude product, Preparation 33 was carried forward to the next step without purification (650 mg). MS (ES+) 422.3 [M-(TBDMSOCH$_2$(c-Pr)CH$_2$O)]$^+$.

Preparation 34: 3-((1-(((tert-Butyldimethylsilyl)oxy)methyl)cyclopropyl)methoxy)-2-(4-chlorobenzyl)-3-(4-chlorophenyl)-6-(1-(dimethylamino)-2-hydroxypropan-2-yl)isoindolin-1-one

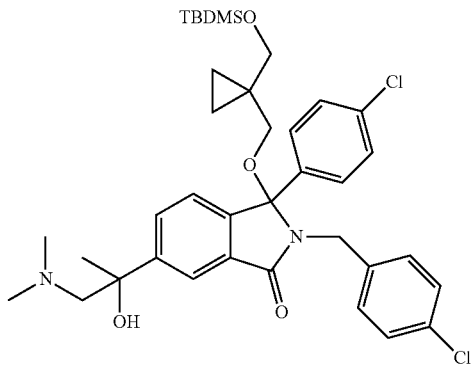 [SMILES: CN(C)CC(C)(O)c1ccc2c(c1)C(=O)N(Cc1ccc(Cl)cc1)C2(OCC1(CO[Si](C)(C)C(C)(C)C)CC1)c1ccc(Cl)cc1]

In a sealed microwave vial, to a solution of 3-((1-(((tert-butyldimethylsilyl)oxy)methyl)cyclopropyl)methoxy)-2-(4-chlorobenzyl)-3-(4-chlorophenyl)-6-(2-methyloxiran-2-yl)isoindolin-1-one, Preparation 33 (1.08 g, 1.69 mmol) in MeOH (3.04 mL) was added dimethylamine (8.45 mL, 16.9 mmol, 2.0 M in MeOH) and the resulting solution heated at 60° C. for 4 h then cooled to RT. The reaction was diluted with water (50 mL), extracted into EtOAc (2×50 mL), washed with brine (100 mL), dried over MgSO$_4$ and concentrated under vacuum. Purified by Biotage using 0-30% MeOH in EtOAc as the eluent gave the title compound as a colourless oil (407 mg, 35%). 1H NMR (500 MHz, CDCl$_3$) −0.02 (3H, m), 0.00 (3H, s), 0.03-0.12 (2H, m), 0.34-0.35 (2H, m), 0.83-0.84 (9H, m), 1.51 (3H, s), 2.19 (6H, s), 2.61-2.64 (1H, m), 2.76-2.83 (3H, m), 3.35-3.39 (1H, m), 3.63-3.67 (1H, m), 4.30-4.40 (2H, m), 7.05-7.10 (5H, m), 7.15 (4H, s), 7.68-7.71 (1H, m), 7.91-7.92 (1H, m).

Preparation 35: (S)-Ethyl 3-amino-3-(4-chlorophenyl)propanoate Hydrochloride

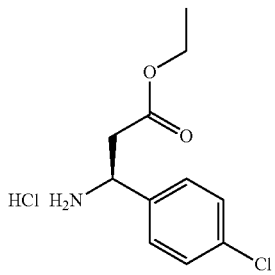

At 0° C., to a solution of s-beta-(p-chlorophenyl)alanine (1.00 g, 5.0 mmol) in EtOH (10 mL) was added dropwise SOCl$_2$ and the resulting solution heated at 78° C. for 1.5 h. The solution was cooled to RT and concentrated under vacuum to give the title compound, Preparation 35 as a white solid (1.31 g, 99%); $^1$H NMR (500 MHz, DMSO) δ 1.08 (3H, t, J=7.1 Hz, CH$_3$), 3.02 (1H, dd, J=9.5 and 16.1 Hz, CHH'C=O), 3.24 (1H, dd, J=5.4 and 16.1 Hz, CHH'C=O), 3.96-4.01 (2H, m, OCH$_2$), 4.59 (1H, dd, J=5.4 and 9.5 Hz, NH₂CH), 7.49 (2H, d, J=8.5 Hz, 2×ArH), 7.62 (2H, d, J=8.5 Hz, 2×ArH), 8.91 (3H, s br)

Preparation 36; (3S)-Ethyl 3-(5-bromo-1-(4-chlorophenyl)-1-hydroxy-3-oxoisoindolin-2-yl)-3-(4-chlorophenyl)propanoate

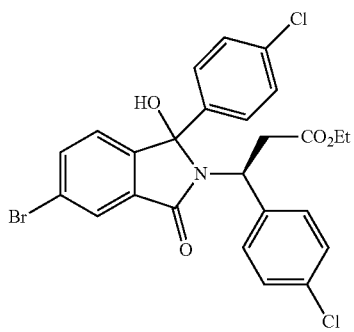 [SMILES: CCOC(=O)C[C@@H](c1ccc(Cl)cc1)N1C(=O)c2cc(Br)ccc2C1(O)c1ccc(Cl)cc1]

Starting from (S)-Ethyl 3-amino-3-(4-chlorophenyl)propanoate hydrochloride, preparation 35 was prepared using similar procedures to those described for Preparation 9. Product was obtained as a diastereoisomeric mixture. MS (ES+) 546.2 [M−H]⁻.

Preparation 37a and 37b: (3S)-Ethyl 3-(5-bromo-1-(4-chlorophenyl)-1-((1-(hydroxymethyl)cyclopropyl)methoxy)-3-oxoisoindolin-2-yl)-3-(4-chlorophenyl)propanoate

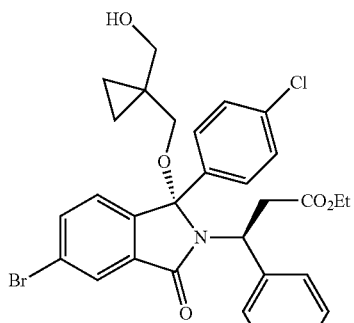
37a

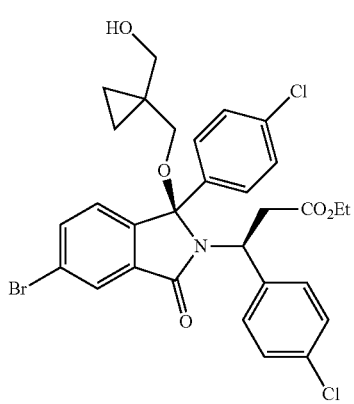
37b

Starting from 3-(5-bromo-1-(4-chlorophenyl)-1-hydroxy-3-oxoisoindolin-2-yl)-3-(4-chlorophenyl)propanoate Preparation 37a and 37b were prepared using similar procedures to those described for Preparation 12. The two products were isolated by SiO₂ chromatography.

37a (S,S): $R_f$=0.67 (1:1 EtOAc/petrol); MS (ES+) 532.2 [M−HOCH₂(c-Pr)CH₂O]⁺.

37b (S,R): $R_f$=0.52 (1:1 EtOAc/petrol); MS (ES+) 530.3 [M−HOCH₂(c-Pr)CH₂O]⁺.

Preparation 38: (S)-Ethyl 3-(4-chlorophenyl)-3-((R)-1-(4-chlorophenyl)-1-((1-(hydroxymethyl)cyclopropyl)methoxy)-3-oxo-5-(prop-1-en-2-yl)isoindolin-2-yl)propanoate

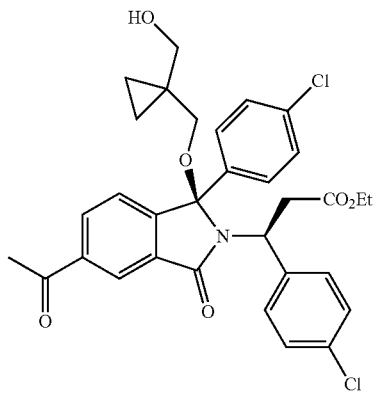 [SMILES: CCOC(=O)C[C@@H](c1ccc(Cl)cc1)N1C(=O)c2cc(C(C)=O)ccc2[C@]1(OCC1(CO)CC1)c1ccc(Cl)cc1]

Starting from preparation 37b, Preparation 38 was prepared using similar procedures to those described for Preparation 13. MS (ES+) 492.4 [M−HOCH₂(c-Pr)CH₂O]⁺.

Preparation 39: (S)-Ethyl 3-((R)-5-acetyl-1-(4-chlorophenyl)-1-((1-(hydroxymethyl)cyclopropyl)methoxy)-3-oxoisoindolin-2-yl)-3-(4-chlorophenyl)propanoate

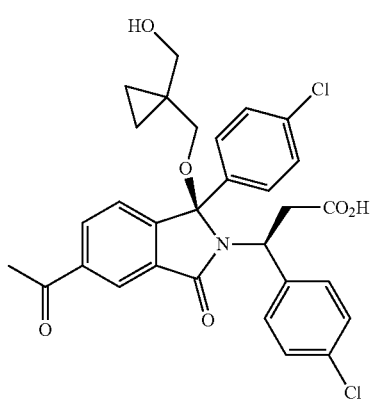 [SMILES: CC(=O)c1ccc2c(c1)C(=O)N([C@@H](CC(=O)O)c1ccc(Cl)cc1)[C@@]2(OCC1(CO)CC1)c1ccc(Cl)cc1]

Starting from Preparation 38, Preparation 39 was prepared using similar procedures to those described for Preparation 15. MS (ES+) 494.3 [M−HOCH₂(c-Pr)CH₂O]⁺.

Preparation 40: (S)-3-((R)-5-Acetyl-1-(4-chlorophenyl)-1-((1-(hydroxymethyl)cyclopropyl)methoxy)-3-oxoisoindolin-2-yl)-3-(4-chlorophenyl)propanoic Acid

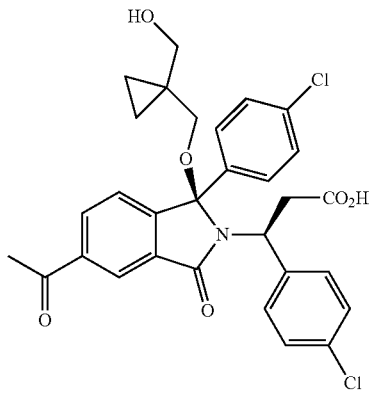 [SMILES: CC(=O)c1ccc2c(c1)C(=O)N([C@@H](CC(=O)O)c1ccc(Cl)cc1)[C@@]2(OCC1(CO)CC1)c1ccc(Cl)cc1]

To a solution of (S)-ethyl 3-((R)-5-acetyl-1-(4-chlorophenyl)-1-((1-(hydroxymethyl)cyclopropyl)methoxy)-3-oxoisoindolin-2-yl)-3-(4-chlorophenyl)propanoate, Preparation 39 (130 mg, 0.22 mmol) in THF/water (1.9 mL/3.0 mL) was added LiOH.H$_2$O (183 mg, 4.36 mmol) and the resulting yellow solution heated at 60° C. for 3 h then cooled to RT. The solution was acidified to pH 5 with aqueous 1.0 M HCl, extracted with EtOAc (3×25 mL), washed with brine (50 mL), dried over MgSO$_4$ and concentrated under vacuum. MPLC (1:1 petrol/EtOAc (0.1% AcOH) to 100% EtOAc (0.1% AcOH)) gave the title compound, Preparation 40 as a white solid (85 mg, 68%); MS (ES+) 566.2 [M−H]$^-$.

Preparation 41: 6-Acetyl-2-(4-chlorobenzyl)-3-(4-chlorophenyl)-3-(3-hydroxy-3-methylbutoxy)isoindolin-1-one

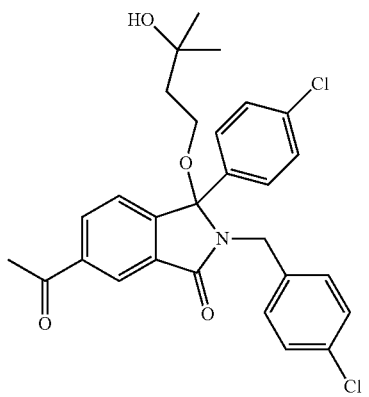 [SMILES: CC(=O)c1ccc2c(c1)C(=O)N(Cc1ccc(Cl)cc1)C2(OCCC(C)(C)O)c1ccc(Cl)cc1]

Starting from 6-acetyl-2-(4-chlorobenzyl)-3-(4-chlorophenyl)-3-hydroxyisoindolin-1-one, Preparation 41 was prepared using similar procedure to those described in Preparation 12.

Preparation 42: 4-[(Triisopropylsilanyl)-ethynyl]-benzylamine

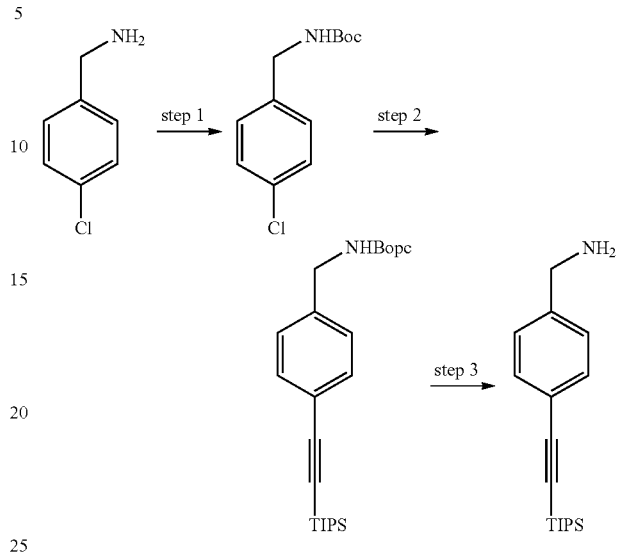

Step 1: (4-Chloro-benzyl)-carbamic Acid Tert-Butyl Ester

4-Chlorobenzylamine (10.5 mL, 86 mmol) was added to a mixture of Amberlyst 15 resin (1.8 g) and di-tert-butyl dicarbonate (18.5 g, 84.7 mmol) and the reaction mixture was stirred at room temperature for 3 hours. The crude mixture was diluted with DCM (200 mL) and the catalyst was removed by filtration. The solvent was removed in vacuo to give the desired product as a white solid (18.9 g). MS: [M-C$_4$H$_9$]$^+$=186. $^1$H NMR (400 MHz, CDCl3): 7.38-7.30 (2H, m), 7.23 (2H, d), 4.87 (1H, s), 4.29 (2H, s), 1.48 (9H, s).

Step 2: {4-[(Triisopropylsilanyl)-ethynyl]-benzyl}-carbamic Acid Tert-Butyl Ester Ethynyl-triisopropyl-silane (13.4 mL, 94.1 mmol) was added to a suspension of (4-chloro-benzyl)-carbamic acid tert-butyl ester (18.9 g, 78.4 mmol), PdCl$_2$(CH$_3$CN)$_2$ (202 mg, 0.78 mmol), XPhos (1.1 g, 2.3 mmol) and Cs$_2$CO3 (53.6 g, 164.6 mmol) in MeCN (170 mL) and the reaction mixture was stirred under N$_2$ at 110° C. for 20 hours. The reaction was then cooled to room temperature, quenched with water (300 mL) and extracted with EtOAc (2×300 mL). The organic phases were collected, dried over Na$_2$SO$_4$. The reaction was then cooled to room temperature, quenched with water (300 mL) and extracted with EtOAc (2×300 mL). The organic phases were collected, dried over Na$_2$SO$_4$, filtered and concentrated in vacuo. The crude material was columned (gradient 0-20% EtOAc in Petrol) to give 15.7 g of a yellow oil. 1H NMR (400 MHz, CDCl3): 7.45 (2H, d), 7.23 (2H, d), 4.83 (1H, s), 4.32 (2H, s), 1.48 (9H, s), 1.20-1.11 (21H, m).

Step 3: 4-[(Triisopropylsilanyl)-ethynyl]-benzylamine

TFA (25 mL, 326 mmol) was added to a solution of {4-[(Triisopropylsilanyl)-ethynyl]-benzyl}-carbamic acid tert-butyl ester (15.6 g, 40.3 mmol) in DCM (50 mL). The reaction was stirred for 16 hours at room temperature and then quenched with water (30 mL) and 2N NaOH until the solution reached pH=11. The product was extracted with DCM (3×). The organic phases were collected, dried over Na$_2$SO$_4$, filtered and concentrated in vacuo to give the desired product (12.5 g) as an orange oil. 1H NMR (400 MHz, CDCl3): 7.46 (2H, d), 7.31-7.24 (2H, m), 3.87 (2H, s), 1.94 (2H, s), 1.15 (21H, s).

Preparation 43:
4-Chloro-2-(methylthio)phenyl)methanamine

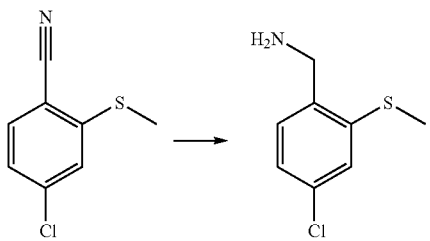

To a solution of 4-chloro-2-(methylthio)benzonitrile (500 mg, 2.72 mmol) in dry THF (10 mL) was added slowly borane-THF complex (1M in THF, 13.6 mL, 13.6 mmol) at 0° C. before refluxing for 1 h. After cooling, 1 M HCl in MeOH (10 mL) was added slowly with ice cooling. The solvent was removed by concentration in vacuo before water (0.61 mmol/mL to benzonitrile) was added, then washed by Et$_2$O (0.61 mmol/mL to benzonitrile) before basifying with 2 M NaOH solution to pH 12. Et$_2$O (0.61 mmol/mL to benzonitrile) was added and the mixture was washed with water (3×0.61 mmol/mL to benzonitrile) and brine (0.4 mol/mL to benzonitrile). The organic layer was dried (MgSO$_4$) and concentrated in vacuo to give the product as a yellow oil (400 mg, 78%). LCMS (ESI$^+$) m/z=171.1 [M-NH$_2$]$^+$.

Preparation 44: (3R)-6-Acetyl-2-[(4-chloro-2-methanesulfonylphenyl)methyl]-3-(4-chlorophenyl)-4-fluoro-3-[(3R)-oxolan-3-yloxy]-2,3-dihydro-1H-isoindol-1-one

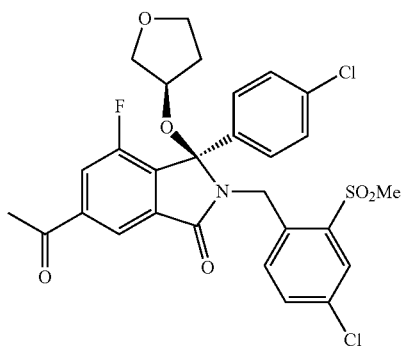 [SMILES: CC(=O)c1cc(F)c2c(c1)C(=O)N(Cc1ccc(Cl)cc1S(C)(=O)=O)[C@@]2(O[C@@H]1CCOC1)c1ccc(Cl)cc1]

The title compound was prepared using a similar method to that described in Example 41, Step 1 and 2; using (3R)-hydroxy-tetrahydrofuran instead of cyclopropane-1,1-dimethanol. The 3(R) isomer was isolated as the slower running fraction from Step 1, using preparative chiral HPLC. MS(ES+) m/z 630 [M+H]$^+$.

Preparation 45: Ethyl (3S)-3-[(1R)-5-acetyl-1-(4-chlorophenyl)-7-fluoro-3-oxo-1-[(3S)-oxolan-3-yloxy]-2,3-dihydro-1H-isoindol-2-yl]-3-(4-chlorophenyl)propanoate

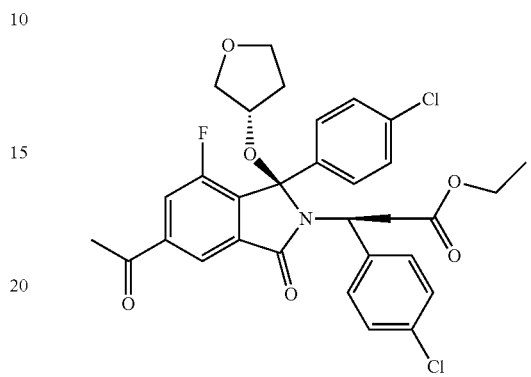

The title compound was prepared in a similar way to Preparation 44, but using ethyl (3S)-3-amino-3-(4-chlorophenyl)propanoate hydrochloride (Preparation 35) instead of (4-chloro-2-(methylsulfonyl)phenyl)methanamine and (3S)-hydroxy-tetrahydrofuran instead of (3R)-hydroxy-tetrahydrofuran. MS(ES+) m/z 598 [M–H]$^-$ Preparation 46: 2-(4-Chlorobenzoyl)-3-fluoro-5-(1-hydroxy-1-methyl-ethyl)benzoic Acid

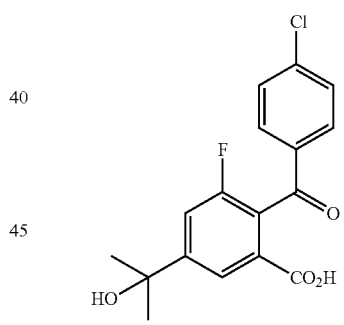

The title compound was prepared in a similar fashion to Example 73 and 74, Step 1; but using acetone instead of 1-methyl-1H-pyrazole-4-carboxaldehyde. MS: [M+H]$^+$= 337.

Preparation 47:
(2-(Aminomethyl)-5-chlorophenyl)dimethylphosphine Oxide

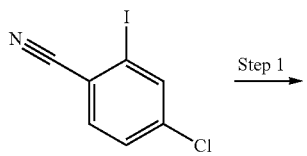

153

-continued

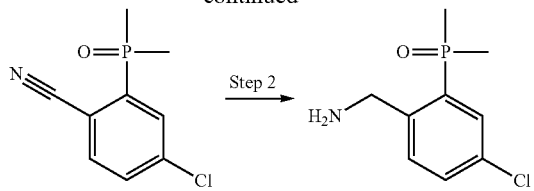

Step 1:
4-Chloro-2-(dimethylphosphoryl)benzonitrile

To a round bottomed flask was added 4-chloro-2-iodo-benzonitrile (2.5 g, 9.50 mmol), dimethylphosphine oxide (1.12 g, 14.30 mmol), Pd$_2$(dba)$_3$ (435 mg, 0.48 mmol), Xantphos (550 mg, 0.95 mmol) and the flask was flushed with N$_2$. The solids were taken up in dioxane (25 mL), triethylamine added (2.10 g, 20.9 mmol) and the reaction was stirred at room temperature for 2 h. To the reaction was added H$_2$O (50 mL) and the aqueous was extracted with EtOAc (2×100 mL). The combined organics were dried (MgSO$_4$), filtered and concentrated in vacuo. The residue was purified on a 50 g SNAP column eluting with MeOH in DCM (0 to 10%) to give the title compound (1.07 g at 80% purity). $^1$H NMR (400 MHz, CDCl$_3$) 8.33-8.29 (1H, m), 7.76-7.73 (1H, m), 7.65-7.62 (1H, m), 1.96 (6H, d);

Step 2:
(2-(Aminomethyl)-5-chlorophenyl)dimethylphosphine Oxide

To a THF solution (10 mL) of 4-chloro-2-(dimethylphosphoryl)benzonitrile (960 mg, 4.50 mmol), under N$_2$, was added BH$_3$.THF (23 mL, 23.00 mmol, 1M THF) and the reaction was stirred for 1 h. The reaction was quenched by the cautious addition of MeOH (10 mL). The solution was concentrated in vacuo., re-dissolved in MeOH and loaded on to a 10 g SCXII cartridge. The cartridge was sequentially flushed with MeOH (3 column volumes) and then 2M NH$_3$ MeOH (3 column volumes). The ammonia wash was concentrated in vacuo. to give the title compound (770 mg). $^1$H NMR (400 MHz, CDCl$_3$) 7.46-7.41 (3H, m), 4.14 (2H, s), 1.83 (6H, d).

Preparation 48: 2-(4-Chlorobenzoyl)-3-fluoro-5-(tetrahydro-2H-pyran-4-carbonyl)benzoic Acid

154

-continued

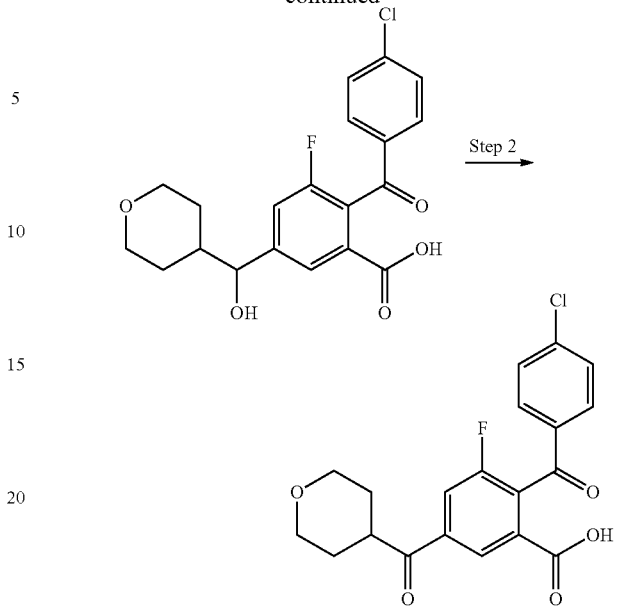

Steps 1 was performed using a procedure similar to that described in Examples 73 and 74; step 1, but using tetrahydro-2H-pyran-4-carbaldehyde instead of 1-methyl-1H-pyrazole-4-carboxaldehyde. Also, Bu$_2$Mg was used in place of methylmagnesium chloride. MS: [M+H]$^+$=393.

Step 2: 2-(4-Chlorobenzoyl)-3-fluoro-5-(tetrahydro-2H-pyran-4-carbonyl)benzoic Acid 2-(4-Chlorobenzoyl)-3-fluoro-5-(hydroxy(tetrahydro-2H-pyran-4-yl)methyl)benzoic acid (17.4 g, 44.4 mmol) was stirred in DCM (400 mL) at RT then TEMPO (0.69 g, 4.44 mmol) and tetra-n-butylammonium chloride (5.72 g, 17.8 mmol) were added followed by OXONE®, monopersulfate compound (30 g, 97.7 mmol). The reaction was allowed to stir at RT for 18 h. TEMPO (0.69 g, 4.44 mmol) was added and the reaction was allowed to stir at RT for an additional 48 h. The solids were removed by filtration and the filter cake was washed with DCM (2×100 mL). The combined filtrates were concentrated under reduced pressure and the resulting residue dissolved in EtOAc (500 mL). The combined organic portions were washed with 2M HCl aqueous solution (2×500 mL) and brine (200 mL), dried (MgSO$_4$), filtered and concentrated to afford the title compound as a pale yellow foam (16 g, 92% yield). MS: [M−H]$^+$=389.

Preparation 49: 4-[(1R)-1-Amino-2-(prop-2-en-1-yloxy)ethyl]benzonitrile

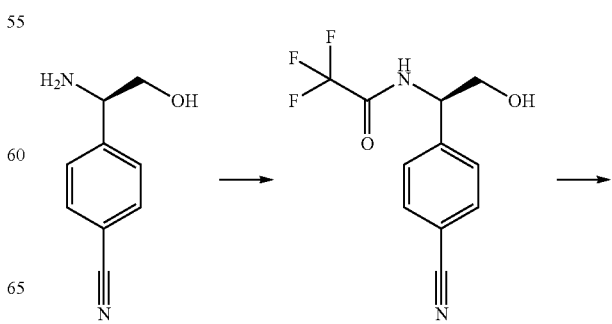

-continued

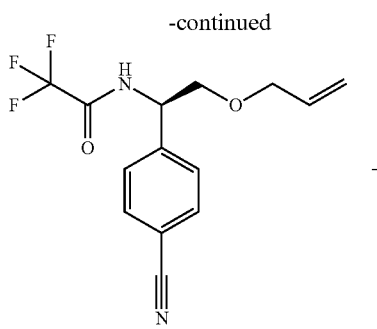

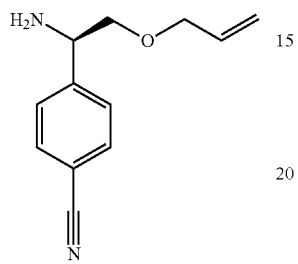

Step 1: N-[(1R)-1-(4-Cyanophenyl)-2-hydroxy-ethyl]-2,2,2-trifluoroacetamide

TFAA (3.6 mL, 25.2 mmol) was added to a solution of 4-[(1R)-1-amino-2-hydroxyethyl]benzonitrile (5.0 g, 25.2 mmol) in DCM (100 mL) containing TEA (10.9 mL, 75.6 mmol) and the solution was stirred for 10 min at room temperature. The reaction was partitioned between DCM and 2N HCl. The aqueous phase was extracted with DCM (2×) and EtOAc (2×). The organic phases were collected, dried over MgSO₄, filtered and concentrated in vacuo to give the desired product as a white solid (4.8 g, 74% yield). LCMS: [M−H]⁻=257.

Step 2: N-[(1R)-1-(4-Cyanophenyl)-2-(prop-2-en-1-yloxy)ethyl]-2,2,2-trifluoroacetamide NaH (60% disp. in oil, 1.5 g, 36.9 mmol) was added in portions to a solution of N-[(1R)-1-(4-cyanophenyl)-2-hydroxyethyl]-2,2,2-trifluoroacetamide (4.76 g, 18.4 mmoL) in DMF (15 mL) at 0° C. under inert atmosphere and the resulting mixture was then stirred for 10 min at room temperature. 3-iodoprop-1-ene (1.7 mL, 18.4 mmol) was then added dropwise, the reaction was stirred for 10 min at room temperature and then quenched with water. The product was extracted with EtOAc (3×), the organic phase was washed 3× with brine and the solvent was removed in vacuo. The crude material was purified by flash chromatography on silica gel (gradient 0-30% EtOAc in petrol) to give the title compound as a colourless liquid (3.5 g, 64% yield). LCMS: [M+H]⁺=299.

Step 3: 4-[(1R)-1-Amino-2-(prop-2-en-1-yloxy)ethyl]benzonitrile

2N NaOH (10 mL) was added to a solution of N-[(1R)-1-(4-cyanophenyl)-2-(prop-2-en-1-yloxy)ethyl]-2,2,2-trifluoroacetamide (3.5 g, 11.7 mmol) in MeOH (10 mL). The reaction was stirred for 16 hours at room temperature after which time 4 mL of 2N NaOH were added to the mixture and stirring was continued for further 2 hours at 45° C. The solvent was removed in vacuo and the residue was partitioned between EtOAc and NaHCO₃. The organic phase was dried over MgSO₄, filtered and concentrated in vacuo to give 2.3 g (96% yield) of the desired compound as a pale yellow oil. LCMS: [M+H]⁺=203.

Preparation 50: 2-(4-Chlorobenzoyl)-3-fluoro-5-(1-methyl-1H-imidazole-4-carbonyl)benzoic Acid

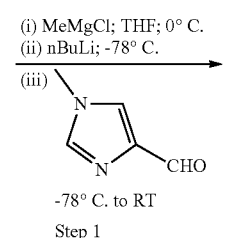

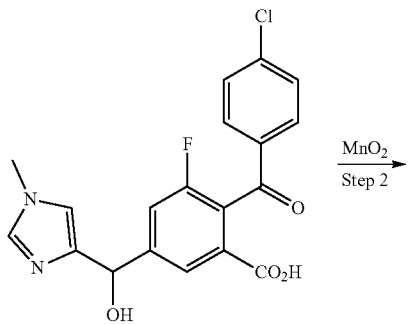

Step 1: 2-(4-Chlorobenzoyl)-3-fluoro-5-(hydroxy(1-methyl-1H-imidazol-4-yl)methyl)benzoic Acid A 10 liter round bottomed flask fitted with an overhead stirrer with a large paddle was charged with 5-bromo-2-(4-chlorobenzoyl)-3-fluorobenzoic acid (178.25 g; 0.5 mol) and anhydrous THF (2610 mL) added. This solution was cooled to −5° C.<T<0° C. and a solution of 3 M methyl magnesium chloride in THF (183 mL; 0.55 mol) was added dropwise at such a rate that the internal temperature

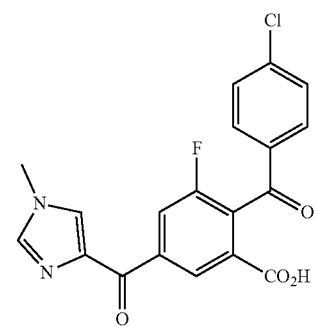

remained below 0° C. On complete addition the mixture was stirred at 0° C. for 15 minutes and then cooled to −78° C. A solution of 2.5 M n-butyllithium in hexanes (259 mL; 0.647 mol) was added drop-wise at such a rate so that the internal temperature remained below −70° C. The reaction deepened in colour and thickened considerably ending up with a sludge like consistency. On complete addition the mixture was stirred at −78° C. for 30 minutes prior to the addition of a solution of 1-methyl-1H-imidazole-4-carbaldehyde (71.3 g; 0.648 mol) in anhydrous THF (500 mL) dropwise at such a rate so that the internal temperature remained below −70° C. On complete addition the mixture was stirred at −78° C. for 30 minutes, the cooling bath removed and the mixture allowed to reach room temperature. The mixture was quenched with 1 M HCl, the pH adjusted to 7 and the whole evaporated under reduced pressure The residue was divided into 4 equal portions and each portion chromatographed on silica gel (300 g) eluting with 0-30% MeOH in DCM gradient to afford the title compound as a yellow solid (151 g; 78%). MS [M+H]$^+$=389

Step 2: 2-(4-Chlorobenzoyl)-3-fluoro-5-(1-methyl-1H-imidazole-4-carbonyl)benzoic Acid To a stirred mixture of 2-(4-chlorobenzoyl)-3-fluoro-5-(hydroxy(1-methyl-1H-imidazol-4-yl)methyl)benzoic acid (24.6 g; 63.4 mmol) in 1,4-dioxane (600 mL) was added activated manganese dioxide (55 g; 634 mmol) and the mixture heated at 110° C. for 1 h. LCMS indicated complete reaction. The reaction was cooled, filtered through celite and GFA filter paper, washed with MeOH. The filtrate and washings were combined and evaporated under reduced pressure to afford a dark solid (24 g). MS [M+H]$^+$=387.

Preparation 51: 3-((Allyloxy)methyl)-4-(aminomethyl)benzonitrile Hydrochloride (4)

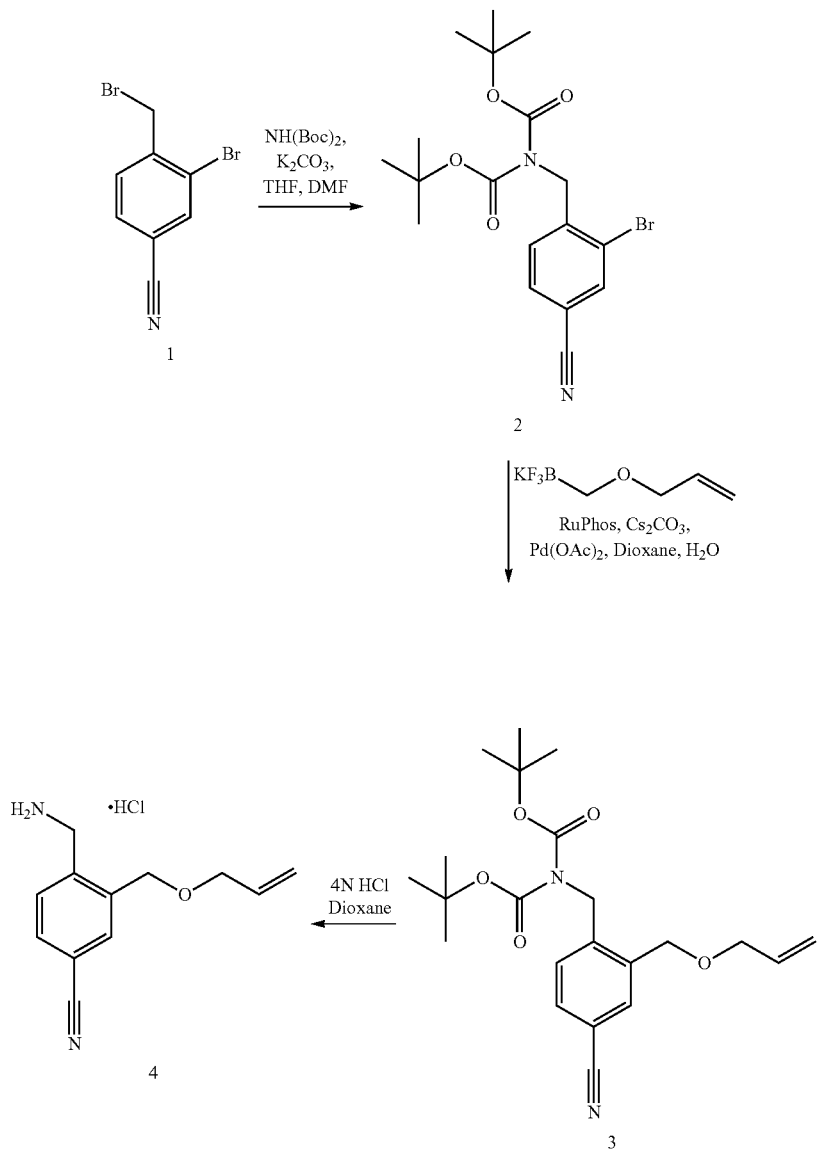

Step 1: tert-Butyl N-[(2-bromo-4-cyano-phenyl) methyl]-N-tert-butoxycarbonyl-carbamate (2)

3-Bromo-4-(bromomethyl)benzonitrile (1) (8 g, 29.1 mmol), was dissolved in THF (80 mL) and DMF (80 mL) and the solution was stirred at room temperature under a nitrogen atmosphere. Di-tert-butylimino carboxylate (9.48 g, 43.6 mmol) and potassium carbonate (6.0 g, 43.6 mmol) were added and the reaction was heated at 100° C. overnight. The mixture was diluted with EtOAc (250 mL) and water (250 mL). The organic phase was collected and the aqueous phase was extracted with EtOAc (250 mL). The combined organic extracts were washed with brine (120 mL), dried (MgSO$_4$), filtered, and evaporated to dryness. The crude product was purified by trituration with the minimal amount of methanol (~20 mL) and the solid was collected via filtration to give the desired product (10.3 g, 86%) as a white solid. $^1$H NMR (400 MHz, CDCl$_3$): 7.84 (1H, d), 7.59 (1H, dd), 7.23 (1H, d), 4.88 (2H, s), 1.46 (18H, s)

Step 2: tert-Butyl N-[[2-(Allyloxymethyl)-4-cyano-phenyl]methyl]-N-tert-butoxycarbonyl-carbamate (3)

tert-Butyl N-[(2-bromo-4-cyano-phenyl)methyl]-N-tert-butoxycarbonyl-carbamate (2) (5 g, 12.1 mmol), RuPhos (0.569 g, 1.21 mmol), potassium [(allyloxy)methyl]trifluoroborane 2.6 g, 14.6 mmol) and cesium carbonate (11.9 g, 36.1 mmoL) were dissolved in dioxane (90 mL) and water (10 mL). The mixture was purged with nitrogen for 5 minutes and then palladium acetate (136 mg, 0.61 mmol) was added. The mixture was purged with nitrogen for a further 5 minutes and then heated at 100° C. for 24 hours. The mixture was concentrated under reduced pressure and the resulting residue was partitioned between EtOAc (150 mL) and water (150 mL). The organic layer was collected and the aqueous phase was extracted with more EtOAc (150 mL). The combined organic extracts were passed through a hydrophobic frit, and evaporated under reduced pressure to give a crude product which was purified by silica column chromatography (gradient elution 0 to 20% EtOAc in iso-Hex), to give the pure product (3.0 g, 53%) as a yellow oil. $^1$H NMR (400 MHz, CDCl$_3$): P 7.68 (1H, d), 7.59-7.56 (1H, m), 7.29 (1H, d), 5.99-5.89 (1H, m), 5.35-5.22 (2H, m), 4.86 (2H, s), 4.56 (2H, s), 4.07-4.04 (2H, m), 1.44 (18H, s), 0.95-0.82 (1H, m)

Step 3: 3-((Allyloxy)methyl)-4-(aminomethyl)benzonitrile Hydrochloride (4)

tert-Butyl N-[[2-(allyloxymethyl)-4-cyano-phenyl] methyl]-N-tert-butoxycarbonyl-carbamate (3) (2.6 g, 6.46 mmol) was dissolved in DCM (83 mL) and 4N HCl in dioxane (28.6 mL) was added. The mixture was stirred at room temperature for 4 hours. The solvents were removed under vacuum and any remaining solvent traces were removed via co-evaporation from chloroform. The desired product (1.6 g) was isolated as a white solid and was deemed to be sufficiently pure for subsequent steps. $^1$H NMR (400 MHz, DMSO): 8.51-8.51 (3H, m), 7.93 (1H, dd), 7.88 (1H, d), 7.71 (1H, d), 6.02-5.92 (1H, m), 5.33 (1H, dd), 5.22 (1H, dd), 4.65 (2H, s), 4.16 (2H, s), 4.06 (2H, d);

Preparation 52: (S)-2-(4-chlorobenzoyl)-3-fluoro-5-(1-hydroxy-1-(tetrahydro-2H-pyran-4-yl)propyl) benzoic Acid

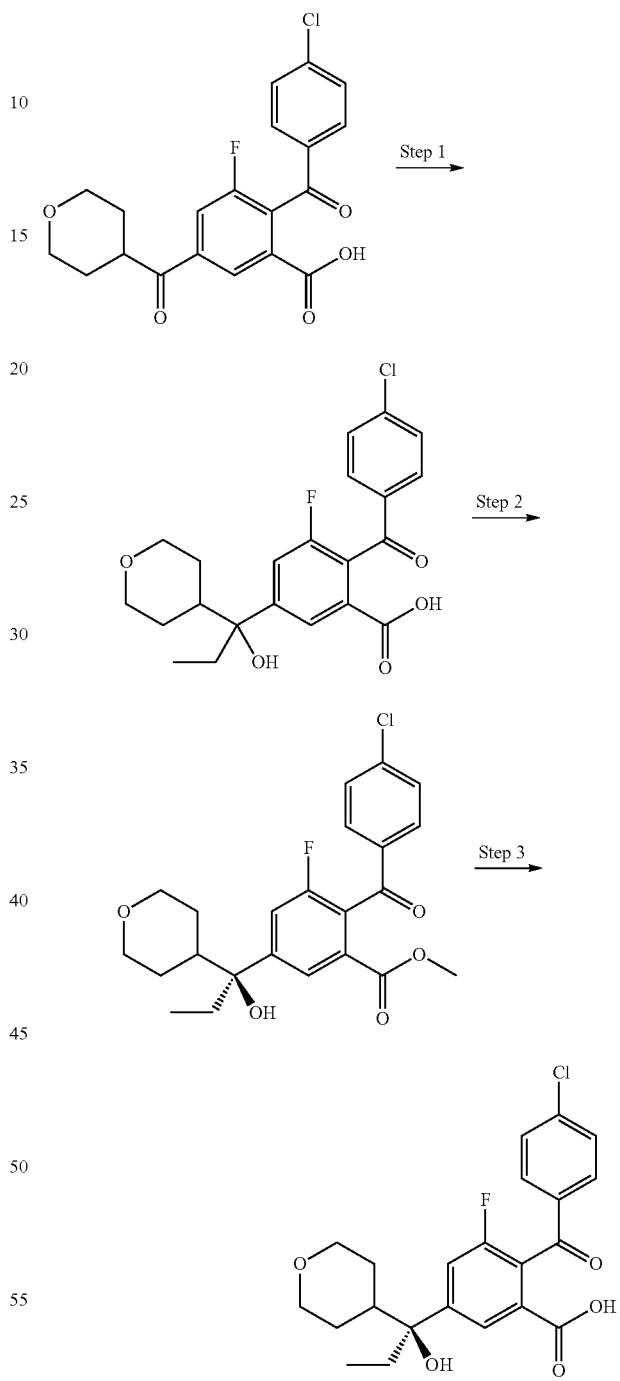

Step 1: 2-(4-Chlorobenzoyl)-3-fluoro-5-(1-hydroxy-1-(tetrahydro-2H-pyran-4-yl)propyl)benzoic Acid To 50 mL of THF at −50° C. under nitrogen atmosphere was added diethylzinc (62 mL, 1M solution in hexanes, 62.0 mmol) and ethyl lithium (36 mL, 1.72 M solution in dibutyl ether, 62.0 mmol). The mixture was stirred at −50° C. for 1 h and then 2-(4-chlorobenzoyl)-3-fluoro-5-(tetrahydro-2H-pyran-4-carbonyl)benzoic acid (Preparation 48, 9.7 g, 24.0 mmol) was added as a THF (100 mL) solution. The mixture turned dark orange immediately and the internal temperature reached −22° C. The mixture was stirred at −50° C. for 20 min before being quenched by slow addition of 2N HCl (500 mL) (Caution). After stirring for 1 h, the pH was adjusted to 1-2 with 2M HCl and the aqueous was extracted with ethyl acetate (200 mL), washed with 2M HCl (75 mL), dried over magnesium sulfate, filtered and concentrated. The crude product was purified by silica column chromatography (gradient elution 0 to 100% EtOAc in iso-hexane) to give the title compound (9.03 g, 90%) as a colourless foam. MS: [M+H]⁺=421

Step 2: Methyl (S)-2-(4-chlorobenzoyl)-3-fluoro-5-(1-hydroxy-1-(tetrahydro-2H-pyran-4-yl)propyl)benzoate To a round bottom flask containing crude 2-(4-chlorobenzoyl)-3-fluoro-5-(1-hydroxy-1-(tetrahydro-2H-pyran-4-yl)propyl)benzoic acid (6.32 g, 15 mmol), K₂CO₃ (2.69 g, 19 mmol) and DMF (50 mL) was added methyl iodide (0.934 mL, 16 mmol). The reaction was stirred for 1.5 h at room temperature, after which point LCMS showed complete conversion to the desired product. The mixture was concentrated under reduced pressure and the residue dissolved in ethyl acetate (150 mL) and washed with water (100 mL), then a 4% aqueous LiCl solution (2×100 mL). The organic layer was dried over magnesium sulfate, filtered and concentrated to give a pale yellow foam. The enantiomers were separated using chiral SFC to give the title compound (8.1 g) as a colourless solid.

Methyl (S)-2-(4-chlorobenzoyl)-3-fluoro-5-(1-hydroxy-1-(tetrahydro-2H-pyran-4-yl)propyl)benzoate: Fast running isomer MS: [M+H]⁺=435. [α]$_D^{20}$=−1.83 (c 1.0, MeOH).

Methyl (R)-2-(4-chlorobenzoyl)-3-fluoro-5-(1-hydroxy-1-(tetrahydro-2H-pyran-4-yl)propyl)benzoate: Slow running isomer MS: [M+H]⁺=435. [α]$_D^{20}$=+1.48 (c 1.0, MeOH).

Step 3: (S)-2-(4-Chlorobenzoyl)-3-fluoro-5-(1-hydroxy-1-(tetrahydro-2H-pyran-4-yl)propyl)benzoic Acid Methyl (S)-2-(4-chlorobenzoyl)-3-fluoro-5-(1-hydroxy-1-(tetrahydro-2H-pyran-4-yl)propyl)benzoate (8.2 g, 18.86 mmol) was dissolved in THF (250 mL), methanol (30 mL) and water (50 mL). Anhydrous LiOH (2.26 g, 94.3 mmol) was added and the mixture was stirred at room temperature for 2 h. The resultant solution was concentrated to approximately 60 mL volume, diluted with water (500 mL) and washed with diethyl ether (400 mL). The aqueous layer was then acidified with 2N HCl and extracted with DCM (3×200 mL). Combined extracts were dried (MgSO₄) and evaporated to afford the title compound (8.1 g, quant.) as a colourless foam. ¹H NMR (400 MHz, CDCl₃) 7.86 (1H, s), 7.71 (2H, d), 7.49-7.41 (3H, m), 4.05 (1H, dd), 3.98-3.93 (1H, m), 3.43-3.28 (2H, m), 1.97-1.89 (2H, m), 1.77-1.74 (1H, m), 1.52-1.40 (2H, m), 1.20-1.13 (1H, m), 0.75 (3H, dd), OH and COOH not observed. MS: [M−H⁺]⁻=419. [α]$_D^{20}$=−2.3 (c 1.0, MeOH).

Preparation 52b: (R)-2-(4-chlorobenzoyl)-3-fluoro-5-(1-hydroxy-1-(tetrahydro-2H-pyran-4-yl)propyl)benzoic Acid

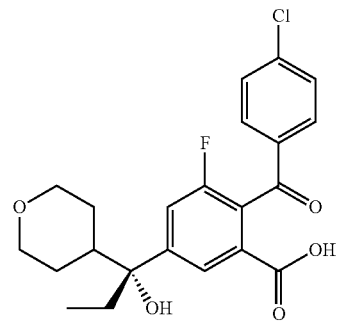 [SMILES: CC[C@](O)(c1cc(F)c(C(=O)c2ccc(Cl)cc2)c(C(=O)O)c1)C1CCOCC1]

The title compound was prepared in a similar fashion to Example 52, but using (R)-2-(4-chlorobenzoyl)-3-fluoro-5-(1-hydroxy-1-(tetrahydro-2H-pyran-4-yl)propyl)benzoate in Step 3. MS: [M−H⁺]⁻=419. [α]$_D^{20}$=+1.8 (c 10, MeOH).

Preparation 53: 2-(4-chlorobenzoyl)-3-fluoro-5-(4-fluorotetrahydro-2H-pyran-4-carbonyl)benzoic Acid

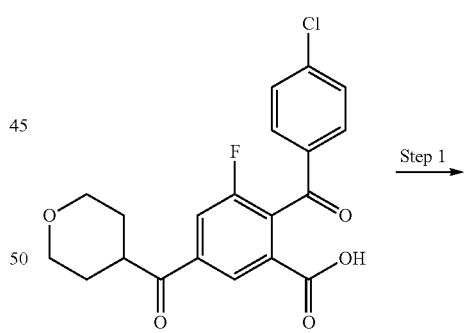

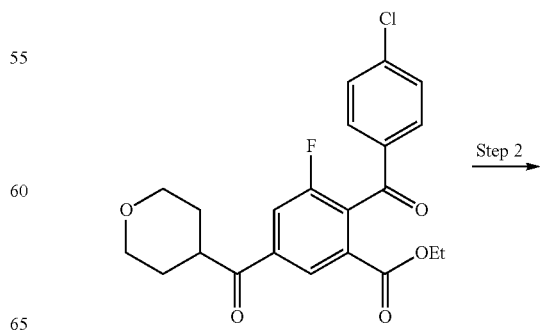

-continued

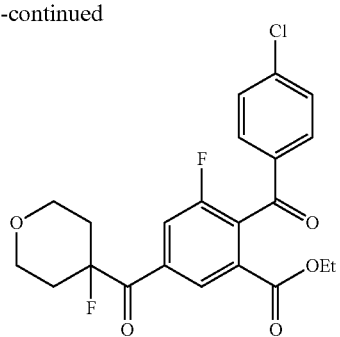

↓ Step 3

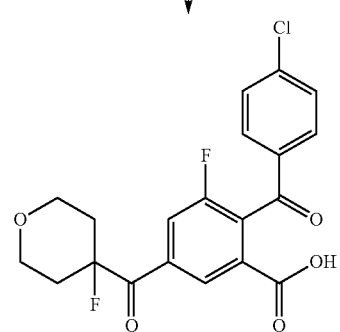

Step 1: Ethyl 2-(4-chlorobenzoyl)-3-fluoro-5-(tetrahydro-2H-pyran-4-carbonyl)benzoate To a stirred solution of 2-(4-chlorobenzoyl)-3-fluoro-5-(tetrahydro-2H-pyran-4-carbonyl)benzoic acid (Preparation 48, 100 g, 258 mmol) in DMF (800 mL) was added potassium carbonate (54.8 g, 396 mmol) followed by iodoethane (26.8 mL, 334 mmol). The mixture was stirred for 18 h at RT and then evaporated to dryness under reduced pressure. The residue was triturated with water (1 L) and the solid was collected by filtration, washing with more water (3×500 mL). The solid was dissolved in DCM (750 mL), dried (MgSO$_4$), filtered and evaporated under reduced pressure to give the title compound (107 g, 99%) as a pale yellow solid. $^1$H NMR (400 MHz, CDCl$_3$) 8.43 (1H, d), 7.90 (1H, dd), 7.75-7.72 (2H, m), 7.47-7.44 (2H, m), 4.21 (2H, q), 4.11-4.05 (2H, m), 3.63-3.48 (3H, m), 1.97-1.79 (4H, m), 1.13 (3H, dd).

Step 2: Ethyl 2-(4-chlorobenzoyl)-3-fluoro-5-(4-fluorotetrahydro-2H-pyran-4-carbonyl)benzoate A three neck flask was fitted with a nitrogen inlet, a thermometer, and a pressure equalizing dropping funnel. The flask was charged with ethyl 2-(4-chlorobenzoyl)-3-fluoro-5-(tetrahydro-2H-pyran-4-carbonyl)benzoate (54.0 g, 129 mmol) and dry THF (560 mL). The mixture was then cooled to −78° C. and LHMDS (170 mL. 170 mmol, 1M in THF) was added at a steady rate such that the internal reaction temperature did not exceed −60° C. The mixture was stirred at −78° C. for 20 min, and then a solution of N-fluorobenzenesulfonimide (53.14 g, 169 mmol) in THF (560 mL) was added steadily ensuring the internal temperature did not exceed −60° C. The mixture was stirred at −78° C. for 20 min, and was then allowed to warm to room temperature (~1 h). The reaction was quenched with water (500 mL) and then extracted with ethyl acetate (3×250 mL). The combined organic extracts were dried (MgSO$_4$), filtered, and evaporated under reduced pressure to give a crude residue which was purified by silica column chromatography (340 g cartridge, gradient elution 0 to 40% EtOAc in iso-hexane) to give the title compound (46.2 g, 82%) as a colourless solid. MS: [M+H]$^+$=437.

Step 3: 2-(4-Chlorobenzoyl)-3-fluoro-5-(4-fluorotetrahydro-2H-pyran-4-carbonyl)benzoic Acid 2-(4-chlorobenzoyl)-3-fluoro-5-(4-fluorotetrahydro-2H-pyran-4-carbonyl)benzoate (46.2 g, 105 mmol) in THF (260 mL) and methanol (260 mL) was added 2M NaOH solution (530 mL). The resulting orange solution was stirred at room temperature for 1 h. Diethyl ether (500 mL) was added and the layers were separated. The aqueous phase was adjusted to pH 1 using concentrated HCl, and the resulting mixture was extracted with ethyl acetate (2×500 mL). The combined organic extracts were dried (MgSO$_4$), filtered and evaporated under reduced pressure to give the title compound (37.4 g, 87%) as a colourless solid. The product was deemed sufficiently pure to be used in the subsequent step. $^1$H NMR (400 MHz, CDCl$_3$) 8.62 (1H, s), 8.08 (1H, dd), 7.71 (2H, d), 7.46-7.43 (2H, m), 4.01-3.84 (4H, m), 2.41-2.22 (2H, m), 2.04-1.96 (2H, m).

Preparation 54: (R)-2-(4-chlorobenzoyl)-3-fluoro-5-(1-(4-fluorotetrahydro-2H-pyran-4-yl)-1-hydroxypropyl)benzoic Acid

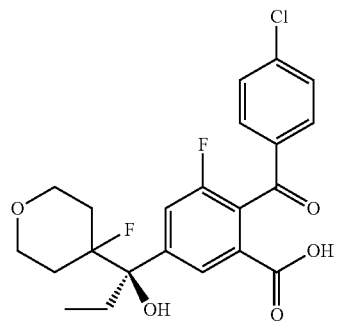 [SMILES: CC[C@@](O)(c1cc(F)c(C(=O)c2ccc(Cl)cc2)c(C(=O)O)c1)C1(F)CCOCC1]

Starting from 2-(4-chlorobenzoyl)-3-fluoro-5-(4-fluorotetrahydro-2H-pyran-4-carbonyl)benzoic acid (Preparation 53). The title compound was prepared using procedures similar to those described in Preparation 52. $^1$H NMR (400 MHz, CDCl$_3$) 7.97 (1H, s), 7.71 (2H, d), 7.57 (1H, d), 7.43 (2H, d), 3.86 (2H, ddd), 3.71-3.59 (3H, m), 2.28-2.18 (1H, m), 2.03-1.60 (5H, m), 0.76 (3H, t). [α]$_D^{20}$=+16.06 (c 1.04, MeOH).

Preparation 55: 2-(4-Chlorobenzoyl)-5-(cyclobutanecarbonyl)-3-fluorobenzoic Acid

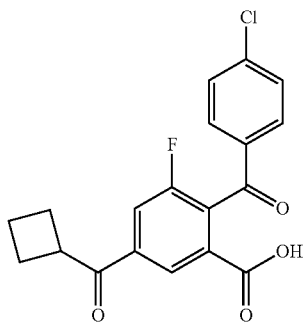 [SMILES: O=C(O)c1cc(C(=O)C2CCC2)cc(F)c1C(=O)c1ccc(Cl)cc1]

Starting from cyclobutylaldehyde, the title compound was prepared using procedures similar to those described in Example 73, steps 1 and 2. MS: [M−H]⁻=359

Preparation 56: trans-4-((tert-Butyldiphenylsilyl)oxy)cyclohexanecarbaldehyde

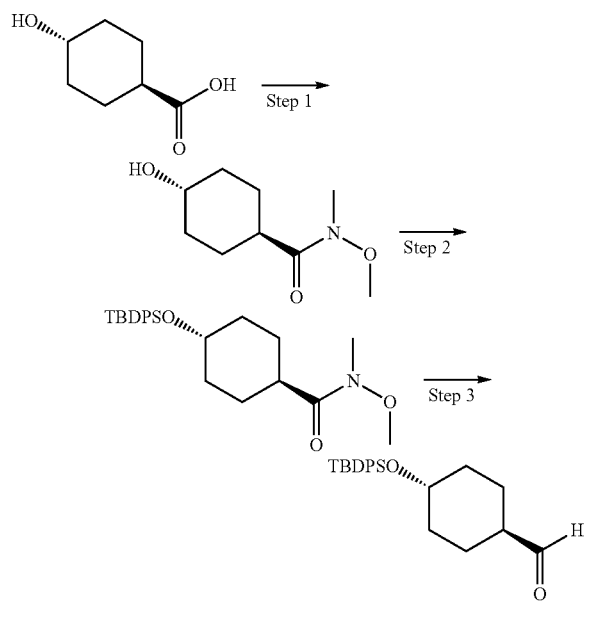

Step 1: trans-4-Hydroxy-N-methoxy-N-methylcyclohexanecarboxamide

To a solution of 4-hydroxycyclohexanecarboxylic acid (25 g, 173 mmol), EDCl (32 g, 208 mmol) and N,O-dimethylhydroxylamine hydrochloride (19 g, 191 mmol) in DCM (500 mL) under nitrogen at room temperature was added DIPEA (91 mL, 520 mmol) and the mixture stirred for 20 h. The reaction was quenched with 2N aqueous HCl (50 mL), partitioned with water (400 mL), layers shaken and separated, the aqueous re-extracted with DCM (2×150 mL). The combined organic extracts were dried (MgSO₄), filtered, and concentrated under reduced pressure to yield the desired product (21 g) as a thick pale yellow oil. ¹H NMR (400 MHz, CDCl₃) 3.70 (3H, s), 3.68-3.59 (1H, m), 3.18 (3H, s), 2.70-2.55 (1H, m), 2.10-2.02 (2H, m), 1.88-1.80 (2H, m), 1.63-1.53 (2H, m), 1.38-1.26 (2H, m), OH missing.

Step 2: trans-4-((tert-Butyldiphenylsilyl)oxy)-N-methoxy-N-methylcyclohexane-1-carboxamide trans-4-Hydroxy-N-methoxy-N-methylcyclohexanecarboxamide (12.2 g, 65 mmol), was dissolved in DMF (200 mL) and stirred at room temperature under a nitrogen atmosphere. tert-butyl(chloro)diphenylsilane (19.7 g, 71 mmol) was added, followed by imidazole (4.88 g, 71 mmol). The reaction was stirred for 18 h. The DMF was evaporated under reduced pressure, and the resulting residue was re-dissolved in EtOAc (250 mL). The organic layer was washed with 4% aqueous LiCl solution (2×150 mL), and then dried (MgSO4), filtered, and evaporated under reduced pressure. The crude residue was purified by silica column chromatography (gradient elution 0 to 60% EtOAc in iso-Hex), to give the pure product as a colourless oil which crystallises upon standing (19.0 g, 69% yield). MS: [M+H]⁺=426.

Step 3: trans-4-((tert-Butyldiphenylsilyl)oxy)cyclohexanecarbaldehyde trans-4-((tert-Butyldiphenylsilyl)oxy)-N-methoxy-N-methylcyclohexanecarboxamide (0.5 g, 1.17 mmol) was dissolved in dry THF (7.5 mL) under a nitrogen atmosphere. The solution was cooled to −78° C., and then DIBAL (1M in hexane, 2.11 mL, 2.11 mmol) was added dropwise. The mixture was stirred at −78° C. for 1.5 h and then quenched with 10% aqueous Rochelle salt solution (10 mL). The mixture was allowed to warm to room temperature and was then diluted further with EtOAc (40 mL) and more Rochelle salt solution (15 mL). The mixture was stirred for 20 mins before being transferred to a separating funnel. The organic phase was collected, and the aqueous phase was extracted with EtOAc (2×30 mL). The combined organic extracts were dried (MgSO₄), filtered, and evaporated under reduced pressure to give a crude residue which was used in next step without further purification. ¹H NMR (400 MHz, CDCl₃) 9.56 (1H, s), 7.67-7.65 (4H, m), 7.43-7.34 (6H, m), 3.64-3.55 (1H, m), 2.20-2.13 (1H, m), 1.95-1.80 (4H, m), 1.48-1.37 (2H, m), 1.28-1.20 (2H, m), 1.05 (9H, s).

Preparation 57: (−)-5-(1-(1-(tert-butoxycarbonyl)-4-fluoropiperidin-4-yl)-1-hydroxypropyl)-2-(4-chlorobenzoyl)-3-fluorobenzoic acid (*Both Isomers Separated and Isolated)

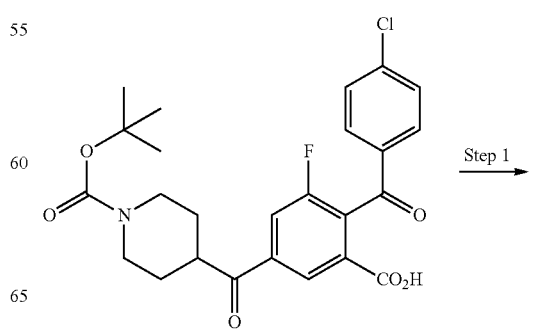

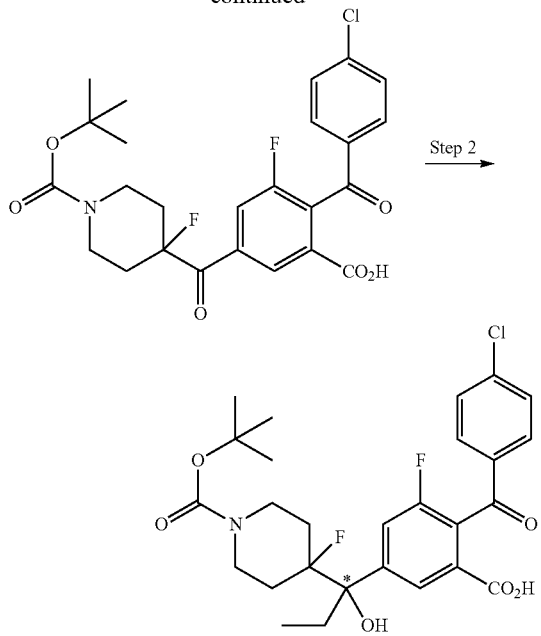

Step 1: 5-(1-(tert-Butoxycarbonyl)-4-fluoropiperidine-4-carbonyl)-2-(4-chlorobenzoyl)-3-fluorobenzoic Acid A mixture of 5-(1-(tert-butoxycarbonyl)piperidine-4-carbonyl)-2-(4-chlorobenzoyl)-3-fluorobenzoic acid (Example 80 step 2, 50 g, 0.102 mol) and NaOH (4.32 g, 0.108 mol) was stirred in anhydrous THF (250 mL) and anhydrous MeOH (90 mL) until all the NaOH dissolved. The solution was evaporated under reduced pressure and the residue dissolved in anhydrous THF (400 mL) and added over 1 minute to a stirred solution of 1M LHMDS in hexanes (125 mL) in anhydrous THF (100 mL) at −40° C. under nitrogen. The mixture was stirred for 20 minutes at −40° C. prior to the addition of a solution of N-fluorobenzenesulfonimide (48.6 g, 0.154 mol) in anhydrous THF (400 mL) in a steady stream over 1 minute. On complete addition the mixture was stirred with cooling in a bath at −40° C. for 20 minutes. The mixture was quenched with water (500 mL), stirred at room temperature for 30 minutes, the pH adjusted to pH2 with 2N HCl and then the aqueous was extracted with EtOAc (2×750 mL). The combined organics were dried (MgSO$_4$) and the solvent evaporated. The residue was triturated with DCM (500 mL) and the solid filtered, washed with DCM and dried to afford the title compound as a colourless solid (31.3 g, 60%). MS [M−H]$^-$=506.

Step 2: (−)-5-(1-(1-(tert-butoxycarbonyl)-4-fluoropiperidin-4-yl)-1-hydroxypropyl)-2-(4-chlorobenzoyl)-3-fluorobenzoic Acid To anhydrous THF (130 mL) at −50° C. under nitrogen was added a 1.72 M solution of EtLi in dibutyl ether (38.4 mL, 65.96 mmol) followed by 1 M diethylzinc in hexanes (66.4 mL). This was stirred at −50° C. for 70 minutes prior to addition of a solution of 5-(1-(tert-butoxycarbonyl)-4-fluoropiperidine-4-carbonyl)-2-(4-chlorobenzoyl)-3-fluorobenzoic acid (13.4 g, 26.38 mmol) in anhydrous THF (130 mL) in a gentle stream over 1 minute. On complete addition the mixture was stirred at −50° C. for 20 minutes, quenched by careful addition of water (200 mL), warmed to room temperature, acidified with 1M HCl and extracted into EtOAc (2×500 mL). Combined extracts were dried (MgSO$_4$) and the solvent evaporated under reduced pressure. The residue was triturated with isohexane (500 mL), the solvent decanted and the colourless solid dried to afford the title compound as the racemate. (13.9 g, 99%). MS [M−H]$^-$=536. The racemate (11.2 g) was separated by SFC to afford the title compound as the slow running isomer (5.11 g, 45% yield).

(+)-5-(1-(1-(tert-butoxycarbonyl)-4-fluoropiperidin-4-yl)-1-hydroxypropyl)-2-(4-chlorobenzoyl)-3-fluorobenzoic Acid Fast running isomer* $^1$H NMR (400 MHz, CDCl$_3$) 7.97 (1H, s), 7.72 (2H, d), 7.54 (1H, d), 7.43 (2H, d), 4.01-4.01 (2H, m), 3.00-2.89 (2H, m), 2.28-2.19 (1H, m), 2.08-1.98 (2H, m), 1.81-1.50 (3H, m), 1.43 (9H, s), 0.75 (3H, dd), exchangeable protons not observed. $[\alpha]_D^{20}$=+31.41° (c 1, MeOH).

(−)-5-(1-(1-(tert-butoxycarbonyl)-4-fluoropiperidin-4-yl)-1-hydroxypropyl)-2-(4-chlorobenzoyl)-3-fluorobenzoic Acid Slow running isomer* $^1$H NMR (400 MHz, CDCl$_3$) 7.97 (1H, s), 7.72 (2H, d), 7.54 (1H, d), 7.43 (2H, d), 4.01-4.01 (2H, m), 3.00-2.89 (2H, m), 2.28-2.19 (1H, m), 2.08-1.98 (2H, m), 1.81-1.50 (3H, m), 1.43 (9H, s), 0.75 (3H, dd), exchangeable protons not observed. $[\alpha]_D^{20}$=−31.33° (c 1, MeOH).

Preparation 58:
(2-Bromo-4-methylphenyl)methanamine

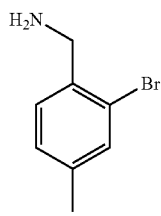

Prepared in a similar manner to that described in Example 33, Step 1; from 2-bromo-4-methylbenzonitrile. $^1$H NMR (400 MHz, CDCl$_3$) 7.37 (1H, s), 7.25 (1H, d), 7.08 (1H, d), 3.86 (2H, s), 2.31 (3H, s).

Preparation 59:
(2-Bromo-4-methoxyphenyl)methanamine

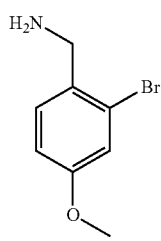

Prepared in a similar manner to that described Example 33, Step 1; from 2-bromo-4-methylbenzonitrile. $^1$H NMR (400 MHz, CDCl$_3$) 7.26 (1H, d), 7.11 (1H, d), 6.84 (1H, dd), 3.85 (2H, s), 3.79 (3H, s), 1.5 (2H, br s).

Preparation 60: (S)-5-(1-(1-(tert-butoxycarbonyl)piperidin-4-yl)-1-hydroxypropyl)-2-(4-chlorobenzoyl)-3-fluorobenzoic Acid

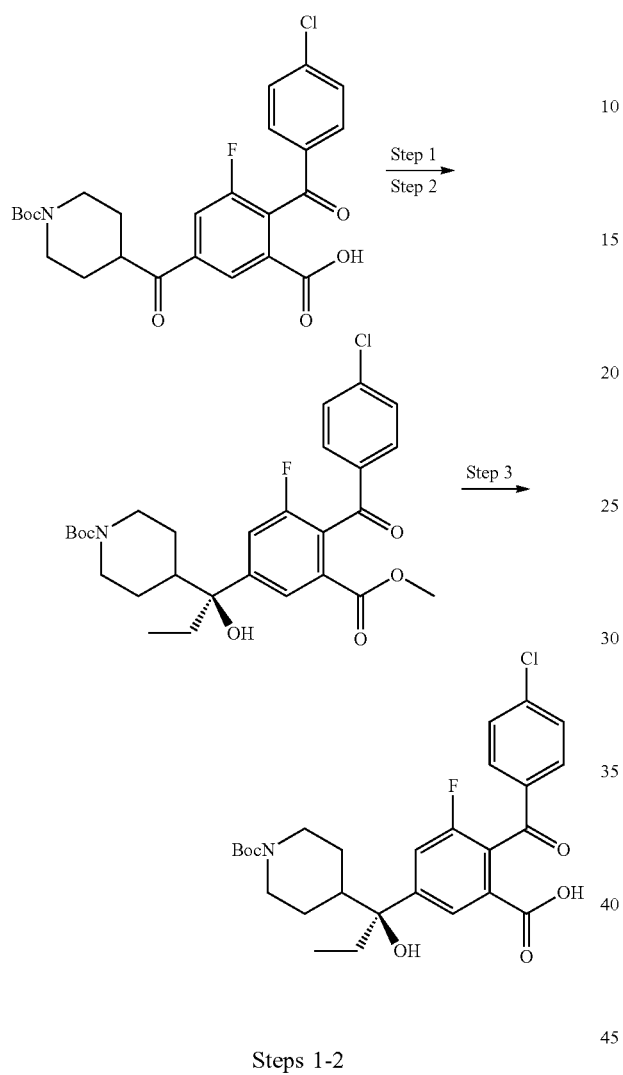

Steps 1-2

Starting from the piperidine ketone (Examples 80 and 81, step 2, 11.0 g, 23 mmol), Steps 1 and 2 were performed using a procedure similar to that described for Preparation 52, Step 1-2, The racemic mixture was separated by chiral SFC to give
(−)-tert-butyl-(S)-4-(1-(4-(4-chlorobenzoyl)-3-fluoro-5-(methoxycarbonyl)phenyl)-1-hydroxypropyl)piperidine-1-carboxylate (3 g). MS: [M+H]$^+$=534, $[\alpha]_D^{20}$=−34.15 (c 1.18, MeOH). and
(+)-tert-butyl-(S)-4-(1-(4-(4-chlorobenzoyl)-3-fluoro-5-(methoxycarbonyl)phenyl)-1-hydroxypropyl)piperidine-1-carboxylate (3.6 g). MS: [M+H]$^+$=534, $[\alpha]_D^{20}$=+24.46 (c 1.02, MeOH).

Step 3: (S)-5-(1-(1-(tert-butoxycarbonyl)piperidin-4-yl)-1-hydroxypropyl)-2-(4-chlorobenzoyl)-3-fluorobenzoic Acid Using procedures similar to those described in Preparation 52 Step 3, (−)-tert-butyl (S)-4-(1-(4-(4-chlorobenzoyl)-3-fluoro-5-(methoxycarbonyl)phenyl)-1-hydroxypropyl)piperidine-1-carboxylate (3.0 g, 5.6 mmol) gave 3.1 g of the title compound. MS: [M+H]$^+$=518, $[\alpha]_D^{20}$=−37.51 (0.97 q/100 mL),

Preparation 61: 2-(4-Chlorobenzoyl)-3-fluoro-5-(pyridine-2-carbonyl)benzoic Acid

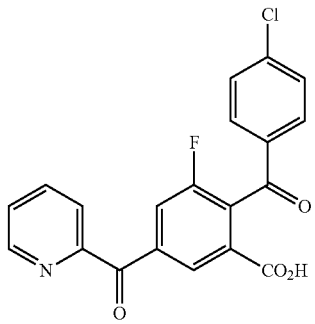 [SMILES: O=C(c1cc(F)c(C(=O)c2ccc(Cl)cc2)c(C(=O)O)c1)c1ccccn1]

The title compound was prepared using procedures similar to those described in Example 73 (step 1-2), but using pyridine-2-carboxaldehyde in step 1. Iodine (2 mol. Eq.), K$_2$CO$_3$ (2 mol eq.), Ki (0.25 mol eq) in water (90° C.) was used as alternative oxidation conditions in Step 2. MS: [M+H]$^+$=384.

Preparation 62: Prop-2-en-1-yl (2S,3S)-3-amino-3-(4-chlorophenyl)-2-methylpropanoate

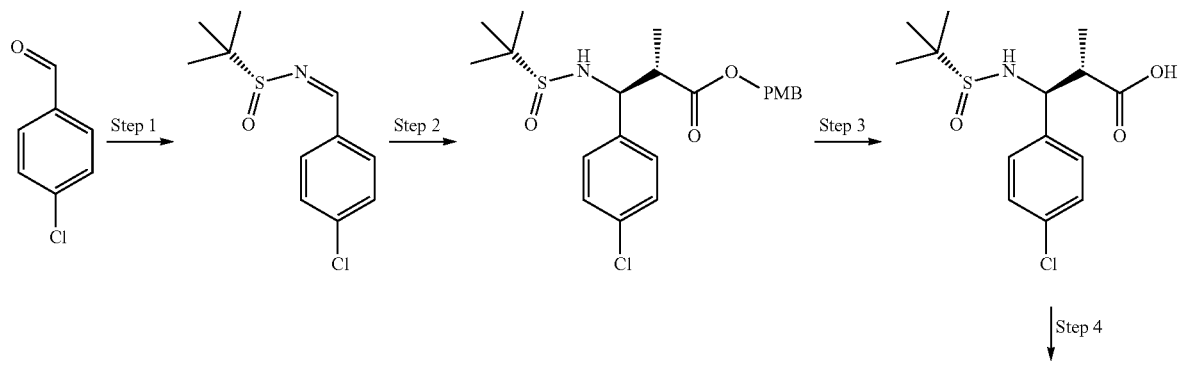

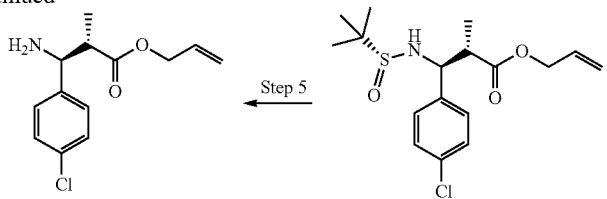

Step 1: N-[(1Z)-(4-Chlorophenyl)methylidene]-2-methylpropane-2-(R)sulfinamide (R)-2-methylpropane-2-sulfinamide (18.1 g, 150 mmol), 4-chlorobenzaldehyde (20.0 g, 143 mmol) and $Cs_2CO_3$ (51.0 g, 157 mmol) were suspended in DCM (150 mL) and stirred at room temperature for 16 h. The mixture was then filtered through Celite and the volatiles were removed in vacuo to give the desired product as a white solid (26.0 g, 75% yield). LCMS: $[M+H]^+=244$.

Step 2: (4-Methoxyphenyl)methyl (2S,3S)-3-(4-chlorophenyl)-2-methyl-3-[(2-methylpropane-2-(R)-sulfinyl)amino]propanoate n-BuLi (2.5 M in hexane, 16.8 mL, 45 mml) was slowly added to a solution of diisopropylamine (6.3 mL, 45 mmol) in THF (20 mL) at 0° C. and the reaction stirred for 30 min. at the same temperature. The mixture was then cooled to −78° C. and (4-methoxyphenyl)methyl propanoate (7.2 mL, 40 mmol) was slowly added, keeping the temperature below −70° C. After 30 min. chlorotriisopropoxytitanium(IV) (1M in hexane, 80 mL, 84 mmol) was added to the reaction mixture and stirring was maintained for further 30 min at −78° C. Finally, a solution of N-[(1Z)-(4-chlorophenyl)methylidene]-2-methylpropane-2-(R)sulfinamide (5.0 g, 20 mmol) in THF (15 mL) was slowly added and the reaction was stirred for further 2 h at −78° C. $NH_4Cl$ (aq), water and EtOAc were added to the reaction, the mixture was wormed up to room temperature and vigorously stirred for 30 min. to dissolve most of the solid. The organic phase was separated and the aqueous phase was extracted with EtOAc (3×). The organic phases were collected, dried over $Na_2SO_4$ and concentrated in vacuo. The residue was columned on silica gel (gradient 0-100% EtOAc in Petrol) to give the desired product as a yellow oil (5.1 g, 58% yield). 1H NMR (400 MHz, DMSO-d6): 7.39-7.27 (2H, m), 7.24 (2H, d), 7.00 (2H, t), 6.91-6.80 (2H, m), 5.72-5.63 (1H, m), 4.88-4.73 (2H, m), 4.24 (1H, t), 3.75 (3H, s), 2.99-2.87 (1H, m), 1.28 (3H, d), 1.02-0.90 (9H, m).

Step 3: (2S,3S)-3-(4-Chlorophenyl)-2-methyl-3-[(2-methylpropane-2-(R)-sulfinyl)amino]propanoic Acid TFA (12 mL) was added to a solution of (4-methoxyphenyl)methyl (2S,3S)-3-(4-chlorophenyl)-2-methyl-3-[(2-methylpropane-2-(R)-sulfinyl)amino]propanoate (6.0 g, 13.7 mmol) in DCM (20 mL) and the reaction was stirred at room temperature for 1 h. The volatiles were removed in vacuo and the residue was partitioned between 1M HCl and EtOAc. The aqueous phase was extracted with EtOAc (3×), the organic phases were collected, dried over $Na_2SO_4$ and concentrated in vacuo to give the give the desired product ad a light brown solid which was used without further purifications in the next step. LCMS: $[M+H]^+=318$.

Step 4: Prop-2-en-1-yl (2S,3S)-3-(4-chlorophenyl)-2-methyl-3-[(2-methylpropane-2-(R)-sulfinyl)amino]propanoate Allyl bromide (2.3 mL, 26 mmol) was added to a suspension of (2S,3S)-3-(4-chlorophenyl)-2-methyl-3-[(2-methylpropane-2-(R)-sulfinyl)amino]propanoic acid (crude from previous step, ca. 13 mmol) and $K_2CO_3$ (5.4 g, 39 mmol) in DMF. The reaction mixture was stirred at room temperature for 2 h, quenched with water and extracted with EtOAc. The organic was dried over $Na_2SO_4$ and concentrated in vacuo. The residue was columned on silica gel (gradient 0-100% EtOAc in Petrol) to give the desired product as a yellow oil (2.8 g, 57% yield over 2 steps). 1H NMR (400 MHz, DMSO-d6): 7.40-7.32 (2H, m), 7.29 (2H, d), 5.74-5.58 (2H, m), 5.15-5.02 (2H, m), 4.41-4.31 (2H, m), 4.27 (1H, t), 3.00-2.88 (1H, m), 1.28 (3H, d), 1.01 (9H, s).

Step 5: Prop-2-en-1-yl (2S,3S)-3-amino-3-(4-chlorophenyl)-2-methylpropanoate HCl (4M in dioxane, 15 mL) was added to a solution of prop-2-en-1-yl (2S,3S)-3-(4-chlorophenyl)-2-methyl-3-[(2-methylpropane-2-(R)-sulfinyl)amino]propanoate (2.8 g, 7.8 mmol) in EtOH (20 mL) and the suspension was stirred at room temperature for 30 min. The volatiles were removed in vacuo and the residue was partitioned between $NaHCO_3$ and EtOAc. The organic was collected, dried over $Na_2SO_4$ and concentrated in vacuo to give the desired product as a yellow oil (1.7 g, 86% yield). 1H NMR (400 MHz, DMSO-d6): 7.34 (4H, s), 5.81-5.68 (1H, m), 5.22-5.06 (2H, m), 4.46-4.33 (2H, m), 4.07-3.94 (1H, m), 2.76-2.60 (1H, m), 1.96 (2H, s), 1.09 (3H, d).

Preparation 63: Ethyl 2-[2-(aminomethyl)-5-chlorophenoxy]acetate hydrochloride

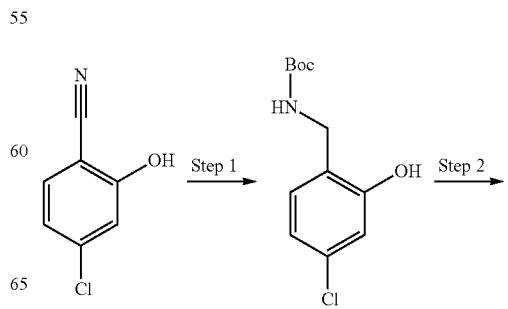

-continued

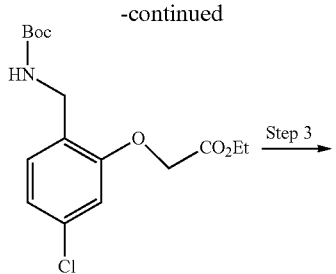

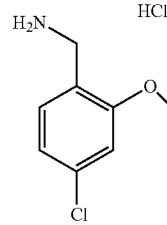

Step 1: tert-Butyl N-[(4-chloro-2-hydroxyphenyl)methyl]carbamate

To a stirred solution of 4-chloro-2-hydroxybenzonitrile (1.57 g, 10.0 mmol) in dry methanol (70 mL), cooled to 0° C., were added Boc$_2$O (4.36 g, 20.0 mmol) and NiCl$_2$.6H$_2$O (0.24 g, 1.0 mmol). NaBH$_4$ (2.65 g, 70.0 mmol) was then added in small portions over 30 min. The reaction was exothermic and effervescent. The resulting reaction mixture containing a finely divided black precipitate was allowed to warm to room temperature and left to stir for a further 1 h, at which point diethylenetriamine (1.1 mL, 20.0 mmol) was added. The mixture was allowed to stir for 30 min before solvent evaporation. The residue was dissolved in DCM (50 mL), piperidine (2 mL) was added and stirred for 30 min, then the organic phase was washed with water and saturated NaHCO$_3$. The organic layer was dried (MgSO$_4$) and the solvent removed in vacuo and the crude product was purified by column chromatography to afford the title compound (1.47 g, 57%). MS: [M+H]$^+$=256.

Step 2: Ethyl 2-[2-({[(tert-butoxy)carbonyl]amino}methyl)-5-chlorophenoxy]acetate To a solution of tert-butyl N-[(4-chloro-2-hydroxyphenyl)methyl]carbamate (1.47 g, 5.7 mmol) in DMF (30 mL) was added K$_2$CO$_3$ (0.95 g, 6.9 mmol) and the mixture was stirred for 30 min. Ethyl bromoacetate (1.4 mL, 8.55 mmol) was added and the stirring was continued for 2 hr. Water was added, the reaction mixture was extracted with EtOAc, the organic phase was washed with brine (3×), dried and the solvent was evaporated. The crude material was purified by column chromatography, eluted with petroleum ether-EtOAc 0-40% to afford the title compound (1.64 g, 84%). MS: [M+H]$^+$=243 (M-Boc).

Step 3: Ethyl 2-[2-(aminomethyl)-5-chlorophenoxy]acetate hydrochloride

To a solution of ethyl 2-[2-({[(tert-butoxy)carbonyl]amino}methyl)-5-chlorophenoxy]acetate (1.8 g, 5.25 mmol) in dioxane (20 mL) was added 4M dioxane —HCl and the mixture was stirred for 16 hr. The solvent was evaporated to afford white solid (1.3 g, 89%). MS: [M+H]$^+$=244.

Preparation 64: 2-(4-chlorobenzoyl)-3-fluoro-5-(1-hydroxy-1-trans-4-hydroxycyclohexyl)propyl)benzoic acid (*Both Isomers Separated and Isolated)

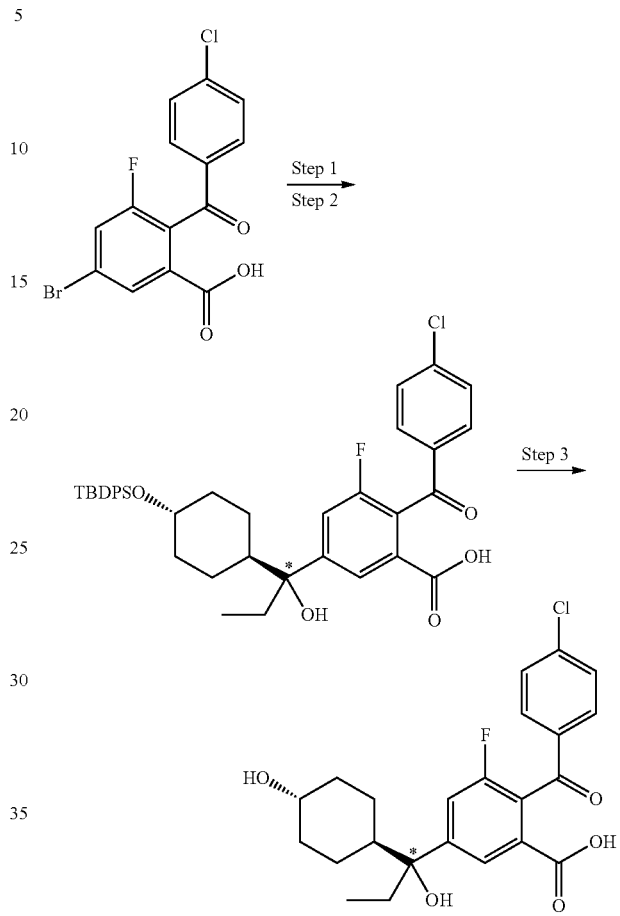

Step 1: 5-(trans-4-((tert-Butyldiphenylsilyl)oxy)cyclohexane-1-carbonyl)-2-(4-chlorobenzoyl)-3-fluorobenzoic Acid Starting from trans-4-((tert-butyldiphenylsilyl)oxy)cyclohexanecarbaldehyde (Preparation 56), the title compound was prepared using procedures similar to those described in Example 73, steps 1 and 2. MS: [M−H]$^-$=641.

Step 2: 5-(1-(trans-4-((tert-butyldiphenylsilyl)oxy)cyclohexyl)-1-hydroxypropyl)-2-(4-chlorobenzoyl)-3-fluorobenzoic Acid The title compound was prepared using the procedure described in Preparation 52, step 1, and the enantiomers were separated by chiral SFC.

(+)-5-(1-(trans-4-((tert-butyldiphenylsilyl)oxy)cyclohexyl)-1-hydroxypropyl)-2-(4-chlorobenzoyl)-3-fluorobenzoic acid: *fast running isomer $^1$H NMR (400 MHz, CDCl$_3$) 7.8 (1H, s), 7.70-7.63 (6H, m), 7.43-7.34 (9H, m), 3.55-3.46 (1H, m), 1.94-1.78 (5H, m), 1.43-1.24 (3H, m), 1.03 (9H, s), 0.96-0.83 (3H, m), 0.69 (3H, t), Exchangeable not observed. MS: [M−H]−=671. [α]$_D^{20}$=+27.65 (c 1.0 MeOH).

(−)-5-(1-(trans-4-((tert-butyldiphenylsilyl)oxy)cyclohexyl)-1-hydroxypropyl)-2-(4-chlorobenzoyl)-3-fluorobenzoic acid: *slow running isomer $^1$H NMR (400 MHz, CDCl₃) 7.79 (1H, s), 7.70-7.63 (6H, m), 7.44-7.33 (9H, m), 3.54-3.48 (1H, m), 1.96-1.75 (5H, m), 1.46-1.16 (3H, m), 1.03 (9H, s), 0.96-0.85 (3H, m), 0.69 (3H, t), Exchangeable not observed. MS: [M−H]−=671. [α]$_D^{20}$=−24.62 (c 1.0, MeOH).

Step 3: 2-(4-chlorobenzoyl)-3-fluoro-5-(1-hydroxy-1-trans-4-hydroxycyclohexyl)propyl)benzoic Acid (−)-5-1-(trans-4-((tert-Butyldiphenylsilyl)oxy)cyclohexyl)-1-hydroxypropyl)-2-(4-chlorobenzoyl)-3-fluorobenzoic acid (3.5 g, 5.2 mmol) was dissolved in THF (70 mL) and the mixture was treated with TBAF (1M in THF, 20.7 mL, 20.7 mmol) and heated overnight at 60° C. The reaction was quenched with saturated aqueous NaHCO₃ solution and extracted with ethyl acetate (2×75 mL). The combined organic layers were dried (MgSO₄), filtered and evaporated to dryness under reduced pressure to give a crude product. The residue was purified by column chromatography (gradient elution, 20 to 100% ethyl acetate in iso-hexane (with 0.1% formic acid)) to give the title compound (1.92 g, 85%) as a colourless oil. MS: [M−H]⁻=433.

Preparation 65: 2-(4-chlorobenzoyl)-3-fluoro-5-(1-methyl-1H-pyrazole-3-carbonyl)benzoic Acid

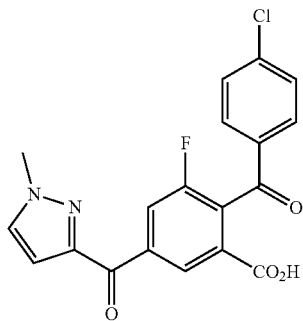 [SMILES: Cn1ccc(C(=O)c2cc(F)c(C(=O)c3ccc(Cl)cc3)c(C(=O)O)c2)n1]

The title compound was prepared using procedures similar to those described in Example 72, Step 1 and Step 2, but using 1-methyl-1H-pyrazole-3-carbaldehyde instead of 1-methyl-1H-pyrazole-4-carboxaldehyde in Step 1; and manganese dioxide in 1,4-dioxane at 100° C. instead of TEMPO/sodium hypochlorite in Step 2. MS [M+H]⁺=387

Example 1: (3R)-3-(4-chlorophenyl)-2-[(4-chlorophenyl)methyl]-3-{[1-(hydroxymethyl)cyclopropyl]methoxy}-6-(2-hydroxypropan-2-yl)-2,3-dihydro-1H-isoindol-1-one

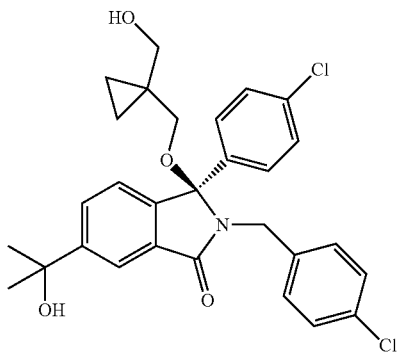 [SMILES: CC(C)(O)c1ccc2c(c1)C(=O)N(Cc1ccc(Cl)cc1)[C@@]2(OCC1(CO)CC1)c1ccc(Cl)cc1]

To a solution of MeMgBr (3M THF, 0.97 mL, 2.91 mmol) in THF (4.0 mL) at room temperature was added Zn(II)Cl₂ (30 mgs, 0.22 mmol) and the resulting solution stirred at this temperature for 1 hour. The solution was cooled to 0° C. before the addition of a cool solution of 6-acetyl-2-(4-chlorobenzyl)-3-(4-chlorophenyl)-3-((3'-(hydroxymethyl)cyclopropyl)methoxy)isoindolin-1-one (Preparation 15) (573 mgs, 1.12 mmol) in THF (4.0 mL) and the resulting mixture stirred at 0° C. for 2 hours. The reaction was quenched by the addition of a saturated solution of NH₄Cl and the resulting mixture extracted with EtOAc (×3). The combined organic phases were washed with brine, dried (MgSO₄), filtered and concentrated in vacuo. Purification on silica gel (Biotage SP4) eluting with 20%-80% EtOAc/Pet gave product as a clear gum (320 mg; 54%). Separation by chiral HPLC (Chrialpak IA 250×10 mm i.d., 75% heptane, 2-propanol, 4.5 mL/min) gave the title compound (Example 1) (R)-2-(4-Chlorobenzyl)-3-(4-chlorophenyl)-3-((3'-(hydroxymethyl)cyclopropyl) methoxy)-6-(2-hydroxypropan-2-yl)isoindolin-1-one. δ$_H$ (500 MHz, CD₃OD) 0.12-0.23 (2H, m, 3'-CH₂), 0.37-0.45 (2H, m, 3'-CH₂'), 1.56 (6H, s, (CH₃)₂), 2.76 (1H, d, J=9.0, 2'-H), 2.88 (1H, d, J=9.0, 2'-H'), 3.42 (1H, d, J=11.2, 4'-H), 3.58 (1H, d, J=11.2, 4'-H'), 4.40 (1H, d, J=15.1, N—CH), 4.45 (1H, d, J=15.1, N—CH'), 7.07-7.14 (4H, m, Ar—H), 7.15-7.22 (5H, m, Ar—H & 4-H), 7.76 (1H, dd, J=1.2, 8.1, 5-H), 8.02 (1H, d, J=1.2, 7-H); HRMS, Found; M⁺ 526.1540/.

Example 2: (3R)-3-(4-chlorophenyl)-2-[(4-chlorophenyl)methyl]-4-fluoro-3-{[1-(hydroxymethyl)cyclopropyl]methoxy}-6-(2-hydroxypropan-2-yl)-2,3-dihydro-1H-isoindol-1-one

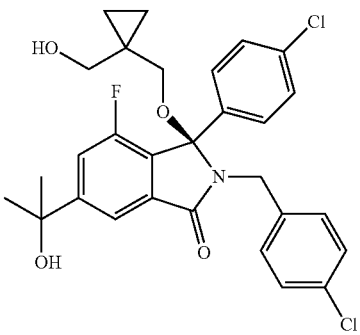 [SMILES: CC(C)(O)c1cc(F)c2c(c1)C(=O)N(Cc1ccc(Cl)cc1)[C@@]2(OCC1(CO)CC1)c1ccc(Cl)cc1]

In a microwave vial was added Hg(OAc)₂ (145 mg, 0.456 mmol) and water (0.3 mL). After stirring for 15 min, THF (0.25 mL) was added, followed by a solution of 2-(4-chlorobenzyl)-3-(4-chlorophenyl)-4-fluoro-3-((1-(hydroxymethyl)cyclopropyl)methoxy)-6-(prop-1-en-2-yl)isoindolin-1-one (Preparation 14) (150 mg, 0.285 mmol) in THF (0.5 mL). The orange solution was stirred at room temperature for 1.5 h, after which time perchloric acid (60%, 7.5 μL) was added, with the orange colour fading to yellow after 2.5 h. 1M aq. NaOH (0.8 mL) was added and the solution turned brown, then NaBH₄ (22 mg, 0.570 mmol) was introduced and the colour changed to metallic grey. The reaction mixture was left to stir for 16 h, then filtered through Celite®, followed by a thiol cartridge and the solvent removed in vacuo. FCC [petrol-ethyl acetate (100: 0)→(80:20)→(50:50)→(20:80)] of the crude residue, followed by preparative HPLC, afforded 28 mg, 20%, of a white solid. Separation of the two enantiomers was carried out by preparative chiral HPLC to give (R)-2-(4-Chlorobenzyl)-3-(4-chlorophenyl)-4-fluoro-3-((1-(hydroxymethyl)cyclopropyl)methoxy)-6-(2-hydroxypropan-2-yl)isoindolin-1-one (Example 2). $^1$H NMR (500 MHz, CDCl$_3$): 7.77 (1H, d, 7-H), 7.37 (1H, dd, ArH), 7.20-7.26 (4H, m, 4×ArH), 7.10-7.16 (4H, m, 4×ArH), 4.55 (1H, d, NC—H'), 4.11 (1H, d, NC—H), 3.53 (1H, d, 4'-H'), 3.34 (1H, d, 4'-H), 2.96 (1H, d, 2'-H'), 2.69 (1H, d, 2'-H), 1.55-1.64 (6H, 2×s, 2×CH$_3$), 0.37-0.44 (2H, m, Cy-Py-H$_2$) and 0.08-0.23 (2H, m, Cy-Py-H). MS: [M-C$_5$H$_9$O$_2$]$^+$ 442

Example 3: (3R)-3-(4-chlorophenyl)-2-[(4-chlorophenyl)methyl]-3-(2-hydroxyethoxy)-6-(2-hydroxypropan-2-yl)-2,3-dihydro-1H-isoindol-1-one

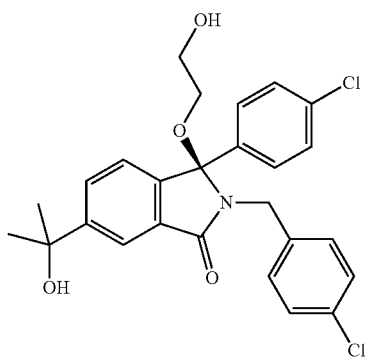 [SMILES: CC(C)(O)c1ccc2c(c1)C(=O)N(Cc1ccc(Cl)cc1)[C@@]2(OCCO)c1ccc(Cl)cc1]

The title compound was prepared from (Preparation 21) (0.062 g, 0.128 mmol), ZnCl$_2$ (0.005 g, 0.035 mmol) and of MeMgCl (3M in THF) (0.15 mL, 0.46 mmol) using a procedure similar to that described for Example 1. The product was obtained as a white foamy solid (0.030 g, 0.062 mmol, 47%). Separation by preparative chiral prep HPLC gave Example 3. $^1$H NMR (500 MHz, CDCl$_3$) δ (ppm) 1.50 (s, 1H), 1.62 (s, 6H), 1.82 (s, 1H), 2.77-2.83 (m, 1H), 2.87-2.95 (m, 1H), 3.33-3.47 (m, 2H), 4.08 (d, 1H), 4.64 (d, 1H), 7.09 (dd, 1H), 7.13-7.20 (m, 4H), 7.20-7.25 (m, 4H), 7.71 (dd, 1H), 8.0 (d, 1H); MS(ES+) m/z 486.3 [M+H]$^+$;

Example 4: (3R)-3-(4-chlorophenyl)-2-[(4-chlorophenyl)methyl]-3-{[3-(hydroxymethyl)oxetan-3-yl]methoxy}-6-(2-hydroxypropan-2-yl)-2,3-dihydro-1H-isoindol-1-one

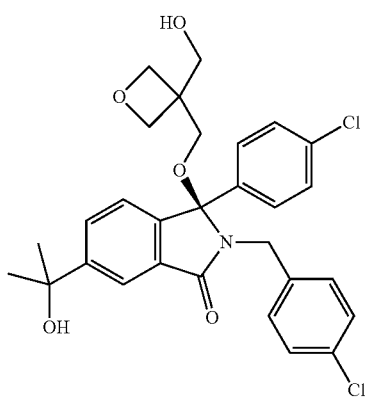 [SMILES: CC(C)(O)c1ccc2c(c1)C(=O)N(Cc1ccc(Cl)cc1)[C@@]2(OCC1(CO)COC1)c1ccc(Cl)cc1]

Starting from Preparation 23. The title compound was prepared in a similar fashion to Example 1, but using 4.5 mol eq. of MeMgCl. $^1$H NMR (500 MHz, CDCl$_3$) δ (ppm) 1.60 (s, 1H, OH), 1.62 (s, 3H, C(CH$_3$)$_2$), 1.63 (s, 3H, C(CH$_3$)$_2$), 1.92 (s, 1H, OH), 2.99 (d, 1H, J=9.2 Hz, OCHHC), 3.03 (d, 1H, J=9.2 Hz, OCHHC), 3.67-3.75 (m, 2H, CCH$_2$OH), 4.18 (d, 1H, J=15.2 Hz, NCHH), 4.25 (d, 1H, J=6.3 Hz, oxetane CHH), 4.30 (d, 1H, J=6.2 Hz, oxetane CHH), 4.33 (d, 1H, J=6.3 Hz, oxetane CHH), 4.36 (d, 1H, J=6.2 Hz, oxetane CHH), 4.56 (d, 1H, J=15.2 Hz, NCHH), 7.07 (d, 1H, J=7.9 Hz, isoindolinone-H), 7.09-7.19 (m, 6H, Ar—H), 7.22 (d, 2H, J=8.9 Hz, Ar—H), 7.73 (dd, 1H, J=8.0, 1.7 Hz, isoindolinone-H), 8.03 (d, 1H, J=1.7 Hz, isoindolinone-H); MS(ES+) m/z 586.3 [M+HCOO$^-$]$^-$;

Example 5: 1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropane-1-carboxylic Acid

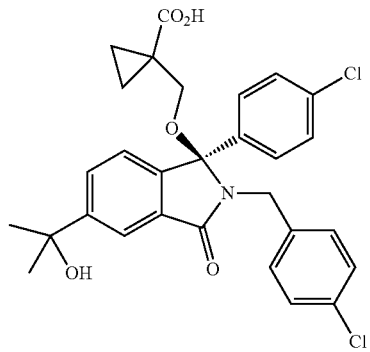 [SMILES: CC(C)(O)c1ccc2c(c1)C(=O)N(Cc1ccc(Cl)cc1)[C@@]2(OCC1(C(=O)O)CC1)c1ccc(Cl)cc1]

To a solution of 2-(4-chlorobenzyl)-3-(4-chlorophenyl)-3-((1-(hydroxymethyl)cyclopropyl)methoxy)-6-(2-hydroxypropan-2-yl)isoindolin-1-one (Example 1) (110 mg, 0.21 mmol), RuCl$_3$.H$_2$O (10 mg, 0.02 mmol) in a mixture of EtOAc (0.7 mmol/mL alcohol), MeCN (0.7 mmol/mL alcohol), and water (0.4 mmol/mL alcohol), was added sodium periodate (4.1 mol eq.) and stirred at rt for 15 min before being diluted with EtOAc (0.04 mmol/mL alcohol) and filtered through a Celite plug. The filtrates were washed with water (0.04 mmol/mL alcohol) and the aqueous was extracted with EtOAc (2×0.04 mmol/mL alcohol). The combined organic phases were washed with brine (0.02 mmol/mL alcohol), dried (MgSO$_4$) and concentrated in vacuo., sodium periodate (185 mg, 0.86 mmol), MeCN (0.6 mL), EtOAc (0.6 mL) and water (1.0 mL). Purification (SP4, silica, EtOAc/petrol (0.1% AcOH), 60%) followed by semi-preparative chiral HPLC (C-18 silica, MeCN/0.1% aq. formic acid, 40%) gave Example 5 as a white solid (54 mg, 48%). $^1$H NMR (500 MHz, CDCl$_3$) δ 0.48-0.52 (1H, m, H-cyclopropane), 0.57-0.61 (1H, m, H-cyclopropane), 1.18-1.21 (1H, m, H-cyclopropane), 1.25-1.29 (1H, m, H-cyclopropane), 1.60 (3H, s, CH$_3$), 1.62 (3H, s, CH$_3$), 2.71 (1H, d, J=9.6 Hz, -iso-OCHH), 3.16 (1H, d, J=9.6 Hz, -iso-OCHH), 4.19 (1H, d, J=15.1 Hz, NCHH), 4.58 (1H, d, J=15.1 Hz, NCHH), 7.09-7.19 (9H, m, H—Ar), 7.71 (1H, dd, J=1.8, 8.0 Hz, H-5), 7.98 (1H, d, J=1.8 Hz, H-7); LRMS (ES$^-$) m/z 538.3 [M−H]$^-$;

Example 6: (3R)-3-(4-chlorophenyl)-2-[(1S)-1-(4-chlorophenyl)ethyl]-3-(2,3-dihydroxy-2-methyl-propoxy)-6-(2-hydroxypropan-2-yl)-2,3-dihydro-1H-isoindol-1-one (*As a Mixture of Isomers at the Position Shown)

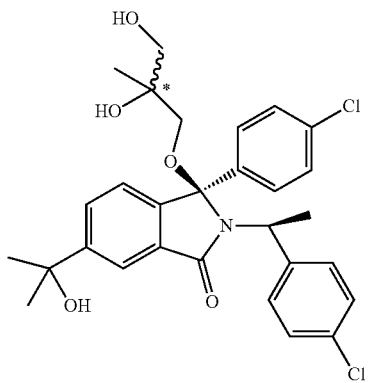 [SMILES: C[C@@H](c1ccc(Cl)cc1)N1C(=O)c2cc(C(C)(C)O)ccc2[C@]1(OCC(C)(O)CO)c1ccc(Cl)cc1]

(S)-3-(4-Chlorophenyl)-2-((S)-1-(4-chlorophenyl)ethyl)-3-((2-(hydroxymethyl)allyl)oxy)-6-(prop-1-en-2-yl)isoindolin-1-one, Preparation 24, (90 mg, 0.18 mmol), Hg(OAc)₂ (140 mg, 0.44 mmol), water (0.5 mL), THF (0.5 mL), 6 M NaOH (0.2 mL) and NaBH₄ (269 mg, 7.1 mmol). Purification (SP4, silica, EtOAc/petrol, 80%) gave Example 6 as a mixture of 2 isomers (27 mg, 28%). ¹H NMR (500 MHz, CDCl₃) δ mixture of diastereoisomers 0.95 (3H, s, -iso-OCH₂C(OHCH₃)CH₂OH), 1.00 (3H, s, -iso-OCH₂C(OHCH₃)CH₂OH), 1.64 (6H, s, C(CH₃)₂OH), 1.65 (6H, s, C(CH₃)₂OH), 1.67 (3H, d, J=7.3 Hz, NCHCH₃), 1.71 (3H, d, J=7.5 Hz, NCHCH₃), 1.87 (2H, br s, OH×2), 2.00 (2H, br s, OH×2), 2.65-2.73 (4H, m, -iso-OCH₂×2), 3.23-3.36 (4H, m, CH₂OH×2), 4.24 (1H, q, J=7.5 Hz, NCHCH₃), 4.28 (1H, q, J=7.3 Hz, NCHCH₃), 7.01 (1H, d, J=7.9 Hz, H-4), 7.02 (1H, d, J=7.9 Hz, H-4), 7.28-7.36 (6H, m, H—Ar), 7.55-7.57 (2H, m, H—Ar), 7.71-7.74 (2H, m, H-5), 7.98-7.99 (2H, m, H-7). LRMS (ES⁺) m/z 566.4 [M+Na]⁺.

Example 7: (3R)-3-(4-chlorophenyl)-2-[(1S)-1-(4-chlorophenyl)ethyl]-3-{[1-(hydroxymethyl)cyclopropyl]methoxy}-6-(2-hydroxypropan-2-yl)-2,3-dihydro-1H-isoindol-1-one

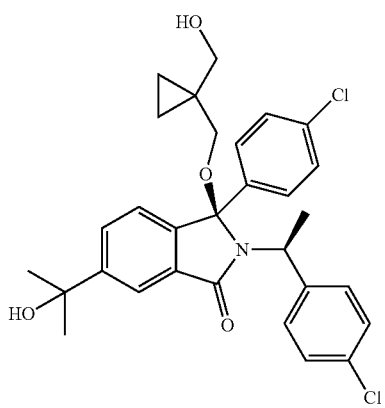 [SMILES: C[C@@H](c1ccc(Cl)cc1)N1C(=O)c2cc(C(C)(C)O)ccc2[C@]1(OCC1(CO)CC1)c1ccc(Cl)cc1]

Example 7 was prepared from Preparation 28 using similar procedure to those described in Example 1. NMR (500 MHz, CDCl₃) δ 0.33-0.36 (1H, m), 0.42-0.45 (1H, m), 0.47-0.54 (2H, m), 1.53 (3H, s), 1.55 (3H, s), 1.84 (3H, d), 2.89 (1H, d), 3.21 (1H, d), 3.56 (2H, d), 4.28 (1H, q)), 6.92-6.98 (9H, m), 7.63 (1H, dd), 7.85 (1H, d); MS (ES+) 540.5 [M+H]⁺

Examples 8 and 9: (3R)-3-(4-chlorophenyl)-2-[(4-chlorophenyl)methyl]-6-(1,2-dihydroxypropan-2-yl)-3-{[1-(hydroxymethyl)cyclopropyl]methoxy}-2,3-dihydro-1H-isoindol-1-one

*The Two Separate Epimers at the Position Shown

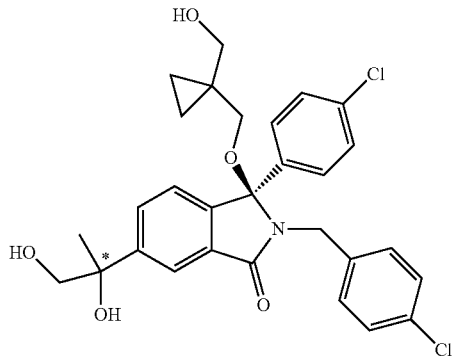 [SMILES: CC(O)(CO)c1ccc2c(c1)C(=O)N(Cc1ccc(Cl)cc1)[C@@]2(OCC1(CO)CC1)c1ccc(Cl)cc1]

To a solution of 2-(4-chlorobenzyl)-3-(4-chlorophenyl)-3-((1-(hydroxymethyl)cyclopropyl)methoxy)-6-(prop-1-en-2-yl)isoindolin-1-one, Preparation 13 (1.20 g, 2.36 mmol) in acetone/water (18 mL/7.1 mL) was added methyl morpholine-N-oxide (318 mg, 2.71 mmol) and OsO₄ (2.5 wt % in tBuOH, 0.90 mL, 0.09 mmol) and the resulting yellow/orange solution stirred at RT for 3.5 h. The reaction was diluted with DCM (125 mL), washed with saturated aqueous sodium sulphite (125 mL), dried over MgSO₄ and concentrated under vacuum. MPLC (1:1 petrol/EtOAc to 100% EtOAc) gave the product as a white solid as a mixture of 4 diastereoisomers (592 mg, 46%). Purification by preparative chiral HPLC (324 mg, Chiralpak IA 250×10 mm, 92.5:7.5 Heptane/Ethanol) gave—

Example 8 (isomer 1): δ_H (500 MHz, CDCl₃) 0.13-0.16 (2H, m, 2×c-PrH), 0.40-0.42 (2H, m, 2×c-PrH), 1.57 (3H, s, CH₃), 2.64 (1H, d, J=9.4 Hz, CHH'), 2.84 (1H, d, J=9.4 Hz, CHH'), 3.35 (1H, d, J=11.3 Hz, CHH'), 3.49 (1H, d, J=11.3 Hz, CHH'), 3.69 (1H, d, J=11.0 Hz, CHH'), 3.79 (1H, d, J=11.0 Hz, CHH'), 4.19 (1H, d, J=14.9 Hz, CHH'), 4.54 (1H, d, J=14.9 Hz, CHH'), 7.12-7.21 (9H, m, 9×ArH), 7.70 (1H, dd, J=1.7 and 7.9 Hz, ArH), 7.97 (1H, d, J=1.7 Hz, ArH).

Example 9 (isomer 2): δ_H (500 MHz, CDCl3) 0.14-0.15 (2H, m, 2×c-PrH), 0.40-0.41 (2H, m, 2×c-PrH), 1.57 (3H, s, CH₃), 2.63 (1H, d, J=9.4 Hz, CHH'), 2.85 (1H, d, J=9.4 Hz, CHH'), 3.34 (1H, d, J=11.3 Hz, CHH'), 3.49 (1H, d, J=11.3 Hz, CHH'), 3.69 (1H, d, J=11.0 Hz, CHH'), 3.81 (1H, d, J=11.0 Hz, CHH'), 4.19 (1H, d, J=14.9 Hz, CHH'), 4.54 (1H, d, J=14.9 Hz, CHH'), 7.13-7.21 (9H, m, 9×ArH), 7.69 (1H, d, J=7.8 Hz, ArH), 7.98 (1H, s, ArH).

Examples 10 and 11: (3R)-3-(4-chlorophenyl)-2-[(1S)-1-(4-chlorophenyl)ethyl]-6-(2-hydroxy-1-methoxypropan-2-yl)-3-{[1-(hydroxymethyl)cyclopropyl]methoxy}-2,3-dihydro-1H-isoindol-1-one

*The Two Separate Epimers at the Position Shown

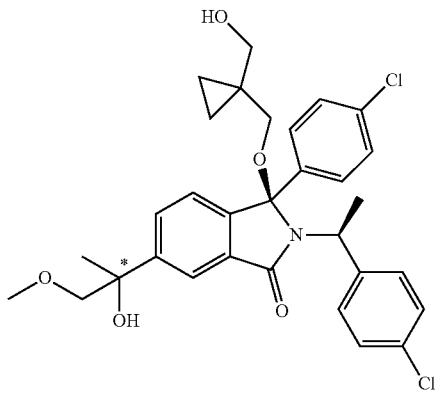 [SMILES: COCC(C)(O)c1ccc2c(c1)C(=O)N([C@@H](C)c1ccc(Cl)cc1)[C@@]2(OCC1(CO)CC1)c1ccc(Cl)cc1]

At 0° C., to a solution of (3R)-3-((1-(((tert-butyldimethylsilyl)oxy)methyl)cyclopropyl) methoxy)-3-(4-chlorophenyl)-2-((S)-1-(4-chlorophenyl)ethyl)-6-(2-hydroxy-1-methoxy propan-2-yl)isoindolin-1-one, Preparation 31 (80 mg, 0.12 mmol), in THF (4 mL) was added TBAF (1.0 M in THF, 0.13 mL, 0.13 mmol) and the reaction stirred at 0° C. for 1 h then at RT for 18 h. The reaction was diluted with water (20 mL), neutralised with 1.0 M aqueous HCl, extracted into EtOAc (2×25 mL), washed with brine (50 mL) and dried over MgSO₄. MPLC (1:1 petrol/EtOAc to 100% EtOAc) and semi-preparative HPLC (ACE 5 C18-AR 150×4.6 mm i.d., 5 um, 55:45 Acetonitrile/Water+0.1% v/v Formic Acid) gave product as a white solid as a diastereoisomeric mixture (36 mg, 53%); MS (ES+) 570.4 [M+H]⁺; Purification by preparative chiral HPLC (82 mg, Chiralpak IC 250×10 mm Mobile Phase: Heptane/Ethanol 87.5:12.5) gave:—

Example 11 (*isomer 1): $\delta_H$ (500 MHz, CDCl3) 0.32-0.36 (1H, m, c-PrH), 0.42-0.46 (1H, m, c-PrH), 0.47-0.53 (2H, m, 2×c-PrH), 1.44 (3H, s, CH₃), 1.83 (3H, d, J=7.3 Hz, CHCH3), 2.89 (1H, d, J=9.5 Hz, CHH'), 3.21 (1H, d, J=9.5 Hz, CHH'), 3.32 (3H, s, OCH3), 3.43 (1H, d, J=9.2 Hz, CHH'), 3.54 (1H, d, J=9.2 Hz, CHH'), 3.56 (2H, s, CH₂), 4.28 (1H, q, J=7.3 Hz, CHCH3), 6.92-6.99 (9H, m, 9×ArH), 7.62 (1H, dd, J=1.7 and 8.0 Hz, ArH), 7.81 (1H, d, J=1.7 Hz, ArH). m/z 468.4 [M-OCH2C(CH₂—CH₂)CH₂OH]⁺

Example 10 (*isomer 2): 1H-NMR $\delta_H$ (500 MHz, CDCl₃) 0.32-0.36 (1H, m, c-PrH), 0.42-0.46 (1H, m, c-PrH), 0.47-0.53 (2H, m, 2×c-PrH), 1.46 (3H, s, CH₃), 1.83 (3H, d, J=7.3 Hz, CHCH₃), 2.87 (1H, d, J=9.5 Hz, CHH'), 3.22 (1H, d, J=9.5 Hz, CHH'), 3.32 (3H, s, OCH₃), 3.41 (1H, d, J=9.2 Hz, CHH'), 3.51 (1H, d, J=9.2 Hz, CHH'), 3.56 (2H, s, CH₂), 4.28 (1H, q, J=7.3 Hz, CHCH₃), 6.92-6.99 (9H, m, 9×ArH), 7.64 (1H, dd, J=1.7 and 7.9 Hz, ArH), 7.79 (1H, d, J=1.7 Hz, ArH).: m/z 468.4 [M-OCH2C(CH₂—CH₂)CH₂OH]⁺

Examples 12 and 13: (3R)-3-(4-chlorophenyl)-2-[(4-chlorophenyl)methyl]-6-[1-(dimethylamino)-2-hydroxypropan-2-yl]-3-{[1-(hydroxymethyl)cyclopropyl]methoxy}-2,3-dihydro-1H-isoindol-1-one (*Two Isomers at the Position Shown)

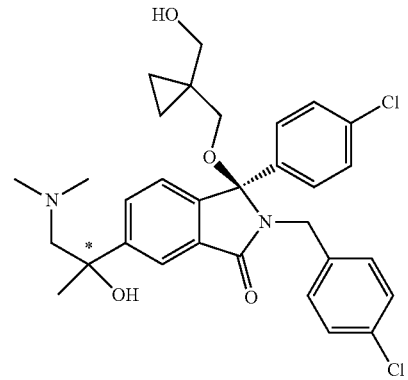 [SMILES: CN(C)CC(C)(O)c1ccc2c(c1)C(=O)N(Cc1ccc(Cl)cc1)[C@@]2(OCC1(CO)CC1)c1ccc(Cl)cc1]

Deprotection of Preparation 34 using a similar procedure to that described for Example 10 followed by purification by preparative chiral HPLC gave the two diastereoisomers:

Example 12 (*isomer 1): 1H NMR (500 MHz, CDCl₃) 0.12-0.20 (2H, m), 0.36-0.45 (2H, m), 1.83 (3H, s), 2.58 (1H, d), 2.68-2.29 (3H, m), 2.89 (1H, d), 2.99-3.00 (3H, m), 3.29 (1H, d), 3.39-3.42 (1H, m), 3.55 (1H, d), 3.62-3.66 (1H, m), 4.18 (1H, d), 4.54 (1H, d), 7.11-7.22 (9H, m), 7.86 (1H, d), 7.94 (1H, s). MS: [M+H]⁺=569.5.

Example 13 (* isomer 2): 1H NMR (500 MHz, CDCl3) 0.12-0.23 (2H, m), 0.36-0.42 (2H, m), 1.80 (3H, s), 2.42 (1H, d), 2.64 (3H, s), 2.92 (1H, d), 2.99-3.00 (3H, m), 3.15 (1H, d), 3.40-3.45 (1H, m), 3.58-3.63 (2H, m), 4.17 (1H, d), 4.53 (1H, d), 7.11-7.15 (4H, m), 7.19-7.23 (5H, m), 7.85 (1H, s), 7.96 (1H, d). MS: [M+H]⁺=569.5.

Example 14: (3S)-3-(4-chlorophenyl)-3-[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]propanoic acid

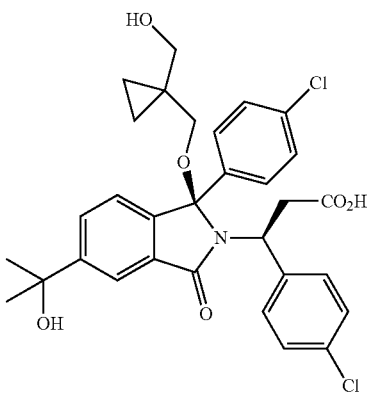 [SMILES: CC(C)(O)c1ccc2c(c1)C(=O)N([C@@H](CC(=O)O)c1ccc(Cl)cc1)[C@@]2(OCC1(CO)CC1)c1ccc(Cl)cc1]

Starting from Preparation 40, Example 14 was prepared using similar procedures to those described for Example 1. ¹H NMR (500 MHz, MeOD) δ 0.40-0.44 (4H, m, 4×c-PrH), 1.47 (6H, s, 2×CH₃), 2.91 (1H, d, J=9.2 Hz, CHH'), 3.09-

3.21 (2H, m, CHH' and CHCHH'), 3.51 (2H, s, CH₂), 3.73 (1H, dd, J=11.1 and 16.2 Hz, CHCHH'), 4.64 (1H, dd, J=3.6 and 11.1 Hz, CHCHH'), 6.89-6.97 (8H, m, 8×ArH), 7.02 (1H, d, J=8.0 Hz, ArH), 7.65 (1H, dd, J=1.7 and 8.0 Hz, ArH), 7.89 (1H, d). MS. 582.1 (M–H⁺)⁻

Example 15: (3R)-3-(4-chlorophenyl)-2-[(1S)-1-(4-chlorophenyl)ethyl]-6-(1,2-dihydroxypropan-2-yl)-3-{[1-(hydroxymethyl)cyclopropyl]methoxy}-2,3-dihydro-1H-isoindol-1-one

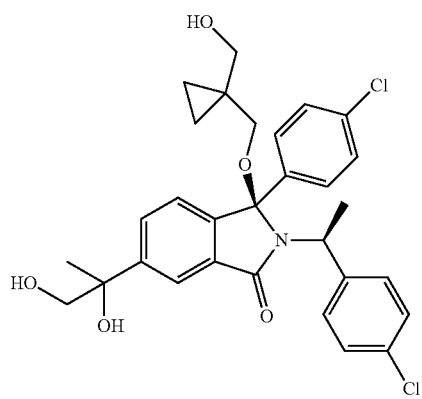 [SMILES: C[C@@H](c1ccc(Cl)cc1)N1C(=O)c2cc(C(C)(O)CO)ccc2[C@]1(OCC1(CO)CC1)c1ccc(Cl)cc1]

Starting from (R)-3-(4-chlorophenyl)-2-((S)-1-(4-chlorophenyl)ethyl)-3-((1-(hydroxymethyl)cyclopropyl)methoxy)-6-(prop-1-en-2-yl)isoindolin-1-one (Preparation 27); Example 15 was prepared by using procedures similar to those described for Example 8. Product was obtained as a white solid as a diastereoisomeric mixture (65 mg, 31 (500 MHz, CDCl₃) δ 0.34-0.36 (1H, m, c-PrH), 0.43-0.52 (3H, m, 3×c-PrH), 1.49-1.50 (3H, m, CH₃), 1.82-1.84 (3H, m, NCHCH₃), 2.89-2.92 (1H, m, alkyl-CH), 3.18-3.21 (1H, m, alkyl-CH), 3.51-3.56 (2H, m, 2×alkyl-CH), 3.58-3.63 (1H, m, alkyl-CH), 3.71-3.75 (1H, m, alkyl-CH), 4.28 (1H, q, J=7.3 Hz, NCHCH₃), 6.92-6.97 (8H, m, 8×ArH), 7.00 (1H, d, J=7.9 Hz, ArH), 7.60-7.62 (1H, m, ArH), 7.84-7.85 (1H, m, ArH); MS (ES+) 454.3 [M–HOCH₂(c-Pr)CH₂O]⁻;

Example 16: (3R)-3-(4-chlorophenyl)-2-[(4-chlorophenyl)methyl]-3-(3-hydroxy-3-methylbutoxy)-6-(2-hydroxypropan-2-yl)-2,3-dihydro-1H-isoindol-1-one

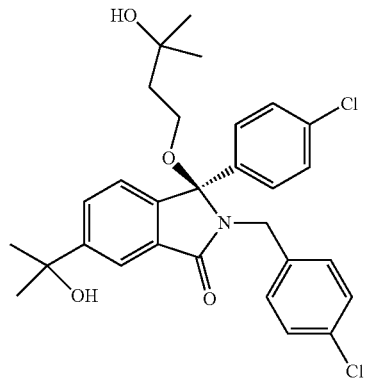 [SMILES: CC(C)(O)CCO[C@]1(c2ccc(Cl)cc2)c2ccc(C(C)(C)O)cc2C(=O)N1Cc1ccc(Cl)cc1]

Starting from Preparation 41, Example 16 was prepared using similar procedure to those described in Example 1. Purification by chiral HPLC (Chiralpak IC 250×10 mm, Mobile Phase: Heptane/Ethanol 80:20): gave Example 16:

(R)-2-(4-Chlorobenzyl)-3-(4-chlorophenyl)-3-(3-hydroxy-3-methylbutoxy)-6-(2-hydroxypropan-2-yl)isoindolin-1-one (39 mg). ¹H NMR (500 MHz, CDCl₃) δ 0.98 (3H, s, CH₃), 1.02 (3H, s, CH₃), 1.13-1.19 (1H, m, CH), 1.35-1.41 (1H, m, CH), 1.55 (3H, s, CH₃), 1.56 (3H, s, CH₃), 2.75-2.80 (1H, m, CH), 2.86-2.91 (1H, m, CH), 3.91 (1H, d, J=14.9 Hz, NCHH'), 4.65 (1H, d, J=14.9 Hz, NCHH'), 7.03 (1H, d, J=7.9 Hz, ArH), 7.11-7.18 (8H, m, 8×ArH), 7.65 (1H, dd, J=1.7 and 7.9 Hz, ArH), 7.93 (1H, d, J=1.7 Hz, ArH); ¹³C (125 MHz, CDCl₃) δ 29.1, 29.9, 31.9, 32.0, 41.5, 42.4, 60.0, 70.0, 72.6, 95.2, 120.0, 122.7, 127.8, 128.4, 128.8, 129.5, 130.7, 131.4, 133.3, 134.7, 136.2, 137.0, 143.4, 151.7, 168.3; MS (ES+) 424.3 [M-(OH)C(CH₃)₂CH₂CH₂O]⁻;

Example 17: (3R)-3-(4-chlorophenyl)-2-[(4-chlorophenyl)methyl]-6-(2-hydroxypropan-2-yl)-3-[(1H-pyrazol-4-yl)methoxy]-2,3-dihydro-1H-isoindol-1-one

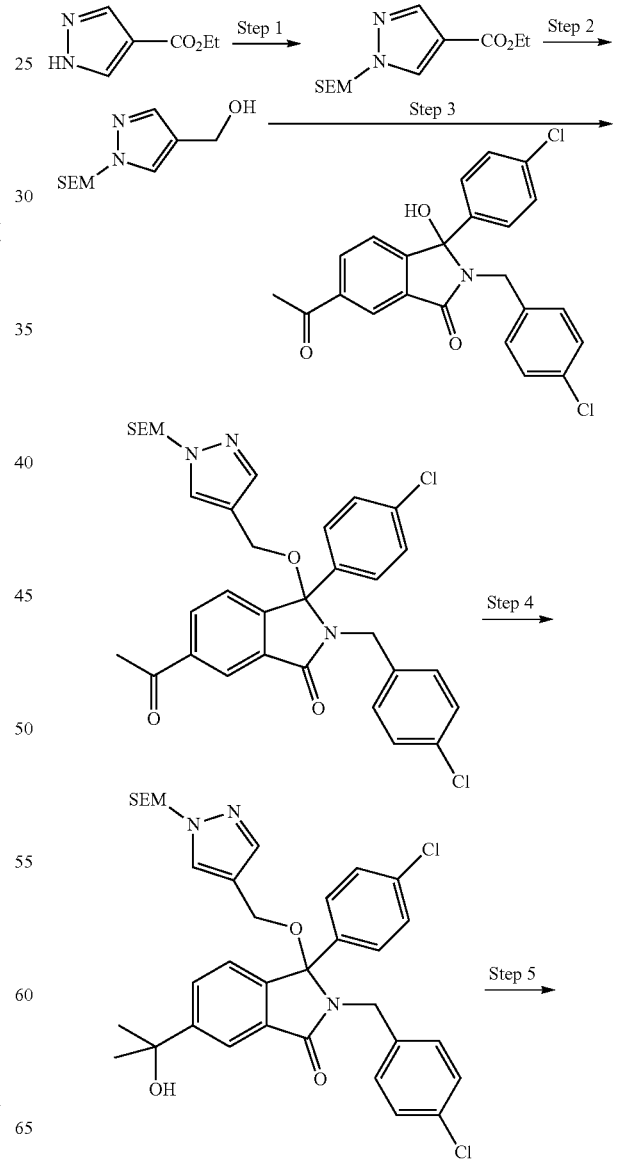

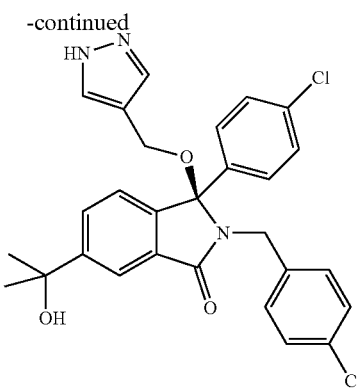

Example 17, Step 1: Ethyl 1-((2-(trimethylsilyl) ethoxy)methyl)-1H-pyrazole-4-carboxylate NaH (80% in oil, 130 mg, 4.3 mmol, 1.5 eq.) was added to 4-ethoxycarbonyl-1H-pyrazole (400 mg, 2.86 mmol, 1 eq.) in THF (8 mL), and the mixture stirred at r.t. for 30 min. SEMCl (556 μL, 3.14 mmol, 1.1 eq.) was added and the reaction stirred at r.t. for 18 h. The mixture was partitioned between EtOAc (2×30 mL) and water (20 mL), the organic layers dried (MgSO$_4$) and the solvent removed in vacuo. The residue was purified by MPLC on silica with gradient elution from 5-20% EtOAc/petrol to give the title compound as a clear oil (657 mg, 85%); HRMS found 271.1468 MH+

Example 17, Step 2: (1-((2-(Trimethylsilyl)ethoxy) methyl)-1H-pyrazol-4-yl)methanol LiAlH$_4$ (1 M in THF, 1.94 mL, 1.94 mmol, 1.5 eq.) was added to ethyl 1-((2-(trimethylsilyl)ethoxy)methyl)-1H-pyrazole-4-carboxylate (350 mg, 1.29 mmol) in THF (4 mL) at 0° C., and the mixture was stirred at r.t. for 4 h. Water (74 μL) was added, followed by NaOH (15% aq, 220 μL) and water (74 μL). The mixture was stirred at r.t. for 1 h, filtered, the solids washed with EtOAc, and the filtrate evaporated in vacuo to give the title compound as a clear oil (330 mg, >100%); HRMS calc for $C_{10}H_{21}O_2N_2Si$, 229.1367, found 229.1361. MH+.

Example 17, Step 3: 6-Acetyl-2-(4-chlorobenzyl)-3-(4-chlorophenyl)-3-((1-((2-(trimethylsilyl)ethoxy) methyl)-1H-pyrazol-4-yl)methoxy)isoindolin-1-one Prepared in a similar manner to Preparation 12 using 6-acetyl-2-(4-chlorobenzyl)-3-(4-chlorophenyl)-3-hydroxy-isoindolin-1-one (Preparation 20) (150 mg, 0.35 mmol, 1 eq.), SOCl$_2$ (51 μL, 0.70 mmol, 2 eq.) and (1-((2-(trimethylsilyl)ethoxy)methyl)-1H-pyrazol-4-yl)methanol (161 mg, 0.70 mmol, 2 eq.) The title compound was obtained as a clear glass (105 mg, 47%); HRMS found 636.1830. MH+.

Example 17, Step 4: 2-(4-Chlorobenzyl)-3-(4-chlorophenyl)-6-(2-hydroxypropan-2-yl)-3-((1-((2-(trimethylsilyl)ethoxy) methyl)-1H-pyrazol-4-yl) methoxy)isoindolin-1-one Prepared in a similar manner to Example 1 using MeMgCl (151 μL, 3 M in THF, 0.45 mmol, 1.5 eq.) and ZnCl$_2$ (8 mg, 0.06 mmol, 0.2 eq.) in THF (1 mL), followed by 6-acetyl-2-(4-chlorobenzyl)-3-(4-chlorophenyl)-3-((1-((2-(trimethylsilyl)ethoxy)methyl)-1H-pyrazol-4-yl) methoxy)isoindolin-1-one (192 mg, 0.30 mmol, 1 eq). The title compound was obtained as a clear gum (78 mg, 40%); HRMS 652.2145. MH+

Example 17, Step 5: (3R)-3-(4-chlorophenyl)-2-[(4-chlorophenyl)methyl]-6-(2-hydroxypropan-2-yl)-3-[(1H-pyrazol-4-yl)methoxy]-2,3-dihydro-1H-isoindol-1-one Et$_4$NF.H$_2$O (149 mg, 1.0 mmol, 10 eq.) and 4 A molecular sieves (50 mg) were added to 2-(4-chlorobenzyl)-3-(4-chlorophenyl)-6-(2-hydroxypropan-2-yl)-3-((1-((2-(trimethylsilyl)ethoxy) methyl)-1H-pyrazol-4-yl)methoxy)isoindolin-1-one (65 mg, 0.1 mmol) in THF (2 mL) and the mixture was heated to 65° C. for 3 h, allowed to cool to r.t., and partitioned between EtOAc (25 mL) and water (3×20 mL). The organic layer was dried (MgSO$_4$) and the solvent removed in vacuo to give a white solid (25 mg, 48%). The enantiomers were separated by chiral HPLC (Daicel Chiralpak IA, 250×10 mm i.d., 5 μm, n-heptane: 2-propanol 5:1; 4.7 mL/min) to give the title compound (6 mg). $^1$H NMR (500 MHz; CDCl$_3$) $\lfloor_H$1.63 (6H, 2×s), 3.66 (1H, d), 3.76 Hz (1H, d), 4.00 (1H, d), 4.72 (1H, d), 7.08-7.27 (9H, m), 7.72 (1H, dd), 8.03 (1H, dd); HRMS found 522.1334. MH+

Example 18: 1-({[(1R)-1-(4-chlorophenyl)-2-[(4-chiorophenyl)methyl]-5-(2-hydroxypropan-2-yl)-3-oxo-2,3-dihydro-1H-isoindol-1-yl]oxy}methyl)cyclopropane-1-carbonitrile

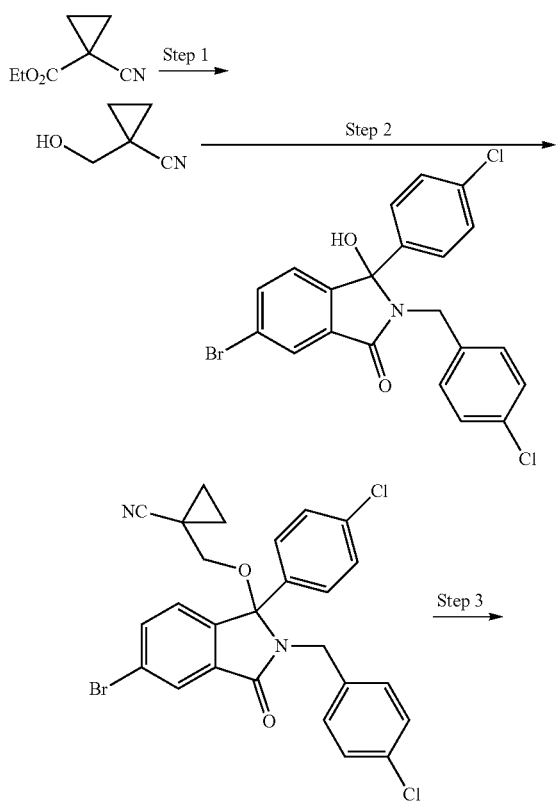

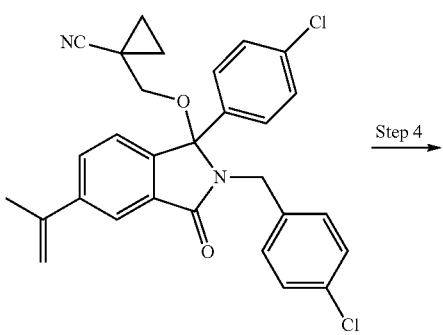

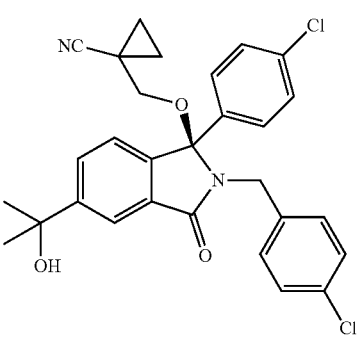

Example 18, Step 1:
1-(Hydroxymethyl)cyclopropanecarbonitrile

LiBH$_4$ (573 mg, 26.3 mmol, 2 eq) was added to ethyl-1-cyanocyclopropane carboxylate (1.7 mL, 13.15 mmol, 1 eq.) in THF (18 mL) and the mixture was heated to 50° C. for 18 h. The reaction was cooled to 0° C. and NaHCO$_3$ (sat'd aq) was added until gas evolution ceased. The mixture was diluted with brine (20 mL) and extracted with EtOAc (1×60 mL), DCM (3×60 mL) and 10% MeOH/DCM (2×60 mL). The organic extracts were combined, dried (MgSO$_4$) and the solvent removed in vacuo to give the title compound as a clear oil (820 mg, 65%); $^1$H NMR (500 MHz; CDCl$_3$): 0.96-1.01 (2H, m), 1.27-1.31 (2H, m), 3.64 (2H, s).

Example 18, Step 2: 1-(((5-Bromo-2-(4-chlorobenzyl)-1-(4-chlorophenyl)-3-oxoisoindolin-1-yl)oxy)methyl)cyclopropane-1-carbonitrile Thionyl chloride (120 µL, 1.64 mmol, 2 eq.) was added to 6-bromo-2-(4-chlorobenzyl)-3-(4-chlorophenyl)-3-hydroxyisoindolin-1-one (Preparation 8) (382 mg, 0.82 mmol, 1 eq.) in THF (4 mL) and the mixture was stirred at r.t. for 4 h. The solvent was removed in vacuo, the residue re-dissolved in THF (2 mL), cyanoalcohol (Example 18, Step 1; 160 mg, 1.64 mmol, 2 eq.) in THF (2 mL) was added and the mixture was stirred at r.t. for 18 h. The mixture was diluted with EtOAc (2×30 mL) and washed with water. The organic layers were combined, dried over MgSO$_4$, and the solvent removed in vacuo. The crude mixture was purified by MPLC on SiO$_2$ with gradient elution from 0-2% Et$_2$O/DCM to give the title compound as a clear gum (390 mg, 87%); MS (ES+) 543.3, 545.3 [M+H]$^+$.

Example 18, Step 3 and 4: 1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropane-1-carbonitrile Using the product from Example 18, Step 2, The title compound was prepared by following procedures similar to those described in Preparation 13 and Example 2: 1H NMR (500 MHz; CDCl3): 0.35-0.42 (1H, m), 0.42-0.49 (1H, m), 1.09-1.20 (2H, m), 1.62 (2×3H, 2×s), 2.31 (1H, d), 2.91 (1H, d), 4.02 (1H, d), 4.72 (1H, d), 7.15-7.22 (5H, m), 7.25-7.30 (4H, m), 7.74 (1H, dd), 8.00 (1H, d); MS (ES+) 521.4, 523.4 [M+H]+.

Example 19: N-{[1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropyl]methyl}methanesulfonamide

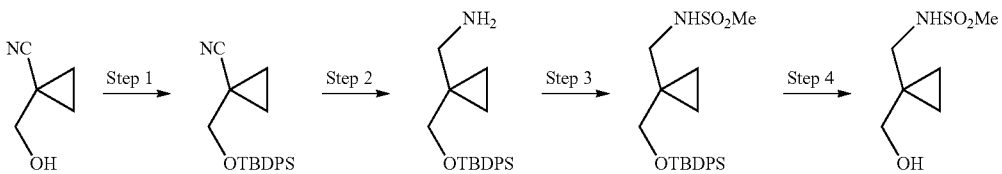

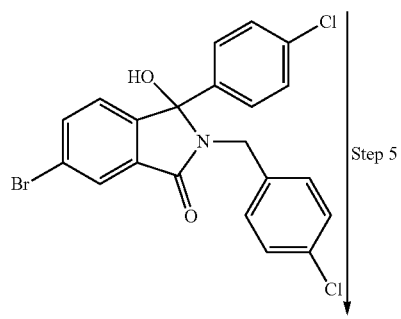

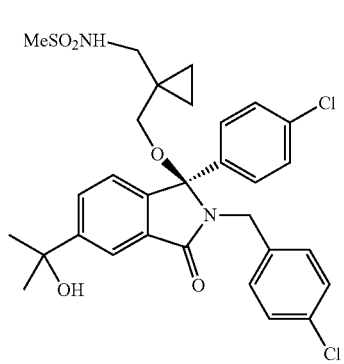 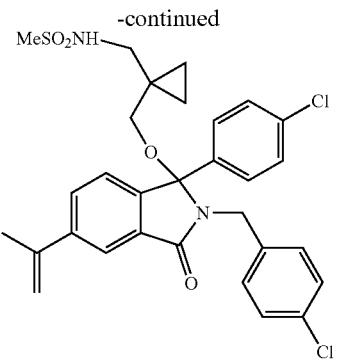

Example 19, Step 1: 1-(((tert-Butyldiphenylsilyl)oxy)methyl) cyclopropanecarbonitrile 1-(Hydroxymethyl)cyclopropanecarbonitrile (1.1 g, 11.3 mmol), TBDPSCl (2.66 mL, 11.3 mmol, 1 eq.), imidazole (926 mg, 13.6 mmol, 1.2 eq.) and DMAP (69 mg, 0.57 mmol, 0.05 eq.) were combined in DCM (15 mL) and stirred at r.t. for 18 h. The mixture was partitioned between EtOAc (2×20 mL) and water (20 mL), washed with brine, dried (MgSO$_4$) and solvent removed in vacuo. The residue was purified by MPLC on silica with gradient elution from 2-40% EtOAc/petrol to give the title compound as a clear oil (2.05 g, 54%); HRMS calc for $C_{21}H_{29}O_1N_2Si$, 353.2044, found 353.2034.

Example 19, Step 2: (1-(((tert-Butyldiphenylsilyl) oxy)methyl)cyclopropyl) methanamine 1-(((tert-Butyldiphenylsilyl)oxy)methyl)cyclopropanecarbonitrile (220 mg, 0.66 mmol) was dissolved in MeOH (10 mL) and hydrogenated through a Raney nickel catcart on Thales H-cube at 20° C., 20 bar for 3 h, with constant recycling of the reaction mixture (1 mL/min flow rate). The solvent was removed in vacuo and the residue purified by MPLC on silica with gradient elution from 0-20% MeOH/EtOAc to give the title compound as a clear gum (78 mg, 46%); $^1$H NMR (500 MHz; CDCl$_3$) 0.30-0.41 (4H, m), 1.06 (9H, s), 2.38 (2H, br s), 2.72 (2H, s), 3.57 (2H, s), 7.35-7.46 (6H, m), 7.62-7.69 (4H, m).

Example 19, Step 3: N-((1-(((tert-Butyldiphenylsilyl)oxy)methyl)cyclopropyl)methyl) methanesulfonamide MsCl (120 µL, 1.54 mmol, 1.1 eq.) was added to a mixture of (1-(((tert-butyldiphenylsilyl)oxy)methyl)cyclopropyl) methanamine (480 mg, 1.4 mmol, 1 eq.) and Et$_3$N (236 µL, 1.69 mmol, 1.2 eq.) in DCM (4 mL) at 0° C. and the mixture was stirred at r.t. for 18 h, partitioned between DCM (2×30 mL) and water (20 mL), washed with brine, dried over MgSO$_4$, and the solvent removed in vacuo. The residue was purified by MPLC on SiO$_2$ with a gradient from 10-35% EtOAc/petrol to give the title compound as a white solid (520 mg, 88%); $^1$H NMR (500 MHz; CDCl$_3$) 0.36-0.40 (2H, m), 0.49-0.54 (2H, m), 1.08 (9H, s), 2.90 (3H, s), 3.15 (2H, d), 3.54 (2H, s), 4.93 (1H, m), 7.36-7.51 (6H, m), 7.62-7.68 (4H, m).

Example 19, Step 4: N-((1-(Hydroxymethyl)cyclopropyl)methyl) methanesulfonamide N-((1-(((tert-Butyldiphenylsilyl)oxy)methyl)cyclopropyl)methyl) methanesulfonamide (500 mg, 1.2 mmol, 1 eq.) and Et$_4$NF (197 mg, 1.32 mmol, 1.1 eq.) were combined in THF (10 mL) and stirred at r.t. for 2 h. The mixture was diluted with water (10 mL) and brine (10 mL) and extracted with EtOAc (2×20 mL) and DCM (4×20 mL). The organic extracts were combined, dried over MgSO$_4$, and the solvent removed in vacuo. Purification by MPLC on SiO$_2$ with a gradient from 70-100% EtOAc/petrol gave the title compound as a clear oil (188 mg, 88%); MS ES– 178.1 [M–H]$^-$.

Example 19, Step 5: N-((1-(((5-Bromo-2-(4-chlorobenzyl)-1-(4-chlorophenyl)-3-oxoisoindolin-1-yl) oxy)methyl)cyclopropyl)methyl)methanesulfonamide Thionyl chloride (117 µL, 1.62 mmol, 2 eq.) was added to 6-bromo-2-(4-chlorobenzyl)-3-(4-chlorophenyl)-3-hydroxyisoindolin-1-one (Preparation 8) (375 mg, 0.81 mmol, 1 eq.) and DMF (1 drop, cat.) in THF (4 mL) and stirred at r.t. for 4 h. The solvent was removed in vacuo, the residue redissolved in THF (2 mL), and the alcohol in THF (2 mL) was added. The mixture was stirred at r.t. for 96 h, partitioned between EtOAc (2×30 mL) and water (20 mL). The organic extracts were combined, dried over MgSO$_4$, and the solvent removed in vacuo. The crude product was purified by MPLC on SiO$_2$ with a gradient from 25-50% EtOAc/petrol to give the title compound as a clear gum (385 mg, 76%); MS ES– 523.2 [M–H]$^-$.

Example 19, Step 6 and 7: N-{[1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropyl]methyl}methanesulfonamide Starting from the product obtained in Step 5; Example 19 was prepared using procedures similar to those described for Preparation 13 and Example 2. $^1$H NMR (500 MHz; CDCl$_3$) 0.08-0.17 (2H, m), 0.38-0.47 (2H, m), 1.61 (3H, s), 1.63 (3H, s), 1.83 (1H, s), 2.53 (1H, d), 2.80 (1H, d), 2.84-2.93 (4H, m), 3.16 (1H, dd), 4.15 (1H, d), 4.30 (1H, t), 4.59 (1H, d), 7.13-7.19 (5H, m), 7.19-7.27 (4H, m), 7.75 (1H, dd), 8.00 (1H, d); MS ES+ 603.4, 605.3 [M+H]$^+$.

Example 20: (3R)-3-(4-chlorophenyl)-2-[(4-ethynyl-phenyl)methyl]-3-{[1-(hydroxymethyl)cyclopropyl]methoxy}-6-(2-hydroxypropan-2-yl)-2,3-dihydro-1H-isoindol-1-one

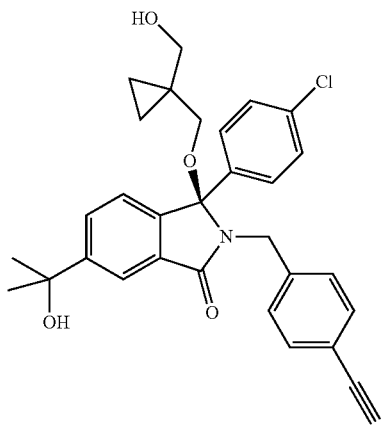 [SMILES: C#Cc1ccc(CN2C(=O)c3cc(C(C)(C)O)ccc3[C@]2(OCC2(CO)CC2)c2ccc(Cl)cc2)cc1]

Example 20, Step 1: 6-Acetyl-3-(4-chlorophenyl)-3-hydroxy-2-(4-((triisopropylsilyl)ethynyl)benzyl)isoindolin-1-one

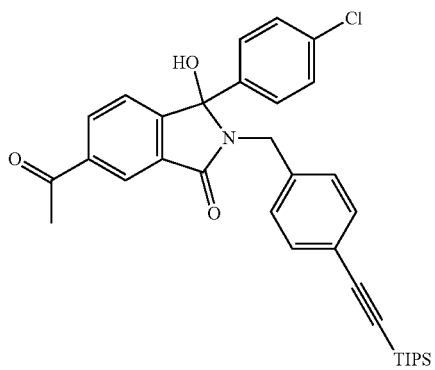

Prepared in a similar manner to that described in Preparation 8 from: 5-acetyl-2-(4-chlorobenzoyl)benzoic acid (Preparation 19) (1 g, 3.303 mmol), SOCl₂ (0.48 mL, 6.607 mmol), (4-((triisopropylsilyl)ethynyl)phenyl)methanamine (Preparation 42) (1.14 g, 3.964 mmol) and DIPEA (1.27 mL, 7.27 mmol) in THF (20 mL). Purified by Biotage using 0-30% EtOAc in petrol as the eluent gave the title compound as a pale yellow solid (1.283 g, 68%). MS: [M+H]⁺=456.4.

Example 20, Step 2: 6-Acetyl-3-(4-chlorophenyl)-3-((1-(hydroxymethyl)cyclopropyl)methoxy)-2-(4-((triisopropylsilyl)ethynyl)benzyl)isoindolin-1-one

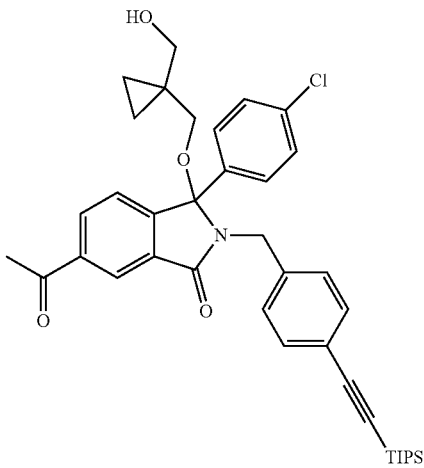

Prepared in a similar manner to that described in Preparation 22 from: 6-acetyl-3-(4-chlorophenyl)-3-hydroxy-2-(4-((triisopropylsilyl)ethynyl)benzyl)isoindolin-1-one (400 mg, 0.70 mmol), SOCl₂ (166 mg, 0.10 mL, 1.40 mmol), 1,1-bis(hydroxymethyl)cyclopropane (104 mg, 0.14 mL, 1.40 mmol) and K₂CO₃ (194 mg, 1.40 mmol) in THF (1.5 mL). Purified by Biotage using 0-40% EtOAc in petrol as the eluent gave the title compound as a colourless oil (205 mg, 45%); 1H NMR (500 MHz, CDCl₃) 0.13-0.17 (2H, m) 0.39-0.43 (2H, m), 1.11 (21H, s), 2.67-2.69 (4H, m), 2.77 (1H, d), 3.35 (1H, d), 3.50 (1H, d), 4.21 (1H, d), 4.59 (1H, d), 7.12-7.13 (2H, m), 7.17-7.26 (5H, m), 7.28 (2H, m), 8.14-8.15 (1H, m), 8.43-8.44 (1H, m).

Example 20, Step 3: 3-(4-Chlorophenyl)-3-((1-(hydroxymethyl)cyclopropyl)methoxy)-6-(2-hydroxypropan-2-yl)-2-(4-((triisopropylsilyl)ethynyl)benzyl)isoindolin-1-one

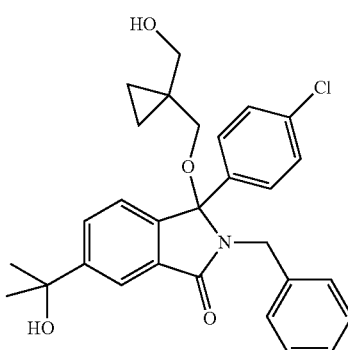

Prepared in a similar manner to that described in Example 1 from: 6-acetyl-3-(4-chlorophenyl)-3-((1-(hydroxymethyl)

cyclopropyl)methoxy)-2-(4-((triisopropylsilyl)ethynyl)benzyl)isoindolin-1-one (180 mg, 0.27 mmol), Zn(II)Cl$_2$ (7.5 mg, 0.055 mmol) and MeMgCl (0.23 mL, 3.0 M in THF, 0.17 mmol) in THF (1.94 mL). The title product was obtained as a white solid (148 mg, 82%); 1H NMR (500 MHz, CDCl$_3$) 0.12-0.18 (2H, m), 0.36-0.43 (2H, m), 1.11 (21H, s), 1.61 (3H, s), 1.62 (3H, s), 2.66 (1H, d), 2.82 (1H, d), 3.35 (1H, d), 3.48 (1H, d), 4.19 (1H, d), 4.57 (1H, d), 7.09-7.13 (3H, m), 7.17-7.21 (4H, m), 7.26-7.28 (2H, m), 7.71 (1H, dd), 7.99 (1H, d).

Example 20, Step 4: (3R)-3-(4-chlorophenyl)-2-[(4-ethynylphenyl)methyl]-3-{[1-(hydroxymethyl)cyclopropyl]methoxy}-6-(2-hydroxypropan-2-yl)-2,3-dihydro-1H-isoindol-1-one Starting from 3-(4-chlorophenyl)-3-((1-(hydroxymethyl)cyclopropyl)methoxy)-6-(2-hydroxypropan-2-yl)-2-(4-((triisopropylsilyl)ethynyl)benzyl)isoindolin-1-one, deprotection using a similar procedure to that described in Example 10 gave Example 20. 1H NMR (500 MHz, CDCl$_3$) 0.09-0.18 (2H, m), 0.37-0.42 (2H, m), 1.61 (3H, s), 1.62 (3H, s), 2.65 (1H, d), 2.82 (1H, d), 3.04 (1H, s), 3.34 (1H, d), 3.47 (1H, d), 4.17 (1H, d), 4.60 (1H, d), 7.11 (1H, d), 7.16-7.22 (6H, m), 7.31 (2H, d), 7.72 (1H, dd), 7.99 (1H, d). MS: [M+H]$^+$=516.4.

Example 21: (3R)-3-(4-chlorophenyl)-2-[(4-ethynylphenyl)methyl]-4-fluoro-3-{[1-(hydroxymethyl)cyclopropyl]methoxy}-6-(2-hydroxypropan-2-yl)-2,3-dihydro-1H-isoindol-1-one Example 21. Step 1: 6-Bromo-3-(4-chloro-phenyl)-4-fluoro-3-hydroxy-2-{4-[(triisopropylsilanyl)-ethynyl]-benzyl}-2,3-dihydro-isoindol-1-one The title compound was prepared from 5-bromo-2-(4-chloro-benzoyl)-3-fluoro-benzoic acid (7.9 g, 22.2 mmol) and 4-[(triisopropylsilanyl)-ethynyl]-benzylamine (7.0 g, 24.4 mmol) in a similar manner to that described for Preparation 9. $^1$H NMR (400 MHz, DMSO-d6): 7.84-7.72 (2H, m), 7.59 (1H, s), 7.33-7.20 (6H, m), 7.12 (2H, d), 4.46-4.37 (1H, m), 4.29 (1H, d), 1.13-1.05 (21H, m).

Example 21. Step 2: 6-Bromo-3-(4-chloro-phenyl)-4-fluoro-3-(1-hydroxymethyl-cyclopropylmethoxy)-2-{4-[(triisopropylsilanyl)-ethynyl]-benzyl}-2,3-dihydro-isoindol-1-one The title compound was prepared from 6-bromo-3-(4-chloro-phenyl)-4-fluoro-3-hydroxy-2-{4-[(triisopropylsilanyl)-ethynyl]-benzyl}-2,3-dihydro-isoindol-1-one (5.0 g, 7.9 mmol) and (1-hydroxymethyl-cyclopropyl)-methanol (4.1 g, 39.9 mmol) in a similar manner to that described for Preparation 10. 1H NMR (400 MHz, DMSO-d6): 7.91 (1H, d), 7.83 (1H, dd), 7.35-7.12 (6H, m), 7.03 (2H, d), 4.51-4.27 (3H, m), 3.44-3.33 (2H, m), 2.86 (2H, s), 1.09 (21H, s), 0.41-0.26 (2H, m), 0.26-0.10 (2H, m).

Example 21, Step 3: 6-Acetyl-3-(4-chloro-phenyl)-2-[4-(3,3-diisopropyl-4-methyl-pent-1-ynyl)-benzyl]-4-fluoro-3-(1-hydroxymethyl-cyclopropylmethoxy)-2,3-dihydro-isoindol-1-one Pd(PPh$_3$)$_4$ (84 mg, 0.07 mmol) and LiCl (178 mg, 4.24 mmol) were added to a solution of 6-bromo-3-(4-chloro-

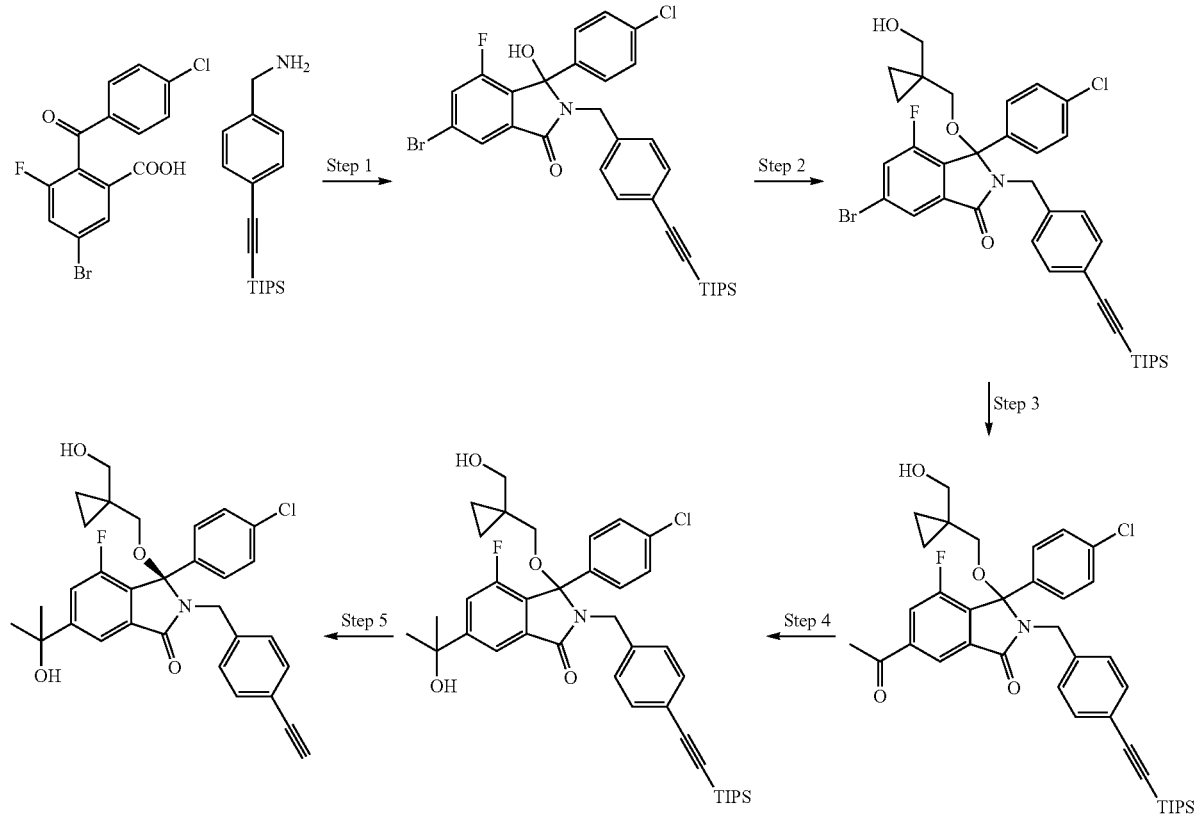

phenyl)-4-fluoro-3-(1-hydroxymethyl-cyclopropyl-methoxy)-2-{4-[(triisopropylsilanyl)-ethynyl]-benzyl}-2,3-dihydro-isoindol-1-one (1.0 g, 1.4 mmol) in dioxane/toluene (1:1, 20 mL) under $N_2$ and the resulting solution was degassed for 10 minutes. Tributyl(1-ethoxyvinyl)tin (475 µL, 1.41 mmol) was added and the reaction was stirred at 110° C. for 1.5 hours. The reaction mixture was cooled to room temperature, quenched with $NaHCO_3$ and extracted with EtOAc. The organic phase was dried over $Na_2SO_4$, filtered and concentrated in vacuo. The crude material was columned (gradient 0-50% EtOAc in Petrol) to give 900 mg of a pale yellow solid which was dissolved in dioxane (10 mL) followed by 2M HCl (6 mL). The solution was stirred at room temperature for 1 hour, quenched with $NaHCO_3$ and extracted with DCM. The organic phase was dried over $Na_2SO_4$, filtered and concentrated in vacuo to give the desired product as a yellow solid. 1H NMR (400 MHz, DMSO-d6): 8.21 (1H, d), 7.95 (1H, dd), 7.37-7.10 (6H, m), 7.06 (2H, d), 4.51-4.28 (3H, m), 3.43-3.33 (2H, m), 2.94-2.77 (2H, m), 2.69 (3H, s), 1.08 (21H, s), 0.41-0.25 (2H, m), 0.23-0.10 (2H, m).

Example 21. Step 4: 3-(4-Chloro-phenyl)-4-fluoro-3-(1-hydroxymethyl-cyclopropylmethoxy)-6-(1-hydroxy-1-methyl-ethyl)-2-{4-[(triisopropylsilanyl)-ethynyl]-benzyl}-2,3-dihydro-isoindol-1-one The title compound was prepared from 6-acetyl-3-(4-chloro-phenyl)-2-[4-(3,3-diisopropyl-4-methyl-pent-1-ynyl)-benzyl]-4-fluoro-3-(1-hydroxymethyl-cyclopropyl-methoxy)-2,3-dihydro-isoindol-1-one (871 mg, 1.29 mmol) in a similar manner to that described for Example 1. $^1$H NMR (400 MHz, DMSO-d6): 7.80 (1H, d), 7.49 (1H, d), 7.36-7.10 (6H, m), 7.05 (2H, d), 5.36 (1H, s), 4.50-4.25 (3H, m), 3.42-3.32 (2H, m), 2.91-2.75 (2H, m), 1.48 (6H, s), 1.09 (21H, s), 0.40-0.25 (2H, m), 0.15 (2H, s).

Example 21. Step 5: (3R)-3-(4-chlorophenyl)-2-[(4-ethynylphenyl)methyl]-4-fluoro-3-{[1-(hydroxymethyl)cyclopropyl]methoxy}-6-(2-hydroxypropan-2-yl)-2,3-dihydro-1H-isoindol-1-one The title compound was prepared by following procedures similar to those described for Example 11. Purification by preparative chiral HPLC gave the title compound (173 mg). $^1$H NMR (400 MHz, DMSO-$d_6$): 7.80 (1H, d), 7.50 (1H, d), 7.37-7.17 (6H, m), 7.09 (2H, d), 5.36 (1H, s), 4.50-4.35 (2H, m), 4.28 (1H, d), 4.11 (1H, s), 3.38 (1H, dd), 3.28 (1H, dd), 2.89 (1H, d), 2.77 (1H, d), 1.48 (6H, s), 0.39-0.24 (2H, m), 0.18-0.00 (2H, m). MS: $[M+H]^+$=534.

Examples 22 and 23: (3R)-3-(4-chlorophenyl)-6-(1,2-dihydroxypropan-2-yl)-2-[(4-ethynylphenyl)methyl]-4-fluoro-3-{[1-(hydroxymethyl)cyclopropyl]methoxy}-2,3-dihydro-1H-isoindol-1-one (*Two Isomers at the Position Shown)

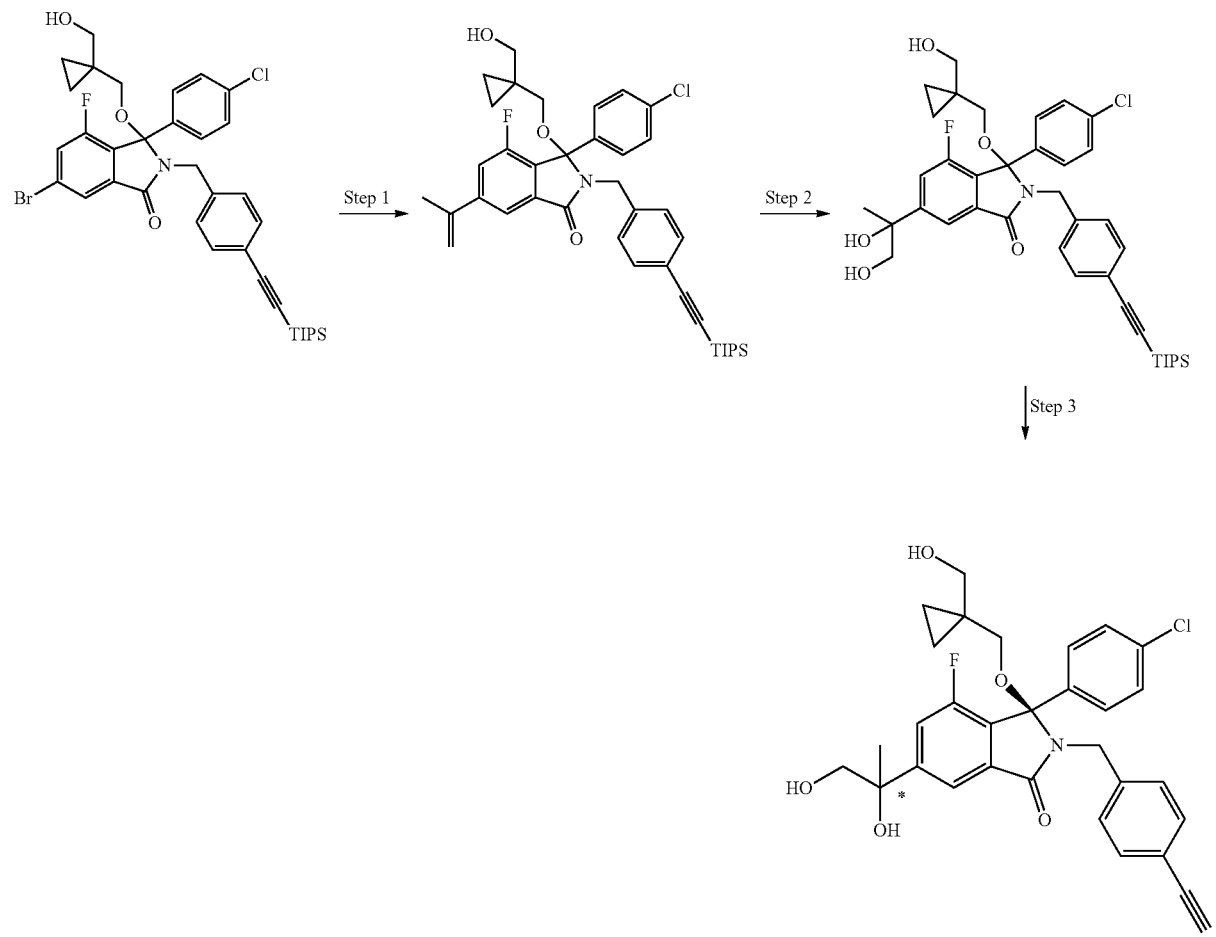

Example 22 and Example 23. Step 1: 3-(4-Chlorophenyl)-4-fluoro-3-(1-hydroxymethyl-cyclopropylmethoxy)-6-isopropenyl-2-{4-[(triisopropylsilanyl)-ethynyl]-benzyl}-2,3-dihydro-isoindol-1-one The title compound was prepared in a similar fashion to Preparation 13. $^1$H NMR (400 MHz, DMSO-d6): 7.79 (1H, d), 7.63-7.55 (1H, m), 7.34-7.09 (6H, m), 7.05 (2H, d), 5.68 (1H, s), 5.30 (1H, s), 4.49- 4.28 (3H, m), 3.36 (2H, d), 2.87 (2H, s), 2.17 (3H, s), 1.16-1.03 (21H, m), 0.42-0.26 (2H, m), 0.17 (2H, d).

Example 22 and Example 23. Step 2: 3-(4-Chlorophenyl)-6-(1,2-dihydroxy-1-methyl-ethyl)-4-fluoro-3-(1-hydroxymethyl-cyclopropylmethoxy)-2-{4-[(triisopropylsilanyl)-ethynyl]-benzyl}-2,3-dihydro-isoindol-1-one The title compound was prepared by using a similar procedure to that described in Example 27 Step 4. $^1$H NMR (400 MHz, DMSO-d6): 7.79 (1H, dd), 7.50-7.42 (1H, m), 7.35-7.10 (6H, m), 7.05 (2H, d), 5.28 (1H, s), 4.86-4.79 (1H, m), 4.42 (1H, t), 4.35 (2H, s), 3.54-3.40 (2H, m), 3.36 (2H, dd), 2.93-2.78 (2H, m), 2.55-2.40 (25H, m), 1.43 (3H, s), 1.14-1.03 (21H, m), 0.40-0.27 (2H, m), 0.21-0.09 (2H, m).

Example 22 and Example 23. Step 3: (3R)-3-(4-chlorophenyl)-6-(1,2-dihydroxypropan-2-yl)-2-[(4-ethynylphenyl)methyl]-4-fluoro-3-{[1-(hydroxymethyl)cyclopropyl]methoxy}-2,3-dihydro-1H-isoindol-1-one (Isomer A and B)

The title compounds were prepared from 3-(4-chlorophenyl)-6-(1,2-dihydroxy-1-methyl-ethyl)-4-fluoro-3-(1-hydroxymethyl-cyclopropylmethoxy)-2-{4-[(triisopropylsilanyl)-ethynyl]-benzyl}-2,3-dihydro-isoindol-1-one (1.0 g, 1.4 mmol) in a similar manner to that described in Example 10. Purification by preparative chiral HPLC gave:—

Example 22 (*isomer 1): 1H NMR (400 MHz, DMSO-d6): 7.78 (1H, s), 7.47 (1H, d), 7.36-7.16 (6H, m), 7.09 (2H, d), 5.29 (1H, s), 4.82 (1H, t), 4.50-4.32 (2H, m), 4.28 (1H, d), 4.12 (1H, s), 3.52-3.34 (3H, m), 3.29 (1H, dd), 2.89 (1H, d), 2.78 (1H, d), 1.43 (3H, s), 0.38-0.25 (2H, m), 0.17-0.00 (2H, m). MS: [M–H]$^-$=548.

Example 23)*isomer 2): 1H NMR (400 MHz, DMSO-d6): 7.79 (1H, d), 7.46 (1H, d), 7.36-7.13 (6H, m), 7.09 (2H, d), 5.42-5.12 (1H, m), 4.98-4.60 (1H, m), 4.41 (1H, d), 4.29 (1H, d), 4.12 (1H, s), 3.50 (1H, d), 3.44 (1H, d), 3.38 (2H, d), 3.29 (1H, d), 2.89 (1H, d), 2.79 (1H, d), 1.43 (3H, s), 0.39-0.29 (2H, m), 0.18-0.00 (2H, m)

Example 24: 4-{[(1R)-1-(4-chlorophenyl)-7-fluoro-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-2-yl]methyl}benzonitrile

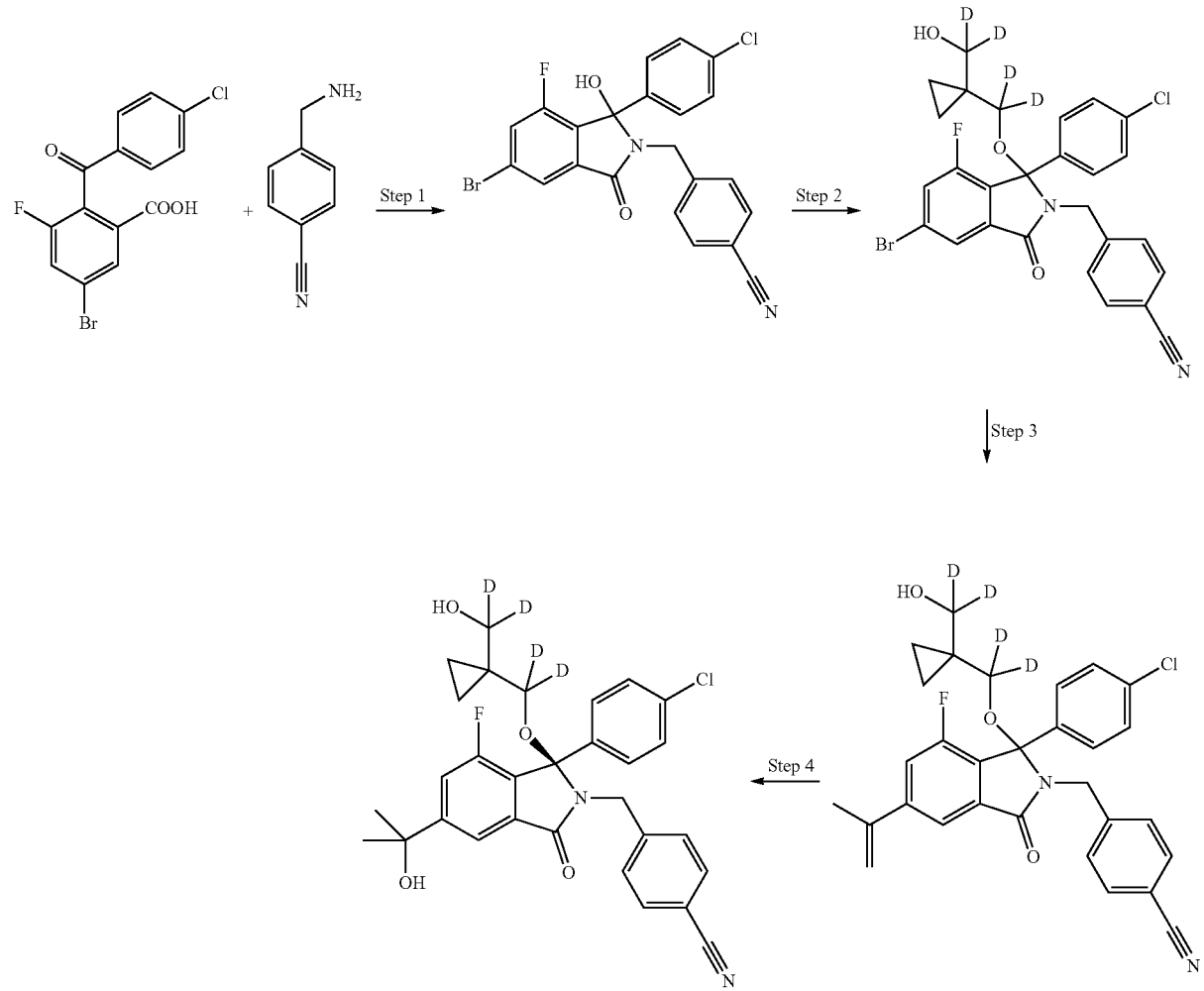

Example 24. Step 1: 4-[5-Bromo-1-(4-chloro-phenyl)-7-fluoro-1-hydroxy-3-oxo-1,3-dihydro-isoindol-2-ylmethyl]-benzonitrile The title compound was prepared from 5-bromo-2-(4-chloro-benzoyl)-3-fluoro-benzoic acid (4.0 g, 11.2 mmol) and 4-aminomethyl-benzonitrile hydrochloride (2.0 g, 11.2 mmol) in a similar manner to that described for Preparation 9 MS: [M–H]⁻=470.

Example 24. Step 2: 4-{[5-Bromo-1-(4-chlorophenyl)-7-fluoro-1-({1-[hydroxy(2H2)methyl]cyclopropyl}(2H2)methoxy)-3-oxo-2,3-dihydro-1H-isoindol-2-yl]methyl}benzonitrile The title compound was prepared from 4-[5-bromo-1-(4-chloro-phenyl)-7-fluoro-1-hydroxy-3-oxo-1,3-dihydro-isoindol-2-ylmethyl]-benzonitrile (1.0 g, 2.1 mmol) and {1-[hydroxy($^2$H$_2$)methyl]cyclopropyl}($^2$H$_2$)methanol (890 mg, 8.4 mmol) in a similar manner to that described for Preparation 10 MS: [M–H]⁻=558.

Example 24. Step 3: 4-{[1-(4-Chlorophenyl)-7-fluoro-1-({1-[hydroxy(2H2)methyl]cyclopropyl}(2H2)methoxy)-3-oxo-5-(prop-1-en-2-yl)-2,3-dihydro-1H-isoindol-2-yl]methyl}benzonitrile The title compound was prepared from 4-{[5-bromo-1-(4-chlorophenyl)-7-fluoro-1-({1-[hydroxy($^2$H$^2$)methyl]cyclopropyl}($^2$H$^2$)methoxy)-3-oxo-2,3-dihydro-1H-isoindol-2-yl]methyl}benzonitrile (750 mg, 1.33 mmol) in a similar manner to that described in Preparation 13. MS: [M–H]⁻=519.

Example 24. Step 4: 4-{[(1R)-1-(4-chlorophenyl)-7-fluoro-1-({1-[hydroxy($^2$H$^2$)methyl]cyclopropyl}($^2$H$_2$)methoxy)-5-(2-hydroxypropan-2-yl)-3-oxo-2,3-dihydro-1H-isoindol-2-yl]methyl}benzonitrile The title compound was prepared from 4-{[1-(4-chlorophenyl)-7-fluoro-1-({1-[hydroxy(2H2)methyl]cyclopropyl}(2H2)meth oxy)-3-oxo-5-(prop-1-en-2-yl)-2,3-dihydro-1H-isoindol-2-yl]methyl}benzonitrile (660 mg, 1.27 mmol) in a similar manner to that described for Example 2. 1H NMR (400 MHz, DMSO-d6): 7.81 (1H, d), 7.61 (2H, d), 7.57-7.46 (1H, m), 7.34-7.15 (6H, m), 5.37 (1H, s), 4.44 (2H, s), 4.40-4.30 (1H, m), 1.48 (6H, s), 0.39-0.26 (2H, m), 0.21-0.03 (2H, m). MS: [M–H]⁻=537.

Example 25: 4-{[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]methyl}benzonitrile

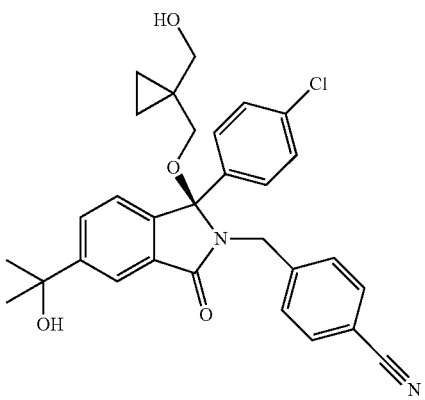 [SMILES: CC(C)(O)c1ccc2c(c1)C(=O)N(Cc1ccc(C#N)cc1)[C@@]2(OCC1(CO)CC1)c1ccc(Cl)cc1]

Example 25, Step 1: 6-Acetyl-2-(4-bromobenzyl)-3-(4-chlorophenyl)-3-hydroxyisoindolin-1-one

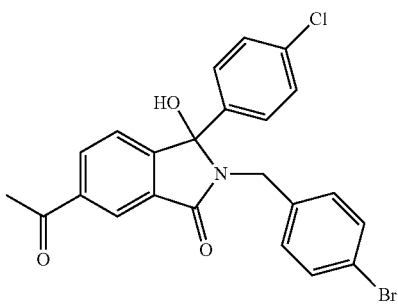 [SMILES: CC(=O)c1ccc2c(c1)C(=O)N(Cc1ccc(Br)cc1)C2(O)c1ccc(Cl)cc1]

Prepared in a similar manner to that described in Preparation 9 from: 5-acetyl-2-(4-chlorobenzoyl)benzoic acid. MS: [M–H]⁻=470.2.

Example 25, Step 2: 6-Acetyl-2-(4-bromobenzyl)-3-(4-chlorophenyl)-3-((1-(hydroxymethyl)cyclopropyl)methoxy)isoindolin-1-one

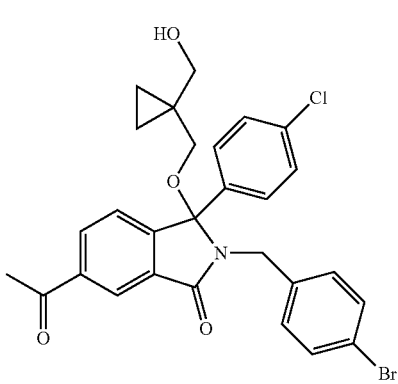 [SMILES: CC(=O)c1ccc2c(c1)C(=O)N(Cc1ccc(Br)cc1)C2(OCC1(CO)CC1)c1ccc(Cl)cc1]

Prepared in a similar manner to that described in Preparation 22 from: 6-acetyl-2-(4-bromobenzyl)-3-(4-chlorophenyl)-3-hydroxyisoindolin-1-one. 1H NMR (500 MHz, CDCl$_3$) 0.09-0.18 (2H, m), 0.40-0.44 (2H, m), 2.67-2.69 (4H, m), 2.78 (1H, d), 3.36 (1H, d), 3.50 (1H, d), 4.19 (1H, d), 4.55 (1H, d), 7.07-7.08 (2H, m), 7.17-7.18 (2H, m), 7.21-7.26 (3H, m), 7.30-7.32 (2H, m), 8.14 (1H, dd), 8.43 (1H, d).

Example 25, Step 3: 2-(4-Bromobenzyl)-3-(4-chlorophenyl)-3-((1-(hydroxymethyl)cyclopropyl)methoxy)-6-(2-hydroxypropan-2-yl)isoindolin-1-one

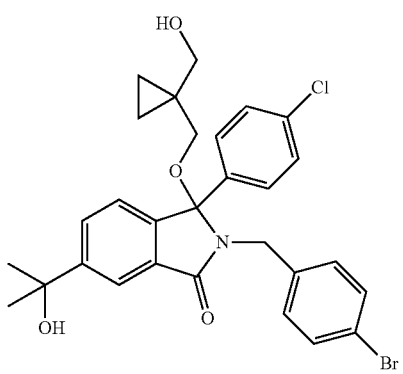 [SMILES: CC(C)(O)c1ccc2c(c1)C(=O)N(Cc1ccc(Br)cc1)C2(OCC1(CO)CC1)c1ccc(Cl)cc1]

Prepared in a similar manner to that described in Example 1 from: 6-acetyl-2-(4-bromobenzyl)-3-(4-chlorophenyl)-3-((1-(hydroxymethyl)cyclopropyl)methoxy)isoindolin-1-on. 1H NMR (500 MHz, CDCl$_3$) 0.12-0.20 (2H, m), 0.39-0.44 (2H, m), 1.61 (3H, s), 1.62 (3H, s), 2.66 (1H, d), 2.83 (1H, d), 3.37 (1H, d), 3.48 (1H, d), 4.17 (1H, d), 4.52 (1H, d), 7.07-7.11 (3H, m), 7.17-7.22 (4H, m), 7.29-2.31 (2H, m), 7.72 (1H, dd), 7.99 (1H, d).

Example 25, Step 4: 4-{[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]methyl}benzonitrile In a microwave vial, a mixture of 2-(4-bromobenzyl)-3-(4-chlorophenyl)-3-((1-(hydroxymethyl)cyclopropyl)methoxy)-6-(2-hydroxypropan-2-yl)isoindolin-1-one (140 mg, 0.25 mmol), zinc powder (3.3 mg, 0.05 mmol), Pd(OAc)$_2$ (11.2 mg, 0.05 mmol), rac-2-(di-tert-butylphosphino)-1,1'-binapthyl (39.8 mg, 0.10 mmol) and Zn(CN)$_2$ (32.3 mg, 0.275 mmol) in MeCN (1.5 mL) was degassed under N$_2$ for 20 min then heated to 120° C. for 1 h. The reaction was cooled to RT, diluted with EtOAc (25 mL) and filtered through Celite. The organic layer was washed with water (100 mL), brine (100 mL), dried over Na$_2$SO$_4$ and concentrated under vacuum. Purified by Biotage 0-50% EtOAc in petrol as the eluent then semi-preparative HPLC gave the racemic mixture as a white solid (55 mg, 43%). Purification by preparative chiral HPLC gave the title compound as a white solid (24.4 mg). 1H NMR (500 MHz, CD$_3$OD-d$_4$) 0.16-0.29 (2H, m), 0.41-0.46 (2H, m), 1.58 (6H, s), 2.84-2.90 (2H, m), 3.48-3.56 (2H, m), 4.44 (1H, d), 4.64 (1H, d), 7.15-7.21 (5H, m), 7.26-7.28 (2H, m), 7.47-7.49 (2H, m), 7.78 (1H, dd), 8.04 (1H, d). MS: [M+H]$^+$=517.4.

Example 26: (3R)-3-(4-chlorophenyl)-2-[(4-chlorophenyl)methyl]-6-(2-hydroxypropan-2-yl)-3-[(3-methyloxetan-3-yl)methoxy]-2,3-dihydro-1H-isoindol-1-one

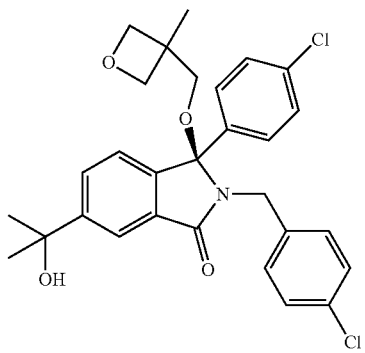 [SMILES: CC1(CO[C@]2(c3ccc(Cl)cc3)c3ccc(C(C)(C)O)cc3C(=O)N2Cc2ccc(Cl)cc2)COC1]

Example 26, Step 1: 2-(Bromomethyl)-2-methylpropane-1,3-diol

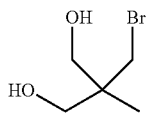

At −10° C., to a solution of 3-methyl-3-oxetanemethanol (1.00 g, 9.8 mmol) in THF (12.3 mL) was added aqueous HBr (48 wt %, 3.9 mL) and the resulting yellow/brown solution was stirred for 4 h at −10° C. then at RT for 12 h. The mixture was diluted with brine (100 mL) and extracted into Et$_2$O (4×100 mL). The combined organic layers were dried over Na$_2$SO$_4$ and concentrated under vacuum to give the title compound as a white solid (1.36 g, 76%); 1H NMR (500 MHz, CDCl$_3$) 0.91 (3H, s), 2.73 (2H, s), 3.53 (2H, s), 3.65 (4H, s).

Example 26, Step 2: 6-Bromo-3-(3-bromo-2-(hydroxymethyl)-2-methylpropoxy)-2-(4-chlorobenzyl)-3-(4-chlorophenyl)isoindolin-1-one

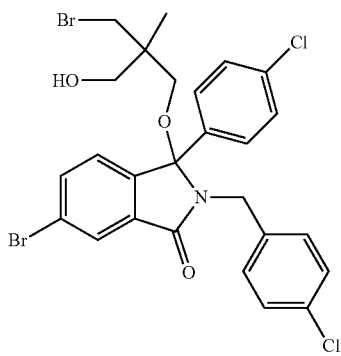 [SMILES: CC(CO)(CBr)COC1(c2ccc(Cl)cc2)c2ccc(Br)cc2C(=O)N1Cc1ccc(Cl)cc1]

Prepared in a similar manner to that described in Preparation 22 from: 6-bromo-2-(4-chlorobenzyl)-3-(4-chlorophenyl)-3-hydroxyisoindolin-1-one (Preparation 9) (635 mg, 1.37 mmol), SOCl₂ (325 mg, 0.20 mL, 2.73 mmol), 2-(bromomethyl)-2-methylpropane-1,3-diol (500 mg, 2.73 mmol) and K₂CO₃ (377 mg, 2.73 mmol) in THF (2.9 mL). Purified by Biotage using 0-20% EtOAc in petrol as the eluent gave the title compound as a white solid (302 mg, 35%). MS: [M+H]⁺=628.3.

Example 26, Step 3: 6-Bromo-2-(4-chlorobenzyl)-3-(4-chlorophenyl)-3-((3-methyloxetan-3-yl)methoxy)isoindolin-1-one

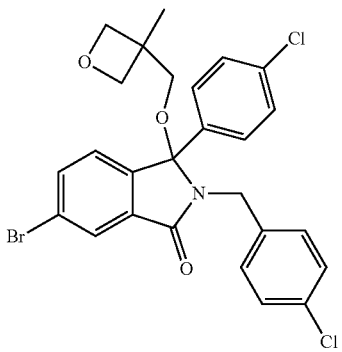 [SMILES: CC1(COC2(c3ccc(Cl)cc3)c3ccc(Br)cc3C(=O)N2Cc2ccc(Cl)cc2)COC1]

To a solution of 6-bromo-3-(3-bromo-2-(hydroxymethyl)-2-methylpropoxy)-2-(4-chlorobenzyl)-3-(4-chlorophenyl)isoindolin-1-one (820 mg, 1.31 mmol) in EtOH (28 mL) was added KOH (88 mg, 1.57 mmol) and the mixture heated at reflux for 6 h then cooled to RT. The reaction was diluted with water (50 mL) and acidified to pH 6 with 1.0 M aqueous HCl solution. The reaction was extracted into EtOAc (3×40 mL), washed with brine, dried over MgSO₄ and concentrated under vacuum. Purified by Biotage using 0-20% EtOAc in petrol as the eluent gave the title compound as a white solid (516 mg, 72%). 1H NMR (500 MHz, CDCl₃) 1.13 (3H, s), 2.75-2.81 (2H, m), 4.16-4.22 (2H, m), 4.26-4.27 (1H, m), 4.32-4.34 (2H, m), 4.51 (1H, d), 6.97 (1H, d), 7.07-7.09 (2H, m), 7.13-7.14 (2H, m), 7.17-7.23 (4H, m), 7.65 (1H, dd), 8.06 (1H, d).

Example 26, Step 4: 2-(4-Chlorobenzyl)-3-(4-chlorophenyl)-3-((3-methyloxetan-3-yl)methoxy)-6-(prop-1-en-2-yl)isoindolin-1-one

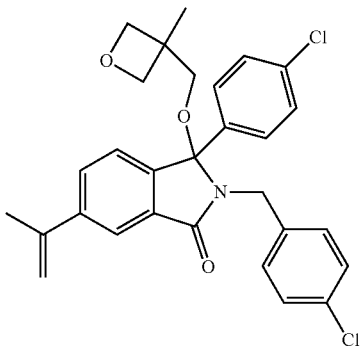 [SMILES: C=C(C)c1ccc2c(c1)C(=O)N(Cc1ccc(Cl)cc1)C2(OCC1(C)COC1)c1ccc(Cl)cc1]

Prepared in a similar manner to that described in Preparation 13 from: 6-bromo-2-(4-chlorobenzyl)-3-(4-chlorophenyl)-3-((3-methyloxetan-3-yl)methoxy)isoindolin-1-one. 1H NMR (500 MHz, CDCl₃) 1.13 (3H, s), 2.20 (3H, s), 2.79 (2H, s), 4.16-4.27 (3H, m), 4.32-4.35 (2H, m), 4.52-4.55 (1H, m), 5.21 (1H, s), 5.48 (1H, s), 7.04 (1H, d), 7.09-7.14 (4H, m), 7.17-7.23 (4H, m), 7.63 (1H, dd), 8.00 (1H, d).

Example 26, Step 5: 6-Acetyl-2-(4-chlorobenzyl)-3-(4-chlorophenyl)-3-((3-methyloxetan-3-yl)methoxy)isoindolin-1-one

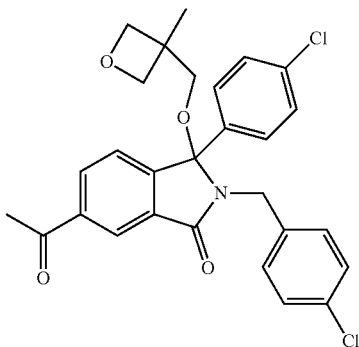

Prepared in a similar manner to that described in Preparation 15 from: 2-(4-chlorobenzyl)-3-(4-chlorophenyl)-3-((3-methyloxetan-3-yl)methoxy)-6-(prop-1-en-2-yl)isoindolin-1-one. MS: [M+H]⁺=510.4.

Example 26, Step 6: (3R)-3-(4-chlorophenyl)-2-[(4-chlorophenyl)methyl]-6-(2-hydroxypropan-2-yl)-3-[(3-methyloxetan-3-yl)methoxy]-2,3-dihydro-1H-isoindol-1-one Prepared in a similar manner to that described in Example 1 from: 6-acetyl-2-(4-chlorobenzyl)-3-(4-chlorophenyl)-3-((3-methyloxetan-3-yl)methoxy)isoindolin-1-one. 1H NMR (500 MHz, CDCl₃) 1.13 (3H, s), 1.63 (3H, s), 1.64 (3H, s), 2.78 (2H, s), 4.16-4.22 (2H, m), 4.25-4.27 (1H, m), 4.34-4.36 (2H, m), 4.54 (1H, d), 7.60 (1H, d), 7.10-7.14 (4H, m), 7.19-7.22 (4H, m), 7.73 (1H, dd), 8.02 (1H, d). MS: [M+H]⁺=526.4.

Examples 27 and 28: 4-{[(1R)-1-(4-chlorophenyl)-5-(1,2-dihydroxypropan-2-yl)-1-{[1-(hydroxymethyl)cyclopropyl]methoxy}-3-oxo-2,3-dihydro-1H-isoindol-2-yl]methyl}benzonitrile (*Both Isomers at Position Shown)

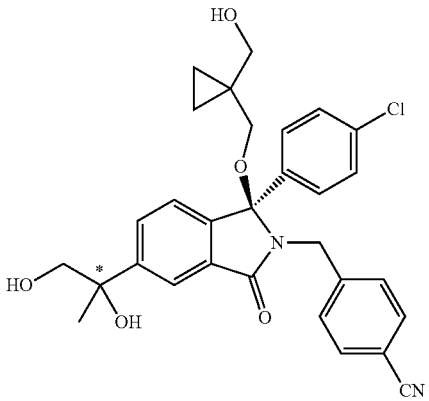

Example 27 and Example 28, Step 2 and 3: 4-((1-(4-Chlorophenyl)-hydroxy-((1-(hydroxymethyl)cyclopropyl)methoxy)-3-oxo-5-(prop-1-en-2-yl)isoindolin-2-yl)methyl)benzonitrile

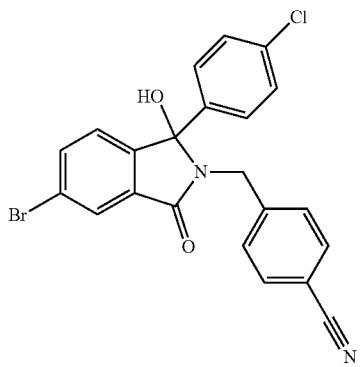 [SMILES: N#Cc1ccc(CN2C(=O)c3cc(Br)ccc3C2(O)c2ccc(Cl)cc2)cc1]

Prepared in a similar manner to that described in Preparation 9 from: 5-bromo-2-(4-chlorobenzoyl)benzoic acid and 4-(aminomethyl)benzonitrile. MS: [M−H]⁻=453.1.

Example 27 and Example 28, Step 2 and 3: 4-((1-(4-Chlorophenyl)-1-((1-(hydroxymethyl)cyclopropyl)methoxy)-3-oxo-5-(prop-1-en-2-yl)isoindolin-2-yl)methyl)benzonitrile

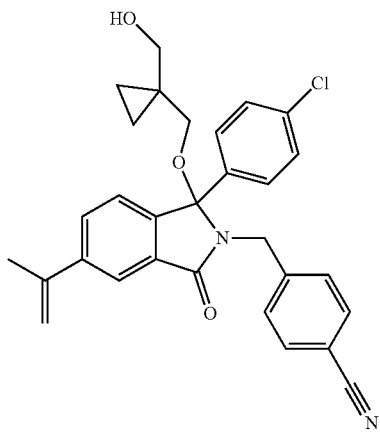 [SMILES: C=C(C)c1ccc2c(c1)C(=O)N(Cc1ccc(C#N)cc1)C2(OCC1(CO)CC1)c1ccc(Cl)cc1]

Starting from: 4-((5-bromo-1-(4-chlorophenyl)-1-hydroxy-3-oxoisoindolin-2-yl)methyl)benzonitrile, the title compound was prepared in a similar manner to that described in Preparation 12 and 13. 1H NMR (500 MHz, CD₃OD) 0.19-0.27 (2H, m), 0.41-0.46 (2H, m), 2.21 (3H, s), 2.85-2.91 (2H, m), 3.49-3.56 (2H, m), 4.45 (1H, d), 4.64 (1H, d), 5.23 (1H, s), 5.51 (1H, s), 7.15-7.22 (5H, m), 7.26-7.28 (2H, m), 7.47-7.48 (2H, m), 7.76 (1H, dd), 7.99 (1H, d).

Example 27 and Example 28, Step 4: 4-{[(1R)-1-(4-chlorophenyl)-5-(1,2-dihydroxypropan-2-yl)-1-{[1-(hydroxymethyl)cyclopropyl]methoxy}-3-oxo-2,3-dihydro-1H-isoindol-2-yl]methyl}benzonitrile At 0° C., to a solution of tert-butanol/water (8.91 mL/8.91 mL) was added AD-mix-β (2.49 g) followed by portion wise addition of 4-((1-(4-chlorophenyl)-1-((1-(hydroxymethyl)cyclopropyl)methoxy)-3-oxo-5-(prop-1-en-2-yl)isoindolin-2-yl)methyl)benzonitrile (900 mg, 1.80 mmol) and the resulting mixture was stirred at 0° C. for 48 h. Na₂SO₃ (0.98 g, 7.78 mmol) was added and the reaction warmed to RT and diluted with water (50 mL). The reaction was extracted with EtOAc (2×50 mL), dried over MgSO₄ and concentrated under vacuum. Purified by Biotage using 0-100% EtOAc in petrol as the eluent gave a diastereoisomeric mixture of product (177 mg, 18%). Chiral HPLC gave the title compounds.

Example 27 (*isomer 1): 1H NMR (500 MHz, CDCl₃) 0.13-0.21 (2H, m), 0.42-0.46 (2H, m), 1.58 (3H, s), 2.64 (1H, s), 2.72 (1H, d), 2.88 (1H, d), 3.40 (1H, d), 3.51 (1H, d), 3.71 (1H, d), 3.82 (1H, d), 4.41 (1H, d), 4.50 (1H, d), 7.14-7.18 (5H, m), 7.26-7.28 (2H, m), 7.44-7.46 (2H, m), 7.72 (1H, dd), 7.99 (1H, d). MS: [M+H]⁺=533.4.

Example 28 (*isomers 2): 1H NMR (500 MHz, CDCl₃) 0.13-0.21 (2H, m), 0.42-0.47 (2H, m), 1.59 (3H, s), 2.64 (1H, s), 2.73 (1H, d), 2.86 (1H, d), 3.41 (1H, d), 3.51 (1H, d), 3.70 (1H, d), 3.81 (1H, d), 4.41 (1H, d), 4.50 (1H, d), 7.14-7.18 (5H, m), 7.27-7.28 (2H, m), 7.44-7.46 (2H, m), 7.72 (1H, dd), 7.98 (1H, d). MS: [M+H]⁺=533.4.

Example 29: (3R)-3-(4-chlorophenyl)-2-[(4-chlorophenyl)methyl]-3-[(1-hydroxycyclopropyl)methoxy]-6-(2-hydroxypropan-2-yl)-2,3-dihydro-1H-isoindol-1-one

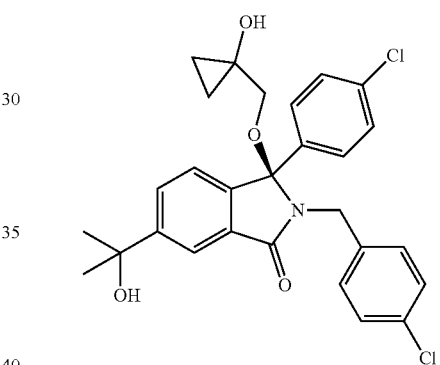

Example 29, Step 1: 6-Acetyl-3-((1-((tert-butyldiphenylsilyl)oxy)cyclopropyl)methoxy)-2-(4-chlorobenzyl)-3-(4-chlorophenyl)isoindolin-1-one

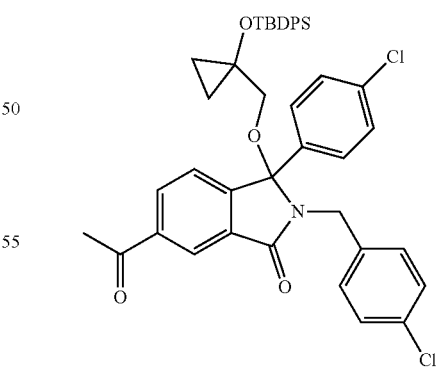

Prepared in a similar manner to that described in Preparation 12 from: 6-acetyl-2-(4-chlorobenzyl)-3-(4-chlorophenyl)-3-hydroxyisoindolin-1-one (Preparation 20) and (1-((tert-butyldiphenylsilyl)oxy)cyclopropyl)methanol). 1H NMR (500 MHz, CDCl₃) 0.07-0.12 (2H, m), 0.66-0.75 (2H, m), 0.99 (9H, s), 2.57 (1H, d), 2.67 (3H, s), 2.76 (1H, d), 4.24 (2H, s), 6.83 (1H, d), 6.97-6.98 (2H, m), 7.06-7.14 (5H, m), 7.25-7.31 (5H, m), 7.37-7.40 (2H, m), 7.56-7.58 (2H, m), 7.65-7.66 (2H, m), 7.99 (1H, dd), 8.34 (1H, d).

Example 29, Step 2: 3-((1-((tert-Butyldiphenylsilyl)oxy)cyclopropyl)methoxy)-2-(4-chlorobenzyl)-3-(4-chlorophenyl)-6-(2-hydroxypropan-2-yl)isoindolin-1-one

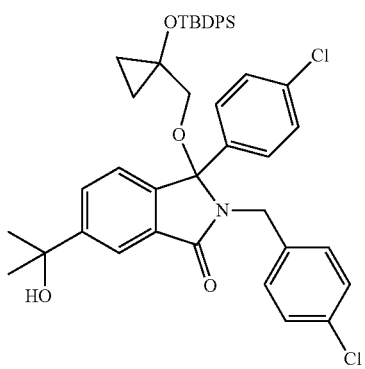

Prepared in a similar manner to that described in Example 1. 1H NMR (500 MHz, CDCl₃) 0.05-0.11 (2H, m), 0.62-0.72 (2H, m), 1.00 (9H, s), 1.61 (6H, s), 2.56 (1H, d), 2.84-2.86 (1H, m), 4.20-4.27 (2H, m), 6.75-6.77 (1H, m), 6.96-6.98 (2H, m), 7.04-7.06 (2H, m), 7.10-7.13 (4H, m), 7.28-7.32 (4H, m), 7.37-7.41 (2H, m), 7.57-7.61 (3H, m), 7.66-7.68 (2H, m), 7.91 (1H, d).

Example 29, Step 3: (3R)-3-(4-chlorophenyl)-2-[(4-chlorophenyl)methyl]-3-[(1-hydroxycyclopropyl)methoxy]-6-(2-hydroxypropan-2-yl)-2,3-dihydro-1H-isoindol-1-one Deprotection in a similar manner to that described for Example 10 gave Example 29. 1H NMR (500 MHz, CDCl₃) 0.19-0.26 (2H, m), 0.70-0.76 (2H, m), 1.61-0.62 (6H, m), 2.71 (1H, d), 2.94 (1H, d), 4.20 (1H, d), 4.54 (1H, d), 7.10 (1H, d), 7.13 (4H, s), 7.20-7.24 (4H, m), 7.71 (1H, dd), 7.99 (1H, d). MS: [M+H]⁺=512.4.

Example 30: 2-{[(1R)-1-(4-Chlorophenyl)-2-[(4-chlorophenyl)methyl]-5-(2-hydroxypropan-2-yl)-3-oxo-2,3-dihydro-1H-isoindol-1-yl]oxy}-N,N-dimethylacetamide

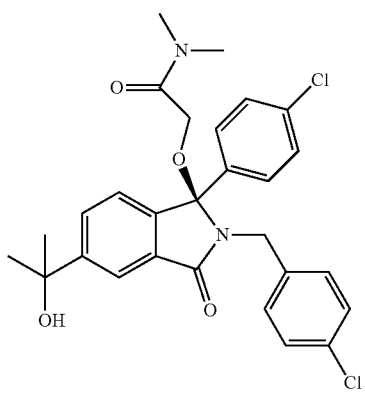 [SMILES: CN(C)C(=O)CO[C@]1(c2ccc(Cl)cc2)c2ccc(C(C)(C)O)cc2C(=O)N1Cc1ccc(Cl)cc1]

Example 30, Step 1: Methyl 2-((5-bromo-2-(4-chlorobenzyl)-1-(4-chlorophenyl)-3-oxoisoindolin-1-yl)oxy)acetate

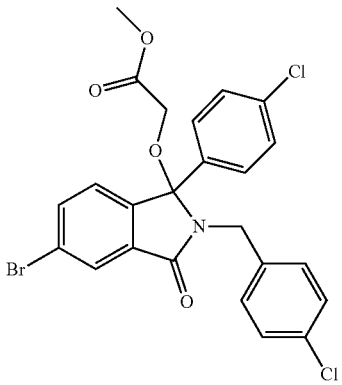 [SMILES: COC(=O)COC1(c2ccc(Cl)cc2)c2ccc(Br)cc2C(=O)N1Cc1ccc(Cl)cc1]

Using methyl glycolate, the title compound was prepared using a procedure similar to that described for Preparation 10. MS: [M-C₃H₅O₃]⁺ 446.

Example 30, Step 2: 2-((5-Bromo-2-(4-chlorobenzyl)-1-(4-chlorophenyl)-3-oxoisoindolin-1-yl)oxy)-N,N-dimethylacetamide

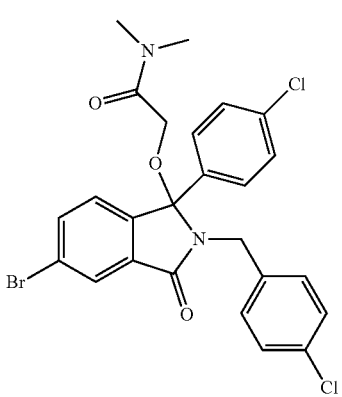 [SMILES: CN(C)C(=O)COC1(c2ccc(Cl)cc2)c2ccc(Br)cc2C(=O)N1Cc1ccc(Cl)cc1]

Methyl 2-((5-bromo-2-(4-chlorobenzyl)-1-(4-chlorophenyl)-3-oxoisoindolin-1-yl)oxy)acetate (756 mg, 1.41 mmol) and 40% aqueous in water dimethylamine (7.6 mL) were mixed and stirred at room temperature for 6.5 h. The solvent was removed in vacuo and FCC [dichloromethane-methanol (100:0)→(94:6)] of the crude residue afforded 2-((5-bromo-2-(4-chlorobenzyl)-1-(4-chlorophenyl)-3-oxoisoindolin-1-yl)oxy)-N,N-dimethylacetamide (524 mg, 68%) as a white foam. MS: [M-C₄H₈NO₂]⁺ 446.

Example 30, Step 3: (R)-2-((2-(4-chlorobenzyl)-1-(4-chlorophenyl)-5-(2-hydroxypropan-2-yl)-3-oxoisoindolin-1-yl)oxy)-N,N-dimethylacetamide The title compound was prepared using similar procedures to those described in Preparation 13 and Example 2. ¹H NMR (500 MHz, CDCl₃): 7.94 (1H, d, 7-H), 7.62 (1H, dd, ArH), 7.35-7.30 (2H, m, 2×ArH), 7.24-7.18 (4H, m, 4×ArH), 7.12-7.07 (3H, m, 3×ArH), 4.74 (1H, d, NC—H'), 3.87 (1H, d, NC—H), 3.20 (1H, d, 4'-H'), 3.08 (1H, d, 4'-H), 2.76 (3H, s, NCH₃), 2.37 (3H, s, NCH₃) and 1.56-1.52 (6H, m, 2×CH₃). MS: [M-C₄H₈NO₂]⁺ 424.

Example 31: (3R)-3-(4-Chlorophenyl)-2-[(4-chlorophenyl)methyl]-6-(2-hydroxypropan-2-yl)-3-{[1-(methoxymethyl)cyclopropyl]methoxy}-2,3-dihydro-1H-isoindol-1-one

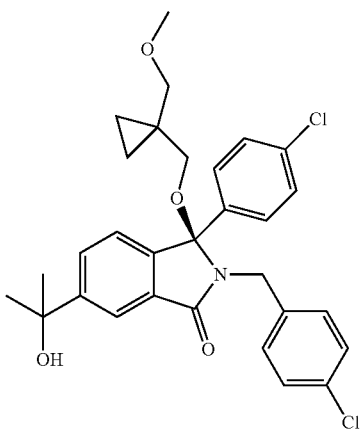 [SMILES: COCC1(CO[C@]2(c3ccc(Cl)cc3)c3ccc(C(C)(C)O)cc3C(=O)N2Cc2ccc(Cl)cc2)CC1]

Example 31, Step 1: 2-(4-Chlorobenzyl)-3-(4-chlorophenyl)-3-((1-(methoxymethyl)cyclopropyl)methoxy)-6-(prop-1-en-2-yl)isoindolin-1-one

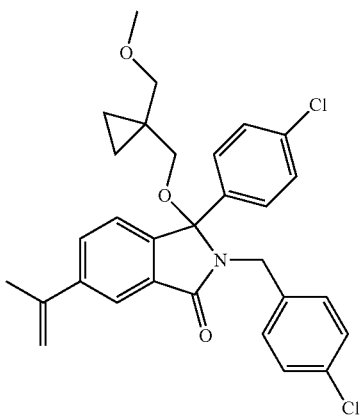 [SMILES: C=C(C)c1ccc2c(c1)C(=O)N(Cc1ccc(Cl)cc1)C2(OCC1(COC)CC1)c1ccc(Cl)cc1]

To a solution of 2-(4-chlorobenzyl)-3-(4-chlorophenyl)-3-((1-(hydroxymethyl)cyclopropyl)methoxy)-6-(prop-1-en-2-yl)isoindolin-1-one, Preparation 13 (318 mg, 0.625 mmol) in anhydrous THF (3 mL) under nitrogen, was added ᵗBuOK (140 mg, 1.25 mmol) at room temperature and the mixture stirred for 1 h before cooling to 0° C. MeI (0.08 mL, 1.25 mol) in anhydrous THF (1 mL) was added dropwise and stirred for 3.5 h. Diluted with EtOAc (10 mL) and washed with water (2×20 mL), brine (20 mL), dried over anhydrous Na₂SO₄, filtered and the solvent removed n vacuo. FCC [petrol-ethyl acetate (100:0)→(80:20)] of the crude residue afforded 2-(4-chlorobenzyl)-3-(4-chlorophenyl)-3-((1-(methoxymethyl)cyclopropyl)methoxy)-6-(prop-1-en-2-yl)isoindolin-1-one (278 mg, 85%) as a colourless gum. MS: [C₆H₁₁O₂]⁺ 406.

Example 31, Step 2: (R)-2-(4-Chlorobenzyl)-3-(4-chlorophenyl)-6-(2-hydroxypropan-2-yl)-3-((1-(methoxymethyl)cyclopropyl)methoxy)isoindolin-1-one The title compound was prepared using similar procedures to those described for Example 2. ¹H NMR (500 MHz, CDCl₃) 8.00 (1H, m, 7-H), 7.73 (1H, dd, ArH), 7.24-7.17 (4H, m, 4×ArH) 7.16-7.10 (4H, m, 4×ArH), 7.08 (1H, d, ArH), 4.46 (1H, d, NC—H'), 4.30 (1H, d, NC—H), 3.43 (1H, d, 4'-H'), 3.31 (3H, s, OCH₃), 3.16 (1H, d, 4'-H), 2.88 (1H, d, 2'-H'), 2.61 (1H, d, 2'-H), 1.67-1.62 (6H, m, 2×CH₃), 0.45-0.38 (2H, m, Cy-Py-H₂) and 0.25-0.15 (2H, m, Cy-Py-H). MS: [M-C₆H₁₁O₂]⁺ 424.

Example 32: (3R)-3-(4-Chlorophenyl)-2-[(4-chlorophenyl)methyl]-3-{[1-(hydroxymethyl) cyclobutyl]methoxy}-6-(2-hydroxypropan-2-yl)-2,3-dihydro-1H-isoindol-1-one

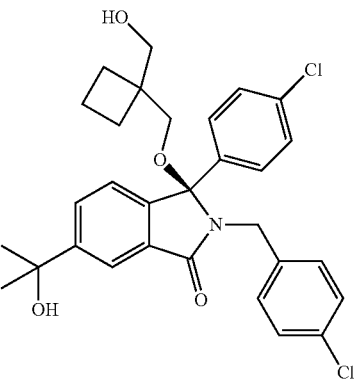 [SMILES: CC(C)(O)c1ccc2c(c1)C(=O)N(Cc1ccc(Cl)cc1)[C@@]2(OCC1(CO)CCC1)c1ccc(Cl)cc1]

Example 32, Step 1: Cyclobutane-1,1-diyldimethanol

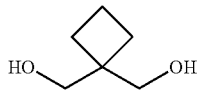

To a solution of diethyl-1,1-cyclobutanedicarboxylate (1.00 g, 4.99 mmol) in anhydrous THF (13 mL) at 0° C. was added LiBH₄ (239 mg, 11.0 mmol) portionwise over 10 min and then stirred for further 10 min before heating to 60° C. for 2 h. The reaction mixture was cooled to room temperature and then to 0° C. Water (2.5 mL) was added cautiously, followed by 1 M HCl until gas evolution ceased, and then neutralised with sat. sol. NaOH. Extracted with EtOAc (3×10 mL) and then combined. To the aqueous layer was added brine (5 mL) and then extracted with EtOAc (2×10 mL). The combined organic phases were washed with brine (15 mL), dried (Na₂SO₄), filtered and concentrated in vacuo to give the title compound as a colourless thick oil (523 mg, 90%), which was used without purification. ¹H NMR (500 MHz, CDCl₃) 3.75 (4H, s, 2×HC₂OH), 2.32 (2H, br s, 2×OH), 1.96-1.90 (2H, m, H-3) and 1.80-1.77 (4H, m, H-2, H-4).

Example 32, Step 2: (R)-2-(4-chlorobenzyl)-3-(4-chlorophenyl)-3-((1-(hydroxymethyl)cyclobutyl)methoxy)-6-(2-hydroxypropan-2-yl)isoindolin-1-one Starting from Preparation 8, the title compound was prepared using procedures similar to those described in Preparation 10, Preparation 13 and Example 2. $^1$H NMR (500 MHz, CDCl$_3$) 8.01 (1H, d, 7-H), 7.72 (1H, dd, ArH) 7.21-7.11 (8H, m, 8×ArH), 7.08 (1H, d, ArH), 4.52 (1H, d, NC—H'), 4.23 (1H, d, NC—H), 3.53 (2H, d, OCH$_2$), 2.88 (1H, d, CH$_2$OH), 2.79 (1H, d, CH$_2$OH) and 1.86-1.51 (12H, m, 2×CH$_3$ and 3×CH$_2$). MS: [M-C$_6$H$_{11}$O$_2$]$^+$ 424.

Example 33: 5-chloro-2-{[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]methyl}benzoic Acid

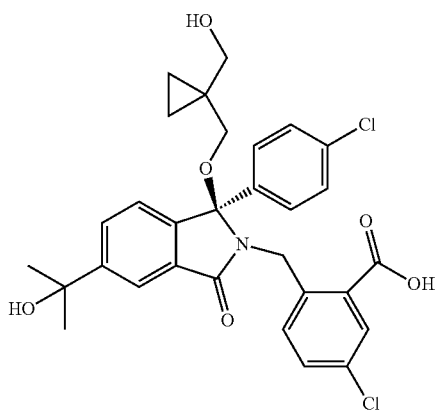 [SMILES: CC(C)(O)c1ccc2c(c1)C(=O)N(Cc1ccc(Cl)cc1C(=O)O)[C@@]2(OCC1(CO)CC1)c1ccc(Cl)cc1]

Example 33, Step 1;
(2-Bromo-4-chlorophenyl)methanamine

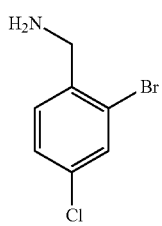

To a solution of 2-bromo-4-chlorobenzonitrile (500 mg, 2.3 mmol), in dry THF (50 mL) was added slowly borane-THF complex (1 M, 12 mL, 11.5 mmol) at 0° C. before refluxing for 1 h. After cooling down, 1 M HCl in MeOH (20 mL) was charged slowly with ice cooling. The solvent was removed by concentration in vacuo before water (0.61 mmol/mL to benzonitrile) was charged, then washed by Et$_2$O (0.61 mmol/mL to benzonitrile) before basifying with 2 M NaOH solution to pH 12. Et$_2$O (15 mL) was added and the mixture was washed with water (3×15 mL) and brine (1 mL). The organic phase was dried (MgSO$_4$) and concentrated in vacuo to give a yellow oil (345 mg, 68%). LCMS (ESI$^+$) m/z=220.1 [M+H]$^+$.

Example 33, Step 2; 6-Acetyl-2-(2-bromo-4-chlorobenzyl)-3-(4-chlorophenyl)-3-hydroxyisoindolin-1-one

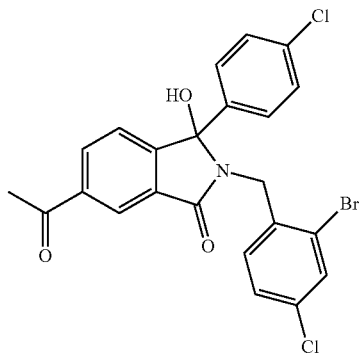 [SMILES: CC(=O)c1ccc2c(c1)C(=O)N(Cc1ccc(Cl)cc1Br)C2(O)c1ccc(Cl)cc1]

The title compound was prepared using procedures similar to those described for Preparation 9. LCMS (ESI$^-$) m/z=502.1 [M−H]$^-$ Example 33, Step 3; 6-Acetyl-2-(2-bromo-4-chlorobenzyl)-3-(4-chlorophenyl)-3-((1-(hydroxymethyl)cyclopropyl)methoxy)isoindolin-1-one

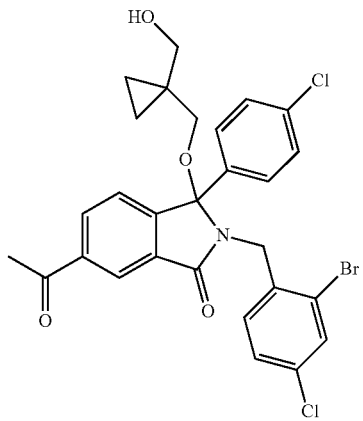 [SMILES: CC(=O)c1ccc2c(c1)C(=O)N(Cc1ccc(Cl)cc1Br)C2(OCC1(CO)CC1)c1ccc(Cl)cc1]

The title compound was prepared using procedures similar to those described for Preparation 10. LCMS (ESI$^+$) m/z=588.3 [M+H]$^+$.

Example 33, Step 4; 6-Acetyl-2-(2-bromo-4-chlorobenzyl)-3-((1-(((tert-butyldimethylsilyl)oxy)methyl)cyclopropyl)methoxy)-3-(4-chlorophenyl)isoindolin-1-one

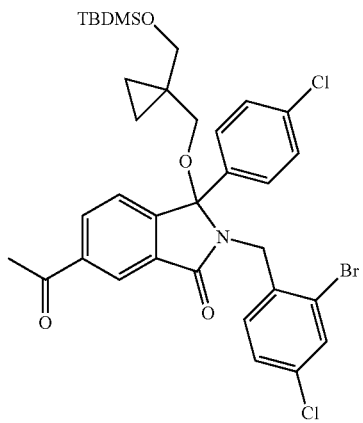 [SMILES: CC(=O)c1ccc2c(c1)C(=O)N(Cc1ccc(Cl)cc1Br)C2(OCC1(CO[Si](C)(C)C(C)(C)C)CC1)c1ccc(Cl)cc1]

The title compound was prepared using procedures similar to those described for Preparation 29. LCMS (ESI⁺) m/z=486.2 [M]⁺.

Example 33, Step 5, 2-((5-Acetyl-1-((1-(((tert-butyldimethylsilyl)oxy)methyl)cyclopropyl)methoxy)-1-(4-chlorophenyl)-3-oxoisoindolin-2-yl)methyl)-5-chlorobenzoic Acid

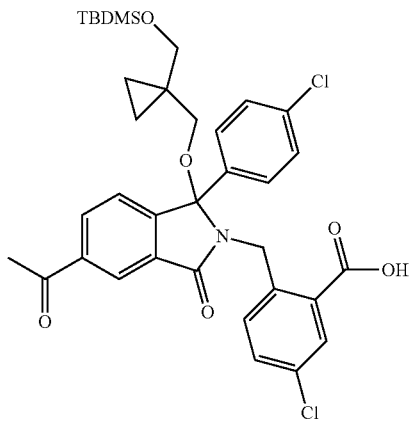 [SMILES: CC(=O)c1ccc2c(c1)C(=O)N(Cc1ccc(Cl)cc1C(=O)O)C2(OCC1(CO[Si](C)(C)C(C)(C)C)CC1)c1ccc(Cl)cc1]

To a solution of the previous compound (306 mg, 0.44 mmol) in dry DMF (4.0 mL) was added Xantphos (104 mg, 0.18 mmol), Pd(OAc)₂ (20 mg, 0.09 mmol), HCOOLi.H₂O (122 mg, 1.74 mmol) and Et₃N (0.25 mL, 1.74 mmol) before degassing for 15 mins, and then Ac₂O (0.17 mL, 1.74 mmol) was introduced before microwave for 30 mins at 140° C. The mixture was gone through a plug of Celite, EtOAc (30 mL) was added and the mixture was washed with water (3×30 mL) and brine (20 mL). The organic phase was dried (MgSO₄) and concentrated in vacuo. Chromatography (silica; EtOAc with 0.1% acetic acid, petrol 20-80%) gave a greasy solid (78 mg, 43%). LCMS (ESI⁻) m/z=666.3 [M−H]⁻.

Example 33, Step 6; 2-((1-((1-(((tert-Butyldimethylsilyl)oxy)methyl)cyclopropyl)methoxy)-1-(4-chlorophenyl)-5-(2-hydroxypropan-2-yl)-3-oxoisoindolin-2-yl)methyl)-5-chlorobenzoic Acid

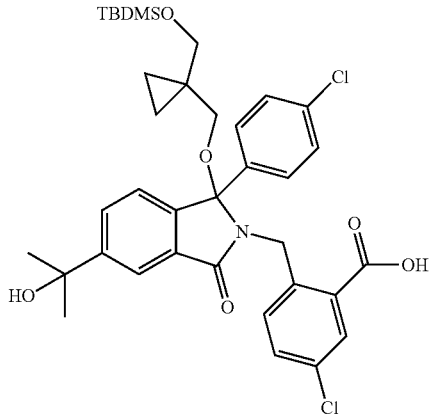 [SMILES: CC(C)(O)c1ccc2c(c1)C(=O)N(Cc1ccc(Cl)cc1C(=O)O)C2(OCC1(CO[Si](C)(C)C(C)(C)C)CC1)c1ccc(Cl)cc1]

The title compound was prepared using procedures similar to those described for Example 1. LCMS (ESI⁻) m/z=682.4 [M−H]⁻.

Example 33, Step 7: 5-chloro-2-{[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]methyl}benzoic Acid The product from Example 33, Step 6 was deprotected using procedures similar to those described for Example 10, to give Example 33. ¹H-NMR (500 MHz, CDCl₃) δ 0.26-0.30 (1H, m, cyclopropane CHHCH₂), 0.36-0.40 (1H, m, cyclopropane CHHCH₂), 0.50-0.59 (2H, m, cyclopropane CH₂CH₂), 1.63 (6H, s, CH₃), 2.50 (1H, d, C—O—CHH), 3.29 (1H, d, C—O—CHH), 3.45 (1H, d, CHHOH), 3.86 (1H, d, CHHOH), 5.01 (1H, d, N—CHH), 5.19 (1H, d, N—CHH), 7.08 (2H, d, H—Ar), 7.12 (1H, d, H—Ar), 7.16 (2H, d, H—Ar), 7.25-7.26 (2H, m, H-4 and H—Ar), 7.73-7.77 (2H, m, H-5 and H—Ar), 8.04 (1H, s, H-7). LCMS (ESI⁻) m/z=568.3[M−H]⁻.

Example 34: (3R)-2-{[4-chloro-2-(morpholine-4-sulfonyl)phenyl]methyl}-3-(4-chlorophenyl)-3-{[1-(hydroxymethyl)cyclopropyl]methoxy}-6-(2-hydroxypropan-2-yl)-2,3-dihydro-1H-isoindol-1-one

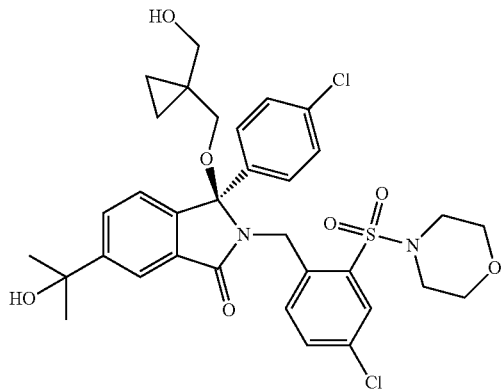 [SMILES: CC(C)(O)c1ccc2c(c1)C(=O)N(Cc1ccc(Cl)cc1S(=O)(=O)N1CCOCC1)[C@@]2(OCC1(CO)CC1)c1ccc(Cl)cc1]

Example 34, Step 1, 4-Chloro-2-mercaptobenzonitrile

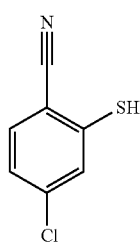

4-Chloro-2-fluorobenzonitrile (200 mg, 1.29 mmol) and Na₂S (110 mg, 1.41 mmol) were added into a microwave vial, DMF (1 mL) was charged into the mixture before stirring for 1 h at room temperature. 1 M NaOH solution was charged to pH 12 then washed by Et₂O (3×10 mL, acidified mixture with 1 M HCl to pH 1-2 and extracted with Et₂O (3×10 mL), the combined extracts were washed by water (30 mL) and brine (20 mL), dried by MgSO₄, concentrate in vacuo to give a yellow solid (156 mg, 72%). ¹H NMR (500 MHz, CDCl₃) δ 4.14 (1H, s, SH), 7.21 (1H, d, J=8.4 Hz, H—Ar), 7.42 (1H, s, H—Ar), 7.52 (1H, d, J=8.3 Hz, H—Ar).

Example 34, Step 2, 4-Chloro-2-(morpholinosulfonyl)benzonitrile

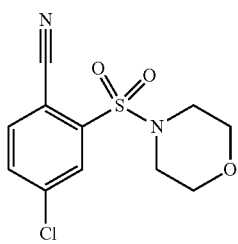 [SMILES: N#Cc1ccc(Cl)cc1S(=O)(=O)N1CCOCC1]

To a stirring mixture of 4-chloro-2-mercaptobenzonitrile (50 mg, 0.30 mmol), t-BuNCl (333 mg, 1.20 mmol) and H$_2$O (0.02 mL) in MeCN (3 mL) was added NCS (120 mg, 0.90 mmol) at 0° C., after 30 mins, morpholine (0.03 mL, 0.30 mmol) was charged into reaction mixture before stirring overnight at room temperature, extracted with EtOAc (3×10 mL), the combined organic extracts were washed with water (30 mL) and brine (20 mL), dried by MgSO$_4$ and concentrated in vacuo. Chromatography (silica; EtOAc, petrol 20-50%) gave a white solid (59 mg, 70%). LCMS (ESI$^+$) m/z=287.2 [M+H]$^+$.

Example 34, Step 3, (4-Chloro-2-(morpholinosulfonyl)phenyl)methanamine

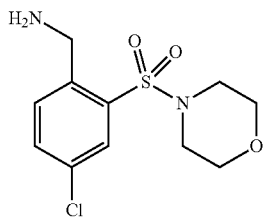

Prepared by the same method as described in Example 33, Step 1 (195 mg, 0.68 mmol), THF (4 mL), 1 mol/L borane-THF complex (3.4 mL, 3.40 mmol) and 1 M HCl in MeOH (4 mL). Concentration in vacuo gave yellow oil (90 mg, 46%). LCMS (ESI$^+$) m/z=291.2 [M+H]$^+$.

Example 34, Step 4, 6-Acetyl-2-(4-chloro-2-(morpholinosulfonyl)benzyl)-3-(4-chlorophenyl)-3-hydroxyisoindolin-1-one

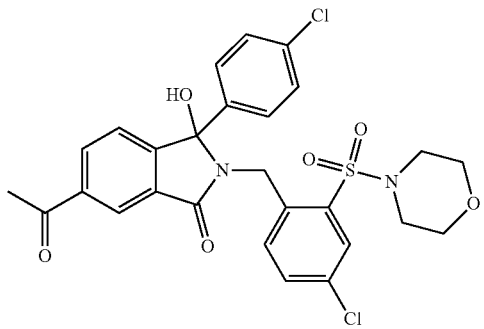 [SMILES: CC(=O)c1ccc2c(c1)C(=O)N(Cc1ccc(Cl)cc1S(=O)(=O)N1CCOCC1)C2(O)c1ccc(Cl)cc1]

The title compound was prepared using procedures similar to those described for Preparation 9. LCMS (ESI$^-$) m/z=573.3 [M−H]$^-$.

Example 34, Step 5, 6-Acetyl-2-(4-chloro-2-(morpholinosulfonyl)benzyl)-3-(4-chlorophenyl)-3-((1-(hydroxymethyl)cyclopropyl)methoxy)isoindolin-1-one

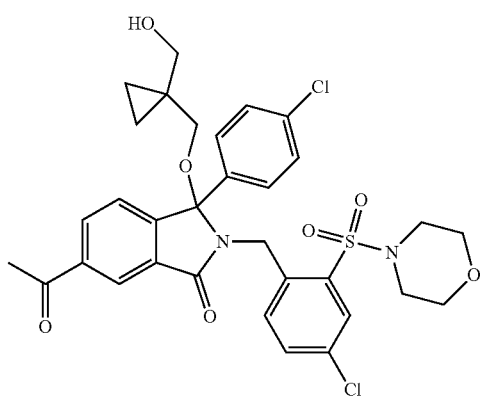 [SMILES: CC(=O)c1ccc2c(c1)C(=O)N(Cc1ccc(Cl)cc1S(=O)(=O)N1CCOCC1)C2(OCC1(CO)CC1)c1ccc(Cl)cc1]

The title compound was prepared using procedures similar to those described in Preparation 22. LCMS (ESI$^+$) m/z=681.4 [M+Na]$^+$.

Example 34, Step 6, (3R)-2-{[4-chloro-2-(morpholine-4-sulfonyl)phenyl]methyl}-3-(4-chlorophenyl)-3-{[1-(hydroxymethyl)cyclopropyl]methoxy}-6-(2-hydroxypropan-2-yl)-2,3-dihydro-1H-isoindol-1-one The title compound was prepared using procedures similar to those described for Example 1. $^1$H-NMR (500 MHz, CDCl$_3$) δ 0.21-0.23 (1H, m, cyclopropane CHHCH$_2$), 0.30-0.32 (1H, m, cyclopropane CHHCH$_2$), 0.44-0.49 (2H, m, cyclopropane CH$_2$CH$_2$), 1.65 (6H, s, CH$_3$), 1.85 (2H, bs, 2H), 2.66 (1H, d, C—O—CHH), 2.96-3.01 (2H, m, H-morpholine), 3.07-3.11 (2H, m, H-morpholine), 3.18 (1H, d, C—O—CHH), 3.33 (1H, d, CHHOH), 3.64-3.71 (4H, m, H-morpholine), 3.82 (1H, d, CHHOH), 4.92 (1H, d, N—CHH), 5.01 (1H, d, N—CHH), 7.11 (2H, d, H—Ar), 7.18-7.24 (5H, m, H—Ar), 7.72 (1H, s, H—Ar), 7.79 (1H, d, H-5), 8.04 (1H, s, H-7). LCMS (ESI$^-$) m/z=673.4 [M−H]$^-$.

Example 35: 1-({[(1R)-2-[(4-chloro-2-methanesulfonylphenyl)methyl]-1-(4-chlorophenyl)-7-fluoro-5-(2-hydroxypropan-2-yl)-3-oxo-2,3-dihydro-1H-isoindol-1-yl]oxy}methyl)cyclopropane-1-carboxamide filtered through celite. The celite was washed with EtOAc and the combined filtrate and washings evaporated to give the title compound as a colourless solid (33.4 g, 71%). $^1$H NMR (400 MHz; DMSO-$d_6$): 7.10-6.85 (2H, m), 4.97 (1H, t), 3.48 (2H, d), 0.90-0.85 (2H, m), 0.61-0.58 (2H, m).

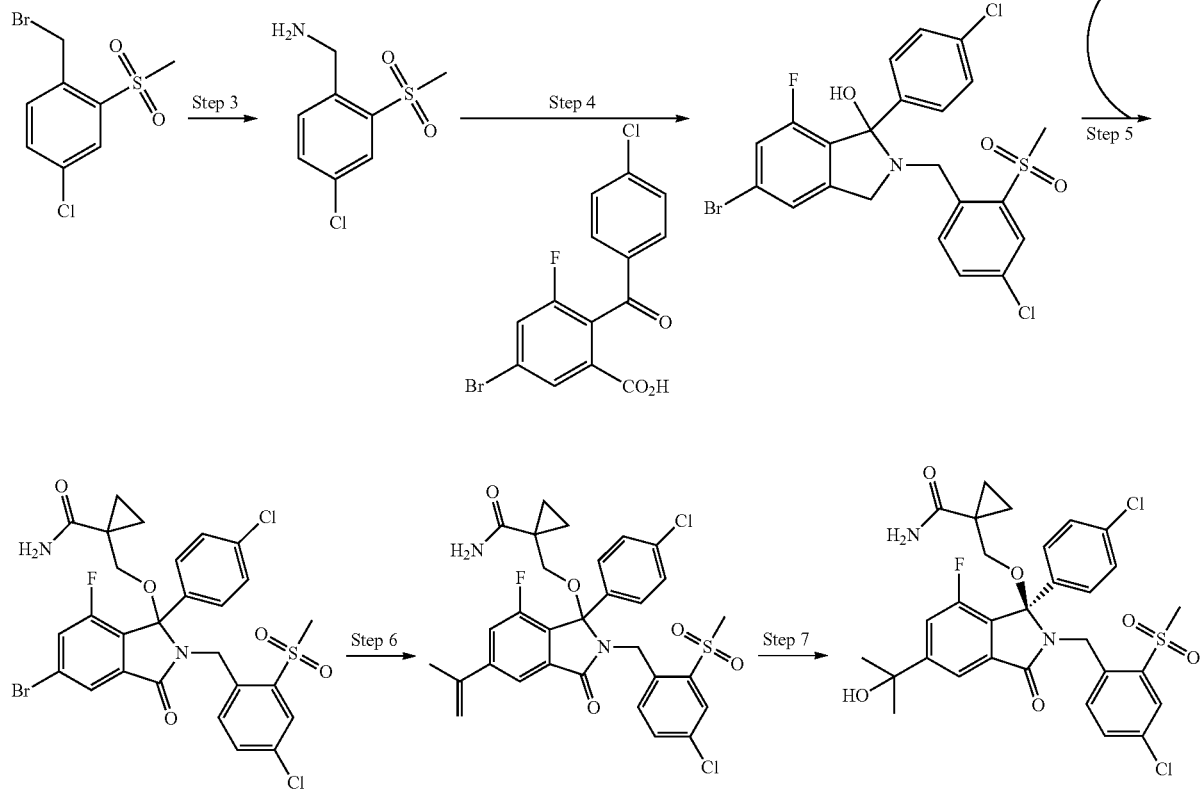

Example 35, Step 1: Methyl 1-carbamoylcyclopropanecarboxylate

A solution of dimethyl cyclopropane-1,1-dicarboxylate (57.8 g, 0.365 mol) in 7M ammonia in methanol was stirred at room temperature for 90 h, then evaporated under reduced pressure to afford the title compound as a colourless solid (52.2 g, 99%). $^1$H NMR (400 MHz; DMSO-$d_6$): 7.82 (1H, s), 7.35 (1H, s), 3.63 (3H, s), 1.34 (4H, s).

Example 35, Step 2: 1-(Hydroxymethyl)cyclopropanecarboxamide

Lithium aluminium hydride (27.2 g, 0.719 mol) was added portionwise over 0.75 h. to a stirred suspension of methyl 1-carbamoylcyclopropanecarboxylate (51.2 g, 0.358 mol) in THF (1.5 L) at 0° C. under nitrogen. On complete addition the mixture was stirred at 0° C. for a further 1.25 h. prior to dropwise addition of water (27 mL), 15% NaOH (27 mL) and water (82 mL) sequentially. The mixture was allowed to warm to room temperature, stirred for 0.5 h. and

Example 35, Step 3: (4-Chloro-2-(methylsulfonyl)phenyl)methanamine

Hexamethylenetetramine (40.8 g, 0.291 mol) was added in one portion to a stirred, room temperature solution of 1-(bromomethyl)-4-chloro-2-(methylsulfonyl)benzene (75 g, 0.264 mol) in EtOAc (1 L). After 1.5 h. the mixture was chilled in ice and the precipitate filtered, washed with cold EtOAc and air dried. This material was suspended in MeOH (375 mL), concentrated HCl (150 mL) added dropwise over 0.33 h. and the mixture heated at 40° C. for 2 h. The mixture was cooled, concentrated under reduced pressure and the residue basified with 5M NaOH, with cooling, and extracted with dichloromethane (3×500 mL). Combined extracts were dried (MgSO$_4$) and evaporated and the residue chromatographed on silica gel eluting with 20-100% EtOAc in isohexane gradient followed by 0-10% MeOH containing 7N NH$_3$ in EtOAc gradient to afford the title compound as a pale brown solid (27.8 g, 48%). 1H NMR (400 MHz, CDCl$_3$): 8.02 (1H, d), 7.58 (1H, dd), 7.51 (1H, d), 4.19 (2H, s), 3.23 (3H, s), 1.64 (2H, s).

Example 35, Step 4: (4-Chloro-2-(methylsulfonyl) phenyl)methanamine6-bromo-2-(4-chloro-2-(methylsulfonyl)benzyl)-3-(4-chlorophenyl)-4-fluoro-3-hydroxyisoindolin-1-one HATU (45.6 g, 0.12 mol) was added to a stirred solution of 5-bromo-2-(4-chlorobenzoyl)-3-fluorobenzoic acid (35.79 g, 0.1 mol) and (4-chloro-2-(methylsulfonyl)phenyl) methanamine (21.95 g, 0.1 mol) in anhydrous DMF (100 mL) at room temperature. The mixture was stirred at room temperature for 18 h, at 60° C. for 18 h, then cooled and concentrated under reduced pressure. The residual oil was poured into water (1.5 L), extracted with dichloromethane (4×500 mL) and the combined extracts washed with water (2×1 L), dried (MgSO$_4$) and evaporated and the residue chromatographed on silica gel eluting with 20-100% EtOAc in isohexane gradient to give the title compound as a pale yellow solid (42.7 g, 76%). 1H NMR (400 MHz, CDCl$_3$): 7.88 (1H, d), 7.70 (1H, d), 7.57 (1H, d), 7.49-7.45 (1H, m), 7.36-7.33 (1H, m), 7.25 (4H, s), 5.13 (1H, d), 4.73 (1H, d), 5.00-4.20 (1H, br s), 3.07 (3H, s).

Example 35, Step 5: 1-(((5-Bromo-2-(4-chloro-2 (methylsulfonyl)benzyl)-1-(4-chlorophenyl)-7-fluoro-3-oxoisoindolin-1 yl)oxy)methyl)cyclopropanecarboxamide The title compound was prepared using procedures similar to those described for Preparation 12. 1H NMR (400 MHz, CDCl$_3$): 7.99 (1H, d), 7.93 (1H, dd), 7.75 (1H, d), 7.51-7.47 (1H, m), 7.30-7.19 (5H, m), 6.98 (1H, s), 6.76 (1H, s), 4.99-4.88 (2H, m), 3.36-3.20 (5H, m), 1.05-0.90 (2H, m), 0.63-0.53 (2H, m).

Example 35, Step 6: 1-(((2-(4-Chloro-2-(methylsulfonyl)benzyl)-1-(4-chlorophenyl)-7-fluoro-3-oxo-5-(prop-1-en-2-yl)isoindolin-1-yl)oxy)methyl)cyclopropanecarboxamide The title compound was prepared using procedures similar to those described for Preparation 13. H NMR (400 MHz; DMSO-d$_6$): 7.87 (1H, d), 7.76 (1H, d), 7.70 (1H, dd), 7.50 (1H, dd), 7.30-7.20 (5H, m), 6.98 (1H, s), 6.70 (1H, s), 5.73 (1H, s), 5.33 (1H, s), 5.00-4.85 (2H, m), 3.36-3.23 (5H, m), 2.20 (3H, s), 0.97-0.85 (2H, m), 0.65-0.45 (2H, m).

Example 35, Step 7: 1-({[(1R)-2-[(4-chloro-2-methanesulfonylphenyl)methyl]-1-(4-chlorophenyl)-7-fluoro-5-(2-hydroxypropan-2-yl)-3-oxo-2,3-dihydro-1H-isoindol-1-yl]oxy}methyl)cyclopropane-1-carboxamide The title compound was prepared using procedures similar to those described for Example 2. Chiral separation using supercritical fluid chromatography gave the title compound as the slower running isomer (0.245 g). 1H NMR (400 MHz, CDCl$_3$): 7.91-7.87 (2H, m), 7.53 (1H, d), 7.37-7.30 (1H, m), 7.78-7.15 (5H, m), 6.53 (1H, s), 5.45 (1H, s), 5.05-4.95 (2H, m), 3.36 (1H, d), 3.00 (3H, s), 2.96 (1H, d), 1.96 (1H, s), 1.65 (6H, s), 1.32-1.15 (2H, m), 0.60-0.30 (2H, m). MS(ES+) m/z 633.3\635.3 [M+H]$^+$.

Example 36: (3R)-2-[(4-chloro-2-methanesulfonylphenyl)methyl]-3-(4-chlorophenyl)-3-({1-[hydroxy ($^2$H$_2$)methyl]cyclopropyl}($^2$H$_2$)methoxy)-6-(2-hydroxypropan-2-yl)-2,3-dihydro-1H-isoindol-1-one

Example 36 Step 1, 6-Bromo-2-(4-chloro-2-(methylsulfonyl)benzyl)-3-(4-chlorophenyl)-3-hydroxyisoindolin-1-one

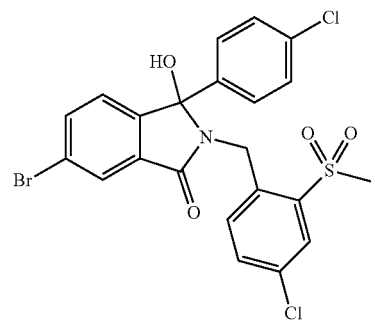 [SMILES: CS(=O)(=O)c1cc(Cl)ccc1CN1C(=O)c2cc(Br)ccc2C1(O)c1ccc(Cl)cc1]

The title compound was prepared using procedures similar to those described for Preparation 9: LCMS (ESI$^-$) m/z=538.0 [M–H]$^-$.

Example 36 Step 2, 6-Bromo-2-(4-chloro-2-(methylsulfonyl)benzyl)-3-(4-chlorophenyl)-3-((1-(deuteratedhydroxymethyl)cyclopropyl)deuteratedmethoxy) isoindolin-1-one

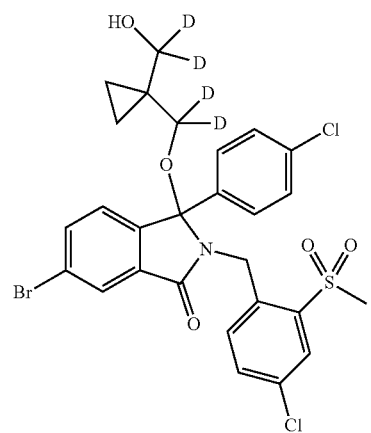 [SMILES: [2H]C([2H])(O)C1(C([2H])([2H])OC2(c3ccc(Cl)cc3)c3ccc(Br)cc3C(=O)N2Cc2ccc(Cl)cc2S(C)(=O)=O)CC1]

The title compound was prepared using procedures similar to those described for Preparation 22 but using 1,1-bis (deuteratedhydroxymethyl)cyclopropane LCMS (ESI$^+$) m/z=650.2 [M+Na]$^+$.

Example 36 Step 3: (3R)-2-[(4-chloro-2-methane-sulfonylphenyl)methyl]-3-(4-chlorophenyl)-3-({1-[hydroxy($^2$H$_2$)methyl]cyclopropyl}($^2$H$_2$)methoxy)-6-(2-hydroxypropan-2-yl)-2,3-dihydro-1H-isoindol-1-one

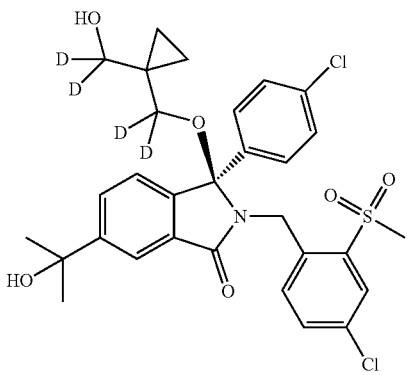 [SMILES: [2H]C([2H])(O)C1(C([2H])([2H])O[C@]2(c3ccc(Cl)cc3)c3ccc(C(C)(C)O)cc3C(=O)N2Cc2ccc(Cl)cc2S(C)(=O)=O)CC1]

Starting from Example 36, Step 2, the title compound was prepared using procedures similar to those described in Preparation 13 and Example 2. $^1$H-NMR (500 MHz, CDCl$_3$) δ 0.22-0.26 (1H, m, cyclopropane CHHCH$_2$), 0.32-0.36 (1H, m, cyclopropane CHHCH$_2$), 0.45-0.51 (2H, m, cyclopropane CH$_2$CH$_2$), 1.65 (6H, s, CH$_3$), 1.83 (2H, bs, 2H), 3.06 (3H, s, SO$_2$CH$_3$), 5.02 (2H, s, N—CH$_3$), 7.13-7.20 (4H, m, H—Ar), 7.24-7.26 (2H, m, H—Ar), 7.30 (1H, d, H—Ar), 7.79 (1H, d, H-5), 7.89 (1H, s, H—Ar), 8.02 (1H, s, H—Ar). LCMS (ESI$^+$) m/z=608.4 [M+H]$^+$ Example 37 and 38: (3R)-3-(4-Chlorophenyl)-2-[(4-chlorophenyl)methyl]-6-(2-hydroxypropan-2-yl)-3-(oxolan-3-yloxy)-2,3-dihydro-1H-isoindol-1-one (*Both Isomers at the Position Shown)

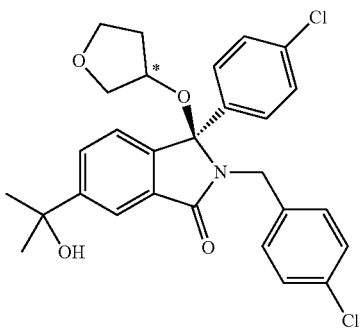 [SMILES: CC(C)(O)c1ccc2c(c1)C(=O)N(Cc1ccc(Cl)cc1)[C@@]2(OC1CCOC1)c1ccc(Cl)cc1]

The title compounds were prepared using procedures similar to those described in Preparations 10 and 13 and Example 2. The two diastereoisomers were isolated by preparative chiral HPLC.

Example 37 (isomer 1): $^1$H-NMR Spectrum: δ$_H$ (500 MHz, CDCl3): 8.01 (1H, d), 7.79 (1H, dd), 7.25-7.13 (9H, m), 4.52 (1H, d), 4.31 (1H, d), 3.88-3.83 (2H, m), 3.59-3.55 (1H, m), 3.27-3.19 (2H, m), 1.79-1.74 (1H, m), 1.59 (6H, s), 1.53-1.46 (1H, m).

Example 38: (isomer 2): $^1$H-NMR Spectrum: δ$_H$ (500 MHz, CDCl$_3$): 8.01 (1H, d), 7.79 (1H, dd), 7.21-7.13 (9H, m), 4.49 (1H, d), 4.43 (1H, d), 3.88-3.82 (2H, m), 3.63-3.59 (1H, m), 3.49 (1H, dd), 3.14 (1H, dd), 1.65-1.61 (2H, m), 1.59 (6H, s).

Example 39 and 40: (3R)-3-(4-chlorophenyl)-2-[(4-chlorophenyl)methyl]-6-(2-hydroxypropan-2-yl)-3-[(oxolan-3-yl)methoxy]-2,3-dihydro-1H-isoindol-1-one (*Both Isomers at the Position Shown)

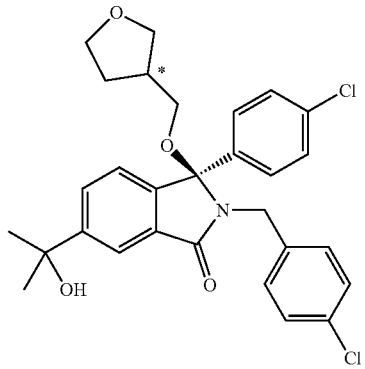 [SMILES: CC(C)(O)c1ccc2c(c1)C(=O)N(Cc1ccc(Cl)cc1)[C@@]2(OCC1CCOC1)c1ccc(Cl)cc1]

Step 1: 3-(Hydroxymethyl)tetrahydrofuran

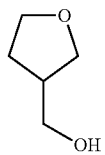

To a solution of tetrahydrofuran-3-carboxylic acid (0.247 mL, 2.58 mmol) in THF (13 mL) at 0° C. was added slowly lithium aluminium hydride (1.0 M in THF, 5.2 mL, 5.16 mmol), stirred for 10 minutes then allowed to attain room temperature and stirred for a further 3 hours. The reaction mixture was cooled to 0° C. and diluted with diethyl ether (15 mL), then treated sequentially with water (0.2 mL), NaOH (15% solution, 0.2 mL) and water (0.6 mL) and stirred for 30 minutes. The white suspension was then treated with sodium sulfate, stirred for a further 20 minutes, filtered over celite, washed with diethyl ether (2×20 mL) and concentrated in vacuo to yield 224 mg (85%) of the title compound as a colourless oil which was carried forward to the next stage without further purification. $^1$H-NMR Spectrum: δ$_H$ (500 MHz, CDCl$_3$): 3.90-3.84 (2H, m), 3.78-3.73 (1H, m), 3.66-3.63 (2H, m), 3.61-3.57 (1H, m), 2.51-2.46 (1H, m), 2.08-2.01 (1H, m), 1.69-1.62 (1H, m)

Step 2: (3R)-3-(4-chlorophenyl)-2-[(4-chlorophenyl)methyl]-6-(2-hydroxypropan-2-yl)-3-[(oxolan-3-yl)methoxy]-2,3-dihydro-1H-isoindol-1-one (*Both Isomers at the Position Shown)

Starting from 3-(hydroxymethyl)tetrahydrofuran and Preparation 8, the title compounds were prepared using procedures similar to those described for Preparations 10 and 13 and Example 2. The two diastereoisomers were isolated by preparative chiral HPLC.

Example 39 (*isomer 1): ¹H-NMR Spectrum: δ$_H$ (500 MHz, (CD$_3$OD): 8.06 (1H, d), 7.79 (1H, dd), 7.31-7.22 (8H, m), 7.16 (1H, d), 4.67 (1H, d), 4.15 (1H, d), 3.77-3.75 (1H, m), 3.68-3.59 (2H, m), 3.49-3.47 (1H, m), 2.79-2.77 (1H, m), 2.69-2.66 (1H, m), 2.10-2.02 (1H, m), 1.83-1.76 (1H, m), 1.59 (6H, s), 1.30-1.24 (1H, m).

Example 40 (*isomer 2): 1H-NMR Spectrum: δ$_H$ (500 MHz, (CD$_3$OD): 7.94 (1H, d), 7.68-7.66 (1H, m), 7.17-7.14 (4H, m), 7.07-7.04 (5H, m), 4.46 (1H, d), 4.13 (1H, d), 3.59-3.55 (3H, m), 3.18-3.15 (1H, m), 2.68-2.60 (2H, m), 2.12-2.04 (1H, m), 1.86-1.79 (1H, m), 1.47 (6H, s), 1.44-1.39 (1H, m).

Examples 41 and 42: (3R)-2-[(4-chloro-2-methanesulfonylphenyl)methyl]-3-(4-chlorophenyl)-4-fluoro-6-[1-hydroxy-1-(oxan-4-yl)ethyl]-3-{[1-(hydroxymethyl)cyclopropyl]methoxy}-2,3-dihydro-1H-isoindol-1-one (*Both Isomers at the Position Shown)

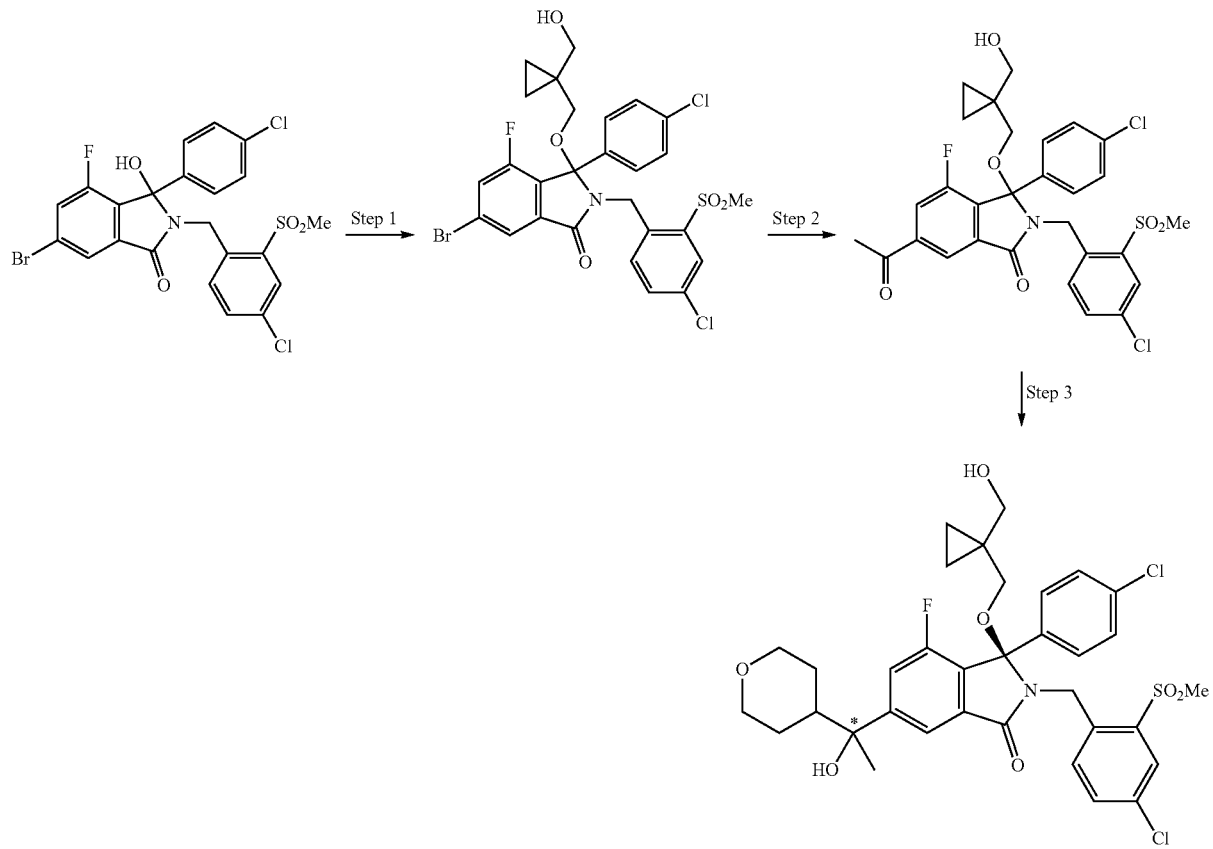 [SMILES: CS(=O)(=O)c1cc(Cl)ccc1CN1C(=O)c2cc(Br)cc(F)c2C1(O)c1ccc(Cl)cc1 ; CS(=O)(=O)c1cc(Cl)ccc1CN1C(=O)c2cc(Br)cc(F)c2C1(OCC1(CO)CC1)c1ccc(Cl)cc1 ; CC(=O)c1cc(F)c2c(c1)C(=O)N(Cc1ccc(Cl)cc1S(C)(=O)=O)C2(OCC1(CO)CC1)c1ccc(Cl)cc1 ; CC(O)(c1cc(F)c2c(c1)C(=O)N(Cc1ccc(Cl)cc1S(C)(=O)=O)[C@@]2(OCC1(CO)CC1)c1ccc(Cl)cc1)C1CCOCC1]

Step 1: 6-Bromo-2-(4-chloro-2-(methylsulfonyl)benzyl)-3-(4-chlorophenyl)-4-fluoro-3-((1-(hydroxymethyl)cyclopropyl)methoxy)isoindolin-1-one Thionyl chloride (3 mL, 42.2 mmol) was added dropwise to a solution of 6-bromo-2-(4-chloro-2-(methylsulfonyl)benzyl)-3-(4-chlorophenyl)-4-fluoro-3-hydroxyisoindolin-1-one (Example 35, Step 4) (4.72 g, 8.44 mmol) in THF (50 mL) at 0° C. under a nitrogen atmosphere. DMF (20 drops) were added and the orange solution was allowed to warm to rt over 1 d. The reaction mixture was concentrated in vacuo and dissolved in THF (40 mL). Cyclopropane-1,1-diyldimethanol (1.72 g, 16.9 mmol) was added followed by K$_2$CO$_3$ (2.33 g, 16.9 mmol) and the orange mixture was stirred at rt under an atmosphere of nitrogen for 1 d. DCM and water were added and the layers separated. The aqueous layer was extracted with DCM and the combined organic layers were dried (phase separator) and concentrated in vacuo. The residue was purified by Biotage (30-35% EtOAc in isohexanes) to give the title compound (3.33 g, 61%) as a pale yellow solid.

¹H NMR (400 MHz, DMSO) 8.01 (1H, d), 7.95 (1H, dd), 7.79 (1H, d), 7.56 (1H, dd), 7.36 (2H, d), 7.30-7.26 (3H, m), 5.01-4.90 (2H, m), 4.45 (1H, t), 3.48-3.31 (2H, m), 3.29 (3H, s), 3.05-2.96 (2H, m), 0.42-0.40 (2H, m), 0.27 (1H, d), 0.19 (1H, dd).

Step 2: 6-Acetyl-2-(4-chloro-2-(methylsulfonyl)benzyl)-3-(4-chlorophenyl)-4-fluoro-3-((1-(hydroxymethyl)cyclopropyl)methoxy)isoindolin-1-one The title compound was prepared in a similar manner to that described in Example 21 Step 3, using 6-bromo-2-(4-chloro-2-(methylsulfonyl)benzyl)-3-(4-chlorophenyl)-4-fluoro-3-((1-(hydroxymethyl)cyclopropyl)methoxy)isoindolin-1-one.

¹H NMR (400 MHz, DMSO) 8.30 (1H, d), 8.06 (1H, d), 7.80 (1H, d), 7.58 (1H, dd), 7.38-7.28 (5H, m), 5.04-4.94

(2H, m), 3.48-3.30 (2H, m), 3.30 (3H, s), 3.06-2.98 (2H, m), 2.75 (3H, s), 0.41 (2H, dd), 0.28-0.25 (1H, m), 0.16 (1H, d).

Step 3: (3R)-2-[(4-chloro-2-methanesulfonylphenyl)methyl]-3-(4-chlorophenyl)-4-fluoro-6-[1-hydroxy-1-(oxan-4-yl)ethyl]-3-{[1-(hydroxymethyl)cyclopropyl]methoxy}-2,3-dihydro-1H-isoindol-1-one LaCl$_3$.2LiCl (0.6 M in THF, 1.93 mL, 1.16 mmol) was added to a solution of 6-acetyl-2-(4-chloro-2-(methylsulfonyl)benzyl)-3-(4-chlorophenyl)-4-fluoro-3-((1-(hydroxymethyl)cyclopropyl)methoxy)isoindolin-1-one (703 mg, 1.16 mmol) in THF (7 mL) under at atmosphere of nitrogen and the yellow solution stirred at rt for 50 min and cooled to 0° C. (Tetrahydro-2H-pyran-4-yl)magnesium chloride (Novel Compound Solutions, 0.5 M in 2-Me-THF, 23.2 mL, 11.6 mmol) was added slowly and the cool bath was removed.

Example 42, Diastereoisomer 2:
$^1$H NMR (400 MHz, CDCl3) 7.91 (1H, d), 7.72 (1H, s), 7.43 (1H, d), 7.36 (1H, dd), 7.31-7.17 (5H, m), 5.07-4.96 (2H, m), 4.07-3.93 (2H, m), 3.81 (1H, dd), 3.40-3.22 (4H, m), 3.03 (3H, s), 2.77 (1H, d), 2.01 (1H, s), 1.86-1.80 (2H, m), 1.62 (3H, s), 1.52-1.39 (2H, m), 1.31-1.25 (2H, m), 0.51 (2H, s), 0.49-0.40 (1H, m), 0.22 (1H, d). MS(ES+) m/z 692 [M+H]$^+$ Examples 43 and 44: (3R)-2-[(4-chloro-2-methanesulfonylphenyl)methyl]-3-(4-chlorophenyl)-4-fluoro-6-[2-hydroxy-1-(piperazin-1-yl)propan-2-yl]-3-{[1-(hydroxymethyl)cyclopropyl]methoxy}-2,3-dihydro-1H-isoindol-1-one (*Both Isomers at the Position Shown)

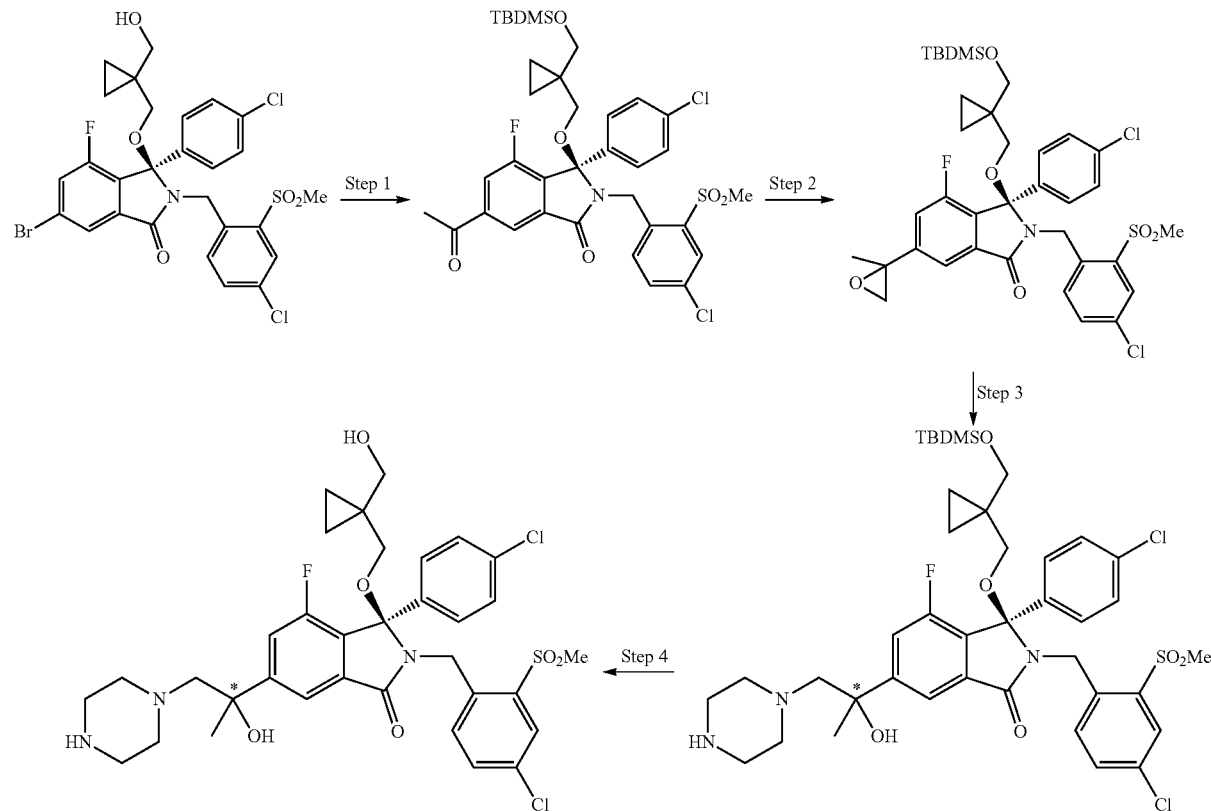

The red solution was allowed to warm to rt over 30 min and quenched with saturated aqueous NH$_4$Cl solution. DCM and water were added and the layers separated. The aqueous layer was extracted with DCM and the combined organic layers were washed with brine, dried (phase separator) and concentrated in vacuo. The residue was purified by Biotage (65-100% EtOAc in iso-hexanes) and submitted for chiral purification by SFC.

Example 41, Diastereoisomer 1:
$^1$H NMR (400 MHz, CDCl3) 7.91 (1H, d), 7.76 (1H, d), 7.40-7.33 (2H, m), 7.30-7.27 (2H, m), 7.24-7.17 (3H, m), 5.06-4.96 (2H, m), 4.07-3.93 (2H, m), 3.80 (1H, dd), 3.42-3.23 (4H, m), 3.04 (3H, s), 2.80 (1H, d), 2.00 (1H, dd), 1.91-1.82 (1H, m), 1.79 (1H, s), 1.61 (3H, s), 1.53-1.40 (2H, m), 1.29-1.22 (2H, m), 0.51 (2H, s), 0.49-0.39 (1H, m), 0.22 (1H, d). MS(ES+) m/z 692 [M+H]$^+$ Step 1
The product from Example 41, Step 1 was purified by preparative chiral HPLC to provide (3R)-6-bromo-2-[(4-chloro-2-methanesulfonylphenyl)methyl]-3-(4-chlorophenyl)-4-fluoro-3-{[1-(hydroxymethyl)cyclopropyl]methoxy}-2,3-dihydro-1H-isoindol-1-one as a single enantiomer. TBDMS protection (following a procedure similar to Preparation 11) gave (R)-6-acetyl-3-((1-(((tert-butyldimethylsilyl)oxy)methyl)cyclopropyl)methoxy)-2-(4-chloro-2-(methylsulfonyl)benzyl)-3-(4-chlorophenyl)-4-fluoroisoindolin-1-one.

Step 2:
60% Sodium Hydride dispersed in mineral oil (0.132 g; 3.44 mmol) was added portionwise over 10 minutes to a stirred solution of (R)-6-acetyl-3-((1-(((tert-butyldimethylsilyl)oxy)methyl)cyclopropyl)methoxy)-2-(4-chloro-2-(methylsulfonyl)benzyl)-3-(4-chlorophenyl)-4-fluoroisoindolin-1-one (1.56 g; 2.17 mmol) and trimethylsulfoxonium iodide (0.533 g; 2.42 mmol) in anhydrous DMSO (9 mL) and anhydrous THF (9 mL), at room temperature, under nitrogen. After 20 hours, water (400 mL) was added, the mixture extracted with EtOAc (2×250 mL) and the combined organics dried (MgSO$_4$) and evaporated under reduced pressure. The residue was purified by chromatography on silica gel (100 g) eluting with 0-50% EtOAc in isohexane gradient to afford 3-((1-(((tert-butyldimethylsilyl)oxy)methyl)cyclopropyl)methoxy)-2-(4-chloro-2-(methylsulfonyl)benzyl)-3-(4-chlorophenyl)-4-fluoro-6-(2-methyloxiran-2-yl)isoindolin-1-one as a pale yellow foam (0.736 g, 46%). 1H NMR (400 MHz, CDCl$_3$): 7.90 (1H, d), 7.77 (1H, d), 7.40-7.27 (2H, m), 7.25-7.20 (2H, m), 7.22-7.10 (3H, m), 5.10-4.85 (2H, m), 3.85-3.70 (1H, m), 3.35-3.20 (2H, m), 3.10-3.00 (1H, m), 2.97 (3H, s), 2.80-2.60 (2H, m), 1.55 (3H, s), 0.82 (9H, s), 0.50-0.35 (2H, m), 0.25-0.05 (2H, m), 0.01 (6H, s).

Step 3 and 4:

Step 3 was performed by following procedures similar to those described in Preparation 34 (but using piperazine instead of dimethylamine). Step 4 was performed by following procedures similar to those described for Example 10. Chiral separation using supercritical fluid chromatography gave Example 43 (the faster running isomer) (74 mg, 30%). 1H NMR (400 MHz, CDCl$_3$): 7.90 (1H, d), 7.77 (1H, d), 7.46 (1H, dd), 7.40-7.30 (1H, m), 7.30-7.10 (5H, m), 5.10-4.98 (2H, m), 3.82 (1H, d), 3.40-3.30 (1H, m), 3.30-3.20 (1H, m), 3.03 (3H, s), 2.85-2.65 (7H, m), 2.55-2.45 (2H, m), 2.38-2.25 (2H, m), 2.20-1.65 (3H, m), 1.51 (3H, s), 0.55-0.45 (2H, m), 0.45-0.35 (1H, m), 0.30-0.15 (1H, m). MS(ES+) m/z 706 [M+H]$^+$.

Example 44 (the slower running isomer) (76 mg, 31%). 1H NMR (400 MHz, CDCl$_3$): 7.90 (1H, d), 7.75 (1H, d), 7.48 (1H, dd), 7.40-7.30 (1H, m), 7.30-7.10 (5H, m), 5.10-4.90 (2H, m), 3.82 (1H, d), 3.40-3.30 (1H, m), 3.30-3.20 (1H, m), 3.03 (3H, s), 2.85-2.65 (7H, m), 2.55-2.45 (2H, m), 2.38-2.25 (2H, m), 2.20-1.65 (3H, m), 1.51 (3H, s), 0.55-0.45 (2H, m), 0.45-0.35 (1H, m), 0.30-0.15 (1H, m). MS(ES+) m/z 706 [M+H]$^+$.

Examples 45 and 46: (3R)-3-(4-Chlorophenyl)-2-[(1S)-1-(4-chlorophenyl)ethyl]-3-{[(3S,4R)-4-hydroxyoxolan-3-yl]oxy}-6-(2-hydroxypropan-2-yl)-2,3-dihydro-1H-isoindol-1-one and (3R)-3-(4-chlorophenyl)-2-[(1S)-1-(4-chlorophenyl)ethyl]-3-{[(3R,4S)-4-hydroxyoxolan-3-yl]oxy}-6-(2-hydroxypropan-2-yl)-2,3-dihydro-1H-isoindol-1-one

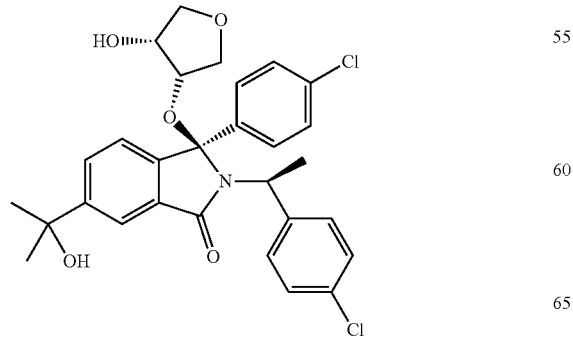

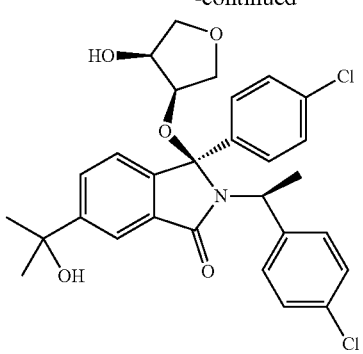

Examples 45 and 46, Step 1

3-(4-Chlorophenyl)-2-[(1S)-1-(4-chlorophenyl)ethyl]-3-[(4-hydroxyoxolan-3-yl)oxy]-6-(prop-1-en-2-yl)-2,3-dihydro-1H-isoindol-1-one

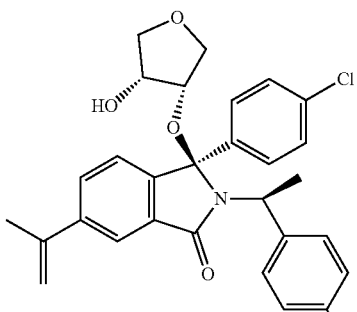

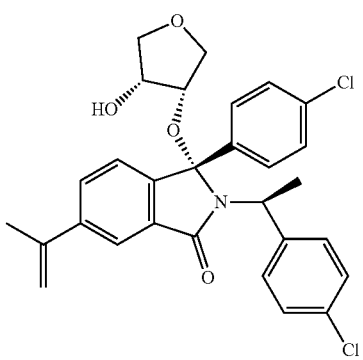

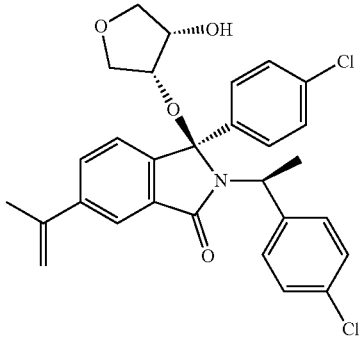

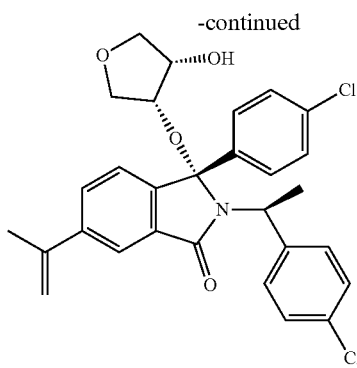

The title compound (as a mixture for 4 isomers) was prepared using a similar procedure as describe for Preparation 10, using 1,4-anhydroerythritol and Preparation 13 The crude material was purified using chromatography on silica (Pet:EtOAc 1:0 to 1:2) to give the desired products as foamy colourless oil. The product (a mixture of 4 isomers) was used directly in the next step.

Example 45 and Example 46, Step 2

Example 45 and Example 46 were prepared using similar procedure to that described for Example 2. The desired products were isolated was using chromatography on silica (Pet:EtOAc 2:1 to 0:1).

Example 45 (isomer 1): $R_f$=0.25 (Pet:EtOAc/1:2). $^1$H NMR (500 MHz, CDCl$_3$) δ (ppm) 1.61 (s, 3H, C(CH$_3$)$_2$), 1.62 (s, 3H, C(CH$_3$)$_2$), 1.85 (s, 1H, C(CH$_3$)$_2$OH), 1.91 (d, 3H, J=7.3 Hz, NCHCH$_3$), 2.49 (d, 1H, J=3.6 Hz, CHOH), 3.27-3.37 (m, 1H, H-b), 3.67 (dd, 1H, J=10.4, 4.0 Hz, H-a), 3.83 (dd, 1H, J=10.3, 1.2 Hz, H'-a), 3.87-4.01 (m, 3H, H-d, H'-d, H-c), 4.28 (q, 1H, J=7.3 Hz, NCH), 6.94 (d, 2H, J=8.5 Hz, Ar—H), 6.97-7.09 (m, 6H, Ar—H); 7.20 (d, 1H, J=8.0 Hz, isoindolinone-H), 7.73 (d, 1H, J=7.9, 1.5 Hz, isoindolinone-H), 7.98 (d, 1H, J=1.3 Hz, isoindolinone-H); MS(ES+) m/z 484.3 [M+H]$^+$;

Example 46 (isomer 2): $R_f$=0.57 (Pet:EtOAc/1:2); $^1$H NMR (500 MHz, CDCl$_3$) δ (ppm) 1.61 (s, 6H, C(CH$_3$)$_2$), 1.74 (d, 3H, J=7.2 Hz, NCHCH$_3$), 1.82 (s, 1H, C(CH$_3$)$_2$OH), 2.06 (s, 1H, CHOH), 2.63-2.68 (m, 1H, H-b), 2.71 (dd, 1H, J=8.5, 7.3 Hz, H-d), 3.28 (dd, 1H, J=8.5, 8.4 Hz, H'-d), 3.42 (dd, 1H, J=10.3, 4.1 Hz, H-a), 3.44-3.49 (m, 1H, H-c), 3.53 (dd, 1H, J=10.4, 1.5 Hz, H'-a), 4.19 (q, 1H, J=7.3 Hz, NCH), 6.97 (d, 1H, J=8.0 Hz, isoindolinone-H), 7.28 (d, 2H, J=8.4 Hz, Ar—H), 7.31-7.44 (m, 4H, Ar—H), 7.57 (d, 2H, J=8.4 Hz, Ar—H), 7.68 (dd, 1H, J=7.9, 1.6 Hz, isoindolinone-H), 7.98 (d, 1H, J=1.3 Hz, isoindolinone-H); MS(ES+) m/z 484.3 [M+H]$^+$;

Example 47: (3R)-3-(4-Chlorophenyl)-2-[(4-chlorophenyl)methyl]-6-(2-hydroxypropan-2-yl)-3-methoxy-2,3-dihydro-1H-isoindol-1-one

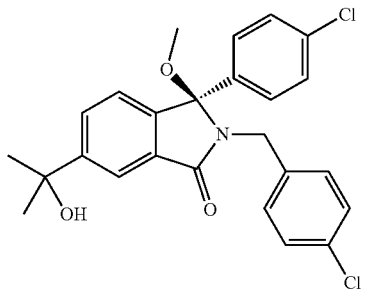 [SMILES: CO[C@]1(c2ccc(Cl)cc2)c2ccc(C(C)(C)O)cc2C(=O)N1Cc1ccc(Cl)cc1]

Starting from Preparation 8 the title compound was prepared using (subsequently) processes similar to those described in Preparation 12; Example 21, step 3 and Example 1. $^1$H-NMR Spectrum: (in CDCl$_3$) δ (ppm) 1.61 (s, 6H, C(CH$_3$)$_2$), 2.12 (s, 1H, OH), 2.62 (s, 3H, OCH$_3$), 4.07 (d, 1H, J=14.8 Hz, NCHH), 4.58 (d, 1H, J=14.8 Hz, NCHH), 7.06 (d, 1H, J=8.0 Hz, Ar—H), 7.12-7.17 (m, 2H, Ar—H), 7.15-7.25 (m, 6H, Ar—H), 7.69 (dd, 1H, J=8.0, 1.7 Hz, Ar—H), 8.00 (d, 1H, J=1.6 Hz, Ar—H. ms (M-H$^+$) m/z=456.4.

Example 48: (3R)-3-(4-Chlorophenyl)-2-[(4-chlorophenyl)methyl]-3-({1-[hydroxy($^2$H$_2$)methyl]cyclopropyl}($^2$H$_2$)methoxy)-6-(2-hydroxypropan-2-yl)-2,3-dihydro-1H-isoindol-1-one

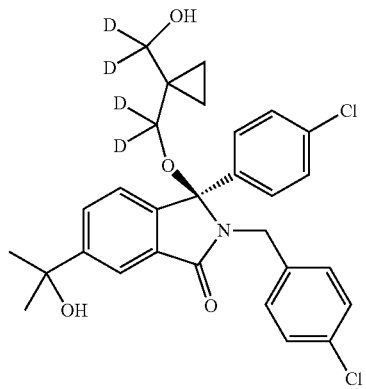 [SMILES: [2H]C([2H])(O)C1(C([2H])([2H])O[C@]2(c3ccc(Cl)cc3)c3ccc(C(C)(C)O)cc3C(=O)N2Cc2ccc(Cl)cc2)CC1]

The title compound was prepared using procedures similar to those described for Example 1. $^1$H NMR (500 MHz; CDCl$_3$) $|_H$ 0.10-0.18 (2H, m, 2×H-cyclopropyl), 0.38-0.44 (2H, m, 2×H-cyclopropyl), 1.52 (1H, br s, OH), 1.61 (3H, s, CH$_3$), 1.63 (3H, s, CH$_3$), 1.75 (1H, br s, OH), 4.18 (1H, d, J=15.0 Hz, CH$_a$H$_b$Ph), 4.55 (1H, d, J=15.0 Hz, CH$_a$H$_b$Ph), 7.10 (1H, d, J=8.0 Hz, H-4), 7.12-7.23 (8H, m, H—Ar), 7.72 (1H, dd, J=1.7 and 8.0 Hz, H-5), 7.99 (1H, d, J=1.7 Hz, H-7). LCMS (ES+) m/z 424.3, 426.3 [(M-c3 sidechain)+H]$^+$ Example 49: (3R)-3-(4-Chlorophenyl)-2-[(4-chlorophenyl)methyl]-6-(2-hydroxypropan-2-yl)-3-(3-hydroxypropoxy)-2,3-dihydro-1H-isoindol-1-one

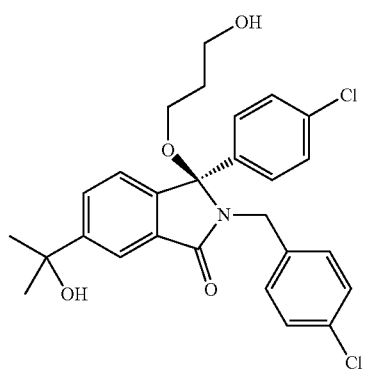 [SMILES: CC(C)(O)c1ccc2c(c1)C(=O)N(Cc1ccc(Cl)cc1)[C@@]2(OCCCO)c1ccc(Cl)cc1]

The title compound was prepared using procedures similar to those described for Example 1. 1H-NMR Spectrum:

δ$_H$ (500 MHz, CDCl3) 1.40-1.55 (2H, m, CH$_2$CH$_2$CH$_2$OH), 1.60-1.64 (6H, m, 2×CH$_3$), 2.79-2.85 (1H, m, CH$_2$CH$_2$CH$_2$OH), 2.85-2.93 (1H, m, CH$_2$CH$_2$CH$_2$OH), 3.57 (2H, t, J=6.1 Hz, CH$_2$CH$_2$CH$_2$OH), 4.05 (1H, d, J=14.8 Hz, NC—H), 4.65 (1H, d, J=14.9 Hz, NC—H'), 7.08 (1H, d, J=7.9 Hz, ArH), 7.14-7.25 (8H, m, 8×ArH), 7.70 (1H, dd, J=1.7 and 7.9 Hz, ArH) and 7.99 (1H, d, J=1.2 Hz, 7-H); (ES+) m/z 424.3 [M-O(CH-2)$_{30}$H]+

Example 50: (3R)-2-[(4-chloro-2-methanesulfonyl-phenyl)methyl]-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one

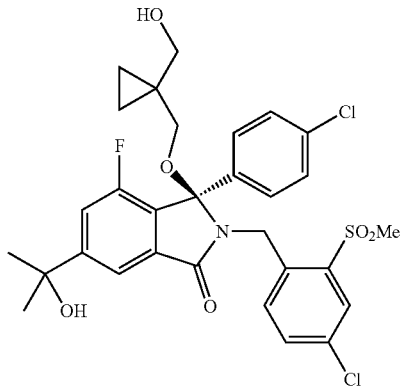 [SMILES: CC(C)(O)c1cc(F)c2c(c1)C(=O)N(Cc1ccc(Cl)cc1S(C)(=O)=O)[C@@]2(OCC1(CO)CC1)c1ccc(Cl)cc1]

The title compound was prepared using procedures similar to those described for Example 36. 1H-NMR Spectrum: δ$_H$ (500 MHz, CDCl3) 0.17-0.25 (1H, m, Cy-Py-H), 0.38-0.42 (1H, m, Cy-Py-H), 0.46-0.53 (2H, m, Cy-Py-H2), 1.60-1.64 (6H, 2×s, 2×CH$_3$), 2.77 (1H, d, J=9.1 Hz, 2'-H), 3.03 (3H, s, SO2CH3), 3.25 (1H, J=9.1 Hz, 2'-H'), 3.36 (1H, d, J=11.2 Hz, 4'-H), 3.81 (1H, d, J=11.1 Hz, 4'-H'), 4.94-5.04 (2H, m, NC—H, NC—H'), 7.14-7.21 (3H, m, 3×ArH), 7.25-7.29 (2H, m, 2×ArH), 7.32 (1H, dd, J=2.3 and 8.4 Hz, ArH), 7.45 (1H, dd, J=1.3 and 10.8 Hz, ArH), 7.81 (1H, d, J=1.4 Hz, ArH) and 7.89 (1H, d, J=2.3, 7-H). (ES+) m/z 520.3 [M-C5H9O2]+

Example 51: (3R)-3-(4-Chlorophenyl)-2-[(4-chlorophenyl)methyl]-3-(2,2-difluoro-3-hydroxypropoxy)-6-(2-hydroxypropan-2-yl)-2,3-dihydro-1H-isoindol-1-one

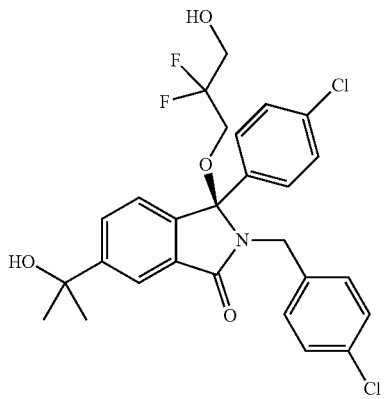 [SMILES: CC(C)(O)c1ccc2c(c1)C(=O)N(Cc1ccc(Cl)cc1)[C@@]2(OCC(F)(F)CO)c1ccc(Cl)cc1]

Starting from Preparation 20 and difluoroprpoanediol, the title compound was prepared by following procedures similar to those described in Preparation 12 and Example 1. 1H-NMR Spectrum: δ$_H$ (500 MHz, CDCl3) 1.55 (3H, s, CH$_3$), 1.56 (3H, s, CH$_3$), 2.93-3.02 (2H, m, CH$_2$), 3.63-3.78 (2H, m, CH$_2$), 4.19 (1H, d, J=15.0 Hz, NCHH'), 4.45 (1H, d, J=15.0 Hz, NCHH'), 7.04-7.11 (7H, m, 7×ArH), 7.13-7.15 (2H, m, 2×ArH), 7.67 (1H, dd, J=1.7 and 8.0 Hz, ArH), 7.94 (1H, d, J=1.7 Hz, ArH). m/z 536.4 [M+H]+

Examples 52 and 53: (3R)-3-(4-Chlorophenyl)-2-[(4-chlorophenyl)methyl]-3-{[2-(hydroxymethyl)cyclobutyl]methoxy}-6-(2-hydroxypropan-2-yl)-2,3-dihydro-1H-isoindol-1-one (Both Isomers as Shown)

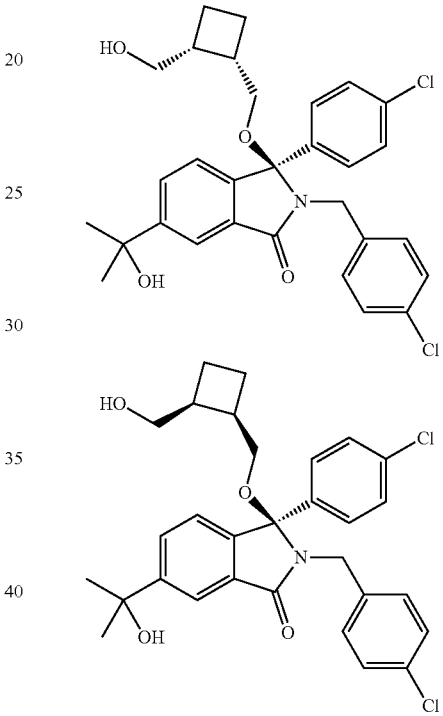

Example 52 and 53, Step 1: (2-Hydroxymethyl-cyclobutyl)-methanol

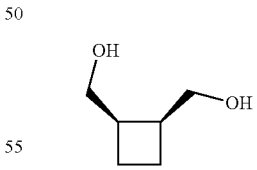

A suspension of cyclobutane dicarboxylic acid (649 mg, 4.50 mmol) in tetrahydrofuran (45 mL) was cooled to 0° C. and treated with lithium aluminium hydride (1M in THF, 18.0 mL, 18.01 mmol) and stirred for 3 hours. Once complete by TLC (SiO2; 30% MeOH in DCM) the reaction was diluted with diethyl ether (45 mL) and treated sequentially with water (0.68 mL), sodium hydroxide (15% aq., 0.68 mL) and water (2.1 mL) then stirred for 30 minutes. Sodium sulphate was added and the solution mixture stirred for a further 30 minutes. Once filtered the organic layer was concentrated in vacuo to yield the title compound (305 mg, 58%) as a colourless oil that was used without the need for further purification.

Example 52 and 53, Step 2

Starting from (2-hydroxymethyl-cyclobutyl)-methanol, Example 52 and 53 were made in a similar manner to Example 1. The two desired isomers were isolated by preparative chiral HPLC.

Example 52 (isomer 1): $\delta_H$ (500 MHz, (CD$_3$OD): 8.05 (1H, d), 7.79 (1H, dd), 7.25-7.21 (4H, m), 7.19-7.14 (5H, m), 4.52 (1H, d), 4.33 (1H, d), 3.54-3.49 (1H, m), 3.44-3.40 (1H, m), 3.06-3.03 (1H, m), 2.91-2.87 (1H, m), 2.53-2.49 (1H, m), 2.37-2.35 (1H, m), 2.04-1.96 (2H, m), 1.73-1.63 (2H, m), 1.59 (6H, s).

Example 53 (isomer 2): $\delta_H$ (500 MHz, (CD$_3$OD): 8.06 (1H, d), 7.79 (1H, dd), 7.25-7.21 (4H, m), 7.19-7.14 (5H, m), 4.52 (1H, d), 4.33 (1H, d), 3.54-3.49 (1H, m), 3.44-3.40 (1H, m), 3.06-3.03 (1H, m), 2.91-2.87 (1H, m), 2.53-2.48 (1H, m), 2.39-2.35 (1H, m), 2.04-1.96 (2H, m), 1.72-1.63 (2H, m), 1.59 (6H, s).

Examples 54 and 55: (3R)-3-(4-chlorophenyl)-2-[(4-chlorophenyl)methyl]-6-[2-hydroxy-1-oxo-1-(pyrrolidin-1-yl)propan-2-yl]-3-{[1-(hydroxymethyl)cyclopropyl]methoxy}-2,3-dihydro-1H-isoindol-1-one (*Both Isomers at the Position Shown)

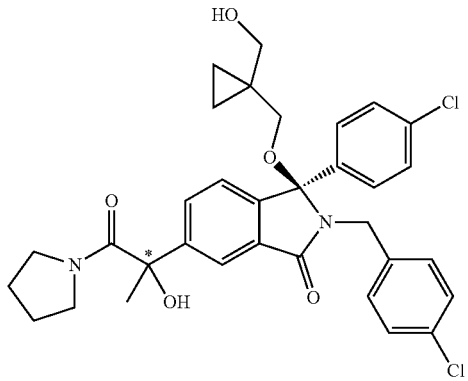 [SMILES: CC(O)(C(=O)N1CCCC1)c1ccc2c(c1)C(=O)N(Cc1ccc(Cl)cc1)[C@@]2(OCC1(CO)CC1)c1ccc(Cl)cc1]

Example 54 and Example 55, Step 1: (R)-3-((1-(((tert-Butyldimethylsilyl)oxy)methyl)cyclopropyl)methoxy)-2-(4-chlorobenzyl)-3-(4-chlorophenyl)-6-(prop-1-en-2-yl)isoindolin-1-one

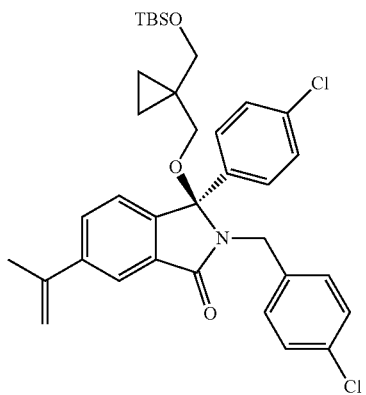 [SMILES: C=C(C)c1ccc2c(c1)C(=O)N(Cc1ccc(Cl)cc1)[C@@]2(OCC1(CO[Si](C)(C)C(C)(C)C)CC1)c1ccc(Cl)cc1]

TBSCl (2.62 g, 17.4 mmol, 1.5 eq.), imidazole (1.19 g, 1.5 eq.) and 2-(4-chlorobenzyl)-3-(4-chlorophenyl)-3-((1-(hydroxymethyl)cyclopropyl) methoxy)-6-(prop-1-en-2-yl)isoindolin-1-one (R-isomer) (5.9 g, 11.6 mmol, 1 eq,) were dissolved in THF (100 mL) and heated to 50° C. for 6 h. Allowed to cool to r.t., and partitioned between EtOAc (2×70 mL) and H$_2$O (70 mL). Organic extracts were combined, dried over MgSO$_4$, and solvent removed in vacuo. The residue was purified by MPLC (1-5% EtOAc/petrol) to give a clear oil (6.045 g, 84%); $^1$H NMR (500 MHz; CDCl$_3$) $\delta$ -0.02 (3H, s, CH$_3$Si), 0.00 (3H, s, CH$_3$Si), 0.07-0.12 (2H, m, cPr), 0.33-0.38 (2H, m, cPr), 0.83 (9H, s, tBu), 1.27 (3H, s, Me), 2.16-2.19 (2H, brs), 2.62 (1H, d, CH$_a$H$_b$O), 2.89 (1H, d, CH$_a$H$_b$O), 3.36 (1H, d, CH$_a$H$_b$O), 3.65 (1H, d, CH$_a$H$_b$O), 4.32 (1H, d, CH$_a$H$_b$N), 4.39 (1H, d, CH$_a$H$_b$N)), 5.18 (1H, m, H-alkene), 5.44 (1H, m, H-alkene), 7.01-7.22 (9H, m, H—Ar), 7.58 (1H, dd, H-5), 7.96 (1H, d, H-7).

Example 54 and Example 55, Step 2

(3R)-3-((1-(((tert-Butyldimethylsilyl)oxy)methyl)cyclopropyl)methoxy)-2-(4-chlorobenzyl)-3-(4-chlorophenyl)-6-(1,2-dihydroxypropan-2-yl)isoindolin-1-one

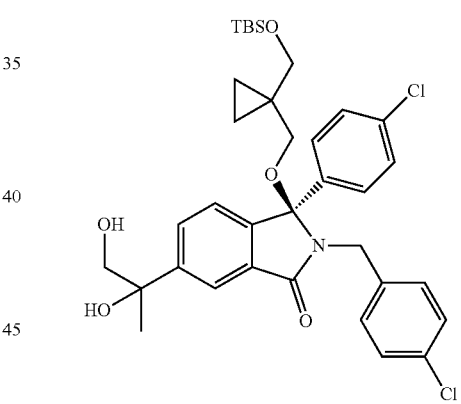

The title compound was prepared using procedures similar to those described for Example 27, giving product as a mixture of 2 diastereoisomers). $^1$H NMR (500 MHz; CDCl$_3$) $\delta$ -0.02 (3H, s, CH$_3$Si), 0.00 (3H, s, CH$_3$Si), 0.07-0.13 (2H, m, cPr), 0.33-0.39 (2H, m, cPr), 0.83 (9H, s, tBu), 1.56 (3H, s, Me), 1.82 (1H, br s, OH), 2.60 (1H, d, CH$_a$H$_b$O), 2.64 (1H, br s, OH), 2.88 (1H, d, CH$_a$H$_b$O), 3.36 (1H, d, CH$_a$H$_b$O), 3.62-3.74 (2H, m, CH$_a$H$_b$O and CH$_a$H$_b$OH), 3.81 (1H, d, CH$_a$H$_b$OH), 4.31 (1H, d, CH$_a$H$_b$N), 4.40 (1H, d, CH$_a$H$_b$N)), 7.03-7.13 (5H, m, H—Ar), 7.13-7.20 (4H, m, H—Ar), 7.67 (1H, dd, H-5), 7.94 (1H, d, J=1.5 Hz, H-7); MS ES+ 440.3, 442.3 [M-sidechain]$^+$.

Example 54 and Example 55, Step 3

2-((R)-1-((1-(((tert-Butyldimethylsilyl)oxy)methyl)cyclopropyl)methoxy)-2-(4-chlorobenzyl)-1-(4-chlorophenyl)-3-oxoisoindolin-5-yl)-2-hydroxypropanoic acid

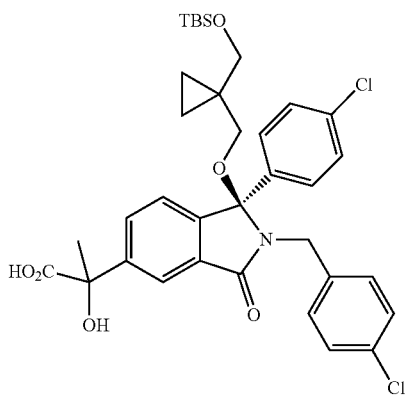 [SMILES: CC(O)(C(=O)O)c1ccc2c(c1)C(=O)N(Cc1ccc(Cl)cc1)[C@@]2(OCC1(CO[Si](C)(C)C(C)(C)C)CC1)c1ccc(Cl)cc1]

TEMPO (161 mg, 1.03 mmol, 0.25 eq.), NaClO$_2$ (744 mg, 8.22 mmol, 2 eq.) and NaOCl (30 µL, 0.08 mmol, 0.02 eq.) were added to (3R)-3-((1-(((tert-butyldimethylsilyl)oxy)methyl)cyclopropyl)methoxy)-2-(4-chlorobenzyl)-3-(4-chlorophenyl)-6-(1,2-dihydroxypropan-2-yl)isoindolin-1-one (2.7 g, 4.11 mmol, 1 eq.) in a mixture of MeCN (20 mL) and sodium phosphate buffer (pH 6.5, 16 mL), and the mixture was stirred at r.t. for 5 days. Water was added, and the pH adjusted to pH 8 with NaOH (1 M aq.). Na$_2$SO$_3$ (aq) was added, and the pH adjusted to pH 2 with HCl (1 M aq). The mixture was extracted with EtOAc (2×50 mL), dried over MgSO$_4$, and the solvent was removed in vacuo. Purification by MPLC on silica with a gradient from 0-10% MeOH/DCM gave a white foam (2.27 g, 83%, ca. 3:1 mixture of diastereoisomers); Major diastereoisomer: $^1$H NMR (500 MHz; CDCl$_3$) δ 0.00 (3H, s, CH$_3$Si), 0.02 (3H, s, CH$_3$Si), 0.10-0.17 (2H, m, cPr), 0.35-0.42 (2H, m, cPr), 0.85 (9H, s, tBu), 1.94 (3H, s, Me), 2.65 (1H, d, CH$_a$H$_b$O), 2.90 (1H, d, CH$_a$H$_b$O), 3.39 (1H, d, CH$_a$H$_b$O), 3.65 (1H, m, CH$_a$H$_b$O), 3.81 (1H, d, CH$_a$H$_b$OH), 4.35 (1H, d, CH$_a$H$_b$N), 4.41 (1H, d, CH$_a$H$_b$N)), 7.00-7.20 (9H, m, H—Ar), 7.96 (1H, dd, H-5), 8.29 (1H, d, H-7); MS ES− 668.3, 670.3 [M−H]$^-$.

Example 54 and Example 55, Step 4

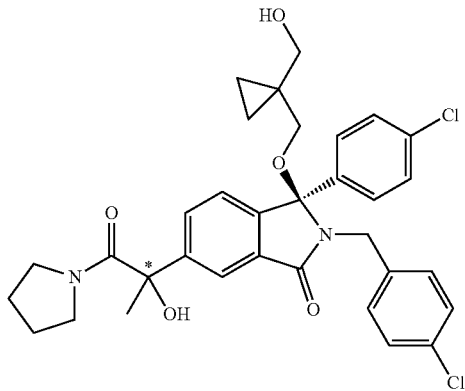 [SMILES: CC(O)(C(=O)N1CCCC1)c1ccc2c(c1)C(=O)N(Cc1ccc(Cl)cc1)[C@@]2(OCC1(CO)CC1)c1ccc(Cl)cc1]

The title compound was prepared from 2-((R)-1-((1-(((tert-butyldimethylsilyl)oxy)methyl)cyclopropyl)methoxy)-2-(4-chlorobenzyl)-1-(4-chlorophenyl)-3-oxoisoindolin-5-yl)-2-hydroxypropanoic acid, using PyBrop and pyrrolidine. Deprotection, using similar procedures to those described for Example 10, followed by preparative HPLC gave the two isomers.

Example 54 (*isomer 1). $^1$H-NMR Spectrum: (500 MHz, CDCl$_3$) δ 0.12-0.18 (2H, m, cyclopropane CH$_2$CH$_2$), 0.40-0.44 (2H, m, cyclopropane CH$_2$CH$_2$), 1.55-1.59 (2H, m, H-pyrrolidine), 1.72-1.77 (3H, m, H-pyrrolidine and OH), 1.85 (3H, s, CH$_3$), 2.56-2.61 (1H, m, H-pyrrolidine), 2.72 (1H, d, J=9.4 Hz, C—O—CHH), 2.76 (1H, d, J=9.4 Hz, C—O—CHH), 3.09-3.14 (1H, m, H-pyrrolidine), 3.39 (1H, d, J=11.4 Hz, CHHOH), 3.47 (1H, d, J=11.4 Hz, CHHOH), 3.51-3.56 (2H, m, H-pyrrolidine), 4.24 (1H, d, J=14.9 Hz, N—CHH), 4.51 (1H, d, J=14.9 Hz, N—CHH), 5.44 (1H, s, OH), 7.11-7.21 (9H, m, H—Ar), 7.51 (1H, d, J=8.0 Hz, H-5), 8.0 (1H, s, H-7). MS (ESI$^+$) m/z=507.4 [M+H]$^+$ Example 55 (*isomer 2): $^1$H-NMR Spectrum: (500 MHz, CDCl$_3$) δ 0.09-0.13 (2H, m, cyclopropane CH$_2$CH$_2$), 0.38-0.43 (2H, m, cyclopropane CH$_2$CH$_2$), 1.51-1.59 (2H, m, H-pyrrolidine), 1.70-1.78 (3H, m, H-pyrrolidine and OH), 1.85 (3H, s, CH$_3$), 2.59-2.66 (2H, m, H-pyrrolidine and C—O—CHH), 2.74 (1H, d, J=9.3 Hz, C—O—CHH), 3.05-3.10 (1H, m, H-pyrrolidine), 3.33 (1H, d, J=11.3 Hz, CHHOH), 3.48 (1H, d, J=11.3 Hz, CHHOH), 3.55-3.58 (2H, m, H-pyrrolidine), 4.17 (1H, d, J=14.8 Hz, N—CHH), 4.54 (1H, d, J=14.8 Hz, N—CHH), 5.38 (1H, s, OH), 7.11-7.22 (9H, m, H—Ar), 7.53 (1H, d, J=8.1 Hz, H-5), 8.0 (1H, s, H-7). MS (ESI$^+$) m/z=507.4 [M+H]$^+$

Examples 56 and 57: 2-[(1R)-1-(4-Chlorophenyl)-2-[(4-chlorophenyl)methyl]-1-{[1-(hydroxymethyl)cyclopropyl]methoxy}-3-oxo-2,3-dihydro-1H-isoindol-5-yl]-2-hydroxy-N,N-dimethylpropanamide (*Both Isomers at the Position Highlighted)

Example 56 and 57, Step 1

2-((R)-1-((1-(((tert-butyldimethylsilyl)oxy)methyl)cyclopropyl)methoxy)-2-(4-chlorobenzyl)-1-(4-chlorophenyl)-3-oxoisoindolin-5-yl)-2-hydroxy-N,N-dimethylpropanamide

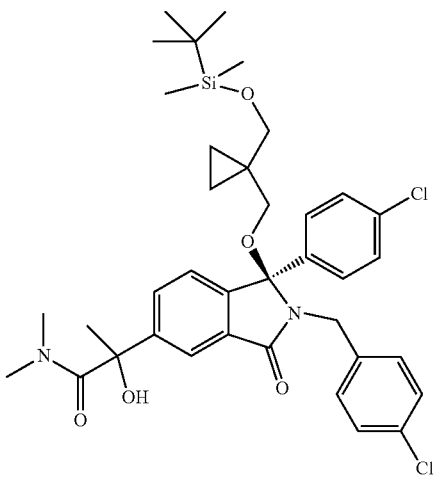 [SMILES: CN(C)C(=O)C(C)(O)c1ccc2c(c1)C(=O)N(Cc1ccc(Cl)cc1)[C@@]2(OCC1(CO[Si](C)(C)C(C)(C)C)CC1)c1ccc(Cl)cc1]

To a solution of 2-((R)-1-((1-(((tert-butyldimethylsilyl)oxy)methyl)cyclopropyl)methoxy)-2-(4-chlorobenzyl)-1-(4-chlorophenyl)-3-oxoisoindolin-5-yl)-2-hydroxypropanoic acid (Example 54 and Example 55, step 3) (400 mg, 0.60 mmol), PyBroP (420 mg, 0.90 mmol) and pyridine (0.05 mL, 0.60 mmol) in MeCN (4 mL) was added dimethylamine solution (2M in MeCN, 0.75 mL, 1.5 mmol) before stirring at room temperature overnight. The reaction was extracted with EtOAc (3×10 mL), the combined organic extracts were washed with water (30 mL) and brine (20 mL), dried by MgSO$_4$ and concentrated in vacuo. Chromatography (silica; EtOAc, petrol 20-90%) gave a white solid (250 mg, 71%). LCMS (ESI$^+$) m/z=719.5 [M+Na]$^+$.

Example 56 and 57, Step 2

2-((1R)-2-(4-Chlorobenzyl)-1-(4-chlorophenyl)-1-((1-(hydroxymethyl)cyclopropyl)methoxy)-3-oxo-2,3-dihydro-1H-isoindol-5-yl)-2-hydroxy-N,N-dimethylpropanamide (*Both Isomers at the Position Highlighted)

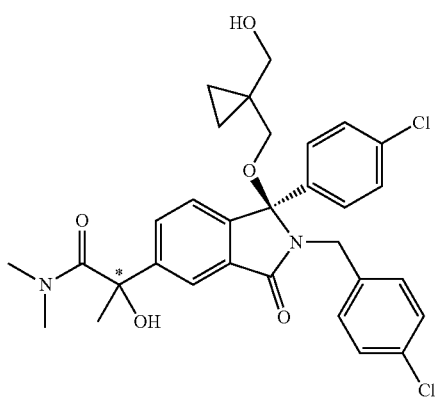 [SMILES: CN(C)C(=O)C(C)(O)c1ccc2c(c1)C(=O)N(Cc1ccc(Cl)cc1)[C@@]2(OCC1(CO)CC1)c1ccc(Cl)cc1]

The title compound was prepared using procedures similar to those described for Example 10. Purification by chiral HPLC gave the title compound:

$^1$H-NMR (500 MHz, CDCl$_3$) δ 0.11-0.15 (2H, m, cyclopropane CH$_2$CH$_2$), 0.39-0.43 (2H, m, cyclopropane CH$_2$CH$_2$), 1.63 (1H, brs, OH), 1.86 (3H, s, CH$_3$), 2.59-2.64 (4H, m, C—O—CHH and N—CH$_3$), 2.80 (1H, d, C—O—CHH), 3.02 (3H, brs, N—CH$_3$), 3.34 (1H, d, CHHOH), 3.50 (1H, d, CHHOH), 4.18 (1H, d, N—CHH), 4.54 (1H, d, N—CHH), 5.39 (1H, s, OH), 7.11-7.18 (7H, m, H—Ar), 7.21 (2H, d, H—Ar), 7.50 (1H, d, H-5), 8.0 (1H, s, H-7). LCMS (ESI$^-$) m/z=627.4 [M+Formate]$^-$.

Example 56 (*isomer 1): $^1$H-NMR Spectrum: (500 MHz, CDCl$_3$) δ 0.12-0.18 (2H, m, cyclopropane CH$_2$CH$_2$), 0.40-0.44 (2H, m, cyclopropane CH$_2$CH$_2$), 1.59 (1H, brs, OH), 1.87 (3H, s, CH$_3$), 2.59 (3H, brs, N—CH$_3$), 2.70 (1H, d, J=9.4 Hz, C—O—CHH), 2.79 (1H, d, J=9.4 Hz, C—O—CHH), 3.00 (3H, brs, N—CH$_3$), 3.38 (1H, d, J=11.4 Hz, CHHOH), 3.48 (1H, d, J=11.4 Hz, CHHOH), 4.24 (1H, d, J=14.8 Hz, N—CHH), 4.51 (1H, d, J=14.8 Hz, N—CHH), 5.44 (1H, s, OH), 7.11-7.17 (7H, m, H—Ar), 7.20 (2H, d, J=8.9 Hz, H—Ar), 7.47 (1H, d, J=8.0 Hz, H-5), 8.0 (1H, s, H-7). MS (ESI$^+$) m/z=481.3 [M+H]$^+$ Example 57 (*isomer 2): $^1$H-NMR Spectrum: (500 MHz, CDCl$_3$) δ 0.11-0.15 (2H, m, cyclopropane CH$_2$CH$_2$), 0.39-0.43 (2H, m, cyclopropane CH$_2$CH$_2$), 1.63 (1H, brs, OH), 1.86 (3H, s, CH$_3$), 2.59-2.64 (4H, m, C—O—CHH and N—CH$_3$), 2.80 (1H, d, J=9.5 Hz, C—O—CHH), 3.02 (3H, brs, N—CH$_3$), 3.34 (1H, d, J=11.3 Hz, CHHOH), 3.50 (1H, d, J=11.3 Hz, CHHOH), 4.18 (1H, d, J=14.8 Hz, N—CHH), 4.54 (1H, d, J=14.8 Hz, N—CHH), 5.39 (1H, s, OH), 7.11-7.18 (7H, m, H—Ar), 7.21 (2H, d, J=8.9 Hz, H—Ar), 7.50 (1H, d, J=8.0 Hz, H-5), 8.0 (1H, s, H-7). MS (ESI$^+$) m/z=481.3 [M+H]$^+$ Examples 58 and 59: 2-[(1R)-1-(4-Chlorophenyl)-2-[(4-chlorophenyl)methyl]-1-{[1-(hydroxymethyl)cyclopropyl]methoxy}-3-oxo-2,3-dihydro-1H-isoindol-5-yl]-2-hydroxy-N-methylpropanamide (*Both Isomers at the Position Highlighted)

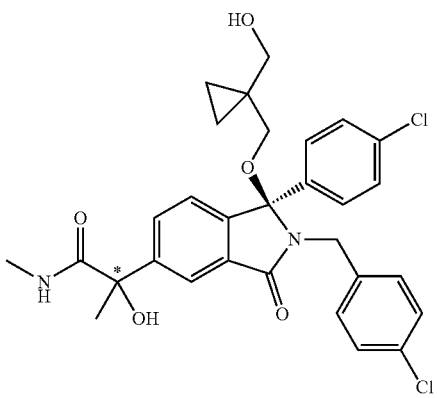 [SMILES: CNC(=O)C(C)(O)c1ccc2c(c1)C(=O)N(Cc1ccc(Cl)cc1)[C@@]2(OCC1(CO)CC1)c1ccc(Cl)cc1]

The title compound was prepared from 2-((R)-1-((1-(((tert-butyldimethylsilyl)oxy)methyl)cyclopropyl)methoxy)-2-(4-chlorobenzyl)-1-(4-chlorophenyl)-3-oxoisoindolin-5-yl)-2-hydroxypropanoic acid, using PyBrop and methylamine. Deprotection, using similar procedures to those described for Example 10, followed by preparative HPLC gave the two isomers.

Example 58 (*isomer 1): $^1$H-NMR: (500 MHz, CDCl$_3$) δ 0.13-0.19 (2H, m), 0.39-0.44 (2H, m), 1.67 (1H, brs), 1.84 (3H, s), 2.66 (1H, d), 2.79 (3H, d), 2.83 (1H, d), 3.36 (1H, d), 3.48 (1H, d), 4.05 (1H, s), 4.21 (1H, d), 4.50 (1H, d), 6.88 (1H, q), 7.08-7.18 (9H, m), 7.82 (1H, d), 8.23 (1H, s). LCMS (ESI$^-$) m/z=567.3 [M–H]$^-$ Example 59 (*isomer 2): $^1$H-NMR: (500 MHz, CDCl$_3$) δ 0.12-0.18 (2H, m), 0.38-0.43 (2H, m), 1.85 (3H, s), 2.63 (1H, d), 2.79 (3H, d), 2.85 (1H, d), 3.34 (1H, d, J=11.4 Hz, CHHOH), 3.50 (1H, d, J=11.4 Hz, CHHOH), 4.19 (1H, d), 4.52 (1H, d), 6.90 (1H, q), 7.09-7.20 (9H, m), 7.81 (1H, d), 8.23 (1H). LCMS (ESI$^-$) m/z=567.3 [M–H]$^-$ Examples 60: (3R)-2-{[4-chloro-2-(methylsulfanyl)phenyl]methyl}-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one

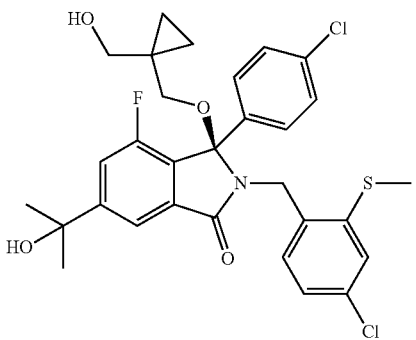 [SMILES: CSc1cc(Cl)ccc1CN1C(=O)c2cc(C(C)(C)O)cc(F)c2[C@]1(OCC1(CO)CC1)c1ccc(Cl)cc1]

Starting from 5-bromo-2-(4-chlorobenzoyl)-3-fluorobenzoic acid and Preparation 43 (4-chloro-2-(methylthio)phenyl)methanamine), the title compound was prepared by following procedures similar to those described in Preparation 9, Preparation 10, Example 21, Step 3 and Example 1; in a sequential manner.

$^1$H NMR (500 MHz, CDCl$_3$) δ7.81 (1H, s, H-7), 7.39 (1H, d5), 7.23 (2H, d, 7.16-7.19 (3H, m), 7.01 (1H, s), 6.96 (1H, d), 4.68 (1H, d), 4.43 (1H, d), 3.49 (1H, q), 3.41 (1H, q), 2.95 (1H, d), 2.89 (1H, d), 2.38 (3H, s), 1.90 (1H, s), 1.71 (1H, t), 1.61 (6H, d), 0.41-0.48 (2H, m), 0.28-0.31 (1H, m), 0.14-0.17 (1H, m). LCMS (ESI$^-$) m/z=634.3 [M+Formate]$^-$ Examples 61 and 62: (3R)-2-[(4-Chloro-2-methanesulfinylphenyl)methyl]-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one (*Both Isomers at Position Highlighted)

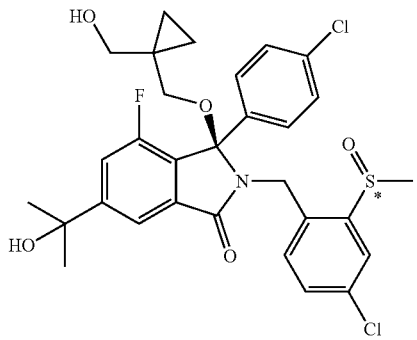 [SMILES: CS(=O)c1cc(Cl)ccc1CN1C(=O)c2cc(C(C)(C)O)cc(F)c2[C@]1(OCC1(CO)CC1)c1ccc(Cl)cc1]

To a solution of (3R)-2-{[4-chloro-2-(methylsulfanyl)phenyl]methyl}-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one (Example 60) (140 mg, 0.24 mmol) in MeOH (3 mL) was added sodium periodate (56 mg, 0.26 mmol) in portions over 3 mins at 0° C. The mixture was stirred overnight, H$_2$O was added, and extracted with EtOAc. The combined organic extracts were washed with brine, dried (MgSO$_4$) and concentrated in vacuo. Chromatography (SP4, silica; MeOH/EtOAc 0-30%) gave the products as white solids (70 mg, 48% and 70 mg, 48%).

Example 61: *fast running isomer: $^1$H NMR (500 MHz, CDCl$_3$) δ 7.85 (1H, d'), 7.81 (1H, d), 7.48 (1H, d), 7.40 (1H, dd), 7.30-7.34 (3H, m), 7.25-7.26 (2H, m), 4.71 (1H, d), 4.28 (1H, d), 3.62 (1H, d), 3.33 (1H, d), 2.82 (1H, d), 2.72 (1H, d), 2.62 (3H, s, CH$_3$), 2.27 (1H, br s), 1.99 (1H, s), 1.62 (3H, s), 1.61 (3H, s), 0.39-0.44 (2H, m), 0.19-0.21 (1H, m), 0.01-0.03 (1H, m). LCMS (ESI$^+$) m/z=682.3 [M+Na]$^+$;

Example 62: *slow running isomer: $^1$H NMR (500 MHz, CDCl$_3$) δ 7.82 (1H, d), 7.78 (1H, d), 7.42 (1H, dd), 7.24 (1H, dd), 7.15-7.19 (4H, m), 7.13 (1H, d), 4.60 (1H, d), 4.46 (1H, d), 3.59 (1H, dd, J=6.1 and 11.5 Hz, CHHOH), 3.49 (1H, dd, J=6.1 and 11.5 Hz, CHHOH), 3.04 (1H, d), 2.91 (1H, d), 1.90 (1H, s), 2.72 (3H, s), 1.67 (1H, t), 1.63 (3H, s), 1.62 (3H, s), 0.41-0.49 (2H, m), 0.30-0.33 (1H, m), 0.05-0.09 (1H, m). LCMS (ESI$^+$) m/z=628.3 [M+Na]$^+$ Examples 63 and 64: (3R)-2-[(4-Chloro-2-methanesulfonylphenyl)methyl]-3-(4-chlorophenyl)-4-fluoro-6-(2-hydroxy-1-methoxypropan-2-yl)-3-{[1-(hydroxymethyl)cyclopropyl]methoxy}-2,3-dihydro-1H-isoindol-1-one (*Both Isomers at the Position Highlighted)

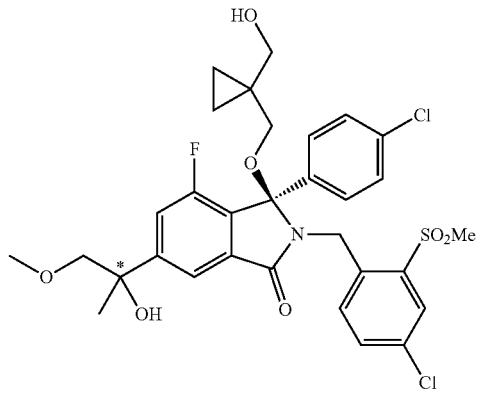 [SMILES: COCC(C)(O)c1cc(F)c2c(c1)C(=O)N(Cc1ccc(Cl)cc1S(C)(=O)=O)[C@@]2(OCC1(CO)CC1)c1ccc(Cl)cc1]

The title compounds were prepared using methods similar to those described in Example 43; but using sodium methoxide instead of piperazine.

Example 63 (the faster running isomer) (31 mg, 14%). 1H NMR (400 MHz, DMSO-d6): 7.85 (1H, d), 7.77 (1H, d), 7.58-7.50 (2H, m), 7.34-7.23 (5H, m), 5.49 (1H, s), 5.02-4.66 (2H, m), 4.39 (1H, t), 3.53-3.44 (2H, m), 3.28 (3H, s), 3.24 (3H, s), 3.02 (1H, d), 2.89 (1H, d), 1.47 (3H, s), 0.41-0.32 (2H, m), 0.26-0.17 (1H, m), 0.06 (1H, d). MS(ES+) m/z 652 [M+H]$^+$.

Example 64 (the slower running isomer) (11 mg, 5%). 1H NMR (400 MHz, DMSO-d6): 7.85 (1H, d), 7.77 (1H, d), 7.57-7.50 (2H, m), 7.33-7.22 (5H, m), 5.49 (1H, s), 5.01-4.81 (2H, m), 4.39 (1H, t), 3.54-3.44 (2H, m), 3.28 (3H, s), 3.24 (3H, s), 3.02 (1H, d), 2.90 (1H, d), 1.47 (3H, s), 0.37 (2H, d), 0.27-0.18 (1H, m), 0.11-0.03 (1H, m). MS(ES+) m/z 652 [M+H]$^+$.

Examples 65 and 66: (3R)-2-[(4-Chloro-2-methanesulfonylphenyl)methyl]-3-(4-chlorophenyl)-6-(1,2-dihydroxypropan-2-yl)-4-fluoro-3-{[1-(hydroxymethyl)cyclopropyl]methoxy}-2,3-dihydro-1H-isoindol-1-one (*Both Isomers at the Position Shown)

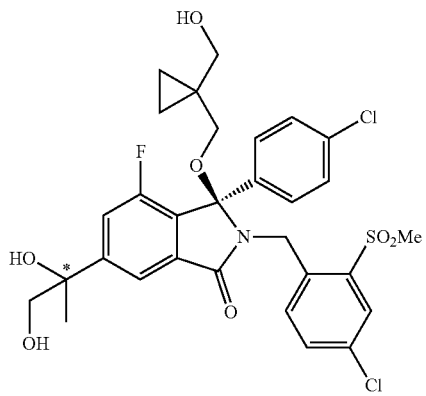 [SMILES: CC(O)(CO)c1cc(F)c2c(c1)C(=O)N(Cc1ccc(Cl)cc1S(C)(=O)=O)[C@@]2(OCC1(CO)CC1)c1ccc(Cl)cc1]

The title compounds were prepared using methods similar to those described in Example 41, Step 1 and Example 27; in a sequential manner.

Example 65 (faster running, major isomer, 174 mg, 26%): 1H NMR (400 MHz, DMSO-d6): 7.84 (1H, d), 7.77 (1H, d), 7.58-7.50 (2H, m), 7.32-7.21 (5H, m), 5.30 (1H, s), 4.98-4.80 (3H, m), 4.39 (1H, t), 3.57-3.40 (3H, m), 3.25 (3H, s), 3.03 (1H, d), 2.90 (1H, d), 1.46 (3H, s), 0.37 (2H, s), 0.27-0.18 (1H, m), 0.07 (1H, d). MS(ES+) m/z 638 [M+H]+.

Example 66 (slower running, minor isomer, 74 mg, 11%): 1H NMR (400 MHz, DMSO-d6): 7.85 (1H, dd), 7.77 (1H, d), 7.57-7.48 (2H, m), 7.32-7.23 (5H, m), 5.30 (1H, s), 4.99-4.79 (3H, m), 4.39 (1H, t), 3.57-3.39 (3H, m), 3.25 (3H, s), 3.02 (1H, d), 2.94-2.87 (1H, m), 1.46 (3H, s), 0.37 (2H, s), 0.28-0.17 (1H, m), 0.08 (1H, d). MS(ES+) m/z 638 [M+H]+.

Examples 67 and 68: (3R)-2-[(4-Chloro-2-methanesulfonylphenyl)methyl]-3-(4-chlorophenyl)-4-fluoro-6-[2-hydroxy-1-(4-methylpiperazin-1-yl)propan-2-yl]-3-[(3R)-oxolan-3-yloxy]-2,3-dihydro-1H-isoindol-1-one (*Both Isomers at the Position Shown)

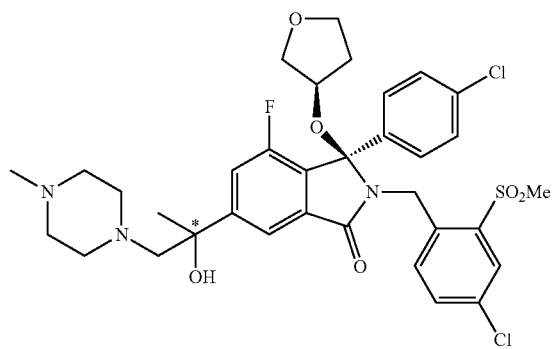 [SMILES: CN1CCN(CC(C)(O)c2cc(F)c3c(c2)C(=O)N(Cc2ccc(Cl)cc2S(C)(=O)=O)[C@@]3(O[C@@H]2CCOC2)c2ccc(Cl)cc2)CC1]

Starting from Preparation 44, the title compounds were prepared using methods similar to those described in Example 43, steps 2 and 3 (but using N-methyl-piperazine instead of piperazine).

Example 67 (faster running isomer, 132 mg, 28%): 1H NMR (400 MHz, DMSO-d6): 7.92 (1H, d), 7.80 (1H, d), 7.60-7.49 (2H, m), 7.36-7.19 (5H, m), 5.26 (1H, s), 5.09-4.67 (2H, m), 4.02-3.94 (1H, m), 3.78 (1H, q), 3.57-3.48 (1H, m), 3.27-3.15 (4H, m), 2.61 (1H, d), 2.34 (4H, s), 2.16 (4H, s), 2.08 (3H, s), 1.74-1.62 (1H, m), 1.59-1.38 (4H, m). MS(ES+) m/z 706 [M+H]+.

Example 68 (slower running isomer, 131 mg, 28%): 1H NMR (400 MHz, DMSO-d6): 7.85 (1H, d), 7.78 (1H, d), 7.62-7.51 (2H, m), 7.32-7.20 (5H, m), 5.23 (1H, s), 4.92 (2H, s), 3.99-3.92 (1H, m), 3.78 (1H, q), 3.58-3.49 (1H, m), 3.43-3.36 (1H, m), 3.24 (3H, s), 2.59 (1H, d), 2.35 (5H, d), 2.16 (4H, s), 2.08 (3H, s), 1.74-1.63 (1H, m), 1.57-1.40 (4H, m). MS(ES+) m/z 706 [M+H]+.

Examples 69 and 70: (3R)-2-[(4-Chloro-2-methanesulfonylphenyl)methyl]-3-(4-chlorophenyl)-4-fluoro-6-[2-hydroxy-1-(4-methylpiperazin-1-yl)propan-2-yl]-3-[(3S)-oxolan-3-yloxy]-2,3-dihydro-1H-isoindol-1-one (*Both Isomers at the Position Shown)

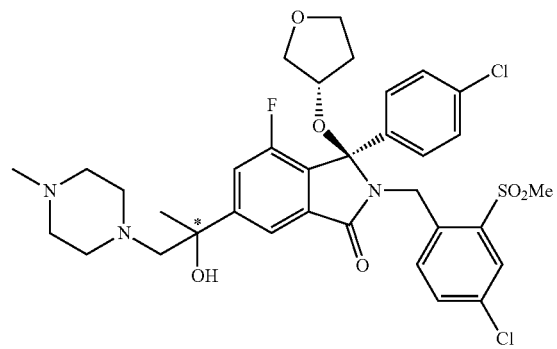 [SMILES: CN1CCN(CC(C)(O)c2cc(F)c3c(c2)C(=O)N(Cc2ccc(Cl)cc2S(C)(=O)=O)[C@@]3(O[C@H]2CCOC2)c2ccc(Cl)cc2)CC1]

The title compounds were prepared using procedures similar to those described in Examples 67 and 68, but using (3S)-hydroxy-tetrahydrofuran.

Example 69 (faster running isomer, 96 mg, 39%): 1H NMR (400 MHz, DMSO-d6): 7.92 (1H, d), 7.78 (1H, d), 7.59-7.50 (2H, m), 7.34-7.19 (5H, m), 5.27 (1H, s), 5.06-4.71 (2H, m), 4.01-3.93 (1H, m), 3.75 (1H, q), 3.60-3.51 (1H, m), 3.45-3.40 (1H, m), 3.24 (3H, s), 3.15 (1H, dd), 2.61 (1H, d), 2.41-2.26 (5H, m), 2.16 (4H, s), 2.07 (3H, s), 1.81-1.64 (1H, m), 1.59 (1H, d), 1.50 (3H, s). MS(ES+) m/z 706 [M+H]+.

Example 70 (slower running isomer, 97 mg, 39%): 1H NMR (400 MHz, DMSO-d6): 7.84 (1H, d), 7.77 (1H, d), 7.63-7.50 (2H, m), 7.30-7.19 (5H, m), 5.23 (1H, s), 4.98 (2H, s), 3.99-3.92 (1H, m), 3.77 (1H, q), 3.62-3.54 (1H, m), 3.46-3.40 (1H, m), 3.25 (3H, s), 3.17 (1H, dd), 2.59 (1H, d), 2.34 (5H, s), 2.16 (4H, s), 2.08 (3H, s), 1.86-1.73 (1H, m), 1.73-1.61 (1H, m), 1.53 (3H, s). MS(ES+) m/z 706 [M+H]+.

Example 71: (3S)-3-(4-Chlorophenyl)-3-[(1R)-1-(4-chlorophenyl)-7-fluoro-5-(2-hydroxypropan-2-yl)-3-oxo-1-[(3S)-oxolan-3-yloxy]-2,3-dihydro-1H-isoindol-2-yl]propanoic Acid

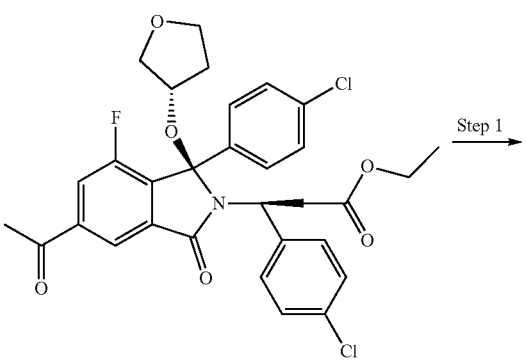

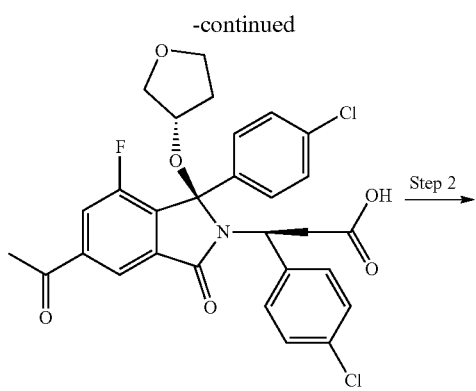

Step 1: (3S)-3-[(1R)-5-Acetyl-1-(4-chlorophenyl)-7-fluoro-3-oxo-1-[(3S)-oxolan-3-yloxy]-2,3-dihydro-1H-isoindol-2-yl]-3-(4-chlorophenyl)propanoic Acid The title compound was prepared from ethyl (3S)-3-[(1R)-5-acetyl-1-(4-chlorophenyl)-7-fluoro-3-oxo-1-[(3S)-oxolan-3-yloxy]-2,3-dihydro-1H-isoindol-2-yl]-3-(4-chlorophenyl)propanoate (Preparation 45) in a similar manner as described in Preparation 40. MS(ES+) m/z 570 [M–H]⁻

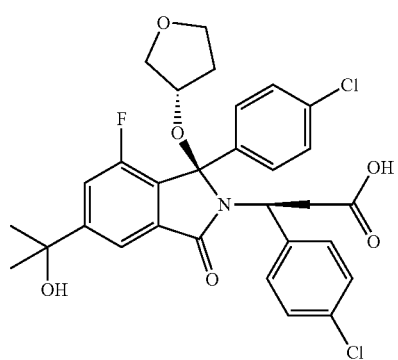

Step 2: (3S)-3-(4-Chlorophenyl)-3-[(1R)-1-(4-chlorophenyl)-7-fluoro-5-(2-hydroxypropan-2-yl)-3-oxo-1-[(3S)-oxolan-3-yloxy]-2,3-dihydro-1H-isoindol-2-yl]propanoic Acid Using the product from Step 1, the title compound was prepared in a similar fashion to Example 1.

1H NMR (400 MHz, DMSO-d6): 12.42 (1H, s), 7.79 (1H, s), 7.51 (1H, d), 7.10 (4H, dd), 6.99 (4H, d), 5.36 (1H, s), 4.62 (1H, dd), 4.21-4.13 (1H, m), 3.92 (1H, q), 3.77-3.63 (2H, m), 3.50 (1H, d), 3.23 (1H, dd), 3.12 (1H, dd), 2.25-2.09 (1H, m), 2.09-1.94 (1H, m), 1.47 (6H, s); MS(ES+) m/z 570 [M–H]⁻

Example 72: 1-({[(1R)-2-{[4-Chloro-2-(hydroxymethyl)phenyl]methyl}-1-(4-chlorophenyl)-7-fluoro-5-(2-hydroxypropan-2-yl)-3-oxo-2,3-dihydro-1H-isoindol-1-yl]oxy}methyl)cyclopropane-1-carbonitrile

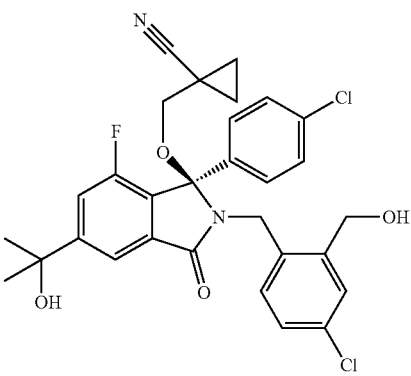 [SMILES: CC(C)(O)c1cc(F)c2c(c1)C(=O)N(Cc1ccc(Cl)cc1CO)[C@@]2(OCC1(C#N)CC1)c1ccc(Cl)cc1]

To a solution of 5-chloro-2-{[(1R)-1-(4-chlorophenyl)-1-[(1-cyanocyclopropyl)methoxy]-7-fluoro-5-(2-hydroxypropan-2-yl)-3-oxo-2,3-dihydro-1H-isoindol-2-yl]methyl}benzoic acid (Example 79) (233 mg, 0.4 mmol) in THF (10 mL) were added triethylamine (0.17 mL, 1.2 mmol) and isobutyl chloroformate (0.08 mL, 0.6 mmol) and the reaction mixture was stirred for 1 h. Water (0.1 mL) was added followed by NaBH₄ (0.045 g, 1.2 mmol) in small portions. Stirred for 1 h, water (10 mL) was added and the product was extracted with EtOAc. The crude product was purified on Silica, eluted with petrol-EtOAc 0-80% to afford the title compound (150 mg, 66%).

1H NMR (400 MHz, DMSO-d6): 7.82 (1H, d), 7.53 (1H, dd), 7.37-7.22 (5H, m), 7.14-7.03 (2H, m), 5.37 (1H, s), 5.21 (1H, t), 4.54-4.36 (3H, m), 4.33 (1H, d), 3.02 (1H, d), 2.80 (1H, d), 1.48 (6H, s), 1.23-1.13 (2H, m), 0.78-0.68 (1H, m), 0.61-0.52 (1H, m). MS(ES+) m/z 472 [3 [M-CN(c-Pr)CH₂O)]⁺.

Examples 73 and 74: 1-({[(1R)-2-[(4-chloro-2-methanesulfonylphenyl)methyl]-1-(4-chlorophenyl)-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide (*Both Isomers at Position Shown)

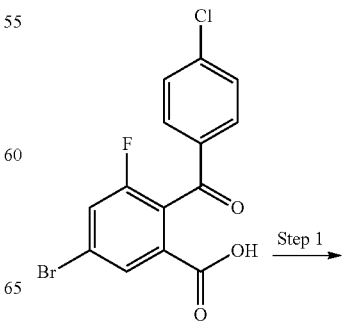

-continued

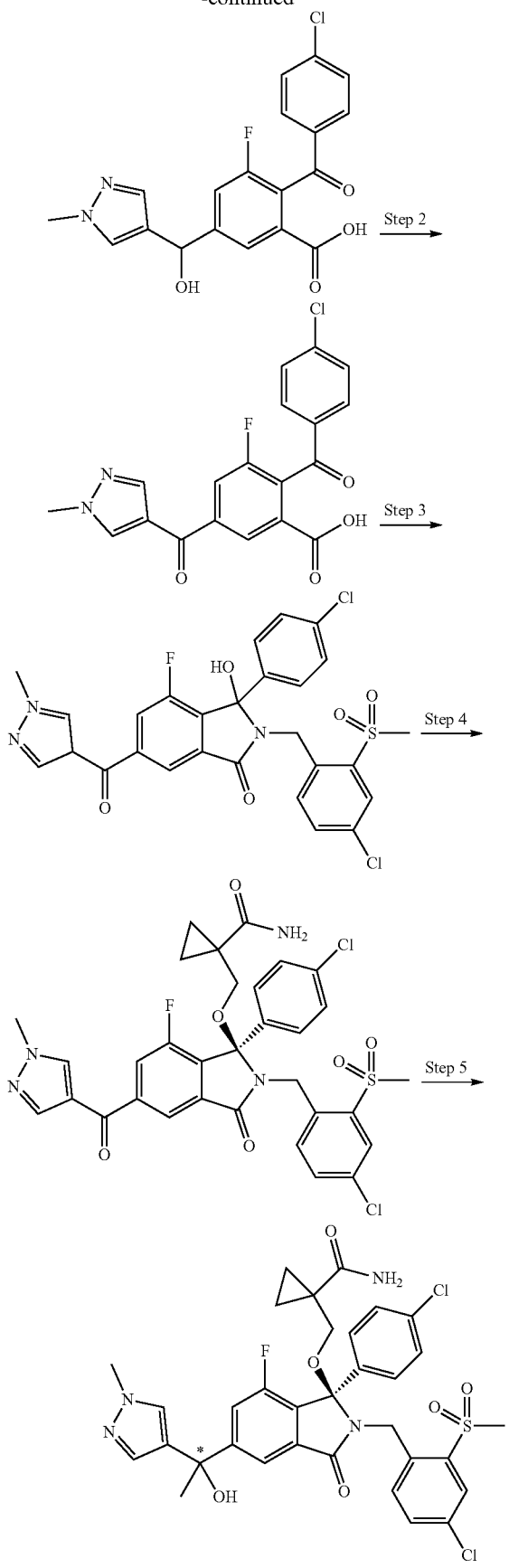

Step 1: 2-(4-Chlorobenzoyl)-3-fluoro-5-(hydroxy(1-methyl-1H-pyrazol-4-yl)methyl)benzoic Acid A 5 liter round bottom flask fitted with an overhead stirrer was charged with 5-bromo-2-(4-chlorobenzoyl)-3-fluorobenzoic acid (100 g, 0.28 mol) and anhydrous THF (1.5 L). The solution was cooled to −3° C. and a solution of methyl magnesium chloride (2.15M in THF, 130 mL, 0.279 mol) was added dropwise at such a rate that the internal temperature remained below −1° C. (25 min). On complete addition, the mixture was stirred at 0° C. for 15 min then cooled to −78° C. A solution of n-butyllithium (2.2M in hexanes, 152 mL; 0.33 mol) was added dropwise over 30 min at such a rate so that the internal temperature remained below −70° C. On complete addition the mixture was stirred at ⌊78° C. for 30 min. A solution of 1-methyl-1H-pyrazole-4-carboxaldehyde (39.7 g, 0.36 mol) in anhydrous THF (500 mL) was added dropwise over 20 min at such a rate so that the internal temperature remained below −70° C. On complete addition the mixture was stirred at −78° C. for 15 min, the cooling bath removed and the mixture allowed to reach RT. The mixture was quenched with 1 M HCl, the pH adjusted to 1-2 and extracted with EtOAc (2×500 mL). Combined organics were dried (MgSO$_4$) and the solvent evaporated. The residue was divided into four equal portions and each portion chromatographed on silica gel (300 g) eluting with 0-20% MeOH in DCM gradient to afford the title compound as a colourless solid (48.33 g, 44.5%). Impure fractions were pooled, evaporated and chromatographed to afford a further quantity of title compound (11.05 g, 10.2%). MS: [M+H]$^+$=389

Step 2: 2-(4-Chlorobenzoyl)-3-fluoro-5-(1-methyl-1H-pyrazole-4-carbonyl)benzoic Acid To a stirred mixture of 2-(4-chlorobenzoyl)-3-fluoro-5-(hydroxy(1-methyl-1H-pyrazol-4-yl)methyl)benzoic acid (20 g, 51.48 mmol) in EtOAc (86 mL) at 0° C. was added 10% aqueous KBr (29.83 mL, 25 mmol) followed by TEMPO (0.82 g, 5.23 mmol). To this stirred mixture was added a solution of sodium hydrogen carbonate (5.40 g, 64.25 mmol) and sodium hypochlorite (89 mL, 5-20% aqueous solution ex Fisher, catalogue number S/5040/PB17) in water (47 mL) at such a rate so that the reaction temperature remained below 5° C. Addition was stopped upon complete oxidation as indicated by LCMS (approximately half of the solution was required). The reaction was quenched by addition of dilute aqueous sodium sulphite solution and the mixture extracted with EtOAc (4×500 mL). Combined organics were dried (MgSO$_4$) and the solvent removed under reduced pressure to give the title compound as a pale orange solid (15.27 g, 76%). The aqueous layer was acidified with 2 M HCl and extracted with EtOAc (500 mL). The organics were dried (MgSO$_4$) and the solvent removed under reduced pressure to give a further quantity of the title compound (3.44 g, 17%). MS: [M+H]$^+$=387.

Step 3: 2-(4-Chloro-2-(methylsulfonyl)benzyl)-3-(4-chlorophenyl)-4-fluoro-3-hydroxy-6-(1-methyl-1H-pyrazole-4-carbonyl)isoindolin-1-one 2-(4-Chlorobenzoyl)-3-fluoro-5-(1-methyl-1H-pyrazole-4-carbonyl)benzoic acid (18.20 g, 46.55 mmol) and (4-chloro-2-(methylsulfonyl)phenyl)methanamine (Example 35, step 3) (19.4 g, 88.30 mmol) were stirred in DMF (90 mL) at RT under nitrogen. HATU (26.80 g, 70.53 mmol) was added and the reaction mixture stirred at RT for 1.25 h.

The reaction mixture was diluted with water, sat. aq. NaHCO$_3$ solution and EtOAc. The layers were separated and the aqueous was extracted with EtOAc. The combined organics were washed with 4% LiCl aq. solution, dried (MgSO$_4$), filtered and concentrated in vacuo. The residue was purified using a 340 g SNAP column eluting with EtOAc in iso-hexanes (0 to 100%) to give the title 8.8 g, 32% yield. MS: [M+H]$^+$=587.

Step 4: (R)-1-(((2-(4-Chloro-2-(methylsulfonyl) benzyl)-1-(4-chlorophenyl)-7-fluoro-5-(1-methyl-1H-pyrazole-4-carbonyl)-3-oxoisoindolin-1-yl)oxy) methyl)cyclopropanecarboxamide The title compound was prepared from 2-(4-chloro-2-(methylsulfonyl)benzyl)-3-(4-chlorophenyl)-4-fluoro-3-hydroxy-6-(1-methyl-1H-pyrazole-4-carbonyl)isoindolin-1-one (2.0 g, 3.40 mmol) in a similar manner to that described in preparation 10. The product was separated using chiral SFC. Slowest eluting isomer. MS: [M+H]$^+$=685.

Step 5: 1-({[(1R)-2-[(4-chloro-2-methanesulfonyl-phenyl)methyl]-1-(4-chlorophenyl)-7-fluoro-5-[1-hydroxy-1-(1-methyl-1H-pyrazol-4-yl)ethyl]-3-oxo-2,3-dihydro-1H-isoindol-1-yl]oxy}methyl) cyclopropane-1-carboxamide (R)-1-(((1-(4-Chlorophenyl)-2-((5-chloropyridin-2-yl) methyl)-7-fluoro-5-(1-methyl-1H-pyrazole-4-carbonyl)-3-oxoisoindolin-1-yl)oxy)methyl)cyclopropanecarbonitrile (620 mg, 0.90 mmol) was stirred in THF (5 mL) at −15° C. under nitrogen. MeMgCl (2.15M in THF, 0.91 mL, 1.96 mmol) was added dropwise forming an orange solution and then stirred for 10 mins at this temperature. The reaction was quenched with sat. aq. NH$_4$Cl solution, water was then added and the reaction was warmed to RT. The aqueous was extracted with DCM (2×50 mL) and the combined organics were dried (phase separator) and concentrated in vacuo. The residue was purified using a 25 g SNAP column, eluting with MeOH in DCM (0 to 5%). Fractions containing the title compound were concentrated in vacuo and the compound was separated using chiral SFC.

Example 73: *faster eluting isomer. $^1$H NMR (400 MHz, CDCl$_3$) 7.90 (1H, d), 7.82 (1H, d), 7.53-7.49 (1H, m), 7.42 (1H, s), 7.37-7.33 (2H, m), 7.25-7.18 (5H, m), 6.52-6.52 (1H, m), 5.42-5.42 (1H, m), 5.04-4.92 (2H, m), 3.90 (3H, s), 3.36 (1H, d), 2.99 (3H, s), 2.91 (1H, d), 2.32 (1H, s), 1.94 (3H, s), 1.32-1.20 (2H, m), 0.53-0.46 (1H, m), 0.39-0.33 (1H, m); MS: [M+H]$^+$=701.

Example 74: *slower eluting isomer. $^1$H NMR (400 MHz, CDCl$_3$) 7.89 (1H, d), 7.82 (1H, s), 7.55-7.50 (1H, m), 7.41 (1H, s), 7.37-7.32 (2H, m), 7.25-7.17 (5H, m), 6.52-6.52 (1H, m), 5.42-5.42 (1H, m), 5.04-4.94 (2H, m), 3.91 (3H, s), 3.36 (1H, d), 3.00 (3H, s), 2.93 (1H, d), 2.34 (1H, s), 1.94 (3H, s), 1.32-1.21 (2H, m), 0.54-0.47 (1H, m), 0.42-0.36 (1H, m); MS: [M+H]$^+$=701.

Example 75 and 76: (3R)-2-[(4-chloro-2-methane-sulfonylphenyl)methyl]-3-(4-chlorophenyl)-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one (*Both Isomers at Position Shown)

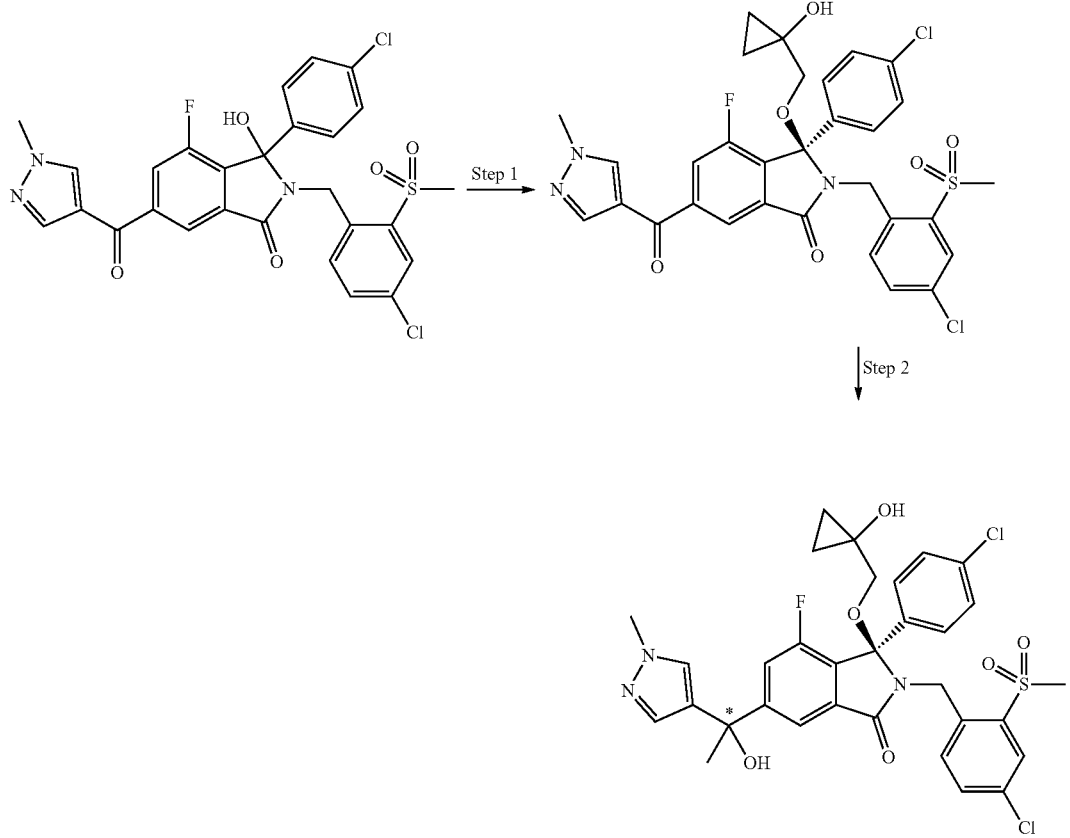

Step 1: (R)-2-(4-Chloro-2-(methylsulfonyl)benzyl)-3-(4-chlorophenyl)-4-fluoro-3-((1-hydroxycyclopropyl)methoxy)-6-(1-methyl-1H-pyrazole-4-carbonyl)isoindolin-1-one The title compound was prepared from 2-(4-chloro-2-(methylsulfonyl)benzyl)-3-(4-chlorophenyl)-4-fluoro-3-hydroxy-6-(1-methyl-1H-pyrazole-4-carbonyl)isoindolin-1-one (2.0 g, 3.4 mmol) in a similar manner to that described in preparation 12. The product was separated using chiral SFC. Slowest eluting isomer. MS: [M+H]$^+$=658.

Step 2: (3R)-2-[(4-chloro-2-methanesulfonylphenyl)methyl]-3-(4-chlorophenyl)-4-fluoro-6-[1-hydroxy-1-(1-methyl-1H-pyrazol-4-yl)ethyl]-3-[(1-hydroxy-cyclopropyl)methoxy]-2,3-dihydro-1H-isoindol-1-one The title compound was prepared from (R)-2-(4-chloro-2-(methylsulfonyl)benzyl)-3-(4-chlorophenyl)-4-fluoro-3-((1-hydroxycyclopropyl)methoxy)-6-(1-methyl-1H-pyrazole-4-carbonyl)isoindolin-1-one (255 mg, 0.39 mmol) in a similar manner to that described in Examples 73 and 74, step 5. The product was separated using chiral SFC.

Example 75: *slower eluting isomer. $^1$H NMR (400 MHz, CDCl$_3$) 7.84 (1H, d), 7.80 (1H, d), 7.45 (1H, dd), 7.40 (1H, s), 7.34-7.20 (5H, m), 7.08 (2H, d), 5.22 (1H, d), 5.02 (1H, d), 3.90 (3H, s), 3.34 (1H, d), 3.24 (1H, s), 3.03 (3H, s), 2.90 (1H, d), 2.27 (1H, s), 1.93 (3H, s), 0.93-0.80 (2H, m), 0.63-0.56 (1H, m), 0.43-0.37 (1H, m); MS: [M+H]+=674.

Example 76: *faster eluting isomer. $^1$H NMR (400 MHz, CDCl$_3$) 7.84 (1H, d), 7.81 (1H, d), 7.45 (1H, dd), 7.40 (1H, d), 7.33-7.21 (5H, m), 7.08 (2H, d), 5.21 (1H, d), 5.01 (1H, d), 3.90 (3H, s), 3.32 (1H, d), 3.21 (1H, s), 3.02 (3H, s), 2.91 (1H, d), 2.28 (1H, s), 1.93 (3H, s), 0.93-0.80 (2H, m), 0.62-0.55 (1H, m), 0.43-0.36 (1H, m); MS: [M+H]+=674.

Examples 77 and 78: (3R)-2-[(4-chloro-2-methanesulfonylphenyl)methyl]-3-(4-chlorophenyl)-4-fluoro-6-[2-hydroxy-1-(4-methylpiperazin-1-yl)propan-2-yl]-3-{[1-(hydroxymethyl)cyclopropyl]methoxy}-2,3-dihydro-1H-isoindol-1-one

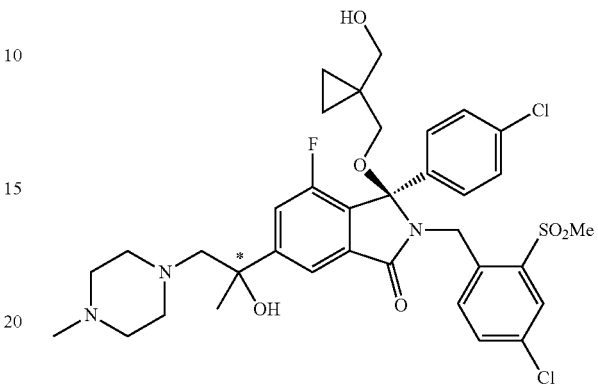

The title compounds were prepared using methods similar to those described in Example 43.

Example 77: *fast running isomer: $^1$H NMR (400 MHz, CDCl3) 7.91 (1H, d), 7.77 (1H, d), 7.46 (1H, dd), 7.35 (1H, dd), 7.29-7.28 (2H, m), 7.22 (1H, d), 7.17 (2H, d), 5.00 (2H, d), 4.40 (1H, s) 3.83 (1H, d), 3.35 (1H, d), 3.27 (1H, d), 3.04 (3H, s), 2.80 (1H, d), 2.71 (2H, dd), 2.53-2.37 (8H, m), 2.25 (3H, s), 2.01-2.01 (1H, m), 1.51 (3H, s), 0.50 (2H, dd), 0.49-0.37 (1H, m), 0.21 (1H, d). MS [M+H]$^+$=720.

Example 78: *slow running isomer: $^1$H NMR (400 MHz, CDCl3) 7.91 (1H, d), 7.76 (1H, d), 7.48 (1H, dd), 7.34 (1H, dd), 7.28 (2H, d), 7.21-7.16 (3H, m), 5.00 (2H, s), 4.47 (1H, d), 3.82 (1H, d), 3.37 (1H, d), 3.26 (1H, d), 3.04 (3H, s), 2.81 (1H, d), 2.73-2.67 (2H, m), 2.52 (2H, s), 2.37 (6H, s), 2.25 (3H, s), 2.00-2.00 (1H, m), 1.51 (3H, s), 0.52-0.37 (3H, m), 0.21-0.17 (1H, m). MS [M+H]$^+$=720.

Example 79: 5-chloro-2-{[(1R)-1-(4-chlorophenyl)-1-[(1-cyanocyclopropyl)methoxy]-7-fluoro-5-(2-hydroxypropan-2-yl)-3-oxo-2,3-dihydro-1H-isoindol-2-yl]methyl}benzoic Acid

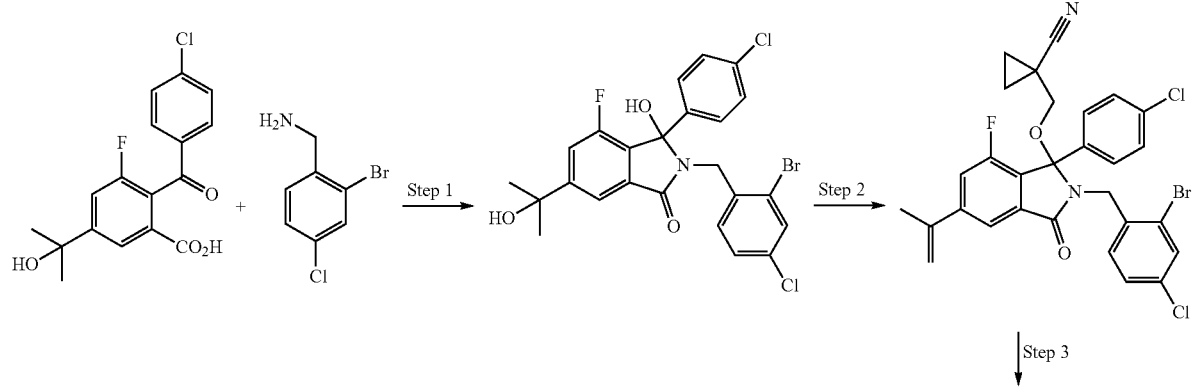

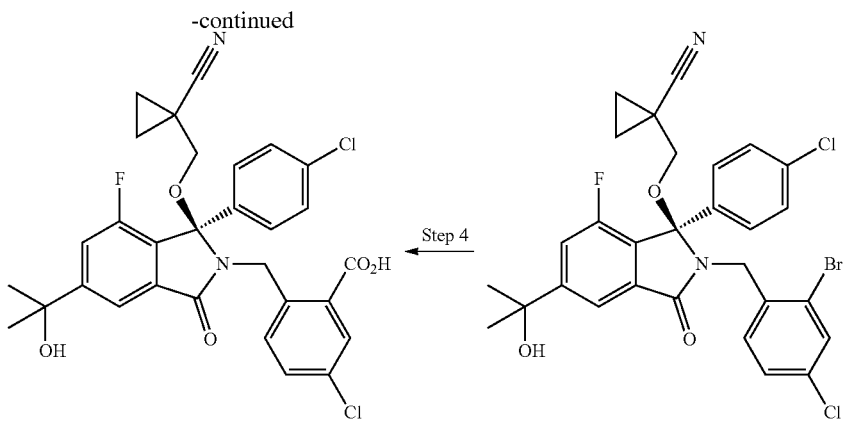

Step 1: 2-(2-Bromo-4-chlorobenzyl)-3-(4-chlorophenyl)-4-fluoro-3-hydroxy-6-(2-hydroxypropan-2-yl)isoindolin-1-one Starting from Preparation 46 and (2-bromo-4-chlorophenyl)methanamine (Example 33, step 1) (1.3 g, 6.24 mmol), the title compound was prepared using methods similar to Example 35, step 4 to afford 2-(2-bromo-4-chlorobenzyl)-3-(4-chlorophenyl)-4-fluoro-3-hydroxy-6-(2-hydroxypropan-2-yl)isoindolin-1-one as a colourless solid (2.15 g, 64%). MS [M+H]$^+$=538.

Step 2: 1-(((2-(2-Bromo-4-chlorobenzyl)-1-(4-chlorophenyl)-7-fluoro-3-oxo-5-(prop-1-en-2-yl)isoindolin-1-yl)oxy)methyl)cyclopropanecarbonitrile The title compound was prepared from 2-(2-bromo-4-chlorobenzyl)-3-(4-chlorophenyl)-4-fluoro-3-hydroxy-6-(2-hydroxypropan-2-yl)isoindolin-1-one (2.1 g, 3.9 mmol) and 1-(hydroxymethyl)cyclopropanecarbonitrile (3.42 g, 9.6 mmol) using the method of Preparation 10 to furnish (1.7 g, 71%). MS [M+H]$^+$=599.

Step 3: (R)-1-(((2-(2-Bromo-4-chlorobenzyl)-1-(4-chlorophenyl)-7-fluoro-5-(2-hydroxypropan-2-yl)-3-oxoisoindolin-1-yl)oxy)methyl)cyclopropanecarbonitrile Step 3 was performed in an analogous fashion to Example 2 to give the title compound as a racemate (1.6 g). Purification by SFC gave the title compound as the fast running isomer. MS [M+H]$^+$=617.

Step 4: 5-chloro-2-{[(1R)-1-(4-chlorophenyl)-1-[(1-cyanocyclopropyl)methoxy]-7-fluoro-5-(2-hydroxypropan-2-yl)-3-oxo-2,3-dihydro-1H-isoindol-2-yl]methyl}benzoic Acid Step 4 was performed in an analogous fashion to Example 33, Step 5. Purification by preparative HPLC afforded (R)-5-chloro-2-((1-(4-chlorophenyl)-7-fluoro-1-((1-(hydroxymethyl)cyclopropyl)methoxy)-5-(2-hydroxypropan-2-yl)-3-oxoisoindolin-2-yl)methyl)benzoic acid (305 mg, 62%). $^1$H NMR (400 MHz, DMSO) 7.84 (1H, s), 7.67 (1H, d), 7.58 (1H, s), 7.56 (1H, s), 7.41 (1H, dd), 7.32-7.22 (5H, m), 4.90 (1H, d), 4.79 (1H, d), 3.16 (1H, d), 2.84 (1H, d), 1.48 (6H, s), 1.27-1.15 (2H, m), 0.86-0.79 (1H, m), 0.69-0.62 (1H, m), OH not observed. MS [M+H]$^+$=583.

Examples 80 and 81: (3R)-2-[(4-chloro-2-methanesulfonylphenyl)methyl]-3-(4-chlorophenyl)-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one (*Both Isomers at Position Shown)

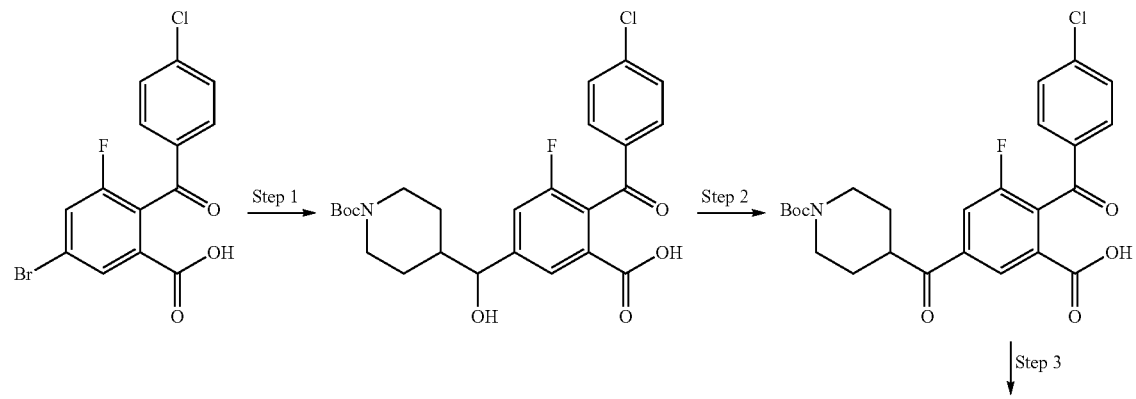

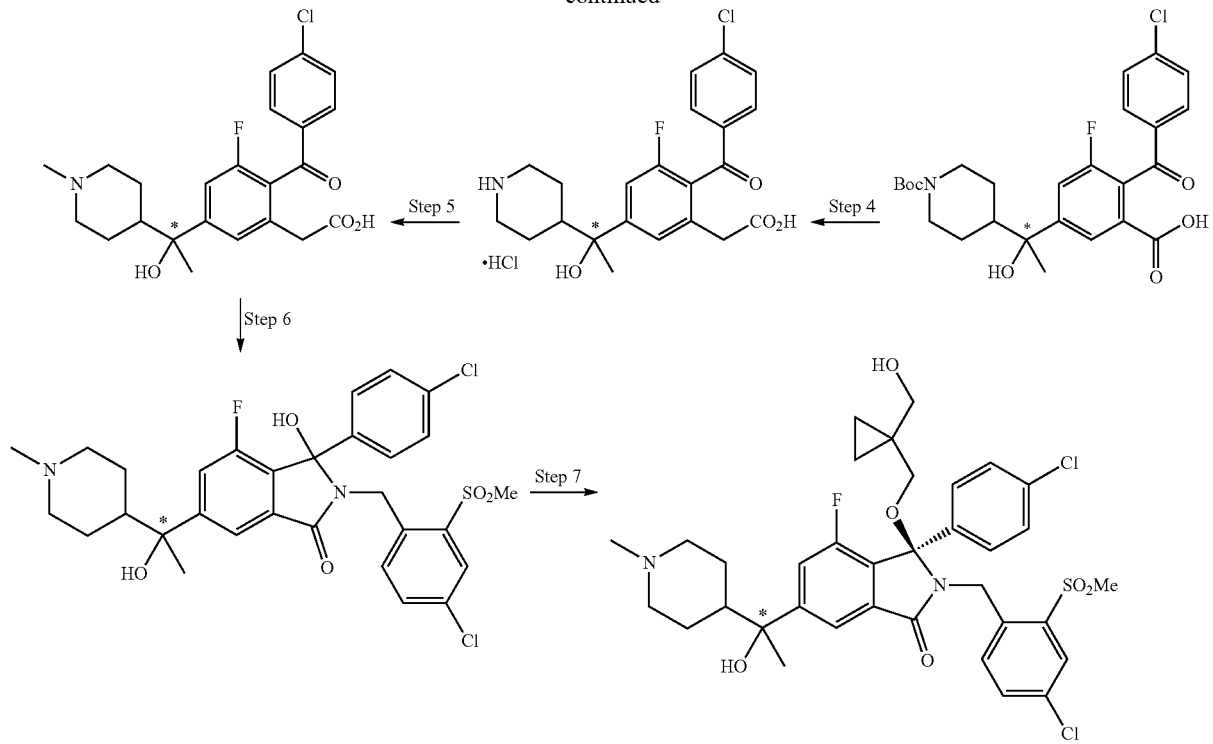

Steps 1 and 2 were performed using procedures similar to those described in Examples 73 and 74; but using tert-butyl 4-formylpiperidine-1-carboxylate instead of 1-methyl-1H-pyrazole-4-carboxaldehyde. Also, Bu$_2$Mg was used in place of methylmagnesium chloride.

Step 3: 5-(1-(1-(tert-Butoxycarbonyl)piperidin-4-yl)-1-hydroxyethyl)-2-(4-chlorobenzoyl)-3-fluorobenzoic Acid To a RB flask containing 5-(1-(tert-butoxycarbonyl)piperidine-4-carbonyl)-2-(4-chlorobenzoyl)-3-fluorobenzoic acid (15.57 g, 31.7 mmol), under N$_2$, was added THF (300 mL) and cooled to −10° C. MeMgCl (34.5 mL, 79.4 mmol, 2.3M in THF) was added over a period of 5 mins. Immediately after the completion of the addition, LCMS analysis showed complete conversion of the starting material. The reaction was quenched with 1 M HCl (200 mL). The reaction was extracted with EtOAc (2×200 mL), dried with MgSO$_4$, filtered and conc. in vacuo. The crude material was purified by column chromatography, Biotage Isolera, 340 g cartridge 0%-60% EtOAc (0.1% formic acid) in DCM (0.1% formic acid) to afford 5-(1-(1-(tert-butoxycarbonyl)piperidin-4-yl)-1-hydroxyethyl)-2-(4-chlorobenzoyl)-3-fluorobenzoic acid as an off white foam (15.1 g, 93%). Purification by chiral preparative LCMS.

* Fast running isomer (Isomer A): MS: [M−H]$^-$=504, [α]$_D^{20}$=+28.7 (c 1.9, MeOH)
* Slow running isomer (Isomer B): MS: [M−H]$^-$=504, [α]$_D^{20}$=−27.8 (c 1.8, MeOH)

Step 4: 2-(4-Chlorobenzoyl)-3-fluoro-5-(1-hydroxy-1-(piperidin-4-yl)ethyl)benzoic Acid Hydrochloride (−)-5-(1-(1-(tert-Butoxycarbonyl)piperidin-4-yl)-1-hydroxyethyl)-2-(4-chlorobenzoyl)-3-fluorobenzoic acid (Isomer B) (6.09 g, 12.0 mmol) was stirred in 4N HCl in dioxane (70 mL) at rt for 10 min. The orange solution was concentrated in vacuo yielding 2-(4-chlorobenzoyl)-3-fluoro-5-(1-hydroxy-1-(piperidin-4-yl)ethyl)benzoic acid hydrochloride (Isomer B) as an orange solid (6.88 g) which was used in the next step without further purification. MS: [M+H]$^+$=406.

In a similar manner (+)-5-(1-(1-(tert-Butoxycarbonyl)piperidin-4-yl)-1-hydroxyethyl)-2-(4-chlorobenzoyl)-3-fluorobenzoic acid (Isomer A) (7.50 g, 14.8 mmol) furnished 2-(4-chlorobenzoyl)-3-fluoro-5-(1-hydroxy-1-(piperidin-4-yl)ethyl)benzoic acid hydrochloride (Isomer A) which was used in the next step without further purification. MS: [M+H]$^+$=406.

Step 5: 2-(4-Chlorobenzoyl)-3-fluoro-5-(1-hydroxy-1-(1-methylpiperidin-4-yl)ethyl)benzoic Acid (−)-2-(4-Chlorobenzoyl)-3-fluoro-5-(1-hydroxy-1-(piperidin-4-yl)ethyl)benzoic acid hydrochloride (Isomer B) (6.88 g, ca. 12.0 mmol) was stirred in MeOH (100 mL) at rt under nitrogen and formaldehyde solution (37% wt in water, 24 mmol, 1.95 mL) was added. The orange solution was stirred at RT for 5 min and NaBH$_3$CN (14.4 mmol, 905 mg) was added. The yellow solution was stirred at RT for 1 d after which time a colourless solid had precipitated. The mixture was concentrated in vacuo to give 2-(4-chlorobenzoyl)-3-fluoro-5-(1-hydroxy-1-(1-methylpiperidin-4-yl)ethyl)benzoic acid (Isomer B) as a yellow solid (6 g) which was used in the next step without further purification.

In a similar manner (+)-2-(4-chlorobenzoyl)-3-fluoro-5-(1-hydroxy-1-(piperidin-4-yl)ethyl)benzoic acid hydrochloride (Isomer A) (6.00 g, ca. 14.8 mmol) furnished 2-(4-chlorobenzoyl)-3-fluoro-5-(1-hydroxy-1-(1-methylpiperidin-4-yl)ethyl)benzoic acid (Isomer A) which was used in the next step without further purification. MS: [M+H]$^+$=419.9.

Step 6: 2-(4-Chloro-2-(methylsulfonyl)benzyl)-3-(4-chlorophenyl)-4-fluoro-3-hydroxy-6-(1-hydroxy-1-(1-methylpiperidin-4-yl)ethyl)isoindolin-1-one Starting from (−)-2-(4-chlorobenzoyl)-3-fluoro-5-(1-hydroxy-1-(1-methylpiperidin-4-yl)ethyl)benzoic acid (Isomer B) (2 g, 4 mmol), Step 6 was performed in a similar fashion to Example 35, Step 4 to give 2-(4-chloro-2-(methylsulfonyl)benzyl)-3-(4-chlorophenyl)-4-fluoro-3-hydroxy-6-(1-hydroxy-1-(1-methylpiperidin-4-yl)ethyl)isoindolin-1-one (Isomer B), 939 mg, 38% as a pale orange solid. MS: [M+H]⁺=621

In a similar manner, (+)-2-(4-Chlorobenzoyl)-3-fluoro-5-(1-hydroxy-1-(1-methylpiperidin-4-yl)ethyl)benzoic acid (Isomer A) (1.55 g, ca. 3.70 mmol) furnished 2-(4-chloro-2-(methylsulfonyl)benzyl)-3-(4-chlorophenyl)-4-fluoro-3-hydroxy-6-(1-hydroxy-1-(1-methylpiperidin-4-yl)ethyl)isoindolin-1-one (Isomer A), 1.05 g, 46%. MS: [M+H]⁺=621.

Step 7: (3R)-2-[(4-chloro-2-methanesulfonylphenyl)methyl]-3-(4-chlorophenyl)-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one Using (−)-2-(4-chloro-2-(methylsulfonyl)benzyl)-3-(4-chlorophenyl)-4-fluoro-3-hydroxy-6-(1-hydroxy-1-(1-methylpiperidin-4-yl)ethyl)isoindolin-1-one (Isomer B) (847 mg, 1.36 mmol), Step 7 was performed in a similar fashion to Example 41, step 1 to give 366 mg of 2-(4-chloro-2-(methylsulfonyl)benzyl)-3-(4-chlorophenyl)-4-fluoro-6-(1-hydroxy-1-(1-methylpiperidin-4-yl)ethyl)-3-((1-(hydroxymethyl)cyclopropyl)methoxy)isoindolin-1-one (Isomer B) as a pale yellow solid which was further purified using preparative HPLC and separated by chiral SFC to yield Example 80 (55 mg, the later running isomer)

Example 80 ¹H NMR (400 MHz, CDCl3) 7.91 (1H, d), 7.72 (1H, d), 7.46-7.42 (1H, m), 7.36 (1H, dd), 7.30 (2H, d), 7.24-7.17 (3H, m), 5.06-4.96 (2H, m), 3.80 (1H, d), 3.38 (1H, d), 3.24 (1H, d), 3.03 (3H, s), 2.92 (2H, dd), 2.78 (1H, d), 2.35-2.35 (3H, m), 2.25 (3H, s), 1.96-1.83 (2H, m), 1.74 (1H, d), 1.61 (3H, s), 1.49-1.35 (3H, m), 0.50 (2H, s), 0.49-0.38 (1H, m), 0.23 (1H, d); MS: [M+H]⁺=705.4.

In a similar manner (+)-2-(4-chloro-2-(methylsulfonyl)benzyl)-3-(4-chlorophenyl)-4-fluoro-3-hydroxy-6-(1-hydroxy-1-(1-methylpiperidin-4-yl)ethyl)isoindolin-1-one (Isomer A) (787 mg, 1.27 mmol) furnished 138 mg 2-(4-chloro-2-(methylsulfonyl)benzyl)-3-(4-chlorophenyl)-4-fluoro-6-(1-hydroxy-1-(1-methylpiperidin-4-yl)ethyl)-3-((1-(hydroxymethyl)cyclopropyl)methoxy)isoindolin-1-one (Isomer A) which was further purified using preparative HPLC and separated by chiral SFC to yield Example 81 (8 mg, the later running isomer).

Example 81 ¹H NMR (400 MHz, CDCl3) 8.40 (1H, s), 7.91 (1H, d), 7.70 (1H, d), 7.45 (1H, dd), 7.35 (1H, dd), 7.30 (2H, d), 7.23 (1H, d), 7.19 (2H, d), 5.00 (2H, s), 3.73-3.67 (1H, m), 3.44 (1H, d), 3.35-3.23 (2H, m), 3.14 (1H, d), 3.03 (3H, s), 2.88 (1H, d), 2.51 (3H, s), 2.28-2.24 (3H, m), 1.94-1.77 (4H, m), 1.62 (3H, s), 1.40-1.31 (1H, m), 0.50 (2H, dd), 0.48-0.38 (1H, m), 0.26 (1H, d); MS: [M+H]⁺=705.

Example 82: (3R)-2-{[4-chloro-2-(dimethylphosphoryl)phenyl]methyl}-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one

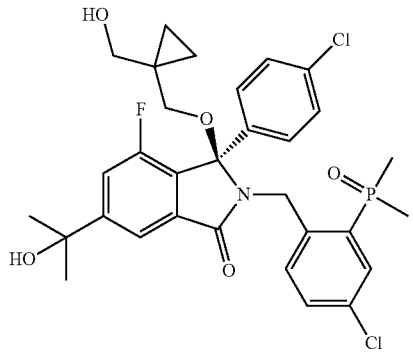 [SMILES: CC(C)(O)c1cc(F)c2c(c1)C(=O)N(Cc1ccc(Cl)cc1P(C)(C)=O)[C@@]2(OCC1(CO)CC1)c1ccc(Cl)cc1]

Starting from 5-bromo-2-(4-chlorobenzoyl)-3-fluorobenzoic acid and Preparation 47: (2-(aminomethyl)-5-chlorophenyl)dimethylphosphine oxide, the title compound was prepared using procedures similar to those described in preparation 9, preparation 10. Example 21 Step 3 and Example 41 Step 3; in a sequential manner.

*fast running isomer: ¹H NMR (400 MHz, CDCl₃) 7.81 (1H, d), 7.45 (1H, dd), 7.31 (2H, d), 7.19-7.13 (2H, m), 7.10-7.06 (3H, m), 5.36 (1H, d), 5.09 (2H, d), 4.37 (1H, dd), 3.84 (1H, d), 2.97 (1H, d), 2.18 (1H, d), 1.89 (1H, s), 1.77 (3H, d), 1.74 (3H, d), 1.65 (3H, s), 1.64 (3H, s), 0.58-0.42 (3H, m), 0.27-0.22 (1H, m). [M+H]+=620.

Examples 83 and 84: (3R)-2-[(4-chloro-2-methanesulfonylphenyl)methyl]-3-(4-chlorophenyl)-4-fluoro-6-[hydroxy(oxan-4-yl)methyl]-3-{[1-(hydroxymethyl)cyclopropyl]methoxy}-2,3-dihydro-1H-isoindol-1-one (*Both Isomers at Position Shown)

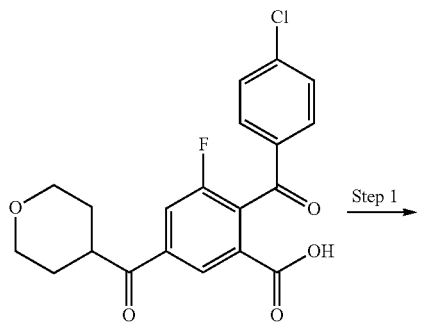

Step 1

-continued

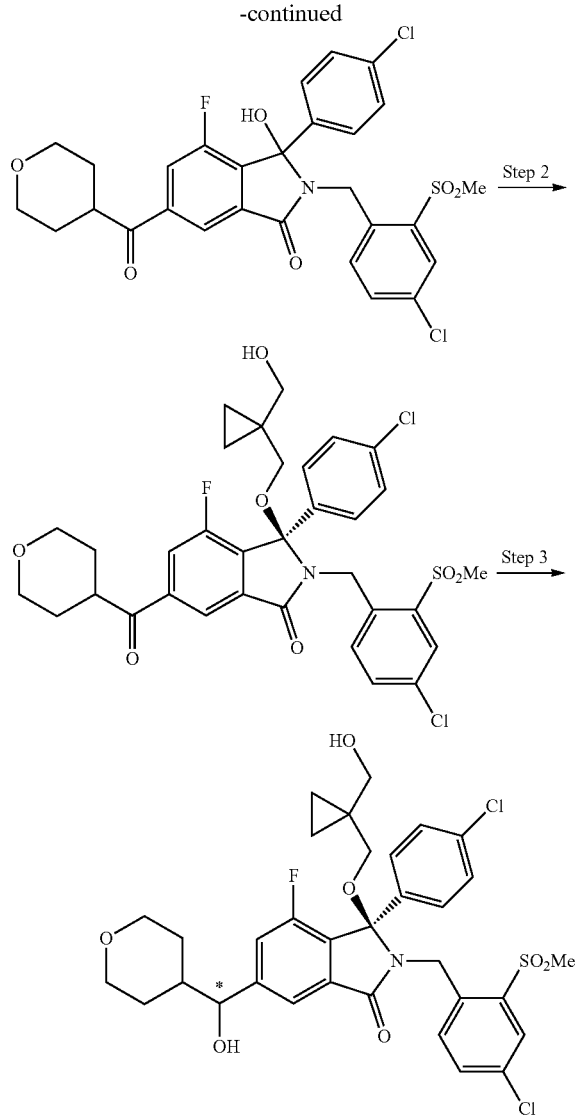

Step 1 and 2: Starting from Preparation 48, Steps 1 and 2 were performed using procedures similar to those described in Examples 73 and 74 Step 3 and Step 4, but using 1,1-bis(hydroxymethyl)cyclopropane instead of 1-(hydroxymethyl)cyclopropane-1-carboxamide. MS: [M-1-(cyclopropane-1,1-diyldimethanol]+=574

Step 3: (3R)-2-[(4-chloro-2-methanesulfonylphenyl) methyl]-3-(4-chlorophenyl)-4-fluoro-6-[hydroxy (oxan-4-yl)methyl]-3-{[1-(hydroxymethyl)cyclopropyl]methoxy}-2,3-dihydro-1H-isoindol-1-one The product from Step 2 (300 mg, 0.44 mmol) was dissolved in methanol (1 mL) under nitrogen at RT with stirring. Sodium borohydride (25 mg, 0.66 mmol) was added to the reaction mixture and the reaction was allowed to stir at room temperature for 10 min then quenched and diluted with water. The reaction was extracted with DCM. The combined organic portions were dried (MgSO$_4$) and concentrated under reduced pressure. The crude residue was purified on a 10 g SNAP silica cartridge, eluting with ethyl acetate in isohexane (10 to 100%). Fractions containing pure product were concentrated under reduced pressure to yield a white solid (247 mg) which was separated using chiral SFC.

Example 83 *slower eluting isomer. $^1$H NMR (400 MHz, CDCl3) 7.91 (1H, d), 7.72 (1H, s), 7.35 (1H, dd), 7.28-7.26 (2H, m), 7.24-7.16 (4H, m), 5.06-4.96 (2H, m), 4.55 (1H, dd), 4.05-3.93 (2H, m), 3.80 (1H, dd), 3.42-3.23 (4H, m), 3.04 (3H, s), 2.78 (1H, d), 2.11 (1H, d), 2.01-1.96 (1H, m), 1.94-1.84 (1H, m), 1.78 (1H, d), 1.54-1.37 (2H, m), 1.29-1.21 (1H, m), 0.54-0.48 (2H, m), 0.46-0.38 (1H, m), 0.22 (1H, d); MS: [M+H]+=678.

Example 84 *faster eluting isomer. $^1$H NMR (400 MHz, CDCl3) 7.91 (1H, d), 7.67 (1H, s), 7.35 (1H, dd), 7.30-7.26 (3H, m), 7.24-7.17 (3H, m), 5.06-4.96 (2H, m), 4.56 (1H, dd), 4.06-3.94 (2H, m), 3.82 (1H, dd), 3.40-3.25 (4H, m), 3.03 (3H, s), 2.75 (1H, d), 2.16 (1H, d), 2.03-1.99 (1H, m), 1.93-1.83 (1H, m), 1.78 (1H, d), 1.55-1.37 (2H, m), 1.28 (1H, d), 0.54-0.47 (2H, m), 0.46-0.40 (1H, m), 0.23 (1H, d); MS: [M+H]+=678.

Example 85 and 86: 1-({[(1R)-2-[(4-chloro-2-methanesulfonylphenyl)methyl]-1-(4-chlorophenyl)-7-fluoro-5-[1-hydroxy-1-(oxan-4-yl)ethyl]-3-oxo-2,3-dihydro-1H-isoindol-1-yl]oxy}methyl)cyclopropane-1-carboxamide (*Both Isomers at Position Shown)

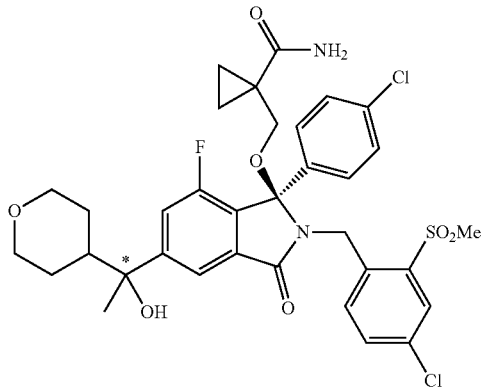 [SMILES: CC(O)(c1cc(F)c2c(c1)C(=O)N(Cc1ccc(Cl)cc1S(C)(=O)=O)[C@@]2(OCC1(C(N)=O)CC1)c1ccc(Cl)cc1)C1CCOCC1]

Using 2-(4-chloro-2-(methylsulfonyl)benzyl)-3-(4-chlorophenyl)-4-fluoro-3-hydroxy-6-(tetrahydro-2H-pyran-4-carbonyl)isoindolin-1-one (Examples 83 and 84; Step 1), the title compound was prepared using methods similar to those described in Preparation 12 (using 1-(hydroxymethyl)cyclopropanecarboxamide instead of 1,1-bis(hydroxymethyl)cyclopropane) and Examples 73 and 74 Step 5.

Example 85 *slower eluting isomer. $^1$H NMR (400 MHz, CDCl3) 7.90 (1H, d), 7.77 (1H, d), 7.50-7.46 (1H, m), 7.36 (1H, dd), 7.28-7.18 (5H, m), 6.52-6.52 (1H, m), 5.42-5.42 (1H, m), 5.06-4.95 (2H, m), 4.07-3.94 (2H, m), 3.41-3.28 (3H, m), 3.00 (3H, s), 2.93 (1H, d), 1.91-1.84 (1H, m), 1.82 (1H, s), 1.63 (3H, s), 1.56 (1H, s), 1.53-1.40 (2H, m), 1.33-1.22 (3H, m), 0.53-0.47 (1H, m), 0.42-0.35 (1H, m); MS: [M+H]+=705.

Example 86 *faster eluting isomer. $^1$H NMR (400 MHz, CDCl3) 7.91 (1H, s), 7.81 (1H, s), 7.44 (1H, d), 7.36 (1H, d), 7.26-7.19 (5H, m), 6.52-6.52 (1H, m), 5.42 (1H, s), 5.05-4.95 (2H, m), 4.06-3.96 (2H, m), 3.39-3.35 (3H, m), 3.00 (3H, s), 2.92 (1H, d), 1.91-1.84 (2H, m), 1.67-1.56 (4H, m), 1.47 (2H, m), 1.26-1.24 (3H, m), 0.51 (1H, s), 0.37-0.37 (1H, m); MS: [M+H]+=705

Example 87: 5-chloro-2-{[(1R)-1-(4-chlorophenyl)-7-fluoro-5-[1-hydroxy-1-(1-methylpiperidin-4-yl)ethyl]-1-methoxy-3-oxo-2,3-dihydro-1H-isoindol-2-yl]methyl}benzoic Acid (Example Isolated as a Single Isomer at the Position Shown*)

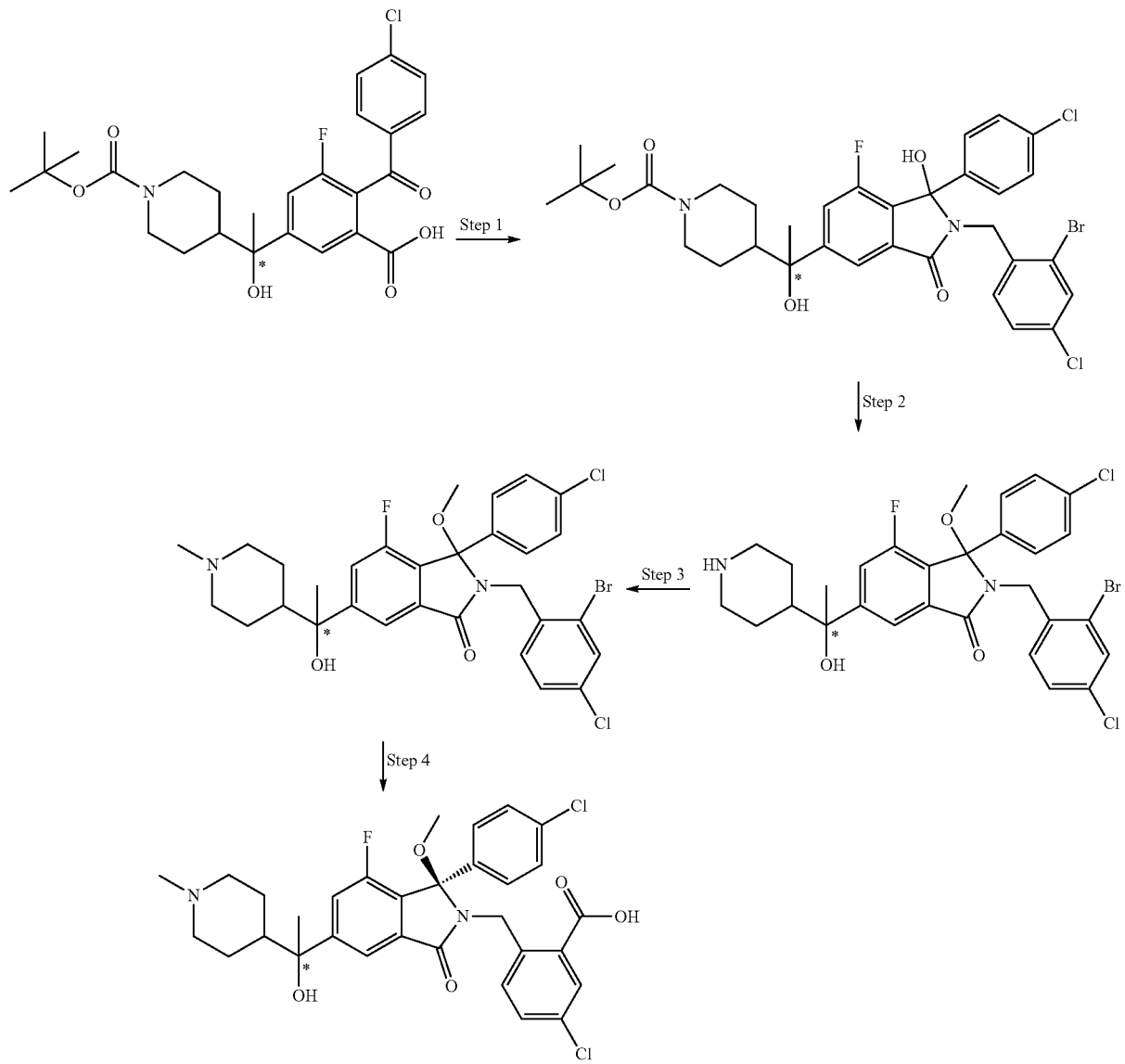

Step 1: tert-Butyl 4-[1-[2-[(2-bromo-4-chloro-phenyl)methyl]-1-(4-chlorophenyl)-7-fluoro-1-hydroxy-3-oxo-isoindolin-5-yl]-1-hydroxy-ethyl]piperidine-1-carboxylate Prepared in a similar manner to that described for Example 35, step 4 from (−)-5-[1-(1-tert-butoxycarbonyl-4-piperidyl)-1-hydroxy-ethyl]-2-(4-chlorobenzoyl)-3-fluoro-benzoic acid and (2-bromo-4-chlorophenyl)methanamine. MS: $[M-H_2O]^+=691$.

Step 2: 2-[(2-Bromo-4-chloro-phenyl)methyl]-3-(4-chlorophenyl)-4-fluoro-6-[1-hydroxy-1-(4-piperidyl)ethyl]-3-methoxy-isoindolin-1-one Prepared in a similar manner to that described in Preparation 10 from tert-butyl 4-[1-[2-[(2-bromo-4-chloro-phenyl)methyl]-1-(4-chlorophenyl)-7-fluoro-1-hydroxy-3-oxo-isoindolin-5-yl]-1-hydroxy-ethyl]piperidine-1-carboxylate and methanol. MS: $[M+H]^+=623$.

Step 3: 2-[(2-Bromo-4-chloro-phenyl)methyl]-3-(4-chlorophenyl)-4-fluoro-6-[1-hydroxy-1-(1-methyl-4-piperidyl)ethyl]-3-methoxy-isoindolin-1-one The title compound was prepared from 2-[(2-bromo-4-chloro-phenyl)methyl]-3-(4-chlorophenyl)-4-fluoro-6-[1-hydroxy-1-(4-piperidyl)ethyl]-3-methoxy-isoindolin-1-one in analogous fashion to Example 81, step 5. MS: $[M+H]^+=637$.

Step 4: 5-Chloro-2-[[(1R)-1-(4-chlorophenyl)-7-fluoro-5-[1-hydroxy-1-(1-methyl-4-piperidyl)ethyl]-1-methoxy-3-oxo-isoindolin-2-yl]methyl]benzoic Acid Prepared in a similar manner to that described for Example 33, step 5 from 2-[(2-bromo-4-chloro-phenyl)methyl]-3-(4-chlorophenyl)-4-fluoro-6-[1-hydroxy-1-(1-methyl-4-piperidyl)ethyl]-3-methoxy-isoindolin-1-one. $^1$H NMR (400 MHz, CDCl3) 7.87 (1H, s), 7.53 (1H, d), 7.49 (1H, d), 7.31 (2H, d), 7.24 (2H, d), 7.19 (1H, d), 7.11 (1H, dd), 4.96 (1H, d), 4.81 (1H, d), 3.47 (1H, d), 3.36-3.32 (1H, m), 2.87 (3H, s), 2.87-2.71 (2H, m), 2.73 (3H, s), 2.11-2.02 (1H, m), 1.99-1.90 (1H, m), 1.80-1.63 (2H, m), 1.62 (3H, s), 1.51 (1H, m). MS: [M+H]$^+$=601.

Examples 88 and 89: (3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic Acid (*Both Isomers Separated and Isolated)

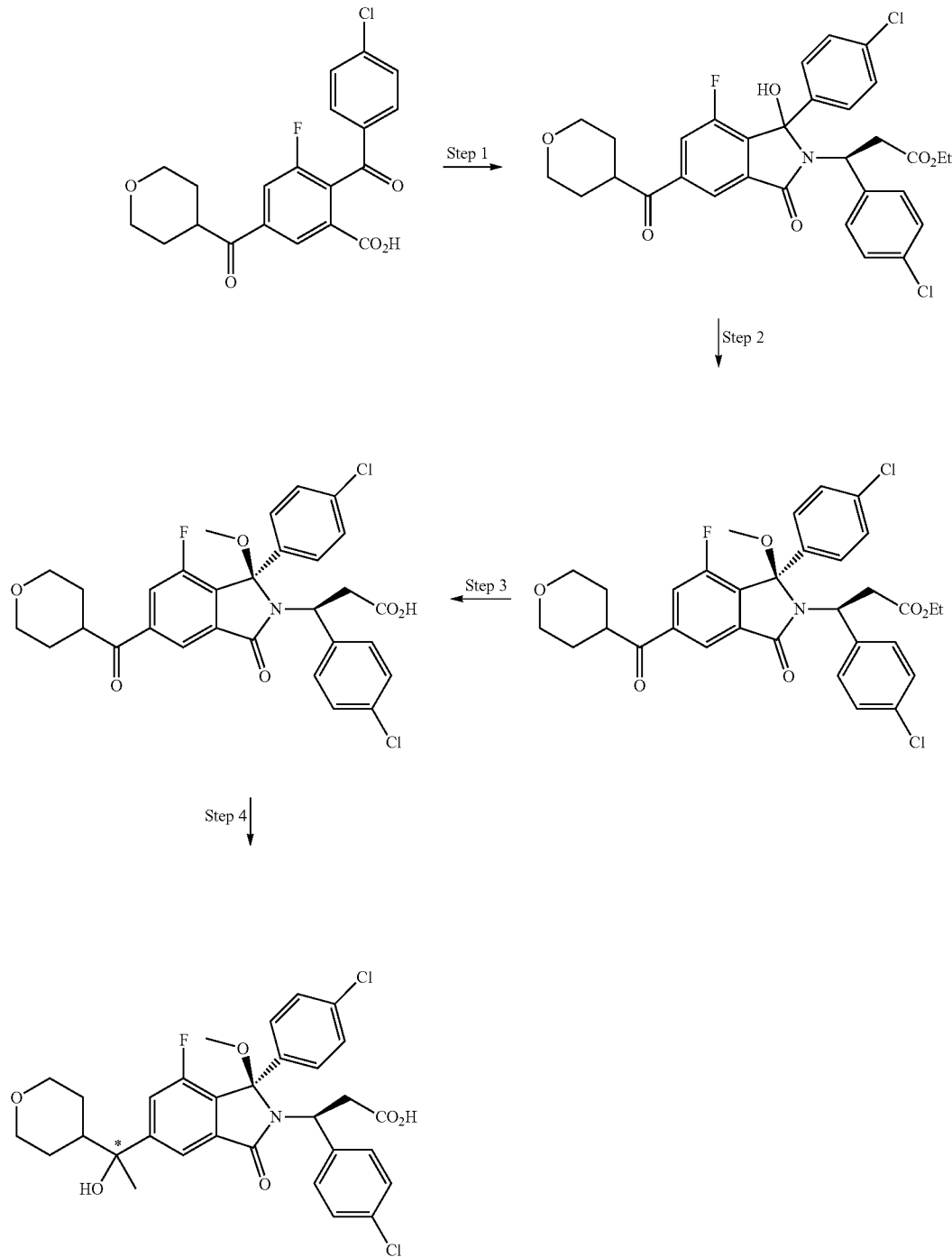

Step 1: (3S)-Ethyl 3-(4-chlorophenyl)-3-(1-(4-chlorophenyl)-7-fluoro-1-hydroxy-3-oxo-5-(tetrahydro-2H-pyran-4-carbonyl)isoindolin-2-yl)propanoate 2-(4-Chlorobenzoyl)-3-fluoro-5-(tetrahydro-2H-pyran-4-carbonyl)benzoic acid (Preparation 48) (3.99 g, 10.2 mmol) was reacted with (S)-ethyl 3-amino-3-(4-chlorophenyl)propanoate hydrochloride (3.5 g, 13.25 mmol) in an analogous fashion as described in Example 35, step 4 to afford the title compound (3.4 g, 50%) as a yellow solid. MS: [M−H]⁻=598.

Step 2: (S)-Ethyl 3-(4-chlorophenyl)-3-((R)-1-(4-chlorophenyl)-7-fluoro-1-methoxy-3-oxo-5-(tetrahydro-2H-pyran-4-carbonyl)isoindolin-2-yl)propanoate The title compound was prepared from (3S)-ethyl 3-(4-chlorophenyl)-3-(1-(4-chlorophenyl)-7-fluoro-1-hydroxy-3-oxo-5-(tetrahydro-2H-pyran-4-carbonyl)isoindolin-2-yl)propanoate and methanol in a similar manner as described in Preparation 12. The diastereoisomers were separated chiral SFC. [M+H]+=614.

Step 3: (S)-3-(4-Chlorophenyl)-3-((R)-1-(4-chlorophenyl)-7-fluoro-1-methoxy-3-oxo-5-(tetrahydro-2H-pyran-4-carbonyl)isoindolin-2-yl)propanoic Acid The title compound was prepared from (S)-ethyl 3-(4-chlorophenyl)-3-((R)-1-(4-chlorophenyl)-7-fluoro-1-methoxy-3-oxo-5-(tetrahydro-2H-pyran-4-carbonyl)isoindolin-2-yl)propanoate in an analogous fashion as described in Preparation 40. [M+H]+=586.

Step 4: (3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid The title compound was prepared from (S)-3-(4-chlorophenyl)-3-((R)-1-(4-chlorophenyl)-7-fluoro-1-methoxy-3-oxo-5-(tetrahydro-2H-pyran-4-carbonyl)isoindolin-2-yl)propanoic acid in a similar manner to that described in Example 1 to give the racemate which was separated by chiral SFC.

Example 88: *fast running isomer ¹H NMR (400 MHz, CDCl3) 7.67 (1H, d), 7.34-7.29 (1H, m), 7.03 (4H, s), 7.00 (4H, s), 4.68 (1H, dd), 4.04-3.90 (2H, m), 3.68 (1H, dd), 3.36-3.24 (3H, m), 3.08 (3H, s), 1.86-1.77 (1H, m), 1.61-1.55 (4H, m), 1.47-1.36 (2H, m), 1.26-1.17 (1H, m), (OH and CO₂H not visible). [M+H]+=602.

Example 89: *slow running isomer ¹H NMR (400 MHz, CDCl3) 7.68 (1H, s), 7.29 (1H, d), 7.03 (4H, s), 7.00 (4H, s), 4.69 (1H, dd), 4.05-3.90 (2H, m), 3.69-3.61 (1H, m), 3.37-3.24 (3H, m), 3.09 (3H, s), 1.87-1.77 (1H, m), 1.63-1.56 (4H, m), 1.50-1.37 (2H, m), 1.20 (1H, d), (OH and CO₂H not visible). [M+H]+=602.

Examples 90 and 91: 4-[(1R)-1-[(1R)-1-(4-Chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]-2-hydroxyethyl]benzonitrile (*Both Isomers Separated and Isolated)

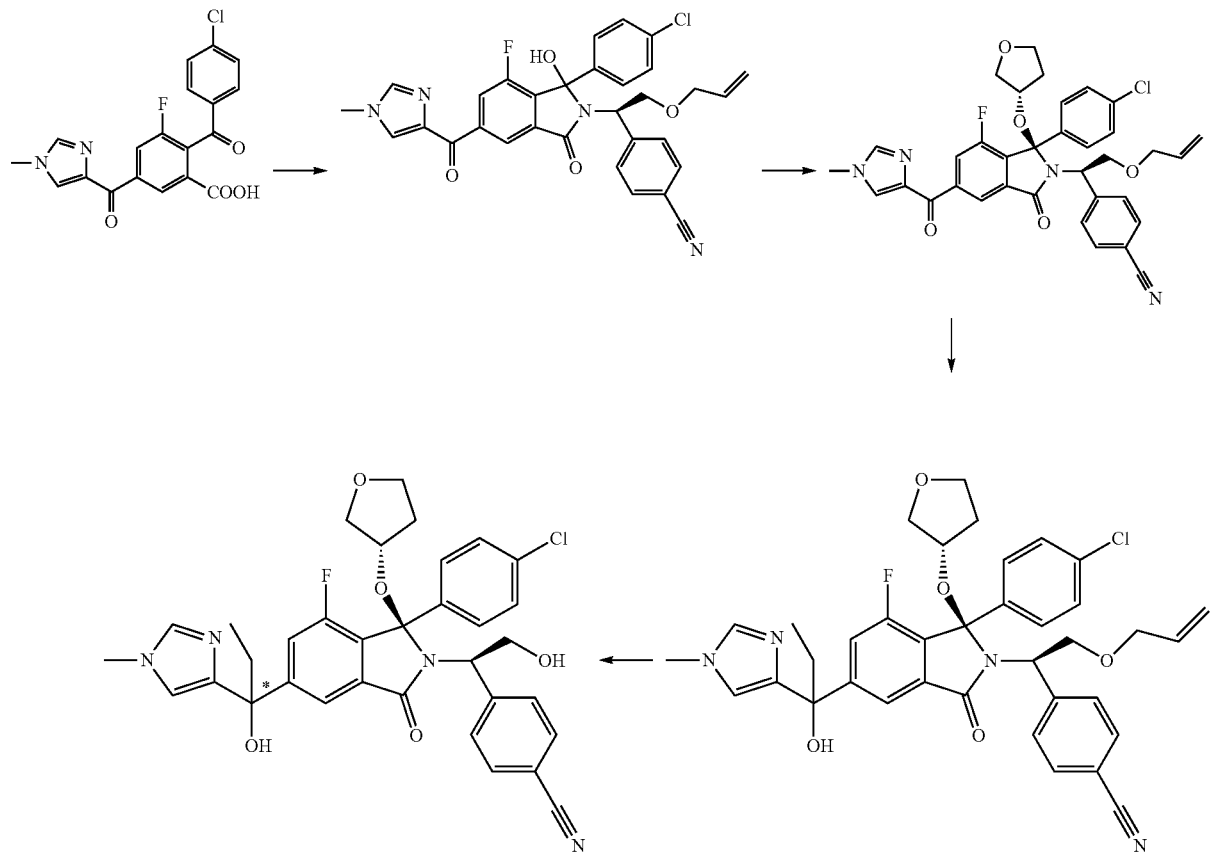

Step 1, 2 and 3: Starting from Preparations 49 and 50, Steps 1, 2 and 3 were performed using procedures similar to those described in Example 73 Step 3, Step 4 and Step 5, but using and (3S)-hydroxy-tetrahydrofuran instead of 1-(hydroxymethyl)cyclopropane-1-carboxamide in Step 2 and EtMgCl instead of MeMgCl in Step 3.

Step 4: 4-[(1R)-1-[(1R)-1-(4-Chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]-2-hydroxyethyl]benzonitrile Pd(PPh$_3$)$_4$ (56 mg, 0.05 mmol) and K$_2$CO$_3$ (252 mg, 1.88 mmol) were added to a solution of 4-[(1R)-1-[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]-2-(prop-2-en-1-yloxy)ethyl]benzonitrile (630 mg, 0.94 mmol) in MeOH (10 mL) and the resulting mixture was stirred at 80° C. for 2 hours. The solvent was then removed in vacuo and the residue was purified by flash chromatography on silica gel (gradient (0-100% EtOAc in petrol). The two diastereoisomers were then separated by chiral HPLC.

Example 90, isomer 1 (73 mg, 12% yield): 1H NMR (400 MHz, DMSO-d6): 7.90 (1H, s), 7.58-7.50 (2H, m), 7.47 (2H, d), 7.18 (2H, d), 7.07-6.82 (5H, m), 5.56 (1H, s), 5.13 (1H, dd), 4.49-4.40 (1H, m), 4.35-4.24 (2H, m), 4.10-3.96 (1H, m), 3.87 (1H, q), 3.69-3.62 (1H, m), 3.61 (3H, s), 3.48-3.42 (1H, m), 3.20-3.08 (1H, m), 2.26-2.05 (4H, m), 0.70 (3H, t); LCMS: [M+H]$^+$=631.

Example 91, isomer 2 (97 mg, 16% yield): 1H NMR (400 MHz, DMSO-d6): 7.85 (1H, s), 7.61-7.51 (2H, m), 7.46 (2H, d), 7.18 (2H, d), 7.10-6.83 (5H, m), 5.56 (1H, s), 5.13 (1H, t), 4.49-4.39 (1H, m), 4.36-4.24 (2H, m), 4.09-3.97 (1H, m), 3.87 (1H, q), 3.70-3.58 (4H, m), 3.43-3.37 (1H, m), 3.11 (1H, dd), 2.25-2.02 (4H, m), 0.70 (3H, t); LCMS: [M+H]$^+$=631.

Examples 92 and 93: 4-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}-3-(hydroxymethyl)benzonitrile (*Both Isomers Separated and Isolated)

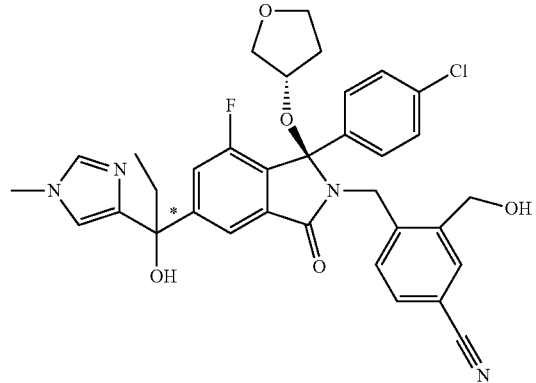 [SMILES: CCC(O)(c1cc(F)c2c(c1)C(=O)N(Cc1ccc(C#N)cc1CO)[C@@]2(O[C@H]1CCOC1)c1ccc(Cl)cc1)c1cn(C)cn1]

The title compounds were prepared in a similar fashion as in Example 90, but using Preparation 51 instead of 49 in step 1.

Example 92: *fast running isomer 1H NMR (400 MHz, CDCl3) 7.81 (1H, d), 7.57 (1H, d), 7.45-7.38 (2H, m), 7.36 (1H, d), 7.28 (1H, d), 7.20 (4H, s), 6.83 (1H, d), 4.74-4.65 (2H, m), 4.58 (1H, dd), 4.42 (1H, d), 3.85-3.70 (2H, m), 3.69 (3H, s), 3.62-3.53 (3H, m), 3.23 (1H, dd), 2.75-2.66 (1H, m), 2.23-2.06 (2H, m), 1.48-1.37 (2H, m), 0.84 (3H, dd). [M+H]$^+$=631.

Example 93: *slow running isomer 1H NMR (400 MHz, CDCl3) 7.69 (1H, d), 7.58-7.51 (2H, m), 7.41-7.36 (2H, m), 7.25-7.23 (1H, m), 7.19 (4H, s), 6.85 (1H, d), 4.73-4.66 (2H, m), 4.58 (1H, d), 4.42 (1H, d), 3.86-3.72 (2H, m), 3.70 (3H, s), 3.62-3.54 (3H, m), 3.22 (1H, dd), 2.23-2.06 (2H, m), 1.50-1.40 (2H, m), 1.27-1.08 (1H, m), 0.84 (3H, dd). [M+H]$^+$=631.

Examples 94 and 95: 4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile (*Both Isomers Separated and Isolated)

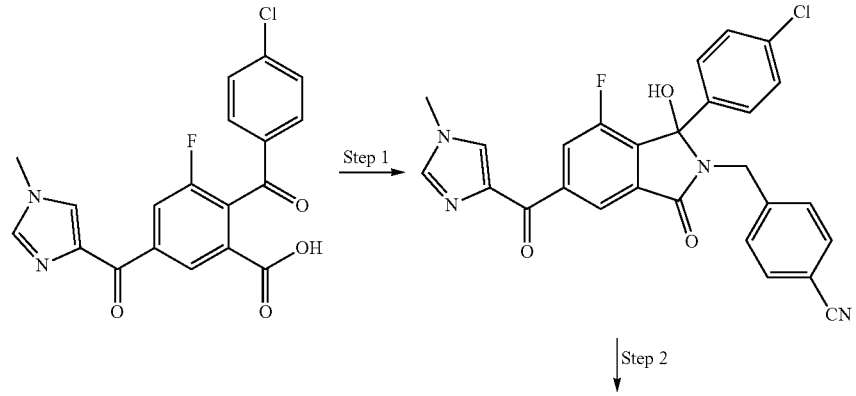

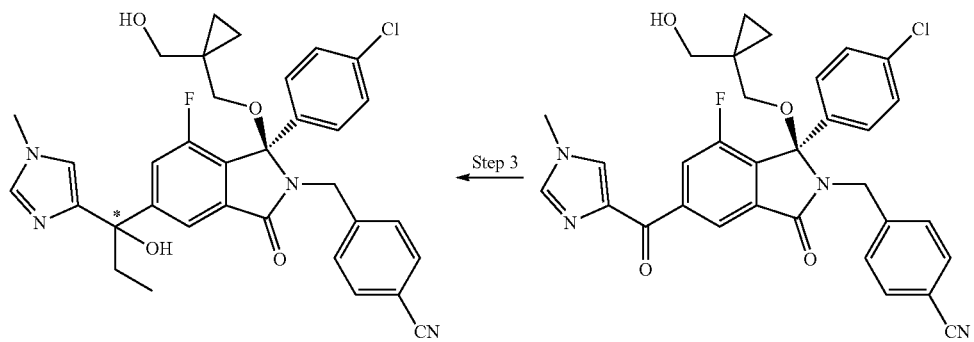

Step 1 and 2: Starting from Preparation 50, Steps 1 and 2 were performed using procedures similar to those described in Examples 73 Step 3 and Step 4 but using 4-(aminomethyl) benzonitrile in Step 1 and [1-(hydroxymethyl)cyclopropyl] methanol in Step 2.

Step 3: 4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile A solution of (R)-4-((1-(4-chlorophenyl)-7-fluoro-1-((1-(hydroxymethyl)cyclopropyl)methoxy)-5-(1-methyl-1H-imidazole-4-carbonyl)-3-oxoisoindolin-2-yl)methyl)benzonitrile) (190 mg, 0.325 mmol), in anhydrous CH$_2$Cl$_2$ (10 mL) was stirred at 0° C. under nitrogen. AlEt$_3$ (2.5 mL, 1M in hexanes, 2.5 mmol) was added drop-wise and the mixture was stirred at 0° C. for 1 h. The reaction was quenched with sat. aq. NH$_4$Cl and diluted with CH$_2$Cl$_2$ (10 mL) and water (7 mL). Solids were removed by filtration and the filtrate was extracted with CH$_2$Cl$_2$ (2×15 mL). Combined organics were dried (MgSO$_4$) and the solvent evaporated. The crude residue was purified by column chromatography, Interchim, 12 g KP-sil cartridge 0-5% MeOH in EtOAc to afford the racemate (98 mg, 49%). Chiral preparative HPLC gave the title compounds:

Example 94 (faster running isomer) $^1$H NMR (400 MHz, CDCl3) 7.71 (1H, s), 7.47 (3H, dd), 7.36 (1H, s), 7.27-7.26 (2H, m), 7.18 (4H, s), 6.84 (1H, s), 4.49 (1H, d), 4.32 (1H, d), 3.69 (3H, s), 3.53 (1H, d), 3.41 (1H, d), 2.97 (1H, d), 2.79 (1H, d), 2.24-2.07 (2H, m), 1.25 (1H, s), 0.86 (3H, dd), 0.45 (2H, dd), 0.28-0.23 (1H, m), 0.15-0.09 (1H, m). MS: [M+H]$^+$=615

Example 95: (slower running isomer) $^1$H NMR (400 MHz, CDCl3) 7.71 (1H, s), 7.49 (3H, dd), 7.36 (1H, s), 7.28-7.27 (2H, m), 7.19 (4H, s), 6.85 (1H, s), 4.51 (1H, d), 4.31 (1H, d), 3.69 (3H, s), 3.55 (1H, s), 3.52-3.47 (1H, m), 3.41 (1H, dd), 2.96 (1H, d), 2.78 (1H, d), 2.22-2.06 (2H, m), 0.85 (3H, dd), 0.44 (2H, dd), 0.29-0.23 (1H, m), 0.15-0.08 (1H, m). MS: [M+H]$^+$=615

Examples 96 and 97: 4-{[(1R)-1-(4-chlorophenyl)-7-fluoro-5-[I-hydroxy-1-(1-methyl-1H-imidazol-4-yl)propyl]-3-oxo-1-[(3S)-oxolan-3-yloxy]-2,3-dihydro-1H-isoindol-2-yl]methyl}benzonitrile (*Both Isomers Separated and Isolated)

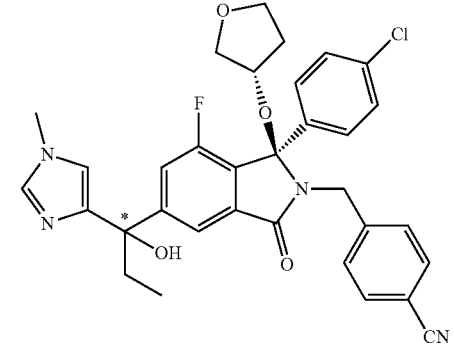 [SMILES: CCC(O)(c1cc(F)c2c(c1)C(=O)N(Cc1ccc(C#N)cc1)[C@@]2(O[C@H]1CCOC1)c1ccc(Cl)cc1)c1cn(C)cn1]

The title compounds were prepared in a similar manner as in Example 94 and Example 95, but using (3S)-hydroxy-tetrahydrofuran in Step 2. Chiral preparative HPLC gave the title compounds.

Example 96: $^1$H NMR (400 MHz, CDCl3) 7.70 (1H, d), 7.55-7.52 (1H, m), 7.46 (2H, d), 7.36 (1H, s), 7.27-7.24 (2H, m), 7.16 (4H, s), 6.85 (1H, d), 4.50 (1H, d), 4.32 (1H, d), 3.84-3.76 (2H, m), 3.70 (3H, s), 3.63-3.52 (3H, m), 3.23 (1H, dd), 2.24-2.07 (2H, m), 1.51-1.44 (2H, m), 0.84 (3H, t). MS: [M+H]$^+$=601

Example 97: $^1$H NMR (400 MHz, CDCl3) 7.81 (1H, d), 7.48-7.42 (3H, m), 7.36 (1H, s), 7.28-7.25 (2H, m), 7.17 (4H, s), 6.83 (1H, d), 4.51 (1H, d), 4.32 (1H, d), 3.82-3.75 (2H, m), 3.69 (3H, s), 3.62-3.54 (3H, m), 3.25 (1H, dd), 2.23-2.07 (2H, m), 1.49-1.42 (2H, m), 0.84 (3H, t). MS: [M+H]$^+$=601.

Examples 98 and 99: (3S)-3-(4-chlorophenyl)-3-[(1R)-1-(4-chlorophenyl)-7-fluoro-5-[1-(4-fluorooxan-4-yl)-1-hydroxyethyl]-1-methoxy-3-oxo-2,3-dihydro-1H-isoindol-2-yl]propanoic Acid (*Both Isomers Separated and Isolated)

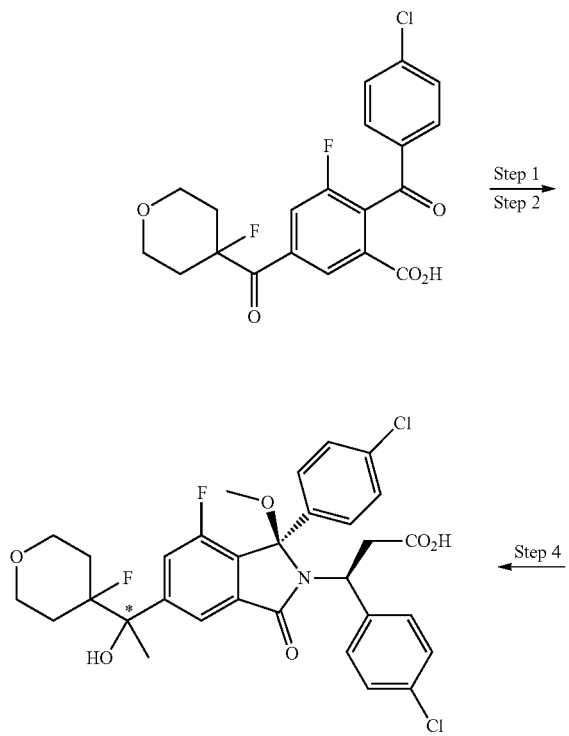
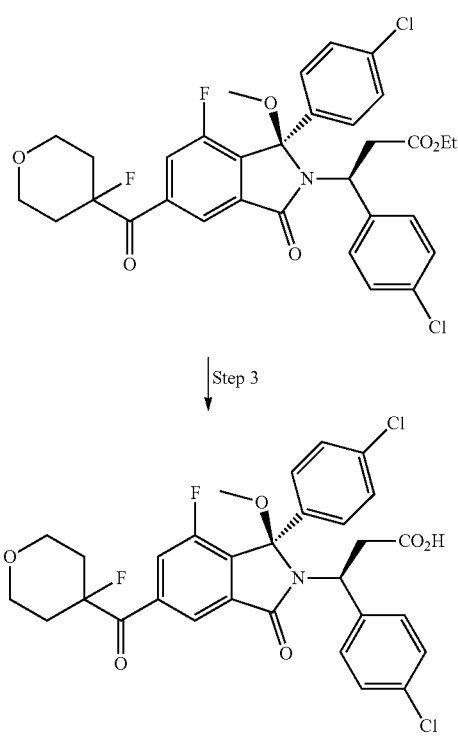

Step 1 and 2: Ethyl (3S)-3-(4-chlorophenyl)-3-(1-(4-chlorophenyl)-7-fluoro-5-(4-fluorotetrahydro-2H-pyran-4-carbonyl)-1-hydroxy-3-oxoisoindolin-2-yl)propanoate Starting from 2-(4-chlorobenzoyl)-3-fluoro-5-(4-fluorotetrahydro-2H-pyran-4-carbonyl)benzoic acid (Preparation 53), (S)-ethyl 3-amino-3-(4-chlorophenyl)propanoate hydrochloride (Preparation 35) and MeOH, Steps 1-2 were performed by following procedures similar to those described in Example 35, step 4 and Preparation 10 respectively. The diastereoisomers were separated using chiral SFC to give ethyl (S)-3-(4-chlorophenyl)-3-((R)-1-(4-chlorophenyl)-7-fluoro-5-(4-fluorotetrahydro-2H-pyran-4-carbonyl)-1-methoxy-3-oxoisoindolin-2-yl)propanoate. MS: [M-MeOH]+=600.

Step 3: (S)-3-(4-Chlorophenyl)-3-((R)-1-(4-chlorophenyl)-7-fluoro-5-(4-fluorotetrahydro-2H-pyran-4-carbonyl)-1-methoxy-3-oxoisoindolin-2-yl)propanoic Acid Step 3 was performed using procedures similar to those described in Preparation 52, Step 3. MS: [M–H]−=602.

Step 4: (3S)-3-(4-chlorophenyl)-3-[(1R)-1-(4-chlorophenyl)-7-fluoro-5-[1-(4-fluorooxan-4-yl)-1-hydroxyethyl]-1-methoxy-3-oxo-2,3-dihydro-1H-isoindol-2-yl]propanoic Acid Step 4 was performed using procedures similar to those described in Example 73, Step 5.

Example 98: *fast running isomer: $^1$H NMR (400 MHz, CDCl$_3$) 7.78 (1H, s), 7.39 (1H, d), 7.04 (4H, s), 7.00 (4H, s), 4.68 (1H, dd), 3.89-3.56 (5H, m), 3.31 (1H, dd), 3.10 (3H, s), 1.98-1.60 (7H, m), 1.44 (1H, dd); COOH missing. MS: [M+H]+=620.

Example 99: * Slow running isomer: $^1$H NMR (400 MHz, CDCl$_3$) 7.79 (1H, s), 7.39 (1H, d), 7.03 (4H, s), 7.00 (4H, s), 4.69 (1H, dd); 3.90-3.56 (5H, m), 3.30 (1H, dd), 3.11 (3H, s), 1.97-1.73 (3H, m), 1.73-1.63 (4H, m), 1.47-1.39 (1H, m); COOH missing. MS: [M+H]+=620.

Example 100: (4S)-4-(4-chlorophenyl)-4-[(1R)-1-(4-chlorophenyl)-7-fluoro-5-[1-hydroxy-1-(1-methyl-1H-pyrazol-3-yl)propyl]-1-methoxy-3-oxo-2,3-dihydro-1H-isoindol-2-yl]butanoic Acid (*Prepared as a Mixture of Epimers at the Position Shown)

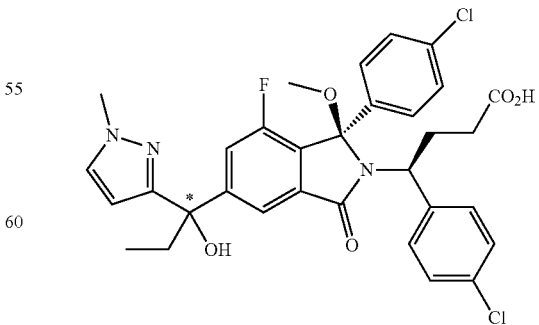

Starting from Preparation 65 and methyl (4S)-4-amino-4-(4-chlorophenyl)butanoate, the title compound was prepared using procedures similar to those described in Example 99; but using EtMgCl/ZnCl₂ instead of MeMgCl in the final step. 1H NMR (400 MHz, CDCl₃): 7.74 (1H, d), 7.49-7.44 (1H, m), 7.34 (1H, d), 7.04-7.00 (8H, m), 6.21 (1H, t), 4.23-4.15 (1H, m), 3.88 (3H, s), 3.19 (3H, d), 3.11-3.02 (1H, m), 2.55-2.44 (2H, m), 2.32-2.11 (6H, m), 0.90-0.85 (4H, m). MS: [M+H]⁺=626.

Example 101 and 102: (3S)-3-(4-chlorophenyl)-3-[(1R)-1-(4-chlorophenyl)-7-fluoro-5-[1-(4-fluorooxan-4-yl)-1-hydroxypropyl]-1-methoxy-3-oxo-2,3-dihydro-1H-isoindol-2-yl]propanoic Acid (*Both Isomers Separated and Isolated)

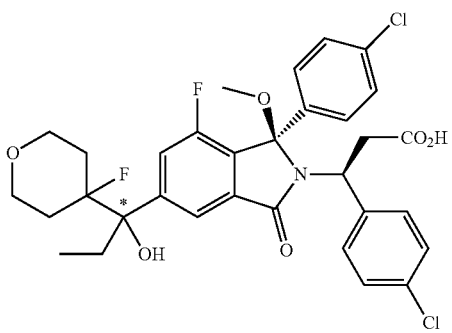 [SMILES: CCC(O)(c1cc(F)c2c(c1)C(=O)N([C@@H](CC(=O)O)c1ccc(Cl)cc1)[C@@]2(OC)c1ccc(Cl)cc1)C1(F)CCOCC1]

Starting from (S)-3-(4-chlorophenyl)-3-((R)-1-(4-chlorophenyl)-7-fluoro-5-(4-fluorotetrahydro-2H-pyran-4-carbonyl)-1-methoxy-3-oxoisoindolin-2-yl)propanoic acid (Example 99 step 3), the title compounds were prepared using procedures similar to those described in Preparation 52, Step 1. The title compounds, prepared as a mixture, were subsequently separated using chiral SFC.

Example 101: *fast running isomer: ¹H NMR (400 MHz, CDCl₃) 7.74 (1H, s), 7.39 (1H, d), 7.04 (4H, s), 7.01 (4H, d), 4.68 (1H, dd), 3.86-3.57 (5H, m), 3.30 (1H, dd), 3.10 (3H, s), 2.25-2.15 (2H, m), 2.05-1.81 (3H, m), 1.66-1.42 (2H, m), 0.69 (3H, t); COOH missing. MS: [M+H]⁺=634.

Example 102: * Slow running isomer: ¹H NMR (400 MHz, CDCl₃) 7.75 (1H, s), 7.37 (1H, d), 7.04 (4H, s), 7.01 (4H, s), 4.70 (1H, dd), 3.87-3.58 (5H, m), 3.29 (1H, dd), 3.11 (3H, s), 2.25-2.15 (2H, m), 2.02-1.80 (3H, m), 1.71-1.51 (1H, m), 1.43 (1H, dd), 0.69 (3H, t); COOH missing. MS: [M+H]⁺=634.

Example 103 and 104: (3S)-3-(4-chlorophenyl)-3-[(1R)-1-(4-chlorophenyl)-5-(1-cyclobutyl-1-hydroxyethyl)-7-fluoro-1-methoxy-3-oxo-2,3-dihydro-1H-isoindol-2-yl]propanoic Acid (*Both Isomers Separated and Isolated)

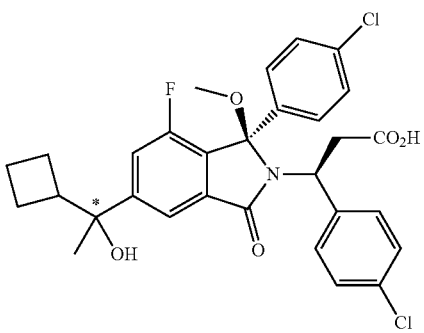 [SMILES: CO[C@]1(c2ccc(Cl)cc2)c2c(F)cc(C(C)(O)C3CCC3)cc2C(=O)N1[C@@H](CC(=O)O)c1ccc(Cl)cc1]

Starting from 2-(4-chlorobenzoyl)-5-(cyclobutanecarbonyl)-3-fluorobenzoic acid (Preparation 55) the title compound was prepared using methods similar to those described for Example 98. Except that 2M aqueous HCl solution was used instead of LiOH in Step 3.

Example 103: *fast running isomer: ¹H NMR (400 MHz, CDCl₃) 7.70 (1H, s), 7.31 (1H, d), 7.04-6.99 (4H, m), 6.98 (4H, s), 4.67 (1H, dd), 3.61-3.60 (1H, m), 3.33-3.25 (1H, m), 3.06 (3H, s), 2.74-2.65 (1H, m), 2.05-1.93 (2H, m), 1.87-1.73 (2H, m), 1.66 (1H, d), 1.56-1.54 (1H, m), 1.44 (3H, s); OH and COOH missing; MS: [M+H]⁺=572.

Example 104: * Slow running isomer: ¹H NMR (400 MHz, CDCl₃) 7.71 (1H, s), 7.29 (1H, d), 7.05-6.93 (8H, m), 4.70 (1H, dd), 3.59 (1H, s), 3.22-3.17 (1H, m), 3.06 (3H, s), 2.74-2.65 (1H, m), 2.07-1.66 (5H, m), 1.61-1.54 (1H, m), 1.44 (3H, s); OH and COOH missing; MS: [M+H]⁺=572.

Example 105: (3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]propanoic Acid

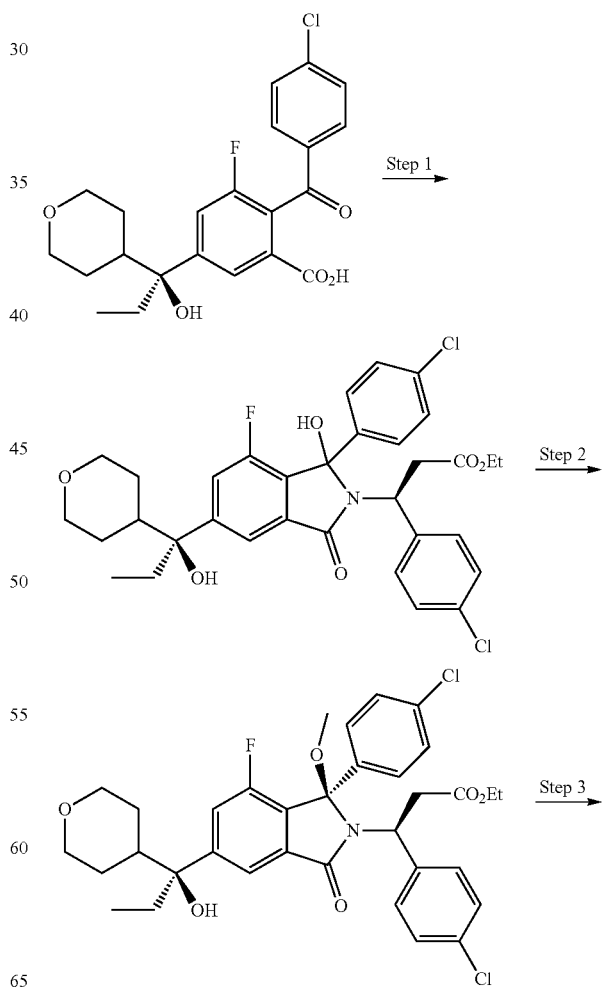

-continued

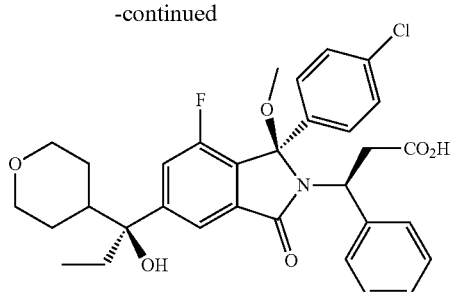

Step 1: Ethyl (3S)-3-(4-chlorophenyl)-3-(1-(4-chlorophenyl)-7-fluoro-1-hydroxy-5-((S)-1-hydroxy-1-(tetrahydro-2H-pyran-4-yl)propyl)-3-oxoisoindolin-2-yl)propanoate (S)-2-(4-Chlorobenzoyl)-3-fluoro-5-(1-hydroxy-1-(tetrahydro-2H-pyran-4-yl)propyl)benzoic acid (Preparation 52, 1.43 g, 3.39 mmol) was reacted with (S)-ethyl 3-amino-3-(4-chlorophenyl)propanoate hydrochloride (Preparation 35, 1.16 g, 4.41 mmol) in an analogous fashion as described in Example 35, step 4 to afford the title compound (1.37 g, 64%) as a colourless foam. MS: [M−H]$^-$=628.

Step 2: Ethyl (S)-3-(4-chlorophenyl)-3-((R)-1-(4-chlorophenyl)-7-fluoro-5-((S)-1-hydroxy-1-(tetrahydro-2H-pyran-4-yl)propyl)-1-methoxy-3-oxoisoindolin-2-yl)propanoate The title compound was prepared from ethyl (3S)-3-(4-chlorophenyl)-3-(1-(4-chlorophenyl)-7-fluoro-1-hydroxy-5-((S)-1-hydroxy-1-(tetrahydro-2H-pyran-4-yl)propyl)-3-oxoisoindolin-2-yl)propanoate (1.3 g, 2.06 mmol) and methanol (0.83 mL, 20 mmol) in a similar manner as described in Preparation 10. The diastereoisomers were separated using chiral SFC giving the title compound (0.39 g) as a pale yellow foam. MS: [M-MeOH]$^+$=612.

Step 3: (3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]propanoic Acid The title compound was prepared from ethyl (S)-3-(4-chlorophenyl)-3-((R)-1-(4-chlorophenyl)-7-fluoro-5-((S)-1-hydroxy-1-(tetrahydro-2H-pyran-4-yl)propyl)-1-methoxy-3-oxoisoindolin-2-yl)propanoate (0.391 g, 0.6 mmol) using procedures similar to those described in Preparation 52, Step 3. The crude product was purified by preparative HPLC to give pure title compound (80 mg) as a white solid. $^1$H NMR (400 MHz, CDCl$_3$) 7.62 (1H, d), 7.29 (1H, dd), 7.04 (4H, s), 7.00 (4H, s), 4.68 (1H, dd), 4.03 (1H, dd), 3.90 (1H, dd), 3.74 (1H, dd), 3.40-3.25 (3H, m), 3.09 (3H, s), 1.97-1.86 (3H, m), 1.73 (1H, d), 1.49-1.35 (2H, m), 1.07 (1H, d), 0.68 (3H, t); OH and COOH missing. MS: [M+H]$^+$=616.

Starting from the appropriate chiral acid intermediate (e.g. Preparation 52, Preparation 52b or Preparation 54), the following Examples were prepared using procedures similar to those described in Example 105 steps 1-3. An appropriately protected α- or β-amino acid was used in Step 1 [e.g. methyl (S)-4-amino-4-(4-chlorophenyl)butanoate or (S)-ethyl 3-amino-3-(4-chlorophenyl)propanoate hydrochloride (Preparation 35)] and an appropriate alcohol (e.g. MeOH, EtOH, CD$_3$OH) was used in Step 2.

In some cases the product was isolated as a tris(hydroxymethyl)aminomethane (TRIS) salt (by dissolving in MeOH, treated with tris(hydroxymethyl)aminomethane and evaporation).

Example 106: (3S)-3-(4-chlorophenyl)-3-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]propanoic Acid

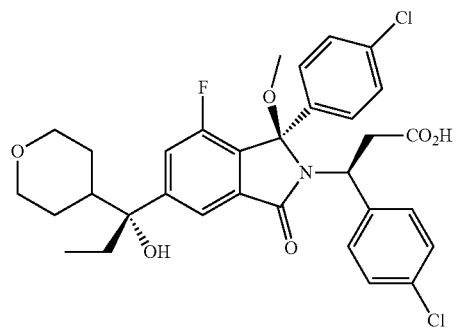 [SMILES: CC[C@](O)(c1cc(F)c2c(c1)C(=O)N([C@@H](CC(=O)O)c1ccc(Cl)cc1)[C@@]2(OC)c1ccc(Cl)cc1)C1CCOCC1]

$^1$H NMR (400 MHz, CDCl$_3$) 7.62 (1H, d), 7.28 (2H, d), 7.04 (4H, s), 7.01 (4H, s), 4.68 (1H, dd), 4.03 (1H, dd), 3.89 (1H, dd), 3.73 (1H, dd), 3.42-3.25 (3H, m), 3.10 (3H, s), 1.96-1.85 (3H, m), 1.74 (1H, d), 1.49-1.36 (2H, m), 1.06 (1H, d), 0.68 (3H, t); COOH missing. MS: [M+H]$^+$=616.

Example 107: (4S)-4-(4-chlorophenyl)-4-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]butanoic Acid

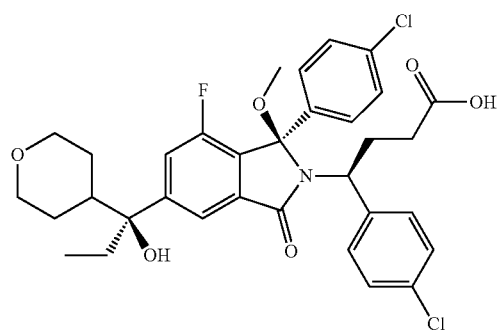 [SMILES: CC[C@@](O)(c1cc(F)c2c(c1)C(=O)N([C@@H](CCC(=O)O)c1ccc(Cl)cc1)[C@@]2(OC)c1ccc(Cl)cc1)C1CCOCC1]

$^1$H NMR (400 MHz, CDCl$_3$) 7.61 (s, 1H), 7.06-7.01 (m, 4H), 6.99 (d, 2H), 4.19 (dd, 1H), 4.02 (dd, 1H), 3.90 (dd, 1H), 3.40-3.24 (m, 2H), 3.19 (s, 3H), 3.13-3.03 (m, 1H), 2.54-2.44 (m, 1H), 2.32-2.11 (m, 2H), 2.07-1.96 (m, 1H), 1.96-1.84 (m, 3H), 1.73 (d, 3H), 1.47-1.36 (m, 3H), 1.27-1.16 (m, 1H), 1.07 (d, 1H), 0.69 (dd, 2H). MS: [M+H]$^+$=630.

Example 108: (4S)-4-(4-chlorophenyl)-4-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]butanoic Acid

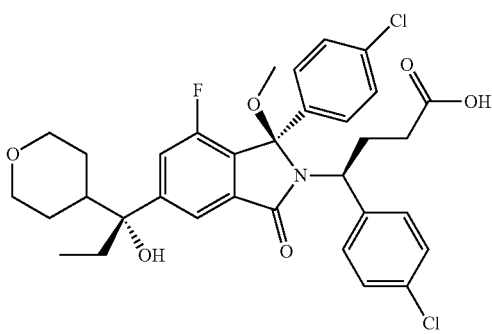 [SMILES: CC[C@](O)(c1cc(F)c2c(c1)C(=O)N([C@@H](CCC(=O)O)c1ccc(Cl)cc1)[C@@]2(OC)c1ccc(Cl)cc1)C1CCOCC1]

¹H NMR (400 MHz, CDCl₃) 7.62-7.59 (3H, m), 7.41 (2H, d), 7.35 (2H, d), 7.31-7.26 (3H, m), 4.09-4.00 (2H, m), 3.91 (1H, dd), 3.41-3.27 (2H, m), 2.88-2.77 (1H, m), 2.51-2.42 (4H, m), 2.03-1.97 (2H, m), 1.97-1.85 (2H, m), 1.73 (1H, d), 1.48-1.38 (2H, m), 1.08 (1H, d), 0.70-0.64 (3H, m); OH and COOH missing. MS: [M+H]⁺=630.

Example 109: (4S)-4-(4-Chlorophenyl)-4-[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]butanoic Acid (tris(hydroxymethyl)aminomethane Salt)

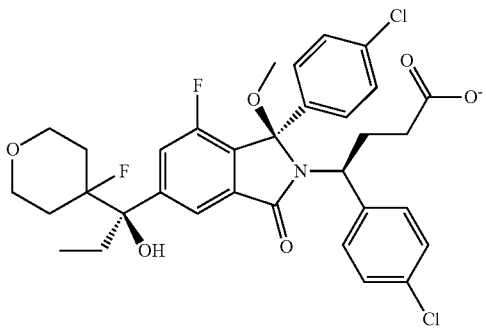

¹H NMR (400 MHz, DMSO) 7.76 (1H, s), 7.48 (1H, d), 7.18-7.12 (4H, m), 7.10-7.02 (4H, m), 4.25 (1H, dd), 3.88 (1H, dd), 3.72 (1H, dd), 3.56-3.50 (1H, m), 3.47-3.39 (1H, m), 3.37 (6H, s), 3.18 (3H, s), 2.84-2.73 (1H, m), 2.48-2.38 (1H, m), 2.26-2.17 (1H, m), 2.05-1.88 (6H, m), 1.07-0.99 (1H, m), 0.63 (3H, t); 7 protons missing (OH×4, NH2 and COOH). MS: [M+H]⁺=648.

Example 110: (3S)-3-(4-chlorophenyl)-3-[(1R)-1-(4-chlorophenyl)-7-fluoro-5-[(1R)-1-(4-fluorooxan-4-yl)-1-hydroxypropyl]-1-trideuteromethoxy-3-oxo-2,3-dihydro-1H-isoindol-2-yl]propanoic Acid

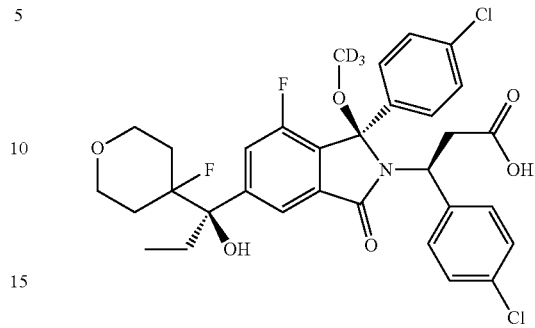

¹H NMR (400 MHz, CDCl₃) 7.61 (1H, s), 7.26 (1H, d), 7.07-6.99 (8H, m), 4.19 (1H, dd), 3.51-3.43 (1H, m), 3.19 (3H, s), 3.14-3.04 (1H, m), 2.53-2.44 (1H, m), 2.30-1.85 (7H, m), 1.67-1.60 (1H, m), 1.31-1.07 (5H, m), 0.66 (3H, dd). MS: [M+H]⁺=637.

Example 111: (3S)-3-(4-chlorophenyl)-3-[(1R)-1-(4-chlorophenyl)-1-ethoxy-7-fluoro-5-[(1R)-1-(4-fluorooxan-4-yl)-1-hydroxypropyl]-3-oxo-2,3-dihydro-1H-isoindol-2-yl]propanoic Acid

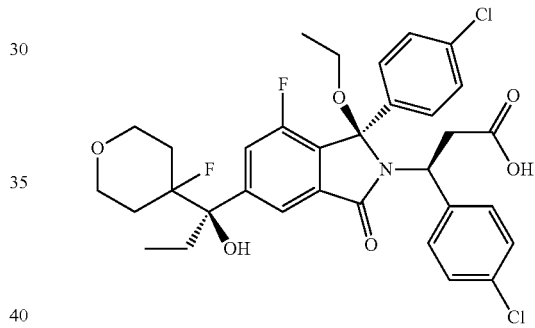

¹H NMR (400 MHz, CDCl₃) 7.73 (1H, s), 7.36 (1H, d), 7.06-7.00 (8H, m), 4.69 (1H, dd), 3.86-3.75 (3H, m), 3.66-3.57 (2H, m), 3.30-3.12 (3H, m), 2.26-2.13 (2H, m), 2.02-1.82 (3H, m), 1.67-1.40 (3H, m), 1.28 (3H, dd), 0.68 (3H, dd). MS: [M+H]⁺=637.

Example 113: (4S)-4-[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]-4-(4-methoxyphenyl)butanoic Acid

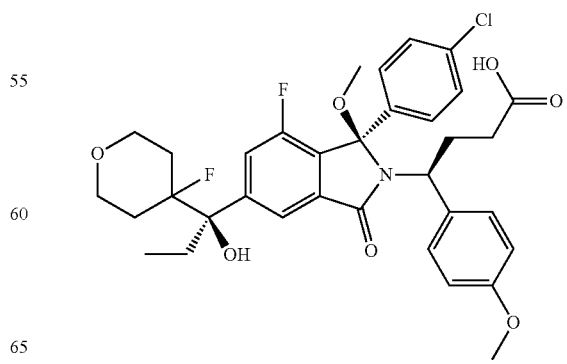

¹H NMR (400 MHz, CDCl3) 7.73 (1H, s), 7.35 (1H, d), 7.05-6.93 (6H, m), 6.58 (2H, d), 4.16 (1H, dd), 3.81 (2H, d), 3.73 (3H, s), 3.66-3.58 (2H, m), 3.17 (3H, s), 3.11-3.10 (1H, m), 2.51-2.42 (1H, m), 2.31-2.28 (4H, m), 2.27-2.13 (3H, m), 1.69-1.44 (2H, m), 0.69 (3H, dd); COOH not observed. MS: [M+H]⁺=644.

Example 114: (4S)-4-(4-chlorophenyl)-4-[(1R)-1-(4-chlorophenyl)-7-fluoro-5-{1-hydroxy-1-[trans-4-hydroxycyclohexyl]propyl}-1-methoxy-3-oxo-2,3-dihydro-1H-isoindol-2-yl]butanoic Acid

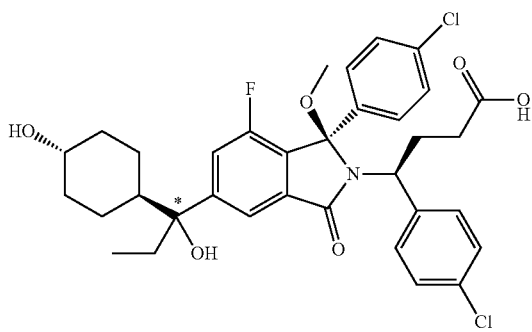

(*Example prepared and isolated as a single isomer at the position shown*)

Starting from the single isomer of 2-(4-chlorobenzoyl)-3-fluoro-5-(1-hydroxy-1-trans-4-hydroxycyclohexyl)propyl)benzoic acid (Preparation 64, Step 3), the title compound was prepared by following procedures similar to those described in Example 105. ¹H NMR (400 MHz, CDCl₃) 7.61 (1H, s), 7.26 (1H, d), 7.07-6.99 (8H, m), 4.19 (1H, dd), 3.51-3.43 (1H, m), 3.19 (3H, s), 3.14-3.04 (1H, m), 2.53-2.44 (1H, m), 2.30-1.85 (7H, m), 1.67-1.60 (1H, m), 1.31-1.07 (5H, m), 0.66 (3H, dd), exchangeable not observed. MS: [M+H]⁺=644.

Example 115: 2-(5-chloro-2-{[1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}phenoxy)acetic Acid (tris(hydroxymethyl)aminomethane salt)

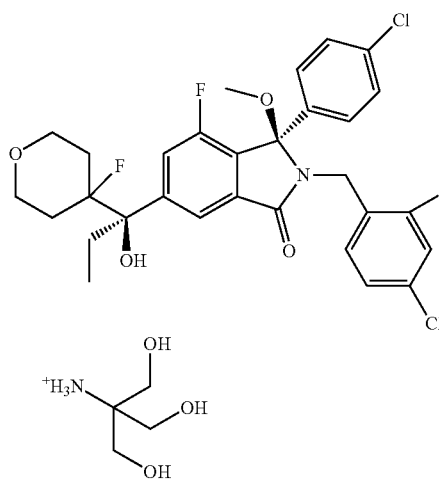

Starting from (R)-2-(4-chlorobenzoyl)-3-fluoro-5-(1-(4-fluorotetrahydro-2H-pyran-4-yl)-1-hydroxypropyl)benzoic acid (Preparation 54) and ethyl 2-[2-(aminomethyl)-5-chlorophenoxy]acetate hydrochloride (Preparation 63), the title compound was prepared by following procedures similar to those described in Example 105. ¹H NMR (400 MHz, DMSO-d₆-D₂O): 7.71 (1H, s), 7.40 (1H, d), 7.26-7.17 (4H, m), 6.91 (1H, d), 6.67 (1H, dd), 6.50 (1H, d), 4.38 (2H, s), 4.19-4.00 (2H, m), 3.84-3.74 (1H, m), 3.66 (1H, dd), 3.46 (7H, s), 2.84 (3H, s), 2.19-2.03 (1H, m), 1.99-1.74 (4H, m), 1.14 (1H, d), 1.04-0.95 (1H, m), 0.56 (3H, t). MS: [M+H]⁺=650.

Example 116: 5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}benzoic Acid

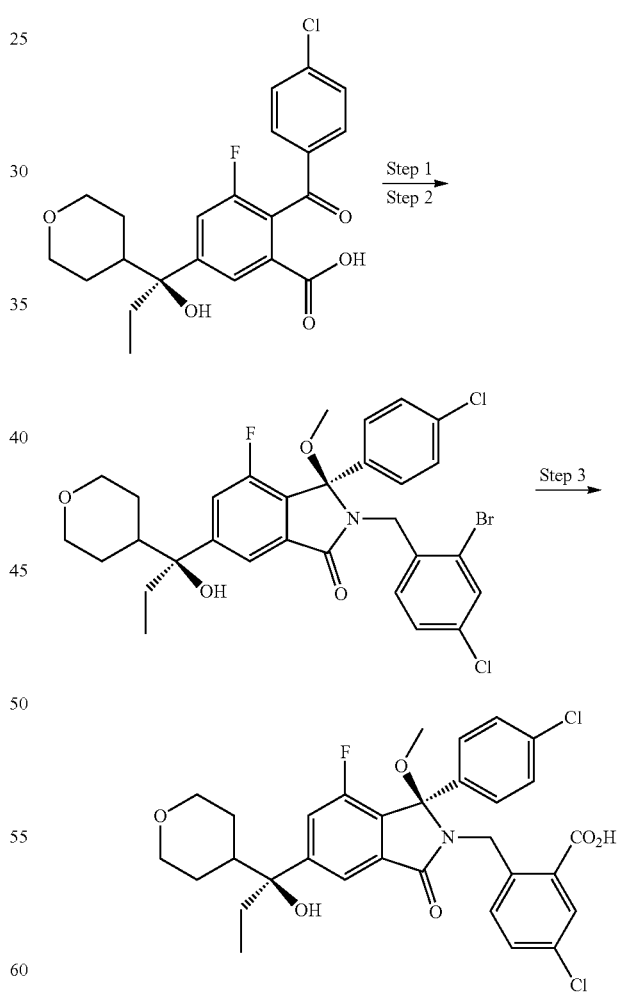

Step 1 and Step 2: Starting from (−)-(S)-2-(4-chlorobenzoyl)-3-fluoro-5-(1-hydroxy-1-(tetrahydro-2H-pyran-4-yl)propyl)benzoic acid (Preparation 52), (2-bromo-4-chlorophenyl)methanamine (Example 33, Step 1) and MeOH, Step 1 and Step 2 were performed by following procedures similar to those described in Example 35, step 4 and Preparation 10 respectively Chiral separation using supercritical fluid chromatography gave (R)-2-(2-bromo-4-chlorobenzyl)-3-(4-chlorophenyl)-4-fluoro-6-((S)-1-hydroxy-1-(tetrahydro-2H-pyran-4-yl)propyl)-3-methoxyisoindolin-1-one. MS: [M+H]$^+$=638

Step 3: 5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}benzoic Acid The title compound was prepared in a similar manner to that described for Example 33, step 5. $^1$H NMR (400 MHz, DMSO) 7.78 (1H, s), 7.69 (1H, s), 7.50 (1H, d), 7.37-7.31 (5H, m), 7.24 (1H, s), 4.98 (1H, s), 4.94-4.81 (2H, m), 3.98-3.93 (1H, m), 3.82 (1H, dd), 3.40-3.30 (1H, m), 3.28-3.21 (1H, m), 2.88 (3H, s), 2.05-1.90 (3H, m), 1.73 (1H, d), 1.48-1.30 (2H, m), 1.02 (1H, d), 0.65 (3H, t), COOH missing. MS: [M+H]$^+$=602.

Starting from the appropriate chiral acid intermediate (e.g. Preparation 52, Preparation 54), the following Examples were prepared using procedures similar to those described in Example 116 steps 1-3. The appropriate benzylamine [e.g. (2-bromo-4-chlorophenyl)methanamine, Preparation 58 or Preparation 59] was used in Step 1 and an appropriate alcohol used in Step 2. In some cases the product was isolated as a tris(hydroxymethyl)aminomethane (TRIS) salt (by dissolving in MeOH, treated with tris(hydroxymethyl)aminomethane and evaporation). Purification by preparative HPLC gave the products as single isomers, with the configuration shown.

Example 117: 5-chloro-2-{[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]methyl}benzoic Acid

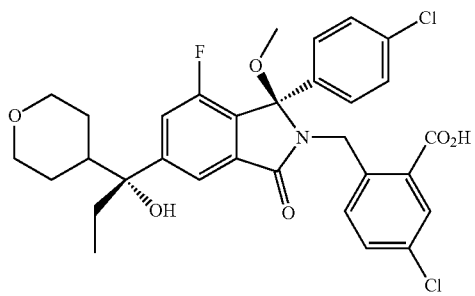 [SMILES: CC[C@](O)(c1cc(F)c2c(c1)C(=O)N(Cc1ccc(Cl)cc1C(=O)O)[C@@]2(OC)c1ccc(Cl)cc1)C1CCOCC1]

Prepared from (+)-(R)-2-(4-chlorobenzoyl)-3-fluoro-5-(1-hydroxy-1-(tetrahydro-2H-pyran-4-yl)propyl)benzoic acid (Preparation 52b). $^1$H NMR (400 MHz, CDCl$_3$) 7.73 (2H, d), 7.30-7.18 (6H, m, overlapping CHCl3), 7.14 (1H, d), 5.12 (1H, d), 4.64 (1H, d), 4.01 (1H, dd), 3.84 (1H, d), 3.37-3.19 (2H, m), 2.81 (3H, s), 1.98-1.71 (4H, m), 1.71 (1H, d), 1.45-1.33 (2H, m), 1.05-0.99 (1H, m), 0.64 (3H, t). COOH missing MS: [M+H]$^+$=602.

Example 118: 5-chloro-2-{[(1R)-1-(4-chlorophenyl)-1-ethoxy-7-fluoro-5-[(1S)-1-hydroxy-1-(oxan-4-yl)propyl]-3-oxo-2,3-dihydro-1H-isoindol-2-yl]methyl}benzoic acid-(tris(hydroxymethyl)aminomethane salt)

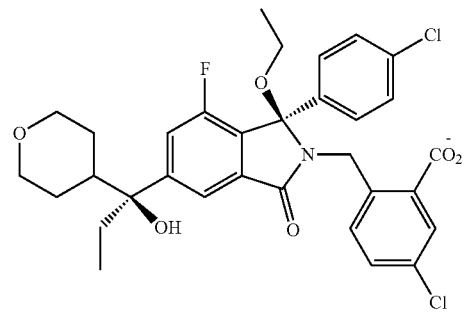

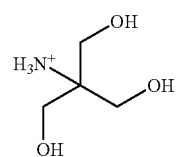

$^1$H NMR (400 MHz, CDCl$_3$) 7.79 (1H, s), 7.50 (1H, s), 7.21 (2H, d), 7.08-7.00 (2H, m), 6.82 (1H, d), 5.02 (2H, s), 4.59-4.59 (3H, m), 3.97-3.94 (1H, m), 3.85-3.81 (1H, m), 3.73 (6H, s), 3.33-3.17 (2H, m), 3.06-2.94 (2H, m), 1.84-1.59 (4H, m), 1.43-1.34 (2H, m), 1.00 (4H, dd), 0.55 (3H, t), one exchangeable proton not observed. MS: [M+H]$^+$=616.

Example 119: 2-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}-5-methylbenzoic Acid

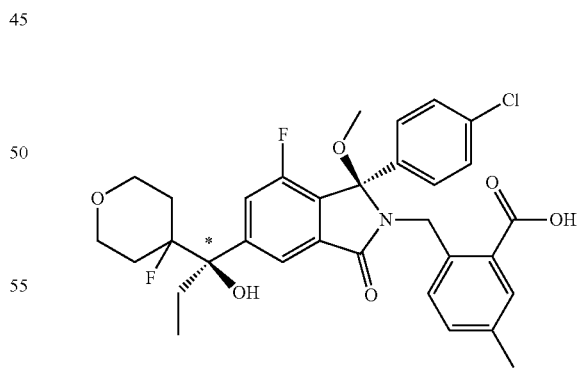

$^1$H NMR (400 MHz, CDCl3) 7.78 (1H, s), 7.69 (1H, s), 7.40-7.31 (4H, m), 7.26-7.19 (3H, m), 4.99 (1H, d, J=15.4 Hz), 4.83 (1H, d, J=15.4 Hz), 3.86-3.77 (2H, m), 3.68-3.57 (2H, m), 2.80 (3H, s), 2.34 (3H, s), 2.25-2.14 (1H, m), 2.00-1.80 (2H, m), 1.70-1.42 (3H, m), 1.26 (1H, s), 0.69 (3H, dd); COOH not observed. [M+H]$^+$=601

Example 120: 2-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}-5-methoxybenzoic acid-tris (hydroxymethyl)aminomethane salt

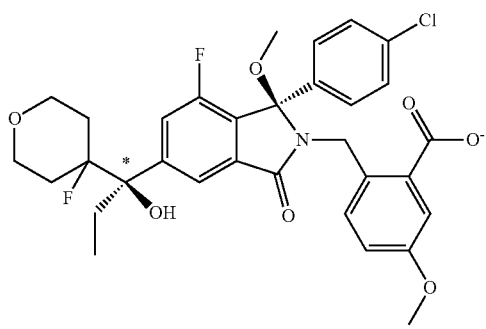

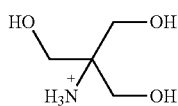

$^1$H NMR (400 MHz, CDCl3) 7.83 (1H, s), 7.32-7.18 (5H, m), 7.13-7.13 (1H, m), 6.95 (1H, d), 6.68 (1H, d), 4.92 (2H, d), 4.65 (1H, d), 3.82-3.78 (1H, m), 3.72 (6H, s), 3.61-3.48 (4H, m), 2.87 (3H, s), 2.62 (1H, s), 2.08-2.00 (1H, m), 1.94-1.60 (6H, m), 1.26-1.16 (1H, m), 0.55 (3H, s). [M+H]+=616

Example 121: 2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)-2-methylpropanoic Acid (tris (hydroxymethyl)aminomethane Salt)

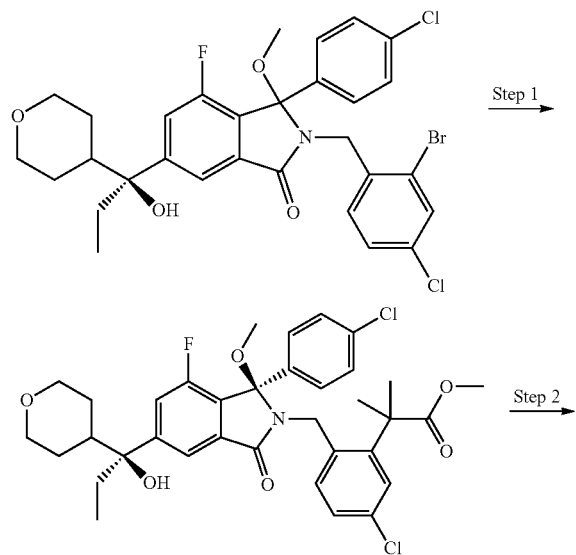

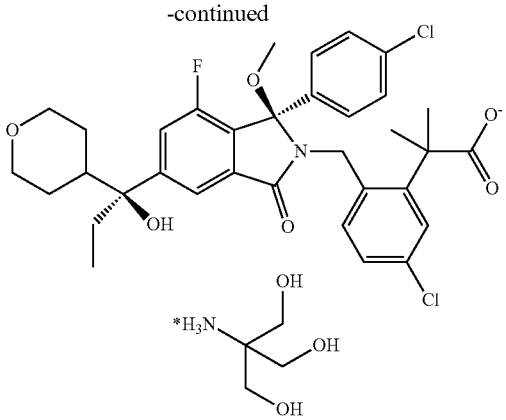

Step 1: Methyl 2-(5-chloro-2-(((R)-1-(4-chlorophenyl)-7-fluoro-5-((S)-1-hydroxy-1-(tetrahydro-2H-pyran-4-yl)propyl)-1-methoxy-3-oxoisoindolin-2-yl)methyl)phenyl)-2-methylpropanoate A diastereomeric mixture at C-3 of 2-(2-bromo-4-chlorobenzyl)-3-(4-chlorophenyl)-4-fluoro-6-((S)-1-hydroxy-1-(tetrahydro-2H-pyran-4-yl)propyl)-3-methoxyisoindolin-1-one (1 g, prepared as in Example 116, Step 2 (omitting chiral separation), methyl trimethylsilyl dimethylketene acetal (820 mg, 4.71 mmol), zinc fluoride (486.6 mg, 4.71 mmol) and di-u-bromobis(tri-t-butylphosphonino) dipalladium (I) {[P(t-Bu)₃]PdBr} (STREM) (243 mg, 0.314 mmol) were placed in a round bottomed flask under nitrogen then degassed DMF (20 mL) was added. The reaction was degassed with nitrogen for a further 5 minutes then heated (using a pre-heated stirrer block set at 70° C.) for 18 h. The reaction was allowed to cool and degassed for 10 min. The reaction was charged with further methyl trimethylsilyl dimethylketene acetal (858 mg, 4.92 mmol), zinc fluoride (500 mg, 4.84 mmol) and {[P(t-Bu)₃]PdBr} (250 mg, 0.32 mmol) then heated (using a pre-heated stirrer block set at 70° C.) for 4 h. The reaction was allowed to cool and then the DMF was removed under reduced pressure. Water (20 mL) and EtOAc (50 mL) was added and the resulting black suspension was filtered. The layers of the filtrate were separated and the organics retained. The aqueous portion was extracted with EtOAc (20 mL) then the combined organic extracts were dried (MgSO₄) and concentrated under reduced pressure to afford a black residue (1.5 g). The residue was dissolved in THF (15 mL) at RT with stirring and 1M TBAF solution in THF (7.75 ml) was added. The reaction was stirred for 15 min at RT. The reaction was diluted with EtOAc (60 mL) and washed with water (20 mL). The organic portion was dried (MgSO₄) and concentrated under reduced pressure to afford a black residue (1.4 g). The crude material was purified by column chromatography using an isocratic gradient of diethyl ether 75% in isohexane, to afford a foam (540 mg). The two diastereoisomers were separated by chiral SFC to yield the title compound as the fast running isomer (300 mg). MS [M-C3 Methoxy]+=626.1

Step 2: 2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)-2-methylpropanoic Acid Methyl 2-(5-chloro-2-(((R)-1-(4-chlorophenyl)-7-fluoro-5-((S)-1-hydroxy-1-(tetrahydro-2H-pyran-4-yl)propyl)-1-methoxy-3-oxoisoindolin-2-yl)methyl)phenyl)-2-methyl-propanoate (300 mg) was dissolved in THF (22 mL) then a solution on lithium hydroxide monohydrate (109.1 mg, 4.5 mmol) in water (7.5 mL) and methanol (4.5 mL) was added at RT with stirring. The reaction was heated at 65° C. for four days then at 75° C. for one day. The reaction was allowed to cool then the volatiles were removed under reduced pressure. The resulting emulsion was diluted with ether (50 mL) and water (20 mL) and the pH adjusted (by the addition of 2M aqueous HCl) to facilitate extraction of the product into the organic layer. The organic portion was passed through a phase separation cartridge and the volatiles were removed under reduced pressure to afford a crude foam (200 mg). The crude material was purified by column chromatography, eluting with a gradient of 0-100% diethyl ether in isohexane followed by washing with 100% EtOAc with 0.1% formic acid additive to afford a crude mixture (70 mg). Further purification by Prep HPLC afforded the title compound (46 mgs) as a colourless foam. The product was then isolated as the TRIS-salt by dissolving in MeOH, treating with TRIS and evaporating. $^1$H NMR (400 MHz, CDCl$_3$) 7.74 (1H, s), 7.31 (1H, s), 7.31-7.28 (1H, m), 7.24 (3H, s), 7.17 (2H, d), 7.08 (1H, d), 7.01 (1H, dd), 4.50-4.37 (2H, m), 4.04 (1H, dd), 3.92 (1H, dd), 3.43 (6H, s), 3.39-3.28 (2H, m), 2.96 (3H, s), 2.73 (1H, dd), 2.01-1.89 (3H, m), 1.73 (1H, s), 1.52-1.50 (6H, m), 1.14-1.07 (1H, m), 0.72 (3H, dd) (7 exchangeable protons not observed). MS [M+H]$^+$=644.

Example 122: 2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)acetic Acid (tris(hydroxymethyl)aminomethane salt)

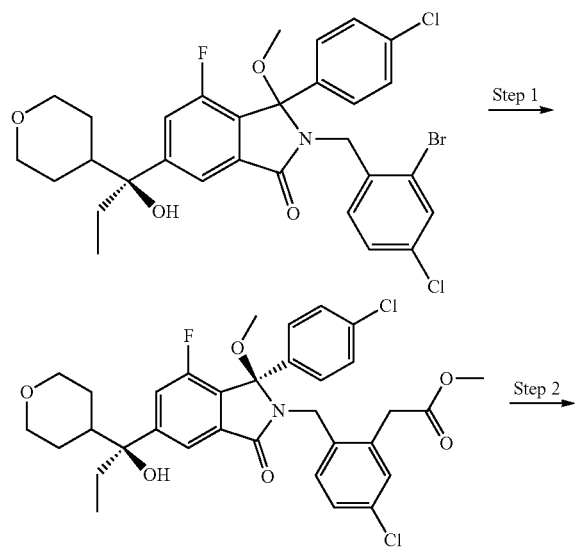

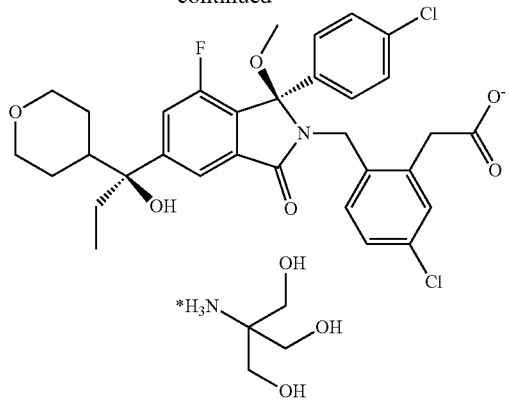

Step 1: Methyl 2-(5-chloro-2-(((R)-1-(4-chlorophenyl)-7-fluoro-5-((S)-1-hydroxy-1-(tetrahydro-2H-pyran-4-yl)propyl)-1-methoxy-3-oxoisoindolin-2-yl)methyl)phenyl)acetate 1-(tert-Butyldimethylsilyloxy)-1-methoxyethene (1270.3 mg, 6.75 mmol), zinc fluoride (697.5 mg, 6.75 mmol), tri-t-butylphosphine (136 mg, 0.67 mmol) and bis(dibenzylideneacetone) palladium(0) (193.9 mg, 0.337 mmol) were divided evenly between two reaction tubes. A degassed solution of a diastereomeric mixture at C-3 of 2-(2-bromo-4-chlorobenzyl)-3-(4-chlorophenyl)-4-fluoro-6-((S)-1-hydroxy-1-(tetrahydro-2H-pyran-4-yl)propyl)-3-methoxy-isoindolin-1-one (860 mg, 1.35 mmol, prepared as in Example 116 Step 2 omitting chiral separation) in DMF (20 mL) was divided evenly between the two reaction tubes. The mixture in each tube was degassed with nitrogen for a further 30 s prior to being sealed then stirred with heating (using a pre-heated stirrer block set at 70° C.) for 18 h. The reaction was allowed to cool to RT and DMF was removed under reduced pressure. Water (20 mL) and EtOAc (50 mL) was added and the resulting black suspension filtered. The layers of the filtrate were separated and the organics retained. The aqueous portion was extracted with EtOAc (20 mL) then the combined organic extracts were dried (MgSO$_4$) and concentrated under reduced pressure to afford a black residue (1.5 g). The crude material was purified by column chromatography with a gradient of 50-90% diethyl ether in isohexane to afford a colourless foam (510 mg). The two diastereoisomers were separated by chiral SFC to yield the title compound as the fast running isomer (140 mg, 33% yield). MS [M-C3 methoxy]$^+$=598.1

Step 2: 2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)acetic Acid (tris(hydroxymethyl)aminomethane salt)

Step 2 was performed using conditions similar to those described in Preparation 52 Step 3 to give the title compound. $^1$H NMR (400 MHz, CDCl$_3$) 7.78 (1H, s), 7.25-7.18 (4H, m), 7.14 (1H, d), 7.06-6.97 (3H, m), 4.70 (1H, d), 4.21 (1H, d), 4.00 (1H, d), 3.86 (1H, d), 3.70 (1H, d), 3.59 (6H, s), 3.54 (1H, d), 3.38-3.22 (3H, m), 2.74 (3H, s), 1.89-1.78 (2H, m), 1.69 (1H, d), 1.48-1.34 (2H, m), 1.05 (1H, d), 0.64 (3H, dd), seven exchangeable protons not observed. MS [M+H]$^+$=616

Example 123: 2-(5-chloro-2-{[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]methyl}phenyl)acetic Acid

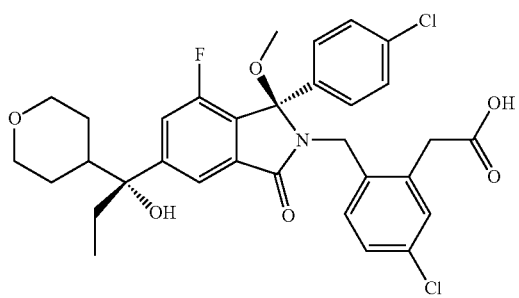 [SMILES: CC[C@](O)(c1cc(F)c2c(c1)C(=O)N(Cc1ccc(Cl)cc1CC(=O)O)[C@@]2(OC)c1ccc(Cl)cc1)C1CCOCC1]

The title compound was prepared in a similar fashion to Example 122, but starting from (+)-(R)-2-(4-chlorobenzoyl)-3-fluoro-5-(1-hydroxy-1-(tetrahydro-2H-pyran-4-yl)propyl)benzoic acid (prepared in a similar fashion to Preparation 52). $^1$H NMR (400 MHz, CDCl$_3$) 7.67 (s, 2H), 7.30-7.10 (m, 7H), 4.71 (d, 1H), 4.15 (d, 1H), 4.03 (dd, 1H), 3.88 (dd, 1H), 3.80 (d, 1H), 3.72 (d, 1H), 3.37 (t, 1H), 3.25 (t, 1H), 2.72 (s, 3H), 1.95-1.82 (m), 1.71 (d, 1H), 1.48-1.32 (m, 2H), 1.10-0.98 (m, 1H), 0.91-0.80 (m, 1H), 0.65 (t, 3H). MS [M-OMe$^-$]$^+$=584

Example 124: (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic Acid

Step 1: Prop-2-en-1-yl (2S,3S)-3-(4-chlorophenyl)-3-[1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate To a solution of (S)-2-(4-chlorobenzoyl)-3-fluoro-5-(1-hydroxy-1-(tetrahydro-2H-pyran-4-yl)propyl)benzoic acid (Preparation 52) (0.686 g, 1.6 mmol), prop-2-en-1-yl (2S,3S)-3-amino-3-(4-chlorophenyl)-2-methylpropanoate (Preparation 62) (0.54 g, 2.12 mmol) and diisopropylethylamine (0.83 mL, 4.8 mmol) in DMF (15 mL) was added HATU (0.91 g, 2.4 mmol) and the reaction mixture was stirred for 2 hrs. Water was added and extracted with ethyl acetate. The organic phase was washed with saturated NaHCO$_3$, brine, dried and the solvent evaporated. The crude product was purified by chromatography to afford the title compound (0.75 g, 72%). MS: [M−H]$^-$=654.

Step 2: Prop-2-en-1-yl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate The title compound was prepared from ethyl (2S,3S)-3-(4-chlorophenyl)-3-[1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate and methanol in a similar manner as described in Preparation 10, but using MeOH instead of 1,1-bis(hydroxymethyl)cyclopropane. The diastereoisomers were separated by chiral SFC, the title compound was the faster eluting isomer. MS: [M+H]$^+$=670.

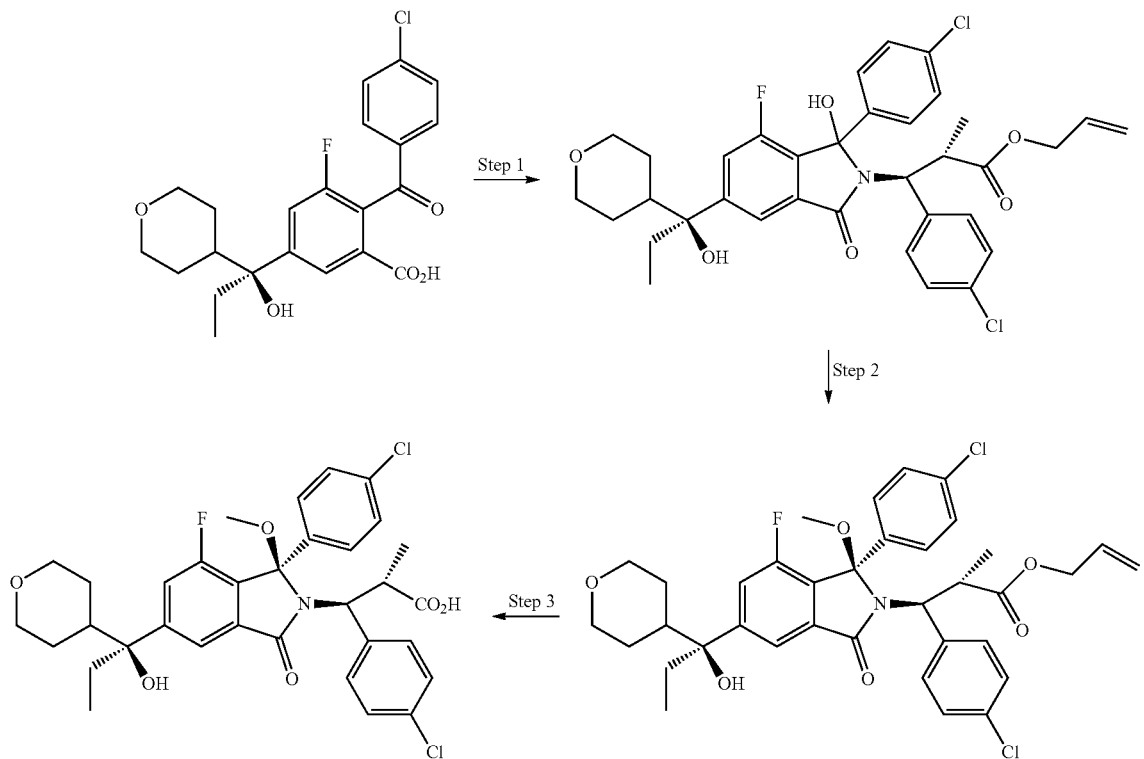

Step 3: (2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic Acid The title compound was prepared from prop-2-en-1-yl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy- 1H), 1.41-1.24 (m, 2H), 1.19 (d, J=6.8 Hz, 3H), 0.93 (d, J=13.2 Hz, 1H), 0.57 (t, J=7.3 Hz, 3H). MS: [M+H]⁺=630.

Example 125 and 126: (3S)-3-(4-chlorophenyl)-3-[(1R)-1-(4-chlorophenyl)-7-fluoro-1-[(3-fluorooxetan-3-yl)methoxy]-5-(2-hydroxybutan-2-yl)-3-oxo-2,3-dihydro-1H-isoindol-2-yl]propanoic acid (*Both Isomers Separated and Isolated)

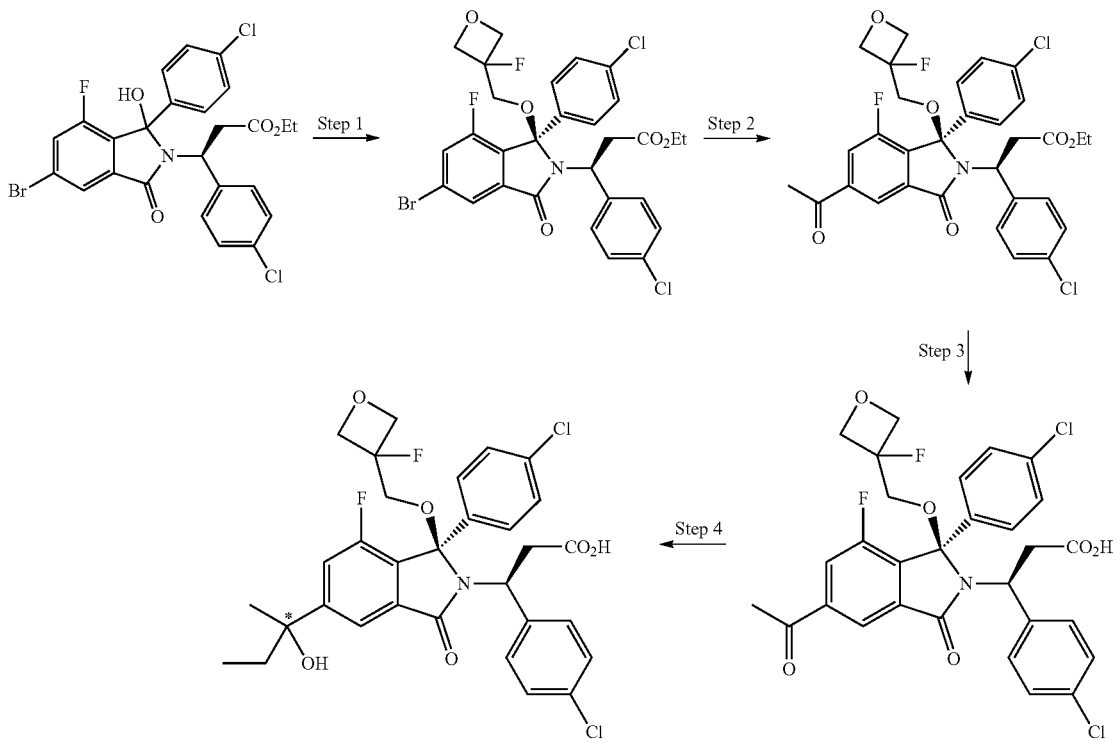

3-oxo-2,3-dihydro-1H-isoindol-2-yl]-2-methylpropanoate in an analogous fashion as described in Example 90, step 4. 1H NMR (400 MHz, DMSO-d6): 12.56-12.00 (1H, m), 7.71 (1H, s), 7.42 (1H, d), 7.02 (4H, d), 6.88 (3H, d), 4.91 (1H, s), 4.23 (1H, d), 3.99-3.85 (2H, m), 3.75 (1H, dd), 3.25-3.10 (5H, m), 2.02-1.90 (1H, m), 1.90-1.78 (2H, m), 1.67 (1H, d), 1.43-1.17 (6H, m), 0.95 (1H, d), 0.58 (3H, t). MS: [M+H]⁺=630.

Example 124a: (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic Acid (tris (hydroxymethyl)aminomethane salt)

Example 124 was dissolved in EtOH and 1 mol. eq. of tris(hydroxymethyl)aminomethane was added. The solvent was removed in vacuo to give a colourless solid. ¹H NMR (500 MHz, DMSO-d6) δ 7.69 (s, 1H), 7.39 (d, J=10.7 Hz, 1H), 7.01 (broad s, 4H), 6.96-6.88 (m, 4H), 4.92 (broad s, 1H), 4.34-4.22 (m, 1H), 3.88 (dd, J=10.9, 4.2 Hz, 1H), 3.74 (dd, J=11.1, 4.2 Hz, 1H), 3.71-3.61 (m, 1H), 3.29 (s, 6H), 3.33-3.22 (m, 1H), 3.21-3.14 (m, 1H), 3.13 (s, 3H), 1.94 (tt, J=12.2, 3.6 Hz, 1H), 1.89-1.78 (m, 2H), 1.66 (d, J=12.8 Hz, Step 1: Ethyl (S)-3-((R)-5-bromo-1-(4-chlorophenyl)-7-fluoro-1-(((3-fluorooxetan-3-yl)methoxy)-3-oxoisoindolin-2-yl)-3-(4-chlorophenyl)propanoate The title compound was prepared from (3S)-ethyl 3-(5-bromo-1-(4-chlorophenyl)-1-hydroxy-3-oxoisoindolin-2-yl)-3-(4-chlorophenyl)propanoate (Preparation 36, 7.19 g, 12.7 mmol) and (3-fluorooxetan-3-yl)methanol (4.00 g, 38 mmol) in a similar manner as described in Preparation 10. The diastereoisomers were separated by column chromatography eluting with DCM. The title compound was obtained as a colourless solid (1.93 g). MS: [M-(3-fluorooxetan-3-yl)methanol]⁺=550.

Step 2: Step 2 was performed by using procedures similar to those described in Example 21 Step 3, to give ethyl (S)-3-((R)-5-acetyl-1-(4-chlorophenyl)-7-fluoro-1-((3-fluorooxetan-3-yl)methoxy)-3-oxoisoindolin-2-yl)-3-(4-chlorophenyl)propanoate (1.29 g) as a yellow solid. MS: [M-(3-fluorooxetan-3-yl)methanol]⁺=512.

Step 3: (S)-3-((R)-5-Acetyl-1-(4-chlorophenyl)-7-fluoro-1-((3-fluorooxetan-3-yl)methoxy)-3-oxoisoindolin-2-yl)-3-(4-chlorophenyl)propanoic Acid The title compound was prepared from ethyl (S)-3-((R)-5-acetyl-1-(4-chlorophenyl)-7-fluoro-1-((3-fluorooxetan-3-yl)methoxy)-3-oxoisoindolin-2-yl)-3-(4-chlorophenyl)propanoate (1.19 g, 1.92 mmol) using procedures similar to those described in Preparation 52, Step 3 The crude product was obtained as a sticky orange solid (1.26 g). MS: [M+H]$^+$=590.

Step 4: (3S)-3-(4-chlorophenyl)-3-[(1R)-1-(4-chlorophenyl)-7-fluoro-1-[(3-fluorooxetan-3-yl)methoxy]-5-(2-hydroxybutan-2-yl)-3-oxo-2,3-dihydro-1H-isoindol-2-yl]propanoic Acid The title compound was prepared by using procedures similar to those described in Example 41, Step 3; except using ethylmagnesium chloride instead of (tetrahydro-2H-pyran-4-yl)magnesium chloride.

Example 125: *fast running isomer: $^1$H NMR (400 MHz, CDCl$_3$) 7.73 (1H, d), 7.38 (1H, dd), 7.04-6.94 (8H, m), 4.93-4.72 (3H, m), 4.68-4.59 (2H, m), 3.73-3.62 (2H, m), 3.52-3.36 (2H, m), 1.89-1.80 (2H, m), 1.59 (3H, s), 0.80 (3H, dd); OH and COOH missing. MS: [M+H]$^+$=620.

Example 126: * Slow running isomer: $^1$H NMR (400 MHz, CDCl$_3$) 7.74 (1H, s), 7.37 (1H, d), 7.02-6.95 (8H, m), 4.93-4.59 (5H, m), 3.72-3.63 (2H, m), 3.52-3.37 (2H, m), 1.89-1.81 (2H, m), 1.58 (3H, s), 0.82 (3H, dd); OH and COOH missing. MS: [M+H]$^+$=620.

Examples 127 and 128: (3S)-3-(4-chlorophenyl)-3-[(1R)-1-(4-chlorophenyl)-7-fluoro-5-[1-hydroxy-1-(pyridin-2-yl)propyl]-1-methoxy-3-oxo-2,3-dihydro-1H-isoindol-2-yl]propanoic Acid (*Both Isomers Separated and Isolated)

Step 1: Ethyl (3S)-3-(4-chlorophenyl)-3-[1-(4-chlorophenyl)-7-fluoro-1-hydroxy-3-oxo-5-(pyridine-2-carbonyl)-2,3-dihydro-1H-isoindol-2-yl]propanoate To a stirred solution of 2-(4-chlorobenzoyl)-3-fluoro-5-(pyridine-2-carbonyl)benzoic acid (preparation 61) (0.48 g, 1.25 mmol), (S)-ethyl 3-amino-3-(4-chlorophenyl)propanoate hydrochloride (0.47 g, 1.87 mmol) and diisopropyl ethylamine (0.9 mL, 5.0 mmol) in DMF (15 mL) was added N-propylphosphonic acid anhydride, cyclic trimer (50% w/w, 1.211 mL, 1.87 mmol) and the reaction mixture was stirred for 1 h. Water was added and the product was extracted with ethyl acetate. The crude product was purified by chromatography, eluted with petrol ether-ethyl acetate 0-50% to afford the title compound (0.36 g, 39%). MS: [M+H]$^+$=384.

Step 2: Ethyl (3S)-3-(4-chlorophenyl)-3-[(1R)-1-(4-chlorophenyl)-7-fluoro-1-methoxy-3-oxo-5-(pyridine-2-carbonyl)-2,3-dihydro-1H-isoindol-2-yl]propanoate The title compound was prepared from ethyl (3S)-3-(4-chlorophenyl)-3-[1-(4-chlorophenyl)-7-fluoro-1-hydroxy-3-oxo-5-(pyridine-2-carbonyl)-2,3-dihydro-1H-isoindol-2-yl]propanoate and methanol in a similar manner as described in Preparation 10. The diastereoisomers were separated by column chromatography [M+H]$^+$=607.

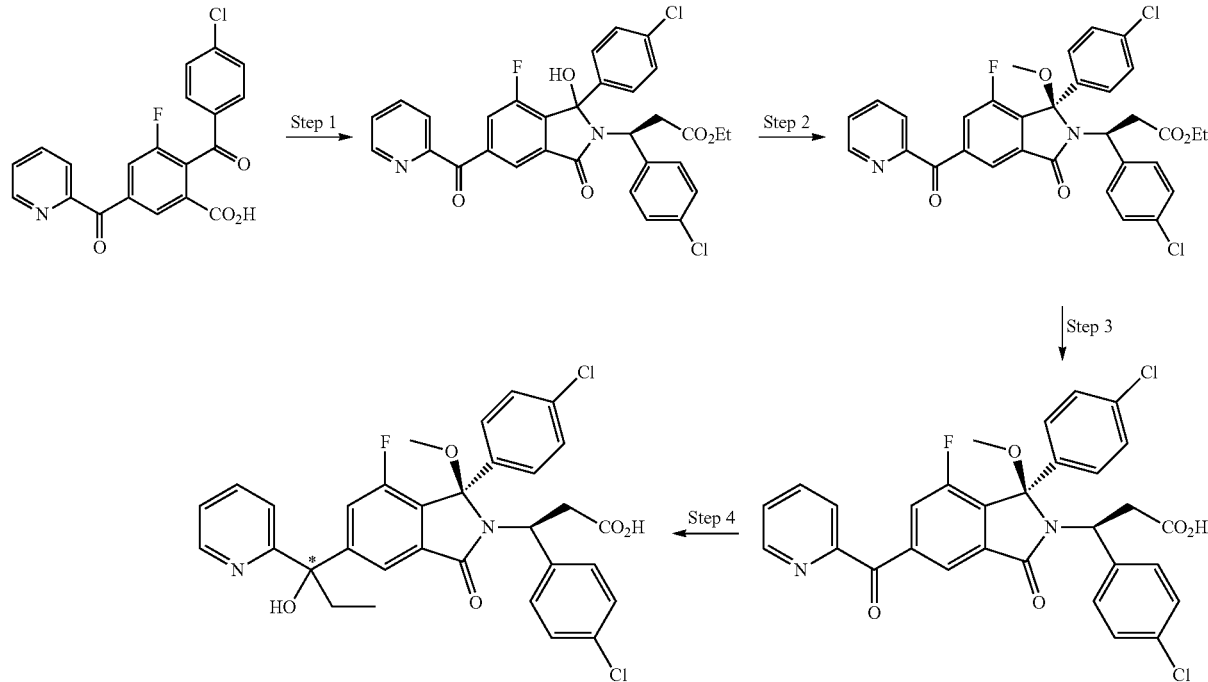

Step 3: (3S)-3-(4-Chlorophenyl)-3-[(1R)-1-(4-chlorophenyl)-7-fluoro-1-methoxy-3-oxo-5-(pyridine-2-carbonyl)-2,3-dihydro-1H-isoindol-2-yl]propanoic Acid The title compound was prepared from ethyl (3S)-3-(4-chlorophenyl)-3-[(1R)-1-(4-chlorophenyl)-7-fluoro-1-methoxy-3-oxo-5-(pyridine-2-carbonyl)-2,3-dihydro-1H-isoindol-2-yl]propanoate in an analogous fashion as described in Preparation 40. [M+H]⁺=579.

Step 4: (3S)-3-(4-chlorophenyl)-3-[(1R)-1-(4-chlorophenyl)-7-fluoro-5-[1-hydroxy-1-(pyridin-2-yl)propyl]-1-methoxy-3-oxo-2,3-dihydro-1H-isoindol-2-yl]propanoic Acid To a solution of (3S)-3-(4-chlorophenyl)-3-[(1R)-1-(4-chlorophenyl)-7-fluoro-1-methoxy-3-oxo-5-(pyridine-2-carbonyl)-2,3-dihydro-1H-isoindol-2-yl]propanoic acid (0.5 g, 0.86 mmol) in THF 10 mL) was added ZnCl₂ (1.7 mL, 0.5 M in THF, 0.85 mmol) and the mixture was stirred for 30 mins, cooled to −30° C. and EtMgCl (1.29 mL, 2 M in THF, 2.58 mmol) was added and stirred for 30 mins. Saturated NH₄Cl solution was added, acidified to pH=4.5 and extracted with ethyl acetate. The diastereoisomers were separated by chiral SFC.

Example 127: fast running isomer
¹H NMR (400 MHz, DMSO-d₆): 12.36 (1H, s), 8.61-8.55 (1H, m), 7.85 (1H, d), 7.82-7.70 (2H, m), 7.63-7.56 (1H, m), 7.30-7.23 (1H, m), 7.17-7.04 (4H, m), 7.04-6.88 (4H, m), 6.08 (1H, s), 4.60 (1H, dd), 3.46 (1H, dd), 3.18 (1H, dd), 3.08-3.00 (3H, m), 2.44-2.34 (1H, m), 2.34-2.24 (1H, m), 0.71 (3H, t). MS: [M+H]⁺=609.

Example 128: slow running isomer
¹H NMR (400 MHz, DMSO-d₆): 12.29 (1H, d), 8.59-8.53 (1H, m), 7.86 (1H, d), 7.83-7.70 (2H, m), 7.59 (1H, dd), 7.28-7.22 (1H, m), 7.17-7.05 (4H, m), 7.05-6.92 (4H, m), 6.07 (1H, s), 4.61 (1H, dd), 3.49-3.41 (1H, m), 3.22-3.09 (1H, m), 3.03 (3H, s), 2.41 (1H, dd), 2.34-2.26 (1H, m), 0.71 (3H, t).
MS: [M+H]⁺=609.

Example 129: (3R)-2-[(4-chloro-2-methanesulfonylphenyl)methyl]-3-(4-chlorophenyl)-4-fluoro-6-[1-(4-fluoropiperidin-4-yl)-1-hydroxypropyl]-3-methoxy-2,3-dihydro-1H-isoindol-1-one (Example Isolated as a Single Isomer at the Position Shown*)

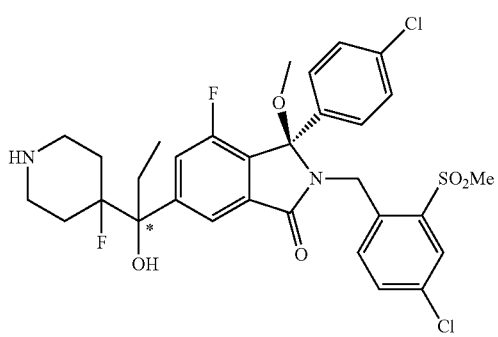 [SMILES: CCC(O)(c1cc(F)c2c(c1)C(=O)N(Cc1ccc(Cl)cc1S(C)(=O)=O)[C@@]2(OC)c1ccc(Cl)cc1)C1(F)CCNCC1]

Starting from (−)-5-(1-(1-(tert-butoxycarbonyl)-4-fluoropiperidin-4-yl)-1-hydroxypropyl)-2-(4-chlorobenzoyl)-3-fluorobenzoic acid (preparation 57) and (4-chloro-2-(methylsulfonyl)phenyl)methanamine (Example 35, step 3), the title compound was prepared using procedures similar to those described in Example 87 (Steps 1-2). ¹H NMR (400 MHz, CDCl3) 7.93 (1H, d), 7.78 (1H, s), 7.49 (1H, d), 7.45-7.38 (2H, m), 7.32 (2H, d), 7.24 (2H, d), 4.96 (2H, q), 3.02 (3H, s), 2.96 (3H, s), 2.95-2.83 (4H, m), 2.26-2.16 (2H, m), 2.09-1.95 (2H, m), 1.86-1.62 (3H, m), 1.44-1.25 (1H, m), 0.71 (3H, dd); MS [M+H]+=653.

Example 130: 4-{[(1R)-1-(4-chlorophenyl)-7-fluoro-5-[(1S)-1-hydroxy-1-(1-methylpiperidin-4-yl)propyl]-3-oxo-1-[cis-3-hydroxycyclobutoxy]-2,3-dihydro-1H-isoindol-2-yl]methyl}benzonitrile

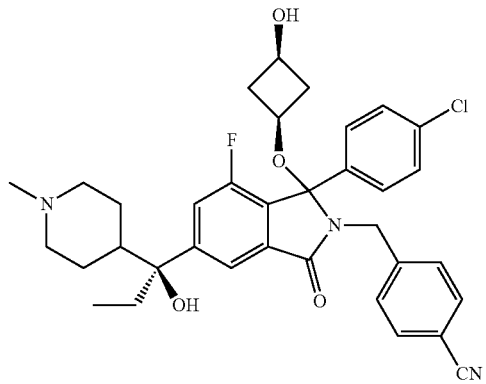 [SMILES: CC[C@@](O)(c1cc(F)c2c(c1)C(=O)N(Cc1ccc(C#N)cc1)C2(O[C@H]1C[C@@H](O)C1)c1ccc(Cl)cc1)C1CCN(C)CC1]

Starting from (S)-5-(1-(1-(tert-butoxycarbonyl)piperidin-4-yl)-1-hydroxypropyl)-2-(4-chlorobenzoyl)-3-fluorobenzoic acid (Preparation 60), 4-aminomethylbenzonitrile and cis-3-((tert-butyldimethylsilyl)oxy)cyclobutan-1-ol, the title compound was prepared using procedures similar to those described in Example 87 (Steps 1-3). Purification by chiral SFC gave the title compound (slow running isomer): ¹H NMR (400 MHz, CDCl₃) 7.62 (1H, d), 7.50 (2H, d), 7.34 (2H, d), 7.30 (1H, dd), 7.28-7.24 (4H, m), 4.62 (1H, d), 4.12 (1H, d), 3.61-3.53 (1H, m), 3.08-3.00 (1H, m), 2.91 (1H, d), 2.80 (1H, d), 2.22 (3H, s), 1.94-7.75 (9H, m), 1.73-1.66 (3H, m), 1.43-1.20 (3H, m), 0.67 (3H, dd). MS: [M+H]⁺=618.

Example 131: (3S)-3-(4-chlorophenyl)-3-[(1R)-1-(4-chlorophenyl)-7-fluoro-5-[1-(4-fluoro-1-methylpiperidin-4-yl)-1-hydroxypropyl]-1-methoxy-3-oxo-2,3-dihydro-1H-isoindol-2-yl]propanoic Acid (*Single Isomer Separated and Isolated)

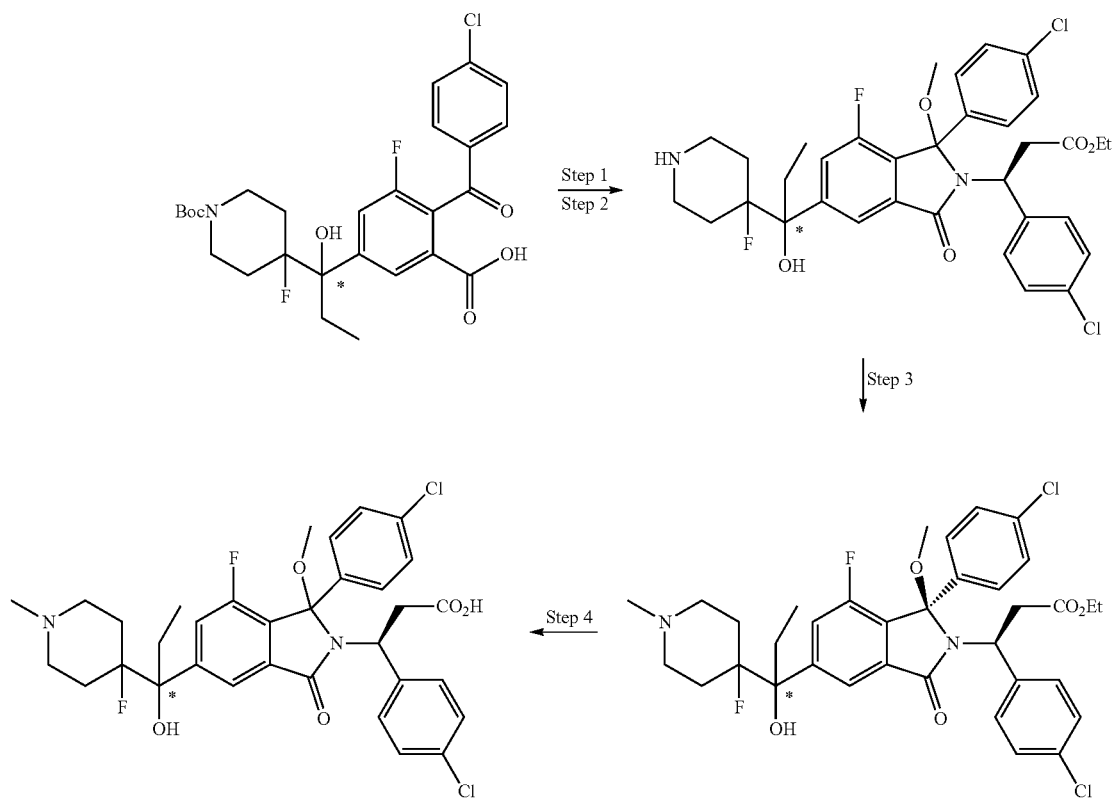

Step 1 and 2: Starting from (−)-5-(1-(1-(tert-butoxycarbonyl)-4-fluoropiperidin-4-yl)-1-hydroxypropyl)-2-(4-chlorobenzoyl)-3-fluorobenzoic acid (Preparation 57), Steps 1 and 2 were performed using methods similar to those described in Example 105. MS: [M+H]$^+$=661.1.

Step 3: ethyl (3S)-3-(4-chlorophenyl)-3-(1-(4-chlorophenyl)-7-fluoro-5-(1-(4-fluoro-1-methylpiperidin-4-yl)-1-hydroxypropyl)-1-methoxy-3-oxoisoindolin-2-yl)propanoate Step 3 was performed using procedures similar to those described in Example 81, Step 5. The desired diastereoisomer was isolated using chiral SFC as the fastest eluting isomer. MS: [M+H]$^+$=675.1.

Step 4: (3S)-3-(4-chlorophenyl)-3-[(1R)-1-(4-chlorophenyl)-7-fluoro-5-[1-(4-fluoro-1-methylpiperidin-4-yl)-1-hydroxypropyl]-1-methoxy-3-oxo-2,3-dihydro-1H-isoindol-2-yl]propanoic Acid Step 4 was performed using methods similar those described in Preparation 52, Step 3 to give the title compound which precipitated and was collected by filtration during the work up. $^1$H NMR (400 MHz, DMSO) 7.70 (1H, s), 7.42 (1H, d), 7.16 (2H, d), 7.09 (3H, d), 7.05 (1H, s), 6.98 (2H, d), 5.53 (1H, s), 4.63 (1H, dd), 3.48 (1H, dd), 3.18 (1H, dd), 3.08 (3H, s), 2.70-2.67 (1H, m), 2.13 (3H, s), 2.05-1.99 (1H, m), 1.95-1.80 (5H, m), 1.78-1.69 (1H, m), 1.11-1.05 (1H, m), 0.55 (3H, t), OH and COOH not observed. MS: [M+H]$^+$=647.3.

Example 132: tert-butyl 2-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetate

Example 133: tert-butyl 2-{4-[(1R)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetate (*Both Isomers Separated and Isolated)

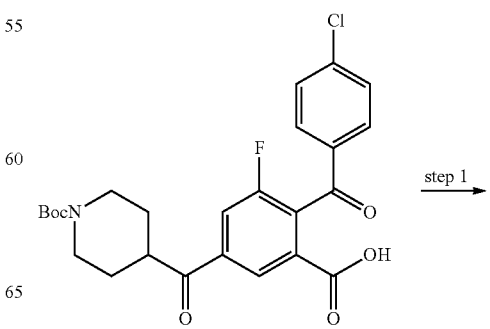

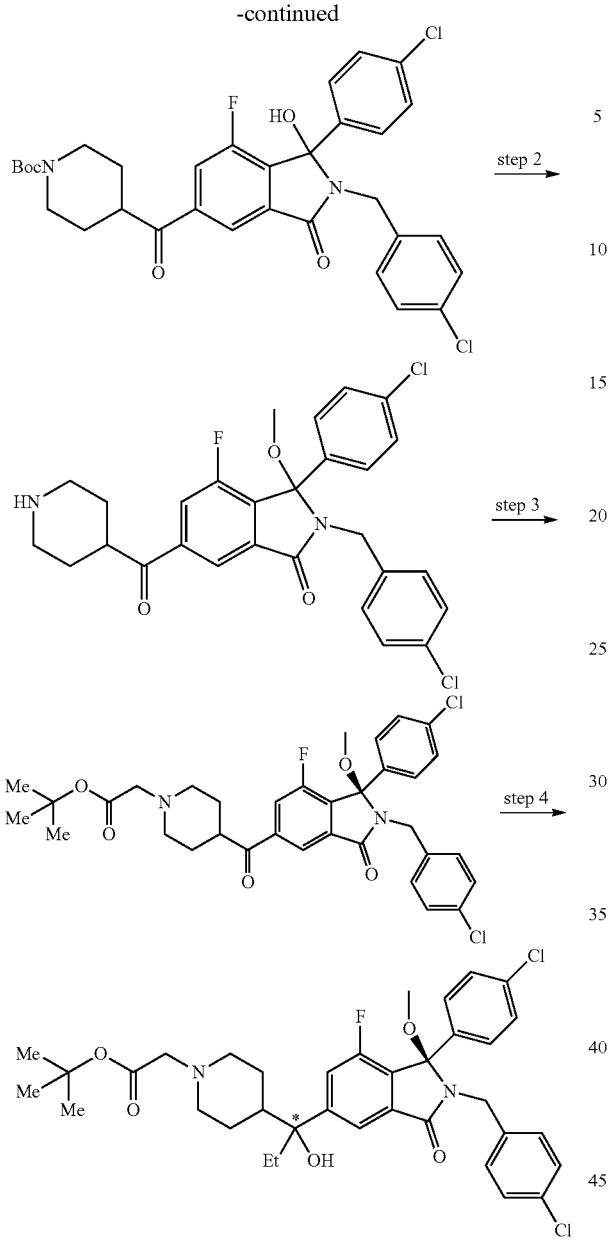

Steps 1-2. Starting from 5-(1-(tert-butoxycarbonyl)piperidine-4-carbonyl)-2-(4-chlorobenzoyl)-3-fluorobenzoic acid (Examples 80 and 81, step 2), steps 1-2 were performed using methods similar to those described in Example 73, Steps 3 and 4 respectively, except $T_3P$ was used instead of HATU in Steps 1 and MeOH instead of 1-(hydroxymethyl)cyclopropane-1-carboxamide in Step 2 to give 3-(4-chlorophenyl)-2-[(4-chlorophenyl)methyl]-4-fluoro-3-methoxy-6-(piperidine-4-carbonyl)-2,3-dihydro-1H-isoindol-1-one. MS $[M+H]^+$=527

Step 3: tert-butyl 2-{4-[1-(4-chlorophenyl)-2-[(4-chlorophenyl)methyl]-7-fluoro-1-methoxy-3-oxo-2,3-dihydro-1H-isoindole-5-carbonyl]piperidin-1-yl}acetate To the reaction flask containing 3-(4-chlorophenyl)-2-[(4-chlorophenyl)methyl]-4-fluoro-3-methoxy-6-(piperidine-4-carbonyl)-2,3-dihydro-1H-isoindol-1-one (1.729 g, 3.28 mmol), $K_2CO_3$ (1.80 g, 13.0 mmol) and DMF (30 mL) was added tert-butyl bromoacetate (0.53 mL, 3.57 mmol). The reaction was stirred at room temperature for 90 minutes at which time LCMS analysis showed complete consumption of starting material. Solvent was then removed and the residue was taken up in EtOAc (10 mL) and sat. $NaHCO_3$. The aqueous layer was further extracted with EtOAc (3×50 mL). The combined organics were dried over anhydrous $Na_2SO_4$, filtered, and concentrated to an oily residue. This material was then purified via $SiO_2$ (petroleum ether:EtOAc) to yield 1.505 g (72%) of the racemic product. The racemic material was then subjected to chiral preparatory separation to yield the enantiomers as white solids.

Fast enantiomer: $^1$H NMR (400 MHz, $CDCl_3$): 8.22 (1H, d), 7.75 (1H, dd), 7.28 (5H, d), 7.26-7.18 (4H, m), 4.66 (1H, d), 4.07 (1H, d), 3.31-3.20 (1H, m), 3.19 (2H, s), 3.04 (2H, d), 2.77 (3H, s), 2.50-2.34 (2H, m), 1.99-1.84 (4H, m), 1.49 (9H, s). MS $[M+NH_4]^+$=641.

Slow enantiomer: $^1$H NMR (400 MHz, $CDCl_3$): 8.22 (1H, s), 7.75 (1H, d), 7.28 (5H, s), 7.26-7.17 (4H, m), 4.66 (1H, d), 4.07 (1H, d), 3.31-3.21 (1H, m), 3.19 (2H, s), 3.04 (2H, d), 2.77 (3H, s), 2.50-2.34 (2H, m), 2.00-1.84 (4H, m), 1.50 (9H, s). MS $[M+NH_4]^+$=641.

Step 4: Taking the slow-eluting isomer from Step 3, Step 4 was performed using a method similar to that described in Preparation 52, Step 1. Purification by preparative chiral HPLC gave the title compounds.

Example 132—fast diastereomer: $^1$H NMR (400 MHz, $CDCl_3$): 7.64 (1H, s), 7.32-7.15 (9H, m), 4.61 (1H, d), 4.05 (1H, d), 3.05 (2H, s), 3.01 (1H, d), 2.89 (1H, d), 2.72 (3H, s), 2.16-1.96 (2H, m), 1.91 (2H, q), 1.82 (1H, d), 1.74 (1H, s), 1.71-1.54 (2H, m), 1.44 (10H, s), 1.41-1.31 (1H, m), 0.68 (3H, t). MS $[M+H]^+$=671.

Example 133—slow diastereomer: 1H NMR (400 MHz, $CDCl_3$): 7.68 (1H, s), 7.33-7.17 (9H, m), 4.64 (1H, d), 4.06 (1H, d), 3.07 (2H, s), 3.04 (1H, d), 2.90 (1H, d), 2.75 (3H, s), 2.19-2.02 (2H, m), 2.02-1.89 (2H, m), 1.89-1.77 (2H, m), 1.77-1.59 (2H, m), 1.59-1.45 (9H, m), 1.45-1.36 (2H, m), 0.70 (3H, t). MS $[M+H]^+$=671.

Example 134: 2-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetic Acid Example 135: 2-{4-[(1R)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetic Acid (*Prepared and Isolated as a Single Isomers)

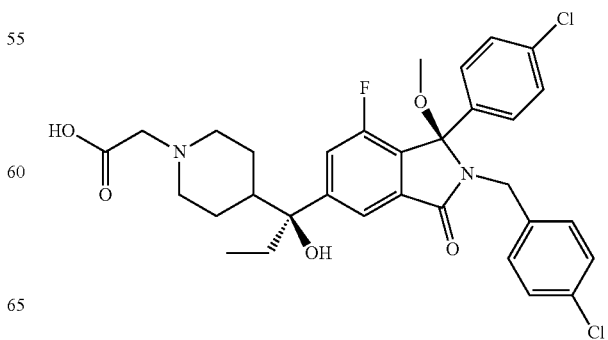

297

-continued

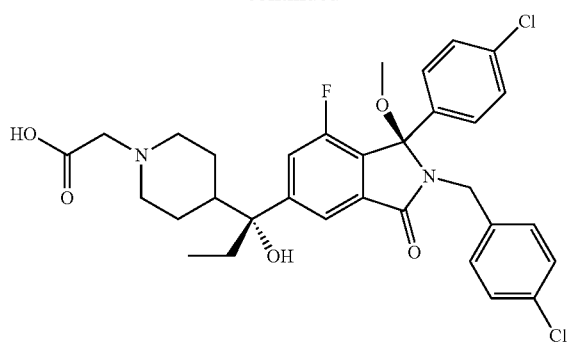

Examples 134: and 135 were prepared from Examples 132 and 133 respectively by using procedures similar to those described in Example 121, Step 2.

Example 134: $^1$H NMR (400 MHz, DMSO-d$_6$): 7.68 (1H, s), 7.43-7.32 (3H, m), 7.32-7.21 (4H, m), 7.17 (2H, d), 4.93 (1H, s), 4.45 (1H, d), 4.14 (1H, d), 3.12 (1H, d), 3.00 (1H, d), 2.92 (2H, s), 2.73 (3H, s), 2.33-2.14 (3H, m), 1.86 (2H, q), 1.82-1.67 (2H, m), 1.42-1.23 (2H, m), 1.16 (1H, d), 0.58 (3H, t). MS [M+H]$^+$=615.

Example 135 1H NMR (400 MHz, DMSO-d6): 7.69 (1H, s), 7.39 (1H, d), 7.34 (2H, d), 7.31-7.21 (4H, m), 7.18 (2H, d), 5.15-4.87 (1H, m), 4.46 (1H, d), 4.13 (1H, d), 3.19 (1H, d), 3.03 (3H, s), 2.73 (3H, s), 2.45-2.26 (3H, m), 1.95-1.69 (4H, m), 1.47-1.31 (2H, m), 1.16 (1H, d), 0.59 (3H, t). MS [M−H]$^−$=613.

Example 136: Methyl 3-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}propanoate

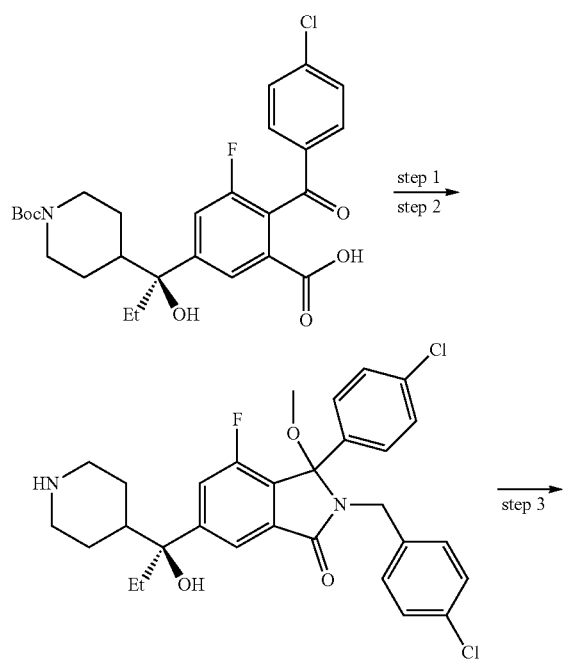

298

-continued

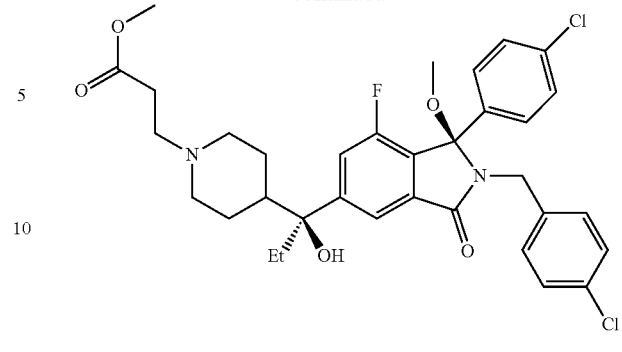

Starting from (S)-5-(1-(1-(tert-butoxycarbonyl)piperidin-4-yl)-1-hydroxypropyl)-2-(4-chlorobenzoyl)-3-fluorobenzoic acid (Preparation 60) and 4-chlorobenzylamine, the title compound was prepared using methods similar to those described for Example 87 (Steps 1-3), except that methyl methacrylate/DBU were used instead of NaBH$_3$CN in step 3. $^1$H NMR (400 MHz, CDCl$_3$): 7.63 (1H, d), 7.31-7.15 (9H, m), 4.61 (1H, d), 4.05 (1H, d), 3.66 (3H, s), 2.96 (1H, d), 2.84 (1H, d), 2.72 (3H, s), 2.69-2.56 (2H, m), 2.47 (2H, t), 2.07-1.79 (5H, m), 1.79-1.55 (3H, m), 1.40-1.28 (2H, m), 0.67 (3H, t). MS [M+H]$^+$=643.

Example 137: 3-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}propanoic Acid

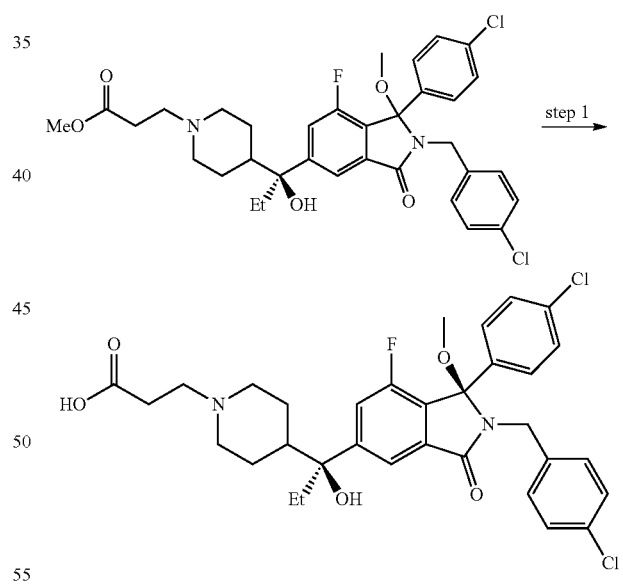

Starting from Example 136, the title compound was prepared using a procedure similar to that described in Preparation 52 (Step 3). $^1$H NMR (400 MHz, DMSO): 7.69 (1H, s), 7.40 (1H, d), 7.35 (2H, d), 7.31-7.21 (3H, m), 7.18 (2H, d), 4.89 (1H, s), 4.46 (1H, d), 4.13 (1H, d), 3.01 (1H, d), 2.87 (1H, d), 2.74 (3H, s), 2.58-2.52 (3H, m), 2.36-2.25 (2H, m), 2.06-1.73 (5H, m), 1.71 (1H, d), 1.35-1.18 (2H, m), 1.09 (1H, d), 0.57 (3H, t). MS [M−H]$^−$=627.

Biological Assays

MDM2-p53 Interaction Using a 96-Well Plate Binding Assay (ELISA)

The ELISA assay was performed in streptavidin coated plates which were preincubated with 200 µl per well of 1 µg ml$^{-1}$ biotinylated IP3 peptide. The plates were ready to use for MDM2 binding after washing the plate with PBS.

Compounds and control solutions in DMSO aliquoted in 96-well plates were pre-incubated in a final 2.5-5% (v/v) DMSO concentration at room temperature (for example 20° C.) for 20 min with 190 µl aliquots of optimized concentrations of in vitro translated MDM2, before transfer of the MDM2-compound mixture to the b-IP3 streptavidin plates, and incubation at 4° C. for 90 min. After washing three times with PBS to remove unbound MDM2, each well was incubated at 20° C. for 1 hour with a TBS-Tween (50 mM Tris pH7.5; 150 mM NaCl; 0.05% Tween 20 nonionic detergent) buffered solution of primary mouse monoclonal anti-MDM2 antibody (Ab-5, Calbiochem, used at a ¹⁄₁₀₀₀₀ or ¹⁄₂₀₀ dilution depending on the antibody stock solution used), then washed three times with TBS-Tween before incubation for 45 mins at 20° C. with a TBS-Tween buffered solution of a goat-anti-mouse horseradish peroxidase (HRP) conjugated secondary antibody (used at ¹⁄₂₀₀₀₀ or ¹⁄₂₀₀₀ depending on the antibody stock solution). The unbound secondary antibody was removed by washing three times with TBS-Tween. The bound HRP activity was measured by enhanced chemiluminescence (ECL™, Amersham Biosciences) using the oxidation of the diacylhydrazide substrate, luminol, to generate a quantifiable light signal. The percentage of MDM2 inhibition at a given concentration is calculated as the [1−(RLU detected in the compound treated sample—RLU negative DMSO control)÷(RLU of DMSO positive and negative controls)]×100 or as the (RLU detected in the compound treated sample÷RLU of DMSO controls)×100. The $IC_{50}$ was calculated using a plot of % MDM2 inhibition vs concentration and is the average of two or three independent experiments.

Western Blot Analysis

SJSA cells were treated for 6 hours with 5, 10 and 20 µM of compounds in 0.5% DMSO. The cells together with 0.5% DMSO only controls were washed with ice-cold phosphate buffered saline (PBS) and protein extracts prepared by lysing the cells in SDS buffer (62.5 mM Tris pH 6.8; 2% sodium dodecyl sulphate (SDS); 10% glycerol) with sonication for 2×5 seconds (Soniprep 150ME) to break down high molecular weight DNA and reduce the viscosity of the samples. The protein concentration of the samples was estimated using the Pierce BCA assay system (Pierce, Rockford, Ill.) and 50 µg aliquots of protein analysed using standard SDS-polyacrylamide gel electrophoresis (SDS-PAGE) and Western immunoblotting procedures. 3-mercaptoethanol (5%) and bromophenol blue (0.05%) were added and the samples, which were then boiled for 5 minutes, followed by brief centrifugation, before loading onto a pre-cast 4-20% gradient Tris-Glycine buffered SDS-polyacrylamide gel (Invitrogen). Molecular weight standards (SeeBlue™, Invitrogen) were included on every gel and electrophoresis was carried out in a Novex XL tank (Invitrogen) at 180 volts for 90 minutes. The separated proteins were transferred electrophoretically overnight from the gel onto a Hybond C nitrocellulose membrane (Amersham) using a BioRad electrophoresis tank and 25 mM Tris, 190 mM glycine and 20% methanol transfer buffer at 30 volts or two hours at 70 volts. Primary antibodies used for immunodetection of the transferred proteins were: mouse monoclonal NCL-p53DO-7 (Novocastra) at 1:1000; MDM2(Ab-1, clone IF2) (Oncogene) at 1:500; WAF1 (Ab-1, clone 4D10) (Oncogene) at 1:100; Actin (AC40) (Sigma) at 1:1000. The secondary antibody used was peroxidase conjugated, affinity purified, goat anti-mouse (Dako) at 1:1000. Protein detection and visualisation was performed by enhanced chemiluminescence (ECL™, Amersham) with light detection by exposure to blue-sensitive autoradiography film (Super RX, Fuji).

Protocol A: SJSA-1 and SN40R2 Assays

The MDM2 amplified cell lines tested were an isogenic matched pair of p53 wild-type and mutated osteosarcoma (SJSA-1 and SN40R2, respectively). All cell cultures were grown in RPMI 1640 medium (Gibco, Paisley, UK) supplemented with 10% fetal calf serum and routinely tested and confirmed negative for mycoplasma infection. The growth of cells and its inhibition was measured using the sulphorhodamine B (SRB) method as previously outlined. 100 µl of 3×10$^4$/ml and 2×10$^4$/ml SJSA-1 and SN40R2 cells, respectively, were seeded into 96-well tissue culture plates and incubated at 37° C. in a 5% $CO_2$ humidified incubator for 24 hrs, after which the medium was replaced with 100 µl of test medium containing a range of MDM2-p53 antagonist concentrations and incubated for a further 72 hrs to allow cell growth before adding 25 µL of 50% trichloroacetic acid (TCA) to fix the cells for 1 h at 4° C. The TCA was washed off with distilled water and 100 µL of SRB dye (0.4% w/v in 1% acetic acid) (Sigma-Aldrich, Poole, Dorset) added to each well of the plate. Following incubation with the SRB dye at room temperature for 30 min, the plates were washed with 1% acetic acid and left to dry. The SRB stained protein, which is a measure of the number of cells in a well, was then resuspended in 100 µL of 10 mM Tris-HCl (pH 10.5) and the absorbance at λ=570 nm measured in each well using a FluoStar Omega Plate reader. The $GI_{50}$ was calculated by non-linear regression analysis of the data using Prism v4.0 statistical software.

Protocol B: SJSA-1 and SN40R2 Assays

The CellTiter-Glo® Luminescent Cell Viability Assay is a homogeneous method to determine the number of viable cells in culture based on quantitation of the ATP present, which signals the presence of metabolically active cells. Both SJSA-1 and SN40R2 were grown in RPMI 1640 (Life Technologies #61870) supplemented with 10% FBS (PAA #A15-204) and 10 U/ml penicillin/streptomycin. 2000 cells in 75 µl were seeded in each well of a 96 well plate and left at 37° C. in a 5% $CO_2$ humidified incubator for 24 hrs. A range of MDM2-p53 antagonist concentrations in DMSO was then added to the cells to a final DMSO concentration of 0.3%, and incubated for a further 72 hrs to allow cell growth. 100 µl of CTG reagent (Promega #G7573) was added to all wells and luminescence was measured on the topcount. The $EC_{50}$ values were determined from a sigmoidal 4 parameter curve fit using XLfit in conjunction with Activity Base (IDBS; Guildford, Surrey, UK).

Anti-Proliferative Activity

Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds (in 0.1% DMSO v/v) for a further 72 hours. At the end of the incubation period 10% (v/v) Alamar Blue is added and incubated for a further 6 hours prior to determination of fluorescent product at 535 nM ex/590 nM em. The anti-proliferative activities of compounds of the invention can be determined by measuring the ability of the compounds to inhibit growth in cancer cell lines for example as available from DSMZ, ECACC or ATCC.

Results

TABLE 1

| biological data obtained from assays as described herein | | | | |
|---|---|---|---|---|
| Patent Example | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
| 1 | 0.012 | 0.49 | 0.55 | 18 | 10% at 10 |
| 2 | 0.0046 | 0.33 | 0.46 | 17 | 22% at 10 |
| 3 | 0.093 | | | | |
| 4 | 0.043 | | | | |
| 5 | 0.14 | | | | |
| 6 | 0.12 | | | | |
| 7 | 0.0066 | | | | |
| 8 | 0.0047 | 0.33 | | 18 | |
| 9 | 0.011 | | | | |
| 10 | 0.0037 | 0.14 | | 7.5 | |
| 11 | 0.033 | | | | |
| 12 | 0.0058 | 0.51 | 0.69 | 5.9 | |
| 13 | 0.12 | 4.6 | | 5.9 | |
| 14 | 0.0050 | 0.83 | 0.49 | 10% at 30 | 9% at 10 |
| 15 | 0.019 | | | | |
| 16 | 0.14 | 2.1 | | 13 | |
| 17 | 0.063 | 0.95 | | 8.1 | |
| 18 | 0.045 | 0.80 | | 18 | |
| 19 | 0.022 | 0.62 | 2.0 | 13 | 13 |
| 20 | 0.011 | 0.33 | | 11 | |
| 21 | 0.0078 | 0.23 | 0.39 | 15 | 51% at 10 |
| 22 | 0.0052 | 0.21 | | 18 | |
| 24 | 0.0075 | 0.37 | 0.63 | 21 | 19% at 10 |
| 25 | 0.0072 | 0.71 | 1.1 | 25 | 14% at 10 |
| 26 | 0.032 | 1.7 | | 17 | |
| 27 | 0.065 | 2.1 | | 29% at 30 | |
| 28 | 0.026 | 0.93 | | 26% at 30 | |
| 29 | 0.11 | 1.4 | | 17 | |
| 30 | 0.086 | 2.4 | | 27 | |
| 31 | 0.038 | 1.2 | | 18 | |
| 32 | | 0.87 | | 15 | |
| 33 | 0.0019 | 9.1 | | 7% at 30 | |
| 34 | 0.0046 | 0.093 | | 9.9 | |
| 35 | 0.0018 | 0.16 | 0.69 | 23 | 13 |
| 36 | 0.0019 | 0.078 | | 17 | |
| 37 | 0.041 | 1.2 | | 13 | |
| 38 | 0.026 | 0.67 | | 17 | |
| 39 | 0.068 | 2.0 | | 18 | |
| 40 | 0.063 | 1.5 | | 17 | |
| 41 | 0.0016 | 0.14 | | 13 | |
| 42 | 34%@0.00030 | 0.011 | 0.03 | 12 | 10 |
| 43 | 47%@0.0010 | 0.57 | | 12 | |
| 44 | 0.0058 | 0.83 | | 6.8 | |
| 45 | 0.23 | | | | |
| 46 | 10.78 | | | | |
| 47 | 0.43 | | | | |
| 48 | 0.0073 | 0.46 | 0.97 | 17 | 24% at 10 |
| 49 | 0.082 | 1.6 | | 18 | |
| 50 | 0.00080 | 0.079 | 0.032 | 17 | 22% at 10 |
| 51 | 0.13 | | | | |
| 52 | 0.15 | 1.8 | | | |
| 53 | 0.12 | 1.9 | | | |
| 54 | 0.15 | | | | |
| 55 | | 1.7 | | 11 | |
| 56 | 0.12 | | | | |
| 57 | 0.061 | 1.4 | | 16 | |
| 58 | 0.018 | 0.59 | | 15 | |
| 59 | 0.0041 | 0.25 | | 19 | |
| 60 | 0.014 | | | | |
| 61 | 0.016 | 0.69 | | 44% at 30 | |
| 62 | 0.0023 | 0.055 | | 55% at 30 | |
| 63 | 71%@0.0010 | | 0.096 | | 19% at 10 |
| 64 | 0.0021 | | | | |
| 65 | 0.0018 | | 0.26 | | |
| 66 | 0.0030 | | | | |
| 67 | 60%@0.0010 | | 0.53 | | 9.4 |
| 68 | 0.0070 | | 1.8 | | 13 |
| 69 | 0.00070 | 0.081 | 0.16 | 15 | 6.6 |
| 70 | 0.0057 | | 0.68 | | 4.9 |
| 71 | 0.0020 | 0.66 | 0.7 | 44 | 3% at 10 |

TABLE 1-continued biological data obtained from assays as described herein

| Patent Example | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 72 | 0.0015 | 0.14 | 0.17 | 16 | 45% at 10 |
| 73 | 0.012 | | 3.6 | | 39% at 30 |
| 74 | 0.00050 | 0.28 | 1.0 | 28 | 13 |
| 75 | 73%@0.0010 | 0.12 | 0.35 | 22 | 12 |
| 76 | 0.0095 | | 1.0 | | 13 |
| 77 | 61%@0.00030 | | 0.46 | | 3.7 |
| 78 | 0.0046 | 0.41 | 1.4 | 5.9 | 4.2 |
| 79 | 0.0022 | | 8.1 | | 10% at 30 |
| 80 | 73%@0.0010 | | 0.83 | | 13 |
| 81 | 0.0026 | | | | |
| 82 | 0.0025 | 0.21 | | 51% at 30 | |
| 83 | 0.0010 | | 0.53 | | 11 |
| 84 | 39%@0.00030 | 0.065 | | 18 | |
| 85 | 0.00049 | | 0.049 | | 13 |
| 86 | 56%@0.10 | | | | |
| 87 | 82%@0.0030 | | 37% at 10 | | 1% at 10 |
| 88 | 0.00079 | 0.15 | 0.23 | 39 | 11% at 10 |
| 89 | 0.012 | | 3.6 | | 3% at 10 |
| 90 | 39%@0.030 | | 97% at 10 | | 6% at 10 |
| 91 | 78%@0.0010 | 0.080 | 0.059 | 26 | 13% at 10 |
| 92 | 76%@0.0010 | 0.080 | 0.084 | 36 | 12% at 10 |
| 93 | 49%@0.030 | | 3.3 | | 12% at 10 |
| 94 | 64%@0.10 | | | | |
| 95 | 87%@0.0010 | 0.036 | 0.022 | 16 | 21% at 10 |
| 96 | 0.00064 | 0.071 | 0.075 | 19 | 17% at 10 |
| 97 | 45%@0.10 | | | | |
| 98 | 0.0008 | 0.081 | 0.13 | 33 | 11% at 10 |
| 99 | 0.012 | | 3.2 | | 4% at 10 |
| 100 | 0.0063 | | 1.7 | | 7% at 10 |
| 101 | 55%@0.00030 | 0.026 | 0.026 | 18 | 11% at 3 |
| 102 | 0.017 | | 1.4 | | 26% at 10 |
| 103 | 55%@0.030 | | 0.8 | | 18% at 10 |
| 104 | 70%@0.10 | | 42% at 10 | | 5% at 10 |
| 105 | 92%@0.0010 | 0.022 | 0.05 | 33 | 20% at 10 |
| 106 | 57%@0.030 | | 3.2 | | 8% at 10 |
| 107 | 78%@0.0010 | 0.021 | 0.038 | 24 | 18% at 10 |
| 108 | 0.0061 | | 27% at 10 | | 29% at 10 |
| 109 | 92%@0.0010 | 0.012 | 0.02 | 26 | 75% at 10 |
| 110 | 76%@0.0010 | 0.026 | 0.013 | 17 | 30% at 10 |
| 111 | 61%@0.0010 | 0.024 | 0.037 | 9 | 51% at 10 |
| 113 | 57%@0.0010 | | 0.02 | | 10% at 10 |
| 114 | 81%@0.0010 | 0.029 | 0.063 | 20 | 15% at 10 |
| 115 | 73%@0.0010 | | 0.22 | | 2% at 10 |
| 116 | 88%@0.0010 | 0.08 | 0.14 | 44 | 12% at 10 |
| 117 | 45% at 0.03 | | 30% at 10 | | 19% at 10 |
| 118 | 87%@0.0010 | | 0.36 | | 8% at 10 |
| 119 | 54%@0.0010 | 0.06 | 0.2 | 39 | 7% at 10 |
| 120 | 76%@0.0010 | 0.063 | 0.095 | 40% at 50 | 4% at 10 |
| 121 | 93%@0.0010 | 0.015 | 0.015 | 26 | 18% at 10 |
| 122 | 88%@0.0010 | | 0.024 | | 20% at 10 |
| 123 | 42%@0.030 | | 107% at 10 | | 16% at 10 |
| 124 | 80%@0.0010 | 0.023 | 0.027 | 23 | 55% at 10 |
| 125 | 18%@0.10 | | | | |
| 126 | 0.0019 | 0.6 | 0.61 | 30 | 7% at 10 |
| 127 | 0.0045 | | 1.4 | | 14% at 10 |
| 128 | 39%@0.10 | | | | |
| 129 | 90%@0.0010 | 0.047 | 0.048 | 6 | 112% at 10 |
| 130 | 98%@0.0010 | | 0.23 | | 87% at 10 |
| 131 | 89%@0.0010 | 0.044 | 0.093 | 22 | −3% at 10 |
| 132 | 43%@0.030 | | 0.75 | | 34% at 10 |
| 133 | 6%@0.10 | | 37% at 10 | | 89% at 10 |
| 134 | 0.0011 | | 0.78 | | 2% at 10 |
| 135 | 40%@0.10 | | 20% at 10 | | 7% at 10 |
| 136 | 0.0013 | | 0.056 | | 86% at 10 |
| 137 | 0.00057 | | 0.15 | | 12% at 10 |

Where more than one data point has been obtained, the table above shows an average (e.g. geometric or arithmetic mean) of these data points.

It is of course to be understood that the invention is not intended to be restricted to the details of the above embodiments which are described by way of example only.

Combination Protocol for Cell Proliferation

The effect of a compound of formula (I) (Compound 1) in combination with an anticancer agent (Compound II) can be assessed using the following technique. Cells from human cells lines (e.g. SJSA-1) were seeded onto 96-well tissue culture plates at a concentration of $2.5 \times 10^3$, $6.0 \times 10^3$, or $4.0 \times 10^3$ cells/well respectively. Cells were allowed to recover for 24-48 hours prior to addition of compound(s) or vehicle control (0.35-0.5% DMSO) as follows:

Compounds were added concurrent for 72-96 hours. Following a total of 72-96 hours compound incubation, cells were fixed with ice-cold 10% (w/v) trichloroacetic acid for 1 hour on ice and then washed four times with $dH_2O$ using a plate washer (Labsystems Wellwash Ascent) and air-dried. Cells were then stained with 0.4% (w/v) Sulforhodamine B (Sigma) in 1% acetic acid for 20 min at room temperature and then washed four times with 1% (v/v) acetic acid and air-dried before the addition of 10 mM Tris buffer to solubilise the dye. Colourmetric product was quantified by reading at Abs490 nm or Abs570 nm on a Wallac Victor$^2$ plate reader (1420 multilabel counter, Perkin Elmer Life Sciences). The $IC_{50}$ for Compound II in the presence of varying doses of Compound I was determined. Synergy was determined when the $IC_{50}$ shifted down in the presence of sub-effective doses of Compound I. Additivity was determined when the response to Compound II and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

Pharmaceutical Formulations Examples (i) Tablet Formulation

A tablet composition containing a compound of the formula (I) is prepared by mixing an appropriate amount of the compound (for example 50-250 mg) with an appropriate diluent, disintegrant, compression agent and/or glidant. One possible tablet comprises 50 mg of the compound with 197 mg of lactose (BP) as diluent, and 3 mg magnesium stearate as a lubricant and compressing to form a tablet in known manner. The compressed tablet may be optionally film coated.

(ii) Capsule Formulation

A capsule formulation is prepared by mixing 100-250 mg of a compound of the formula (I) with an equivalent amount of lactose and filling the resulting mixture into standard hard gelatin capsules. An appropriate disintegrant and/or glidant can be included in appropriate amounts as required.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then made isotonic, sterilised by filtration or by terminal sterilisation, filled into an ampoule or vial or pre-filled syringe, and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution or by terminal sterilisation, and filling into sealable 1 ml vials or ampoules or pre-filled syringe.

(v) Injectable Formulation III

A formulation for i.v. delivery by injection or infusion can be prepared by dissolving the compound of formula (I) (e.g. in a salt form) in water at 20 mg/ml and then adjusted for isotonicity. The vial is then sealed and sterilised by autoclaving or filled into an ampoule or vial or pre-filled syringe, sterilised by filtration and sealed.

(vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial, ampoule or pre-filled syringe is then sealed and sterilised by autoclaving or sterilized by filtration and sealed.

(vii) Subcutaneous or Intramuscular Injection Formulation

A composition for sub-cutaneous or intramuscular administration is prepared by mixing a compound of the formula (I) with pharmaceutical grade corn oil to give a concentration of 5-50 mg/ml. The composition is sterilised and filled into a suitable container.

(viii) Lyophilised Formulation I

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation II

Aliquots of formulated compound of formula (I) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(x) Lyophilised Formulation for Use in i.v. Administration III

An aqueous buffered solution is prepared by dissolving a compound of formula I in a buffer. The buffered solution is filled, with filtration to remove particulate matter, into a container (such as a Type 1 glass vial) which is then partially sealed (e.g. by means of a Fluorotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle. On completion of the freeze drying cycle the vials are back filled with nitrogen to atmospheric pressure, stoppered and secured (e.g. with an aluminium crimp). For intravenous administration, the freeze dried solid can be reconstituted with a pharmaceutically acceptable diluent, such as 0.9% saline or 5% dextrose. The solution can be dosed as is, or can be diluted further into an infusion bag (containing a pharmaceutically acceptable diluent, such as 0.9% saline or 5% dextrose), before administration.

(xii) Powder in a Bottle

A composition for oral administration is prepared by filling a bottle or vial with a compound of the formula (I). The composition is then reconstituted with a suitable diluent for example water, fruit juice, or commercially available vehicle such as OraSweet or Syrspend. The reconstituted solution may be dispensed into dosing cups or oral syringes for administration.

The invention claimed is:
1. A compound of formula (Ir):

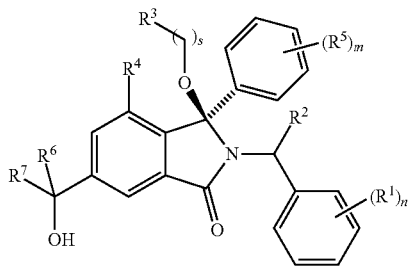

or a tautomer or a solvate or a pharmaceutically acceptable salt thereof, wherein:

$R^1$ is independently selected from hydroxy, halogen, nitro, nitrile, $C_{1-4}$ alkyl, halo$C_{1-4}$alkyl, hydroxy$C_{1-4}$ alkyl, $C_{2-6}$alkenyl, $C_{1-4}$ alkoxy, halo$C_{1-4}$ alkoxy, $C_{2-4}$alkynyl, —$O_{0,1}$—$(CR^xR^y)_v$—$CO_2H$, —$(CR^xR^y)_v$—$CO_2C_{1-4}$ alkyl, —$(CR^xR^y)_v$—$CON(C_{1-4}$ alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$;

$R^2$ is selected from hydrogen, $C_{1-4}$ alkyl, $C_{2-6}$alkenyl, hydroxy$C_{1-4}$alkyl, —$(CR^xR^y)_u$—$CO_2H$, —$(CR^xR^y)_u$—$CO_2C_{1-4}$alkyl, and —$(CR^xR^y)_u$—$CONR^xR^y$;

s is selected from 0 and 1;

$R^3$ is hydrogen or -$(A)_t$-$(CR^xR^y)_q$—X;

t is selected from 0 and 1;

q is selected from 0, 1 and 2;

wherein when $R^3$ is -$(A)_t$-$(CR^xR^y)_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more heteroatoms selected from N, O, S and oxidised forms thereof;

X is selected from hydrogen, halogen, —CN, —$OR^9$, —$(CH_2)_v$—$CO_2H$, —$(CH_2)_v$—$CO_2C_{1-4}$alkyl, —$S(O)_d$—$R^x$, —$C(=O)$—$C_{1-4}$alkyl, —$S(O)_d$—$N(H)_e$ $(C_{1-4}$alkyl$)_{2-e}$, —$NR^xR^y$, —$NHSO_2R^x$, —$NR^xCOR^y$, and —$C(=O)NR^xR^y$;

$R^4$ and $R^5$ are independently selected from halogen, nitrile, $C_{1-4}$ alkyl, halo$C_{1-4}$alkyl, $C_{1-4}$alkoxy and halo$C_{1-4}$ alkoxy;

$R^6$ is selected from hydrogen and $C_{1-6}$alkyl;

$R^7$ is

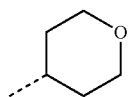

optionally substituted by one $R^z$ group;

$R^8$ and $R^9$ are independently selected from hydrogen, $C_{1-6}$alkyl, halo$C_{1-6}$alkyl, hydroxy$C_{1-6}$alkyl, —$(CH_2)_k$—O—$C_{1-6}$alkyl, —$(CH_2)_k$—O—(hydroxy$C_{1-6}$alkyl), hydroxy$C_{1-6}$alkoxy, —$(CH_2)_k$— $CO_2C_{1-6}$alkyl, —$(CH_2)_k$—$CO_2H$, —$C_{1-6}$ alkyl-$N(H)_e$ $(C_{1-4}$alkyl$)_{2-e}$, —$(CH_2)_j$—$C_{3-8}$cycloalkyl and —$(CH_2)_j$ —$C_{3-8}$cycloalkenyl;

$R^x$ and $R^y$ are independently selected from hydrogen, halogen, nitro, nitrile, $C_{1-6}$ alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —$(CH_2)_k$—O—$C_{1-6}$alkyl, hydroxy$C_{1-6}$ alkoxy, —$COOC_{1-6}$alkyl, —$N(H)_e(C_{1-4}$alkyl$)_{2-e}$, —$C_{1-6}$ alkyl-$N(H)_e(C_{1-4}$alkyl$)_{2-e}$, —$(CH_2)_k$—$C(=O)$ $N(H)_e(C_{1-4}$alkyl$)_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group;

$R^z$ is independently selected from halogen, nitro, nitrile, $C_{1-6}$ alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —$C(=O)C_{1-6}$alkyl, —$C(=O)C_{1-6}$alkyl-OH, —$C(=O)C_{1-6}$alkyl-$N(H)_e(C_{1-4}$alkyl$)_{2-e}$, —$C(=O)N$ $(H)_e(C_{1-4}$alkyl$)_{2-e}$, —$(CH_2)_r$—$CO_2C_{1-6}$alkyl, —$(CH_2)_r$—$CO_2H$, —$N(H)_e(C_{1-4}$alkyl$)_{2-e}$, —$C_{1-6}$alkyl-$N(H)_e(C_{1-4}$alkyl$)_{2-e}$, heterocyclyl group with 3 to 6 ring members, heterocyclyl group with 3 to 6 ring members substituted by —$C(=O)C_{1-4}$alkyl, heterocyclyl group with 3 to 6 ring members substituted by —$C(=O)$ $OC_{1-4}$ alkyl, heterocyclyl group with 3 to 6 ring members substituted by —$C(=O)N(H)_e(C_{1-4}$alkyl$)_{2-e}$, —$C(=O)$heterocyclyl group with 3 to 6 ring members, $C_{3-8}$ cycloalkyl and $C_{3-8}$cycloalkenyl;

j, d, e, n, r and p are independently selected from 0, 1 and 2;

k and m are independently selected from 1 and 2;

u is selected from 0, 1, 2 and 3; and v is selected from 0 and 1.

2. A compound according to claim 1, or a tautomer or a solvate or a pharmaceutically acceptable salt thereof, wherein $R^1$ is:

(i) halogen, hydroxy, nitrile, $C_{1-4}$alkyl, $C_{2-4}$alkynyl, or $C_{1-4}$alkoxy, for example wherein n is 1 and $R^1$ is chloro or nitrile e.g. chloro; or (ii) hydroxy, halogen, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$ alkoxy, $C_{2-4}$ alkynyl, —$(CH_2)_v$—$CO_2H$, —$O_{0,1}$— $(CR^xR^y)_v$—$CO_2C_{1-4}$alkyl, —$(CH_2)_v$—$CON(C_{1-4}$ alkyl$)_2$, —$P(=O)(R^x)_2$, —$S(O)_d$—$C_{1-6}$alkyl, —$S(O)_d$-heterocyclic group with 3 to 6 ring members or —$S(O)_d$—$N(R^8)_2$.

3. A compound according to claim 1, or a tautomer or a solvate or a pharmaceutically accepttale salt thereof, wherein $R^2$ is:

(i) hydrogen, $C_{1-4}$alkyl, $C_{2-6}$alkenyl or hydroxy$C_{1-4}$alkyl; or (ii) hydrogen or —$(R^xR^y)_u$—$CO_2H$.

4. A compound according to claim 1, or a tautomer or a solvate or a pharmaceutically acceptable salt thereof, wherein:

(i) $R^3$ is —$(A)_t$—$(CR^xRY)_q$—X and A is either a $C_{3-6}$cycloalkyl group or a heterocyclic group with 3 to 5 ring members; or (ii) $R^3$ is —$(A)_t$—$(CR^xR^y)_q$—X and A is a heterocyclic group with 3 to 5 ring members.

5. A compound according to claim 1, or a tautomer or a solvate or a pharmaceutically acceptable salt thereof, wherein s is 1.

6. A compound according to claim 1, or a tautomer or a solvate or a pharmaceutically acceptable salt thereof, wherein X is hydrogen, halogen, -CN, -OR$^9$, or -C(=O)NR$^x$R$^y$.

7. A compound according to claim 1, wherein the compound is a compound of the formula

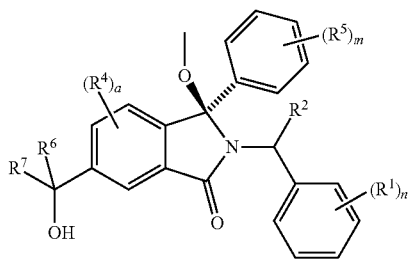

wherein a is 1 and R$^4$ is at the 4-position of the isoindolinone ring, or a tautomer or a solvate or a pharmaceutically acceptable salt thereof.

8. A compound according to claim 1, or a tautomer or a solvate or a pharmaceutically acceptable salt thereof, wherein R$^4$ is F.

9. A compound according to claim 1, or a tautomer or a solvate or a pharmaceutically acceptable salt thereof, wherein R$^5$ is chloro and m is 1 and the substituent R$^5$ is at the para-position of the phenyl group.

10. A compound according to claim 1, or a tautomer or a solvate or a pharmaceutically acceptable salt thereof, wherein R$^6$ is methyl or ethyl.

11. A compound according to claim 1, wherein the compound is a compound of formula (bb) or a tautomer or a solvate or a pharmaceutically acceptable salt thereof:

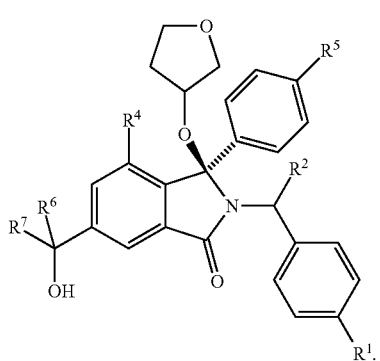

12. A compound according to claim 1, or a tautomer, pharmaceutically acceptable salt or solvate thereof, wherein the compound is selected from:

(3R)-2- [(4-chloro-2-methanesulfonylphenyl)methyl]-3- (4-chlorophenyl)-4-fluoro-6-[1-hydroxy-1-(oxan-4-yl)ethyl]-3 -{[1-(hydroxymethyl)cyclopropyl]methoxy}-2,3-dihydro -1H-isoindol-1-one;

(3R)-2-[(4-chloro-2-methanesulfonylphenyl)methyl]-3- (4-chlorophenyl)-4-fluoro-6-[hydroxy(oxan-4-yl) methyl]-3-{[1-(hydroxymethyl)cyclopropyl] methoxy}-2,3 -dihydro-1H -isoindol-1-one;

1-({[(1R)-2-[(4-chloro-2-methanesulfonylphenyl) methyl]-1-(4-chlorophenyl)-7-fluoro-5 - [1-hydroxy-1- (oxan-4-yl)ethyl]-3 -oxo-2,3 -dihydro-1H-isoindol -1- yl]oxy}methyl)cyclopropane-1-carboxamide;

(3 S)-3-(4-chlorophenyl)-3-[(1R)-1-(4-chlorophenyl)-7- fluoro-5-[1-hydroxy-1-(oxan-4- yl)ethyl]-1-methoxy- 3-oxo-2,3 -dihydro-1H-isoindol-2-yl]propanoic acid;

(3 S)-3-(4-chlorophenyl)-3-[(1R)-1-(4-chlorophenyl)-7- fluoro-5-[1-(4-fluorooxan-4-yl)-1- hydroxyethyl]-1- methoxy-3-oxo-2,3-dihydro-1H-isoindol-2-yl]propanoic acid;

(3 S)-3-(4-chlorophenyl)-3-[(1R)-1-(4-chlorophenyl)-7- fluoro-5-[1-(4-fluorooxan-4-yl)-1- hydroxypropyl]-1- methoxy-3-oxo-2,3-dihydro-1H-isoindol-2-yl]propanoic acid;

(3S)-3-(4-chlorophenyl)-3-[(1R)-1-(4-chlorophenyl)-7- fluoro-5-[(1S)-1-hydroxy-1-(oxan- 4-yl)propyl]-1- methoxy-3-oxo-2,3-dihydro-1H-isoindol-2-yl]propanoic acid;

(3S)-3-(4-chlorophenyl)-3-[(1R)-1-(4-chlorophenyl)-7- fluoro-5-[(1R)-1-hydroxy-1-(oxan- 4-yl)propyl]-1- methoxy-3-oxo-2,3-dihydro-1H-isoindol-2-yl]propanoic acid;

(4S)-4-(4-chlorophenyl)-4-[(1R)-1-(4-chlorophenyl)-7- fluoro-5-[(1S)-1-hydroxy-1-(oxan- 4-yl)propyl]-1- methoxy-3-oxo-2,3-dihydro-1H-isoindol-2-yl]butanoic acid;

(4S)-4-(4-chlorophenyl)-4-[(1R)-1-(4-chlorophenyl)-7- fluoro-5-[(1R)-1-hydroxy-1-(oxan- 4-yl)propyl]-1- methoxy-3-oxo-2,3-dihydro-1H-isoindol-2-yl]butanoic acid;

(4S)-4-(4-Chlorophenyl)-4-[(1R)-1-(4-chlorophenyl)-7- fluoro-5-R1R)-1-(4-fluorooxan-4- yl)-1-hydroxypropyl]-1-methoxy-3-oxo-2,3-dihydro-1H-isoindol-2-yl] butanoic acid;

(3S)-3-(4-chlorophenyl)-3-[(1R)-1-(4-chlorophenyl)-7- fluoro-5-[(1R)-1-(4-fluorooxan-4- yl)-1-hydroxypropyl]-1-trideuteromethoxy-3-oxo-2, 3-dihydro-1H-isoindol -2-yl]propanoic acid;

(3S)-3-(4-chlorophenyl)-3-[(1R)-1-(4-chlorophenyl)-1- ethoxy-7-fluoro-5-[(1R)-1-(4- fluorooxan-4-yl)-1-hydroxypropyl]-3-oxo-2,3 -dihydro-1H-isoindol-2-yl] propanoic acid;

(4S)-4-[(1R)-1-(4-chlorophenyl)-7-fluoro-5-[(1R)-1-(4- fluorooxan-4-yl)-1-hydroxypropyl]- 1-methoxy-3-oxo- 2,3 -dihydro-1H-isoindol-2-yl]-4-(4-methoxyphenyl) butanoic acid;

2-(5-chloro-2-{[1-(4-chlorophenyl)-7-fluoro-5-[(1R)-1- (4-fluorooxan-4-yl)- 1- hydroxypropyl]-1-methoxy-3- oxo-2, 3-dihydro-1H-isoindol -2-yl]methyl }phenoxy) acetic acid;

5-chloro-2-{[(1R)-1-(4-chlorophenyl)-7-fluoro-5-[(1S)- 1-hydroxy- 1-(oxan-4-yl)propyl]-1- methoxy-3-oxo-2, 3-dihydro-1H-isoindol-2-yl]methyl}benzoic acid;

5-chloro-2-{[(1R)-1-(4-chlorophenyl)-7-fluoro-5-[(1R)- 1-hydroxy-1-(oxan-4-yl)propyl]-1- methoxy-3-oxo-2, 3-dihydro-1H-isoindol-2-yl]methyl}benzoic acid;

5 -chloro-2-{[(1R)-1-(4-chlorophenyl)- 1-ethoxy-7- fluoro-5-[(1S)- 1-hydroxy-1-(oxan-4- yl)propyl]-3- oxo-2, 3-dihydro-1H-isoindol-2-yl]methyl}benzoic acid;

2-{[(1R)- 1-(4-chlorophenyl)-7-fluoro-5-[(1R)- 1-(4-fluorooxan-4-yl)-1-hydroxypropyl]-1- methoxy-3-oxo-2, 3-dihydro-1H-isoindol-2-yl]methyl}-5-methylbenzoic acid;

2-{[(1R)-1-(4-chlorophenyl)-7-fluoro-5-[(1R)-1-(4-fluo-rooxan-4-yl)-1-hydroxypropyl]-1-methoxy-3-oxo-2,3-dihydro-1H-isoindol-2-yl]methyl}-5-methoxybenzoic acid;

2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)-2-methylpropanoic acid;

2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl) acetic acid;

2-(5-chloro-2-{[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]methyl}phenyl) acetic acid; and (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid.

13. A compound according to claim 1, or a tautomer, pharmaceutically acceptable salt or solvate thereof, wherein the compound is selected from:

(2S,3S)-3-(4-chlorophenyl)-3-[(1R)-1-(4-chlorophenyl)-7-fluoro-5-[(1S)-1-hydroxy-1-(oxan-4-y1)propyl]-1-methoxy-3-oxo-2,3-dihydro-1H-isoindol-2-yl]-2-methylpropanoic acid;

(3S)-3-(4-chlorophenyl)-3-[(1R)-1-(4-chlorophenyl)-7-fluoro-5-[1-hydroxy-1-(oxan-4-y1)ethyl]-1-methoxy-3-oxo-2,3-dihydro-1H-isoindol-2-yl]propanoic acid; and 2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)-2-methylpropanoic acid.

14. A combination comprising a compound of formula (Ir) as defined in claim 1, or a tautomer or a solvate or a pharmaceutically acceptable salt thereof, with one or more other therapeutic agents.

15. A pharmaceutical composition comprising a compound of formula (Ir) as defined in claim 1, or a tautomer or a solvate or a pharmaceutically acceptable salt thereof.

16. A pharmaceutical composition comprising a compound of formula (Ir) as defined in claim 1, or a tautomer or a solvate or a pharmaceutically acceptable salt thereof, one or more other therapeutic agents, and a pharmaceutically acceptable carrier.

17. A method for treating cancer, said method comprising administering to a patient a compound of formula (Ir) as defined in claim 1, or a tautomer or a solvate or a pharmaceutically acceptable salt thereof, wherein the cancer is selected from colon cancer, colorectal cancer, lung cancer, mesothelioma, breast cancer, osteosarcoma, fibrosarcoma, melanoma, liver cancer, leukemia, and lymphoma.

18. A method of inhibiting the interaction of p53 with MDM2 in a subject, the method comprising administering to the subject a compound as defined in claim 1, or a tautomer or a solvate or a pharmaceutically acceptable salt thereof.

19. A process for the preparation of a compound of formula (Ir) as defined in claim 1, or a tautomer, pharmaceutically acceptable salt, or solvate thereof which comprises:

(a) reacting a compound of formula (XXIX) with an organometallic reagent:

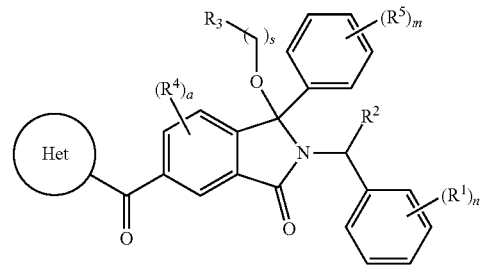

(XXIX)

wherein $R^1$ $R^2$, $R^3$, $R^4$, $R^5$, s, m and n are as defined in claim 1;

Het is

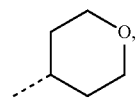

optionally substituted by one $R^z$ group;
a is 1; and
$R^4$ is at the 4-position of the isoindolinone ring; and/or (b) interconversion of a compound of formula (Ir) or protected derivative thereof to a further compound of formula (Ir) or protected derivative thereof; and/or (c) deprotection of a protected derivative of a compound of formula (Ir); and/or (d) providing a compound of formula (Ir) and forming a pharmaceutically acceptable salt of the compound.

20. A compound according to claim 1, or a tautomer or a solvate or a pharmaceutically acceptable salt thereof, wherein n is 1 and $R^1$ is chloro or nitrile.

21. A compound according to claim 20, or a tautomer or a solvate or a pharmaceutically acceptable salt thereof, wherein $R^1$ is chloro.

22. A compound according to claim 1, or a tautomer or a solvate or a pharmaceutically acceptable salt thereof, wherein $R^2$ is -COOH, -CH$_2$COOH, -CH$_2$CH$_2$-CO$_2$H, -(CH(CH$_3$))-CO$_2$H or -(C(CH$_3$)2)-CO$_2$H.

23. A compound according to claim 1, or a tautomer or a solvate or a pharmaceutically acceptable salt thereof, wherein $R^3$ is -(A)$_r$-(CR$^x$ P$^y$)$_q$-X and A is a cyclopropyl group.

24. A compound according to claim 1, or a tautomer or a solvate or a pharmaceutically acceptable salt thereof, wherein $R^3$ is -(A)$_r$-(CR$^x$R$^y$)$_q$-X and A is a heterocyclic group with 5 ring members.

25. A compound according to claim 1, wherein the compound is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid or a tautomer, pharmaceutically acceptable salt or solvate thereof.

26. A compound according to claim 1, wherein the compound is (3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid or a tautomer, pharmaceutically acceptable salt or solvate thereof.

27. A compound according to claim 1, wherein the compound is 2-(5-chloro-2-{[(1R)-1-(4-chlorophenyl)-7- fluoro-5-[(1S)-1-hydroxy-1-(oxan-4-yl)propyl]-1-methoxy-3-oxo-2,3-dihydro-1H-isoindol-2-yl]methyl}phenyl)-2-methylpropanoic acid or a tautomer, pharmaceutically acceptable salt or solvate thereof.

* * * * *

UNITED STATES PATENT AND TRADEMARK OFFICE
CERTIFICATE OF CORRECTION

PATENT NO. : 10,544,132 B2  
APPLICATION NO. : 15/763698  
DATED : January 28, 2020  
INVENTOR(S) : Chessari et al.

Page 1 of 3

It is certified that error appears in the above-identified patent and that said Letters Patent is hereby corrected as shown below:

In the Claims

Column 308, Line 21: Claim 1, Delete "$R^z$ is independently selected" and insert -- $R^z$ is selected --

Column 308, Line 22: Claim 1, Delete "$C_{1-6}$ alkyl" and insert -- $C_{1-6}$alkyl --

Column 308, Lines 46-47: Claim 2, Delete "$C_{1-4}$alkoxy, for example wherein n is 1 and $R^1$ is chloro or nitrile e.g. chloro; or" and insert -- $C_{1-4}$alkoxy; or --

Column 308, Line 60: Claim 3, Delete "-$(R^xR^y)_u$-$CO_2H$." and insert -- -$(CR^xR^y)_u$-$CO_2H$. --

Column 309, Line 6: Claim 6, Delete "or -C=O)" and insert -- or -C(=O) --

Column 309, Line 60: Claim 12, Delete "(3R)-2- [(4-" and insert -- (3R)-2-[(4- --

Column 309, Line 62: Claim 12, Delete "ethyl]-3 -{[1-" and insert -- ethyl]-3-{[1- --

Column 310, Line 5: Claim 12, Delete "(3 S)" and insert -- (3S) --

Column 310, Line 6: Claim 12, Delete "-(oxan-4- yl)ethyl]" and insert -- -(oxan-4-yl)ethyl] --

Column 310, Line 9: Claim 12, Delete "(3 S)" and insert -- (3S) --

Column 310, Line 10: Claim 12, Delete "4-yl)-1- hydroxyethyl]" and insert -- 4-yl)-1-hydroxyethyl] --

Column 310, Line 13: Claim 12, Delete "(3 S)" and insert -- (3S) --

Column 310, Line 14: Claim 12, Delete "4-yl)-1- hydroxypropyl]" and insert -- 4-yl)-1-hydroxypropyl] --

Signed and Sealed this  
Ninth Day of June, 2020

Andrei Iancu  
*Director of the United States Patent and Trademark Office*

CERTIFICATE OF CORRECTION (continued)
U.S. Pat. No. 10,544,132 B2

Column 310, Line 18: Claim 12, Delete "1-(oxan- 4-yl)propyl]" and insert -- 1-(oxan-4-yl)propyl] --

Column 310, Line 22: Claim 12, Delete "1-(oxan- 4-yl)propyl]" and insert -- 1-(oxan-4-yl)propyl] --

Column 310, Line 26: Claim 12, Delete "1-(oxan- 4-yl)propyl]" and insert -- 1-(oxan-4-yl)propyl] --

Column 310, Line 30: Claim 12, Delete "1-(oxan- 4-yl)propyl]" and insert -- 1-(oxan-4-yl)propyl] --

Column 310, Line 35: Claim 12, Delete "fluoro-5-R1R)-1-(4-fluorooxan-4- yl)" and insert -- fluoro-5-[(1R)-1-(4-fluorooxan-4-yl) --

Column 310, Line 39: Claim 12, Delete "-(4-fluorooxan-4- yl)-1" and insert -- -(4-fluorooxan-4-yl)-1 --

Column 310, Line 40: Claim 12, Delete "-3-oxo-2, 3-dihydro" and insert -- 3-oxo-2,3-dihydro --

Column 310, Line 43: Claim 12, Delete "4- fluorooxan-4-yl" and insert -- 4-fluorooxan-4-yl --

Column 310, Line 44: Claim 12, Delete "2,3 -dihydro" and insert -- 2,3-dihydro --

Column 310, Line 48: Claim 12, Delete "2,3 -dihydro" and insert -- 2,3-dihydro --

Column 310, Line 52: Claim 12, Delete "oxo-2, 3-dihydro-1H-isoindol -2-yl]methyl }phenoxy )" and insert -- oxo-2,3-dihydro-1H-isoindol-2-yl]methyl}phenoxy) --

Column 310, Line 58: Claim 12, Delete "propyl]-1- methoxy" and insert -- propyl]-1-methoxy --

Column 310, Lines 60-63: Claim 12, Delete "5 -chloro-2-{[(1R)-1-(4-chlorophenyl)- 1-ethoxy-7-fluoro-5-[(1S)- 1-hydroxy-1-(oxan-4- yl)propyl]-3-oxo-2, 3-dihydro-1H-isoindol-2-yl]methyl} benzoic acid;" and insert -- 5-chloro-2-{[(1R)-1-(4-chlorophenyl)-1-ethoxy-7-fluoro-5-[(1S)-1-hydroxy-1-(oxan-4-yl)propyl]-3-oxo-2,3-dihydro-1H-isoindol-2-yl]methyl}benzoic acid; --

Column 310, Line 65: Claim 12, Delete "hydroxypropyl]-1- methoxy" and insert -- hydroxypropyl]-1-methoxy --

Column 311, Line 2: Claim 12, Delete "hydroxypropyl]-1- methoxy" and insert -- hydroxypropyl]-1-methoxy --

Column 311, Line 11: Claim 12, Delete "1H-isoindol -2-yl" and insert -- 1H-isoindol-2-yl --

Column 311, Line 16: Claim 12, Delete "1H-isoindol -2-yl" and insert -- 1H-isoindol-2-yl --

Column 311, Line 20: Claim 12, Delete "3-oxo-2, 3-dihydro" and insert -- 3-oxo-2,3-dihydro --

Column 311, Line 26: Claim 13, Delete "oxan-4- yl)propyl" and insert -- oxan-4-yl)propyl --

CERTIFICATE OF CORRECTION (continued)
U.S. Pat. No. 10,544,132 B2

Column 311, Line 36: Claim 13, Delete "1H-i soindol-2yl]" and insert -- 1H-isoindol-2yl] --

Column 312, Line 38: Claim 20, Delete "$R^1$" and insert -- $R^1$ --

Column 312, Line 41: Claim 21, Delete "$R^1$" and insert -- $R^1$ --

Column 312, Line 45: Claim 22, Delete "or -(C(CH$_3$)2)-CO$_2$H" and insert -- or -(C(CH$_3$)$_2$)-CO$_2$H --

Column 312, Line 48: Claim 23, Delete "-(A)$_t$-(CR$^x$ P$^y$)$_q$-X" and insert -- -(A)$_t$-(CR$^x$ R$^y$)$_q$-X --

Column 312, Line 55: Claim 25, Delete "(2S,3S)-3- (4-chlorophenyl)" and insert -- (2S,3S)-3-(4-chlorophenyl) --

Column 312, Line 57: Claim 25, Delete "propyl]-1- methoxy" and insert -- propyl]-1-methoxy --

Column 312, Line 61: Claim 26, Delete "3-(4- chlorophenyl)" and insert -- 3-(4-chlorophenyl) --

Column 312, Line 63: Claim 26, Delete "methoxy-3- oxo" and insert -- methoxy-3-oxo --

Column 312, Line 67: Claim 27, Delete "2-(5-chloro- 2-" and insert -- 2-(5-chloro-2- --

Column 313, Line 2: Claim 27, Delete "3-oxo-2,3- dihydro" and insert -- 3-oxo-2,3-dihydro --